(12) United States Patent
Kim et al.

(10) Patent No.: US 12,161,722 B2
(45) Date of Patent: Dec. 10, 2024

(54) BIFUNCTIONAL HETEROCYCLIC COMPOUND HAVING BTK DEGRADATION FUNCTION VIA UBIQUITIN PROTEASOME PATHWAY, AND USE THEREOF

(71) Applicants: KOREA RESEARCH INSTITUTE OF CHEMICAL TECHNOLOGY, Daejeon (KR); UBIX THERAPEUTICS, INC., Seoul (KR)

(72) Inventors: Pil Ho Kim, Daejeon (KR); Sung Yun Cho, Daejeon (KR); Jae Du Ha, Daejeon (KR); Chi Hoon Park, Daejeon (KR); Jong Yeon Hwang, Daejeon (KR); Hyun Jin Kim, Daejeon (KR); Song Hee Lee, Seoul (KR); Ye Seul Lim, Seoul (KR); Han Wool Kim, Seoul (KR); Sun Mi Yoo, Seoul (KR); Beom Seon Suh, Seongnam-si (KR); Ji Youn Park, Seongnam-si (KR); Je Ho Ryu, Seongnam-si (KR); Jung Min Ahn, Incheon (KR); Hee Jung Moon, Incheon (KR); Ho Hyun Lee, Siheung-si (KR)

(73) Assignees: KOREA RESEARCH INSTITUTE OF CHEMICAL TECHNOLOGY, Daejeon (KR); UBIX THERAPEUTICS, INC., Seoul (KR)

( * ) Notice: Subject to any disclaimer, the term of this patent is extended or adjusted under 35 U.S.C. 154(b) by 0 days.

(21) Appl. No.: 18/573,904

(22) PCT Filed: Jun. 24, 2022

(86) PCT No.: PCT/KR2022/009087
§ 371 (c)(1),
(2) Date: Dec. 22, 2023

(87) PCT Pub. No.: WO2022/270994
PCT Pub. Date: Dec. 29, 2022

(65) Prior Publication Data
US 2024/0285778 A1  Aug. 29, 2024

(30) Foreign Application Priority Data

Jun. 25, 2021 (KR) .......... 10-2021-0083326
Jun. 23, 2022 (KR) .......... 10-2022-0077174

(51) Int. Cl.
*A61K 47/55* (2017.01)
*A61K 47/54* (2017.01)
*A61K 47/60* (2017.01)

(52) U.S. Cl.
CPC ............ *A61K 47/55* (2017.08); *A61K 47/545* (2017.08); *A61K 47/60* (2017.08)

(58) Field of Classification Search
CPC .................................................. A61K 47/55
See application file for complete search history.

(56) References Cited

U.S. PATENT DOCUMENTS

| 9,624,224 | B2 | 4/2017 | Chen et al. |
| 11,084,824 | B2* | 8/2021 | Kim ................... A23L 33/10 |
| 11,155,561 | B2 | 10/2021 | Shu et al. |
| 2009/0203690 | A1 | 8/2009 | Akritopoulou-Zanze et al. |
| 2022/0105188 | A1 | 4/2022 | Hwang et al. |

FOREIGN PATENT DOCUMENTS

| KR | 10-2016-0062103 A | 6/2016 |
| KR | 10-2128018 B2 | 6/2020 |
| WO | 2008/141976 A1 | 11/2008 |
| WO | 2008/147831 A1 | 12/2008 |
| WO | 2008/154241 A1 | 12/2008 |
| WO | 2012/084704 A1 | 6/2012 |
| WO | 2014/189466 A1 | 11/2014 |
| WO | 2015/092431 A1 | 6/2015 |
| WO | 2017/197051 A1 | 11/2017 |
| WO | 2018/071606 A1 | 4/2018 |
| WO | 2018/119441 A1 | 6/2018 |
| WO | 2018/140809 A1 | 8/2018 |
| WO | 2018-208132 A1 | 11/2018 |
| WO | 2019-042445 A1 | 3/2019 |
| WO | 2019/136016 A1 | 7/2019 |
| WO | 2019/148055 A1 | 8/2019 |
| WO | 2019/149922 A1 | 8/2019 |
| WO | 2019/186358 A1 | 10/2019 |
| WO | 2020/012337 A1 | 1/2020 |
| WO | 2020/038415 A1 | 2/2020 |

(Continued)

OTHER PUBLICATIONS

Tinworth, Med. Chem. Commun.,2016, 7, 2206-2216.*
Lim, Blood Adv. Jan. 10, 2023;7(1):92-105.*
International Search Report with Written Opinion issued for International Application No. PCT/KR2022/009087 on Sep. 30, 2022, 16 pages.
Lee, Sang Ho et al. "Next-generation Drug Discovery Platform: Target Protein Degradation", Keit PD Issue Report, 2018; 18(3), 18-40.

*Primary Examiner* — Nizal S Chandrakumar
(74) *Attorney, Agent, or Firm* — ROTHWELL, FIGG, ERNST & MANBECK, P.C.

(57) ABSTRACT

The present invention relates to a novel heterocyclic compound and a composition, for preventing or treating a cancer, an autoimmune disease, and an inflammatory disease, comprising same. The novel heterocyclic compound of the present invention is a bifunctional compound having a Bruton's tyrosine kinase (BTK) degradation function via a ubiquitin proteasome pathway, and may be utilized as a composition for preventing or treating a cancer, an autoimmune disease, and Parkinson's disease.

2 Claims, No Drawings

(56) References Cited

FOREIGN PATENT DOCUMENTS

| | | |
|---|---|---|
| WO | 2020/051235 A1 | 3/2020 |
| WO | 2020/051564 A1 | 3/2020 |
| WO | 2020-081450 A1 | 4/2020 |
| WO | 2020/160192 A1 | 8/2020 |
| WO | 2020/160193 A2 | 8/2020 |
| WO | 2020/160198 A1 | 8/2020 |
| WO | 2020/162725 A1 | 8/2020 |
| WO | 2020/167518 A1 | 8/2020 |
| WO | 2020/200291 A1 | 10/2020 |
| WO | 2020/263935 A1 | 12/2020 |
| WO | 2021/058017 A1 | 4/2021 |
| WO | 2021-068380 A1 | 4/2021 |

\* cited by examiner

BIFUNCTIONAL HETEROCYCLIC COMPOUND HAVING BTK DEGRADATION FUNCTION VIA UBIQUITIN PROTEASOME PATHWAY, AND USE THEREOF

CROSS REFERENCE TO RELATED APPLICATION

This application is a 35 U.S.C. 371 National Phase Entry Application from PCT/KR2022/009087, filed on Jun. 24, 2022, which claims the benefit of Korean Patent Application Nos. 10-2021-0083326 filed on Jun. 25, 2021, and 10-2022-0077174 filed on Jun. 23, 2022, the disclosures of which are incorporated herein in their entirety by reference.

TECHNICAL FIELD

The present disclosure relates to a novel bifunctional compound having Bruton's tyrosine kinase (BTK) degradation activity through the ubiquitin proteasome pathway.

BACKGROUND ART

Among tissues that proliferate uncontrollably in the human body and destroy organs, cancer refers to a life-threatening neoplasm with strong reproductivity and high metastasis and is also called a malignant tumor. Cancer is characterized by uncontrollable proliferation and invasion. When metastasized, cancer spreads to a different part in the body from where it started. That is, cancer spreads from a primary site to various secondary sites, such as the liver, the lungs, bones, the brain, etc. through lymph nodes or blood vessels, eventually threatening life.

Although the causes and origins of cancer have not been fully elucidated despite the development of modern medicine, carcinogenic chemicals (about 1,500 species), radiation, continuous stimulation and damage, hereditary factors, and viruses are currently recognized as causes. About 80 to 90% of cancer occurrence is directly or indirectly related to environmental factors, and it is recognized that more than 90% of exogenous carcinogens are various compounds that exist in the natural environment. In addition, cancer is complex because there are many types, and there are differences in stages for each type, and there are differences in treatment methods and principles. In the treatment of cancer, surgery or radiation therapy and chemotherapy using chemotherapeutic agents that inhibit cell proliferation are mainly used.

Among them, chemotherapy provokes side effects due to cytotoxicity and induces drug resistance when repetitively used because chemotherapeutic agents are not target agents that act directly on each cancer target. Despite an initial successful response by an anticancer drug used in chemotherapy, when the cancer treatment period is prolonged or recurrence occurs, side effects due to cytotoxicity and resistance to the drug makes the treatment ending in failure. There is therefore a continuing need for the development of targeted therapies with clear mechanisms of anticancer action in order to overcome the limitations of such chemotherapeutic agents. In this regard, many studies are being conducted on specific molecular biological factors involved in oncogenesis in order to develop targeted therapeutic agents. In particular, molecular biological factors are widely used to prognose cancer or to determine whether chemotherapy or radiotherapy should be undertaken.

Bruton's tyrosine kinase (BTK), which is a member of the TEC family of tyrosine kinases, affects the development of early B-cells and the activation of mature B-cells and functions as a regulatory factor to regulate signal transduction and cell survival. BTK is activated by B-cell signaling through the B cell antigen receptor (BCR) and involved in various intracellular signal transduction pathways essential for cell survival, playing a crucial role in the signaling and development of B cells.

However, when BTK is overexpressed by abnormal signal transduction of BCR in B cells, cascade phosphorylation occurs on molecules downstream of the BCR signaling pathway, leading to the abnormal proliferation of B cells and the formation of pathological autoantibodies. As a result, it can induce autoimmune diseases such as systemic lupus erythematosus and rheumatoid arthritis, cancer, B cell malignancies, and inflammatory diseases.

In addition, BTK is known to be overexpressed in B-lineage malignant lymphoid tumors such as B-cell precursor-acute lymphocytic leukemia, chronic lymphocytic leukemia, and non-Hodgkin's lymphoma. When BTK is inhibited in B cells that are abnormally proliferating, signal transduction by BCR is blocked to interfere with the progression of B cell-mediated diseases. Thus, the use of BTK inhibitors can be a useful approach for treating B cell-mediated diseases. Conventionally, since advantageous effects have been demonstrated through BTK inhibition in experimental animal models for autoimmune diseases or B-cell malignancies, BTK inhibitors have attracted attention as therapeutic drugs for these diseases.

The proteolysis-targeting chimaera (PROTAC) technology of the present disclosure is a small molecule compound-based new drug development platform technology, and consists of an E3 ligase binding module-linker-target protein binding module that is designed to degrade target proteins responsible for the onset of diseases in vivo through ubiquitination. With such mechanisms, the technology can degrade over 80% of disease-causing proteins that are difficult to target with existing drug development techniques, and can overcome the resistance problem of existing drugs.

Therefore, the PROTAC can take, as targets, proteins associated with incurable diseases such as dementia and cancer, which have not been accessible through existing drug development methods, whereby it is expected to accelerate the development of new treatments, which do not currently exist, for diseases.

With respect to Bruton's tyrosine kinase (BTK) inhibitors, reference may be made to Korean Patent No. 10-2016-0062103 A and Korean Patent No. 2128018. However, these related literatures are different from the present disclosure that is adapted to remove disease-causing target proteins by inducing in vivo degradation through ubiquitination.

In addition, the International Patent No. WO 2020081450 discloses compounds for degrading BTK via a ubiquitin proteasome pathway, which are different from the compounds of the present disclosure in terms of structure and activity.

Under this background, intensive and thorough research conducted by the present inventors resulted in the finding that novel compounds as in Chemical Formula 1 can selectively and effectively degrade target proteins responsible for the onset of diseases and can be developed into a pharmaceutical composition for prevention, treatment, or alleviation of cancer, autoimmune diseases, and Parkinson's disease, leading to the present disclosure.

DISCLOSURE OF INVENTION

Technical Problem

An aspect of the present disclosure is to provide a novel bifunctional compound having BTK degradation activity through a ubiquitin proteasome pathway and a composition including same for prevention or treatment of cancer, an autoimmune disease, and Parkinson's disease. More specifically, the present disclosure aims to provide a novel bifunctional compound having BTK degradation activity via a ubiquitin proteasome pathway, with an excellent degradation effect selective for disease-causing target proteins, and a composition including same for prevention or treatment of cancer, an autoimmune disease, and Parkinson's disease.

Solution to Problem

The present disclosure is drawn to a bifunctional compound, represented by the following Chemical Formula 1, consisting of a targeting ligand-linker(L)-binder(B), or an enantiomer, diastereomer, stereoisomer, hydrate, solvate, prodrug, or pharmaceutically acceptable salt thereof:

[Chemical Formula 1]

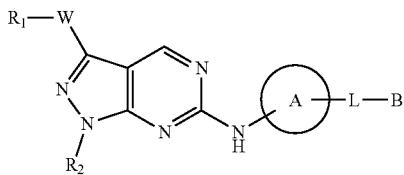

wherein,

W is —NH—, —N($C_1$-$C_6$ alkyl)-, —O—, or —NHC(O)—;

$R_1$ is a substituted or unsubstituted phenyl, a substituted or unsubstituted indanyl, or a substituted or unsubstituted heteroaryl, more specifically, $R_1$ is a substituted or unsubstituted phenyl, a substituted or unsubstituted indanyl, or a substituted or unsubstituted 4- to 12-membered heteroaryl, the substituted phenyl, indanyl, or heteroaryl having a $C_1$-$C_6$ alkyl, a $C_2$-$C_8$ alkenyl, a $C_2$-$C_8$ alkynyl, a halogen, a $C_1$-$C_6$ haloalkyl, a $C_1$-$C_6$ alkoxy, a $C_1$-$C_6$ haloalkoxy, a $C_1$-$C_6$ alkoxy $C_1$-$C_6$ alkoxy, or a substituted or unsubstituted—NHC(O)phenyl as an independent substituent on at least one of the ring members thereof, the substituted —NHC(O)phenyl having a $C_1$-$C_6$ alkyl, a $C_1$-$C_6$ haloalkyl, or a halogen as an independent substituent on at least one of the phenyl ring members;

or $R_1$—W is a pyrrolidinyl or a piperidinyl;

$R_2$ is —H, a $C_1$-$C_6$ alkyl, a $C_1$-$C_6$ haloalkyl, a $C_1$-$C_6$ hydroxyalkyl, a $C_1$-$C_6$ alkoxy $C_1$-$C_6$ alkyl, a substituted or unsubstituted 3- to 12-membered carbocyclyl, or a substituted or unsubstituted heterocyclyl, more specifically $R_2$ is —H, a $C_1$-$C_6$ alkyl, a $C_1$-$C_6$ haloalkyl, a $C_1$-$C_6$ hydroxyalkyl, a $C_1$-$C_6$ alkoxy $C_1$-$C_6$ alkyl, a substituted or unsubstituted 3- to 12-membered carbocyclyl, or a substituted or unsubstituted 3- to 12-membered heterocyclyl, the substituted carbocyclyl or heterocyclyl having a $C_1$-$C_6$ alkyl, a $C_1$-$C_6$ haloalkyl, a $C_1$-$C_6$ alkoxy, a $C_1$-$C_6$ haloalkoxy, a $C_1$-$C_6$ alkylamine, a halogen, —CN, —OH, or —NH$_2$ as an independent substituent on at least one of the ring members thereof;

A is a substituted or unsubstituted 3- to 12-membered carbocyclyl, a substituted or unsubstituted heterocyclyl, a substituted or unsubstituted 6- to 12-membered aryl, or a substituted or unsubstituted heteroaryl, more specifically, A is a substituted or unsubstituted 3- to 12-membered carbocyclyl, a substituted or unsubstituted 3- to 12-membered heterocyclyl, a substituted or unsubstituted 6- to 12-membered aryl, or a substituted or unsubstituted 4- to 12-membered heteroaryl, the substituted carbocyclyl, heterocyclyl, aryl, or heteroaryl having a $C_1$-$C_6$ alkyl, a $C_1$-$C_6$ haloalkyl, a $C_1$-$C_6$ alkoxy, a $C_1$-$C_6$ haloalkoxy, a $C_1$-$C_6$ alkylamine, a halogen, —CN, —OH, or —NH$_2$ as an independent substituent on at least one of the ring members thereof;

L is represented by the following Chemical Formula 2,

[Chemical Formula 2]

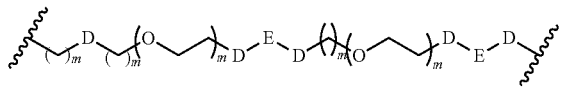

wherein,

D is each independently a direct bond, —C(O)—, —O—, —NH—, —CH(OH)—, —C(O)NH—, —NHC(O)—, —NHC(O)CH$_2$O—, —NHC(O)CH$_2$NH—, —C(O)CH$_2$NH—, —C(=S)—, or —C(CN)=CH—;

E is each independently a direct bond, a substituted or unsubstituted 3- to 12-membered carbocyclyl, a substituted or unsubstituted heterocyclyl, a substituted or unsubstituted 6- to 12-membered aryl, or a substituted or unsubstituted heteroaryl, more specifically, E is each independently a direct bond, a substituted or unsubstituted 3- to 12-membered carbocyclyl, a substituted or unsubstituted 3- to 12-membered heterocyclyl, a substituted or unsubstituted 6- to 12-membered aryl, or a substituted or unsubstituted 4- to 12-membered heteroaryl, the substituted carbocyclyl, heterocyclyl, aryl, or heteroaryl having a $C_1$-$C_6$ alkyl, a halogen, a $C_1$-$C_6$ haloalkyl, a $C_1$-$C_6$ alkoxy, a $C_1$-$C_6$ haloalkoxy, —CN, —OH, or —NH$_2$ as an independent substituent on at least one of the ring members thereof;

m is each independently an integer of 0 to 12;

B is represented by one of the following Chemical Formulas 3 to 7,

[Chemical Formula 3]

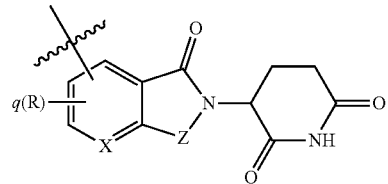

[Chemical Formula 4]

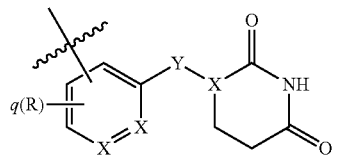

-continued

[Chemical Formula 5]

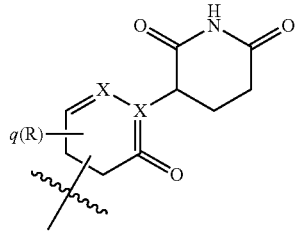

[Chemical Formula 6]

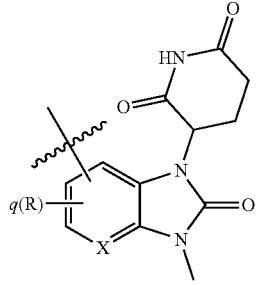

[Chemical Formula 7]

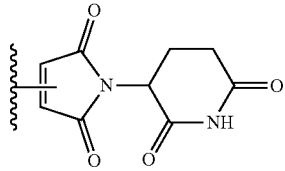

wherein,

Z is —C($R^A$)$_2$—, —C(O)—, —C($R^A$)$_2$—C($R^A$)$_2$—, —C($R^A$)═C($R^A$)—, —C($R^A$)═N—, —N═C($R^A$)—, or —N═N—;

Y is a direct bond, —C($R^A$)$_2$—, —N($R^A$)—, —C(O)NH—, —SO$_2$NH—, or —O—;

X is each independently C, CH, or N;

$R^A$ is each independently —H, a halogen, a $C_1$-$C_6$ alkyl, a $C_1$-$C_6$ haloalkyl, a $C_1$-$C_6$ alkoxy, or a $C_1$-$C_6$ haloalkoxy;

R is each independently —H, a halogen, a $C_1$-$C_6$ alkyl, a $C_1$-$C_6$ haloalkyl, a $C_1$-$C_6$ alkoxy, a $C_1$-$C_6$ haloalkoxy, —CN, —OH, or —NH$_2$; and q is an integer of 0 to 3.

In addition, the present disclosure provides a bifunctional compound represented by Chemical Formula 1, or an enantiomer, diastereomer, stereoisomer, hydrate, solvate, prodrug, or pharmaceutically acceptable salt thereof, wherein W, $R_1$, $R_2$, and A in Chemical Formula 1 are as defined below:

in Chemical Formula 1,

W is —NH—;

$R_1$ is a substituted or unsubstituted phenyl or a substituted or unsubstituted indanyl, the substituted phenyl or indanyl having a $C_1$-$C_6$ alkyl, a halogen, a $C_1$-$C_6$ haloalkyl, a $C_1$-$C_6$ alkoxy, a $C_1$-$C_6$ alkoxy $C_1$-$C_6$ alkoxy, or a substituted or unsubstituted —NHC(O)phenyl as an independent substituent on at least one of the ring members thereof, the substituted —NHC(O)phenyl having a $C_1$-$C_6$ haloalkyl as an independent substituent on at least one of the phenyl ring members;

$R_2$ is H or a $C_1$-$C_6$ alkyl;

A is represented by the following Chemical Formula 8 or 9,

[Chemical Formula 8]

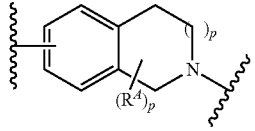

[Chemical Formula 9]

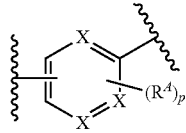

wherein,

X is each independently CH or N;

$R^A$ is each independently —H, a halogen, a $C_1$-$C_6$ alkyl, a $C_1$-$C_6$ alkoxy, or a $C_1$-$C_6$alkylamine; and p is each independently an integer of 0 to 2.

Also, the present disclosure provides a bifunctional compound represented by Chemical Formula 1, or an enantiomer, diastereomer, stereoisomer, hydrate, solvate, prodrug, or pharmaceutically acceptable salt thereof, wherein L in Chemical Formula 2 is as defined below:

in Chemical Formula 2,

D is each independently a direct bond, —C(O)—, —O—, —NH—, —CH(OH)—, —C(O)NH—, —NHC(O)—, —NHC(O)CH$_2$O—, —NHC(O)CH$_2$NH—, —C(O)CH$_2$NH—, —C(═S)—, or —C(CN)═CH—;

m is each independently an integer of 0 to 12;

E is each independently a direct bond, phenyl, cyclopropyl, cyclohexyl, triazolyl, a substituted or unsubstituted piperazinyl, a substituted or unsubstituted piperidinyl, a pyrrolidinyl, a substituted or unsubstituted azetidinyl, 1,2,3,6-tetrahydropyridinyl, or a compound represented by the following Chemical Formula 10 or 11, the substituted piperazinyl, piperidinyl, or azetidinyl having a substituent independently selected from the group consisting of a hydroxy, a halogen, and a $C_1$-$C_6$ alkyl on at least one of the ring members thereof:

[Chemical Formula 10]

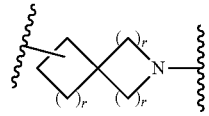

[Chemical Formula 11]

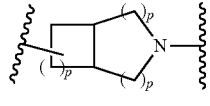

wherein, p is each independently an integer of 0 to 2; and r is each independently an integer of 1 to 2.

Furthermore, the present disclosure provides a bifunctional compound represented by Chemical Formula 1 or an enantiomer, diastereomer, stereoisomer, hydrate, solvate, prodrug, or pharmaceutically acceptable salt thereof wherein B in Chemical Formula 1 is selected from the following Chemical Formula 3, Chemical Formula 4, Chemical Formula 6, or Chemical Formula 7:

[Chemical Formula 3]

[Chemical Formula 4]

[Chemical Formula 5]

[Chemical Formula 6]

[Chemical Formula 7]

wherein,

X is each independently C, CH, or N;

Y is a direct bond, —C(R$^A$)$_2$—, —N(R$^A$)—, —C(O)NH—, or —SO$_2$NH—;

Z is —C(R$^A$)$_2$—, —C(O)—, or —N=N—;

R$^A$ is each independently —H or a C$_1$-C$_6$ haloalkoxy;

R is each independently —H, a halogen, a C$_1$-C$_6$ alkyl, or C$_1$-C$_6$ alkoxy; and q is an integer of 0 to 3.

Moreover, the present disclosure provides a bifunctional compound represented by the following Chemical Formula 1, or an enantiomer, diastereomer, stereoisomer, hydrate, solvate, prodrug, or pharmaceutically acceptable salt thereof:

[Chemical Formula 1]

wherein,

W is —NH—;

R$_1$ is a substituted or unsubstituted phenyl or a substituted or unsubstituted indanyl, the substituted phenyl or indanyl having a C$_1$-C$_6$ alkyl, a halogen, a C$_1$-C$_6$ haloalkyl, a C$_1$-C$_6$ alkoxy, a C$_1$-C$_6$ alkoxy C$_1$-C$_6$ alkoxy, or a substituted or unsubstituted —NHC(O)phenyl as an independent substituent on at least one of the ring members thereof, the substituted —NHC(O)phenyl having a C$_1$-C$_6$ haloalkyl as an independent substituent on at least one of the phenyl ring members;

R$_2$ is H or a C$_1$-C$_6$ alkyl;

A is represented by the following Chemical Formula 8 or 9,

[Chemical Formula 8]

[Chemical Formula 9]

wherein,

X is each independently CH or N;

R$^A$ is each independently —H, a halogen, a C$_1$-C$_6$ alkyl, a C$_1$-C$_6$ alkoxy, or a C$_1$-C$_6$ alkylamine;

p is each independently an integer of 0 to 2;

L is represented by the following Chemical Formula 2,

[Chemical Formula 2]

wherein,

D is each independently a direct bond, —C(O)—, —O—, —NH—, —CH(OH)—, —C(O)NH—, —NHC(O)—, —NHC(O)CH$_2$O—, —NHC(O)CH$_2$NH—, —C(O)CH$_2$NH—, —C(=S)—, or —C(CN)=CH—;

m is each independently an integer of 0 to 12;

E is each independently selected from a direct bond, phenyl, cyclopropyl, cyclohexyl, triazolyl, a substituted or unsubstituted piperazinyl, a substituted or unsubstituted piperidinyl, pyrrolidinyl, a substituted or unsubstituted azetidinyl, 1,2,3,6-tetrahydropyridinyl, or a compound represented by the following Chemical Formula 10 or 11, the substituted piperazinyl, piperidinyl, or azetidinyl having a substituent selected from the group consisting of a hydroxy, a halogen, or a $C_1$-$C_6$ alkyl on at least one of the ring members,

[Chemical Formula 10]

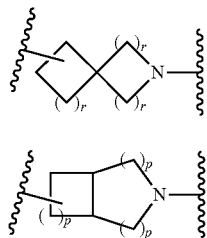

[Chemical Formula 11]

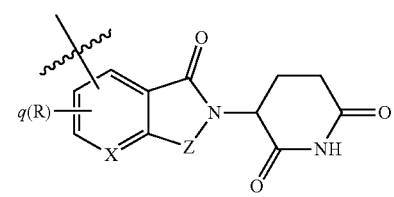

wherein,
p is each independently an integer of 0 to 2;
r is each independently an integer of 1 to 2;
B is selected from the following Chemical Formula 3, Chemical Formula 4, Chemical Formula 6, or Chemical Formula 7,

[Chemical Formula 3]

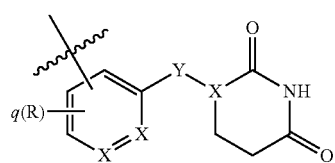

[Chemical Formula 4]

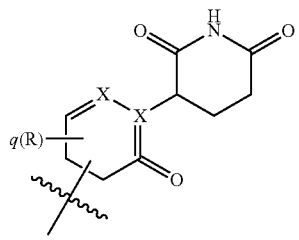

[Chemical Formula 5]

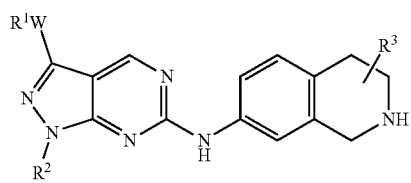

[Chemical Formula 6]

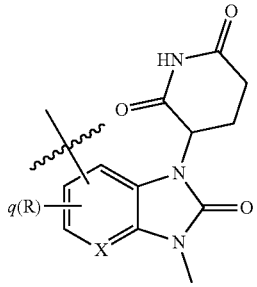

[Chemical Formula 7]

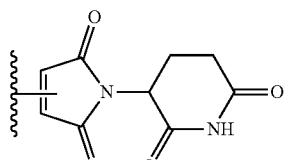

wherein,
X is each independently C, CH, or N;
Y is a direct bond, —C($R^A$)$_2$—, —N($R^A$)—, —C(O)NH—, or —SO$_2$NH—;
Z is —C($R^A$)$_2$—, —C(O)—, or —N=N—;
$R^A$ is each independently —H or a $C_1$-$C_6$ haloalkoxy;
R is each independently —H, a halogen, a $C_1$-$C_6$ alkyl, or $C_1$-$C_6$ alkoxy; and
q is each independently an integer of 0 to 3.

The preparation method and reaction condition for the "BTK-targeting ligand-L (linker)-B (E3 ligase binder)" having various structures of Chemical Formula 1, which is the final compound of the present disclosure, are as follows.

In the context of preparing the compound of Chemical Formula 1 of the present disclosure, the "BTK-targeting ligand" is constructed with reference to Korean Patent No. 2128018, issued to the present inventors, that discloses a preparation method of pyrazolopyrimidine.

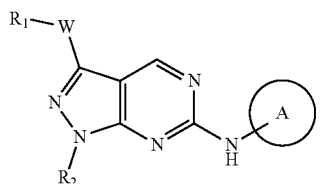

<BTK-targeting ligand>

The targeting ligand-linker (L)-binder (B) compound is prepared as illustrated in the following Schemes 1 to 4:

[Scheme 1]

R = CH$_2$Cl, CH$_2$Br, CH$_2$I, CH$_2$OTs, COOH, CHO

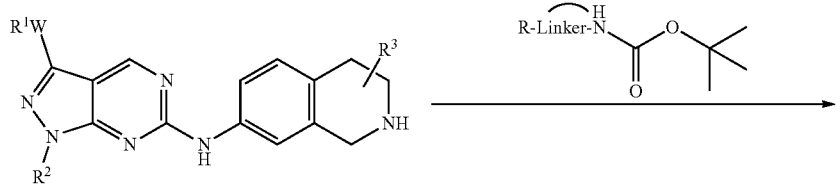

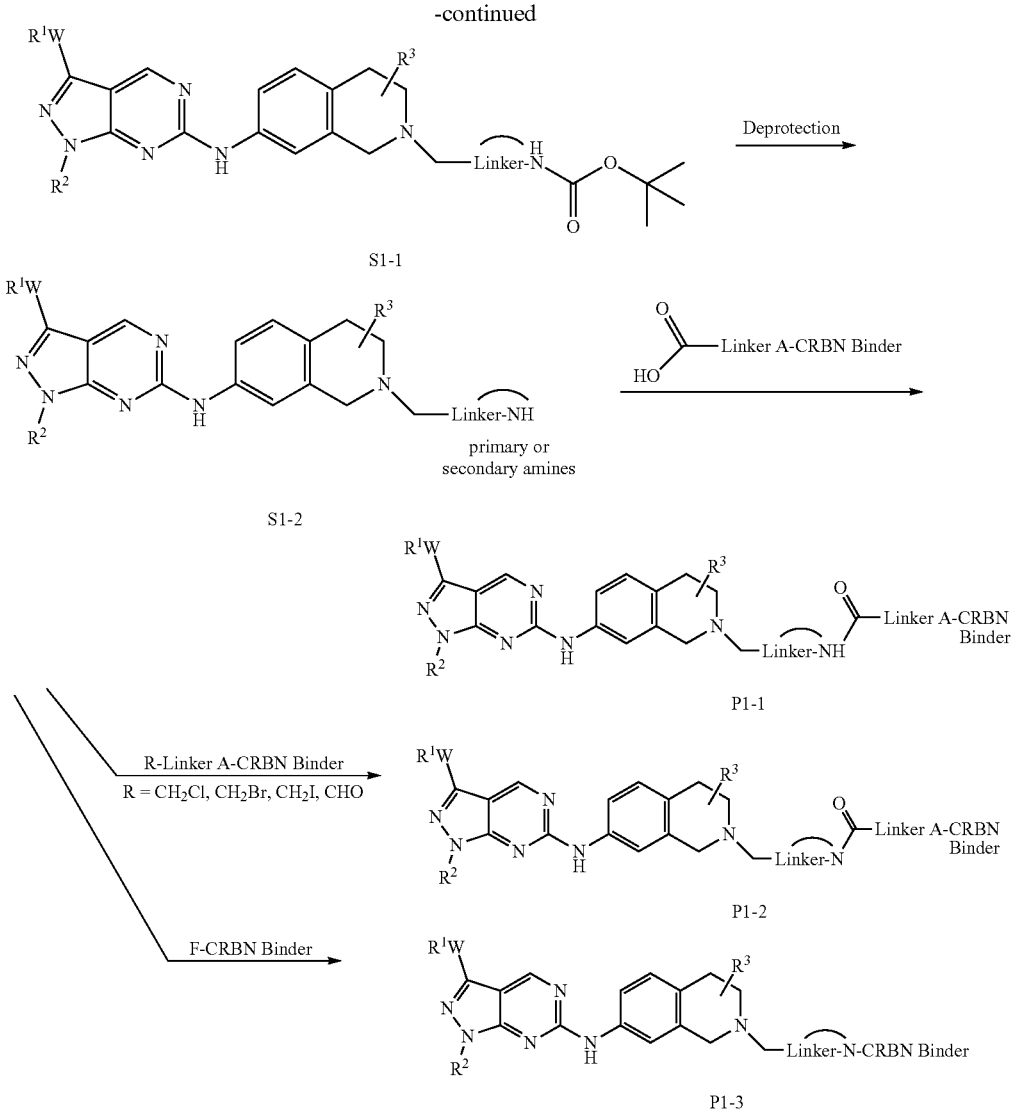

The BTK inhibitor S1 is reacted with a primary or secondary amine-protected electrophile to synthesize S1-1 which is then deprotected to give a primary or secondary amine S1-2. S1-2 is reacted with a CRBN binder containing a carboxylic acid-linker to synthesize PROTAC P1-1. Also, S1-2 is reacted with a CRBN binder containing an electrophile-linker to synthesize PROTAC P1-2. $S_N Ar$ (nucleophilic aromatic substitution) reaction between S1-2 and a fluoro-CRBN binder leads to the synthesis of PROTAC P1-3.

[Scheme 2]

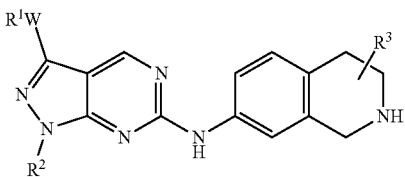

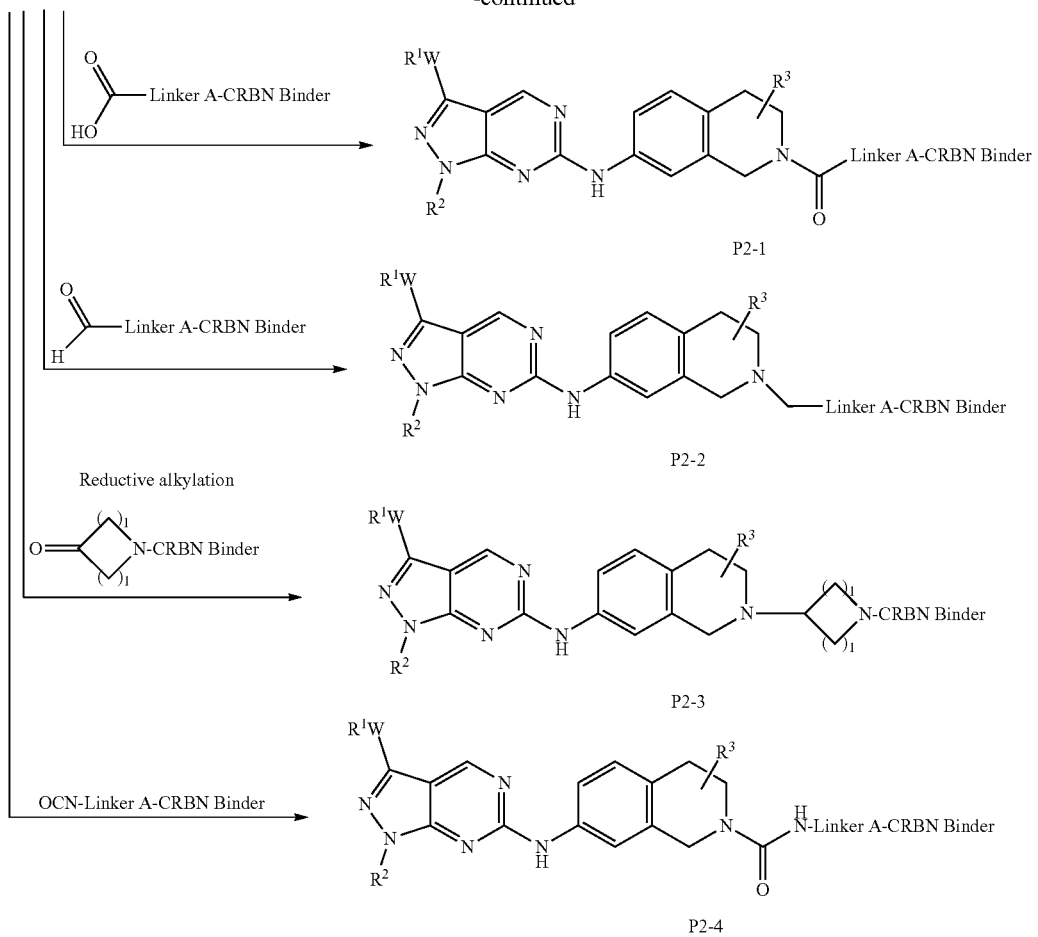

The BTK inhibitor S1 is reacted with CRBN binder containing a carboxylic acid-linker to synthesize PROTAC P2-1. The reductive alkylation of S1 with CRBN containing an aldehyde-linker synthesizes PROTAC P2-2. Also, the reductive alkylation of S1 with a CRBN binder containing a cyclic ketone synthesizes PROTAC P2-3. When reacted with a CRBN binder containing an isocyanate-linker, S1 is converted into the adduct PROTAC P2-4.

[Scheme 3]

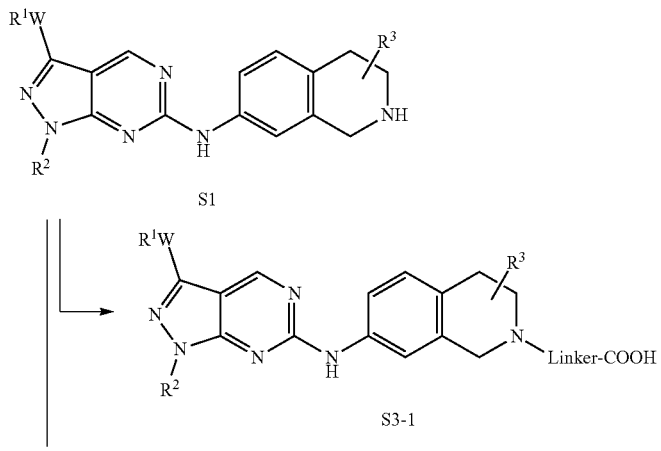

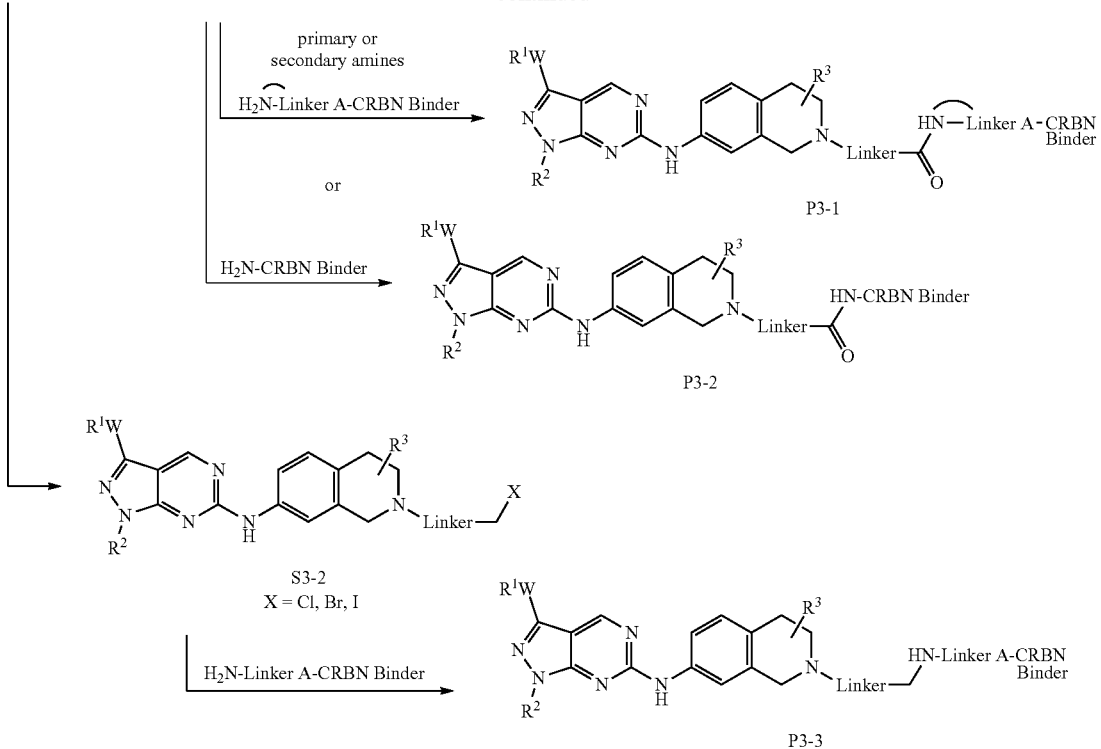

The BTK inhibitor S1 is reacted with a linker containing a carboxylic acid to give S3-1. S3-1 is reacted with a CRBN binder containing a primary or secondary amine-linker to synthesize PROTAC P3-1 or with a CRBN binder containing a primary amine to synthesize PROTAC P3-2. S1 is reacted with a linker containing a halogen to give S3-2 which is then reacted with a CRBN binder containing a primary amine-linker to synthesize PROTAC P3-3.

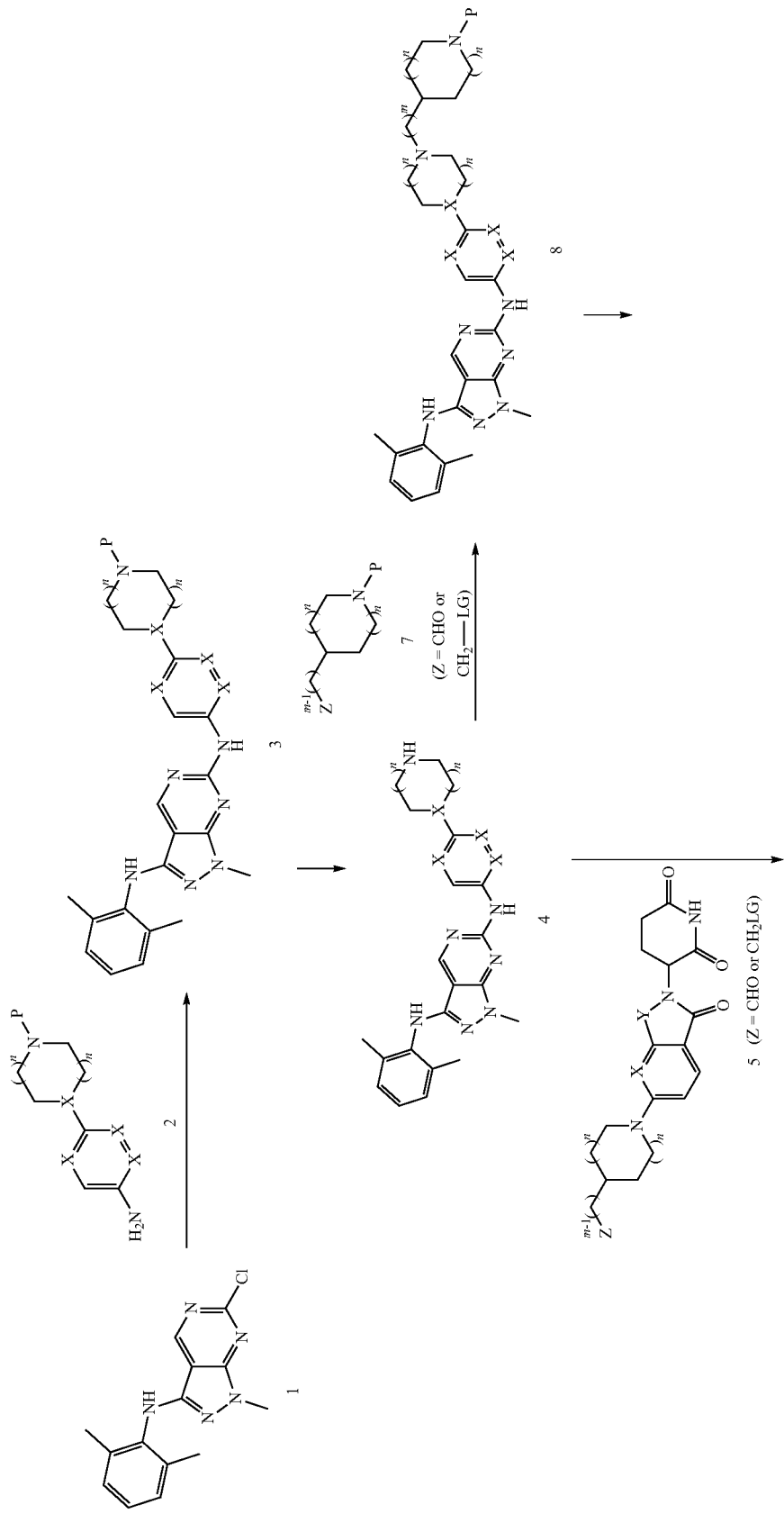

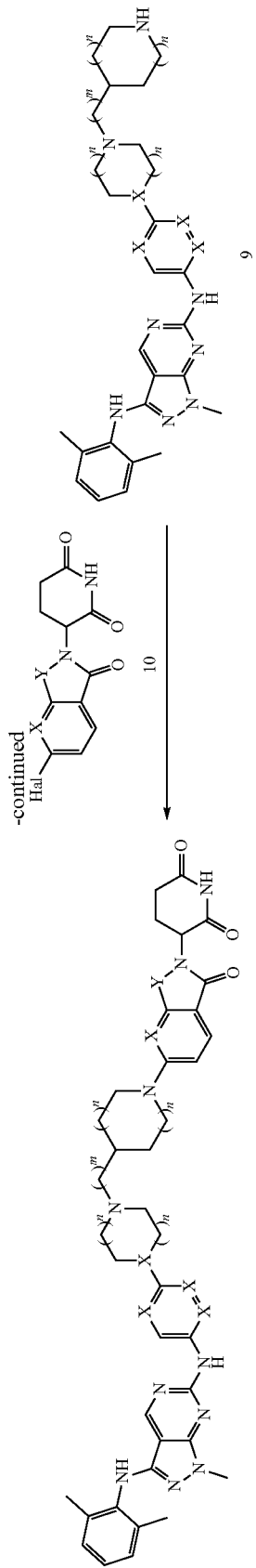

In Scheme 4, starting material 1 (Korean Patent No. 10-2128018) is reacted with amine 2 protected with a suitable protecting group in the presence of an acid, a base, or a metal catalyst to give intermediate 3 which is then deprotected to afford intermediate 4. Intermediate 4 is subjected to reductive amination or N-alkylation with intermediate 5 (WO2018/140809, WO2019/149922) in which a CRBN ligand is bonded to a heterocyclyl having an aldehyde or a leaving group (LG) introduced thereto, to effectively synthesize the final compound 6.

On the other hand, the reductive amination or N-alkylation of intermediate 4 with compound 7 in which a heterocyclyl protected with a suitable protecting group (P) has an aldehyde or a leaving group (LG) gives intermediate 8 which is then deprotected to obtain intermediate 9. This intermediate is reacted at a high temperature with compound 10 (WO2017/197051, WO2018/140809) in which a CRBN ligand is halogenated (Hal), to afford the final compound 6.

In addition, the present disclosure pertains to a compound of Chemical Formula 1, selected from the group of the compound listed below, or an enantiomer, diastereomer, stereoisomer, hydrate, solvate, prodrug, or pharmaceutically acceptable salt thereof:

4-((6-(7-((3-((2,6-dimethylphenyl)amino)-1-methyl-1H-pyrazolo[3,4-d]pyrimidin-6-yl)amino)-3,4-dihydroisoquinolin-2 (1H)-yl)-6-oxohexyl)amino)-2-(2,6-dioxopiperidin-3-yl)isoindoline-1,3-dione (Compound 1), 5-((2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl) amino)-2-(2,6-dioxopiperidin-3-yl)isoindoline-1,3-dione (Compound 2), 4-((2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl) amino)-2-(2,6-dioxopiperidin-3-yl)isoindoline-1,3-dione (Compound 3), N-(2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)-1-(2-(2,6-dioxopiperidin-3-yl)-1,3-dioxoisoindolin-4-yl) piperidine-4-carboxamide (Compound 4), N-(14-(7-((3-((2,6-dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)-1-(2-(2,6-dioxopiperidin-3-yl)-1,3-dioxoisoindolin-4-yl) piperidine-4-carboxamide (Compound 5), N-(4-(2-(2-(2-(2-((2-(2,6-dioxopiperidin-3-yl)-1,3-dioxoisoindolin-4-yl)amino)ethoxy)ethoxy)ethoxy)phenyl)-4-(7-((3-((4-(2-methoxyethoxy)-2,6-dimethylphenyl)amino)-1-methyl-1H-pyrazolo[3,4-d]pyrimidin-6-yl) amino)-1,1-dimethyl-3,4-dihydroisoquinolin-2 (1H)-yl)-4-oxobutanamide (Compound 6), 4-((12-(7-((3-((2,6-dimethylphenyl)amino)-1-methyl-1H-pyrazolo[3,4-d]pyrimidin-6-yl)amino)-3,4-dihydroisoquinolin-2 (1H)-yl)-12-oxododecyl)amino)-2-(2,6-dioxopiperidin-3-yl)isoindoline-1,3-dione (Compound 7), 5-((14-(7-((3-((2,6-dimethylphenyl)amino)-1-methyl-H-pyrazolo[3,4-d]pyrimidin-6-yl)amino)-3,4-dihydroisoquinolin-2 (1H)-yl)-14-oxo-3,6,9,12-tetraoxatetradecyl) amino)-2-(2,6-dioxopiperidin-3-yl)isoindoline-1,3-dione (Compound 8), N-(14-(7-((3-((2,6-dimethylphenyl)amino)-1-methyl-H-pyrazolo[3,4-d]pyrimidin-6-yl)amino)-3,4-dihydroisoquinolin-2 (1H)-yl)-14-oxo-3,6,9,12-tetraoxatetradecyl)-2-((2-(2,6-dioxopiperidin-3-yl)-1,3-dioxoisoindolin-5-yl) oxy)acetamide (Compound 9), N-(14-(7-((3-((2,6-dimethylphenyl)amino)-1-methyl-H-pyrazolo[3,4-d]pyrimidin-6-yl)amino)-3,4-dihydroisoquinolin-2 (1H)-yl)-14-oxo-3,6,9,12-tetraoxatetradecyl)-2-((2-(2,6-dioxopiperidin-3-yl)-1,3-dioxoisoindolin-4-yl) amino)acetamide (Compound 10), tert-butyl 1-((2-(2,6-dioxopiperidin-3-yl)-1,3-dioxoisoindolin-4-yl)amino)-2-oxo-6,9,12,15-tetraoxa-3-azaheptadecan-17-oate (Compound 11), N-(2-(2-(2-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)-1H-1,2,3-triazol-1-yl)ethoxy)ethoxy)ethyl)-2-((2-(2,6-dioxopiperidin-3-yl)-1,3-dioxoisoindolin-5-yl)amino)acetamide (Compound 12), 4-((14-(7-((3-((2,6-dimethylphenyl)amino)-1-methyl-H-pyrazolo[3,4-d])pyrimidin-6-yl)amino)-3,4-dihydroisoquinolin-2 (1H)-yl)-14-oxo-3,6,9,12-tetraoxatetradecyl) amino)-2-(2,6-dioxopiperidin-3-yl)isoindoline-1,3-dione (Compound 13), tert-butyl 2-(2-(2-((2-(2,6-dioxopiperidin-3-yl)-1,3-dioxoisoindolin-5-yl)amino)ethoxy)ethoxy)acetate (Compound 14), 5-((15-(7-((3-((2,6-dimethylphenyl)amino)-1-methyl-H-pyrazolo[3,4-d]pyrimidin-6-yl)amino)-3,4-dihydroisoquinolin-2 (1H)-yl)-15-oxo-3,6,9,12-tetraoxapentadecyl) amino)-2-(2,6-dioxopiperidin-3-yl)isoindoline-1,3-dione (Compound 15), N-(15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-5-yl) oxy)acetamide (Compound 16), N-(15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-4-yl) oxy)acetamide (Compound 17), N-(15-(7-((3-((2,6-dimethylphenyl)amino)-1-methyl)-1H-pyrazolo[3,4-d]pyrimidin-6-yl)amino)-3,4-dihydroisoquinolin-2 (1H)-yl)-15-oxo-3,6,9,12-tetraoxapentadecyl)-2-(4-(2-(2,6-dioxopiperidin-3-yl)-1,3-dioxoisoindolin-5-yl)piperazin-1-yl)acetamide (Compound 18), N-(2-(2-(2-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-1H-1,2,3-triazol-1-yl)ethoxy)ethoxy)ethoxy)ethyl)-2-((2-(2,6-dioxopiperidin-3-yl)-1,3-dioxoisoindolin-4-yl)amino) acetamide (Compound 19), N-(2-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl)piperazin-1-yl) acetamide (Compound 20), N-(2-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-5-yl)piperidine-4-carboxamide (Compound 21), N-(15-(7-((3-((2,6-dimethylphenyl)amino)-1-methyl-H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-5-yl) amino)acetamide (Compound 22), 2-(2-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethoxy)ethoxy)-N-(2-(2,6-dioxopiperidin-3-yl)-1,3-dioxoisoindolin-5-yl)acetamide (Compound 23), N-(2-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-4-yl)piperidine-4-carboxamide (Compound 24), N-(2-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethoxy)ethyl)-2-((2-(2,6-dioxopiperidin-3-yl)-1,3-dioxoisoindolin-5-yl)oxy)acetamide (Compound 25), 5-(4-((R)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl)isoindoline-1,3-dione (Compound 26), N-(2-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-5-yl)azetidine-3-carboxamide (Compound 27), 5-(4-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidine-1-carbonyl)piperidin-1-yl)-2-(2,6-dioxopiperidin-3-yl)isoindoline-1,3-dione (Compound 28), 5-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 29), 5-(2-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidin-1-yl)-2-oxoethoxy)-2-(2,6-dioxopiperidin-3-yl)isoindoline-1,3-dione (Compound 30), 5-(4-(2-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidin-1-yl)-2-oxoethyl)piperazin-1-yl)-2-(2,6-dioxopiperidin-3-yl)isoindoline-1,3-dione (Compound 31), 5-(4-(2-((R)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)piperazin-1-yl)-2-(2,6-dioxopiperidin-3-yl)isoindoline-1,3-dione (Compound 32), 5-(4-(2-((S)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)piperazin-1-yl)-2-(2,6-dioxopiperidin-3-yl)isoindoline-1,3-dione (Compound 33), 5-(2-((S)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethoxy)-2-(2,6-dioxopiperidin-3-yl)isoindoline-1,3-dione (Compound 34), 5-((2-((S)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)amino)-2-(2,6-dioxopiperidin-3-yl)isoindoline-1,3-dione (Compound 35), 5-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-2-(2,6-dioxopiperidin-3-yl)isoindoline-1,3-dione (Compound 36), 3-(6-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidine-2,6-dione (Compound 37), 1-(5-(4-((7-((3-((2,6-dimethylphenyl))amino)-1-methyl-1H-pyrazolo[3,4-d]pyrimidin-6-yl)amino)-3,4-dihydroisoquinolin-2 (1H)-yl)methyl)piperidine-1-carbonyl)-2-methoxyphenyl)dihydropyrimidine-2,4 (1H,3H)-dione (Compound 38), 5-(4-(2-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethyl)piperazin-1-yl)-2-(2,6-dioxopiperidin-3-yl)isoindoline-1,3-dione (Compound 39), 5-(4-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidine-1-carbonyl)piperidin-1-yl)-2-(2,6-dioxopiperidin-3-yl)isoindoline-1,3-dione (Compound 40), 5-(4-(((3-((3-((2,6-dimethylphenyl)amino)-1-methyl-H-pyrazolo[3,4-d]pyrimidin-6-yl)amino)benzyl)amino)methyl)piperidin-1-yl)-2-(2,6-dioxopiperidin-3-yl)isoindoline-1,3-dione (Compound 41), 5-(4-(4-(((3-((3-((2,6-dimethylphenyl)amino)-1-methyl-H-pyrazolo[3,4-d]pyrimidin-6-yl)amino)benzyl)amino)methyl)piperidine-1-carbonyl)piperidin-1-yl)-2-(2,6-dioxopiperidin-3-yl)isoindoline-1,3-dione (Compound 42), 5-(2-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)piperidin-1-yl)-2-oxoethoxy)-2-(2,6-dioxopiperidin-3-yl)isoindoline-1,3-dione (Compound 43), 5-(4-(2-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)piperidin-1-yl)-2-oxoethyl)piperazin-1-yl)-2-(2,6-dioxopiperidin-3-yl)isoindoline-1,3-dione (Compound 44), 5-((2-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)piperidin-1-yl)-2-oxoethyl)amino)-2-(2,6-dioxopiperidin-3-yl)isoindoline-1,3-dione (Compound 45), 3-(6-((4-((7-((3-((2,6-dimethylphenyl))amino)-1-methyl-H-pyrazolo[3,4-d]pyrimidin-6-yl)amino)-3,4-dihydroisoquinolin-2 (1H)-yl)methyl)piperidin-1-yl)methyl)-4-oxobenzo[d][1,2,3]triazin-3 (4H)-yl)piperidin-2,6-dione (Compound 46), 5-(3-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)azetidin-1-yl)-2-(2,6-dioxopiperidin-3-yl)isoindoline-1,3-dione (Compound 47), 3-(6-(2-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidin-1-yl)-2-oxoethoxy)-4-oxobenzo[d][1,2,3]triazin-3 (4H)-yl)piperidin-2,6-dione (Compound 48), 5-(2-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethoxy)-2-(2,6-dioxopiperidin-3-yl)isoindoline-1,3-dione (Compound 49), 5-(3-((4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)methyl)azetidin-1-yl)-2-(2,6-dioxopiperidin-3-yl)isoindoline-1,3-dione (Compound 50), 5-((2-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethyl)amino)-2-(2,6-dioxopiperidin-3-yl)isoindoline-1,3-dione (Compound 51), 3-(6-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-4-oxobenzo[d][1,2,3]triazin-3 (4H)-yl)piperidin-2,6-dione (Compound 52), 3-(7-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-4-oxobenzo[d][1,2,3]triazin-3 (4H)-yl)piperidin-2,6-dione (Compound 53), 5-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidine-1-carbonyl)piperidin-1-yl)-2-(2,6-dioxopiperidin-3-yl)isoindoline-1,3-dione (Compound 54), 3-(6-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethoxy)-4-oxobenzo[d][1,2,3]triazin-3 (4H)-yl)piperidin-2,6-dione (Compound 55), 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-(2,6-dioxopiperidin-3-yl)isoindoline-1,3-dione (Compound 56), 3-(6-((2-(4-(7-((3-((2,6-dimethylphenyl)amino)-1-methyl-1H-pyrazolo[3,4-d])pyrimidin-6-yl)amino)-1,2,3,4-tetrahydroisoquinoline-2-carbonyl)piperidin-1-yl)-2-oxoethyl)amino)-4-oxobenzo[d][1,2,3]triazin-3 (4H)-yl)piperidin-2,6-dione (Compound 57), 3-(6-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3 (4H)-yl)piperidin-2,6-dione (Compound 58), 3-(5-(4-(7-((3-((2,6-dimethylphenyl))amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3 (4H)-yl)piperidin-2,6-dione (Compound 59), 3-(7-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidine-1-carbonyl)piperidin-1-yl)-4-oxobenzo[d][1,2,3]triazin-3 (4H)-yl)piperidin-2,6-dione (Compound 60), 3-(7-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-dione (Compound 61), 3-(5-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-dione (Compound 62), 3-(7-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-4-oxobenzo[d][1,2,3]triazin-3 (4H)-yl)piperidin-2,6-dione (Compound 63), 3-(4-(3-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-3-oxopropyl)-1-oxoisoindolin-2-yl)piperidin-2,6-dione (Compound 64), 3-(4-(3-(7-((3-((2,6-dimethylphenyl)amino)-1-methyl-H-pyrazolo[3,4-d]pyrimidin-6-yl)amino)-3,4-dihydroisoquinolin-2 (1H)-yl)-3-oxopropyl)-1-oxoisoindolin-2-yl)piperidin-2,6-dione (Compound 65), 5-(3-(7-((3-((2,6-dimethylphenyl))amino)-1-methyl-1H-pyrazolo[3,4-d]pyrimidin-6-yl)amino)-1,2,3,4-tetrahydroisoquinoline-2-carbonyl)pyrrolidin-1-yl)-2-(2,6-dioxopiperidin-3-yl)isoindoline-1,3-dione (Compound 66), 5-(4-(3-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl)isoindoline-1,3-dione (Compound 67), 3-(7-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)amino)-4-oxobenzo[d][1,2,3]triazin-3 (4H)-yl)piperidin-2,6-dione (Compound 68), 3-(7-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3 (4H)-yl)piperidin-2,6-dione (Compound 69), 5-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-(2,6-dioxopiperidin-3-yl)isoindoline-1,3-dione (Compound 70), 3-(7-(7-((3-((2,6-dimethylphenyl)amino)-1-methyl-1H-pyrazolo[3,4-d]pyrimidin-6-yl)amino)-3,4-dihydroisoquinolin-2 (1H)-yl)-4-oxobenzo[d][1,2,3]triazin-3 (4H)-yl)piperidin-2,6-dione (Compound 71), 5-((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)amino)-2-(2,6-dioxopiperidin-3-yl)isoindoline-1,3-dione (Compound 72), 5-(4-((5-((3-((2,6-dimethylphenyl)amino)-1-methyl-1H-pyrazolo[3,4-d]pyrimidin-6-yl)amino)isoindolin-2-yl)methyl)piperidin-1-yl)-2-(2,6-dioxopiperidin-3-yl)isoindoline-1,3-dione (Compound 73), 3-(7-(4-((5-((3-((2,6-dimethylphenyl)amino)-1-methyl-1H-pyrazolo[3,4-d]pyrimidin-6-yl)amino)isoindolin-2-yl)methyl)piperidin-1-yl)-4-oxobenzo[d][1,2,3]triazin-3 (4H)-yl)piperidin-2,6-dione (Compound 74), 5-(4-((7-((3-((2,6-dimethylphenyl)amino)-1-methyl-1H-pyrazolo[3,4-d]pyrimidin-6-yl)amino)-1-methyl-3,4-dihydroisoquinolin-2 (1H)-yl)methyl)piperidin-1-yl)-2-(2,6-dioxopiperidin-3-yl)isoindoline-1,3-dione (Compound 75), 2-(2,6-dioxopiperidin-3-yl)-5-(4-((7-((3-((4-(2-methoxyethoxy)-2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 76), 5-((3-((2,6-dimethylphenyl)amino)-1-methyl-1H-pyrazolo[3,4-d]pyrimidin-6-yl)amino)-2'-(2,6-dioxopiperidin-3-yl)-[2,5'-biisoindoline]-1',3'-dione (Compound 77), 5-(4-((7-((3-((2,6-dimethylphenyl)amino)-1-methyl-1H-pyrazolo[3,4-d]pyrimidin-6-yl)amino)-1-isopropyl-3,4-dihydroisoquinolin-2 (1H)-yl)methyl)piperidin-1-yl)-2-(2,6-dioxopiperidin-3-yl)isoindoline-1,3-dione (Compound 78), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(1-methyl-2,6-dioxopiperidin-3-yl)isoindoline-1,3-dione (Compound 79), 3-(5-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-1-oxoisoindolin-2-yl)piperidin-2,6-dione (Compound 80), 3-(5-((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)amino)-1-oxoisoindolin-2-yl)piperidin-2,6-dione (Compound 81), 5-(4-((7-((3-((2,6-dichlorophenyl)amino)-1-methyl-H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 82), 5-(4-((7-((3-((2,4-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 83), 2-(2,6-dioxopiperidin-3-yl)-5-(4-((7-((1-methyl-3-(o-tolylamino)-1H-pyrazolo[3,4-d]pyrimidin-6-yl)amino)-3,4-dihydroisoquinolin-2 (1H)-yl)methyl)piperidin-1-yl)isoindoline-1,3-dione (Compound 84), 5-(4-((7-((3-((2-chloro-6-methylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 85), 5-(4-((7-((3-((2,6-dimethylphenyl)amino)-1-isopropyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 86), 5-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)-2-(2,6-dioxopiperidin-3-yl)isoindoline-1,3-dione (Compound 87), 5-(4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)-2-(2,6-dioxopiperidin-3-yl)isoindoline-1,3-dione (Compound 88), 5-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)pyrrolidin-1-yl)-2-(2,6-dioxopiperidin-3-yl)isoindoline-1,3-dione (Compound 89), 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1,3-dioxoisoindolin-5-yl)acetamide (Compound 90), 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1-oxoisoindolin-5-yl)acetamide (Compound 91), 4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-N-(2-(2,6-dioxopiperidin-3-yl)-1-oxoisoindolin-5-yl)piperidine-1-carboxamide (Compound 92), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperazin-1-yl)-2-(2,6-dioxopiperidin-3-yl)isoindoline-1,3-dione (Compound 93), 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-((2-(2,6-dioxopiperidin-3-yl)-1-oxoisoindolin-5-yl)methyl)acetamide (Compound 94), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-2-(2,6-dioxopiperidin-3-yl)isoindoline-1,3-dione (Compound 95), 7-((3-((2,6-dimethylphenyl)amino)-1-methyl-1H-pyrazolo[3,4-d]pyrimidin-6-yl)amino)-N-(2-(2,6-dioxopiperidin-3-yl)-1-oxoisoindolin-5-yl)-3,4-dihydroisoquinoline-2 (1H)-carboxamide (Compound 96), 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-(1-(2-(2,6-dioxopiperidin-3-yl)-1,3-dioxoisoindolin-5-yl)piperidin-4-yl)acetamide (Compound 97), 3-(5-(((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)amino)methyl)-1-oxoisoindolin-2-yl)piperidin-2,6-dione (Compound 98), 7-((3-((2,6-dimethylphenyl)amino)-1-methyl-1H-pyrazolo[3,4-d]pyrimidin-6-yl)amino)-N-((2-(2,6-dioxopiperidin-3-yl)-1-oxoisoindolin-5-yl)methyl)-3,4-dihydroisoquinoline-2 (1H)-carboxamide (Compound 99), N-(4-((3-((2,6-dimethylphenyl)amino)-1-methyl-1H-pyrazolo[3,4-d]pyrimidin-6-yl)amino)phenethyl)-1-(2-(2,6-dioxopiperidin-3-yl)-1,3-dioxoisoindolin-5-yl)piperidine-4-carboxamide (Compound 100), N-(4-((3-((2,6-dimethylphenyl)amino)-1-methyl-1H-pyrazolo[3,4-d]pyrimidin-6-yl)amino)phenethyl)-1-(2-((2-(2,6-dioxopiperidin-3-yl)-1,3-dioxoisoindolin-5-yl)amino)-2-oxoethyl)piperidine-4-carboxamide (Compound 101), N4-(4-((3-((2,6-dimethylphenyl)amino)-1-methyl-1H-pyrazolo[3,4-d]pyrimidin-6-yl)amino)phenethyl)-N1-(2-(2,6-dioxopiperidin-3-yl)-1-oxoisoindolin-5-yl)piperidine-1,4-dicarboxamide (Compound 102), 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-1-oxoisoindolin-2-yl)piperidin-2,6-dione (Compound 103), 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperazin-1-yl)-1-oxoisoindolin-2-yl)piperidin-2,6-dione (Compound 104), 3-(5-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)-1-oxoisoindolin-2-yl)piperidin-2,6-dione (Compound 105), 3-(5-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)oxy)-1-oxoisoindolin-2-yl)piperidin-2,6-dione (Compound 106), (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methyl pivalate (Compound 107), 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-(2-(2,6-dioxopiperidin-3-yl)-1-oxoisoindolin-5-yl)acetamide (Compound 108), 5-(4-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 109), 5-((2-(4-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-2-(2,6-dioxopiperidin-3-yl)isoindoline-1,3-dione (Compound 110), 1-(5-(4-(2-(6-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidine-1-carbonyl)-2-methoxyphenyl)dihydropyrimidine-2,4 (1H,3H)-dione (Compound 111), 1-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidine-1-carbonyl)-2-methoxyphenyl)dihydropyrimidine-2,4 (1H,3H)-dione (Compound 112), N-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)-3-(2,4-dioxotetrahydropyrimidin-1 (2H)-yl)-4-methoxybenzamide (Compound 113), N-(4-((3-((2,6-dimethylphenyl)amino)-1-methyl-1H-pyrazolo[3,4-d]pyrimidin-6-yl)amino)phenethyl)-1-(2-((2-(2,6-dioxopiperidin-3-yl)-1,3-dioxoisoindolin-5-yl)amino)-2-oxoethyl)piperidine-4-carboxamide (Compound 114), 3-(5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperazin-1-yl)-1-oxoisoindolin-2-yl)piperidin-2,6-dione (Compound 115), 3-(6-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)oxy)-1-oxoisoindolin-2-yl)piperidin-2,6-dione (Compound 116), 3-(6-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidin-4-yl)oxy)-1-oxoisoindolin-2-yl)piperidin-2,6-dione (Compound 117), 2-(2,6-dioxopiperidin-3-yl)-5-(4-((7-((3-((4-methoxy-2-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 118), 5-(4-((7-((3-((2,3-dihydro-1H-inden-4-yl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 119), 2-(2,6-dioxopiperidin-3-yl)-5-(4-((7-((3-((2-fluoro-4-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 120), 2-(2,6-dioxopiperidin-3-yl)-5-(4-((7-((3-((4-fluoro-2-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 121), N-(4-((6-((2-((1-(2-(2,6-dioxopiperidin-3-yl)-1,3-dioxoisoindolin-5-yl)piperidin-4-yl)methyl)-1,2,3,4-tetrahydroisoquinolin-7-yl)amino)-1-methyl-1H-pyrazolo[3,4-d]pyrimidin-3-yl)amino)-3-methylphenyl)-3-(trifluoromethyl)benzamide (Compound 122), 5-((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)amino)-2-(2,6-dioxopiperidin-3-yl)isoindoline-1,3-dione (Compound 123), 5-(2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-7-azaspiro[3.5]nonan-7-yl)-2-(2,6-dioxopiperidin-3-yl)isoindoline-1,3-dione (Compound 124), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidin-1-yl)-2-(2,6-dioxopiperidin-3-yl)isoindoline-1,3-dione (Compound 125), 5-(4-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)-3-oxopropyl)piperidin-1-yl)-2-(2,6-dioxopiperidin-3-yl)isoindoline-1,3-dione (Compound 126), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)piperidin-1-yl)-2-(2,6-dioxopiperidin-3-yl)isoindoline-1,3-dione (Compound 127), 5-(4-(((1r,4r)-4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)cyclohexyl)oxy)piperidin-1-yl)-2-(2,6-dioxopiperidin-3-yl)isoindoline-1,3-dione (Compound 128), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)-4-hydroxypiperidin-1-yl)-2-(2,6-dioxopiperidin-3-yl)isoindoline-1,3-dione (Compound 129), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidin-1-yl)-2-(2,6-dioxopiperidin-3-yl)isoindoline-1,3-dione (Compound 130), 5-(4-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethyl)-4-hydroxypiperidin-1-yl)-2-(2,6-dioxopiperidin-3-yl)isoindoline-1,3-dione (Compound 131), 3-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-5-oxo-5,7-dihydro-6H-pyrrolo[3,4-b]pyridin-6-yl)piperidin-2,6-dione (Compound 132), 3-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidin-1-yl)-5-oxo-5,7-dihydro-6H-pyrrolo[3,4-b]pyridin-6-yl)piperidin-2,6-dione (Compound 133), 5-(4-((4-(5-((3-((2,6-dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione (Compound 134), 5-(4-((1-(5-((3-((2,6-dimethylphenyl)amino)-1-methyl-1H-pyrazolo[3,4-d]pyrimidin-6-yl)amino)pyridin-2-yl)piperidin-4-yl)methyl)piperazin-1-yl)-2-(2,6-dioxopiperidin-3-yl)isoindoline-1,3-dione (Compound 135), 5-(4-((4-(3-((3-((2,6-dimethylphenyl)amino)-1-methyl-1H-pyrazolo[3,4-d]pyrimidin-6-yl)amino)phenyl)piperazin-1-yl)methyl)piperidin-1-yl)-2-(2,6-dioxopiperidin-3-yl)isoindoline-1,3-dione (Compound 136), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2,6-dioxopiperidin-3-yl)picolinamide (Compound 137), 5-(3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)azetidin-1-yl)-2-(2,6-dioxopiperidin-3-yl)isoindoline-1,3-dione (Compound 138), 5-(4-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)piperidin-1-yl)-2-(2,6-dioxopiperidin-3-yl)isoindoline-1,3-dione (Compound 139), 5-((R)-3-((4-(7-((3-((2,6-dimethylphenyl)amino)-1-methyl-H-pyrazolo[3,4-d]pyrimidin-6-yl)amino)-3,4-dihydroisoquinolin-2 (1H)-yl)piperidin-1-yl)methyl)piperidin-1-yl)-2-(2,6-dioxopiperidin-3-yl)isoindoline-1,3-dione (Compound 140), 5-((S)-3-((4-(7-((3-((2,6-dimethylphenyl)amino)-1-methyl-H-pyrazolo[3,4-d]pyrimidin-6-yl)amino)-3,4-dihydroisoquinolin-2 (1H)-yl)piperidin-1-yl)methyl)piperidin-1-yl)-2-(2,6-dioxopiperidin-3-yl)isoindoline-1,3-dione (Compound 141), 5-((R)-3-((4-(7-((3-((2,6-dimethylphenyl)amino)-1-methyl-H-pyrazolo[3,4-d]pyrimidin-6-yl)amino)-3,4-dihydroisoquinolin-2 (1H)-yl)piperidin-1-yl)methyl)pyrrolidin-1-yl)-2-(2,6-dioxopiperidin-3-yl)isoindoline-1,3-dione (Compound 142), 5-((S)-3-((4-(7-((3-((2,6-dimethylphenyl)amino)-1-methyl-H-pyrazolo[3,4-d]pyrimidin-6-yl)amino)-3,4-dihydroisoquinolin-2 (1H)-yl)piperidin-1-yl)methyl)pyrrolidin-1-yl)-2-(2,6-dioxopiperidin-3-yl)isoindoline-1,3-dione (Compound 143), 5-((R)-3-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione (Compound 144), 5-((S)-3-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione (Compound 145), 5-(4-(2-(7-((3-((2,6-dimethylphenyl)amino)-1-methyl-H-pyrazolo[3,4-d]pyrimidin-6-yl)amino)-3,4-dihydroisoquinolin-2 (1H)-yl)ethyl)piperidin-1-yl)-2-(2,6-dioxopiperidin-3-yl)isoindoline-1,3-dione (Compound 146), 5-(3-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidin-1-yl)azetidin-1-yl)-2-(2,6-dioxopiperidin-3-yl)isoindoline-1,3-dione (Compound 147), 5-((1R,5S,6S)-6-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-3-azabicyclo[3.1.0]hexan-3-yl)-2-(2,6-dioxopiperidin-3-yl)isoindoline-1,3-dione (Compound 148), 5-(4-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)piperidin-1-yl)-2-(2,6-dioxopiperidin-3-yl)isoindoline-1,3-dione (Compound 149), 5-((R)-3-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)pyrrolidin-1-yl)-2-(2,6-dioxopiperidin-3-yl)isoindoline-1,3-dione (Compound 150), 5-((S)-3-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)pyrrolidin-1-yl)-2-(2,6-dioxopiperidin-3-yl)isoindoline-1,3-dione (Compound 151), 5-(3-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)azetidin-1-yl)-2-(2,6-dioxopiperidin-3-yl)isoindoline-1,3-dione (Compound 152), 5-((1R,5S,6S)-6-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)-3-azabicyclo[3.1.0]hexan-3-yl)-2-(2,6-dioxopiperidin-3-yl)isoindoline-1,3-dione (Compound 153), 5-((R)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)pyrrolidin-1-yl)-2-(2,6-dioxopiperidin-3-yl)isoindoline-1,3-dione (Compound 154), 5-((S)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)pyrrolidin-1-yl)-2-(2,6-dioxopiperidin-3-yl)isoindoline-1,3-dione (Compound 155), 5-(4-(4-(5-((3-((2,6-dimethylphenyl)amino)-1-methyl-H-pyrazolo[3,4-d]pyrimidin-6-yl)amino)pyridin-2-yl)piperazin-1-yl)piperidin-1-yl)-2-(2,6-dioxopiperidin-3-yl)isoindoline-1,3-dione (Compound 156), 5-(4-(2-(4-(5-((3-((2,6-dimethylphenyl)amino)-1-methyl-1H-pyrazolo[3,4-d]pyrimidin-6-yl)amino)pyridin-2-yl)piperazin-1-yl)ethyl)piperidin-1-yl)-2-(2,6-dioxopiperidin-3-yl)isoindoline-1,3-dione (Compound 157), 5-(3-(4-(5-((3-((2,6-dimethylphenyl)amino)-1-methyl-1H-pyrazolo[3,4-d]pyrimidin-6-yl)amino)pyridin-2-yl)piperazin-1-yl)azetidin-1-yl)-2-(2,6-dioxopiperidin-3-yl)isoindoline-1,3-dione (Compound 158), 5-(3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)azetidin-1-yl)-2-(2,6-dioxopiperidin-3-yl)isoindoline-1,3-dione (Compound 159), 5-((R)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione (Compound 160), 5-((S)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione (Compound 161), 5-(4-((4-(6-((3-((2,6-dimethylphenyl)amino)-1-methyl-1H-pyrazolo[3,4-d]pyrimidin-6-yl)amino)pyridin-3-yl)piperazin-1-yl)methyl)piperidin-1-yl)-2-(2,6-dioxopiperidin-3-yl)isoindoline-1,3-dione (Compound 162), 5-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidin-1-yl)-2-(2,6-dioxopiperidin-3-yl)isoindoline-1,3-dione (Compound 163), 5-(4-((4-(5-((3-((2,6-dimethylphenyl)amino)-1-methyl-1H-pyrazolo[3,4-d]pyrimidin-6-yl)amino)pyridin-2-yl)piperidin-1-yl)methyl)piperidin-1-yl)-2-(2,6-dioxopiperidin-3-yl)isoindoline-1,3-dione (Compound 164), 5-(4-((4-(4-((3-((2,6-dimethylphenyl)amino)-1-methyl-1H-pyrazolo[3,4-d]pyrimidin-6-yl)amino)phenyl)piperidin-1-yl)methyl)piperidin-1-yl)-2-(2,6-dioxopiperidin-3-yl)isoindoline-1,3-dione (Compound 165), 5-((R)-3-((4-(4-((3-((2,6-dimethylphenyl)amino)-1-methyl-H-pyrazolo[3,4-d]pyrimidin-6-yl)amino)phenyl)piperidin-1-yl)methyl)pyrrolidin-1-yl)-2-(2,6-dioxopiperidin-3-yl)isoindoline-1,3-dione (Compound 166), 5-((S)-3-((4-(4-((3-((2,6-dimethylphenyl)amino)-1-methyl-1H-pyrazolo[3,4-d]pyrimidin-6-yl)amino)phenyl)piperidin-1-yl)methyl)pyrrolidin-1-yl)-2-(2,6-dioxopiperidin-3-yl)isoindoline-1,3-dione (Compound 167), 5-(4-(4-((3-((2,6-dimethylphenyl)amino)-1-methyl-1H-pyrazolo[3,4-d]pyrimidin-6-yl)amino)phenyl)-[1,4'-bipiperidin]-1'-yl)-2-(2,6-dioxopiperidin-3-yl)isoindoline-1,3-dione (Compound 168), 5-(3-((4-(4-((3-((2,6-dimethylphenyl)amino)-1-methyl-1H-pyrazolo[3,4-d]pyrimidin-6-yl)amino)phenyl)piperidin-1-yl)methyl)azetidin-1-yl)-2-(2,6-dioxopiperidin-3-yl)isoindoline-1,3-dione (Compound 169), 3-(2-(4-((4-(4-((3-((2,6-dimethylphenyl)amino)-1-methyl-1H-pyrazolo[3,4-d]pyrimidin-6-yl)amino)phenyl)piperidin-1-yl)methyl)piperidin-1-yl)-5-oxo-5,7-dihydro-6H-pyrrolo[3,4-b]pyridin-6-yl)piperidin-2,6-dione (Compound 170), 5-(4-((4-(5-((3-((2,6-dimethylphenyl)amino)-1-methyl-1H-pyrazolo[3,4-d]pyrimidin-6-yl)amino)pyrimidin-2-yl)piperazin-1-yl)methyl)piperidin-1-yl)-2-(2,6-dioxopiperidin-3-yl)isoindoline-1,3-dione (Compound 171), 5-(4-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 172), 5-((R)-3-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione (Compound 173), 5-((S)-3-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione (Compound 174), 5-(4-((3-(4-((3-((2,6-dimethylphenyl)amino)-1-methyl-1H-pyrazolo[3,4-d]pyrimidin-6-yl)amino)phenyl)azetidin-1-yl)methyl)piperidin-1-yl)-2-(2,6-dioxopiperidin-3-yl)isoindoline-1,3-dione (Compound 175), 5-((R)-3-((3-(4-((3-((2,6-dimethylphenyl)amino)-1-methyl-1H-pyrazolo[3,4-d]pyrimidin-6-yl)amino)phenyl)azetidin-1-yl)methyl)pyrrolidin-1-yl)-2-(2,6-dioxopiperidin-3-yl)isoindoline-1,3-dione (Compound 176), 5-((S)-3-((3-(4-((3-((2,6-dimethylphenyl)amino)-1-methyl-1H-pyrazolo[3,4-d]pyrimidin-6-yl)amino)phenyl)azetidin-1-yl)methyl)pyrrolidin-1-yl)-2-(2,6-dioxopiperidin-3-yl)isoindoline-1,3-dione (Compound 177), 5-(4-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-hydroxypropyl)piperazin-1-yl)-2-(2,6-dioxopiperidin-3-yl)isoindoline-1,3-dione (Compound 178), 5-((R)-3-((4-(4-((3-((2,6-dimethylphenyl)amino)-1-methyl-1H-pyrazolo[3,4-d]pyrimidin-6-yl)amino)phenyl)piperazin-1-yl)methyl)pyrrolidin-1-yl)-2-(2,6-dioxopiperidin-3-yl)isoindoline-1,3-dione (Compound 179), 5-((S)-3-((4-(4-((3-((2,6-dimethylphenyl)amino)-1-methyl-1H-pyrazolo[3,4-d]pyrimidin-6-yl)amino)phenyl)piperazin-1-yl)methyl)pyrrolidin-1-yl)-2-(2,6-dioxopiperidin-3-yl)isoindoline-1,3-dione (Compound 180), 5-(3-((4-(4-((3-((2,6-dimethylphenyl)amino)-1-methyl-1H-pyrazolo[3,4-d]pyrimidin-6-yl)amino)phenyl)piperazin-1-yl)methyl)azetidin-1-yl)-2-(2,6-dioxopiperidin-3-yl)isoindoline-1,3-dione (Compound 181), 5-(3-((3-(4-((3-((2,6-dimethylphenyl)amino)-1-methyl-1H-pyrazolo[3,4-d]pyrimidin-6-yl)amino)phenyl)azetidin-1-yl)methyl)azetidin-1-yl)-2-(2,6-dioxopiperidin-3-yl)isoindoline-1,3-dione (Compound 182), 5-(3-(((S)-4-(4-((3-((2,6-dimethylphenyl)amino)-1-methyl-1H-pyrazolo[3,4-d]pyrimidin-6-yl)amino)phenyl)-3-methylpiperazin-1-yl)methyl)azetidin-1-yl)-2-(2,6-dioxopiperidin-3-yl)isoindoline-1,3-dione (Compound 183), 5-(3-(((R)-4-(4-((3-((2,6-dimethylphenyl)amino)-1-methyl-1H-pyrazolo[3,4-d]pyrimidin-6-yl)amino)phenyl)-3-methylpiperazin-1-yl)methyl)azetidin-1-yl)-2-(2,6-dioxopiperidin-3-yl)isoindoline-1,3-dione (Compound 184), 5-(3-(((S)-4-(4-((3-((2,6-dimethylphenyl)amino)-1-methyl-1H-pyrazolo[3,4-d]pyrimidin-6-yl)amino)phenyl)-2-methylpiperazin-1-yl)methyl)azetidin-1-yl)-2-(2,6-dioxopiperidin-3-yl)isoindoline-1,3-dione (Compound 185), 5-(3-(((R)-4-(4-((3-((2,6-dimethylphenyl)amino)-1-methyl-1H-pyrazolo[3,4-d]pyrimidin-6-yl)amino)phenyl)-2-methylpiperazin-1-yl)methyl)azetidin-1-yl)-2-(2,6-dioxopiperidin-3-yl)isoindoline-1,3-dione (Compound 186), 3-(2-(3-((4-(4-((3-((2,6-dimethylphenyl)amino)-1-methyl-1H-pyrazolo[3,4-d]pyrimidin-6-yl)amino)phenyl)piperazin-1-yl)methyl)azetidin-1-yl)-5-oxo-5,7-dihydro-6H-pyrrolo[3,4-b]pyridin-6-yl)piperidin-2,6-dione (Compound 187), 3-(2-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidin-1-yl)-5-oxo-5,7-dihydro-6H-pyrrolo[3,4-b]pyridin-6-yl)piperidin-2,6-dione (Compound 188), 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(3-(N-(2,6-dioxopiperidin-3-yl)sulfamoyl)-4-methylphenyl)acetamide (Compound 189), 7-((3-((2,6-dimethylphenyl)amino)-1-methyl-1H-pyrazolo[3,4-d]pyrimidin-6-yl)amino)-N-(3-(N-(2,6-dioxopiperidin-3-yl)sulfamoyl)-4-methylphenyl)-3,4-dihydroisoquinoline-2 (1H)-carboxamide (Compound 190), 3-(3-((3-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)phenyl)amino)-2,5-dioxo-2,5-dihydro-1H-pyrrol-1-yl)piperidin-2,6-dione (Compound 192), 3-(3-((3-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)phenyl)amino)-2,5-dioxo-2,5-dihydro-1H-pyrrol-1-yl)piperidin-2,6-dione (Compound 193), 5-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)-2-(2,6-dioxopiperidin-3-yl)isoindoline-1,3-dione (Compound 194), 5-(4-((7-((3-((2-bromo-6-methylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 195), 5-(4-(((1-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)cyclopropyl)amino)methyl)piperidin-1-yl)-2-(2,6-dioxopiperidin-3-yl)isoindoline-1,3-dione (Compound 199), 3-(3-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2,5-dioxo-2,5-dihydro-1H-pyrrol-1-yl)piperidin-2,6-dione (Compound 201), N-(1-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)cyclopropyl)-1-(2-(2,6-dioxopiperidin-3-yl)-1,3-dioxoisoindolin-5-yl)piperidine-4-carboxamide (Compound 204), N-(1-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)cyclopropyl)-2-((2-(2,6-dioxopiperidin-3-yl)-1,3-dioxoisoindolin-5-yl)oxy) acetamide (Compound 205), (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methyl piperidine-4-carboxylate bistrifluoroacetic acid (Compound 206), (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methyl 4-methylpentanoate (Compound 207), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)-6-fluoroisoindoline-1,3-dione (Compound 208), 3-(5-(1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)-1-oxoisoindolin-2-yl)piperidin-2,6-dione (Compound 209), 5-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-2-(2,6-dioxopiperidin-3-yl)-6-fluoroisoindoline-1,3-dione (Compound 210), 5-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-2-(2,6-dioxopiperidin-3-yl)-6-fluoroisoindoline-1,3-dione (Compound 211), 5-(4-((7-((3-((2,6-dibromophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 217), 5-(4-((7-((3-((2-bromo-6-chlorophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 218), 5-(4-((7-((3-((2-chloro-6-iodophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 219), 3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-6-fluoro-1-oxoisoindolin-2-yl)piperidin-2,6-dione (Compound 220), 2-(2,6-dioxopiperidin-3-yl)-5-(4-((7-((3-((4-fluoro-2,6-dimethylphenyl)amino)-1-methyl-1H-pyrazolo[3,4-d]pyrimidin-6-yl)amino)-3,4-dihydroisoquinolin-2 (1H)-yl) methyl)piperidin-1-yl)isoindoline-1,3-dione (Compound 221), 5-(4-(2-(4-(4-((3-((2,6-dimethylphenyl)amino)-1-methyl-1H-pyrazolo[3,4-d]pyrimidin-6-yl)amino)phenyl)piperidin-1-yl)-2-oxoethyl)piperidin-1-yl)-2-(2,6-dioxopiperidin-3-yl)isoindoline-1,3-dione (Compound 222), 5-(4-(2-(4-(4-((3-((2,6-dimethylphenyl)amino)-1-methyl-1H-pyrazolo[3,4-d]pyrimidin-6-yl)amino)phenyl)piperidin-1-yl)-2-oxoethyl)piperazin-1-yl)-2-(2,6-dioxopiperidin-3-yl)isoindoline-1,3-dione (Compound 225), 5-(4-(2-(4-(4-((3-((2,6-dimethylphenyl)amino)-1-methyl-1H-pyrazolo[3,4-d]pyrimidin-6-yl)amino)-2-fluorophenyl)piperidin-1-yl)-2-oxoethyl)piperazin-1-yl)-2-(2,6-dioxopiperidin-3-yl)isoindoline-1,3-dione (Compound 226), 5-(4-(2-(4-(4-((3-((2,6-dimethylphenyl)amino)-1-methyl-H-pyrazolo[3,4-d]pyrimidin-6-yl)amino)-2-fluorophenyl)piperidin-1-yl)-2-oxoethyl)piperidin-1-yl)-2-(2,6-dioxopiperidin-3-yl)isoindoline-1,3-dione (Compound 227), 5-(3-(4-(4-((3-((2,6-dimethylphenyl)amino)-1-methyl-H-pyrazolo[3,4-d]pyrimidin-6-yl)amino)phenyl)piperidine-1-carbonyl)azetidin-1-yl)-2-(2,6-dioxopiperidin-3-yl) isoindoline-1,3-dione (Compound 228), 5-(3-(4-(4-((3-((2,6-dimethylphenyl)amino)-1-methyl-H-pyrazolo[3,4-d]pyrimidin-6-yl)amino)-2-fluorophenyl)piperidine-1-carbonyl)azetidin-1-yl)-2-(2,6-dioxopiperidin-3-yl)isoindoline-1,3-dione (Compound 229), 5-(4-((4-(4-((3-((2,6-dimethylphenyl)amino)-1-methyl-H-pyrazolo[3,4-d]pyrimidin-6-yl)amino)phenyl)-3,6-dihydropyridin-1 (2H)-yl)methyl)piperidin-1-yl)-2-(2,6-dioxopiperidin-3-yl)isoindoline-1,3-dione (Compound 230), 5-(4-((4-(4-((3-((2,6-dimethylphenyl)amino)-1-methyl-H-pyrazolo[3,4-d]pyrimidin-6-yl)amino)-3-fluorophenyl)piperidin-1-yl)methyl)piperidin-1-yl)-2-(2,6-dioxopiperidin-3-yl)isoindoline-1,3-dione (Compound 231), 5-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonothioyl)piperidin-1-yl)-2-(2,6-dioxopiperidin-3-yl)isoindoline-1,3-dione (Compound 232), 5-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonothioyl)piperidin-1-yl)-2-(2,6-dioxopiperidin-3-yl)-6-fluoroisoindoline-1,3-dione (Compound 233), 5-(4-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonothioyl)piperidine-1-carbonyl)piperidin-1-yl)-2-(2,6-dioxopiperidin-3-yl)isoindoline-1,3-dione (Compound 234), 5-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-oxoethyl)amino)-2-(2,6-dioxopiperidin-3-yl)isoindoline-1,3-dione (Compound 235), 5-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-oxoethoxy)-2-(2,6-dioxopiperidin-3-yl)isoindoline-1,3-dione (Compound 236), 3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1-oxoisoindolin-2-yl)piperidin-2,6-dione (Compound 237), 5-(4-(4-((3-((2,6-dimethylphenyl)amino)-1-methyl-1H-pyrazolo[3,4-d]pyrimidin-6-yl)amino)phenyl)piperazin-1-yl)-2-(2,6-dioxopiperidin-3-yl)isoindoline-1,3-dione (Compound 238), 5-(4-(4-((3-((2,6-dimethylphenyl)amino)-1-methyl-1H-pyrazolo[3,4-d]pyrimidin-6-yl)amino)phenyl)piperazin-1-yl)-2-(2,6-dioxopiperidin-3-yl)-6-fluoroisoindoline-1,3-dione (Compound 239), (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(1-(1-(2-(2,6-dioxopiperidin-3-yl)-1,3-dioxoisoindolin-5-yl)piperidine-4-carbonyl)piperidin-4-yl)acrylonitrile (Compound 240), (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(1-(2-((2-(2,6-dioxopiperidin-3-yl)-1,3-dioxoisoindolin-5-yl)oxy)acetyl)piperidin-4-yl)acrylonitrile (Compound 241), 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-(2,6-dioxopiperidin-3-yl)isoindoline-1,3-dione (Compound 243), 5-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)-4-fluoropiperidin-1-yl)-2-(2,6-dioxopiperidin-3-yl)-6-fluoroisoindoline-1,3-dione (Compound 244), 3-(5-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidin-1-yl)-6-fluoro-1-oxoisoindolin-2-yl)piperidin-2,6-dione (Compound 245), 5-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidine-1-carbonyl)piperidin-1-yl)-2-(2,6-dioxopiperidin-3-yl)isoindoline-1,3-dione (Compound 246), 5-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-oxoethyl)amino)-2-(2,6-dioxopiperidin-3-yl)isoindoline-1,3-dione (Compound 247), 5-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-oxoethoxy)-2-(2,6-dioxopiperidin-3-yl)isoindoline-1,3-dione (Compound 248), 5-(4-((4-(5-((3-((2,6-dimethylphenyl)amino)-1-methyl-1H-pyrazolo[3,4-d]pyrimidin-6-yl)amino)-2-fluorophenyl)-3,6-dihydropyridin-1 (2H)-yl)methyl)piperidin-1-yl)-2-(2,6-dioxopiperidin-3-yl)isoindoline-1,3-dione (Compound 250), 5-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidin-1-yl)-2-(2,6-dioxopiperidin-3-yl)isoindoline-1,3-dione (Compound 253), 5-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidin-1-yl)-2-(2,6-dioxopiperidin-3-yl)-6-fluoroisoindoline-1,3-dione (Compound 254), 3-(5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidine-1-carbonyl)-1-oxoisoindolin-2-yl)piperidin-2,6-dione (Compound 255), 3-(5-(4-((4-(4-((3-((2,6-dimethylphenyl)amino)-1-methyl-H-pyrazolo[3,4-d]pyrimidin-6-yl)amino)phenyl)piperazin-1-yl)methyl)piperidine-1-carbonyl)-1-oxoisoindolin-2-yl)piperidin-2,6-dione (Compound 256), 3-(5-(4-(4-((3-((2,6-dimethylphenyl)amino)-1-methyl-H-pyrazolo[3,4-d]pyrimidin-6-yl)amino)phenyl)piperidine-1-carbonyl)-1-oxoisoindolin-2-yl)piperidin-2,6-dione (Compound 257), 3-(5-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidine-1-carbonyl)-1-oxoisoindolin-2-yl)piperidin-2,6-dione (Compound 258), (E)-2-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)-3-(1-(2-(2,6-dioxopiperidin-3-yl)-1-oxoisoindoline-5-carbonyl)piperidin-4-yl)acrylonitrile (Compound 259), (E)-2-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)-3-(1-((2-(2,6-dioxopiperidin-3-yl)-1,3-dioxoisoindolin-5-yl)glycyl)piperidin-4-yl)acrylonitrile (Compound 260), (E)-2-(4-(4-((3-((2,6-dimethylphenyl)amino)-1-methyl-H-pyrazolo[3,4-d]pyrimidin-6-yl)amino)phenyl)piperidine-1-carbonyl)-3-(1-((2-(2,6-dioxopiperidin-3-yl)-1,3-dioxoisoindolin-5-yl)glycyl)piperidin-4-yl)acrylonitrile (Compound 261), 3-(5-(4-(4-(4-((3-((2,6-dimethylphenyl)amino)-1-methyl-H-pyrazolo[3,4-d]pyrimidin-6-yl)amino)phenyl)piperidine-1-carbonyl)piperidin-1-yl)-3-methyl-2-oxo-2,3-dihydro-1H-benzo[d]imidazol-1-yl)piperidin-2,6-dione (Compound 262), 5-(3-(4-(5-((3-((2,6-dimethylphenyl)amino)-1-methyl-H-pyrazolo[3,4-d]pyrimidin-6-yl)amino)-2-fluorophenyl)-1,2,3,6-tetrahydropyridine-1-carbonyl)azetidin-1-yl)-2-(2,6-dioxopiperidin-3-yl)isoindoline-1,3-dione (Compound 263), 3-(5-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)piperidin-1-yl)-3-methyl-2-oxo-2,3-dihydro-1H-benzo[d]imidazol-1-yl)piperidin-2,6-dione (Compound 264), 5-(4-((4-(6-((3-((2,6-dimethylphenyl)amino)-1-methyl-H-pyrazolo[3,4-d]pyrimidin-6-yl)amino)pyridazin-3-yl)piperazin-1-yl)methyl)piperidin-1-yl)-2-(2,6-dioxopiperidin-3-yl)isoindoline-1,3-dione (Compound 268), and 3-(5-(4-((4-(4-((3-((2,6-dimethylphenyl)amino)-1-methyl-H-pyrazolo[3,4-d]pyrimidin-6-yl)amino)phenyl)piperidin-1-yl)methyl)piperidin-1-yl)-6-fluoro-1-oxoisoindolin-2-yl)piperidin-2,6-dione (Compound 272).

The following terms in the present disclosure have the meanings set forth below unless otherwise indicated. Any terms not directly defined herein shall be understood to have the meanings commonly associated with them as understood within the art of the invention.

As used herein, the term "alkyl" refers to a linear or branched, saturated aliphatic hydrocarbon of 1 to 20 carbon atoms and preferably 1 to 6 carbon atoms, as exemplified by methyl, ethyl, n-propyl, isopropyl, n-butyl, isobutyl, tert-butyl, 1-methylpropyl, pentyl, hexyl, and so on.

As used herein, the term "alkenyl" refers to a linear or branched hydrocarbon of 2 to 16 carbon atoms and preferably 2 to 8 carbon atoms having at least one double bond between carbon atoms.

As used herein, the "alkynyl" refers to a linear or branched hydrocarbon of 2 to 16 carbon atoms and preferably 2 to 8 carbon atoms having at least one triple bond between carbon atoms.

As used herein, "alkoxy" refers to a linear or branched, saturated hydrocarbon of 1 to 20 carbon atoms and preferably 1 to 6 carbon atoms with an oxygen atom singularly bonded thereto, as exemplified by methoxy, ethoxy, propoxy, n-butoxy, tert-butoxy, 1-methylpropoxy, and so on.

The term "alkoxyalkoxy", as used herein, refers to an alkoxy as defined above, with an alkoxy radical substituted for at least one hydrogen carbon bonded thereto.

The terms "halo" and "halogen" are used in the conventional sense to refer to a chloro, bromo, fluoro, or iodo substituent.

As used herein, the term "haloalkyl" refers to an alkyl radical as defined above, with a halogen substituted for at least one hydrogen of the alkyl.

As used herein, the term "haloalkoxy" refers to an alkoxy radical as defined above, with a halogen substituted for at least one hydrogen of the alkoxy.

As used herein, the terms "cyclic" and "ring" refer to alicyclic or aromatic groups that may or may not be substituted and/or may or may not contain a heteroatom, and that may be monocyclic, bicyclic, polycyclic, or spirocyclic.

As used herein, the term "carbocyclyl" refers to a stable non-aromatic monocyclic or polycyclic hydrocarbon radical consisting solely of carbon and hydrogen atoms, which can include fused or bridged ring systems, having from 3 to 10 carbon atoms. In certain embodiments, a carbocyclyl comprises 3 to 12 carbon atoms. The carbocyclyl is attached to the rest of the molecule by a single bond. Carbocyclyl may be saturated, (i.e., containing single C—C bonds only) or unsaturated (i.e., containing one or more double bonds or triple bonds). A fully saturated carbocyclyl radical is also referred to as "cycloalkyl". Examples of monocyclic cycloalkyls include, but are not limited to, cyclopropyl, cyclobutyl, cyclopentyl, cyclohexyl, cycloheptyl, and cyclooctyl. An unsaturated carbocyclyl is also referred to as "cycloalkenyl". Examples of monocyclic cycloalkenyls include, but are not limited to, cyclopentenyl, cyclohexenyl, cycloheptenyl, and cyclooctenyl. Polycyclic carbocyclyl radicals include, but are not limited to, indanyl, adamantyl, decalinyl, 7,7-dimethyl-bicyclo[2.2.1]heptanyl, and the like.

As used herein, the term "heterocyclic" or "heterocyclyl" refers to a stable 3- to 12-membered non-aromatic ring radical that comprises two to eleven carbon atoms and from one to four heteroatoms selected from nitrogen, oxygen and sulfur. Unless stated otherwise specifically in the specification, the heterocyclyl radical is a monocyclic, bicyclic, tricyclic, or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring (s).

Examples of such heterocyclyl radicals include, but are not limited to, pyrrolidinyl, piperidinyl, piperazinyl, azetidinyl, 1,2,3,6-tetrahydropyridinyl, isoindolinyl, tetrahydroisoindolinyl, 2-azaspiro[3.4]octanyl, 6-azaspiro[3.4]octanyl, azaspirodecanyl, 2-azabicyclo[2.1.0]pentanyl, octahydrdo-1H-cyclopenta[c]pyridinyl, 7-azaspiro[3.5]nonanyl, 3-azabicyclo[3.1.0]hexanyl, and 3-azabicyclo[4.2.0]octanyl.

As used herein, the term "aryl" refers to an aromatic substituent that has at least one ring with a pi-system of electrons delocalized therein, as exemplified by phenyl, benzyl, naphthyl, anthryl, indanyl, biphenyl, triphenyl, and so on.

As used herein, the term, "heteroaryl" refers to a mono-, bi-, or tricyclic aromatic ring compound bearing at least one heteroatom such as N, O, or S as a ring member. According to numbers and kinds of heteroatoms and numbers of carbon atoms within the ring, there are various radicals including pyrazolopyridinyl, pyridazinyl, pyridinyl, pyrimidinyl, triazolyl, pyridyl, pyrrolyl, pyrrolidinyl, furanyl, quinolidinyl, indolyl, imidazolyl, 1,2,4-triazolyl, tetrazolyl, pyranyl, thiophenyl, thiazolyl, dibenzothiophenyl, dibenzofuranyl, dibenzoselenophenyl, benzofuranyl, benzothiophenyl, benzoselenophenyl, carbazolyl, indolocarbazolyl, pyridylindolyl, pyrrolodipyridinyl, pyrazolyl, imidazolyl, oxazolyl, thiazolyl, oxadiazolyl, oxatriazolyl, dioxazolyl, thiadiazolyl, pyrazinyl, triazinyl, oxazinyl, oxathiazinyl, oxadiazinyl, benzimidazolyl, indazolyl, indoxazinyl, benzoxazolyl, benzisoxazolyl, benzothiazolyl, quinolinyl, isoquinolinyl, cinnolinyl, quinazolinyl, quinoxalinyl, naphthyridinyl, phthalazinyl, pteridinyl, xanthenyl, acridinyl, phenazinyl, phenothiazinyl, phenoxazinyl, benzofuropyridinyl, furopyridinyl, benzothienopyridinyl, thienodipyridinyl, benzoselenophenopyridinyl, and selenophenodipyridinyl.

Furthermore, the compound of the present disclosure may contain at least one asymmetric carbon atom and may exist in a racemic form or an optically active form. All of the compounds and diastereomers fall within the scope of the present disclosure.

As used herein, the term "pharmaceutically acceptable salt thereof" indicates a salt or complex of Chemical Formula 1 that retains a desired biological activity. Examples of the salt include, but are not limited to, acid addition salts formed with inorganic acids (e.g., hydrochloric acid, hydrobromic acid, sulfuric acid, phosphoric acid, nitric acid, etc.), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. The compound may also be administered in the form of a pharmaceutically acceptable quaternary salt. Among others, the salt includes chloride, bromide, iodide, —O-alkyl, toluene sulfonate, methylsulfonate, sulfonate, phosphate, or carboxylate (e.g., benzoate, succinate, acetate, glycolate, maleate, malate, fumarate, citrate, tartrate, ascorbate, cinnamate, mandelate, and diphenylacetate). The compound of Chemical Formula 1 according to the present disclosure is intended to encompass any salt, hydrate, solvate, and prodrug that can be prepared using typical methods.

The acid addition salts according to the present disclosure can be prepared using typical methods. For instance, a derivative of Chemical Formula 1 may be dissolved in an organic solvent, such as methanol, ethanol, acetone, dichloromethane, acetonitrile, etc., and added with an organic acid or an inorganic acid to form a precipitate which may be then filtered and dried to obtain an acid addition salt. Alternatively, the solvent and the excess of acid are evaporated at a reduced pressure and the residue is crystalized in an organic solvent to afford the acid addition salt.

In addition, a pharmaceutically acceptable metal salt may be prepared using a base. An alkali metal or alkaline earth metal salt may be obtained, for example, by dissolving a compound in an excess amount of alkali metal hydroxide or alkaline earth metal hydroxide solution, filtering out the undissolved salt, and then evaporating and drying the filtrate. As the metal salts, sodium, potassium or calcium salts are pharmaceutically suitable. Also, the corresponding silver salts may be obtained by reacting an alkali metal or alkaline earth metal salt with a proper silver salt (e.g., silver nitrate).

The cancer may be a solid cancer or blood cancer. The solid cancer may be selected from the group consisting of brain tumor, low-grade astrocytoma, high-grade astrocytoma, pituitary adenoma, meningioma, CNS lymphoma, oligodendroglioma, craniopharyngioma, ependymoma, brain stem tumor, head & neck tumor, laryngeal cancer, oropharyngeal cancer, nasal cavity/PNS tumor, nasopharyngeal tumor, salivary gland tumor, hypopharyngeal cancer, thyroid cancer, oral cavity tumor, chest tumor, small cell lung cancer, non-small cell lung cancer, thymoma, mediastinal tumor, esophageal cancer, breast cancer, male breast cancer, abdomen-pelvis tumor, stomach cancer, hepatoma, gall bladder cancer, biliary tract tumor, pancreatic cancer, small intestinal tumor, large intestinal tumor, anal cancer, bladder cancer, renal cell carcinoma, male genital tumor, penile cancer, prostatic cancer, female genital tumor, cervix cancer, endometrial cancer, ovarian cancer, uterine sarcoma, vaginal cancer, vulva cancer, female urethral cancer, and skin cancer, but with no limitations thereto. The blood cancer may be selected from the group consisting of leukemia, malignant lymphoma, multiple myeloma, and aplastic anemia, but with no limitations thereto.

In addition, the autoimmune disease may be selected from the group consisting of, but not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myoclonus syndrome, ankylosing spondylitis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

The pharmaceutical composition according to the present disclosure may be formulated into suitable dosage forms using a pharmaceutically acceptable carrier which is commonly used. The term "pharmaceutically acceptable" refers to a composition that is physiologically acceptable and does not cause an allergic reaction or a similar reaction thereto, such as gastrointestinal disorder, dizziness, etc., when administered to humans. In addition, the composition may be formulated and used in the form of oral formulations such as powders, granules, tablets, capsules, suspensions, emulsions, syrups, aerosols, etc., external preparations, suppositories, and sterile injectable solutions according to a general method.

Carriers, excipients, and diluents that may be included in the composition may include lactose, dextrose, sucrose, sorbitol, mannitol, xylitol, erythritol, maltitol, starch, Arabic rubber, alginate, gelatin, calcium phosphate, calcium silicate, cellulose, methyl cellulose, microcrystalline cellulose, polyvinylpyrrolidone, water, methyl paraoxybenzoate, propyl paraoxybenzoate, talc, magnesium stearate, and mineral oil, but are not limited thereto. The formulations may be prepared by using a diluent or an excipient, such as a filler, a stabilizer, a binder, a disintegrating agent, a surfactant, etc., which are commonly used. Solid formulations for oral administration include a tablet, a pill, a powder, a granule, a capsule, and the like, and these solid formulations may be prepared by mixing at least one or more excipients, for example, starch, microcrystalline cellulose, sucrose or lactose, low-substituted hydroxypropyl cellulose, hypromellose, and the like with the compound of the present disclosure. Further, lubricants such as magnesium stearate and talc may also be used in addition to simple excipients. Liquid formulations for oral administration may correspond to suspensions, liquids for internal use, emulsions, syrups, and the like, and may include various excipients, for example, a humectant, a sweetener, an aromatic agent, a preservative, and the like, in addition to water and liquid paraffin which are commonly used as simple diluents. Formulations for parenteral administration include a sterile aqueous solution, a non-aqueous solution, a suspension, an emulsion, a lyophilizing agent, and a suppository. As the non-aqueous solution and the suspension, propylene glycol, polyethylene glycol, vegetable oil such as olive oil, injectable ester such as ethyl oleate, and the like may be used. As a base of the suppository, witepsol, macrogol, Tween 61, cacao butter, laurin butter, glycerol, gelatin, and the like may be used. For preparation as formulations for parenteral administration, the pyrimidine derivative compound of Chemical Formula 1 or a pharmaceutically acceptable salt is sterilized and/or mixed with a preservative, a stabilizer, a wettable powder or emulsifier, an adjuvant such as salts and/or buffers for regulation of osmotic pressure, and other therapeutically useful materials in water to be prepared by a solution or suspension, and the prepared solution or suspension may be prepared by an ampoule or vial unit dose type The pharmaceutical composition comprising the compound of Chemical Formula 1 disclosed in the present disclosure as an active ingredient may be administered to mammals such as rats, livestock, and humans in various routes. All modes of administration may be contemplated and, for example, the pharmaceutical composition may be administered by oral, rectal or intravenous, intramuscular, subcutaneous, intrauterine dural, or cerebrovascular injection. A dose may vary according to the age, sex, and body weight of a subject to be treated, a specific disease or pathology to be treated, the severity of disease or pathology, an administration time, an administration route, the absorption of a drug, distribution and excretion rate, types of other drugs to be used, judgment of prescribers, etc. The dose determination based on these factors is within a level of those skilled in the art, and in general, the dose is in the range of 0.01 mg/kg/day to about 2000 mg/kg/day. A more preferable dose is 1 mg/kg/day to 500 mg/kg/day. The administration may be performed once a day or several times a day. The dose does not limit the scope of the present disclosure in any way.

The pharmaceutical composition of the present disclosure may be used alone or in combination with surgery, hormone therapy, chemotherapy, and a biological response modulator, for prevention or treatment of cancer, autoimmune diseases, and Parkinson's disease.

Advantageous Effects of Invention

The present disclosure is drawn to a novel bifunctional compound and a composition comprising same for prevention or treatment of cancer, autoimmune diseases, and Parkinson's disease. With excellent selectively inhibitory activity against Bruton's tyrosine kinase (BTK), the bifunctional compound finds advantageous applications in pharmaceutical compositions for prevention and treatment of cancer, autoimmune diseases, and Parkinson's disease.

BEST MODE FOR CARRYING OUT THE INVENTION

Hereinafter, embodiments of the disclosure will be described in detail. This disclosure may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art.

Example 1. Synthesis and Physicochemical Characterization of Compounds

Synthesis procedures for compounds 1 to 272 of the present disclosure are as follows Compound 1. 4-((6-(7-((3-((2,6-Dimethylphenyl)amino)-1-methyl-1H-pyrazolo[3,4-d]pyrimidin-6-yl)amino)-3,4-dihydroisoquinolin-2(1H)-yl)-6-oxohexyl)amino)-2-(2,6-dioxopiperidin-3-yl)isoindoline-1,3-dione

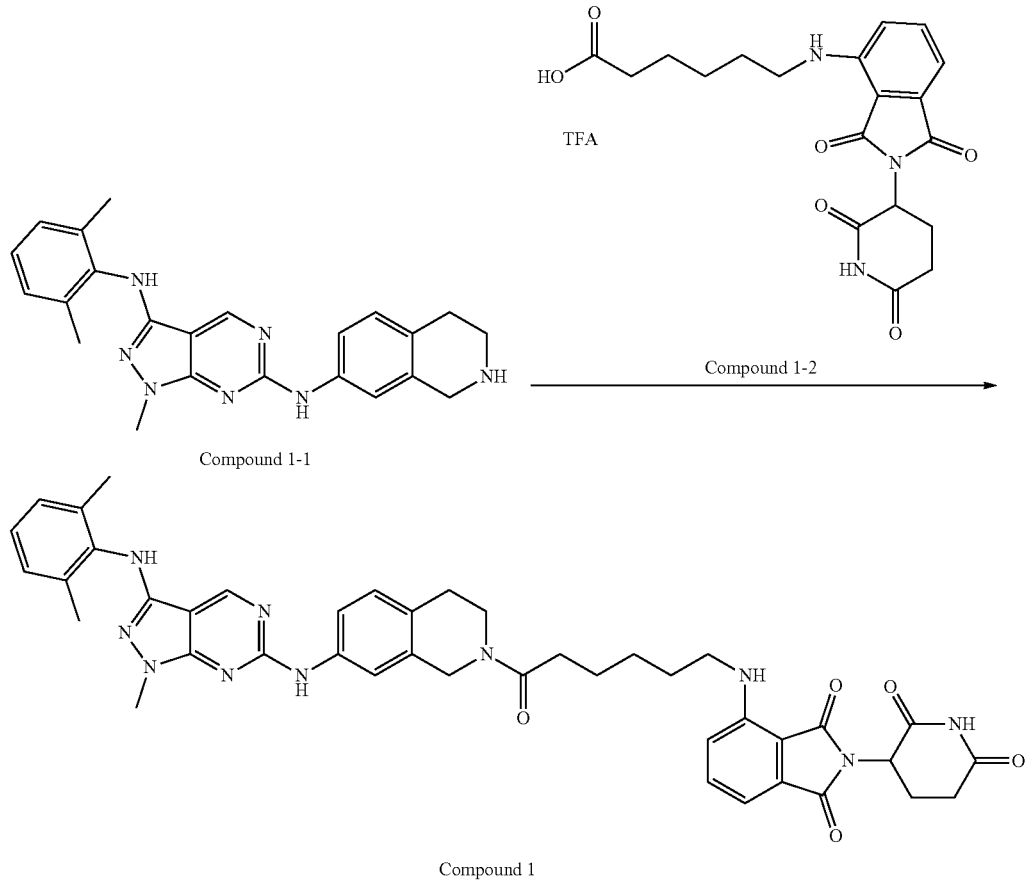

To a solution of Compound 1-1 (Korean Patent No. 2128018) (10 mg, 0.021 mmol) in DMF (1 mL) were added EDCI (20.1 mg, 0.105 mmol), HOBt (14.1 mg, 0.105 mmol), Compound 1-2 (WO2020/200291) (10.0 mg, 0.021 mmol), and DIPEA (21.7 mg, 0.168 mmol), and the mixture was heated at 40° C. for 16 hours. The reaction mixture was added with cold water, followed by extraction with 5% MeOH/dichloromethane. The organic layer thus formed was washed with cold water and brine and concentrated in a vacuum to give a crude product (31 mg). The crude product was purified through preparative TLC to afford Compound 1 as a brown oil (6 mg).

Compound 2. 5-((2-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)amino)-2-(2,6-dioxopiperidin-3-yl)isoindoline-1,3-dione

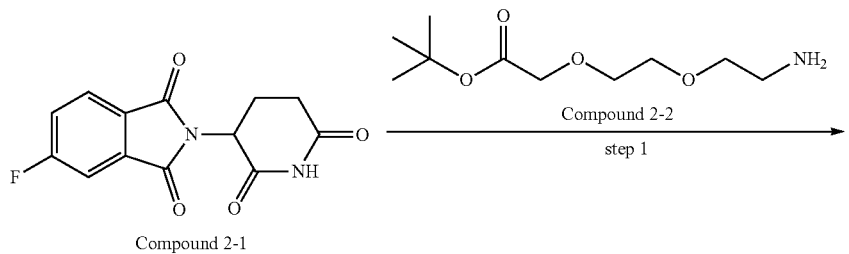

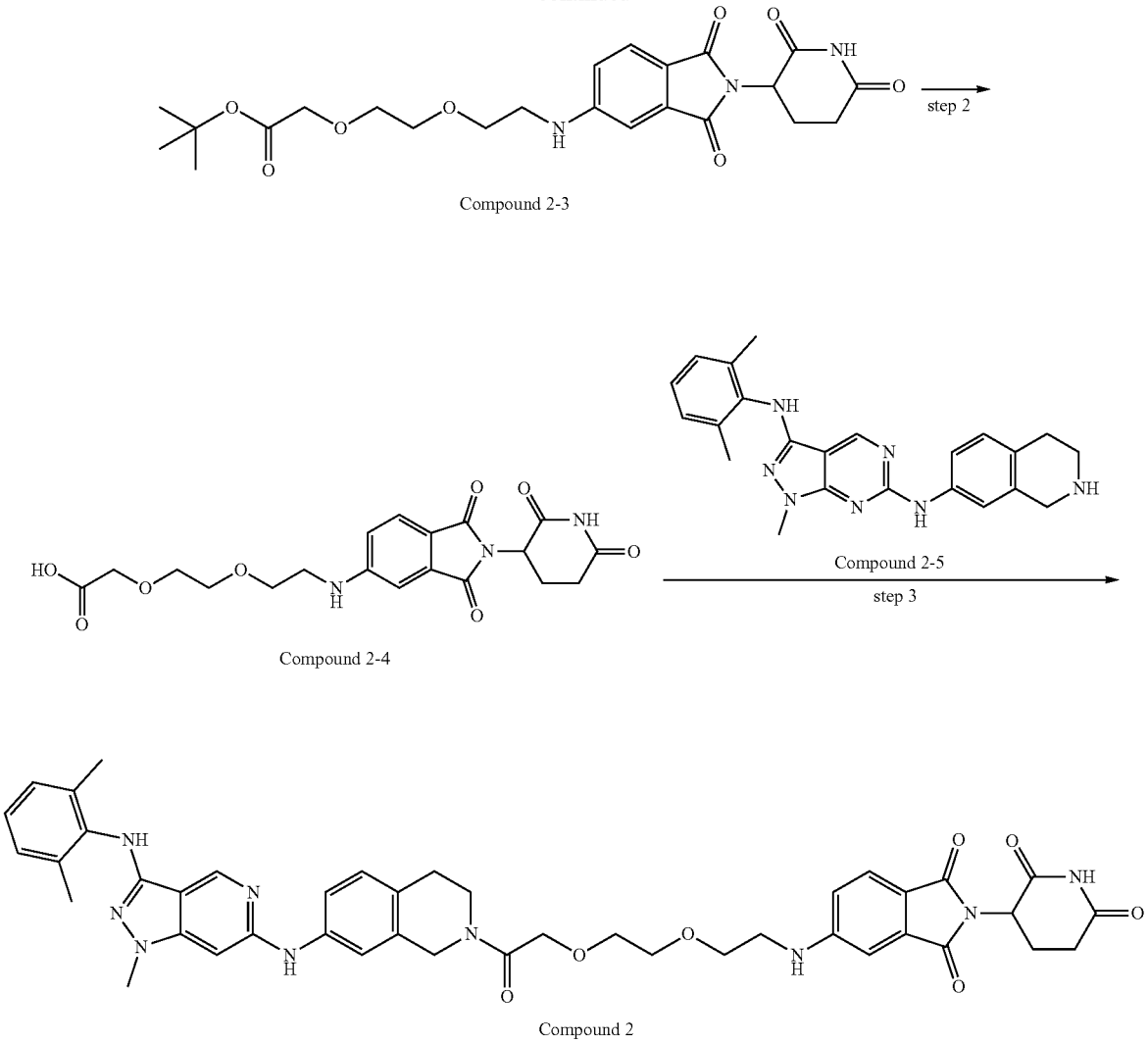

Compound 2-3

Compound 2-4

Compound 2-5

Compound 2

Step 1: Synthesis of tert-butyl-2-(2-(2-((2-(2,6-di-oxopiperidin-3-yl)-1,3-dioxoisoindolin-5-yl)amino)ethoxy)ethoxy)acetate (Compound 2-3)

A solution of Compound 2-2 (Angene, AG01C1H7) (tert-butyl 2-(2-(2-aminoethoxy)ethoxy)acetate; 83.3 mg, 0.380 mmol) in DMSO (1.0 mL) was added with DIPEA (187.6 mg, 1.488 mmol) and stirred for 10 minutes. After addition of Compound 2-1 (Combi-Blocks, HD-3240) (5-fluorothalidomide; 100 mg, 0.362 mmol), the mixture was heated at 90° C. and stirred to complete the reaction. The reaction mixture was added with cold water, followed by extraction with EtOAc. The organic layer thus formed was washed with water and brine and concentrated in a vacuum. The crude product was purified by preparative TLC to afford Compound 2-3 as a brown oil (26 mg).

Step 2: Synthesis of 2-(2-(2-((2-(2,6-dioxopiperidin-3-yl)-1,3-dioxoisoindolin-5-yl)amino)ethoxy)ethoxy)acetic acid (Compound 2-4)

A solution of Compound 2-3 (25 mg, 0.05 mmol) in dichloromethane (5.0 mL) was added with TFA (30.0 mg, 0.26 mmol) and stirred at room temperature for 16 hours. The organic solvent was removed by vacuum concentration and the crude product thus obtained was neutralized with a saturated sodium bicarbonate solution, followed by extraction with EtOAc. The organic layer was concentrated in a vacuum to afford Compound 2-4 (15.0 mg).

Step 3: Synthesis of Synthesis of 5-((2-(2-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)-2-oxoethoxy)ethoxy)ethyl)amino)-2-(2,6-dioxopiperidin-3-yl)isoindoline-1,3-dione (Compound 2)

A solution of Compound 2-4 (10.0 mg, 0.02 mmol) in DMF (0.5 mL) was added with HATU (30.4 mg, 0.08 mmol) and TEA (16.1 mg, 0.16 mmol) and stirred for 10 minutes. Addition of Compound 2-5 (Korean Patent No. 2128018) (9.25 mg, 0.02 mmol) was followed by stirring at 40° C. for 16 hours. The reaction mixture was quenched with iced water, and the solid thus formed was filtered and dissolved in ethyl acetate (10 mL). The organic layer was washed with water and brine. After vacuum concentration, the crude product thus formed was purified by MPLC to afford Compound 2 as a brown solid (6.0 mg).

Compound 3. 4-((2-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)amino)-2-(2,6-dioxopiperidin-3-yl)isoindoline-1,3-dione
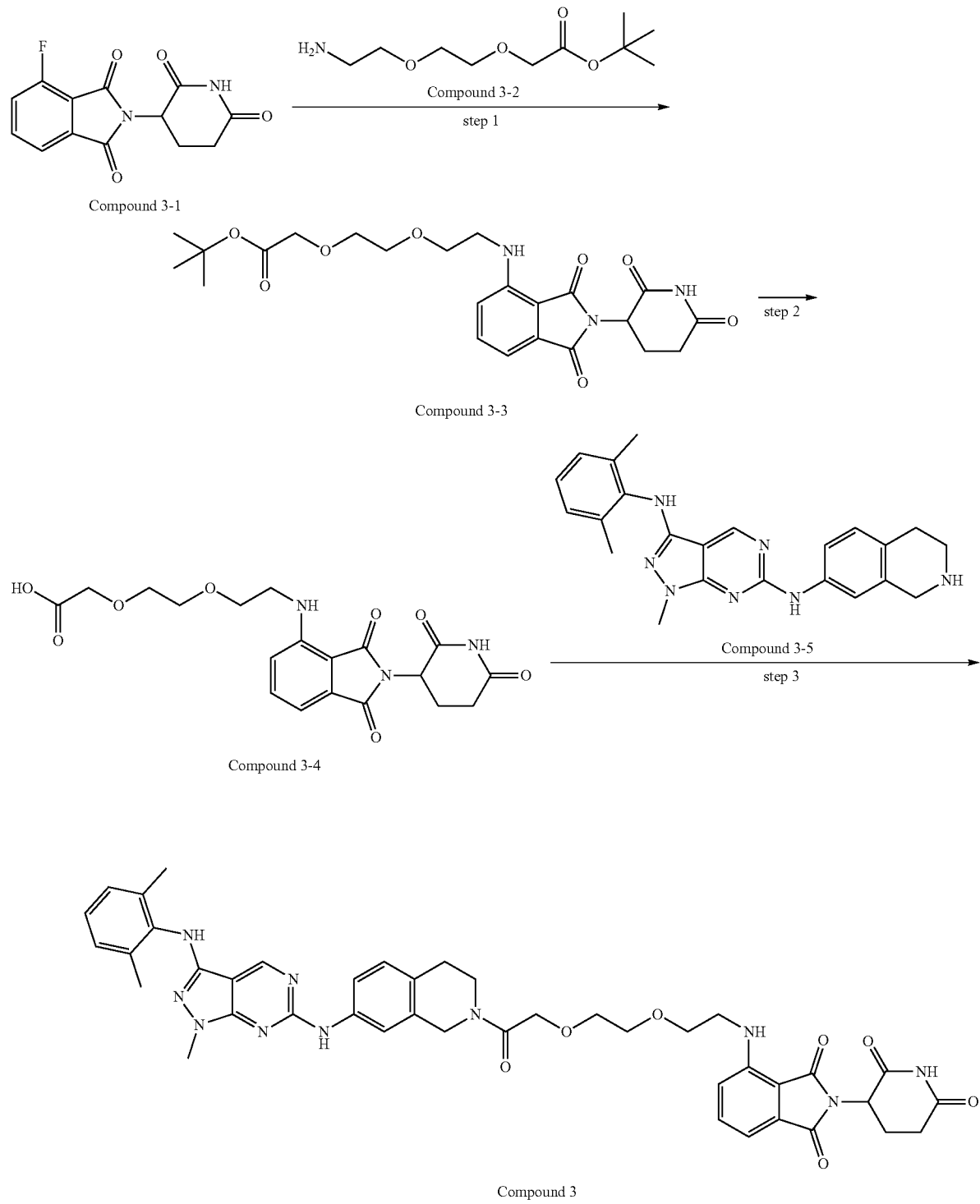

Step 1: Synthesis of tert-butyl 2-(2-(2-((2-(2,6-di-oxopiperidin-3-yl)-1,3-dioxoisoindolin-4-yl)amino)ethoxy)ethoxy)acetate (Compound 3-3)

A solution of Compound 3-2 (Angene, AG01C1H7) (41.6 mg, 0.190 mmol) in DMSO (1.0 mL) was added with DIPEA (93.8 mg, 0.721 mmol) and stirred for 10 minutes. After addition of Compound 3-1 (Axis Pharm, AP12129) (4-fluorothalidomide; 50.0 mg, 0.181 mmol), the mixture was heated to 90° C. and stirred for 16 hours. The reaction mixture was added with cold water, followed by extraction with EtOAc. The organic layer thus formed was washed with water and brine and concentrated in a vacuum. The crude product was purified by preparative TLC to afford Compound 3-3 as a brown oil (40.0 mg, 0.08 mmol).

Step 2: Synthesis of 2-(2-(2-((2-(2,6-dioxopiperi-din-3-yl)-1,3-dioxoisoindolin-4-yl)amino)ethoxy)ethoxy)acetic acid (Compound 3-4)

To a solution of Compound 3-3 (25 mg, 0.084 mmol) in DCM (5.0 mL) was added TFA (48 mg, 0.42 mmol), followed by stirring at room temperature for 16 hours. Evaporation of the solvent in a vacuum afforded Compound 3-4 as a brown oil (46 mg).

Step 3: Synthesis of Synthesis of 4-((2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)amino)-2-(2,6-dioxopiperidin-3-yl)isoindoline-1,3-dione (Compound 3)

A solution of Compound 3-4 (45.0 mg, 0.0946 mmol) in DMF (2 mL) was added with HATU (144.0 mg, 0.378 mmol) and TEA (76.1 mg, 0.752 mmol) and stirred for 10 minutes. After addition of Compound 3-5 (Korean Patent No. 2128018) (37.5 mg, 0.0946 mmol), stirring was conducted at 40° C. until completion of the reaction. The reaction mixture was quenched with iced water, and the solid thus formed was filtered and dissolved in ethyl acetate. The organic layer was washed with water and brine and concentrated in a vacuum. The crude product was purified by MPLC to afford Compound 3 as a yellow solid (26 mg).

Compound 4. N-(2-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)-1-(2-(2,6-dioxopiperidin-3-yl)-1,3-dioxoisoindolin-4-yl)piperidine-4-carboxamide

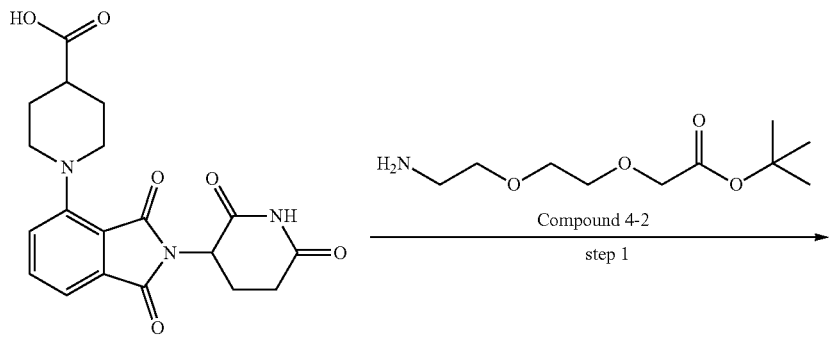

Compound 4-1

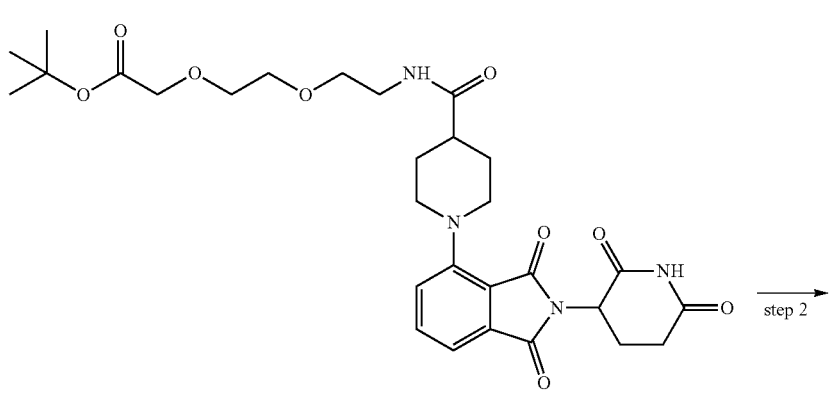

Compound 4-3

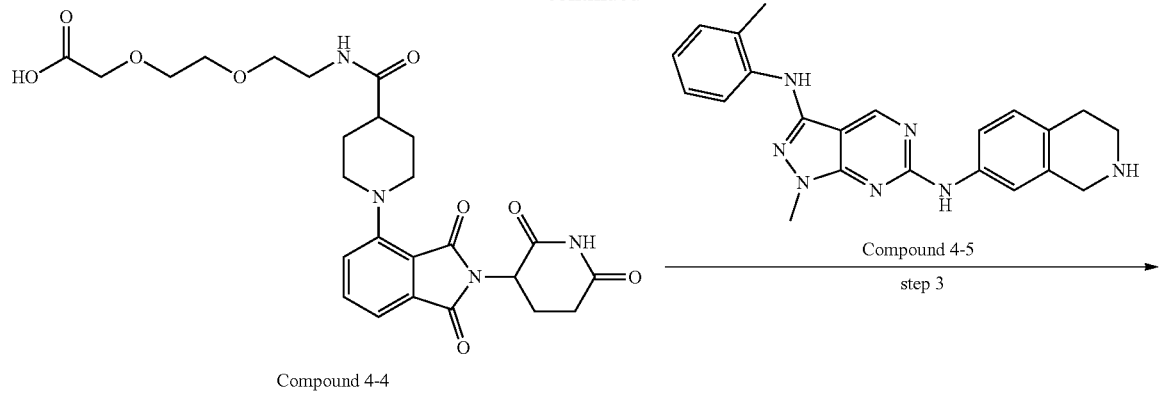

Compound 4-4

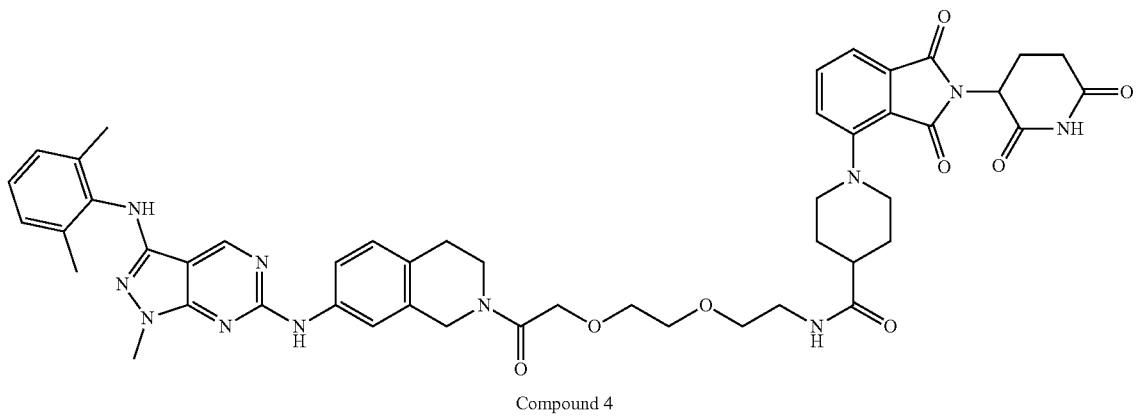

Compound 4

Step 1: Synthesis of tert-butyl 2-(2-(2-(1-(2-(2,6-dioxopiperidin-3-yl)-1,3-dioxoisoindolin-4-yl)pyrimidine-4-carboxamido)ethoxy)ethoxy)acetate (Compound 4-3)

To a solution of Compound 4-1 (WO 2020/162725) (50.0 mg, 0.129 mmol) in DMF (1 mL) were added EDCI (38.5 mg, 0.285 mmol), HOBt·H$_2$O (49.4 mg, 0.285 mmol), Compound 4-2 (Angene, AG01C1H$_7$) (28.5 mg, 0.129 mmol), and DIPEA (66.8 mg, 0.516 mmol) at room temperature. The mixture was stirred at room temperature for 7 hours. The reaction was terminated by quenching with water. After extraction with EtOAc, the organic layer was concentrated in a vacuum. The crude product was purified by column chromatography to afford Compound 4-3 as a yellow solid (44 mg).

Step 2: Synthesis of 2-(2-(2-(1-(2-(2,6-dioxopiperidin-3-yl)-1,3-dioxoisoindolin-4-yl)pyrimidine-4-carboxamido)ethoxy)ethoxy)acetic acid (Compound 4-4)

A solution of Compound 4-3 (39 mg, 0.066 mmol) in DCM (1 mL) was added with TFA (38 mg, 0.33 mmol) at room temperature and stirred for 12 hours. After vaporization of the volatile material in a vacuum, the residual solvent was removed by a high-vacuum pump to afford Compound 4-4 as a yellow solid (34 mg).

Step 3: Synthesis of Synthesis of N-(2-(2-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)-2-oxoethoxy)ethoxy)ethyl)-1-(2-(2,6-dioxopiperidin-3-yl)-1,3-dioxoisoindolin-4-yl)piperidine-4-carboxamide (Compound 4)

A solution of Compound 4-4 (15 mg, 0.028 mmol) in DMF (2 mL) was added with HATU (42 mg, 0.11 mmol) and TEA (33 mg, 0.11 mmol) and stirred for 10 minutes. After addition of Compound 4-5 (Korean Patent No. 2128018) (11.3 mg, 0.0280 mmol), stirring was conducted at 40° C. for 16 hours. The reaction mixture was quenched with iced water, and the solid thus formed was filtered and dissolved in ethyl acetate (10 mL). The organic layer was washed with water and brine and concentrated in a vacuum. The crude product was purified by MPLC to afford Compound 4 as a reddish yellow solid (10 mg).

Compound 5. N-(14-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)-1-(2-(2,6-dioxopiperidin-3-yl)-1,3-dioxoisoindolin-4-yl)piperidine-4-carboxamide
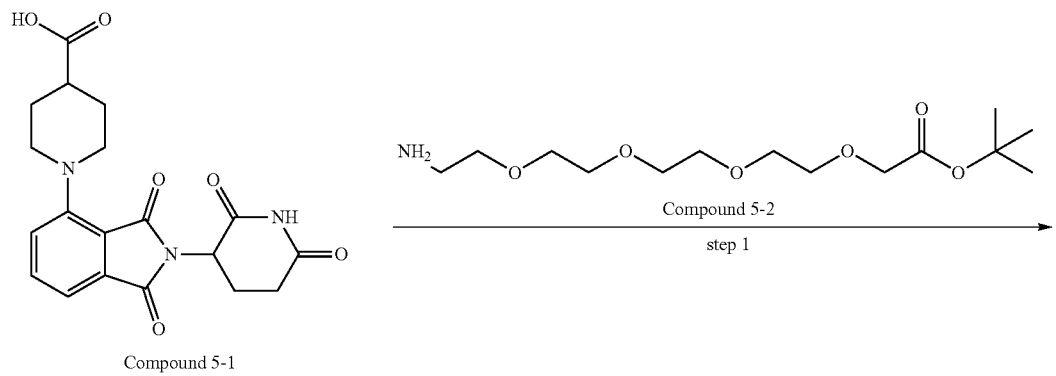
Compound 5-1
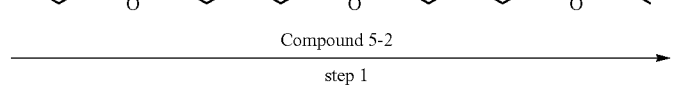
Compound 5-2, step 1
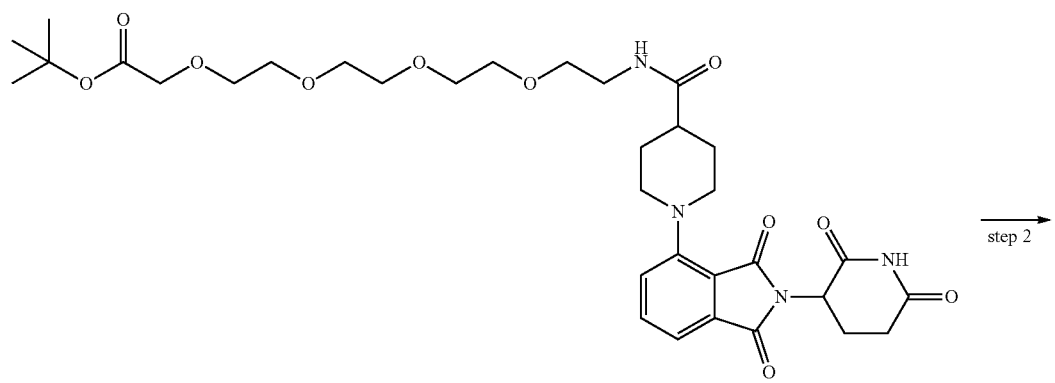
Compound 5-3
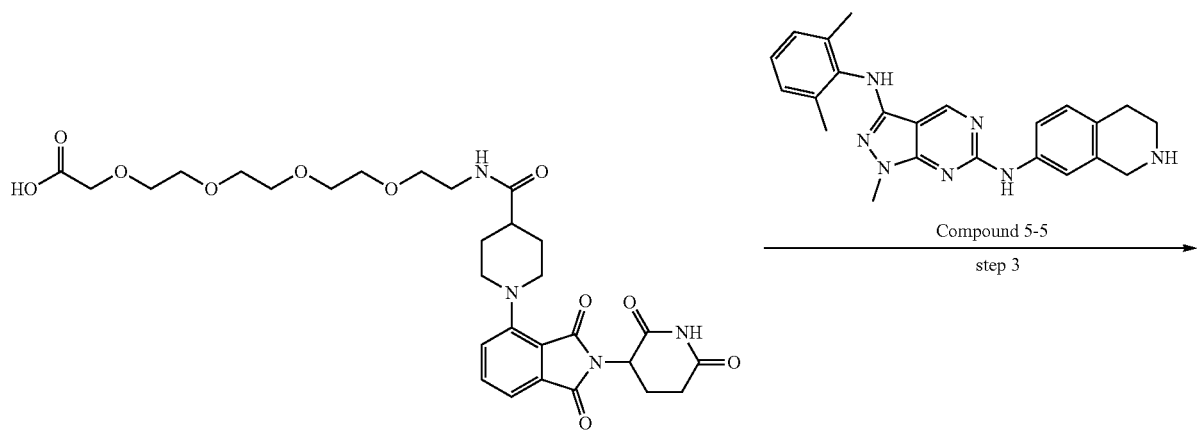
Compound 5-4
Compound 5-5, step 3

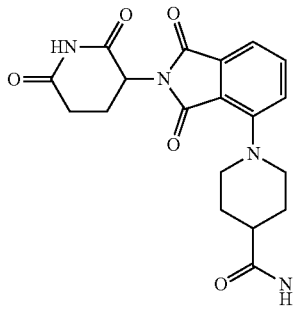

Compound 5

Step 1: Synthesis of tert-butyl 1-(1-(2-(2,6-dioxopiperidin-3-yl)-1,3-dioxoisoindolin-4-yl)piperidin-4-yl)-1-oxo-5,8,11,14-tetraoxa-2-azahexadecan-16-oate (Compound 5-3)

A solution of Compound 5-1 (WO 2020/162725) (50.0 mg, 0.129 mmol) in DMF (1 mL) was added with EDCI (38.5 mg, 0.285 mmol), HOBt·H$_2$O (49.4 mg, 0.285 mmol), Compound 5-2 (Combi-Blocks, HD-3240) (40.0 mg, 0.129 mmol), and DIPEA (66.8 mg, 0.516 mmol) at room temperature and stirred at room temperature for 4 hours. The reaction mixture was quenched with water, followed by extraction with EtOAc. The organic layer thus formed was concentrated in a vacuum to give a crude material which was then purified by silica gel column chromatography to afford Compound 5-3 as a yellow oil (21 mg).

Step 2: Synthesis of 1-(1-(2-(2,6-dioxopiperidin-3-yl)-1,3-dioxoisoindolin-4-yl)piperidin-4-yl)-1-oxo-5,8,11,14-tetraoxa-2-azahexadecan-16-oic acid (Compound 5-4)

A solution of Compound 5-3 (20 mg, 0.029 mmol) in DCM (1 mL) was added at room temperature with TFA (17 mg, 0.14 mmol) and stirred for 16 hours. After vaporization of the volatile material in a vacuum, the residual solvent was removed by a high-vacuum pump to afford Compound 5-4 as a dark brown oil (17 mg).

Step 3: Synthesis of Synthesis of N-(14-(7-((3-((2,6-dimethylphenyl)amino)-1-methyl-1H-pyrazolo[3,4-d]pyrimidin-6-yl)amino)-3,4-dihydroisoquinolin-2(1H)-yl)-14-oxo-3,6,9,12-tetraoxatetradecyl)-1-(2-(2,6-dioxopiperidin-3-yl)-1,3-dioxoisoindolin-4-yl)piperidine-4-carboxamide (Compound 5)

A solution of Compound 5-4 (10 mg, 0.016 mmol) in DMF (2 mL) was added with HATU (24 mg, 0.064 mmol) and TEA (13 mg, 0.13 mmol) and stirred for 10 minutes. After addition of Compound 5-5 (Korean Patent No. 2128018) (6.3 mg, 0.016 mmol), stirring was conducted at 40° C. for 16 hours. The reaction mixture was quenched with iced water, and the solid thus formed was filtered and dissolved in ethyl acetate. The organic layer was washed with water and brine and concentrated in a vacuum. The crude product was purified by MPLC to afford Compound 5 as a yellow solid (8.0 mg).

Compound 6. N-(4-(2-(2-(2-(2-((2-(2,6-Dioxopiperidin-3-yl)-1,3-dioxoisoindolin-4-yl)amino)ethoxy)ethoxy)ethoxy)ethoxy)phenyl)-4-(7-((3-((4-(2-methoxyethoxy)-2,6-dimethylphenyl)amino)-1-methyl-1H-pyrazolo[3,4-d]pyrimidin-6-yl)amino)-1,1-dimethyl-3,4-dihydroisoquinolin-2(1H)-yl)-4-oxobutanamide

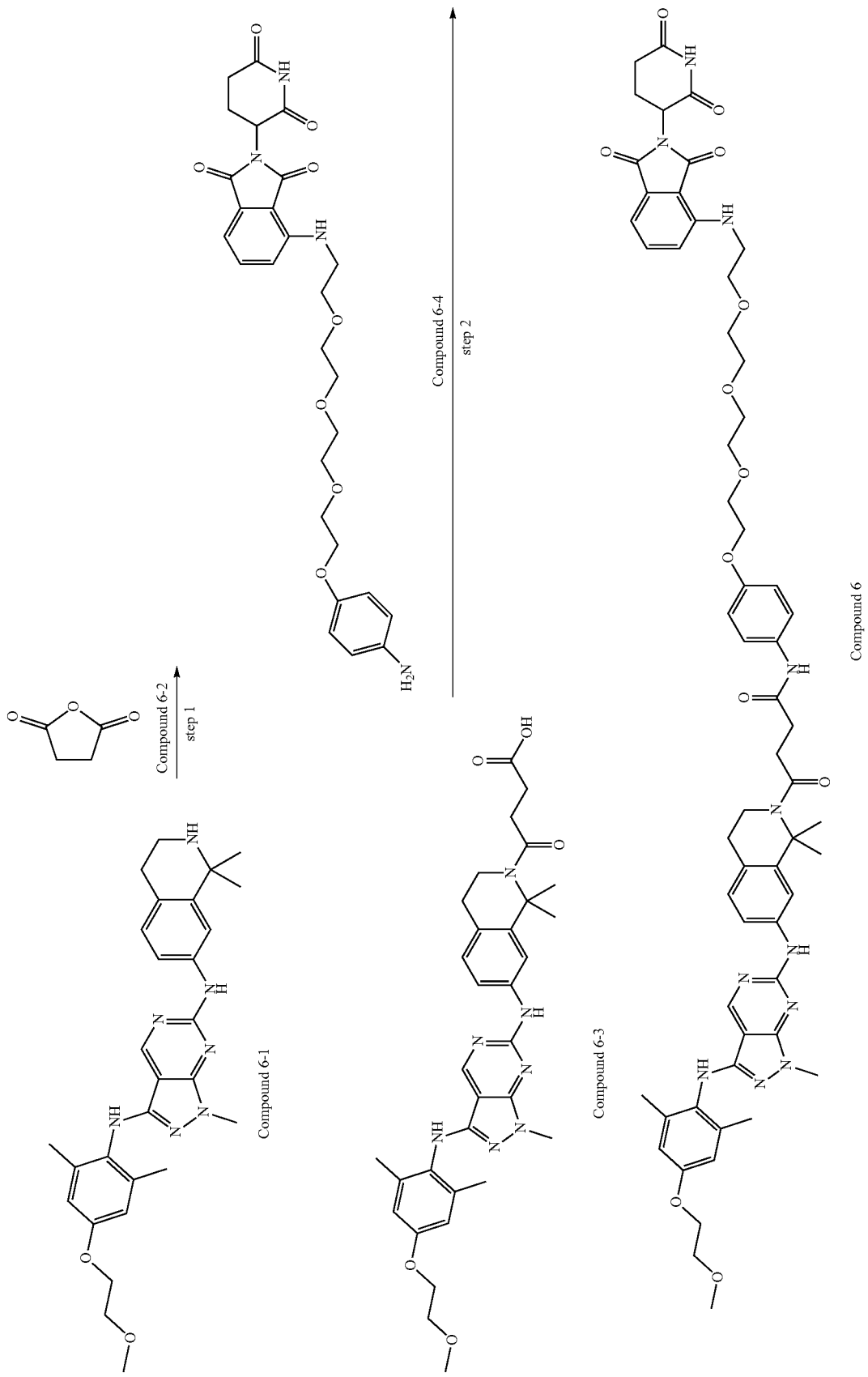

Step 1: Synthesis of 4-(7-((3-((4-(2-methoxyethoxy)-2,6-dimethylphenyl)amino)-1-methyl-1H-pyrazolo[3,4-d]pyrimidin-6-yl)amino)-1,1-dimethyl-3,4-dihydroisoquinolin-2 (1H)-yl)-4-oxobutanoic acid (Compound 6-3)

To a stirred solution of Compound 6-1 (Korean Patent No. 2128018) (100 mg, 0.199 mmol) in anhydrous THF, the succinate anhydride Compound 6-2 (TCI, S0107) (100 mg, 0.997 mmol) was added at 0° C. over one hour. The temperature was elevated to 40° C. and two drops of TEA were added to dissolve the reactants, followed by stirring for 26 hours. When the reaction was completed under TLC monitoring, THF was removed by evaporation in a vacuum. The residue was dissolved in DCM and washed with water. The DCM layer was dried over sodium sulfate and the solvent was evaporated in a vacuum. The crude product thus formed was purified by silica gel column chromatography using 5% MeOH:DCM as an eluent to afford Compound 6-3 as a brown solid (98 mg, 0.163 mmol, 90%).

Step 2: Synthesis of N(4-(2-(2-(2-(2-((2-(2,6-dioxopiperidin-3-yl)-1,3-dioxoisoindolin-4-yl)amino)ethoxy)ethoxy)ethoxy)ethoxy)phenyl)-4-(7-((3-((4-(2-methoxyethoxy)-2,6-dimethylphenyl)amino)-1-methyl-1H-pyrazolo[3,4-d]pyrimidin-6-yl)amino)-1,1-dimethyl-3,4-dihydroisoquinolin-2 (1H)-yl)-4-oxobutanamide (Compound 6)

A solution of Compound 6-3 (10.0 mg, 0.016 mmol) in DMF (2 mL) was added with HATU (25 mg, 0.064 mmol) and TEA (13 mg, 0.13 mmol) and stirred for 10 minutes. After addition of Compound 6-4 (WO 2019/148055) (9.0 mg, 0.016 mmol), stirring was conducted at 40° C. for 16 hours. The reaction mixture was quenched with iced water and the solid thus formed was filtered and dissolved in ethylacetate. The organic layer was washed with water and brine and concentrated in a vacuum to give a crude material which was then purified by MPLC to afford Compound 6 as a reddish yellow solid (10 mg).

Compound 7. 4-((12-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-12-oxododecyl)amino)-2-(2,6-dioxopiperidin-3-yl)isoindoline-1,3-dione

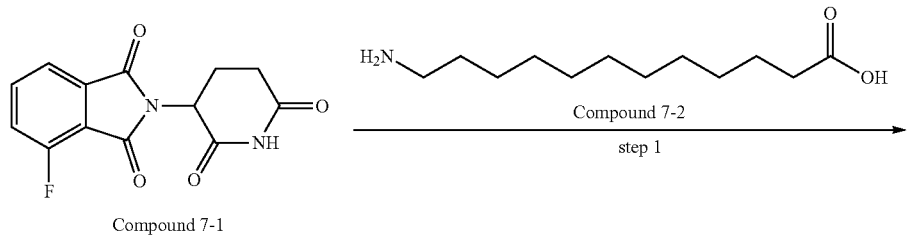

Compound 7-1

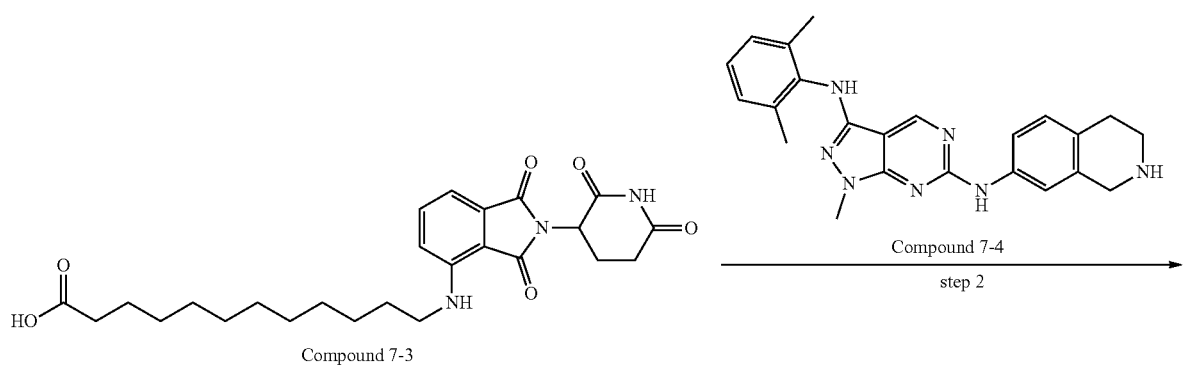

Compound 7-3

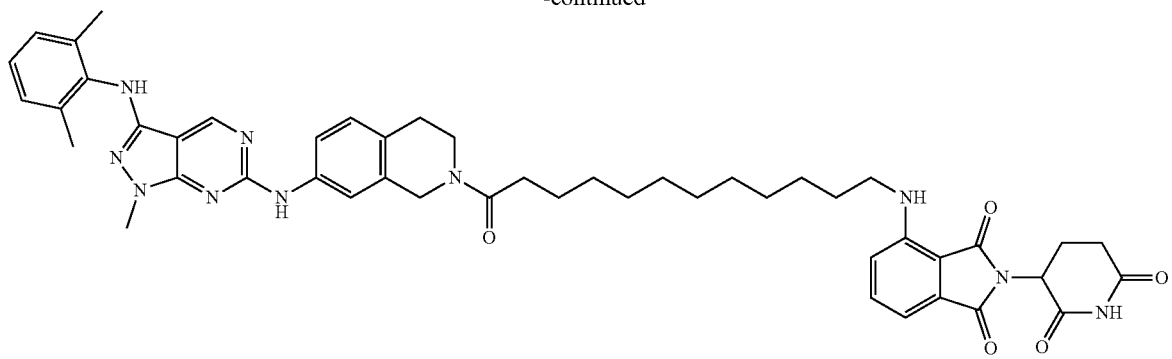

Compound 7

Step 1: Synthesis 12-((2-(2,6-dioxopiperidin-3-yl)-1,3-dioxoisoindolin-4-yl)amino)dodecanoic acid (Compound 7-3)

A solution of Compound 7-2 (Combi-Blocks, QB-6982) (12-aminododecanoic acid; 4.7 mg, 0.021 mmol) in DMSO (0.5 mL) was added with DIPEA (14 mg, 0.11 mmol) and stirred for 10 minutes. To the mixture was added Compound 7-1 (Axis Pharm, AP12129) (4-pomalidomide; 5.0 mg, 0.018 mmol) which was then heated to 90° C. and stirred for 16 hours. The reaction mixture was added to cold water, followed by extraction with EtOAc. The organic layer was washed with water and brine and dried over sodium sulfate. The organic layer was concentrated in a vacuum and the crude product was purified by MPLC to afford Compound 7-3 as a green solid (7 mg).

Step 2: Synthesis of 4-((12-(7-((3-((2,6-dimethylphenyl)amino)-1-methyl-1H-pyrazolo[3,4-d]pyrimidin-6-yl)amino)-3,4-dihydroisoquinolin-2 (1H)-yl)-12-oxododecyl)amino)-2-(2,6-dioxopiperidin-3-yl)isoindoline-1,3-dione (Compound 7)

A solution of Compound 7-3 (7.0 mg, 0.014 mmol) in DMF (0.5 mL) was added with HATU (21.2 mg, 0.0561 mmol) and TEA (11.3 mg, 0.112 mmol) and stirred for 10 minutes. After addition of Compound 7-4 (Korean Patent No. 2128018) (5.9 mg, 0.014 mmol) stirring was conducted at 40° C. for 16 hours. The reaction mixture was quenched with iced water and the solid thus formed was filtered and dissolved in ethylacetate. The organic layer was washed with water and brine and concentrated in a vacuum to give a crude material which was then purified by MPLC to afford Compound 7 as a reddish yellow solid (7.1 mg).

Compound 8. 5-((14-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)amino)-2-(2,6-dioxopiperidin-3-yl)isoindoline-1,3-dione

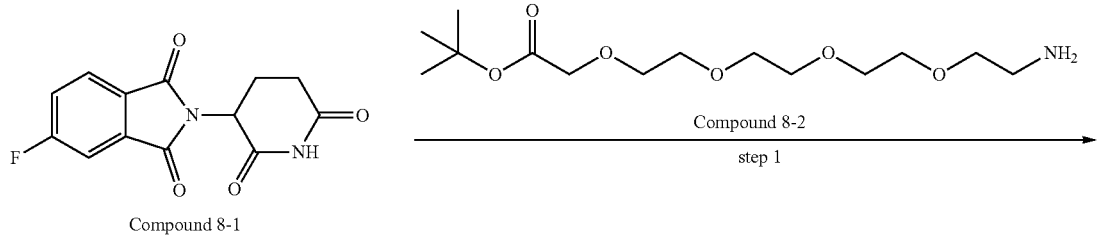

Compound 8-1     Compound 8-2     step 1

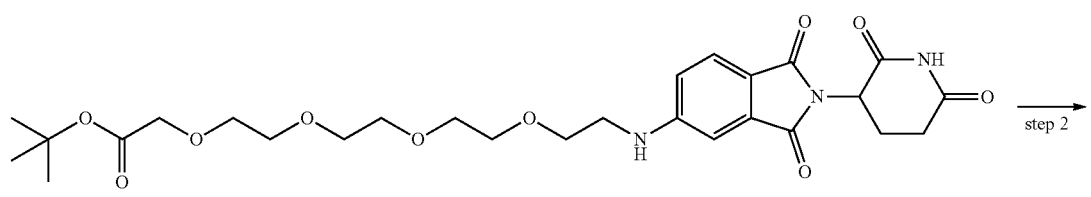

Compound 8-3     step 2

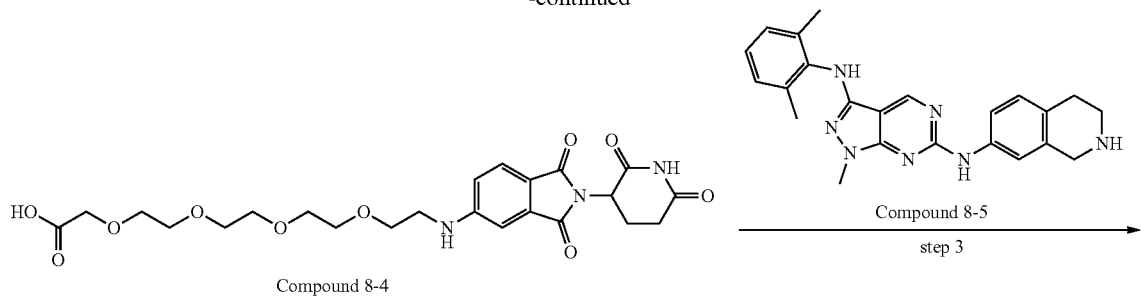

Compound 8-4

Compound 8-5 step 3

Compound 8

Step 1: Synthesis of tert-butyl-2-(2-(2-((2-(2,6-di-oxopiperidin-3-yl)-1,3-dioxoisoindolin-5-yl)amino)ethoxy)ethoxy)acetate (Compound 8-3)

A solution of Compound 8-1 (Combi-Blocks, HD-3240) (5-fluoro pomalidomide; 50 mg, 0.18 mmol) in DMSO (1.0 mL) was added with DIPEA (188 mg, 1.45 mmol) and stirred for 10 minutes. The mixture was added with Compound 8-2 (BLDpharm, BD00927562) (58 mg, 0.19 mmol), heated to 90° C., and stirred for 24 hours. The reaction mixture was diluted with ice and water, followed by extraction with EtOAc. The organic layer was washed with water and brine and concentrated in a vacuum to give a crude material which was then purified by MPLC to afford Compound 8-3 as a green oil (18 mg).

Step 2: Synthesis of 14-((2-(2,6-dioxopiperidin-3-yl)-1,3-dioxoisoindolin-5-yl)amino)-3,6,9,12-tetraoxatetradecanoic acid (Compound 8-4)

A solution of Compound 8-3 (18 mg, 0.031 mmol) in DCM (0.2 mL) was added at room temperature with TFA (0.2 mL) and stirred for 16 hours. The volatile material was evaporated in a vacuum and the residual solvent was removed by vacuum concentration to afford Compound 8-4 as a dark brown oil (13 mg).

Step 3: Synthesis of Synthesis of 5-((14-(7-((3-((2,6-dimethylphenyl)amino)-1-methyl-1H-pyrazolo[3,4-d]pyrimidin-6-yl)amino)-3,4-dihydroisoquinolin-2(1H)-yl)-14-oxo-3,6,9,12-tetraoxatetradecyl)amino)-2-(2,6-dioxopiperidin-3-yl)isoindoline-1,3-dione (Compound 8)

A solution of Compound 8-4 (13.0 mg, 0.0250 mmol) in DMF (0.5 mL) was added with HATU (38.2 mg, 0.100 mmol) and TEA (20.2 mg, 0.200 mmol) and stirred for 10 minutes. After addition of Compound 8-5 (Korean Patent No. 2128018) (10.3 mg, 0.0250 mmol), stirring was conducted at 40° C. for 6 hours. The reaction mixture was quenched with iced water, and the solid thus formed was filtered and dissolved in ethyl acetate. The organic layer was washed with water and brine and concentrated in a vacuum. The crude product was purified by MPLC to afford Compound 8 as a pale brown solid (8.0 mg).

Compound 9. N-(14-(7-((3-((2,6-Dimethylphenyl)amino)-1-methyl-1H-pyrazolo[3,4-d]pyrimidin-6-yl)amino)-3,4-dihydroisoquinolin-2(1H)-yl)-14-oxo-3,6,9,12-tetraoxatetradecyl)-2-((2-(2,6-dioxopiperidin-3-yl)-1,3-dioxoisoindolin-5-yl)oxy)acetamide

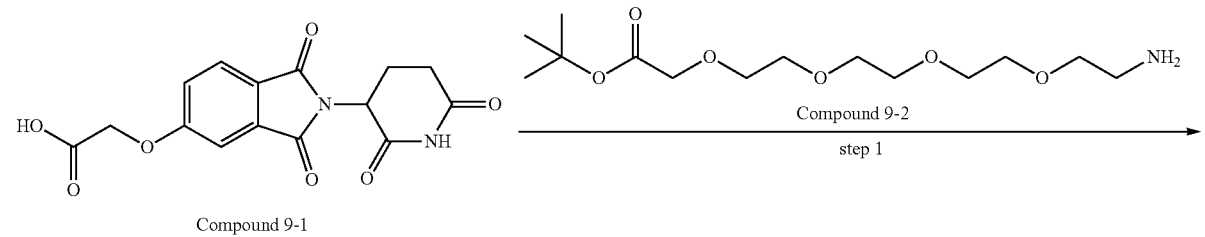

Compound 9-1

Compound 9-2 step 1

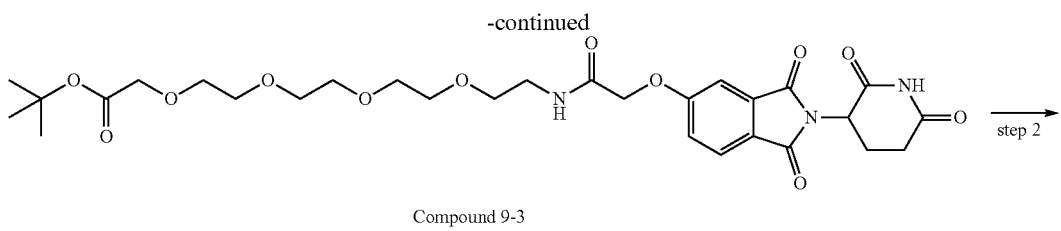

Compound 9-3

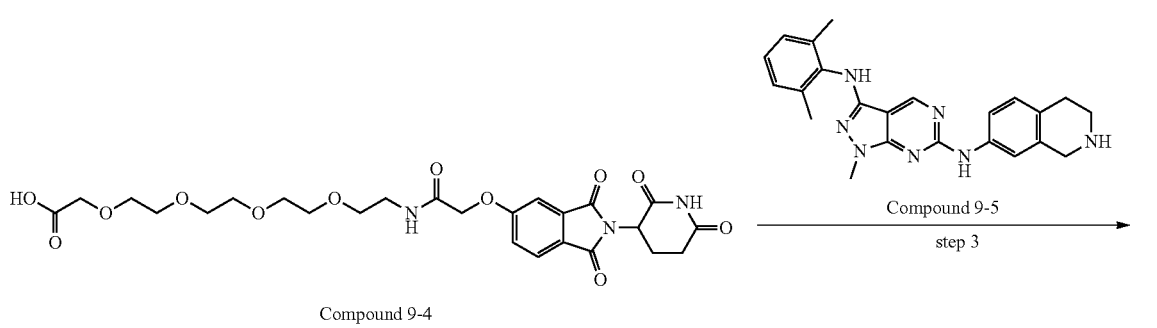

Compound 9-4

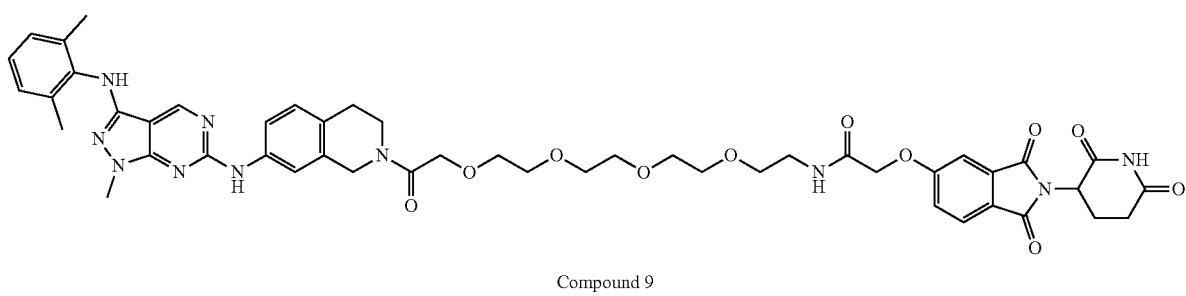

Compound 9

Step 1: Synthesis of tert-butyl-1-((2-(2,6-dioxopiperidin-3-yl)-1,3-dioxoisoindolin-5-yl)oxy)-2-oxo-6,9,12,15-tetraoxa-3-azaheptadecan-17-oate (Compound 9-3)

A solution of Compound 9-1 (WO 2020/160198) (30 mg, 0.0903 mmol) in DMF (1 mL) was added at room temperature with EDCI (24.2 mg, 0.180 mmol), HOBt·H₂O (34.5 mg, 0.180 mmol), Compound 9-2 (BLDpharm, BD00927562) (30.5 mg, 0.993 mmol), and DIPEA (46.6 mg, 0.360 mmol) and stirred at room temperature for 4 hours. The reaction mixture was quenched with water, followed by extraction with EtOAc. The organic layer was concentrated in a vacuum and the crude material thus obtained was purified by silica gel column chromatography to afford Compound 9-3 as a transparent oil (22 mg).

Step 2: Synthesis of 1-((2-(2,6-dioxopiperidin-3-yl)-1,3-dioxoisoindolin-5-yl)oxy)-2-oxo-6,9,12,15-tetraoxa-3-azaheptadecan-17-oic acid (Compound 9-4)

A solution of Compound 9-3 (22 mg, 0.038 mmol) in DCM (2 mL) was added at room temperature with TFA (1 mL) and stirred for 16 hours. The volatile material was removed by vacuum concentration to afford Compound 9-4 as an off-white oil (19 mg).

Step 3: Synthesis of Synthesis of N-(14-(7-((3-((2,6-dimethylphenyl)amino)-1-methyl-1H-pyrazolo[3,4-d]pyrimidin-6-yl)amino)-3,4-dihydroisoquinolin-2(1H)-yl)-14-oxo-3,6,9,12-tetraoxatetradecyl)-2-((2-(2,6-dioxopiperidin-3-yl)-1,3-dioxoisoindolin-5-yl)oxy)acetamide (Compound 9)

A solution of Compound 9-4 (14.0 mg, 0.0247 mmol) in DMF (0.5 mL) was added with HATU (40.3 mg, 0.106 mmol) and TEA (85.8 mg, 0.850 mmol) and stirred for 10 minutes. After addition of Compound 9-5 (Korean Patent No. 2128018) (10.0 mg, 0.0247 mmol), stirring was conducted at 40° C. for 6 hours. The reaction mixture was quenched with iced water, and the solid thus formed was filtered and dissolved in ethyl acetate. The organic layer was washed with water and brine and concentrated in a vacuum. The crude product was purified by MPLC to afford Compound 9 as a bright brown solid (7.0 mg).

Compound 10. N-(14-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)-2-((2-(2,6-dioxopiperidin-3-yl)-1,3-dioxoisoindolin-4-yl)amino)acetamide

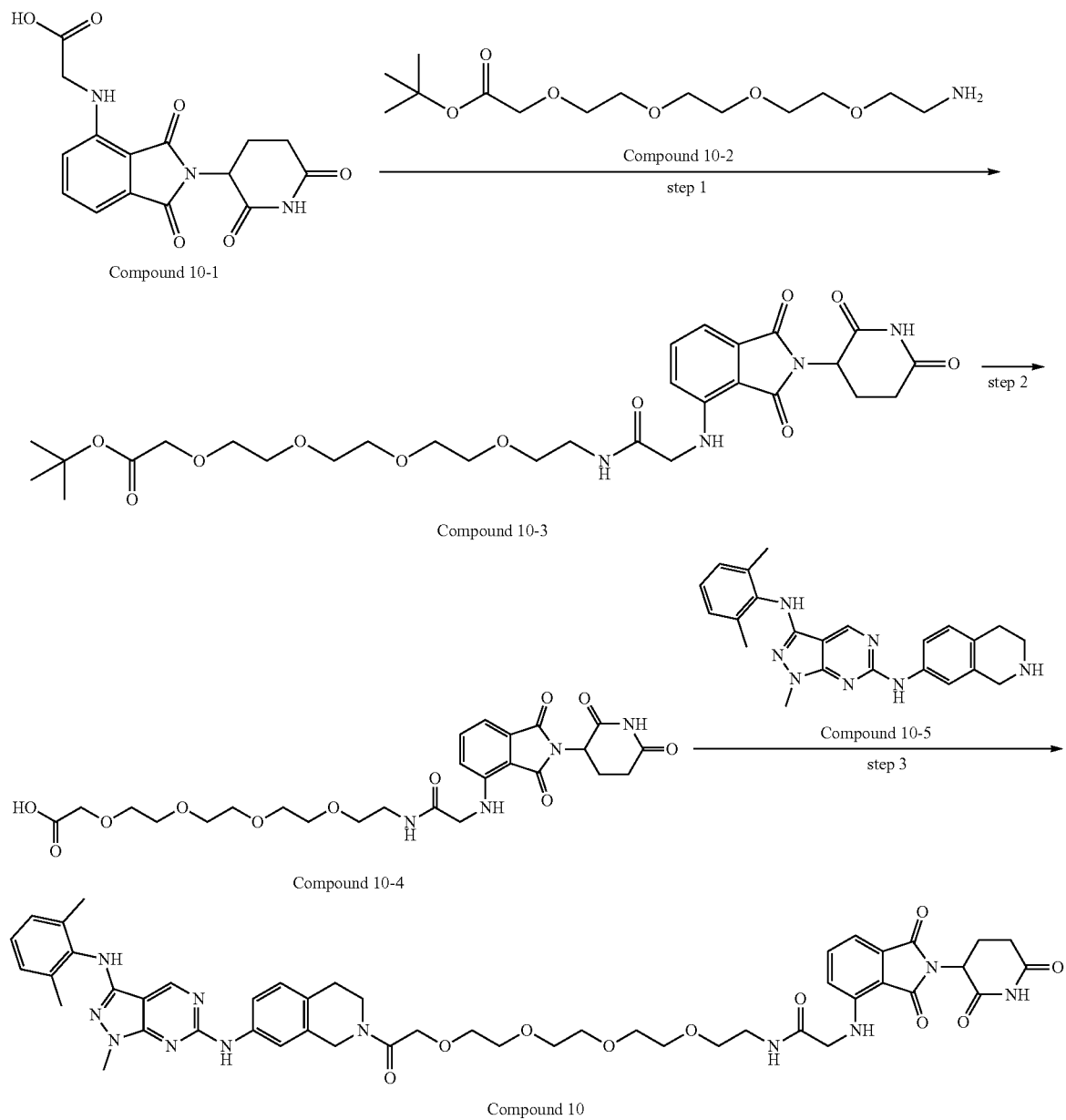

Step 1: Synthesis of tert-butyl 1-((2-(2,6-dioxopiperidin-3-yl)-1,3-dioxoisoindolin-4-yl)amino)-2-oxo-6,9,12,15-tetraoxa-3-azaheptadecan-17-oate (Compound 10-3)

A solution of Compound 10-1 (WO 2020/162725) (30 mg, 0.090 mmol) in DMF (1 mL) was added at room temperature with EDCI (24.5 mg, 0.180 mmol), HOBt·H₂O (34.7 mg, 0.181 mmol), Compound 10-2 (BLDpharm, BD00927562) (30.6 mg, 0.996 mmol) and DIPEA (47.0 mg, 0.362 mmol) and stirred at room temperature for 4 hours. The organic layer thus formed was concentrated in a vacuum to give a crude material which was then purified by silica gel column chromatography to afford Compound 10-3 as a yellow oil (26 mg).

Step 2: Synthesis of 1-((2-(2,6-dioxopiperidin-3-yl)-1,3-dioxoisoindolin-4-yl)amino)-2-oxo-6,9,12,15-tetraoxa-3-azaheptadecan-17-oic acid (Compound 10-4)

A suspension of Compound 10-3 (26 mg, 0.041 mmol) in DCM (1 mL) was added at room temperature with TFA (1 mL) and stirred for 16 hours. After vaporization of the volatile material in a vacuum, the residual solvent was removed by a high-vacuum pump to afford Compound 10-4 as a yellow solid (22 mg).

Step 3: Synthesis of Synthesis of N-(14-(7-((3-((2,6-dimethylphenyl)amino)-1-methyl-1H-pyrazolo[3,4-d]pyrimidin-6-yl)amino)-3,4-dihydroisoquinolin-2(1H)-yl)-14-oxo-3,6,9,12-tetraoxatetradecyl)-2-((2-(2,6-dioxopiperidin-3-yl)-1,3-dioxoisoindolin-4-yl)amino)acetamide (Compound 10)

A solution of Compound 10-4 (15.0 mg, 0.0246 mmol) in DMF (0.5 mL) was added with HATU (40.3 mg, 0.106 mmol) and TEA (85.8 mg, 0.850 mmol) and stirred for 10 minutes. After addition of Compound 10-5 (Korean Patent No. 2128018) (10.6 mg, 0.0265 mmol), stirring was conducted until the completion of the reaction. The reaction mixture was quenched with iced water, and the solid thus formed was filtered and dissolved in ethyl acetate (10 mL). The organic layer was washed with water and brine and concentrated in a vacuum. The crude product was purified by MPLC to afford Compound 10 as a bright brown solid (14 mg).

Compound 11. Tert-butyl 1-((2-(2,6-dioxopiperidin-3-yl)-1,3-dioxoisoindolin-4-yl)amino)-2-oxo-6,9,12,15-tetraoxa-3-azaheptadecan-17-oate

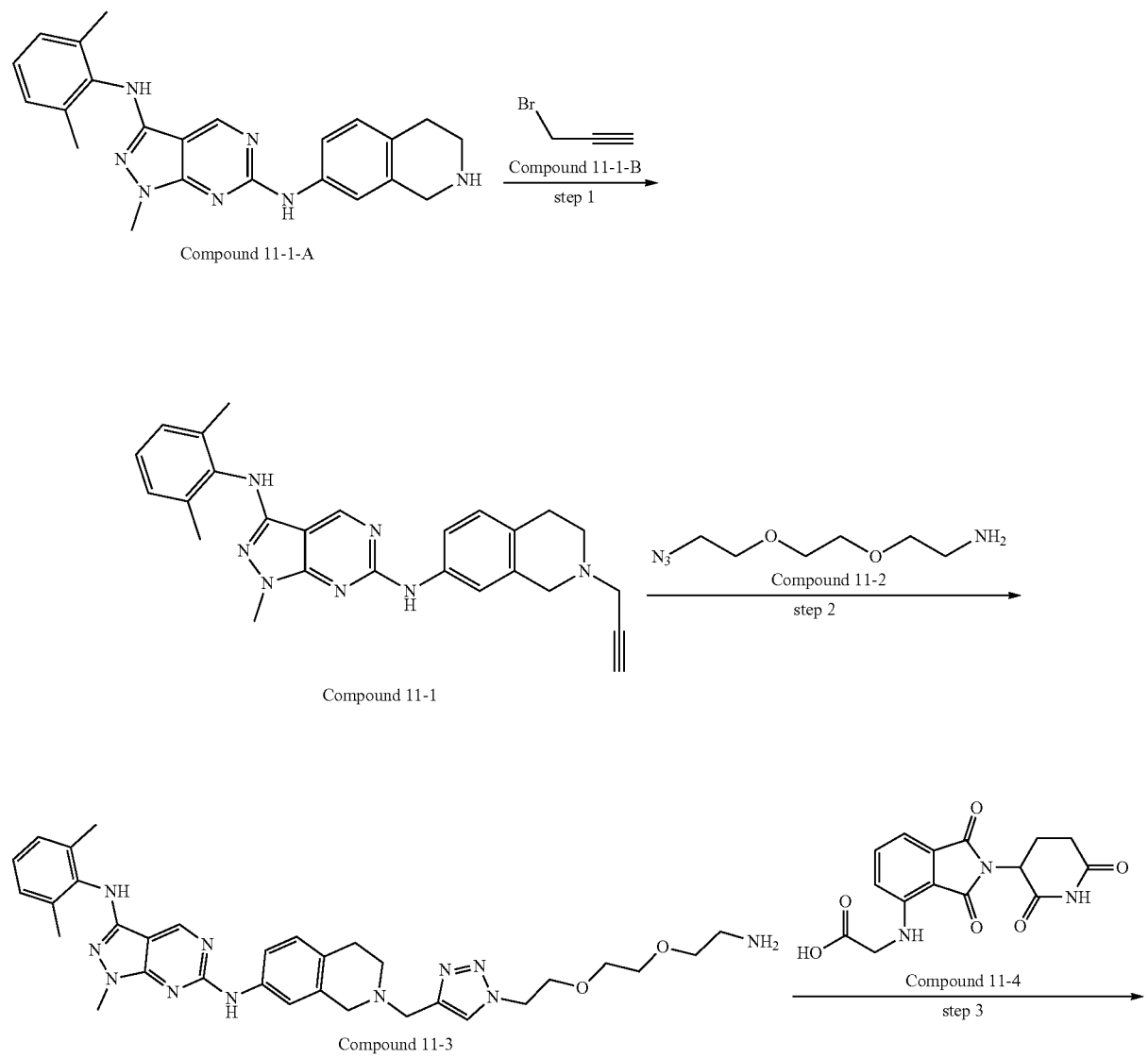

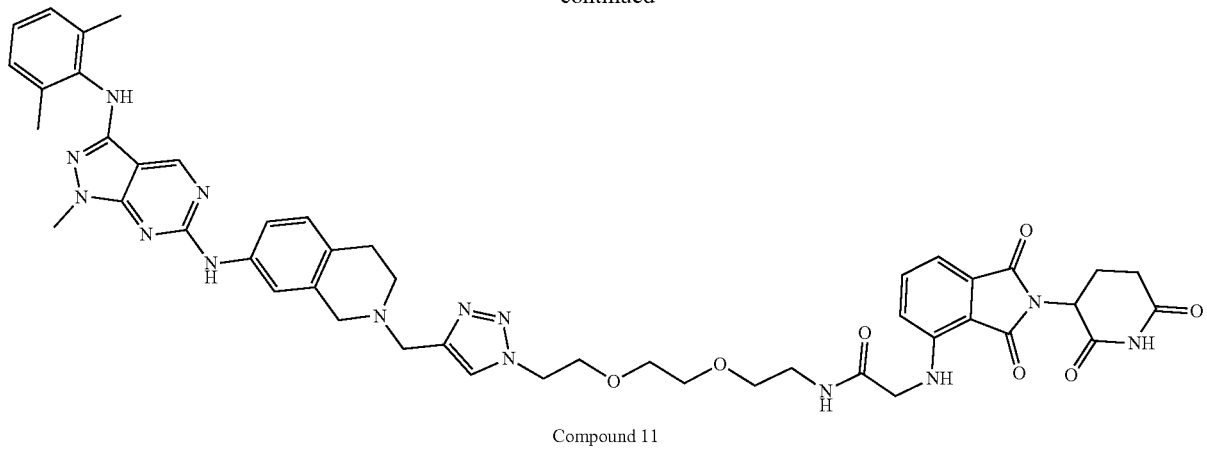

Compound 11

Step 1: Synthesis of N3-(2,6-dimethylphenyl)-1-methyl-N6-(2-(pro-2-pin-1-yl)-1,2,3,4-tetrahydroisoquinolin-7-yl)-1H-pyrazolo[3,4-d]pyrimidine-3,6-diamine (Compound 11-1)

A solution of Compound 11-1-A (Korean Patent No. 2128018) (20 mg, 0.050 mmol) in DMF (0.5 mL) was added at room temperature with Compound 11-1-B (TCI, P1272) (propargyl bromide; 7.1 mg, 0.060 mmol) and cesium carbonate (20 mg, 0.060 mmol) and stirred at room temperature for 4 hours. The consumption of the starting material was monitored by TLC. The reaction mixture was added, followed by extraction with EtOAc (3×15 mL). The pooled organic layer was washed with water (3×10 mL) and brine. The organic layer was dried over sodium sulfate and the solvent was evaporated in a vacuum to afford Compound 11-1 as an off-white solid (15 mg, 0.034 mmol, 71%).

Step 2: Synthesis of N6-(2-((1-(2-(2-(2-aminoethoxy)ethoxy)ethyl)-1H-1,2,3-triazol-4-yl)methyl)-1,2,3,4-tetrahydroisoquinolin-7-yl)-N3-(2,6-dimethylphenyl)-1-methyl-1H-pyrazolo[3,4-d]pyrimidine-3,6-diamine (Compound 11-3)

A suspension of Compound 11-1 (5.0 mg, 0.011 mmol) in water/t-BuOH (1:1) was added with Compound 11-2 (BroadPharm, BP-20692) (azido-PEG2-amine; 2.4 mg, 0.013 mmol), sodium ascorbate (0.87 mg, 0.0044 mmol, 3 eq.), and copper sulfate (0.35 mg, 0.0022 mmol, 1 eq.). The mixture was heated to 70° C. and stirred for 3 hours under a nitrogen atmosphere. The volatile material was evaporated in a vacuum and the residue was added with DCM. The DCM layer was washed with water and the organic layer was concentrated in a vacuum to afford Compound 11-3 as a dark brown oil (11 mg, crude).

Step 3: Synthesis of tert-butyl 1-((2-(2,6-dioxopiperidin-3-yl)-1,3-dioxoisoindolin-4-yl)amino)-2-oxo-6,9,12,15-tetraoxa-3-azaheptadecan-17-oate (Compound 11)

A solution of Compound 11-4 (WO 2020/162725) (5.30 mg, 16.1 mmol) in DMF (1 mL) was added at room temperature with EDCI (4.8 mg, 35.8 mmol), HOBt·H$_2$O (6.86 mg, 35.8 mmol), Compound 11-3 (11.0 mg, 17.9 mmol), and DIPEA (9.20 mg, 71.6 mmol) and stirred at 40° C. for 4 hours. The organic layer thus formed was concentrated in a vacuum to give a crude material which was then purified by silica gel column chromatography to afford Compound 11 as a brown solid (3.0 mg).

Compound 12. N-(2-(2-(2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)-1H-1,2,3-triazol-1-yl)ethoxy)ethoxy)ethyl)-2-((2-(2,6-dioxopiperidin-3-yl)-1,3-dioxoisoindolin-5-yl)amino)acetamide

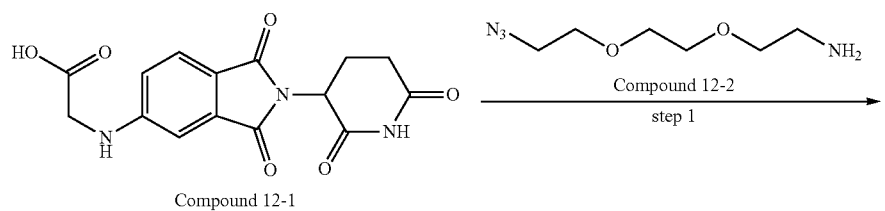

Compound 12-1     Compound 12-2 step 1

-continued

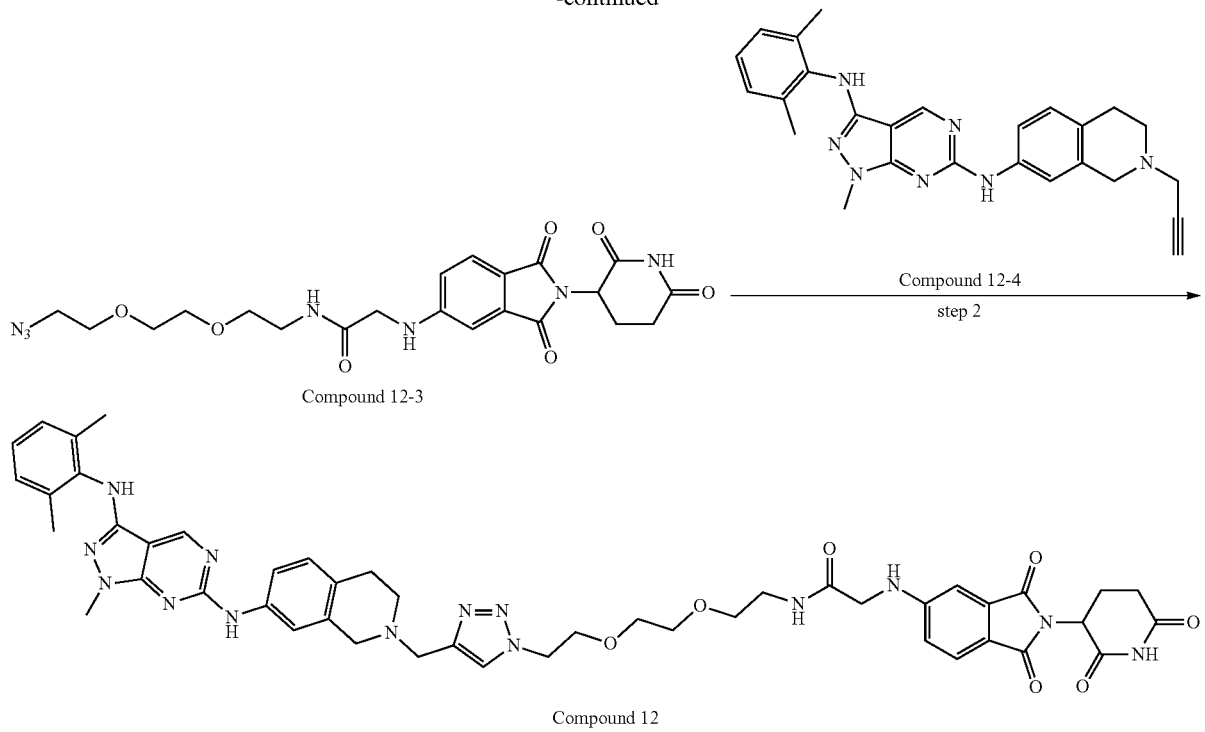

Step 1: Synthesis of N-(2-(2-(2-azidoethoxy)ethoxy)ethyl)-2-((2-(2,6-dioxopiperidin-3-yl)-1,3-dioxoisoindolin-5-yl)amino)acetamide (Compound 12-3)

A solution of Compound 12-1 (WO 2020/162725) (30.0 mg, 90.6 mmol) in DMF (1 mL) was added at room temperature with EDCI (24.48 mg, 181.2 mmol), HOBt·H$_2$O (34.73 mg, 181.2 mmol), Compound 12-2 (BroadPharm, BP-20692) (azido-2PEG-amine; 17.3 mg, 99.6 mmol), and DIPEA (46.93 mg, 962.2 mmol) and stirred at 40° C. for 4 hours. The organic layer thus formed was concentrated in a vacuum to give a crude material which was then purified by silica gel column chromatography to afford Compound 12-3 as a brown oil (20 mg).

Step 2: Synthesis of N-(2-(2-(2-(4-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)-1H-1,2,3-triazol-1-yl)ethoxy)ethoxy)ethyl)-2-((2-(2,6-dioxopiperidin-3-yl)-1,3-dioxoisoindolin-5-yl)amino)acetamide (Compound 12)

A suspension of Compound 12-4 (identical to Compound 11-1) (10 mg, 22.0 mmol) in water/t-BuOH (1:1) was added with Compound 12-3 (11.8 mg, 24.0 mmol), sodium ascorbate (13.0 mg, 66.0 mmol), and copper sulfate (3.70 mg, 22.0 mmol). The mixture was stirred at 70° C. for 14 hours in a nitrogen atmosphere. The volatile material was evaporated in a vacuum and the residue was added with DCM. The organic layer was washed with water and concentrated in a vacuum, and the crude material thus obtained was purified by silica gel column chromatography to afford Compound 12 as a brown solid (4.0 mg).

Compound 13. 4-((14-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)amino)-2-(2,6-dioxopiperidin-3-yl)isoindoline-1,3-dione

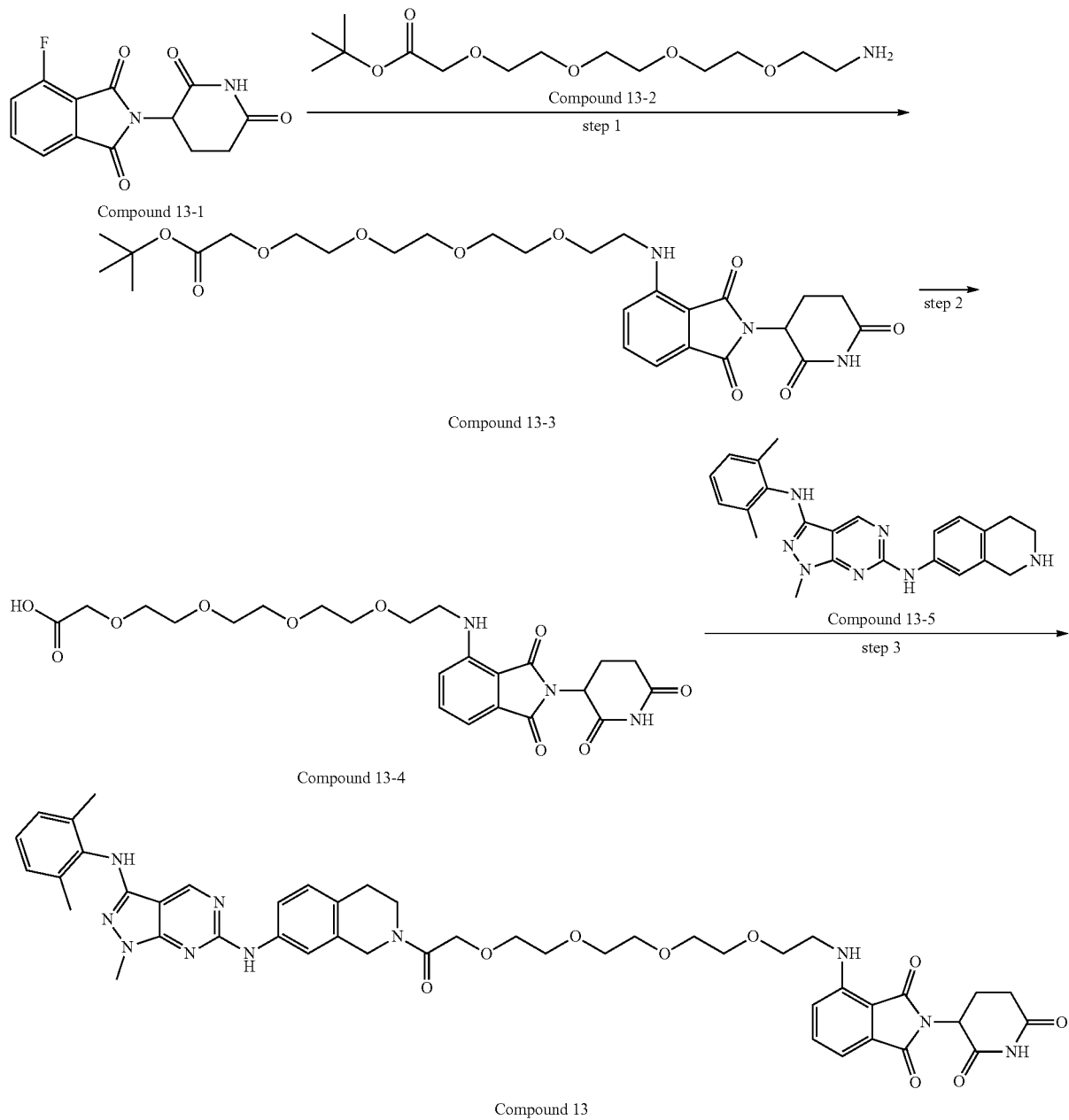

Step 1: Synthesis of tert-butyl-2-(2-(2-((2-(2,6-dioxopiperidin-3-yl)-1,3-dioxoisoindolin-5-yl)amino)ethoxy)ethoxy)acetate (Compound 13-3)

A solution of Compound 13-1 (Axis Pharm, AP12129) (4-fluoropomalidomide; 30 mg, 0.10 mmol) in DMSO (1.0 mL) was added with DIPEA (111 mg, 0.860 mmol) and stirred for 10 minutes. The mixture was added with Compound 13-2 (BLDpharm, BD00927562) (58 mg, 0.19 mmol), heated to 90° C., and stirred for 12 hours. The reaction mixture was added with ice and diluted with water before extraction with EtOAc. The organic layer was washed with water and brine and concentrated in a vacuum to give a crude material which was then purified by MPLC to afford Compound 13-3 as a brown oil (17 mg).

Step 2: Synthesis of tert-butyl (15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)carbamate (Compound 13-4)

A solution of Compound 13-3 (17 mg, 0.030) in 40% TFA/DCM (2 mL) (1 mL) was stirred at room temperature for 2 hours. The solvent was evaporated in a vacuum to afford Compound 13-4 as a brown oil (15 mg, 0.029, 98%).

Step 3: Synthesis of 4-((14-(7-((3-((2,6-dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)amino)-2-(2,6-dioxopiperidin-3-yl)isoindoline-1,3-dione (Compound 13)

A solution of Compound 13-4 (15 mg, 0.029 mmol) in DMF (0.5 mL) was added with HATU (44 mg, 0.12 mmol) and TEA (23 mg, 0.23 mmol) and stirred for 10 minutes. After addition of Compound 13-5 (Korean Patent No. 2128018) (12 mg, 0.030 mmol), stirring was conducted at 40° C. for 14 hours. The reaction mixture was quenched with iced water, and the solid thus formed was filtered and dissolved in ethyl acetate. The organic layer was washed with water and brine and concentrated in a vacuum. The crude product was purified by MPLC to afford Compound 13 as a yellow solid (6 mg).

Compound 14. tert-Butyl 2-(2-(2-((2-(2,6-dioxopiperidin-3-yl)-1,3-dioxoisoindolin-5-yl)amino)ethoxy)ethoxy)acetate

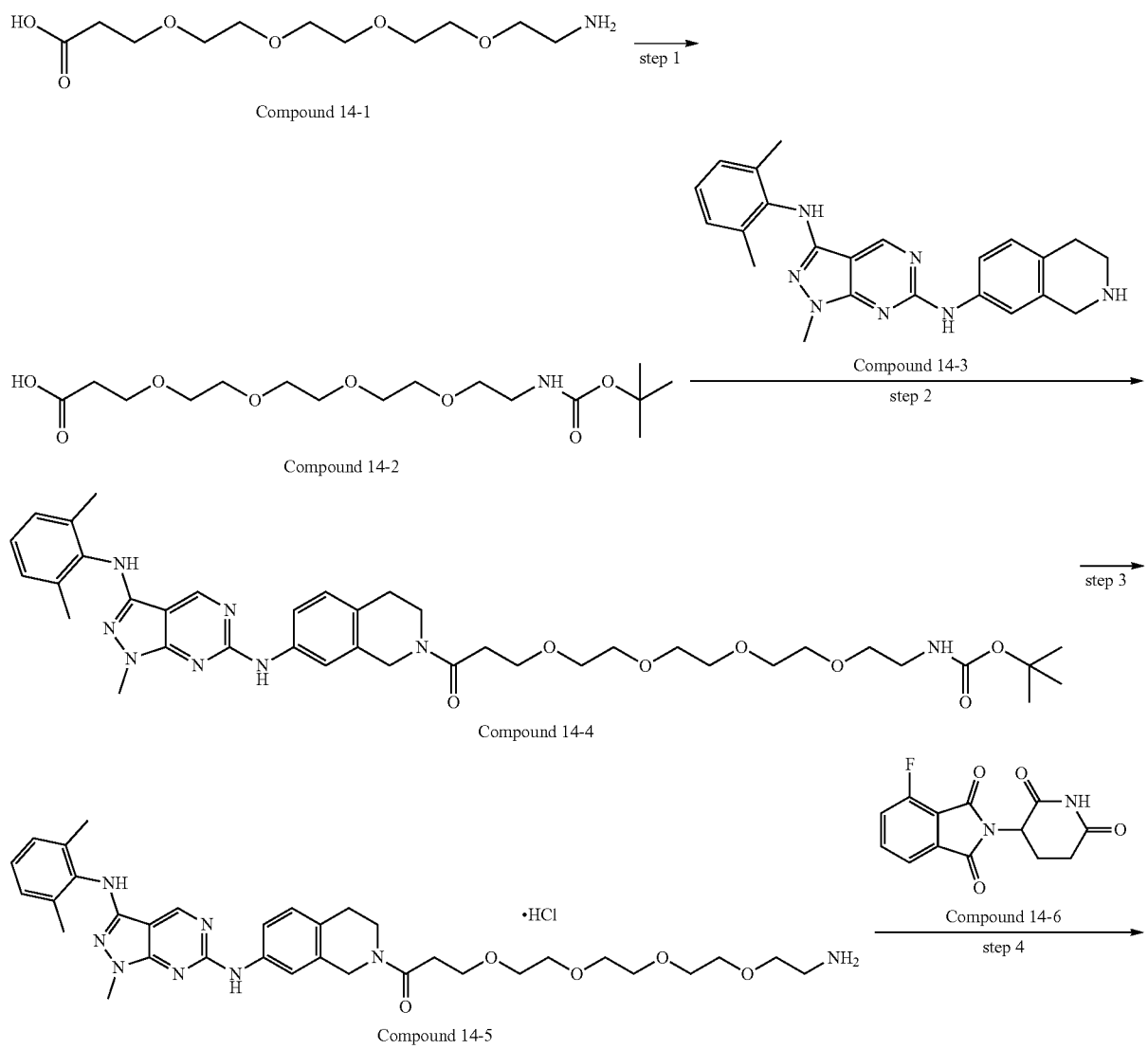

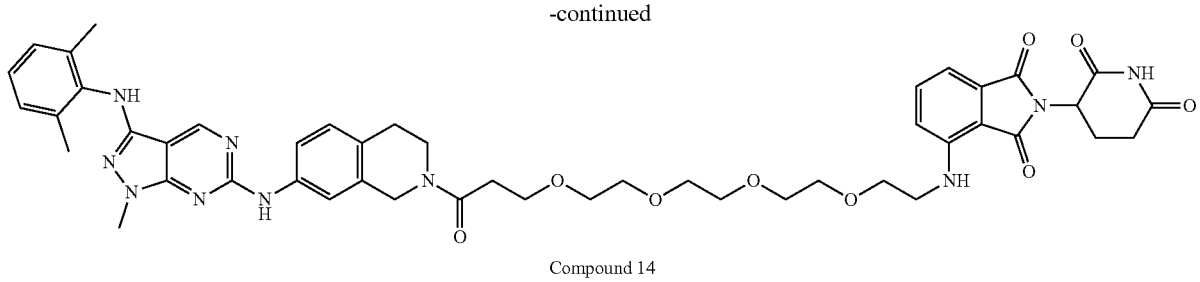

Compound 14

Step 1: Synthesis of 2,2-dimethyl-4-oxo-3,8,11,14,17-pentaoxa-5-azaicosan-20-oic acid (Compound 14-2)

A solution of Compound 14-1 (BroadPharm, BP-20423) (4-PEG amino acid; 200 mg, 0.753 mmol) in THF (25 mL) was added with TEA (91.4 mg, 0.904 mmol) and (Boc)$_2$O (197 mg, 0.904 mmol) and stirred at room temperature for 6 hours. After concentration of the organic solvent, the residue was added with DCM and washed with 0.5 N—HCl. The organic layer was concentrated in a vacuum to give a crude material which was then purified by MPLC to afford Compound 14-2 as a transparent oil (230 mg).

Step 2: Synthesis of tert-butyl (15-(7-((3-((2,6-dimethylphenyl)amino)-1-methyl-1H-pyrazolo[3,4-d]pyrimidin-6-yl)amino)-3,4-dihydroisoquinolin-2(1H)-yl)-15-oxo-3,6,9,12-tetraoxapentadecyl)carbamate (Compound 14-4)

A solution of Compound 14-2 (151 mg, 0.413 mmol) in DMF (5 mL) was added with HATU (428.0 mg, 1.12 mmol) and TEA (190 mg, 1.87 mmol) and stirred for 10 minutes. After addition of Compound 14-3 (Korean Patent No. 2128018) (150 mg, 0.375 mmol), stirring was conducted overnight at 40° C. The reaction mixture was quenched with iced water, and the solid thus formed was filtered and dissolved in ethyl acetate (10 mL). The organic layer was washed with water and brine and concentrated in a vacuum. The crude product was purified by MPLC to afford Compound 14-4 as a reddish yellow solid (190 mg).

Step 3: Synthesis of 1-amino-15-(7-((3-((2,6-dimethylphenyl)amino)-1-methyl-1H-pyrazolo[3,4-d]pyrimidin-6-yl)amino)-3,4-dihydroisoquinolin-2(1H)-yl)-3,6,9,12-tetraoxapentadecan-15-one hydrochloride (Compound 14-5)

A solution of Compound 14-4 (180 mg, 0.241 mmol) in DCM (5 mL) was added at 0° C. with HCl/dioxane (1.5 equivalents) and stirred at room temperature for 4 hours. Evaporation of the solvent in a vacuum afforded Compound 14-5 as a brown solid (161 mg).

Step 4: Synthesis of tert-butyl 2-(2-(2-((2-(2,6-dioxopiperidin-3-yl)-1,3-dioxoisoindolin-5-yl)amino)ethoxy)ethoxy)acetate (Compound 14)

A solution of Compound 14-5 (20 mg, 0.031 mmol) in DMSO (1.0 mL) was added with DIPEA (32 mg, 0.24 mmol) and stirred for 10 minutes. The mixture was added with Compound 14-6 (Axis Pharm, AP12129) (10.3 mg, 0.0371 mmol), heated to 90° C., and stirred for 12 hours. The reaction mixture was added with ice and diluted with water before extraction with EtOAc. The organic layer was concentrated in a vacuum to give a crude material which was then purified by MPLC to afford Compound 14 as a yellow oil (7.4 mg).

Compound 15. 5-((15-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)amino)-2-(2,6-dioxopiperidin-3-yl)isoindoline-1,3-dione

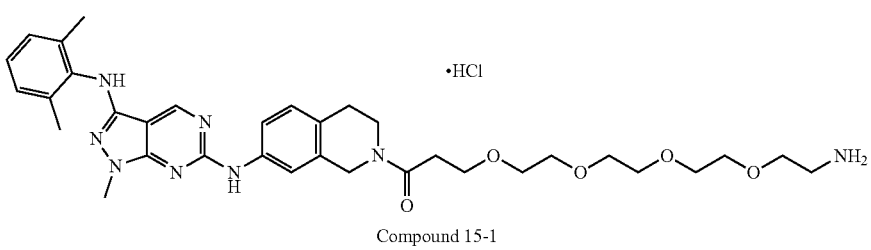

Compound 15-1

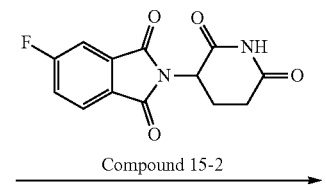

Compound 15-2

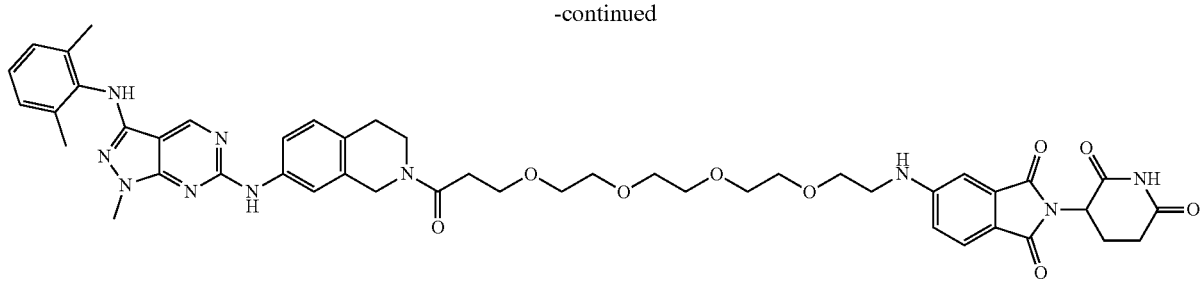

Compound 15

A solution of Compound 15-1 (identical to Compound 14-5) (20 mg, 0.031 mmol) in DMSO (1.0 mL) was added with DIPEA (32 mg, 0.24 mmol) and stirred for 10 minutes. The mixture was added with Compound 15-2 (Combi-Blocks, HD-3240) (10.3 mg, 0.0371 mmol), heated to 90° C., and stirred for 12 hours. The reaction mixture was added with water and ice before extraction with EtOAc. The organic layer was washed with water and brine and concentrated in a vacuum to give a crude material which was then purified by MPLC to afford Compound 15 as a yellow oil (7 mg).

Compound 16. N-(15-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-5-yl)oxy)acetamide

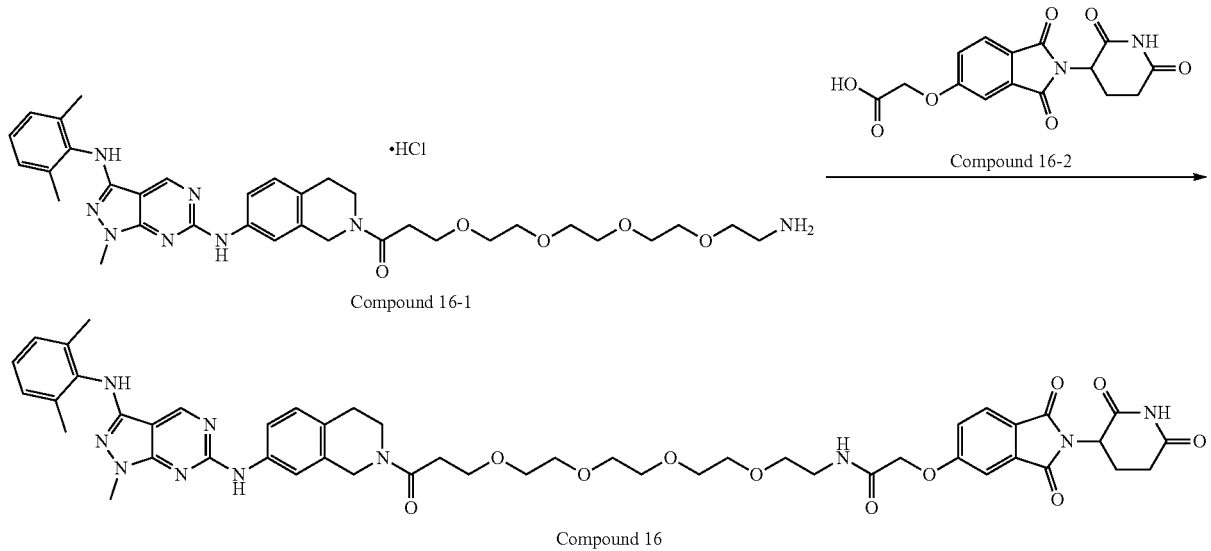

Compound 16-2

Compound 16-1

Compound 16

A solution of Compound 16-2 (WO 2020/160198) (9.0 mg, 0.027 mmol) in DMF (0.5 mL) was added at room temperature with EDCI (11 mg, 0.058 mmol), HOBt·H$_2$O (7.8 mg, 0.058 mmol), Compound 16-1 (identical to Compound 14-5) (20 mg, 0.029 mmol), and DIPEA (18 mg, 0.14 mmol) and stirred at room temperature for 4 hours. The reaction mixture was quenched with water before extraction with EtOAc. The organic layer was concentrated in a vacuum to give a crude material which was then purified by silica gel column chromatography to afford Compound 16 as an off-white solid (14 mg).

Compound 17. N-(15-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-4-yl)oxy)acetamide

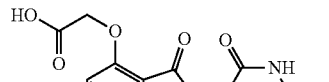

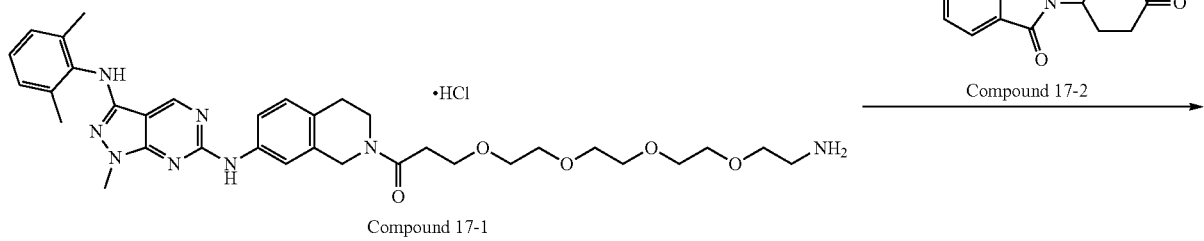

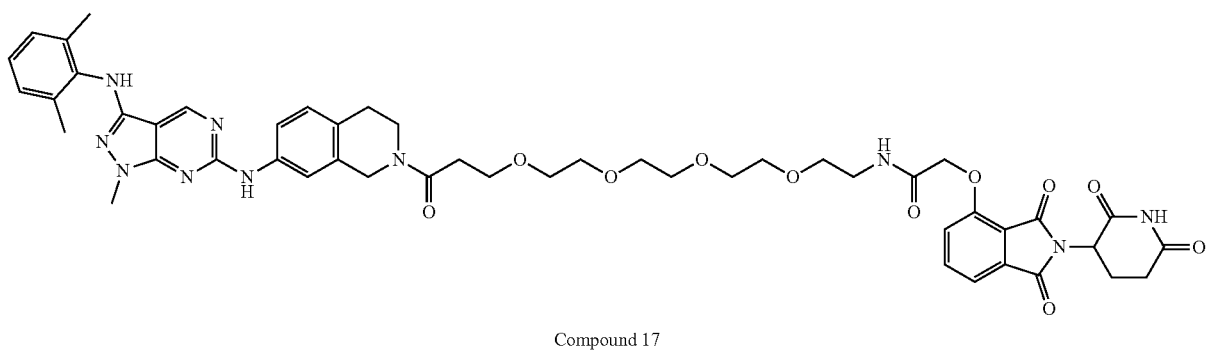

A solution of Compound 17-2 (WO 2020/263935) (9.0 mg, 0.027 mmol) in DMF (0.5 mL) was added at room temperature with EDCI (11 mg, 0.058 mmol), HOBt·H$_2$O (7.8 mg, 0.058 mmol), Compound 17-1 (identical to Compound 14-5) (20 mg, 0.029 mmol), and DIPEA (18 mg, 0.14 mmol) and stirred at 40° C. for 4 hours. The reaction was quenched with water before extraction with EtOAc. The organic layer was concentrated in a vacuum to give a crude material which was then purified by silica gel column chromatography to afford Compound 17 as an off-white solid (16 mg).

Compound 18. N-(15-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-(4-(2-(2,6-dioxopiperidin-3-yl)-1,3-dioxoisoindolin-5-yl)piperazin-1-yl)acetamide

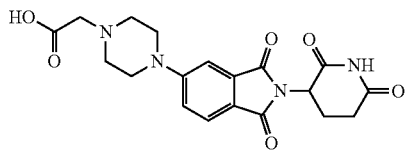

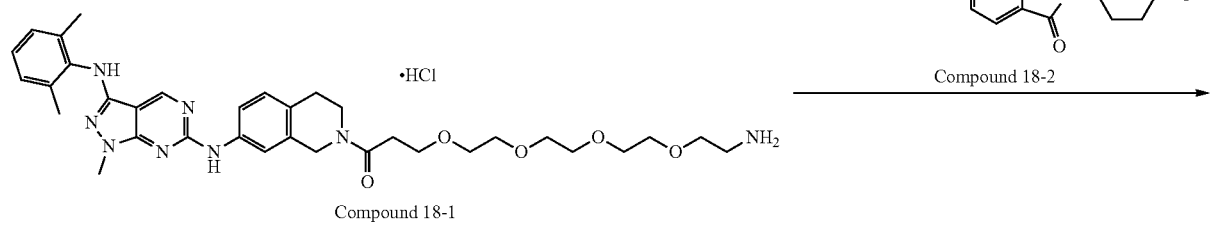

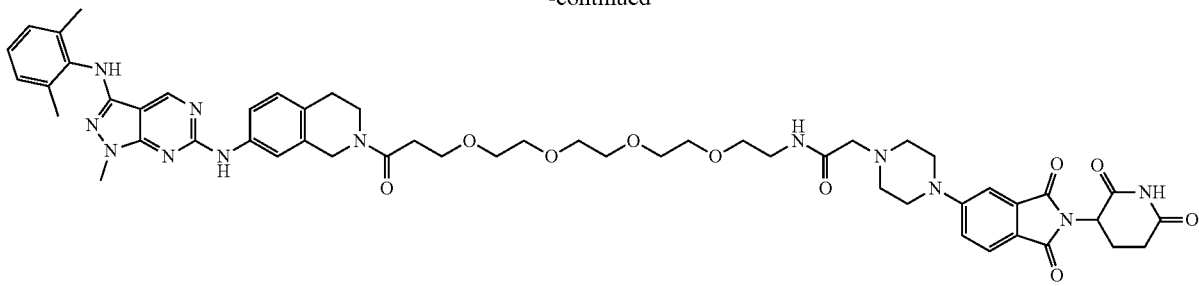

Compound 18

A solution of Compound 18-2 (WO 2020/160193) (8.0 mg, 0.020 mmol) in DMF (0.5 mL) was added at room temperature with EDCI (8.0 mg, 0.042 mmol), HOBt·H$_2$O (5.6 mg, 0.042 mmol), Compound 18-1 (identical to Compound 14-5) (15 mg, 0.021 mmol), and DIPEA (13.6 mg, 0.105 mmol) and stirred at 40° C. for 4 hours. The reaction was quenched with water before extraction with EtOAc. The organic layer was concentrated in a vacuum and the crude material thus obtained was purified by silica gel column chromatography to afford Compound 18 as an off-white solid (10 mg).

Compound 19. N-(2-(2-(2-(2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)-1H-1,2,3-triazol-1-yl)ethoxy)ethoxy)ethyl)-2-((2-(2,6-dioxopiperidin-3-yl)-1,3-dioxoisoindolin-4-yl)amino)acetamide

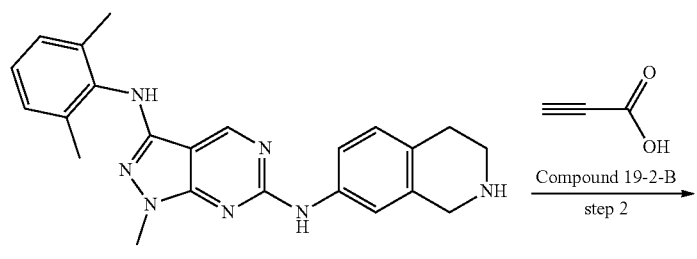

Compound 19-2-A

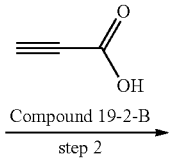

Compound 19-2-B step 2

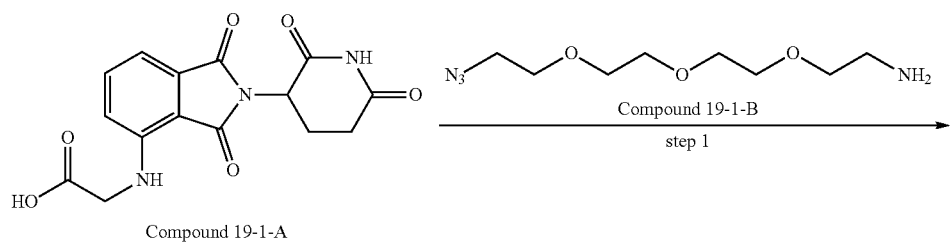

Compound 19-2

Compound 19-1-A

Compound 19-1-B step 1

-continued

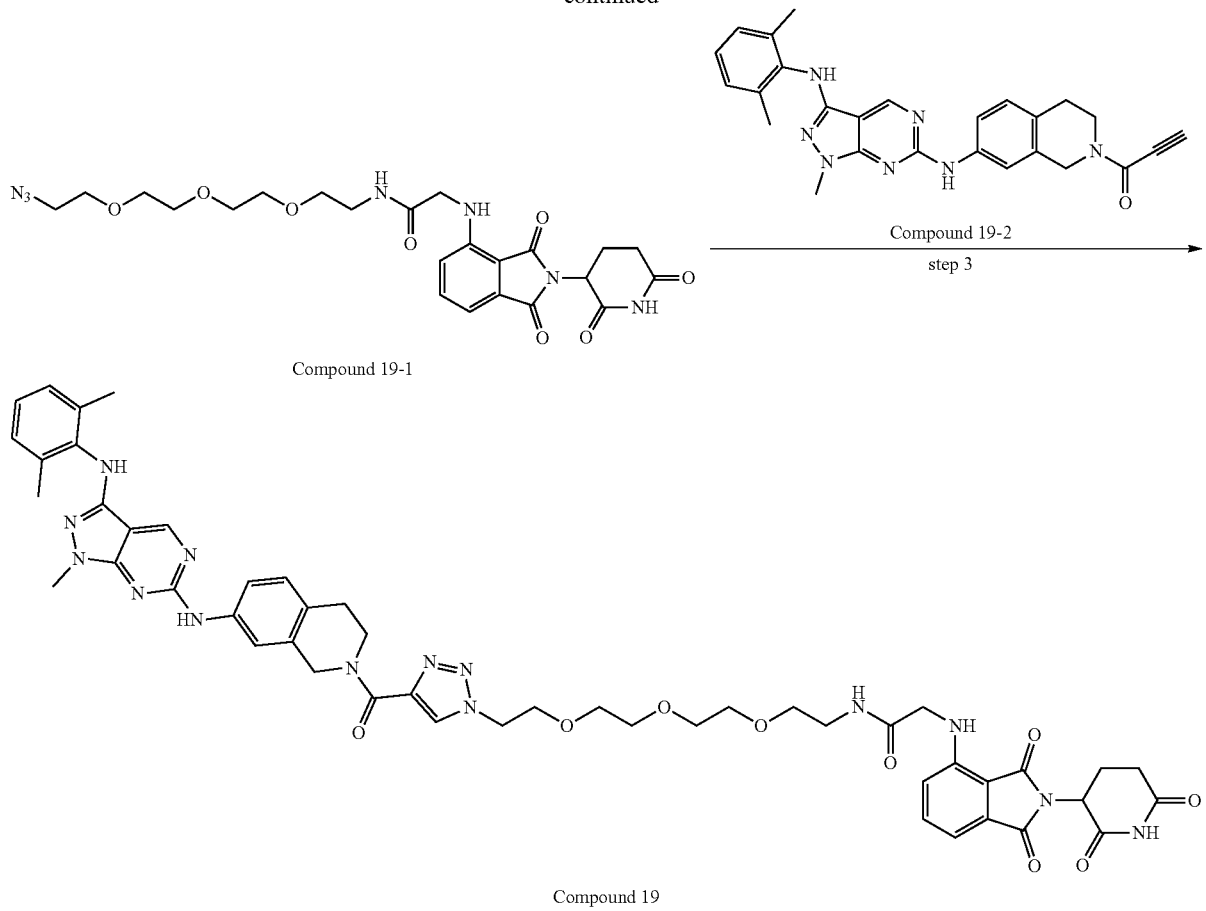

Compound 19-1

Compound 19

Step 1: Synthesis of N-(2-(2-(2-azidoethoxy)ethoxy)ethyl)-2-((2-(2,6-dioxopiperidin-3-yl)-1,3-dioxoisoindolin-5-yl)amino)acetamide (Compound 19-1)

A solution of Compound 19-1-A (WO 2020/162725) (50.0 mg, 0.151 mmol) in DMF (1 mL) was added at room temperature with EDCI (57.9 mg, 0.302 mmol), HOBt·H$_2$O (40.8 mg, 0.302 mmol), Compound 19-1-B (BROAD-PHARM, BP-20580) (azido-2PEG amine; 36.2 mg, 0.166 mmol), and DIPEA (78.2 mg, 0.604 mmol) and stirred at 40° C. for 4 hours. The reaction was quenched before extraction with EtOAc. The pooled organic layer was dried over Na$_2$SO$_4$ and the solvent was removed in a vacuum. The crude material was purified by silica gel column chromatography using 10% MeOH/DCM as an eluent to afford Compound 19-1 as a yellow oil (34 mg, 0.064 mmol).

Step 2: Synthesis of 1-(7-((3-((2,6-dimethylphenyl)amino)-1-methyl-1H-pyrazolo[3,4-d]pyrimidin-6-yl)amino)-3,4-dihydroisoquinolin-2(1H)-yl)pro-2-pi-1-one (Compound 19-2)

A solution of Compound 19-2-B (TCI, P0497) (propiolic acid; 21 mg, 0.30 mmol) in DMF (2 mL) was added with HATU (380 mg, 1.00 mmol) and TEA (156 mg, 0.400 mmol) and stirred for 10 minutes. After addition of Compound 19-2-A (Korean Patent No. 2128018) (20 mg, 0.050 mmol), stirring was continued at room temperature for 4 hours. The consumption of the starting materials was monitored by TLC. The reaction mixture was quenched with iced water, and the solid thus formed was filtered and dissolved in ethyl acetate (10 mL). The organic layer was washed with water and brine and dried over sodium sulfate, and the solvent was evaporated in a vacuum. The crude product was purified by MPLC using 10% MeOH/DCM as an eluent to afford Compound 19-2 as a reddish yellow solid (91 mg, 0.20 mmol, 80%).

Step 3: Synthesis of N-(2-(2-(2-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-1H-1,2,3-triazol-1-yl)ethoxy)ethoxy)ethyl)-2-((2-(2,6-dioxopiperidin-3-yl)-1,3-dioxoisoindolin-4-yl)amino)acetamide (Compound 19)

A suspension of Compound 19-1 (10 mg, 22.0 mmol) in t-BuOH (1 mL) was added with Compound 19-2 (11.8 mg, 24.0 mmol), sodium ascorbate (13.0 mg, 66.0 mmol), copper sulfate (3.70 mg, 22.0 mmol), and TEA (2.9 mg, 0.018 mmol), heated to 70° C., and stirred for 14 hours under an argon atmosphere. The consumption of the starting materials was monitored by TLC. The volatile material was evaporated in a vacuum and the residue was added with DCM. The DCM layer was washed with water. The organic layer was dried over sodium sulfate and the solvent was evaporated in a vacuum. The crude material was purified by silica gel column chromatography using 10% MeOH/DCM as an eluent to afford Compound 19 as a brown solid (4.0 mg, 0.0040 mmol, 22%).

Compound 20. N-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl)piperazin-1-yl)acetamide

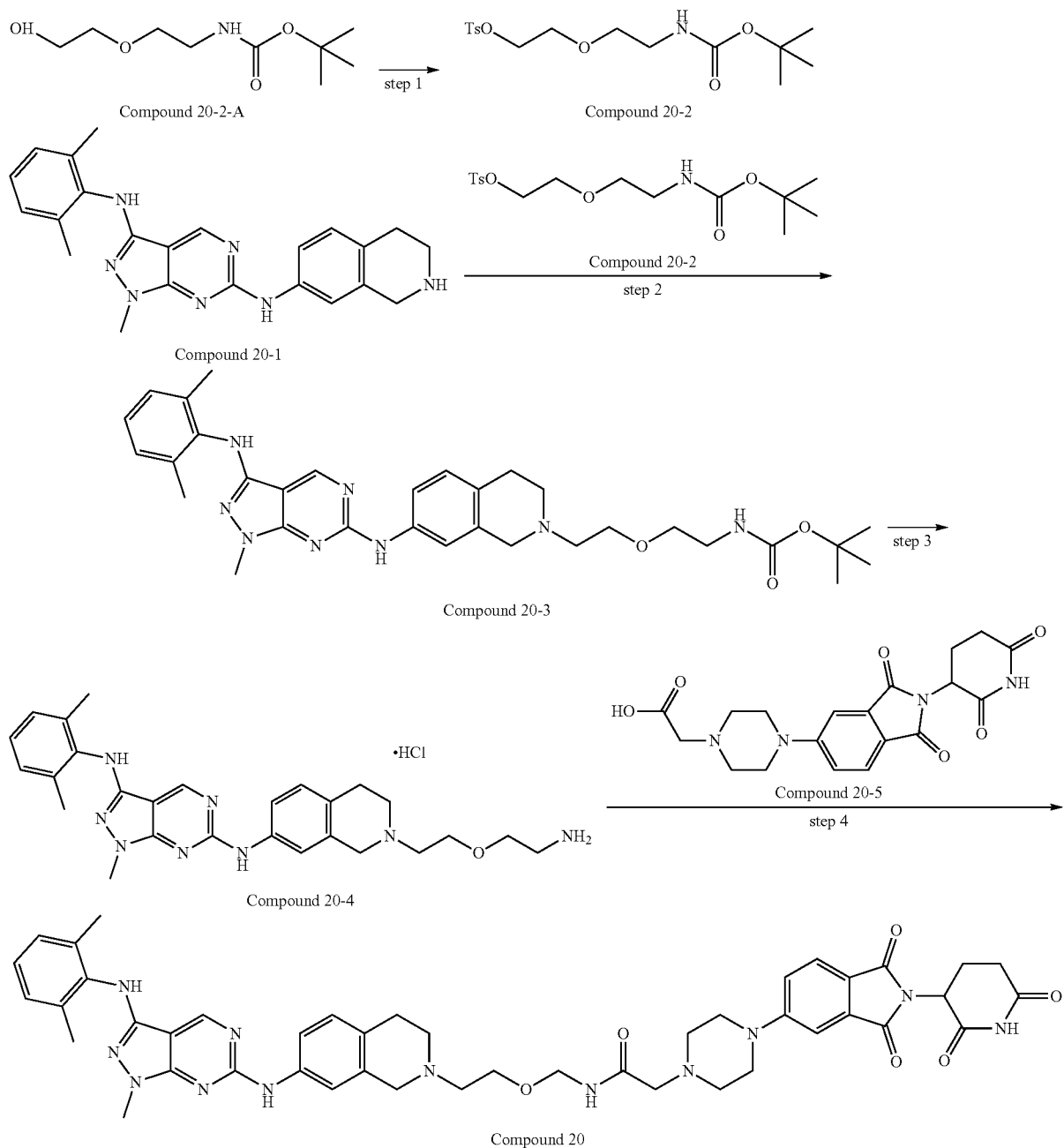

Step 1: Synthesis of 2-(2-((tert-butoxycarbonyl)amino)ethoxy)ethyl 4-methylbenzenesulfonate (Compound 20-2)

A stirred solution of Compound 20-2-A (BROADPHARM, BP-23275) (tert-butyl (2-(2-hydroxyethoxy)ethyl) carbamate; 1.0 g, 4.8 mmol) in DCM (20 mL) was cooled to 0° C. and added with TEA (0.97 g, 9.6 mmol) and DMAP (0.29 g, 2.4 mmol) and then slowly with p-toluene sulfonyl chloride (1.4 g, 7.3 mmol) while stirring at room temperature for 16 hours. After completion of the reaction, the reaction mixture was diluted with DCM (20 mL) and washed with water. The aqueous layer was subjected to extraction with DCM (25 mL×2), and the pooled organic layer was washed with 10% NaOH and brine. The organic layer was dried over sodium sulfate and the solvent was evaporated in a vacuum. The crude material was purified by silica gel column chromatography using 50% EA:HEX mixture as an eluent to afford Compound 20-2 as a transparent oil (1.1 g, 3.0 mmol, 62%).

Step 2: Synthesis of tert-butyl (2-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)ethoxy)ethyl)carbamate (Compound 20-3)

A solution of Compound 20-2 (20 mg, 0.056 mmol) in DMF (0.5 mL) was added at room temperature with Compound 20-1 (Korean Patent No. 2128018) (30 mg, 0.051 mmol) and potassium carbonate (14 mg, 0.10 mmol) and stirred at 70° C. for 16 hours. After completion of the reaction, water was added to form a white precipitate which was then filtered and dissolved in DCM. The organic layer was concentrated in a vacuum to give a crude material which was then purified by MPLC to afford Compound 20-3 as a white solid (23 mg).

Step 3: Synthesis of N6-(2-(2-(2-aminoethoxy)ethyl)-1,2,3,4-tetrahydroisoquinolin-7-yl)-N3-(2,6-dimethylphenyl)-1-methyl-1H-pyrazolo[3,4-d]pyrimidine-3,6-diamine hydrochloride (Compound 20-4)

A solution of Compound 20-3 (23 mg, 0.039 mmol) in DCM (1 mL) was added with 4 N—HCl/dioxane (0.23 mL, 0.058 mmol) and the temperature was elevated from 0° C. to room temperature before stirring for one hour. The volatile material was evaporated. The yellow solid thus formed was washed with diethylether. The volatile material was distilled under a vapor to afford Compound 20-4 as a yellow solid (18 mg).

Step 4: Synthesis of N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl)piperazin-1-yl)acetamide (Compound 20)

A solution of Compound 20-5 (WO 2020/160193) (7.2 mg, 0.018 mmol) in DMF (0.5 mL) was added at room temperature with EDCI (6.9 mg, 0.036 mmol), HOBt·H₂O (4.8 mg, 0.036 mmol), Compound 20-4 (10 mg, 0.018 mmol), and DIPEA (12 mg, 0.090 mmol) and stirred at 40° C. for 16 hours. The reaction mixture was quenched with water, followed by extraction with EtOAc. The organic layer was concentrated in a vacuum to give a crude material which was then purified by silica gel column chromatography to afford Compound 20 as a yellow solid (4 mg).

Compound 21. N-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-5-yl)piperidine-4-carboxamide

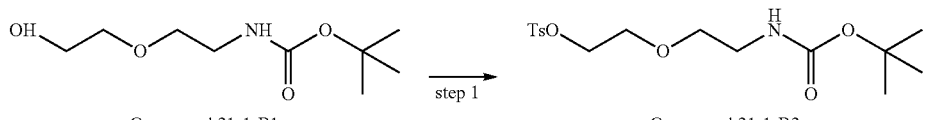

Compound 21-1-B1    step 1    Compound 21-1-B2

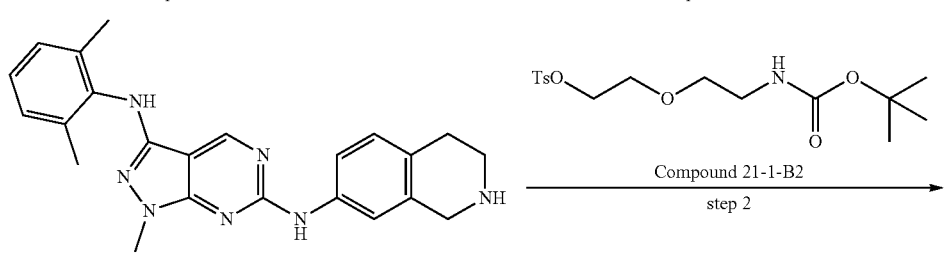

Compound 21-1-A

Compound 21-1-B2    step 2

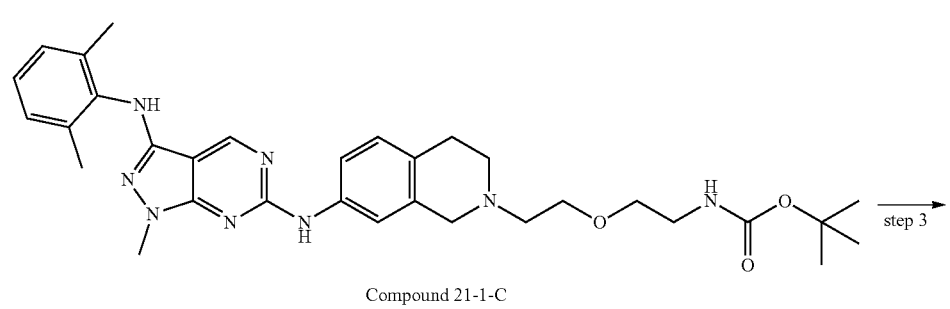

Compound 21-1-C

-continued

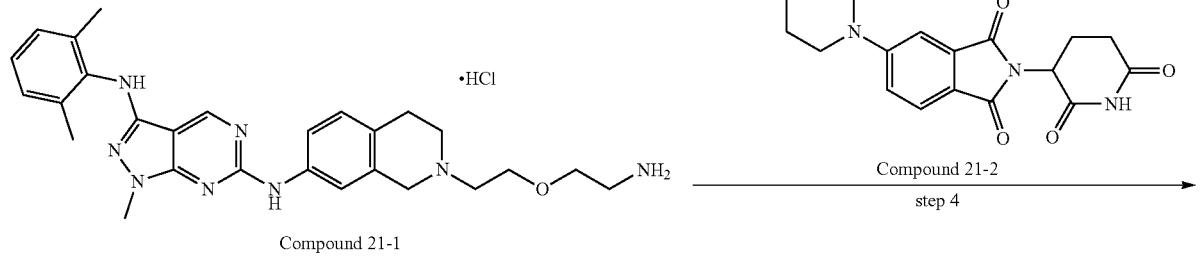

Compound 21-1 · HCl

Compound 21-2 step 4

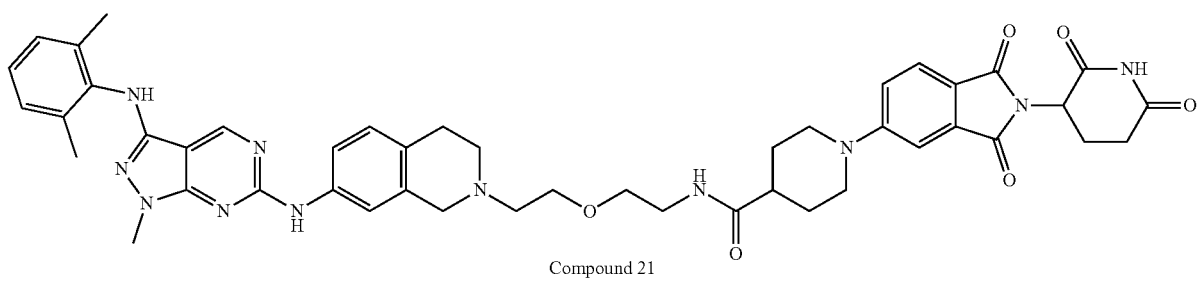

Compound 21

Step 1: Synthesis of 2-(2-((tert-butoxycarbonyl)amino)ethoxy)ethyl 4-methylbenzenesulfonate (Compound 21-1-B2)

A stirred solution of Compound 21-1-B1 (tert-butyl (2-(2-hydroxyethoxy)ethyl)carbamate) (Sigma-Aldrich, 749648) (1.0 g, 4.8 mmol) in DCM (20 mL) was refrigerated to 0° C. and added with TEA (0.97 g, 9.6 mmol) and DMAP (0.29 g, 2.4 mmol) and slowly with p-toluene sulfonyl chloride (1.4 g, 7.3 mmol) before stirring at room temperature for 16 hours. After completion of the reaction, the reaction mixture was diluted with DCM (20 mL) and washed with water. The aqueous layer was subjected to extraction with DCM (25 mL×2). The pooled organic layer was washed with NaOH and brine and dried over sodium sulfate before the solvent was evaporated in a vacuum. The crude residue was purified through silica gel column using the solvent mixture 50% EA:HEX as an eluent to afford Compound 21-1-B2 as a transparent oil (1.1 g, 3.0 mmol, 62%).

Step 2: Synthesis of tert-butyl (2-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)ethoxy)ethyl)carbamate (Compound 21-1-C)

A solution of Compound 21-1-B2 (20 mg, 0.056 mmol) in DMF (0.5 mL) was added at room temperature with Compound 21-1-A (Korean Patent No. 2128018) and potassium carbonate (14 mg, 0.10 mmol) and stirred at 70° C. for 16 hours. When the starting material was completely consumed as monitored by TLC, water was added to the reaction mixture. The white precipitate thus formed was filtered, washed thrice with water, and dissolved in DCM. The organic layer was dried over sodium sulfate and the organic solvent evaporated under a pressure. The crude residue was purified using 5% MeOH:DCM as an eluent to afford Compound 21-1-C as a white solid (23 mg, 0.039 mmol, 47%).

Step 3: Synthesis of N6-(2-(2-(2-aminoethoxy)ethyl)-1,2,3,4-tetrahydroisoquinolin-7-yl)-N3-(2,6-dimethylphenyl)-1-methyl-1H-pyrazolo[3,4-d]pyrimidine-3,6-diamine hydrochloride (Compound 21-1)

A solution of Compound 21-1-C (23 mg, 0.039 mmol) in DCM (1 mL) was added with 4 N HCl/dioxane (0.23 mL, 0.058 mmol) and the temperature was elevated from 0° C. to room temperature before stirring for one hour. The volatile material was evaporated to give a yellow solid. This solid was washed with diethylether and the volatile material was distilled in a vapor to afford Compound 21-1 as a yellow solid (18 mg, 0.037 mmol, 94%).

Step 4: Synthesis of N-(2-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)ethoxy)ethyl)-1-(2-(2,6-dioxopiperidin-3-yl)-1,3-dioxoisoindolin-5-yl)piperidine-4-carboxamide (Compound 21)

A solution of Compound 21-2 (WO 2020/162725) (8.8 mg, 0.022 mmol) in DMF (0.5 mL) was added at room temperature with EDCI (8.4 mg, 0.044 mmol), HOBt·H₂O (5.9 mg, 0.044 mmol), Compound 21-1 (12 mg, 0.022 mmol), and DIPEA (14 mg, 0.11 mmol) and stirred at 40° C. for 16 hours. The reaction mixture was quenched with water, followed by extraction with EtOAc. The organic layer was concentrated in a vacuum to give a crude material which was then purified by silica gel column chromatography to afford Compound 21 as a yellow solid (4 mg).

Compound 22. N-(15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-5-yl)amino)acetamide

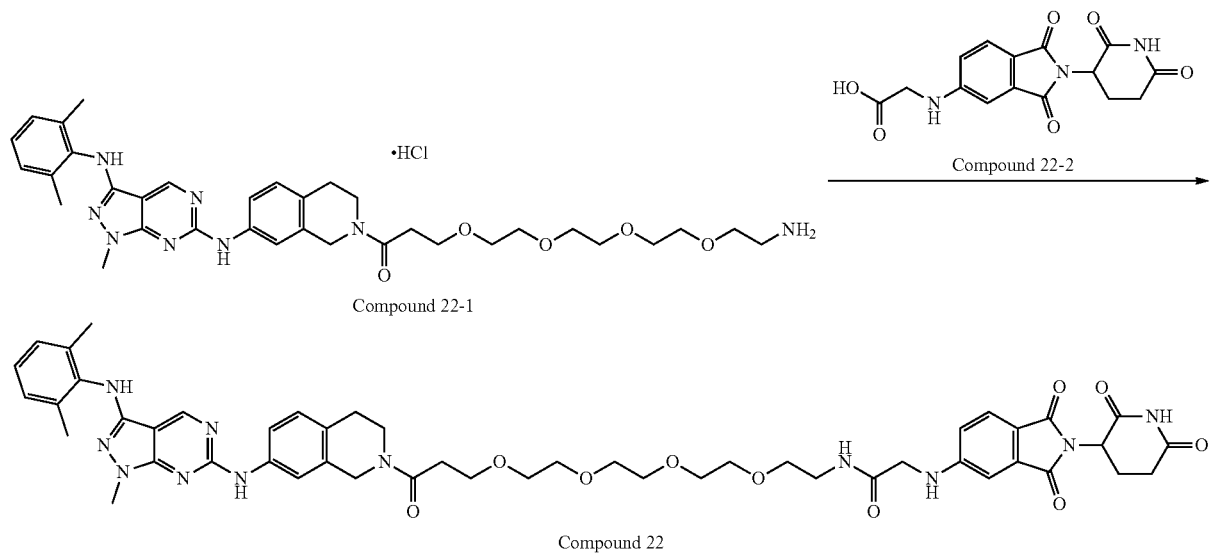

A solution of Compound 22-2 (WO 2020/162725) (4.6 mg, 0.014 mmol) in DMF (0.5 mL) was added at room temperature with EDCI (5.3 mg, 0.028 mmol), HOBt·H₂O (3.7 mg, 0.028 mmol), Compound 22-1 (identical to Compound 14-5) (10 mg, 0.014 mmol), and DIPEA (9.0 mg, 0.070 mmol) and stirred at 40° C. for 4 hours. The organic layer thus formed was concentrated in a vacuum to give a crude material which was then purified by silica gel column chromatography to afford Compound 22 as an off-white solid (10 mg).

Compound 23. 2-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)ethoxy)ethoxy)-N-(2-(2,6-dioxopiperidin-3-yl)-1,3-dioxoisoindolin-5-yl)acetamide

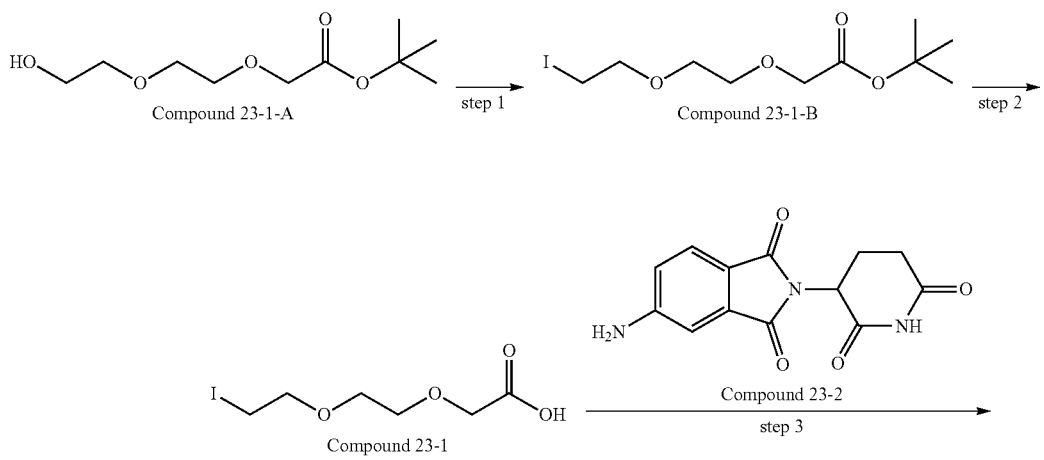

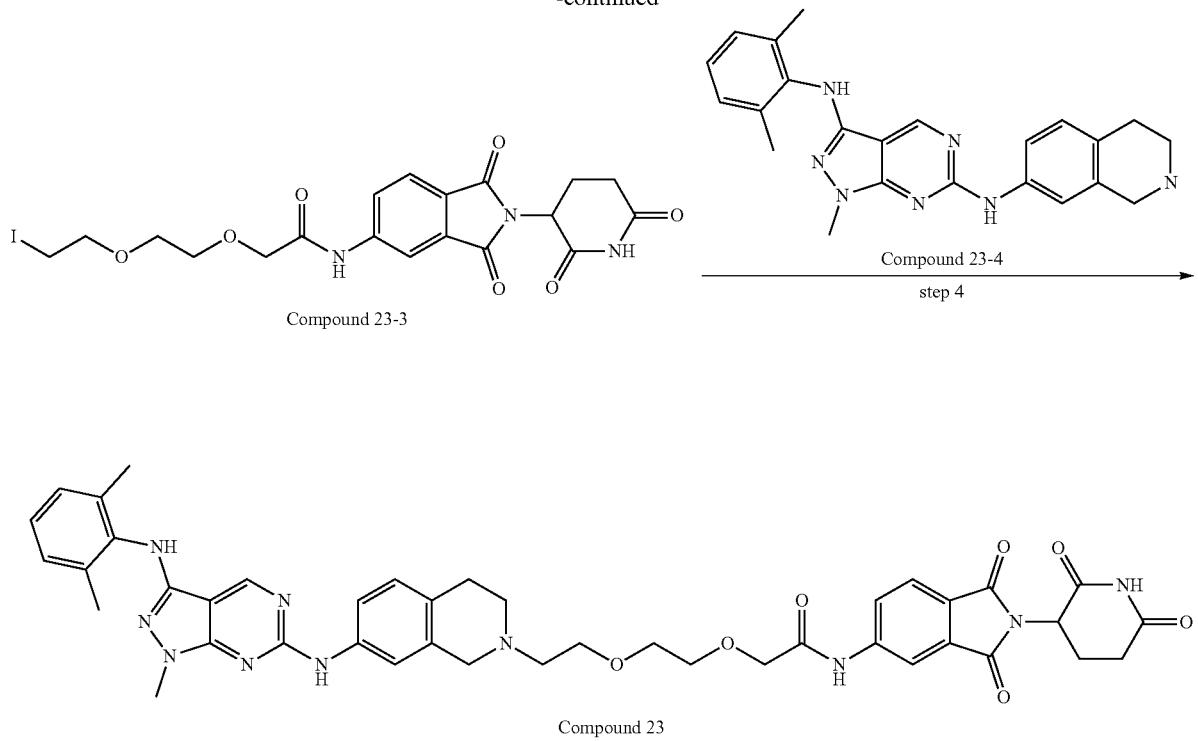

Compound 23

Step 1: Synthesis of tert-butyl 2-(2-(2-iodoethoxy) ethoxy)acetate (Compound 23-1-B)

To a solution of triphenylphosphene (70.8 mg, 0.27 mmol) in anhydrous DCM (3 mL) was added at 0° C. imidazole (22.46 mg, 0.33 mmol) which was stirred until it was dissolved. The addition of iodine (68.5 mg, 0.33 mmol) turned the solution yellow. A solution of Compound 23-1-A (BLDpharm, MFCD25959245) (tert-butyl 2-(2-(2-hydroxyethoxy)ethoxy)acetate; 50 mg, 0.22 mmol) in DCM (2 mL) was added before the mixture was stirred at 23° C. for 16 hours. When the reaction was completed as analyzed by TLC, the reaction mixture was diluted with DCM and washed with 1N HCl. The DCM layer was dried over sodium sulfate and the solvent was concentrated in a vacuum. The crude product was purified by silica gel flash chromatography using the 1:1 EA:HEX elution system to afford Compound 23-1-B as a white liquid (44 mg, 0.13 mmol).

Step 2: Synthesis of 2-(2-(2-iodoethoxy)ethoxy)acetic acid (Compound 23-1)

A solution of Compound 23-1-B (500 mg, 1.51 mmol) in DCM (5 mL) was added with TFA (5 mL) and stirred at room temperature to complete the reaction. Then, the solvent was evaporated to afford Compound 23-1 as a brown oil (410 mg, 1.49 mmol, 98%).

Step 3: Synthesis of N-(2-(2,6-dioxopiperidin-3-yl)-1,3-dioxoisoindolin-5-yl)-2-(2-(2-iodoethoxy)ethoxy)acetamide (Compound 23-3)

A solution of Compound 23-1 (250 mg, 0.0366 mmol) in anhydrous THE (10 mL) was added at 0° C. with thionyl chloride (342 mg, 2.86 mmol) and stirred at 60° C. for 2 hours to form hydrochloride. After formation of hydrochloride, the solvent was evaporated, together with excess thionyl chloride, in a vacuum. The residue was dissolved in THE and added with Compound 23-2 (WO 2019/148055) (100 mg, 0.366 mmol). The mixture was heated at 80° C. for 4 hours until the reaction was completed. THE was evaporated in a vacuum, and the residue was dissolved in ethylacetate and washed with sodium bicarbonate. The organic layer was concentrated in a vacuum and the crude material was purified by MPLC to afford Compound 23-3 as a white solid (112 mg).

Step 4: Synthesis of 2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethoxy)-N-(2-(2,6-dioxopiperidin-3-yl)-1,3-dioxoisoindolin-5-yl)acetamide (Compound 23)

A solution of Compound 23-4 (Korean Patent No. 2128018) (15 mg, 0.037 mmol) was added at 50° C. with Compound 23-3 (20 mg, 0.037 mmol) and TEA (15 mg, 0.11 mmol) and stirred 50° C. for 16 hours. The reaction mixture was added with water. The white precipitate thus formed was filtered and dissolved in DCM. The organic layer was concentrated in a vacuum to give a crude material which was then purified by MPLC to afford Compound 23 as a yellow solid (9 mg).

Compound 24. N-(2-(2-(7-((3-((2,6-Dimethylphenyl)amino)-1-methyl-1H-pyrazolo[3,4-d]pyrimidin-6-yl)amino)-3,4-dihydroisoquinolin-2(1H)-yl)ethoxy)ethyl)-1-(2-(2,6-dioxopiperidin-3-yl)-1,3-dioxoisoindolin-4-yl)piperidine-4-carboxamide
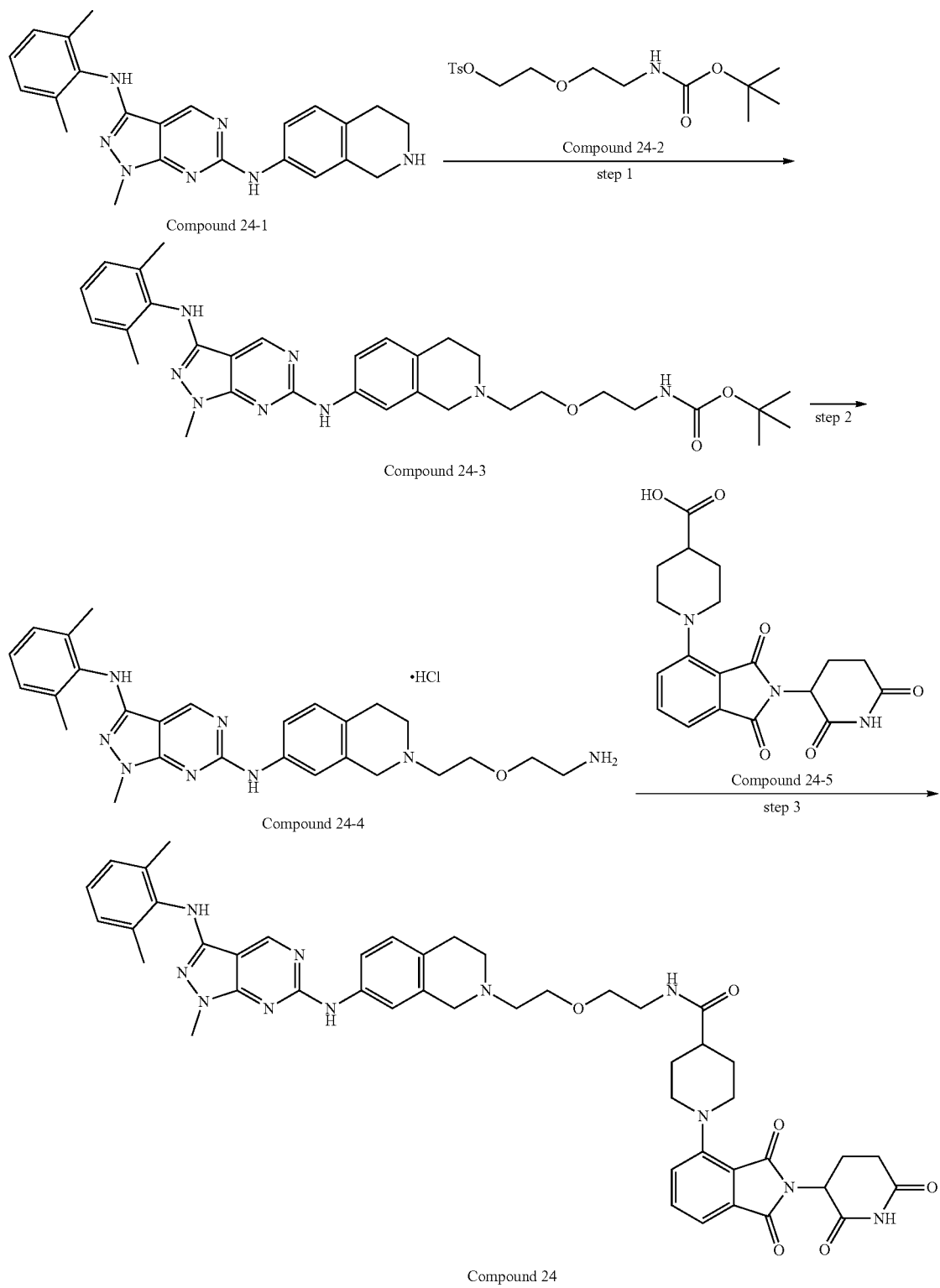

Step 1: Synthesis of tert-butyl (2-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)ethoxy)ethyl)carbamate (Compound 24-3)

A solution of Compound 24-2 (identical to Compound 20-2) (99.0 mg, 0.275 mmol) in DMF (0.5 mL) was added at room temperature with Compound 24-1 (Korean Patent No. 2128018) (100 mg, 0.250 mmol) and potassium carbonate (39.1 mg, 0.500 mmol) and stirred at 70° C. for 16 hours. After completion of the reaction, the reaction mixture was added with water. The white precipitate thus formed was filtered and dissolved in DCM. The organic layer was concentrated in a vacuum to give a crude material which was then purified by MPLC to afford Compound 24-3 as an off-white solid (89 mg).

Step 2: Synthesis of N6-(2-(2-(2-aminoethoxy)ethyl)-1,2,3,4-tetrahydroisoquinolin-7-yl)-N3-(2,6-dimethylphenyl)-1-methyl-1H-pyrazolo[3,4-d]pyrimidine-3,6-diamine hydrochloride (Compound 24-4)

A solution of Compound 24-3 (23 mg, 0.039 mmol) in DCM (1 mL) was added at room temperature with 4 N—HCl/dioxane (0.050 mL, 0.20 mmol). The temperature was elevated from 0° C. to room temperature before stirring for 1 hour. The volatile material was evaporated and the yellow solid thus formed was washed with diethylether. The volatile material was evaporated in a vacuum to afford Compound 24-4 as a yellow solid (80 mg).

Step 3: Synthesis of N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-4-yl)piperidine-4-carboxamide (Compound 24)

A solution of Compound 24-5 (WO 2020/162725) (6.2 mg, 0.028 mmol) in DMF (0.5 mL) was added at room temperature with EDCI (11 mg, 0.056 mmol), HOBt·H₂O (7.5 mg, 0.056 mmol), Compound 24-4 (15 mg, 0.028 mmol), and DIPEA (18 mg, 0.14 mmol). The mixture was stirred at room temperature for 16 hours. The reaction mixture was quenched with ice and the precipitate thus formed was washed with water and dissolved in DCM. The organic layer was concentrated in a vacuum and the crude material thus obtained was purified by silica gel column chromatography to afford Compound 24 as a yellow solid (10 mg).

Compound 25. N-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-((2-(2,6-dioxopiperidin-3-yl)-1,3-dioxoisoindolin-5-yl)oxy)acetamide

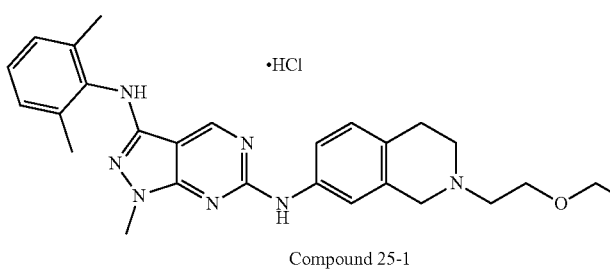

Compound 25-1

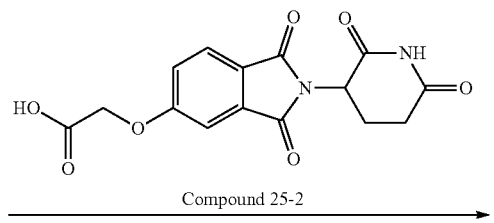

Compound 25-2

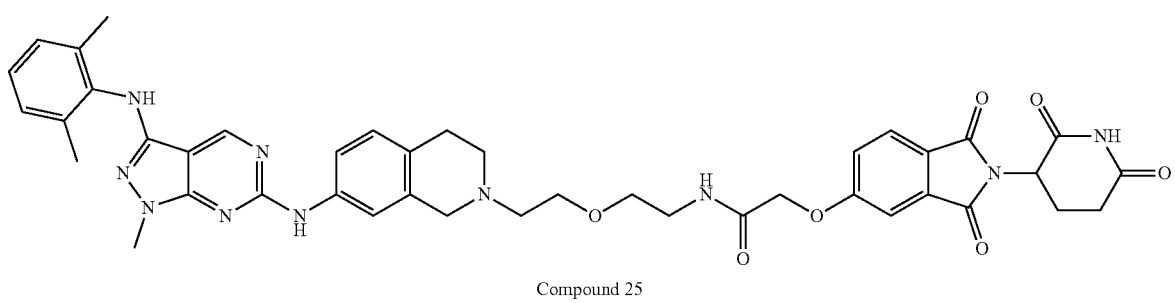

Compound 25

A solution of Compound 25-2 (WO 2020/160198) (6.0 mg, 0.018 mmol) in DMF (0.5 mL) was added at room temperature with EDCI (7.2 mg, 0.038 mmol), HOBt·H₂O (5.1 mg, 0.038 mmol), Compound 25-1 (identical to Compound 21-1) (10 mg, 0.019 mmol), and DIPEA (12 mg, 0.095 mmol) and stirred at room temperature for 4 hours. The reaction mixture was quenched with water, followed by extraction with EtOAc. The organic layer was concentrated in a vacuum and the crude material thus obtained was purified by silica gel column chromatography to afford Compound 25 as an off-white solid (4.0 mg).

Compound 26. 5-(4-((R)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl)isoindoline-1,3-dione

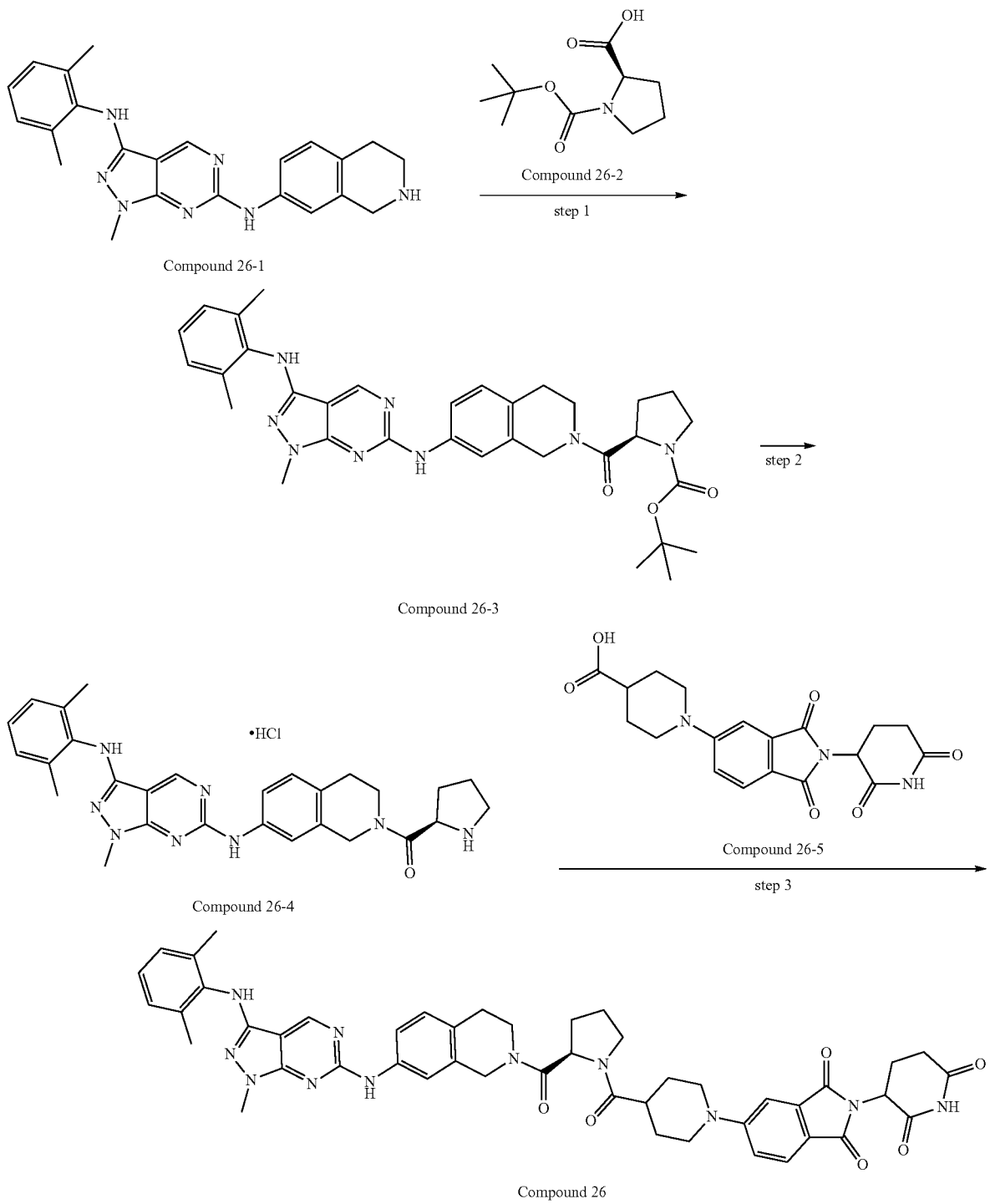

Step 1: Synthesis of N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl)piperazin-1-yl)acetamide (Compound 26-3)

A solution of Compound 26-2 (Sigma Aldrich, 483818) (26 mg, 0.12 mmol) in DMF (0.5 mL) was added at room temperature with EDCI (47 mg, 0.24 mmol), HOBt·H$_2$O (33 mg, 0.24 mmol), Compound 26-1 (Korean Patent No. 2128018) (50 mg, 0.12 mmol), and DIPEA (78 mg, 0.60 mmol) and stirred at 40° C. for 16 hours. The reaction mixture was quenched with water, and the precipitate thus formed was filtered and washed four times with water. The precipitate was dissolved in DCM. The organic layer was concentrated in a vacuum and the crude material thus obtained was purified by silica gel column chromatography to afford Compound 26-3 as a yellow solid (70 mg).

Step 2: Synthesis of N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl)piperazin-1-yl)acetamide hydrochloride (Compound 26-4)

A solution of Compound 26-3 (23 mg, 0.039 mmol) in DCM (1 mL) was added with 4 N—HCl/dioxane (0.050 mL, 0.20 mmol) and stirred at room temperature for 1 hour. The volatile material was evaporated to give a yellow solid which was then washed with diethylether. Evaporation of the volatile material afforded Compound 26-4 as a yellow solid (50 mg).

Step 3: Synthesis of 5-(4-((R)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl)isoindoline-1,3-dione (Compound 26)

A solution of Compound 26-5 (WO 2020/162725) (4 mg, 0.009 mmol) in DMF (0.5 mL) was added at room temperature with 50% T3P/EA (17 mg, 0.027 mmol), Compound 26-4 (10 mg, 0.018 mmol), and TEA (4.5 mg, 0.14 mmol. The mixture was stirred at room temperature for 16 hours until the reaction was completed. The reaction mixture was added with water, followed by extraction with MC. The organic layer was washed with water and brine and concentrated in a vacuum to give a crude product which was then purified by MPLC to afford Compound 26 as an off-white solid (1 mg).

Compound 27. N-(2-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-5-yl)azetidine-3-carboxamide

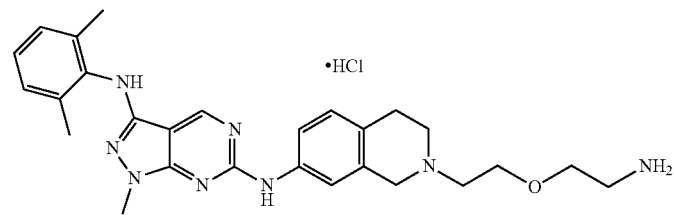

Compound 27-1

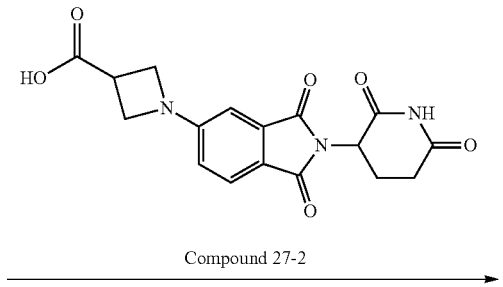

Compound 27-2

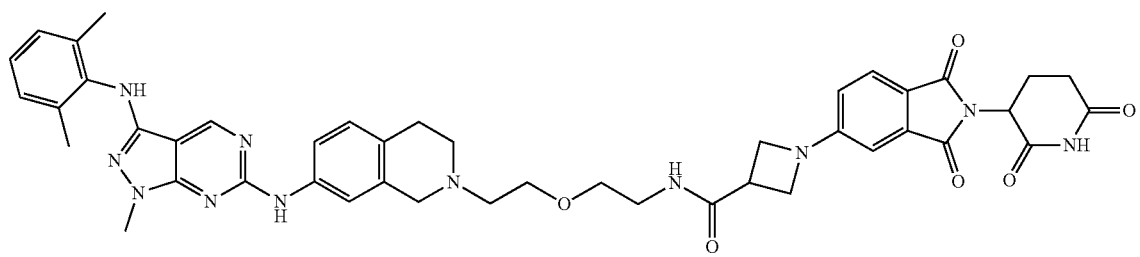

Compound 27

A solution of Compound 27-2 (WO 2020/038415) (6.7 mg, 0.019 mmol) in DMF (0.5 mL) was added at room temperature with 50% T3P/EA (36 mg, 0.057 mmol), Compound 27-1 (identical to Compound 21-1) (10 mg, 0.019 mmol), and TEA (12 mg, 0.095 mmol) and stirred at room temperature for 2 hours. The reaction mixture was added with water, subjected to extraction with MC, and washed with water and brine. The organic layer was concentrated in a vacuum to give a crude material which was then purified by MPLC to afford Compound 27 as a green solid (1.7 mg).

Compound 28. 5-(4-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-2-(2,6-dioxopiperidin-3-yl)isoindoline-1,3-dione

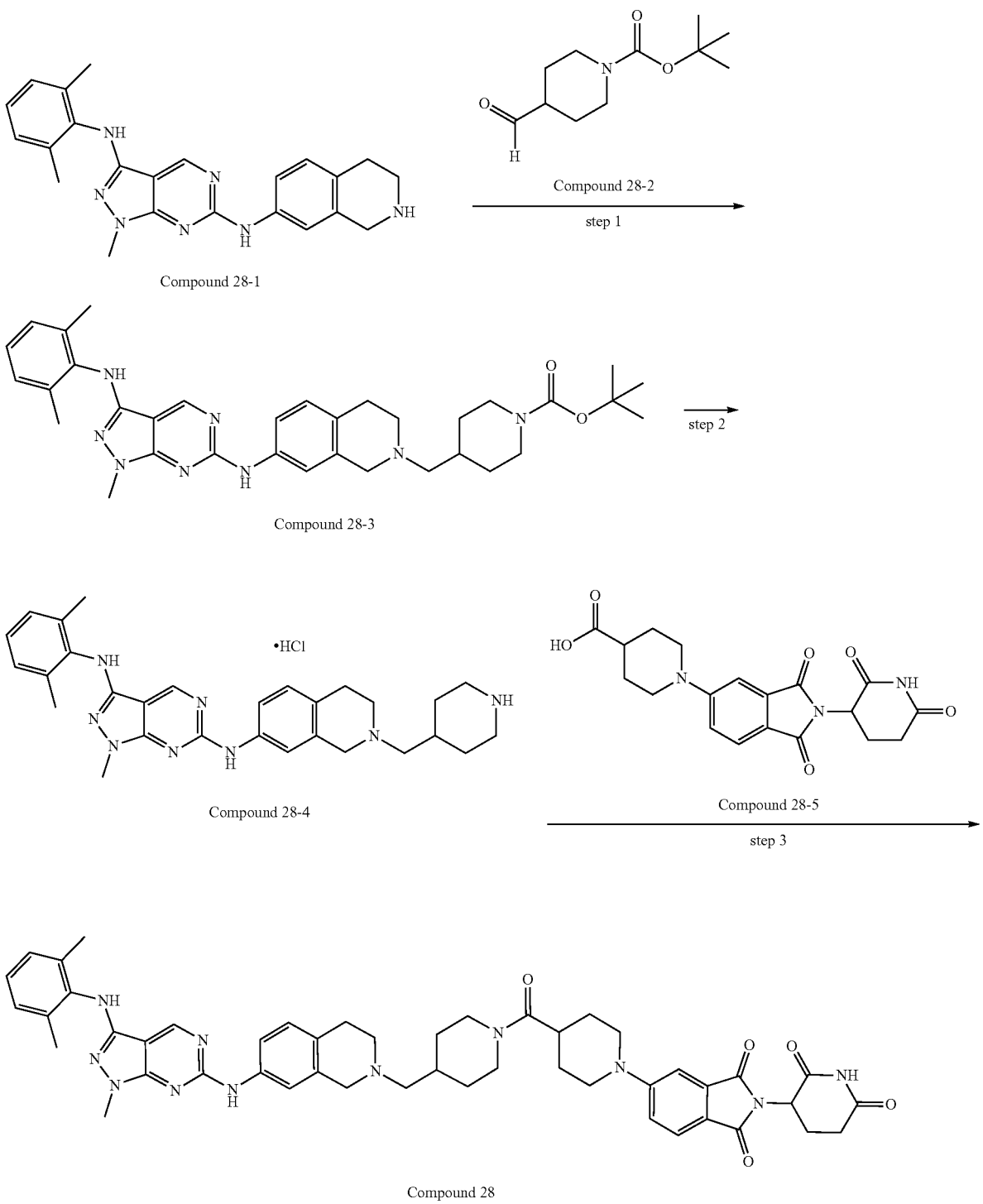

Step 1: Synthesis of tert-butyl 4-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidine-1-carboxylate (Compound 28-3)

A solution of Compound 28-2 (TCI, B3873) (1-Boc-piperidine-4-carboxaldehyde; 120 mg, 0.56 mmol) in MeOH (4.0 mL) was added with Compound 28-1 (Korean Patent No. 2128018) (200 mg, 0.52 mmol) and stirred at room temperature for 1 hour in the presence of AcOH (0.5 mL) as a catalyst. Then, sodium cyanoborohydride (48 mg, 0.76 mmol) was added before stirring was conducted at room temperature for 1 hour until the reaction was completed. MeOH was evaporated. The reaction was quenched by adding water and EA. The aqueous layer was subjected to extraction with EA. Then, the organic layer was concentrated in a vacuum to give a crude material which was then purified by silica gel column chromatography to afford Compound 28-3 as a green solid (175.8 mg).

Step 2: Synthesis of N3-(2,6-dimethylphenyl)-1-methyl-N6-(2-(piperidin-4-ylmethyl)-1,2,3,4-tetrahydroisoquinolin-7-yl)-1H-pyrazolo[3,4-d]pyrimidine-3,6-diamine hydrochloride (Compound 28-4)

A solution of Compound 28-3 (159 mg, 0.27 mmol) in DCM (10.0 mL) was added with 4 N—HCl/dioxane (0.13 mL, 0.054 mmol) and stirred at room temperature for 3 hours. After completion of the reaction, the solvent was evaporated in a vacuum to afford Compound 28-4 as a yellow solid (137.6 mg).

Step 3: Synthesis of 5-(4-(4-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidine-1-carbonyl)piperidin-1-yl)-2-(2,6-dioxopiperidin-3-yl)isoindoline-1,3-dione (Compound 28)

A solution of Compound 28-5 (WO 2020/162725) (7.0 mg, 0.018 mmol) in DMF (0.5 mL) was added at room temperature with HATU (21 mg, 0.056 mmol), Compound 28-4 (10 mg, 0.018 mmol), and TEA (10 mg, 0.090 mmol). The mixture was stirred at room temperature for 16 hours. The reaction mixture was added with water, subjected to extraction with EA, and washed with water and brine. The organic layer was concentrated in a vacuum to give a crude material which was then purified by MPLC to afford Compound 28 as an off-white solid (3.5 mg).

Compound 29. 5-(4-((7-((3-((2,6-Dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-2-(2,6-dioxopiperidin-3-yl)isoindoline-1,3-dione

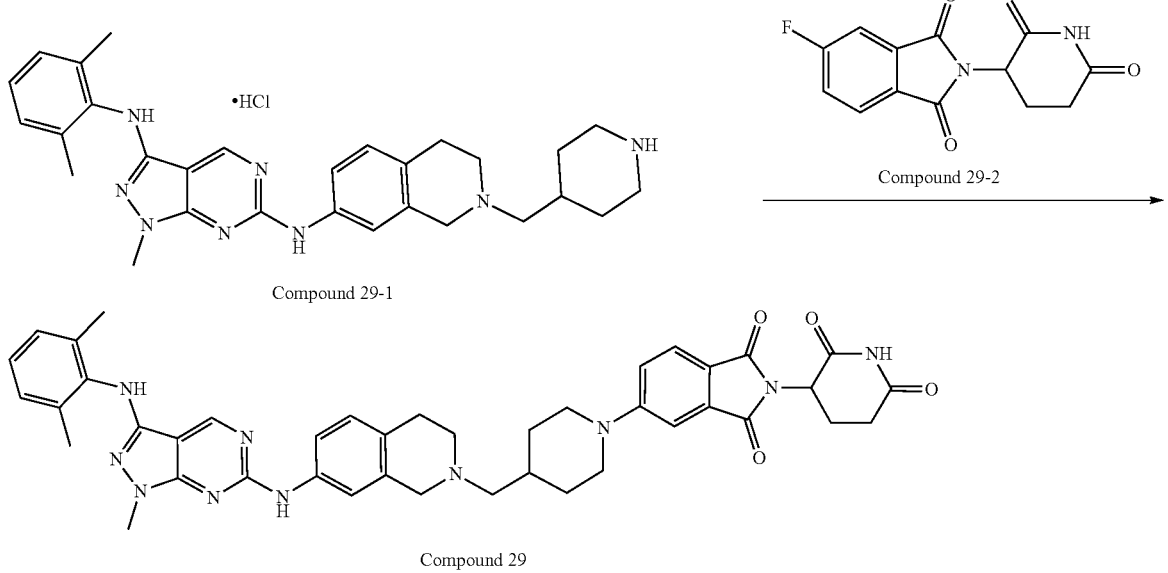

Compound 29-2 (Combi-Blocks, HD-3240) (167 mg, 0.604 mmol) in DMSO (5 mL) was added at room temperature with Compound 29-1 (identical to Compound 28-4) (300 mg, 0.604 mmol) and DIPEA (234 mg, 1.18 mmol). The mixture was stirred at 90° C. for 6 hours. The reaction mixture was added with water, subjected to extraction with EA, and washed with water and brine. Then, the organic layer was concentrated in a vacuum to give a crude material which was then purified by MPLC to afford Compound 29 as a fluorescent green solid (304 mg).

Compound 30. 5-(2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethoxy)-2-(2,6-dioxopiperidin-3-yl)isoindoline-1,3-dione

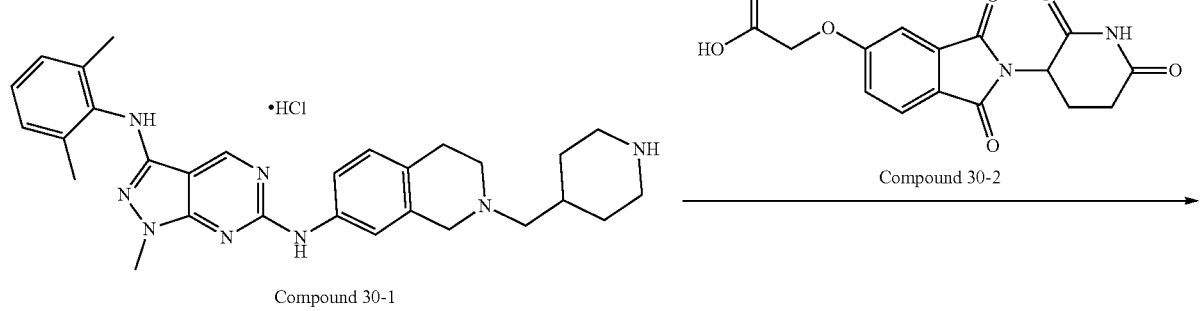

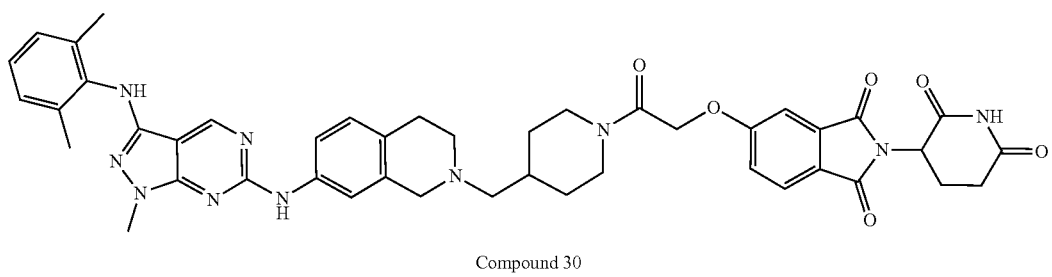

Compound 30

A solution of Compound 30-2 (WO 2020/160198) (6.0 mg, 0.018 mmol) in DMF (0.5 mL) was added at room temperature with HATU (21 mg, 0.056 mmol), Compound 30-1 (identical to Compound 29-1) (10 mg, 0.018 mmol), and TEA (10 mg, 0.090 mol). The mixture was stirred at room temperature for 16 hours. When the product was formed as analyzed by TLC, the reaction mixture was added with water, subjected to extraction with EA (15 mL×3), and washed with water (3×) and brine. The pooled organic layer was dried over sodium sulfate and purified by MPLC using 10% MeOH/MC to afford Compound 30 as a white solid (3.5 mg, 0.0040 mmol, 22%).

Compound 31. 5-(4-(2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)piperazin-1-yl)-2-(2,6-dioxopiperidin-3-yl)isoindoline-1,3-dione

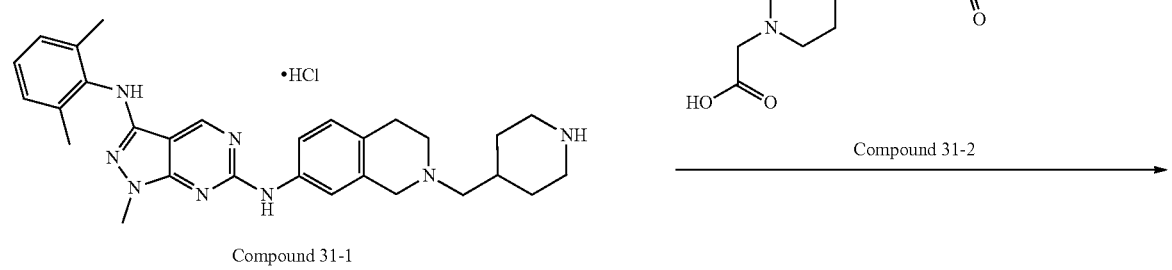

-continued

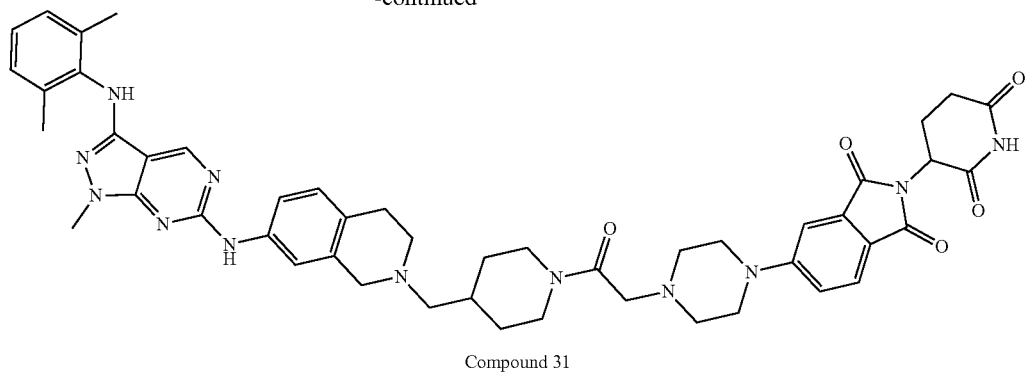

Compound 31

A solution of Compound 31-2 (WO 2020/160193) (2-(4-(2-(2,6-dioxopiperidin-3-yl)-1,3-dioxoisoindolin-5-yl)piperazin-1-yl)acetic acid; 8.4 mg, 0.021 mmol) in DMF (0.5 mL) was added with HATU (28.8 mg, 0.076 mmol) and TEA (16.1 mg, 0.16 mmol) and stirred for 10 minutes. Finally, after addition of Compound 31-1 (identical to Compound 29-1) (10 mg, 0.019 mmol), stirring was conducted at 40° C. for 16 hours. After completion of the reaction, the reaction mixture was diluted with DCM and washed water. The organic layer was washed with brine and concentrated in a vacuum to give a crude material which was then purified by silica gel column chromatography to afford Compound 31 as a yellow solid (4.0 mg).

Compound 32. 5-(4-(2-((R)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)piperazin-1-yl)-2-(2,6-dioxopiperidin-3-yl)isoindoline-1,3-dione A solution of Compound 32-2 (WO 2020/160193) (11 mg, 0.028 mmol) in DMF (0.5 mL) was added at room temperature with 50% T3P/EA (34 mg, 0.034 mmol), Compound 32-1 (identical to Compound 26-4) (10 mg, 0.018 mmol), and TEA (14 mg, 0.14 mmol). The mixture was stirred at room temperature until the reaction was completed. When the product was formed as analyzed by TLC, the reaction mixture was added with water, subjected to extraction with MC (15 mL×3), and washed with water (3×) and brine. The pooled organic layer was dried over sodium sulfate and purified by MPLC using 10% MeOH/MC to afford Compound 32 as an off-white solid (2.0 mg, 0.002 mmol, 12%).

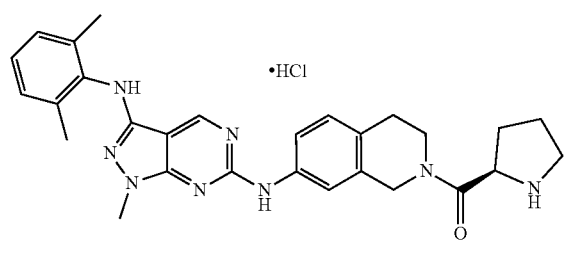

Compound 32-1

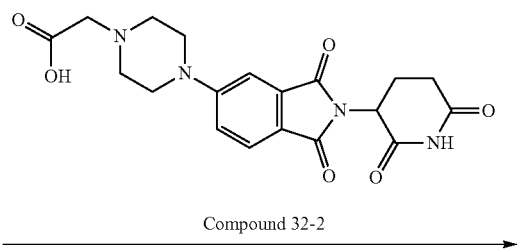

Compound 32-2

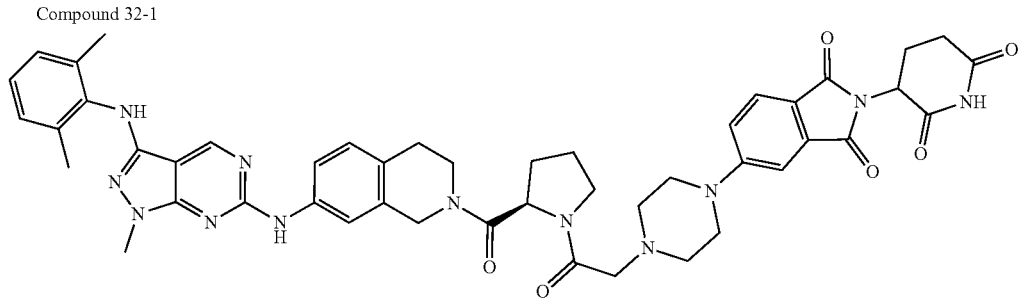

Compound 32

Compound 33. 5-(4-(2-((S)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)piperazin-1-yl)-2-(2,6-dioxopiperidin-3-yl)isoindoline-1,3-dione
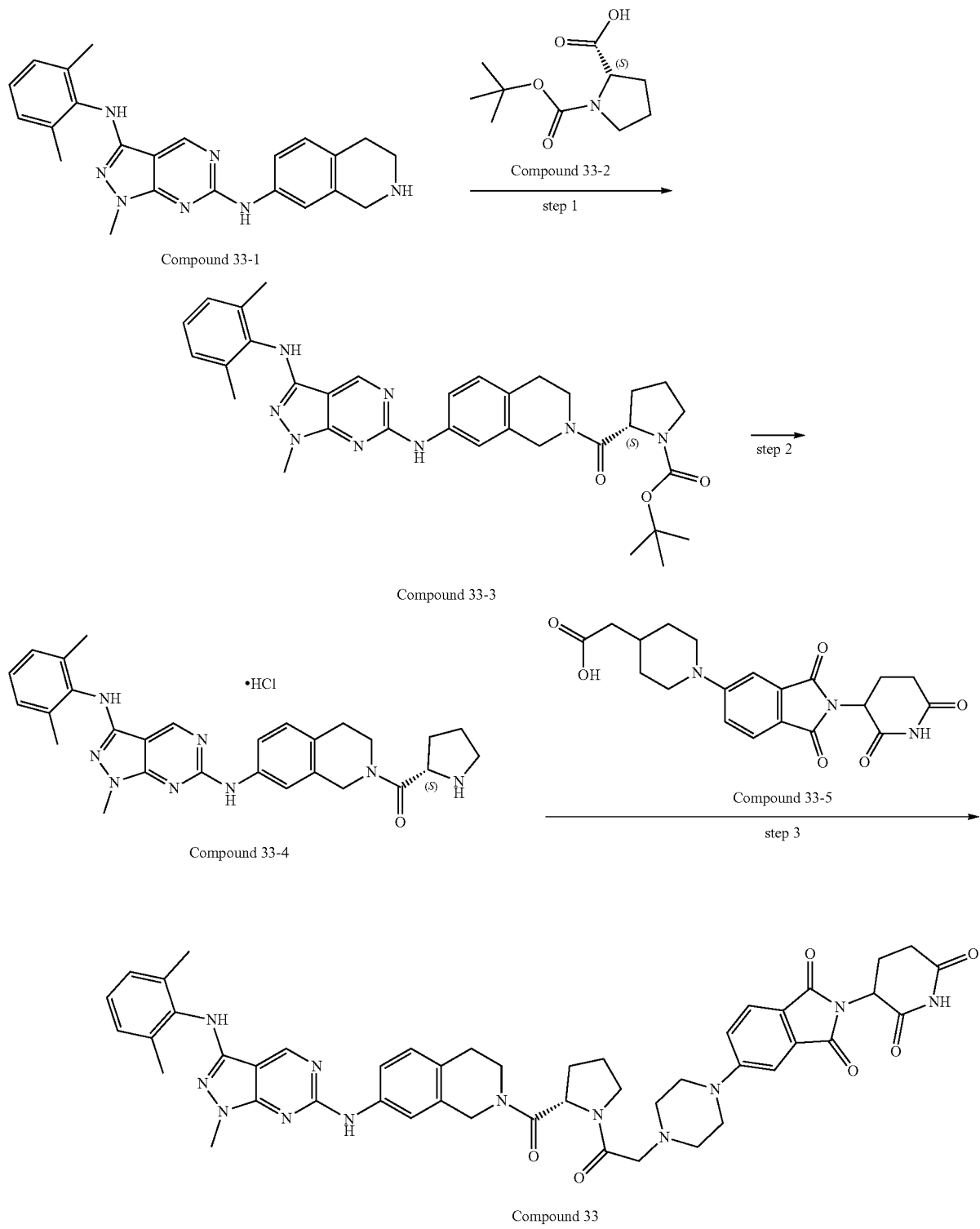

Step 1: Synthesis of N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl)piperazin-1-yl)acetamide (Compound 33-3)

A solution of Compound 33-2 (TCI, B1188) (26 mg, 0.12 mmol) in DMF (0.5 mL) was added at room temperature with EDCI (47 mg, 0.24 mmol), HOBt·H$_2$O (33 mg, 0.24 mmol), Compound 33-1 (Korean Patent No. 2128018) (50 mg, 0.12 mmol), and DIPEA (78 mg, 0.60 mmol) and stirred at 40° C. for 2 hours. The reaction mixture was quenched with water and the precipitate thus formed was filtered and washed four times with water. The precipitate was dissolved in DCM. The organic layer was concentrated in a vacuum to give a crude material which was then purified by silica gel column chromatography to afford Compound 33-3 as a yellow solid (70 mg).

Step 2: Synthesis of N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl)piperazin-1-yl)acetamide hydrochloride (Compound 33-4)

A solution of Compound 33-3 (60 mg, 0.10 mmol) in DCM (1 mL) was added with 4 N—HCl/dioxane (0.050 mL, 0.20 mmol) and stirred at room temperature for 3 hours. The volatile material was evaporated to give a yellow solid which was then washed with diethyl ether. The volatile material was distilled under a vapor to afford Compound 33-4 as a yellow solid (44 mg).

Step 3: Synthesis of 5-(4-(2-((S)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)piperazin-1-yl)-2-(2,6-dioxopiperidin-3-yl)isoindoline-1,3-dione (Compound 33)

A solution of Compound 33-5 (WO 2020/160193) (6.9 mg, 0.018 mmol) in DMF (0.5 mL) was added at room temperature with 50% T3P/EA (34 mg, 0.034 mmol), Compound 33-4 (10 mg, 0.018 mmol), and TEA (14 mg, 0.14 mmol). The mixture was stirred at room temperature for 16 hours until the reaction was completed. The reaction mixture was added with water, subjected to extraction with MC, and washed with water and brine. The organic layer was concentrated in a vacuum to give a crude material which was then purified by MPLC to afford Compound 33 as an off-white solid (5.4 mg).

Compound 34. 5-(2-((S)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethoxy)-2-(2,6-dioxopiperidin-3-yl)isoindoline-1,3-dione

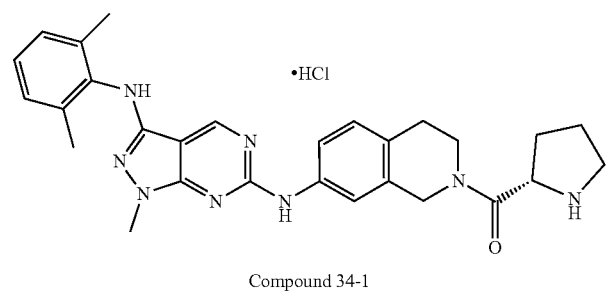

Compound 34-1

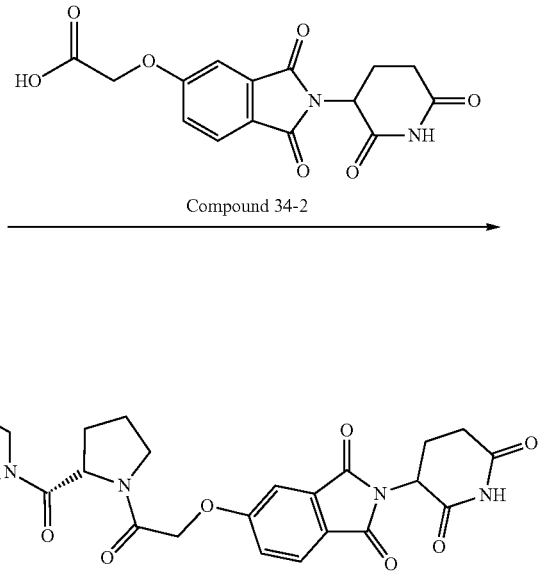

Compound 34-2

Compound 34

A solution of Compound 34-2 (WO 2020/160198) (6.0 mg, 0.018 mmol) in DMF (0.5 mL) was added at room temperature with 50% T3P/EA (34 mg, 0.034 mmol), Compound 34-1 (identical to Compound 33-4) (10 mg, 0.018 mmol) and TEA (14 mg, 0.14 mmol). The mixture was stirred at room temperature for 16 hours until the reaction was completed. The reaction mixture was added with water, subjected to extraction with MC, and washed with water and brine. The organic layer was concentrated in a vacuum to give a crude material which was then purified by MPLC to afford Compound 34 as an off-white solid (2 mg).

Compound 35. 5-((2-((S)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)amino)-2-(2,6-dioxopiperidin-3-yl)isoindoline-1,3-dione

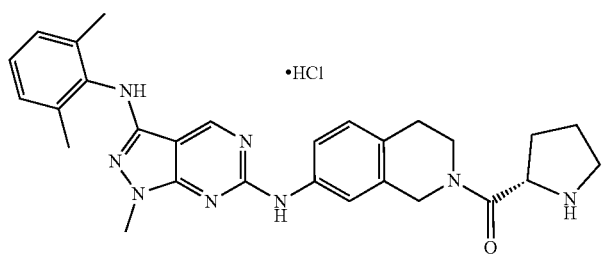

Compound 35-1

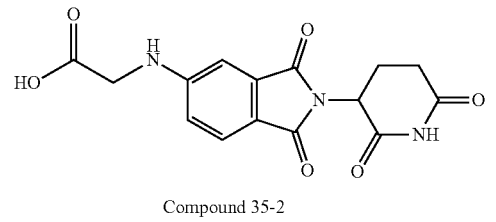

Compound 35-2

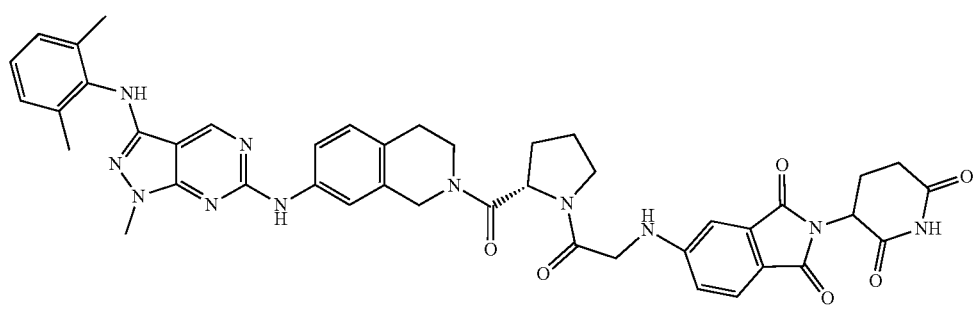

Compound 35

A solution of Compound 35-2 (WO 2020/162725) (6.0 mg, 0.018 mmol) in DMF (0.5 mL) was added at room temperature with 50% T3P/EA (34 mg, 0.034 mmol), Compound 35-1 (identical to Compound 33-4) (10 mg, 0.018 mmol) and TEA (14 mg, 0.14 mmol). The mixture was stirred at room temperature for 16 hours until the reaction was completed. The reaction mixture was added with water, subjected to extraction with MC, and washed with water and brine. The organic layer was concentrated to give a crude product which was then purified by MPLC to afford Compound 35 as an off-white solid (4.4 mg).

Compound 36. 5-((2-(4-((7-((3-((2,6-Dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-2-oxoethyl)amino)-2-(2,6-dioxopiperidin-3-yl)isoindoline-1,3-dione

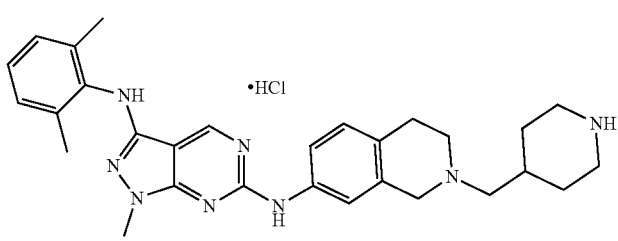

Compound 36-1

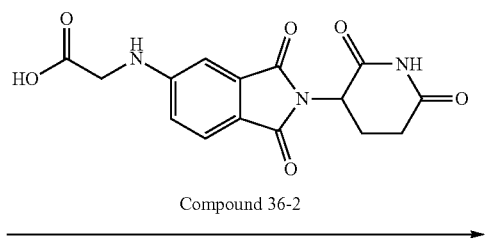

Compound 36-2

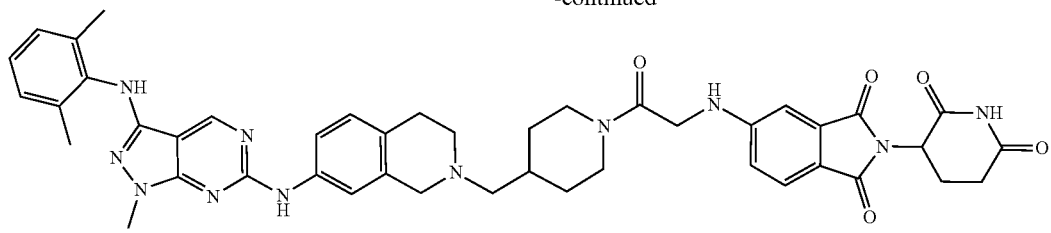

Compound 36

A solution of Compound 36-2 (WO 2020/162725) (6.0 mg, 0.018 mmol) in DMF (0.5 mL) was added at room temperature with 50% T3P/EA (35 mg, 0.056 mmol), Compound 36-1 (identical to Compound 28-4) (10 mg, 0.018 mmol) and TEA (10 mg, 0.090 mmol). The mixture was stirred at room temperature for 16 hours until the reaction was completed. The reaction mixture was added with water, subjected to extraction with MC, and washed with water and brine. The organic layer was concentrated in a vacuum to give a crude material which was then purified by MPLC to afford Compound 36 as an off-white solid (2 mg).

Compound 37. 3-(6-(4-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-one

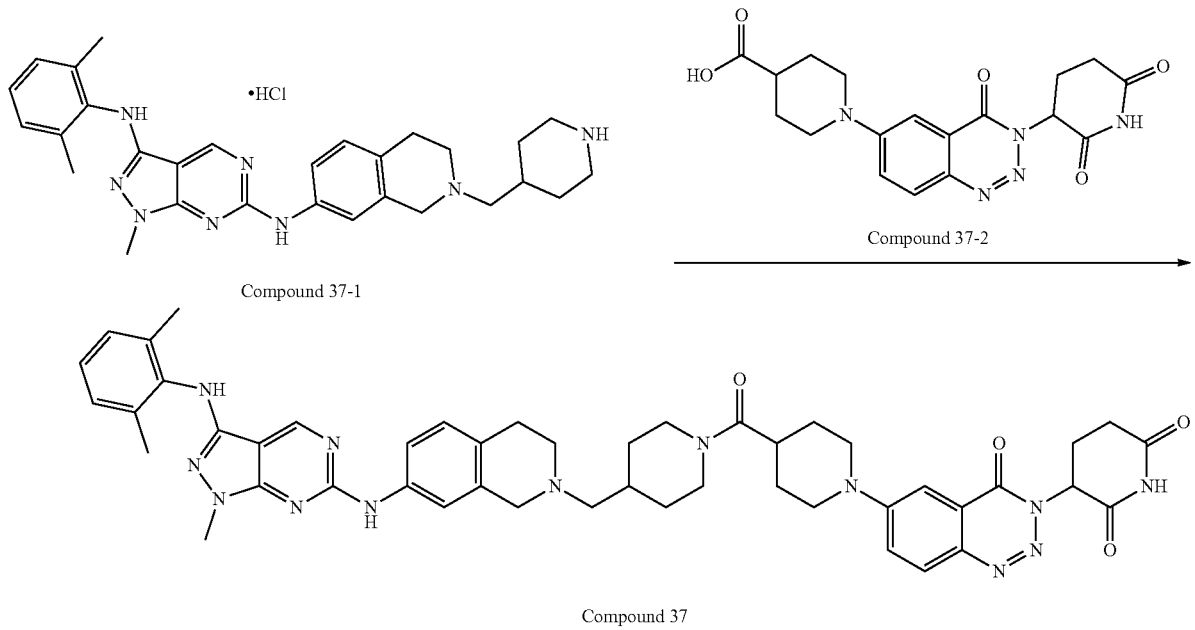

Compound 37

A solution of Compound 37-2 (WO 2020/162725) (6.5 mg, 0.018 mmol) in DMF (0.5 mL) was added at room temperature with 50% T3P/EA (35 mg, 0.056 mmol), Compound 37-1 (identical to Compound 28-4) (10 mg, 0.018 mmol), and TEA (10 mg, 0.090 mmol). The mixture was stirred at room temperature for 16 hours until the reaction was completed. The reaction mixture was added with water, subjected to extraction with MC, and washed with water and brine. The organic layer was concentrated in a vacuum to give a crude material which was then purified by silica gel column chromatography to afford Compound 37 as an off-white solid (6 mg).

Compound 38. 1-(5-(4-((7-((3-((2,6-Dimethylphenyl))amino)-1-methyl-1H-pyrazolo[3,4-d]pyrimidin-6-yl)amino)-3,4-dihydroisoquinolin-2 (1H)-yl) methyl)piperidine-1-carbonyl)-2-methoxyphenyl) dihydropyrimidine-2,4 (1H,3H)-dione

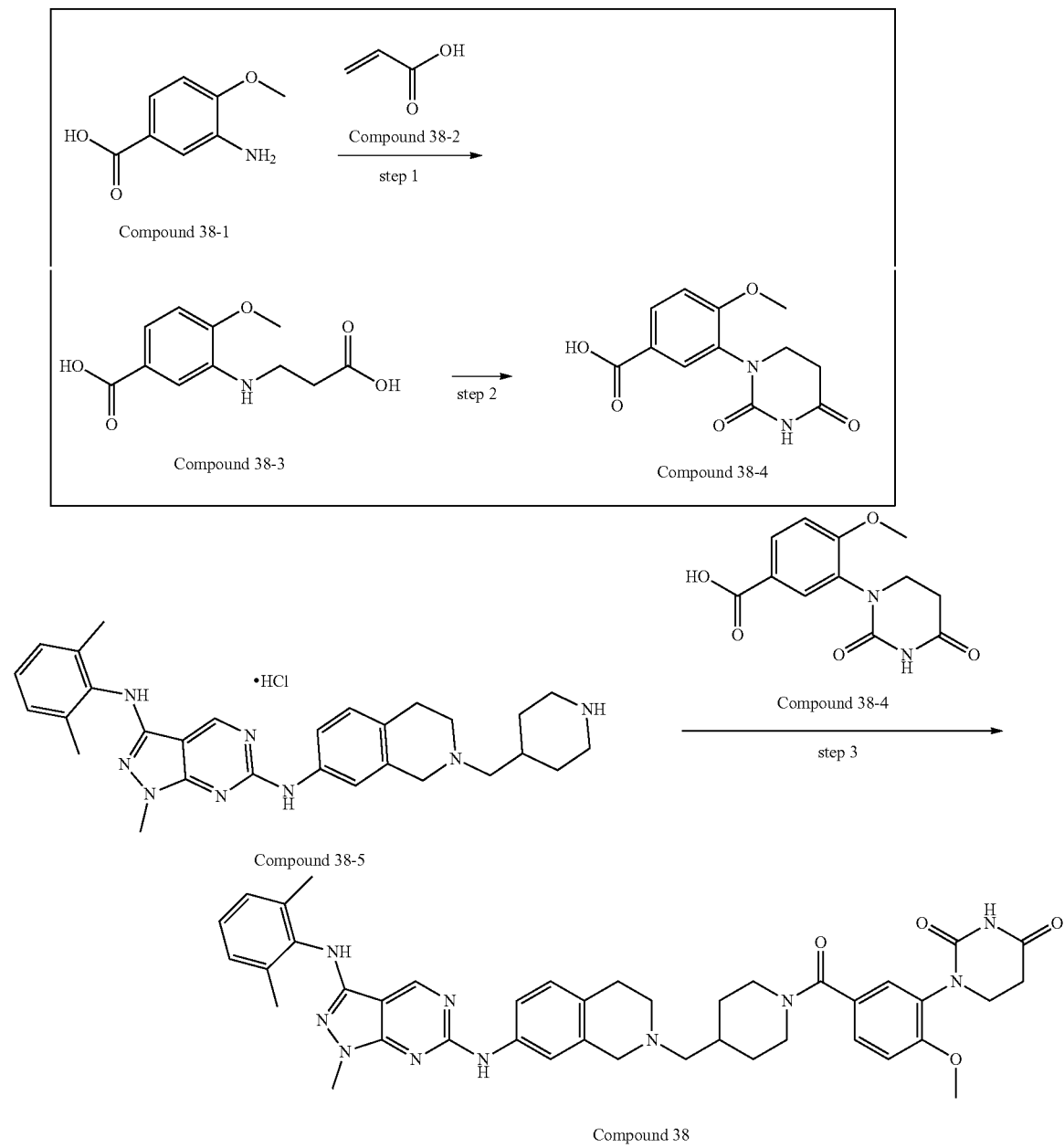

Step 1: Synthesis of 3-((2-carboxyethyl)amino)-4-methoxybenzoic acid (Compound 38-3)

A suspension of Compound 38-1 (TCI, A1955) (3-amino-4-methoxybenzoic acid, 5.0 g, 29 mmol) in Compound 38-2 (TCI, A0141) (acrylic acid, 8.05 mL, 117 mmol) was heated to 100° C. and stirred for 10 minutes. Thereafter, while the stirring was slow down to 150 rpm, the reaction was maintained at 100° C. for 3 hours. When the reaction was completed as analyzed by TLC, the reaction mixture was quenched to give a gray suspension to be used in the next step.

Step 2: Synthesis of 3-(2,4-dioxotetrahydropyrimidin-1 (2H)-yl)-4-methoxybenzoic acid (Compound 38-4)

To the residue of Compound 38-3 was added acetic acid (35 mL) and urea (11.3 g, 188 mmol) before heating at 100°

C. for 12 hours. When the reaction was completed under the monitoring of TLC, the reaction mixture was quenched and added with 1 N—HCl (150 mL) and water (50 mL). The reaction mass was maintained overnight at 5° C. The temperature of the reaction mass was elevated to room temperature and filtered. The filtered cake was decomposed with 0.05 N—HCl (50 mL) and the solid was dried to afford Compound 38-4 as a purple solid (3.0 g).

Step 3: Synthesis of 1-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)-2-methoxyphenyl) dihydropyrimidine-2,4 (1H,3H)-dione (Compound 38)

A solution of Compound 38-4 (4.7 mg, 0.018 mmol) in DMF (0.5 mL) was added at room temperature with HATU (21 mg, 0.056 mmol), Compound 38-5 (identical to Compound 28-4) (10 mg, 0.018 mmol), and TEA (10 mg, 0.090 mmol). The mixture was stirred at room temperature for 16 hours. The reaction mixture was added with water, subjected to extraction with EA, and washed with water and brine. Then, the organic layer was concentrated in a vacuum to give a crude material which was then purified by MPLC to afford Compound 38 as an off-white solid (2.5 mg).

Compound 39. 5-(4-(2-(3-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethyl)piperazin-1-yl)-2-(2,6-dioxopiperidin-3-yl)isoindoline-1,3-dione

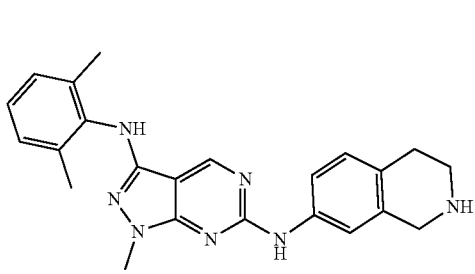

Compound 39-1

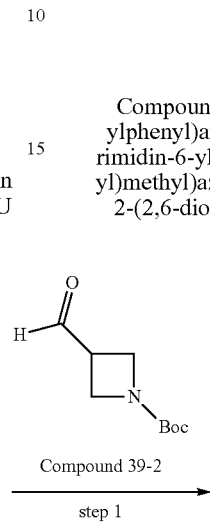

Compound 39-2 step 1

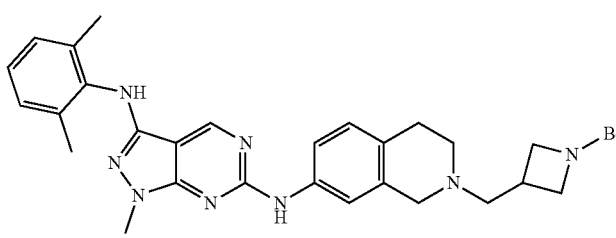

Compound 39-3 step 2

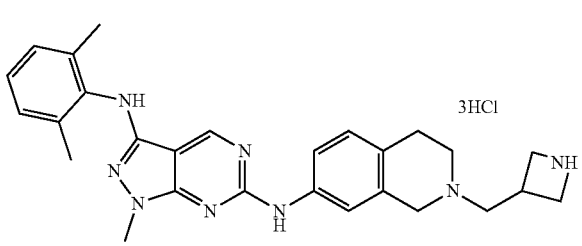

Compound 39-4

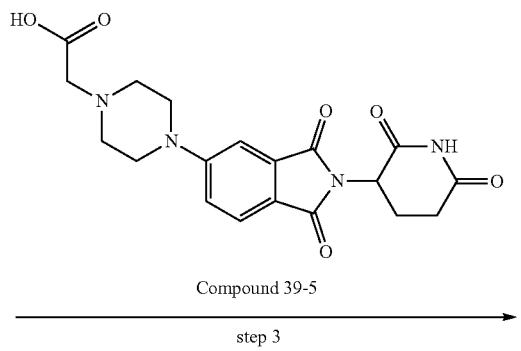

Compound 39-5 step 3

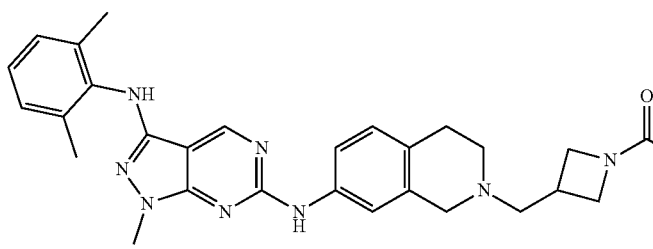

Compound 39

Step 1: Synthesis of tert-butyl 3-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)azetidine-1-carboxylate (Compound 39-3)

A solution of Compound 39-2 (TCI, B5160) (102 mg, 0.550 mmol) in MeOH (25 mL) was added with Compound 39-1 (Korean Patent No. 2128018) (200 mg, 0.500 mmol) and acetic acid (6 mg, 0.10 mmol) and stirred for 1 hour. The mixture was added with NaCNBH$_3$ (47.2 mg, 0.750 mmol) and stirred at room temperature for 4 hours. When the reaction was completed as analyzed by TLC, the solvent was completely evaporated. The residue was dissolved in MC and washed with water. The organic layer was concentrated in a vacuum to give a crude material which was then purified by MPLC to afford Compound 39-3 as a yellow solid (160 mg).

Step 2: Synthesis of N6-(2-(azetidin-3-ylmethyl)-1,2,3,4-tetrahydroisoquinolin-7-yl)-N3-(2,6-dimethylphenyl)-1-methyl-1H-pyrazolo[3,4-d]pyrimidine-3,6-diamine hydrochloride (Compound 39-4)

A solution of Compound 39-3 (150 mg, 0.263 mmol) in DCM (10 mL) was added with 4 N—HCl/dioxane (0.131 mL, 0.527 mmol) and stirred at room temperature for 1 hour. After completion of the reaction, the solvent was evaporated and the residual dioxane was subjected to extraction with CHCl$_3$ (20 mL). Drying the residue afforded Compound 39-4 as a yellow solid (140 mg).

Step 3: Synthesis of 5-(4-(2-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethyl)piperazin-1-yl)-2-(2,6-dioxopiperidin-3-yl)isoindoline-1,3-dione (Compound 39)

Compound 39-5 (WO 2020/160193) (6.8 mg, 0.017 mmol) in DMF (0.5 mL) was added at room temperature with HATU (20.0 mg, 0.052 mmol), Compound 39-4 (10 mg, 0.017 mmol), and TEA (8.6 mg, 0.085 mmol). The mixture was stirred at room temperature for 16 hours. The reaction mixture was added with water, subjected to extraction with DCM, and washed with water and brine. The organic layer was concentrated in a vacuum to give a crude material which was then purified by MPLC to afford Compound 39 as a green solid (3.0 mg).

Compound 40. 5-(4-(3-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)azetidine-1-carbonyl)piperidin-1-yl)-2-(2,6-dioxopiperidin-3-yl)isoindoline-1,3-dione

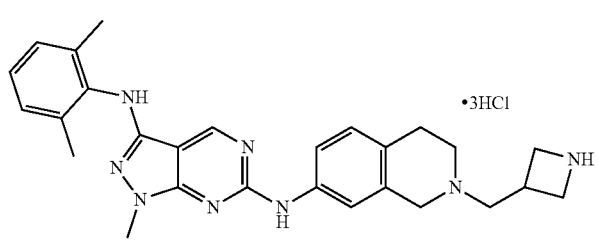

Compound 40-1

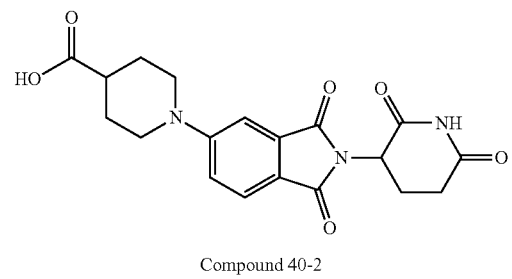

Compound 40-2

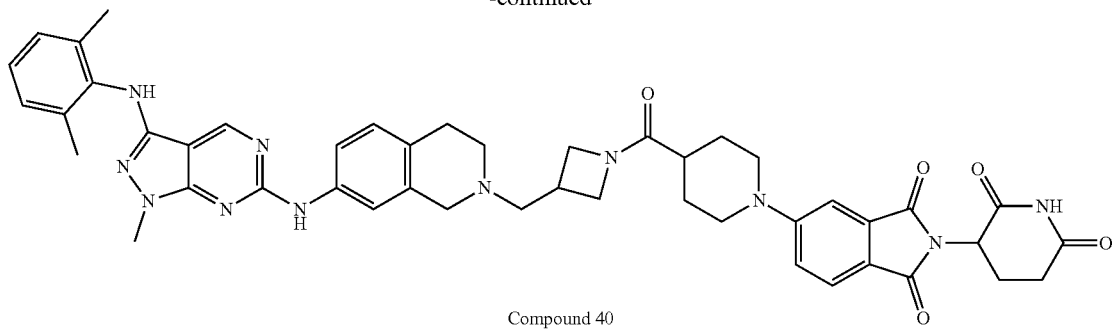

Compound 40

A solution of Compound 40-2 (WO 2020/162725) (7.3 mg, 0.019 mmol) in DMF (0.5 mL) was added at room temperature with T3P (38 mg, 0.0.059 mmol), Compound 40-1 (identical to Compound 39-4) (10 mg, 0.019 mmol), and TEA (9.3 mg, 0.095 mmol). The mixture was stirred at room temperature for 16 hours. The reaction mixture was added with water, subjected to extraction with EA, and washed with water and brine. Then, the organic layer was concentrated in a vacuum to give a crude material which was then purified by MPLC to afford Compound 40 as a brown solid (4.0 mg).

Compound 41. 5-(4-(((3-((3-((2,6-Dimethylphenyl)amino)-1-methyl-TH-pyrazolo[3,4-d]pyrimidin-6-yl)amino)benzyl)amino)methyl)piperidin-1-yl)-2-(2,6-dioxopiperidin-3-yl)isoindoline-1,3-dione

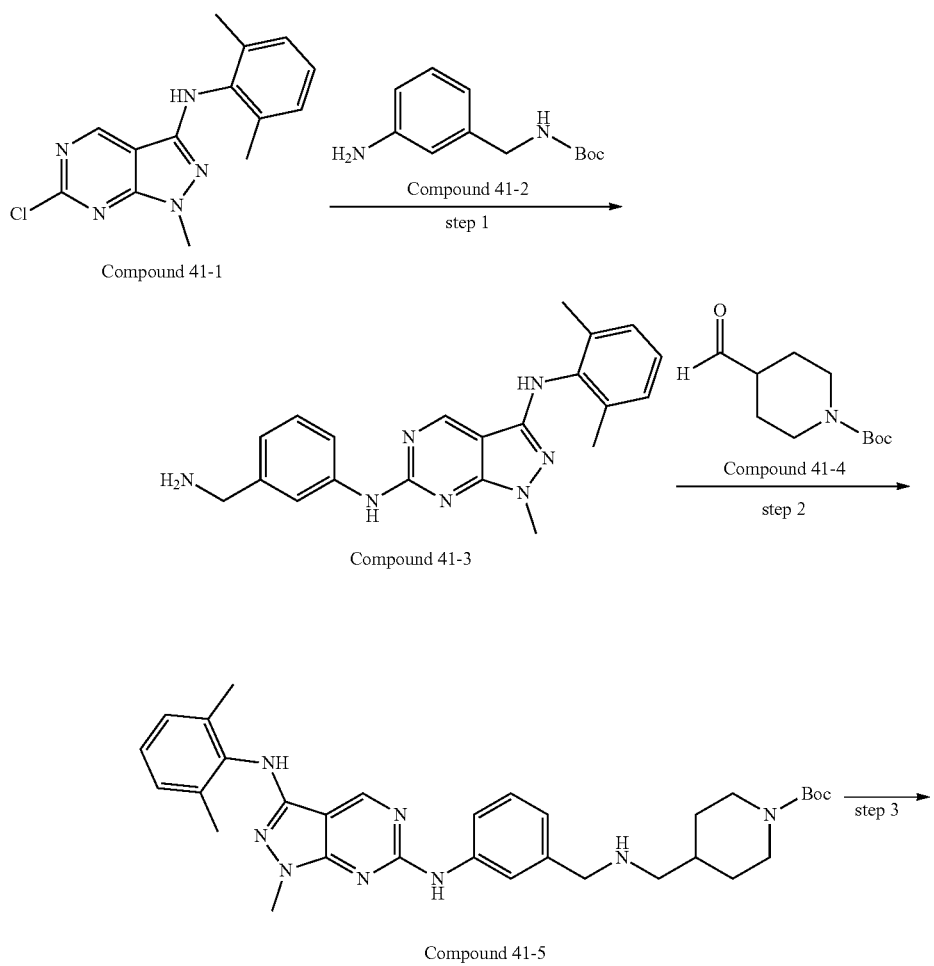

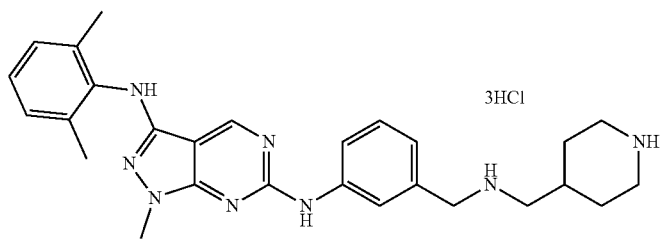
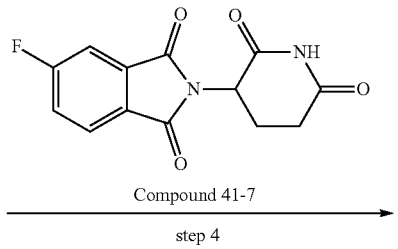

Compound 41-6     3HCl     Compound 41-7 step 4

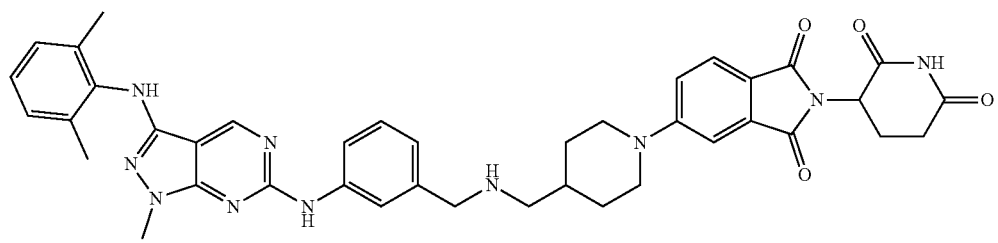

Compound 41

Step 1: Synthesis of N6-(3-(aminomethyl)phenyl)-N3-(2,6-dimethylphenyl)-1-methyl-1H-pyrazolo[3,4-d]pyrimidine-3,6-diamine (Compound 41-3)

A suspension of Compound 41-1 (Korean Patent No. 2128018) (100 mg, 0.347 mmol) and Compound 41-2 (TCI, A2718) (84.8 mg, 0.347 mmol) in IPA (25 mL) was added with p-TSA-H$_2$O (72.6 g, 0.381 mmol) and heated at 90° C. while being stirred for 12 hours. The solid thus formed in the reaction mixture was filtered and washed with ethanol (50 mL) to give a pTSA salt of the title compound as a yellow solid which was then neutralized with a sodium carbonate solution to afford Compound 41-3 as an off-white solid (95.0 mg).

Step 2: Synthesis of tert-butyl 3-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)azetidine-1-carboxylate (Compound 41-5)

A solution of Compound 41-4 (TCI, B3873) (Boc-piperidine aldehyde; 63.0 mg, 0.894 mmol) in MeOH (25 mL) was added with Compound 41-3 (100 mg, 0.267 mmol) and acetic acid (3.2 mg, 0.053 mmol) and stirred for 3 hours (imine generation). The mixture was added with NaBH$_3$CN (25.2 mg, 0.400 mmol) and stirred at room temperature for 1 hour. After completion of the reaction, the solvent was completely evaporated. The residue was dissolved in MC and washed with water. The organic layer was concentrated in a vacuum to give a crude material which was then purified by MPLC to afford Compound 41-5 as a yellow solid (80.2 mg).

Step 3: Synthesis of N3-(2,6-dimethylphenyl)-1-methyl-N6-(3-(((piperidin-4-ylmethyl)amino)methyl)phenyl)-1H-pyrazolo[3,4-d]pyrimidine-3,6-diamine hydrochloride (Compound 41-6)

A solution of Compound 41-5 (70 mg, 0.123 mmol) in DCM (2 mL) was added with 4 N—HCl/dioxane (0.123 mL, 0.246 mmol) and stirred at room temperature for 1 hour. After completion of the reaction, the solvent was evaporated and the residual dioxane layer was subjected to extraction with CHCl$_3$ (20 mL). Drying in a vacuum afforded Compound 41-6 as a yellow solid (50 mg).

Step 4: Synthesis of 5-(4-(((3-((3-((2,6-dimethylphenyl)amino)-1-methyl-1H-pyrazolo[3,4-d]pyrimidin-6-yl)amino)benzyl)amino)methyl)piperidin-1-yl)-2-(2,6-dioxopiperidin-3-yl)isoindoline-1,3-dione (Compound 41)

A solution of Compound 41-7 (Combi-Blocks, HD-3240) (5.5 mg, 0.019 mmol) in DMSO (0.5 mL) was added at room temperature with Compound 41-6 (10 mg, 0.019 mmol) and DIPEA (12.3 mg, 0.0950 mmol). The mixture was stirred at 90° C. for 16 hours. The mixture was stirred at room temperature until the reaction was completed. The reaction mixture was added with water, subjected to extraction with MC, and washed with water and brine. The organic layer was concentrated in a vacuum to give a crude material which was then purified by MPLC to afford Compound 41 as a yellow solid (3.0 mg).

Compound 42. 5-(4-(4-(((3-((3-((2,6-Dimethylphenyl)amino)-1-methyl-1H-pyrazolo[3,4-d]pyrimidin-6-yl)amino)benzyl)amino)methyl)piperidine-1-carbonyl)piperidin-1-yl)-2-(2,6-dioxopiperidin-3-yl)isoindoline-1,3-dione

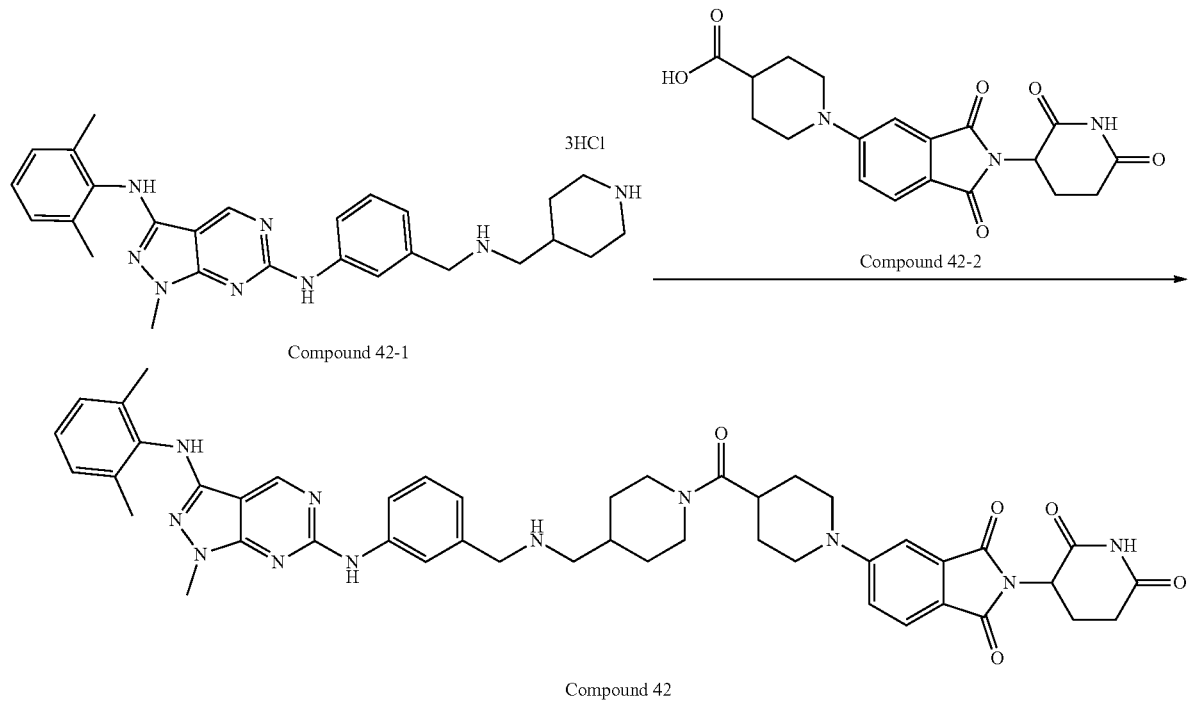

A solution of Compound 42-2 (WO 2020/162725) (7.3 mg, 0.019 mmol) in DMF (0.5 mL) was added at room temperature with HATU (22 mg, 0.057 mmol), Compound 42-1 (identical to Compound 41-6) (10 mg, 0.019 mmol), and TEA (10 mg, 0.095 mmol). The mixture was stirred at 35° C. for 4 hours. The reaction mixture was added with water, subjected to extraction with DCM, and washed with water and brine. The organic layer was concentrated in a vacuum to give a crude material which was then purified by MPLC to afford Compound 42 as a yellow solid (3.6 mg).

Compound 43. 5-(2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethoxy)-2-(2,6-dioxopiperidin-3-yl)isoindoline-1,3-dione

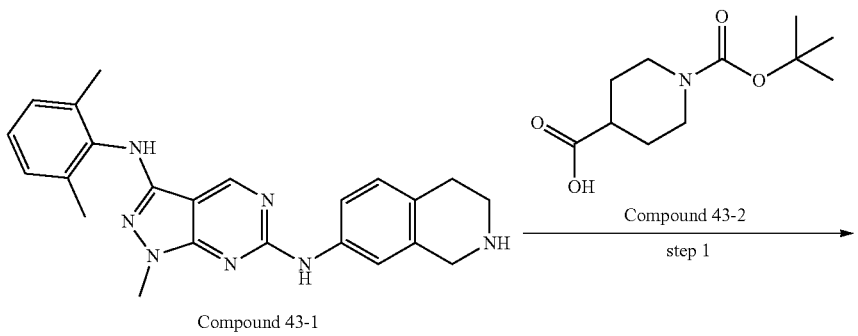

-continued

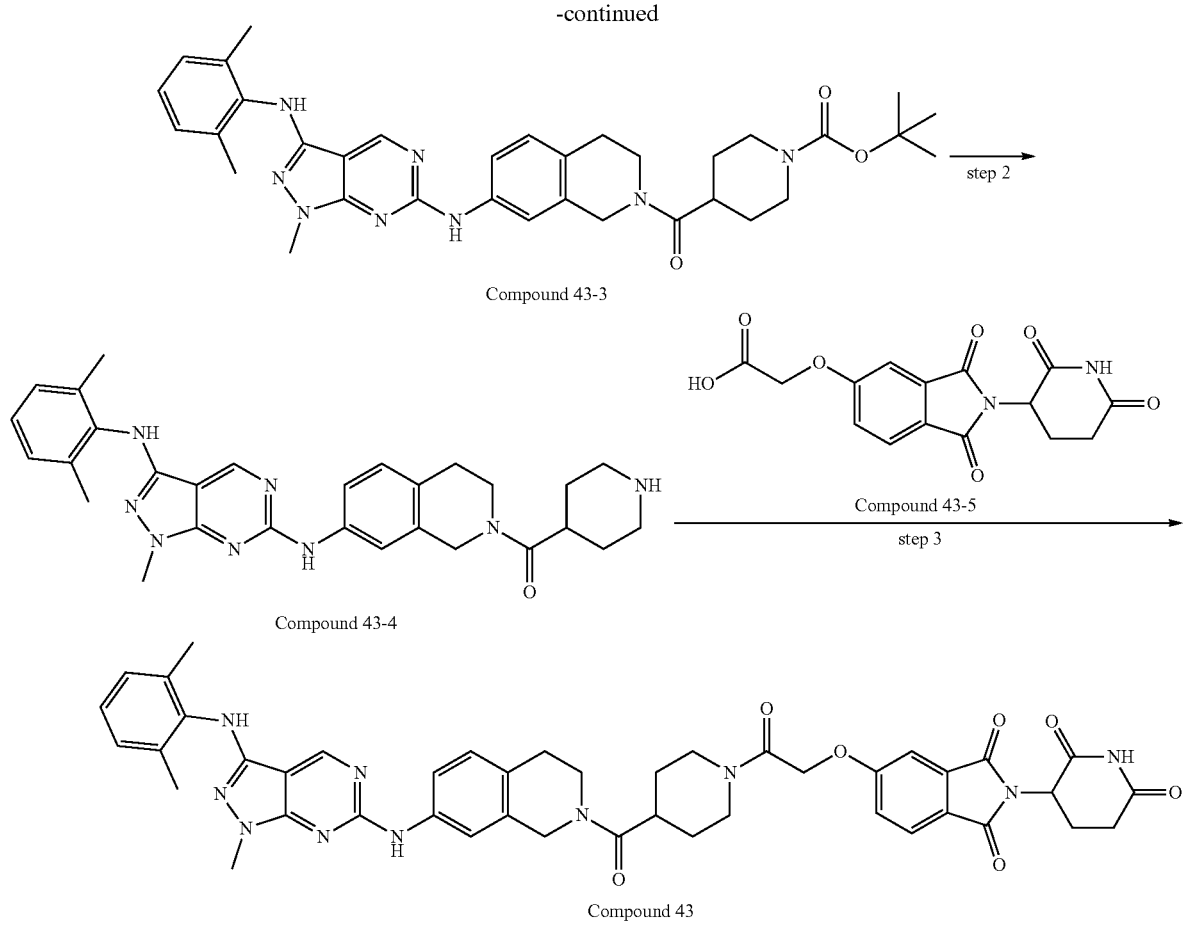

Compound 43-3

Compound 43-4

Compound 43-5

Compound 43

Step 1: Synthesis of tert-butyl 4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)piperidine-1-carboxylate (Compound 43-3)

A solution of Compound 43-2 (BLDPharm, BD00948389) (1-(tert-butoxycarbonyl)piperidine-4-carboxylic acid; 32.8 mg, 0.14 mmol) in DMF (1 mL) was added with HATU (148.2 mg, 0.39 mmol) and TEA (52.6 mg, 0.52 mmol) and stirred for 10 minutes. Finally, after addition of Compound 43-1 (Korean Patent No. 2128018) (50 mg, 0.13 mmol), stirring was conducted at 30° C. for 12 hours. The reaction mixture was quenched with water (10 mL) and ice, followed by filtration. The compound was washed with water and extracted with DCM. The organic layer was concentrated in a vacuum to give a crude material which was then purified by silica gel column chromatography to afford Compound 43-3 as a brown solid (74.4 mg).

Step 2: Synthesis of (7-((3-((2,6-dimethylphenyl)amino)-1-methyl-1H-pyrazolo[3,4-d]pyrimidin-6-yl)amino)-3,4-dihydroisoquinolin-2 (1H)-yl) (piperidin-4-yl)methanone hydrochloride (Compound 43-4)

A solution of Compound 43-3 (60 mg, 0.10 mmol) in DCM (3.0 mL) was added with 4 N—HCl/dioxane (0.05 mL, 0.20 mmol) and stirred at room temperature for 3 hours. When the starting material was not observed in the TLC profile, the solvent was evaporated in a vacuum to afford Compound 43-4 as a yellow solid (46 mg).

Step 3: Synthesis of 5-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethoxy)-2-(2,6-dioxopiperidin-3-yl)isoindoline-1,3-dione (Compound 43)

A solution of Compound 43-5 (WO 2020/160198) (6.9 mg, 0.021 mmol) in DMF (2 mL) was added with HATU (28.8 mg, 0.076 mmol) and TEA (16.1 mg, 0.16 mmol) and stirred for 10 minutes. Finally, after addition of Compound 43-4 (10 mg, 0.018 mmol), stirring was conducted at 35° C. for 12 hours. After completion of the reaction, the reaction mixture was quenched with water and ice. A yellow solid was formed in the solution. The solid was diluted with DCM. The organic layer was concentrated in a vacuum to give a crude material which was then purified by silica gel column chromatography to afford Compound 43 as a pale yellow solid (9.2 mg).

Compound 44. 5-(4-(2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)piperazin-1-yl)-2-(2,6-dioxopiperidin-3-yl)isoindoline-1,3-dione

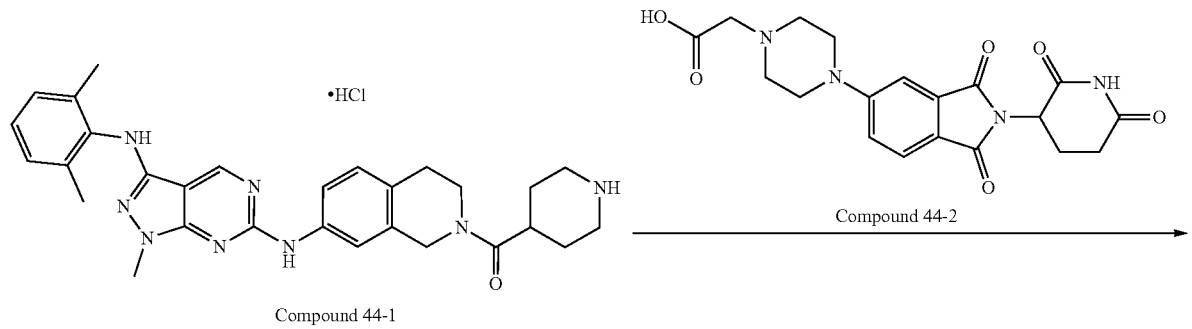

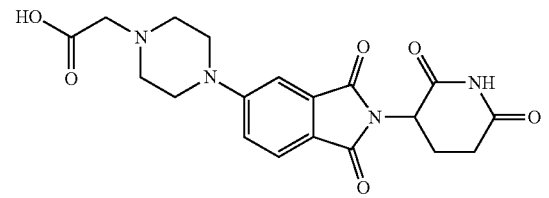

Compound 44-2

Compound 44-1

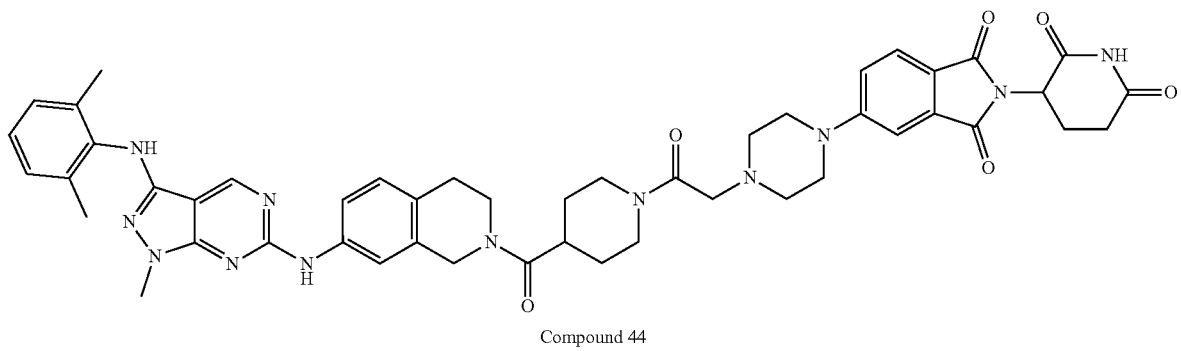

Compound 44

A solution of Compound 44-2 (WO 2020/160193) (8.4 mg, 0.021 mmol) in DMF (2 mL) was added with HATU (28.8 mg, 0.076 mmol) and TEA (16.1 mg, 0.16 mmol) and stirred for 10 minutes. Finally, after addition of Compound 44-1 (identical to Compound 43-4) (10 mg, 0.018 mmol), stirring was conducted at 35° C. for 12 hours. After completion of the reaction, the reaction mixture was quenched with water and ice. The compound was formed as a yellow solid in the solution. The solid was filtered and washed with water and brine. The compound was extracted with DCM. The organic layer was concentrated in a vacuum to give a crude material which was then purified by silica gel column chromatography to afford Compound 44 as a pale yellow solid (4.8 mg).

Compound 45. 5-((2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)amino)-2-(2,6-dioxopiperidin-3-yl)isoindoline-1,3-dione

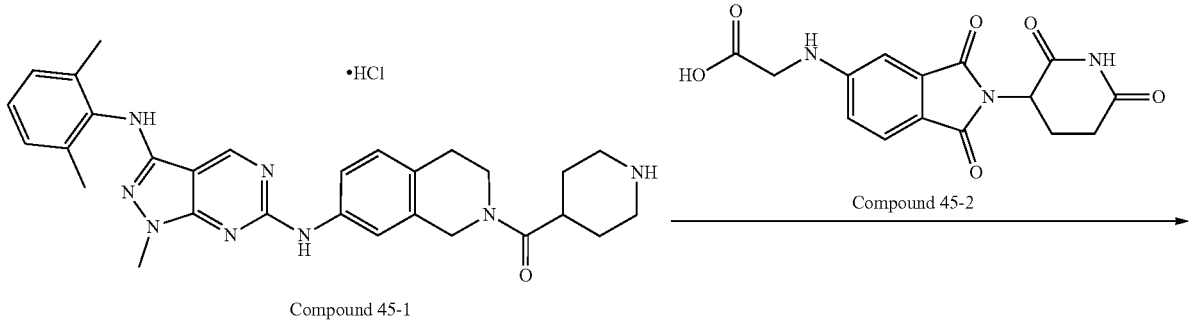

Compound 45-2

Compound 45-1

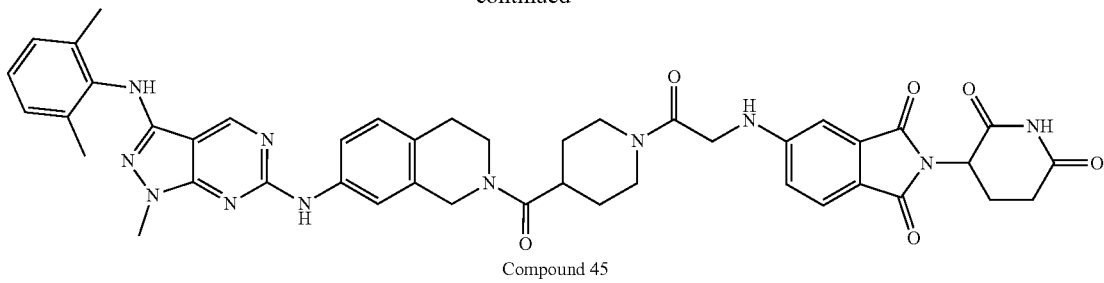

Compound 45

A solution of Compound 45-2 (WO 2020/162725) (6.9 mg, 0.021 mmol) in DMF (2 mL) was added with HATU (28.8 mg, 0.0757 mmol) and TEA (16.1 mg, 0.160 mmol) and stirred for 10 minutes. Finally, after addition of Compound 45-1 (identical to Compound 43-4) (10 mg, 0.018 mmol), stirring was conducted at 35° C. for 12 hours. When the reaction was completed, the reaction mixture was quenched with water and ice. The compound was formed as a yellow solid in the solution. The solid was filtered and washed with water and brine. The compound was extracted, and the organic layer was concentrated in a vacuum to give a crude material which was then purified by silica gel column chromatography to afford Compound 45 as a bright yellow solid (3.8 mg).

Compound 46. 3-(6-((4-((7-((3-((2,6-Dimethylphenyl))amino)-1-methyl-1H-pyrazolo[3,4-d]pyrimidin-6-yl)amino)-3,4-dihydroisoquinolin-2 (1H)-yl)methyl)piperidin-1-yl)methyl)-4-oxobenzo[d][1,2,3]triazin-3 (4H)-yl)piperidin-2,6-one

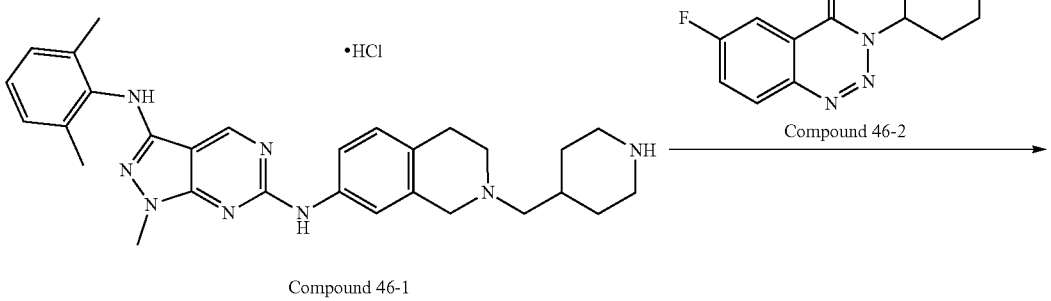

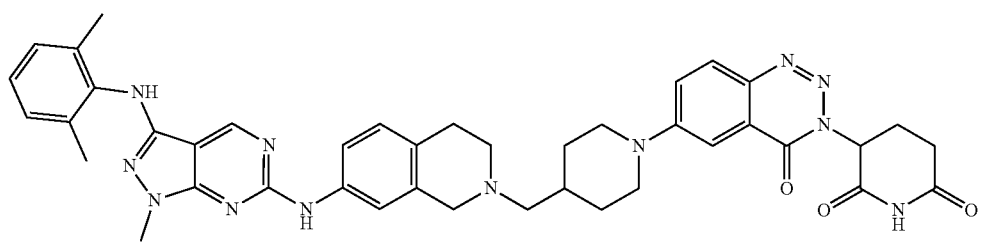

Compound 46

A solution of Compound 46-2 (WO 2020/162725) (10 mg, 0.020 mmol) in DMSO (1.0 mL) was added with Compound 46-1 (identical to Compound 28-4) (10 mg, 0.018 mmol) and DIPEA (9.3 mg, 0.072 mmol) and stirred at 90° C. for 13 hours to complete the reaction. After completion of the reaction, the reaction mixture was quenched with water and ice and subjected to extraction with EA. The pooled organic layer was washed and brine and concentrated in a vacuum to give a crude material which was then purified by silica gel column chromatography to afford Compound 46 as a brown solid (4.6 mg).

Compound 47. 5-(3-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-(2,6-dioxopiperidin-3-yl)isoindoline-1,3-dione

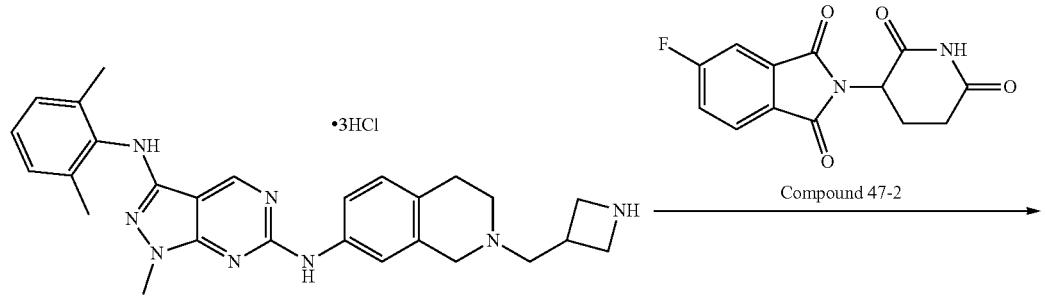

Compound 47-1      Compound 47-2

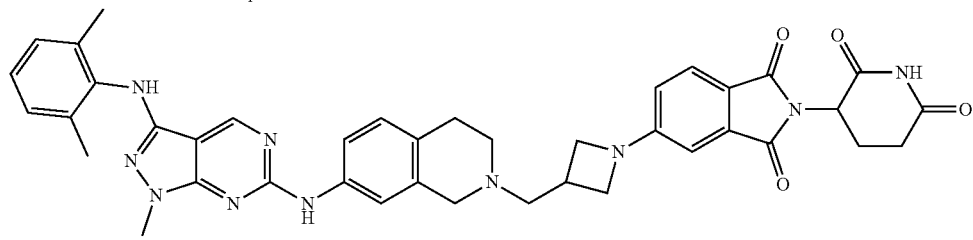

Compound 47

A solution of Compound 47-2 (Combi-Blocks, HD-3240) (8.6 mg, 0.031 mmol) in DMSO (2.0 mL) was added with Compound 47-1 (identical to Compound 40-1) (15 mg, 0.031 mmol) and DIPEA (13.4 mg, 0.104 mmol) and stirred 90° C. for 12 hours to complete the reaction. After completion of the reaction, the reaction mixture was quenched with water and ice and subjected to extraction with DCM. The pooled organic layer was washed with water and brine and concentrated in a vacuum to give a crude material which was then purified by silica gel column chromatography to afford Compound 47 as a brown solid (3.5 mg).

Compound 48. 3-(6-(2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethoxy)-4-oxobenzo[d][1,2,3]triazin-3 (4H)-yl)piperidin-2,6-one

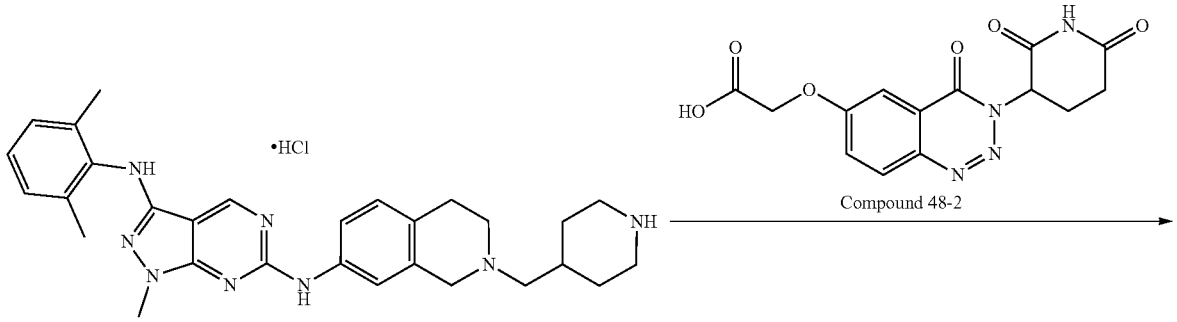

Compound 48-1      Compound 48-2

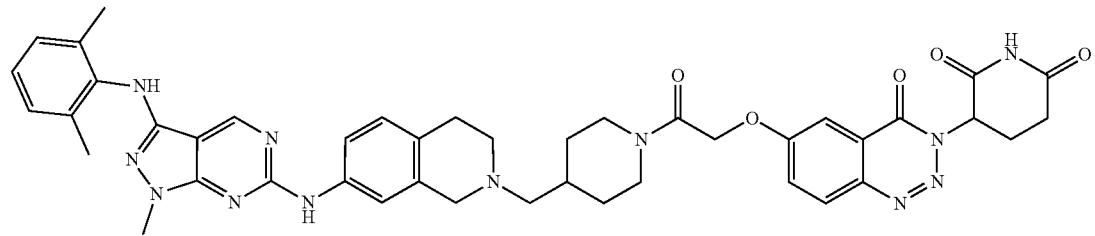

Compound 48

A solution of Compound 48-2 (WO 2020/162725) (6.9 mg, 0.021 mmol) in DMF (1 mL) was added with T3P (36.3 mg, 0.0570 mmol) and TEA (16.1 mg, 0.160 mmol) and stirred for 10 minutes. Finally, after addition of Compound 48-1 (identical to Compound 29-1) (10 mg, 0.019 mmol), stirring was conducted at 35° C. for 12 hours. After completion of the reaction, the reaction mixture was quenched with water. The aqueous layer was subjected to extraction with DCM and the organic layer was washed with water and brine. The organic layer was concentrated in a vacuum to give a crude material which was then purified by silica gel column chromatography to afford Compound 48 as a green solid (3.8 mg).

Compound 49. 5-(2-(3-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethoxy)-2-(2,6-dioxopiperidin-3-yl)isoindoline-1,3-dione

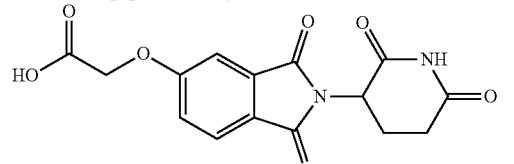

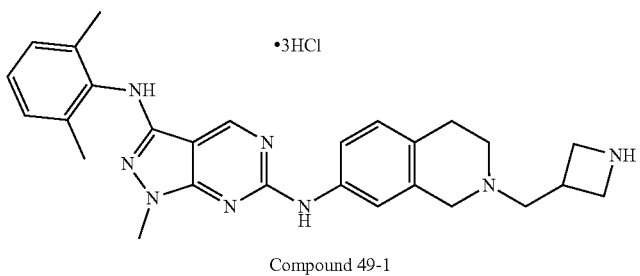

Compound 49-1

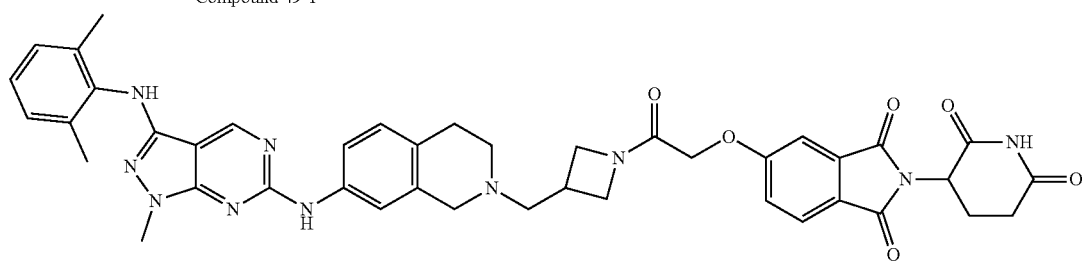

Compound 49

A solution of Compound 49-2 (WO 2020/160198) (6.3 mg, 0.019 mmol) in DMF (1 mL) was added with T3P (38 mg, 0.059 mmol) and TEA (9.6 mg, 0.095 mmol) and stirred for 10 minutes. Finally, after addition of Compound 49-1 (identical to Compound 40-1) (10 mg, 0.019 mmol), stirring was conducted overnight at 30° C. After completion of the reaction, the reaction mixture was quenched with water. The aqueous layer was subjected to extraction with DCM. The organic layer was washed with water and brine and concentrated in a vacuum to give a crude material which was then purified by silica gel column chromatography to afford Compound 49 as a white solid (2.9 mg).

Compound 50. 5-(3-((4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)methyl)azetidin-1-yl)-2-(2,6-dioxopiperidin-3-yl)isoindoline-1,3-dione

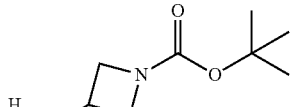

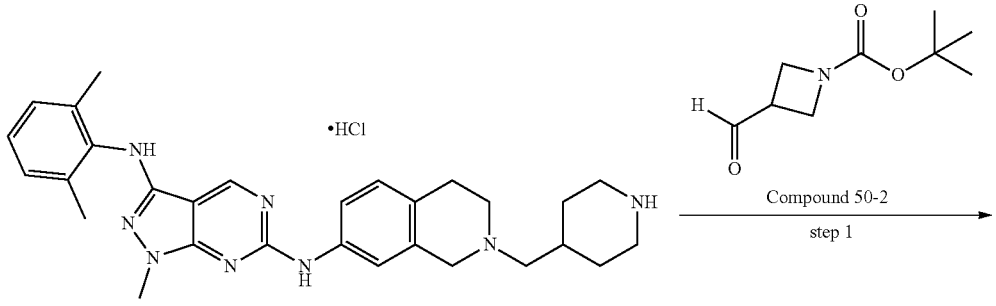

Compound 50-1

-continued

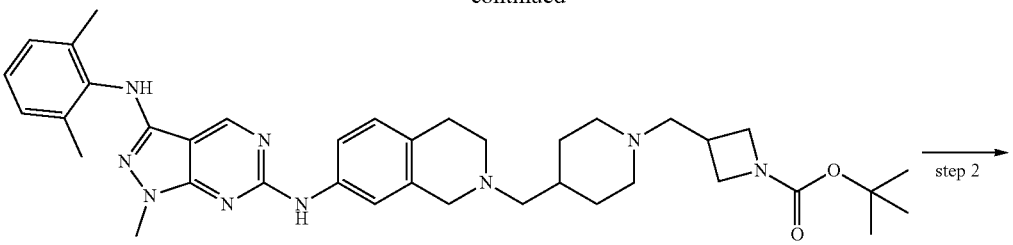

Compound 50-3

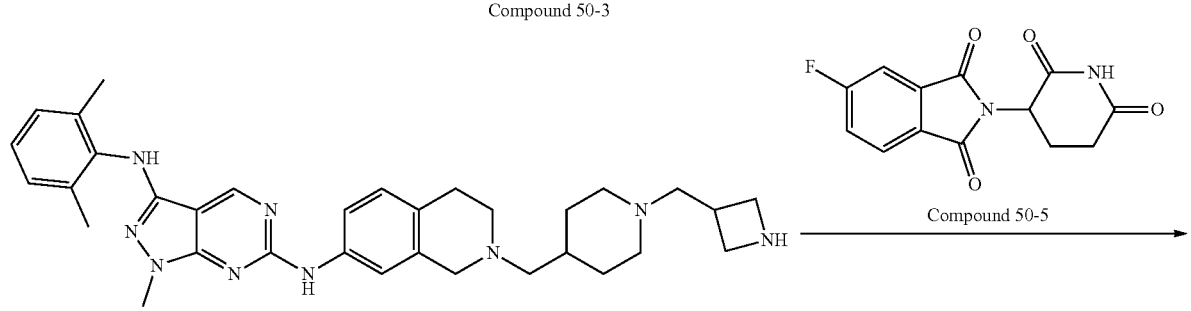

Compound 50-4

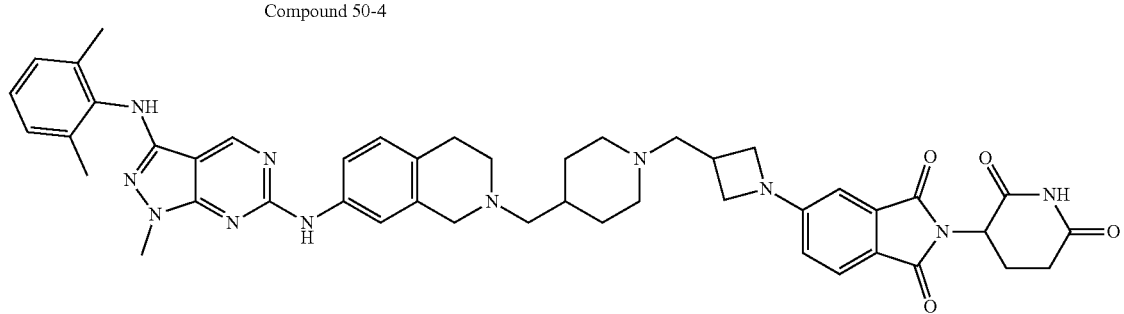

Compound 50

Step 1: Synthesis of tert-butyl 3-((4-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidin-1-yl)methyl)azetidine-1-carboxylate (Compound 50-3)

A solution of Compound 50-2 (TCI, B5160) (tert-butyl 3-formylazetidine-1-carboxylate; 19.3 mg, 0.104 mmol) in MeOH (5.0 mL) was added at 0° C. with Compound 50-1 (identical to Compound 29-1) (47.1 mg, 0.0948 mmol) and stirred at room temperature for 3 hours in the presence of AcOH (0.1 mL) as a catalyst (imine generation). Sodium cyanoborohydride (8.9 mg, 0.14 mmol) was added before additional one hours of stirring. After completion of the reaction, the reaction mixture was quenched with water and MeOH was evaporated. The aqueous layer was subjected to extraction with EA. The crude residue was purified by silica gel column chromatography to afford Compound 50-3 as a green solid (28.5 mg).

Step 2: Synthesis of N6-(2-((1-(azetidin-3-ylmethyl)piperidin-4-yl)methyl)-1,2,3,4-tetrahydroisoquinolin-7-yl)-N3-(2,6-dimethylphenyl)-1-methyl-1H-pyrazolo[3,4-d]pyrimidine-3,6-diamine (Compound 50-4)

A solution of Compound 50-3 (20 mg, 0.030 mmol) in DCM (5.0 mL) was added with 4 N—HCl/dioxane (0.02 mL, 0.060 mmol) and stirred at room temperature for 3 hours. After completion of the reaction, the solvent was evaporated in a vacuum to produce a yellow solid (15 mg). This compound was neutralized with NaHCO₃ and the aqueous layer was subjected to extraction with MC and the organic layer was concentrated in a vacuum to afford Compound 50-4 as a white solid (16.0 mg).

Step 3: Synthesis of 5-(3-((4-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidin-1-yl)methyl)azetidin-1-yl)-2-(2,6-dioxopiperidin-3-yl)isoindoline-1,3-dione (Compound 50)

A solution of Compound 50-5 (Combi-Blocks, HD-3240) (5.9 mg, 0.021 mmol) in DMSO (2.0 mL) was added with Compound 50-4 (10 mg, 0.018 mmol) and DIPEA (7.0 mg, 0.54 mmol). Stirring was conducted at 90° C. for 12 hours to complete the reaction. After completion of the reaction, the reaction mixture was quenched with water and ice and subjected to extraction with DCM. The organic layer was washed with water and brine (25 mL×3) and concentrated in a vacuum to give a crude material which was then purified by silica gel column chromatography to afford Compound 50 as a green solid (6.4 mg).

Compound 51. 5-((2-(3-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethyl)amino)-2-(2,6-dioxopiperidin-3-yl)isoindoline-1,3-dione

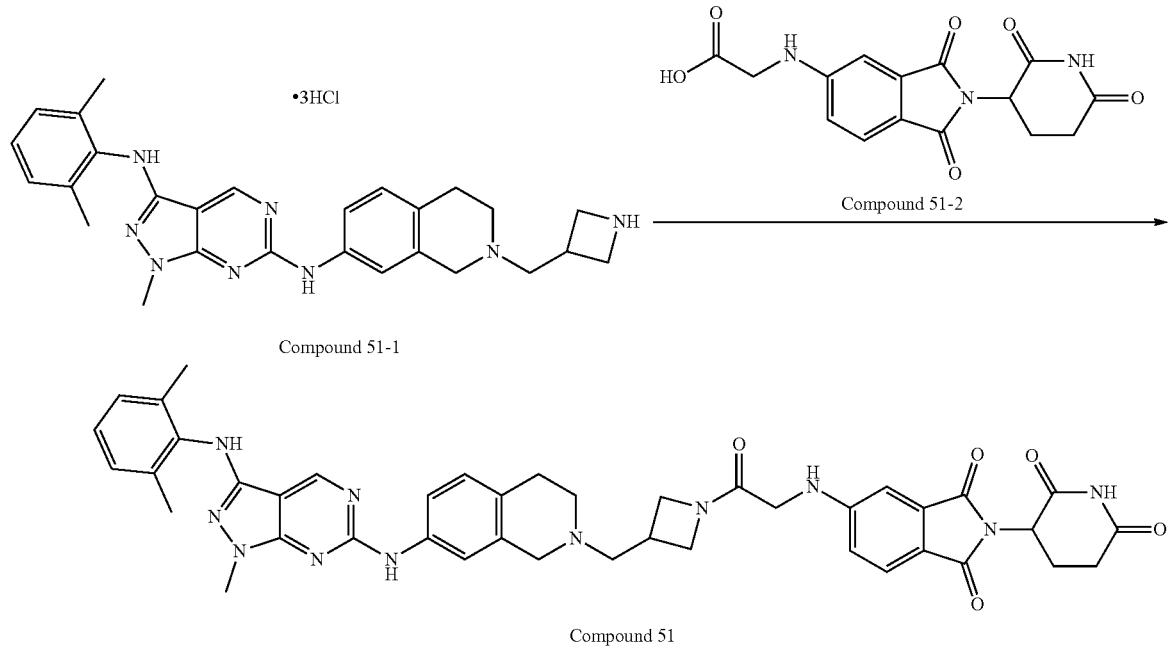

A solution of Compound 51-2 (WO 2020/162725) (5.6 mg, 0.017 mmol) in DMF (1 mL) was added with T3P (32.4 mg, 0.0510 mmol) and TEA (8.6 mg, 0.085 mmol) and stirred for 10 minutes. Finally, after addition of Compound 51-1 (identical to Compound 40-1) (10 mg, 0.017 mmol), stirring was conducted overnight at 30° C. After completion of the reaction, the reaction mixture was quenched with water and the aqueous layer was subjected to extraction with DCM. The organic layer was washed with water and brine and concentrated in a vacuum to give a crude material which was then purified by silica gel column chromatography to afford Compound 51 as a yellow solid (3.5 mg).

Compound 52. 3-(6-((2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-4-oxobenzo[d][1,2,3]triazin-3 (4H)-yl)piperidin-2,6-one

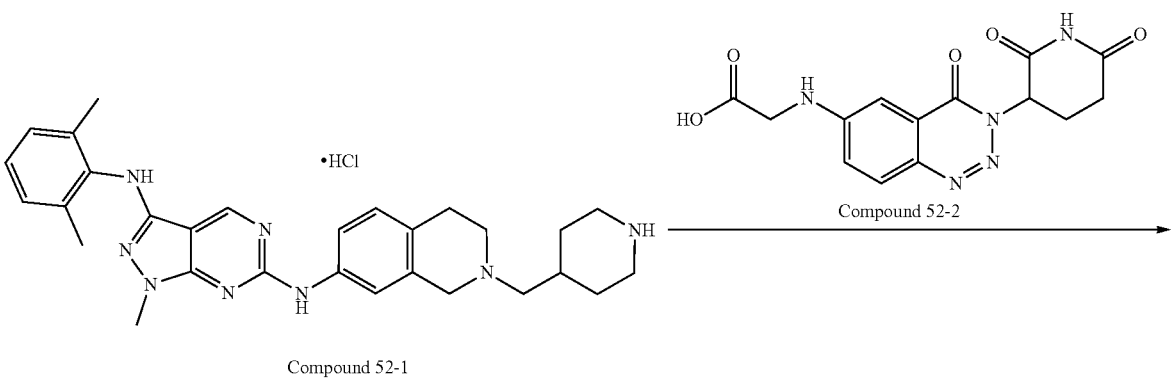

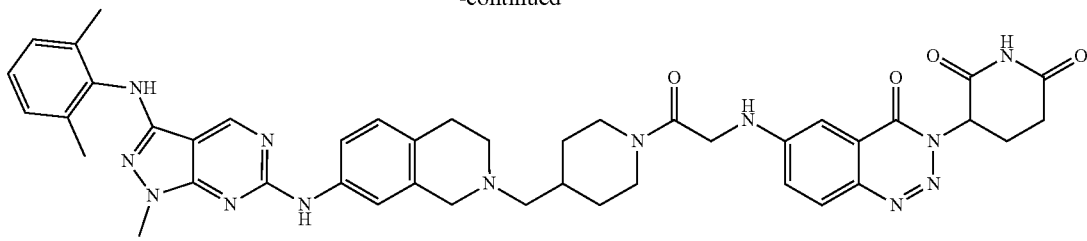

Compound 52

A solution of Compound 52-2 (WO 2020/162725) (7.3 mg, 0.022 mmol) in DMF (1 mL) was added with HATU (30.4 mg, 0.0805 mmol) and TEA (16.2 mg, 0.161 mmol) and stirred for 10 minutes. Finally, after addition of Compound 52-1 (identical to Compound 29-1) (10 mg, 0.020 mmol), stirring was conducted at 35° C. for 12 hours. After completion of the reaction, the reaction mixture was quenched with water and subjected to extraction with DCM. The organic layer was washed with water and brine and concentrated in a vacuum to give a crude material which was then purified by silica gel column chromatography to afford Compound 52 as a reddish yellow solid (6.4 mg).

Compound 53. 3-(7-(4-(((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-4-oxobenzo[d][1,2,3]triazin-3(4H)-yl)piperidin-2,6-one

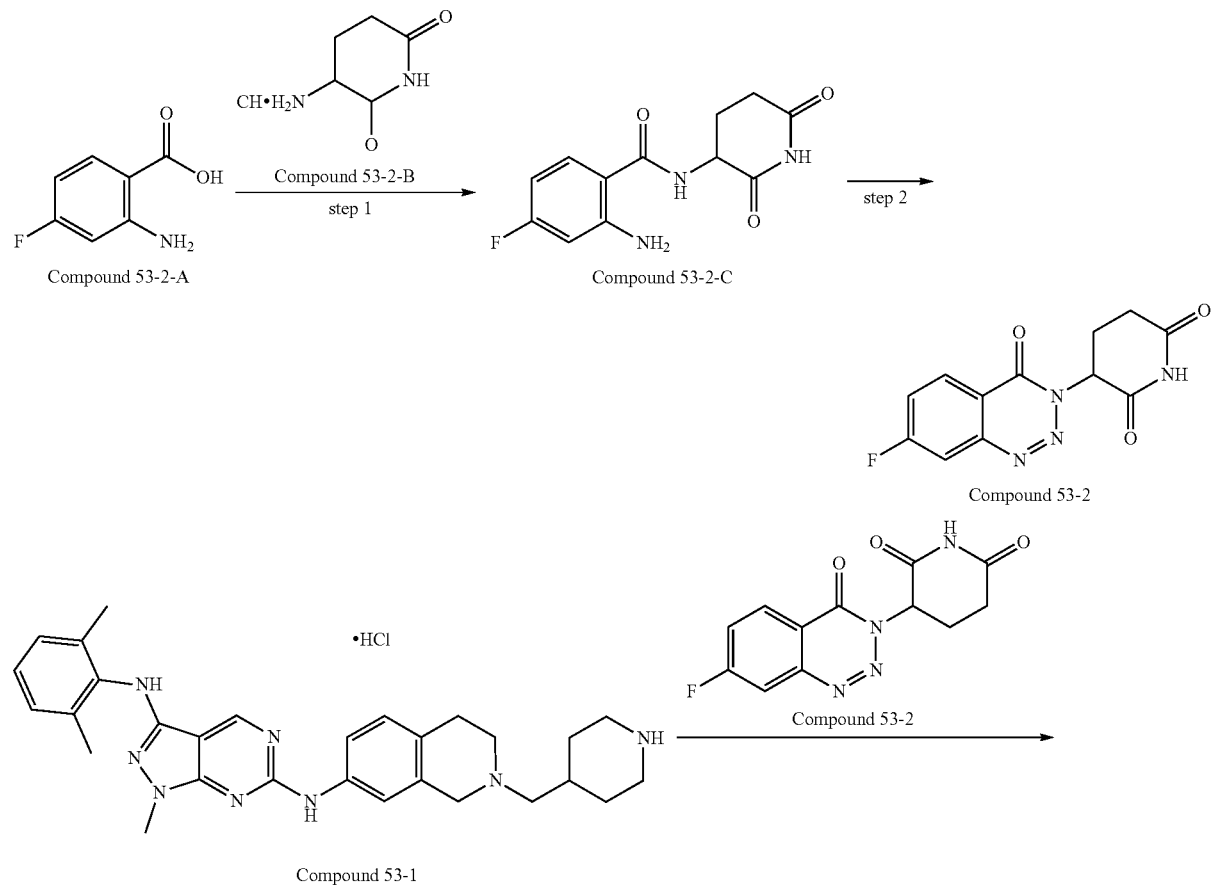

-continued

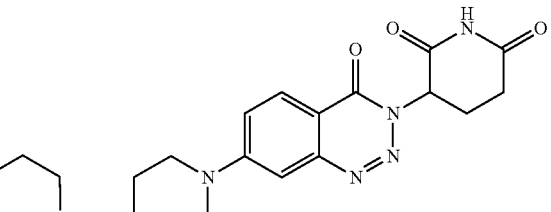

Compound 53

Step 1: Synthesis of 2-amino-N-(2,6-dioxopiperidin-3-yl)-4-fluorobenzamide (Compound 53-2-C)

To a solution of Compound 53-2-A (BLDpharm, MFCD00075553) (2-amino-4-fluorobenzoic acid; 12.5 g, 80.5 mmol) in DMF (150 mL) was added a solution of Compound 53-2-B (3-aminopiperidin-2,6-one hydrochloride; 19.9 g, 120.8 mmol) in DCM (50 mL), together with EDCI·HCl (30.8 g, 161 mmol), HOBt (24.6 g, 161 mmol), and DIPEA (31.3 g, 241.5 mmol), at room temperature, and the mixture was stirred for 12 hours. The reaction mixture was concentrated to remove DCM and added with water before extraction with EtOAc (2×450 mL). The organic layer was washed with brine (2×250 mL), dried over sodium sulfate, and concentrated in a vacuum to give a crude product. This crude product was crystallized and purified using MC and hexane (1:9) to afford Compound 53-2-C as a white solid (18 g, 67.86 mmol, 84%).

Step 2: Synthesis of 3-(7-fluoro-4-oxobenzo[d][1,2,3]triazin-3 (4H)-yl)piperidin-2,6-one (Compound 53-2)

A solution of Compound 53-2-C (18 g, 67.86 mmol) in glacial acetic acid (300 mL) was added with sodium nitrite (9.36 g, 135.7 mmol) and stirred at room temperature for 2 hours. The reaction mixture was quenched before extraction with EtOAc (2×250 mL). The pooled organic layer was dried over $Na_2SO_4$ and the solvent was removed in a vacuum. The crude product was crystallized and purified using MC and hexane (1:9) to afford Compound 53-2 as a white solid (16.5 g, 59.7 mmol, 88%).

Step 3: Synthesis of 3-(7-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-4-oxobenzo[d][1,2,3]triazin-3 (4H)-yl)piperidin-2,6-one (Compound 53)

A solution of Compound 53-2 (8.0 mg, 0.029 mmol) in DMSO (2.0 mL) was added with Compound 53-1 (identical to Compound 29-1) (12 mg, 0.024 mmol) and DIPEA (9.3 mg, 0.72 mmol) and stirred at 90° C. for 4 hours until the reaction was completed. After completion of the reaction, the reaction mixture was quenched with water and subjected to extraction with DCM. The organic layer was washed with water and brine and concentrated in a vacuum to give a crude material which was then purified by silica gel column chromatography to afford Compound 53 as a bright green solid (9.7 mg).

Compound 54. 5-(4-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidine-1-carbonyl)piperidin-1-yl)-2-(2,6-dioxopiperidin-3-yl)isoindoline-1,3-dione

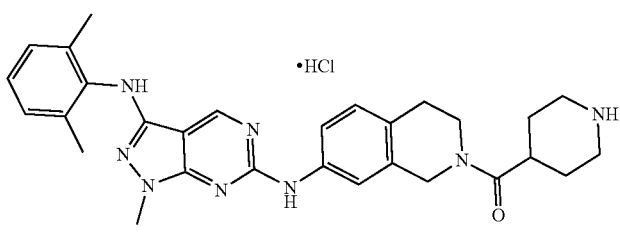

Compound 54-1

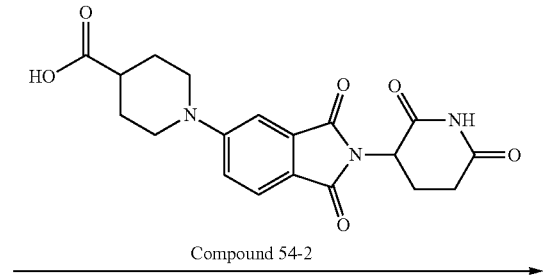

Compound 54-2

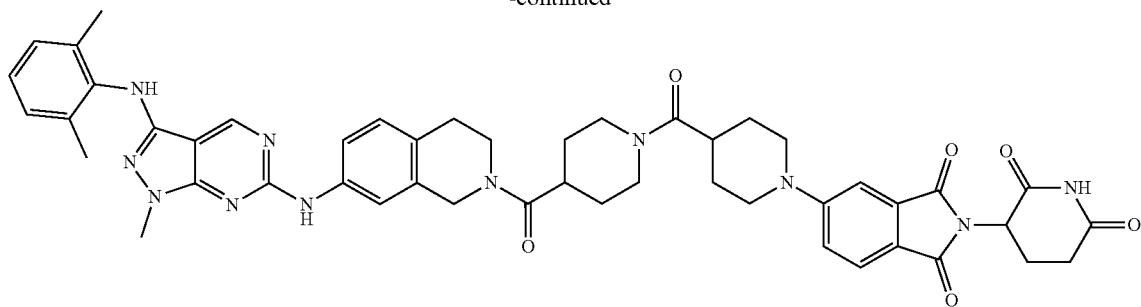

Compound 54

A solution of Compound 54-2 (WO 2020/162725) (8.0 mg, 0.021 mmol) in DMF (1 mL) was added at room temperature with HATU (22 mg, 0.057 mmol), Compound 54-1 (identical to Compound 43-4) (10 mg, 0.019 mmol) and TEA (6.0 mg, 0.057 mmol) and the mixture was stirred at room temperature for 16 hours. The reaction mixture was added with water, subjected to extraction with EA, and washed with water and brine. Then, the organic layer was concentrated in a vacuum to give a crude material which was then purified by MPLC to afford Compound 54 as a brown solid (6.0 mg).

Compound 55. 3-(6-(2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethoxy)-4-oxobenzo[d][1,2,3]triazin-3 (4H)-yl)piperidin-2,6-one

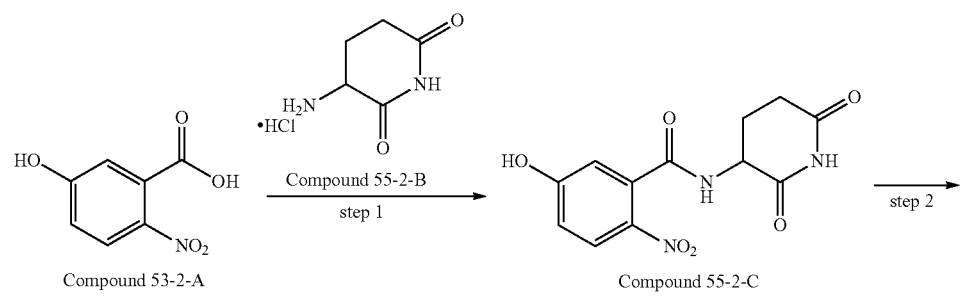

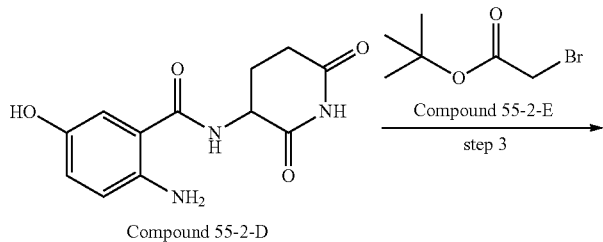

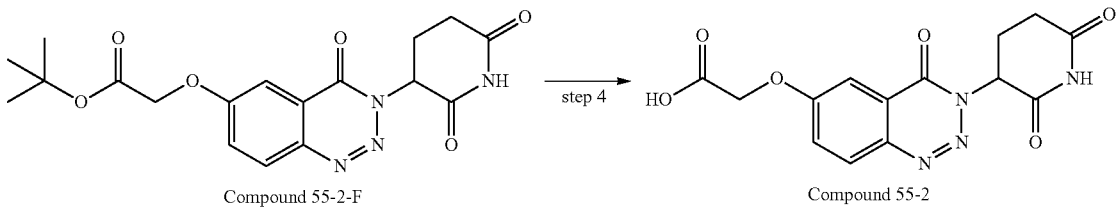

-continued

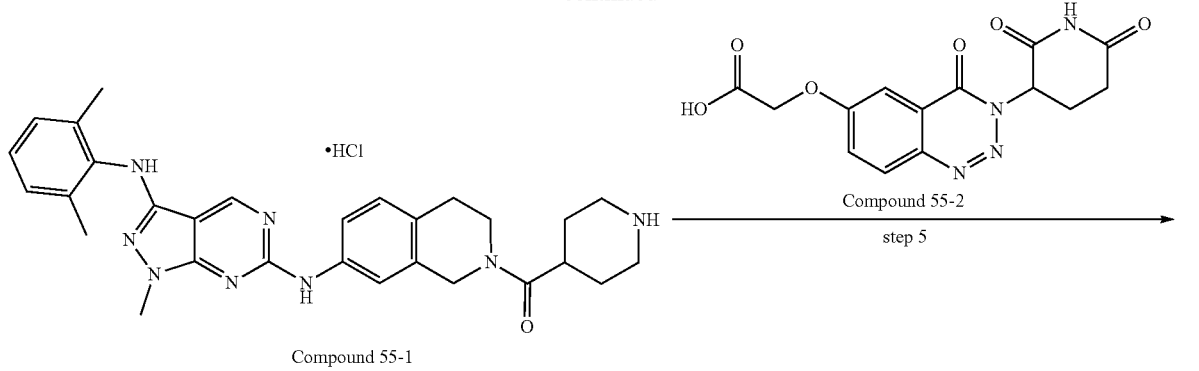

Compound 55-1

Compound 55

Step 1: Synthesis of N-(2,6-dioxopiperidin-3-yl)-5-hydroxy-2-nitrobenzamide (Compound 55-2-C)

A solution of Compound 55-2-A (BLDPharm, BD21759) (5-hydroxy-2-nitrobenzoic acid; 200 mg, 1.08 mmol) in DMF (5 mL) was added with Compound 55-2-B (BLDPharm, BD170886) (glutarimide; 178 mg, 1.08 mmol), EDCI·HCl (228 mg, 1.18 mmol), HOBt·H$_2$O (182 mg, 1.18 mmol), and DIPEA (0.564 mL, 3.24 mmol) and stirred overnight at room temperature. The reaction mixture was concentrated in a vacuum and filtered twice with methanol. Then, the filtrate was concentrated in a vacuum to give an oil. This crude mixture was purified by silica gel column chromatography using 7% DCM/MeOH to afford Compound 55-2-C as a yellow oil (380 mg, mixture).

Step 2: Synthesis of 2-amino-N-(2,6-dioxopiperidin-3-yl)-5-hydroxybenzamide (Compound 55-2-D)

A solution of Compound 55-2-C (380 mg, 1.08 mmol) in MeOH (4 mL) was added with 10% Pd/C (38 mg) and stirred overnight at room temperature in a hydrogen gas atmosphere. The solution was filtered through a celite pad, followed by removal in a vacuum to give an oil. This crude mixture was purified by silica gel column chromatography using 7% DCM/MeOH to afford Compound 55-2-D as a yellow solid (105 mg, 0.399 mmol, 37%).

Step 3: Synthesis of tert-butyl 2-((3-(2,6-dioxopiperidin-3-yl)-4-oxo-3,4-dihydrobenzo[d][1,2,3]triazin-6-yl)oxy)acetate (Compound 55-2-F)

A solution of Compound 55-2-D (48 mg, 0.175 mmol) in DMF (1 mL) was added with Compound 55-2-E (TCI, B1473) (tert-butyl bromoacetate; 0.026 mL, 0.175 mmol) and potassium carbonate (36 mg, 0.262 mmol) and stirred at room temperature for 3 hours. The reaction mixture was quenched with H$_2$O, followed by extraction with EtOAc. The pooled organic layer was dried over MgSO$_4$ and the solvent was removed in a vacuum. The crude mixture was purified by silica gel column chromatography (MPLC, Hex/EtOAc 55%) to afford Compound 55-2-F as a white solid (33 mg, 0.085 mmol, 48%).

Step 4: Synthesis of 2-((3-(2,6-dioxopiperidin-3-yl)-4-oxo-3,4-dihydrobenzo[d][1,2,3]triazin-6-yl)oxy)acetic acid (Compound 55-2)

A solution of Compound 55-2-F (30 mg, 0.077 mmol) in 40% TFA/DCM (0.7 mL) was stirred at room temperature for 1 hour. The reaction mixture was concentrated in a vacuum to afford Compound 55-2 as a white solid (33 mg, crude).

Step 5: Synthesis of 3-(6-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethoxy)-4-oxobenzo[d][1,2,3]triazin-3 (4H)-yl)piperidin-2,6-one (Compound 55)

A solution of Compound 55-2 (6.6 mg, 0.021 mmol) in DMF (1 mL) was added at room temperature with HATU (22 mg, 0.057 mmol), Compound 55-1 (identical to Compound 43-4) (10 mg, 0.019 mmol), and TEA (6.0 mg, 0.057 mmol), and the mixture was stirred at room temperature for 16 hours. The reaction mixture was added with water, subjected to extraction with EA, and washed with water and brine. Then, the organic layer was concentrated in a vacuum to give a crude material which was then purified by MPLC to afford Compound 55 as a brown solid (5.0 mg).

Compound 56. 5-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-(2,6-dioxopiperidin-3-yl)isoindoline-1,3-dione

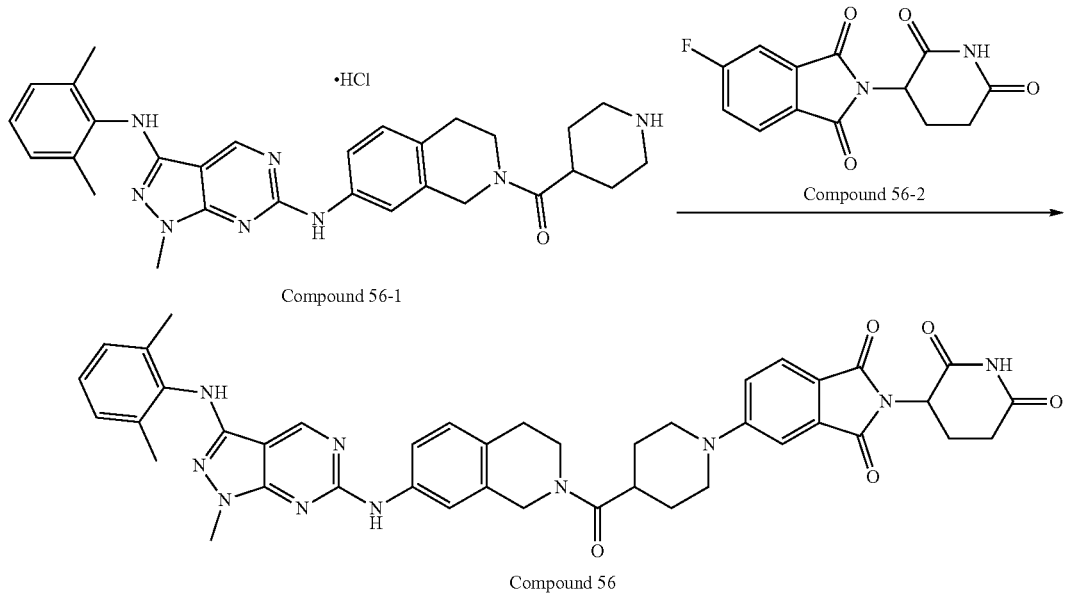

A solution of Compound 56-2 (WO 2020/162725) (5.2 mg, 0.019 mmol) in DMSO (2 mL) was added at room temperature with Compound 56-1 (identical to Compound 43-4) (10 mg, 0.019 mmol) and DIPEA (12 mg, 0.095 mmol). The mixture was stirred at 90° C. for 3 hours. The reaction mixture was added with water, subjected to extraction with EA, and washed with water and brine. Then, the organic layer was concentrated in a vacuum to give a crude material which was then purified by MPLC to afford Compound 56 as a yellow solid (6.0 mg).

Compound 57. 3-(6-((2-(4-(7-((3-((2,6-Dimethylphenyl)amino)-1-methyl-1H-pyrazolo[3,4-d])pyrimidin-6-yl)amino)-1,2,3,4-tetrahydroisoquinoline-2-carbonyl)piperidin-1-yl)-2-oxoethyl)amino)-4-oxobenzo[d][1,2,3]triazin-3 (4H)-yl)piperidin-2,6-one

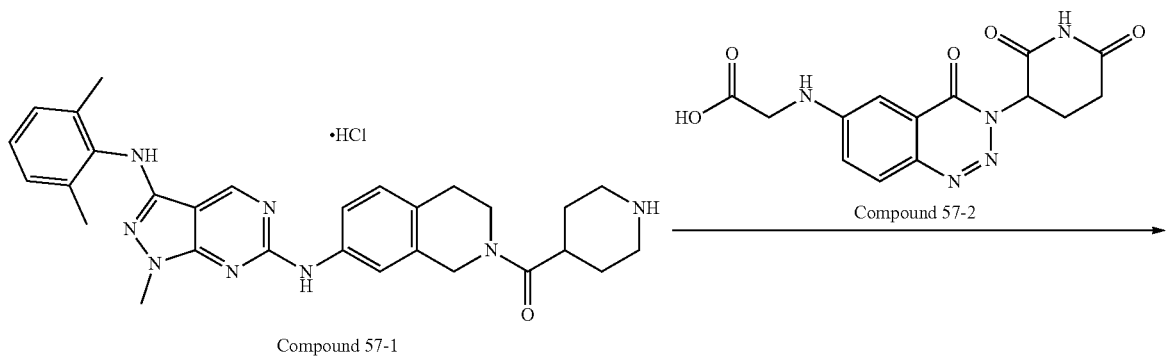

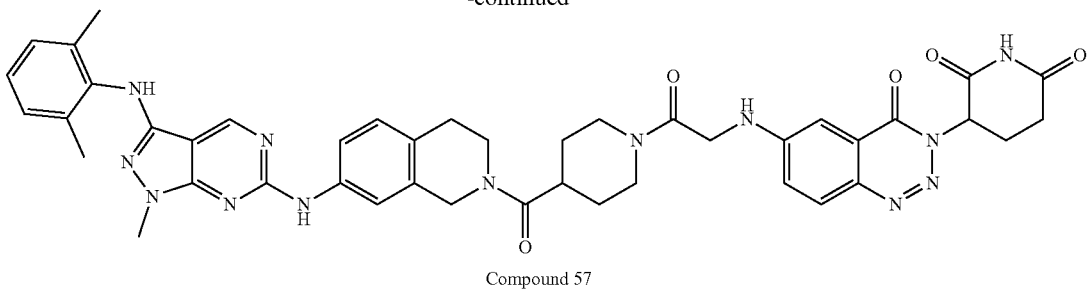

Compound 57

A solution of Compound 57-2 (WO 2020/162725) (6.9 mg, 0.021 mmol) in DMF (1 mL) was added at room temperature with HATU (22 mg, 0.057 mmol), Compound 57-1 (identical to Compound 43-4) (10 mg, 0.019 mmol), and TEA (6.0 mg, 0.057 mmol) and stirred at room temperature for 16 hours. The reaction mixture was added with water, subjected to extraction with EA, and washed with water and brine. Then, the organic layer was concentrated in a vacuum to give a crude material which was then purified by MPLC to afford Compound 57 as a brown solid (5.0 mg).

Compound 58. 3-(6-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3 (4H)-yl)piperidin-2,6-one

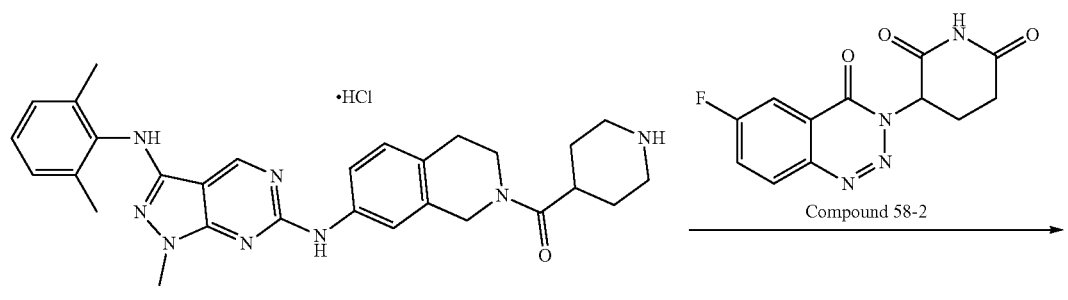

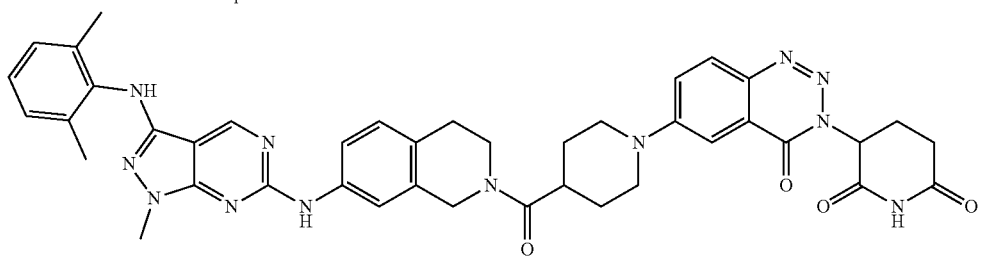

Compound 58

A solution of Compound 58-2 (WO 2020/162725) (5.8 mg, 0.021 mmol) in DMSO (1 mL) was added at room temperature with Compound 58-1 (identical to Compound 43-4) (10 mg, 0.019 mmol) and DIPEA (7.4 mg, 0.057 mmol). The resulting mixture was stirred at 90° C. for 12 hours. The reaction mixture was added with water, subjected to extraction with EA, and washed with water and brine. Then, the organic layer was concentrated in a vacuum to give a crude material which was then purified by MPLC to afford Compound 58 as an off-white solid (6.0 mg).

Compound 59. 3-(5-(4-(7-((3-((2,6-Dimethylphenyl))amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3(4H)-yl)piperidin-2,6-one

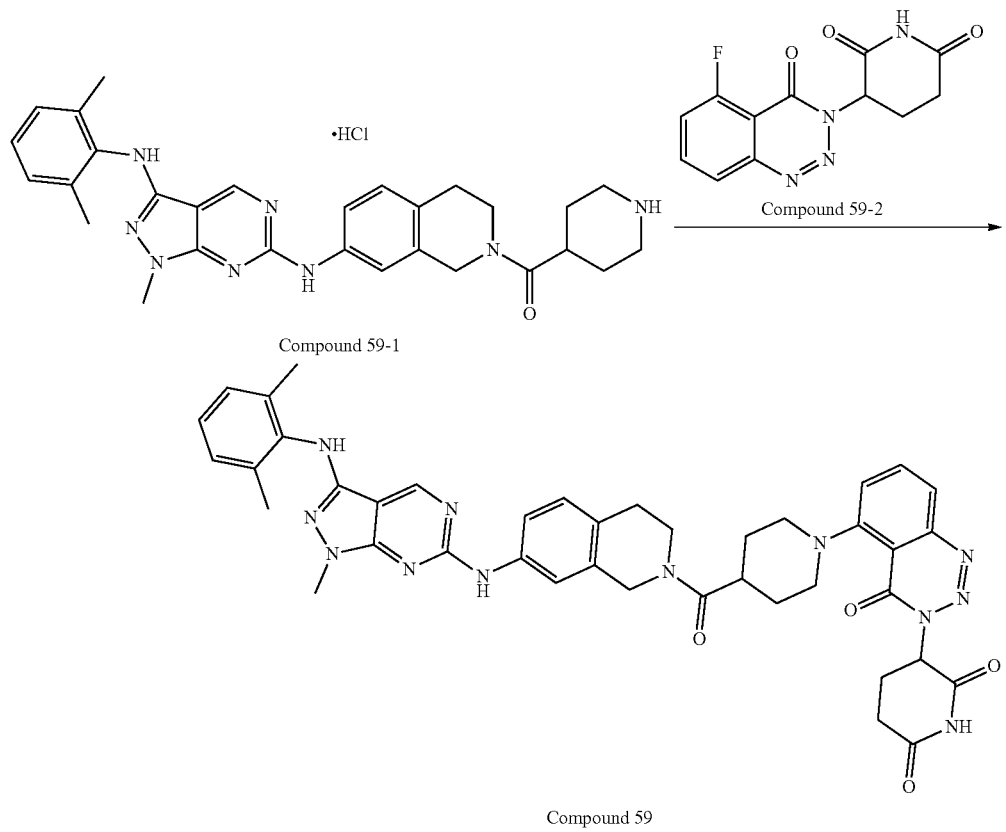

A solution of Compound 59-2 (WO 2020/162725) (5.8 mg, 0.021 mmol) in DMSO (1 mL) was added at room temperature with Compound 59-1 (identical to Compound 43-4) (10 mg, 0.019 mmol) and DIPEA (7.4 mg, 0.057 mmol). The resulting mixture was stirred at 90° C. for 12 hours. The reaction mixture was added with water, subjected to extraction with EA, and washed with water and brine. Then, the organic layer was concentrated in a vacuum to give a crude material which was then purified by MPLC to afford Compound 59 as a yellow solid (12 mg).

Compound 60. 3-(7-(4-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidine-1-carbonyl)piperidin-1-yl)-4-oxobenzo[d][1,2,3]triazin-3 (4H)-yl)piperidin-2,6-one

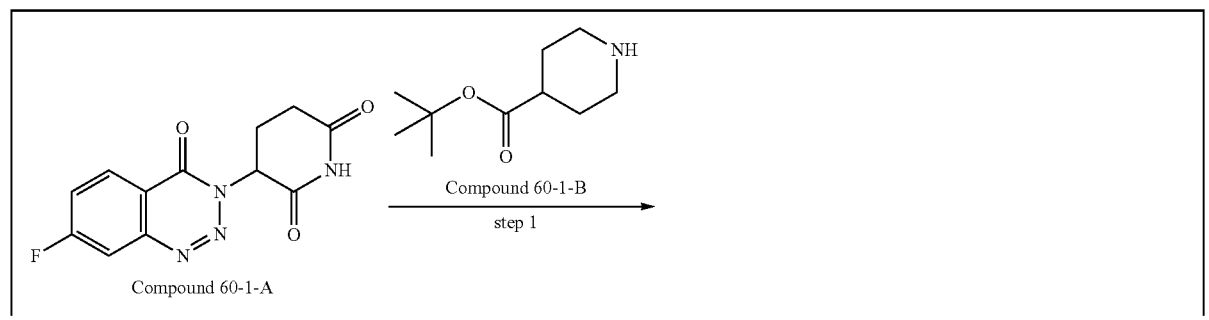

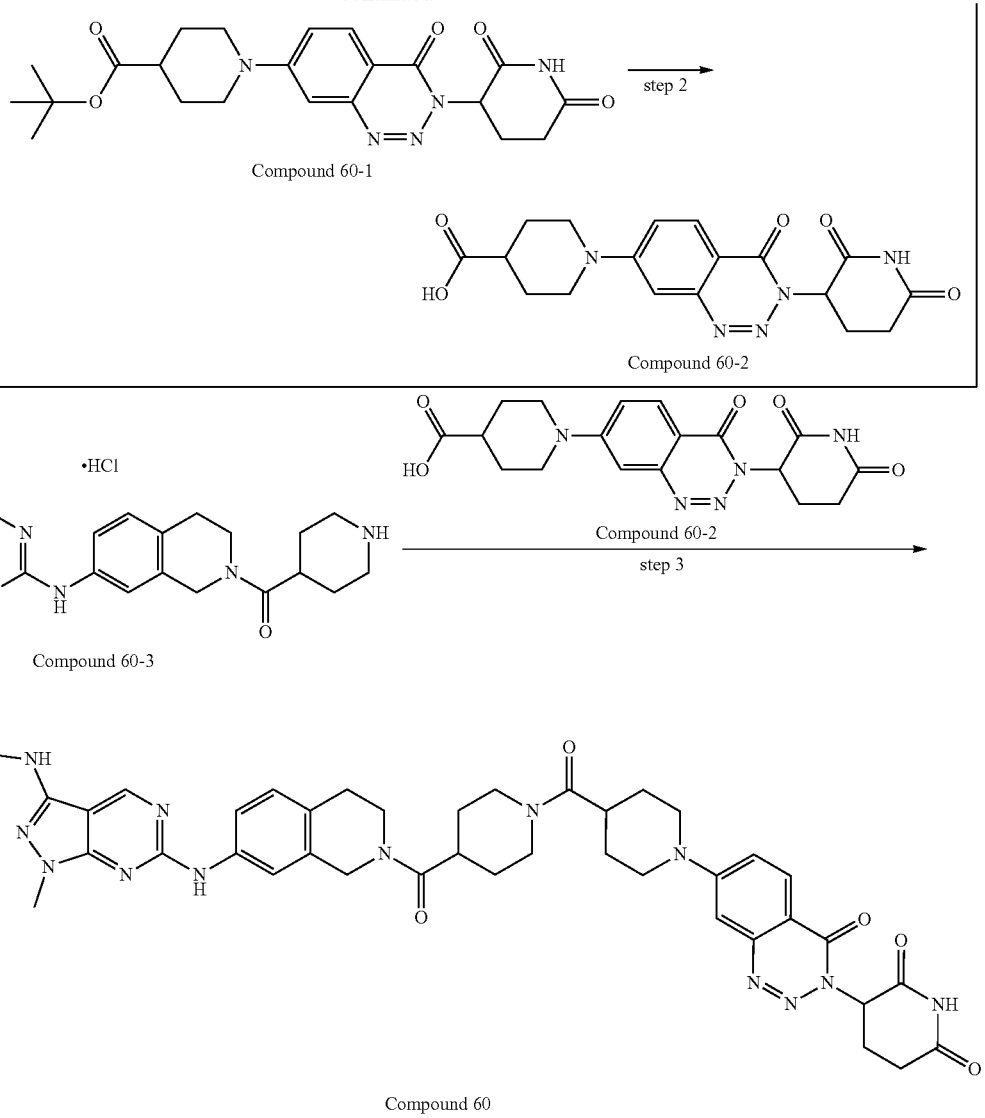

Compound 60

Step 1: Synthesis of tert-butyl 1-(3-(2,6-dioxopiperidin-3-yl)-4-oxo-3,4-dihydrobenzo[d][1,2,3]triazin-7-yl)piperidine-4-carboxylate (Compound 60-1)

A solution of Compound 60-1-A (identical to Compound 53-2) (1.0 g, 3.62 mmol) in DMSO (10 mL) was added with Compound 60-1-B (TCI, B3873) (tert-butyl piperidine-4-carboxylate; 1.06 g, 5.43 mmol) and DIPEA (1.9 mL, 10.8 mmol). The resulting mixture was stirred at 90° C. for 2 hours. The reaction mixture was quenched with water before extraction with DCM (25 ml×2). The organic layer was washed with saturated brine. The pooled layer was concentrated in a vacuum to give a crude mixture which was then purified by column chromatography using MeOH/DCM to afford Compound 60-1 as a yellow solid (1.1 g, 2.49 mmol, 69%).

Step 2: Synthesis of 1-(3-(2,6-dioxopiperidin-3-yl)-4-oxo-3,4-dihydrobenzo[d][1,2,3]triazin-7-yl)piperidine-4-carboxylic acid (Compound 60-2)

A solution of Compound 60-1 (100 mg, 0.226 mmol) in DCM (1 mL) was added with TFA (0.25 mL) and stirred at room temperature for 1 hour. After completion of the reaction, the solvent was evaporated to give the free base Compound 60-2 as a yellow fluffy solid (80.0 mg).

Step 3: Synthesis of 3-(7-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidine-1-carbonyl)piperidin-1-yl)-4-oxobenzo[d][1,2,3]triazin-3 (4H)-yl)piperidin-2,6-one (Compound 60)

A solution of Compound 60-2 (8.5 mg, 0.022 mmol) in DMF (1 mL) was added at 30° C. with Compound 60-3 (identical to Compound 43-4) (10 mg, 0.019 mmol), HATU (23 mg, 0.060 mmol), and TEA (6.0 mg, 0.060 mmol). The mixture was stirred at 30° C. for 12 hours. When the product was formed as analyzed by TLC, the reaction mixture was added with water, subjected to extraction with EA (20 mL×3), and washed with water (3×) and brine. The pooled organic layer was dried over sodium sulfate and purified by MPLC using 10% MeOH/MC to afford Compound 60 as a yellow solid (6.0 mg, 0.015 mmol, 40%).

Compound 61. 3-(7-(4-(4-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-one

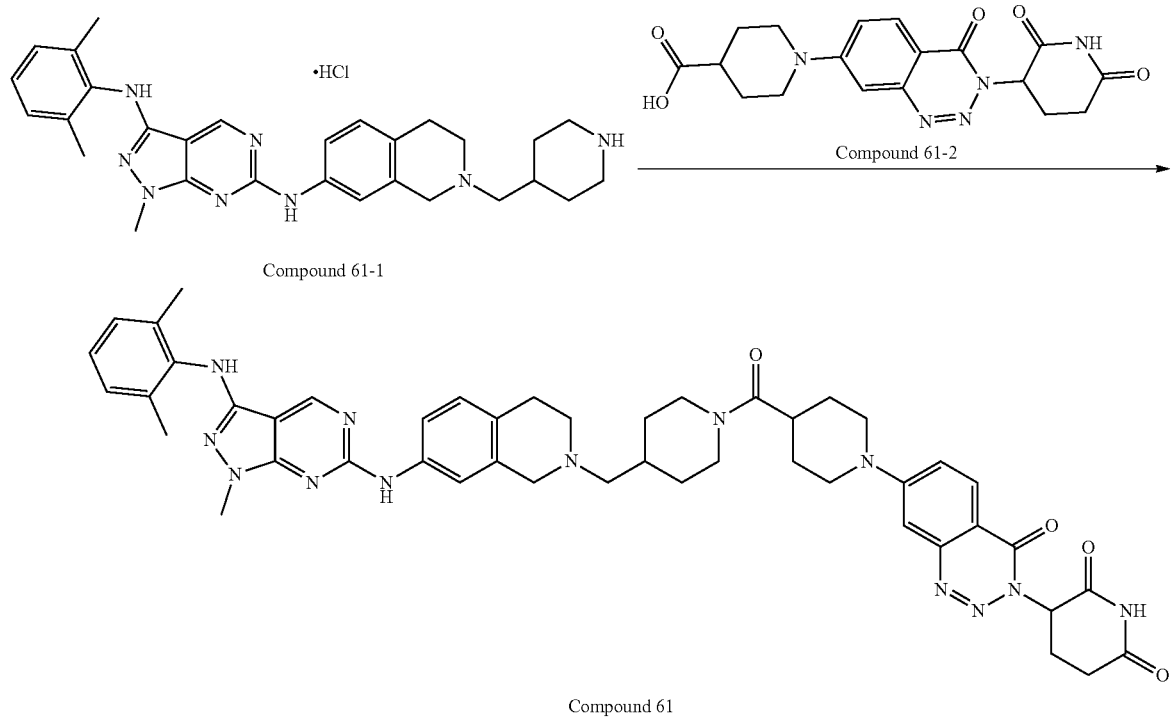

A solution of Compound 61-2 (identical to Compound 60-2) (8.5 mg, 0.022 mmol) in DMF (1 mL) was added at 30° C. with Compound 61-1 (identical to Compound 29-1) (10 mg, 0.019 mmol), HATU (23 mg, 0.060 mmol), and TEA (6.0 mg, 0.060 mmol), and the resulting mixture was stirred at 30° C. for 12 hours. When the product was formed as analyzed by TLC, the reaction mixture was added with water, subjected to extraction with EA (20 mL×3), and washed with water (3×) and brine. The pooled organic layer was dried over sodium sulfate and purified by MPLC using 10% MeOH/MC to afford Compound 61 as a yellow solid (7.0 mg, 0.015 mmol, 42%).-

Compound 62. 3-(5-(4-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-one
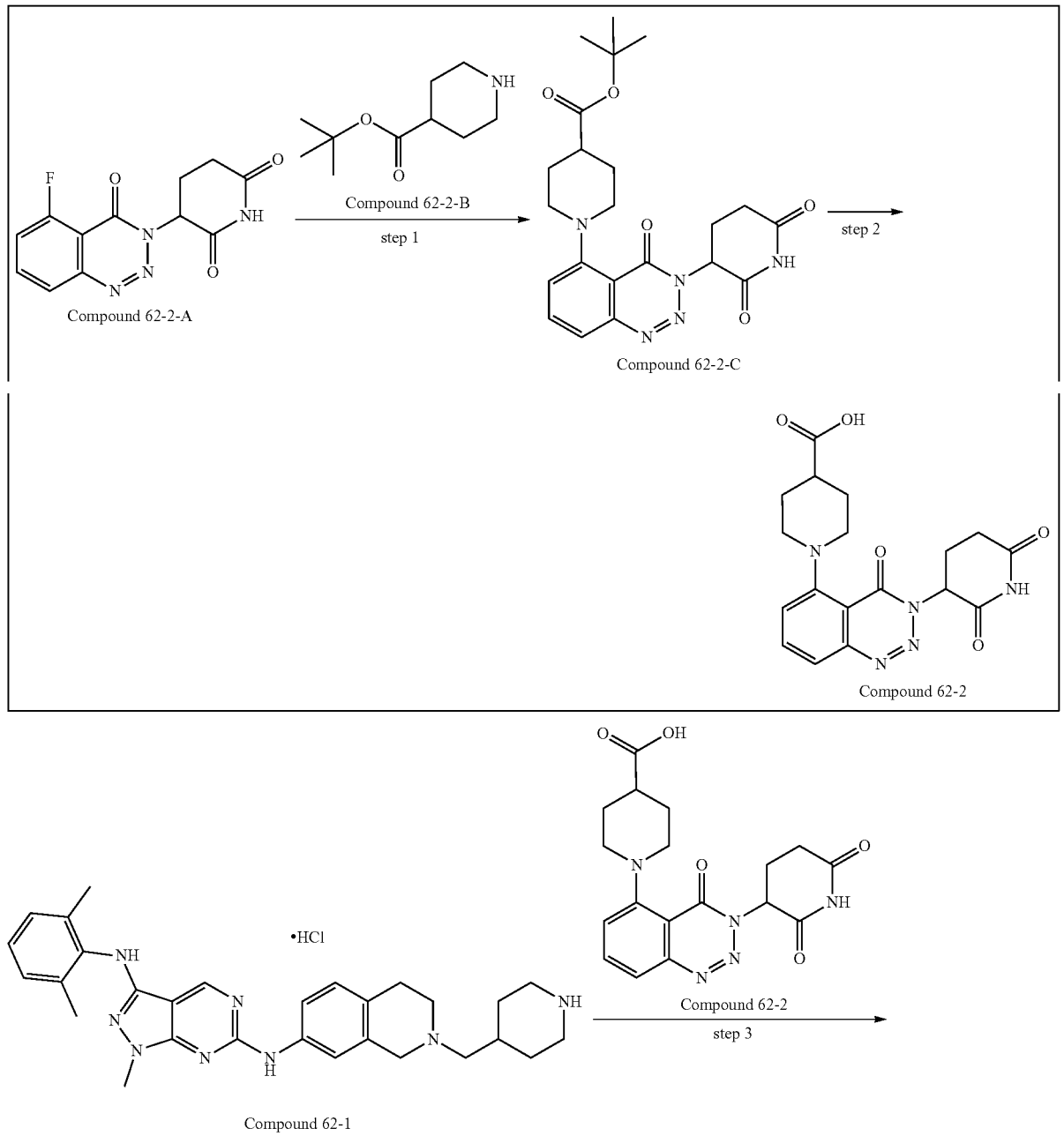

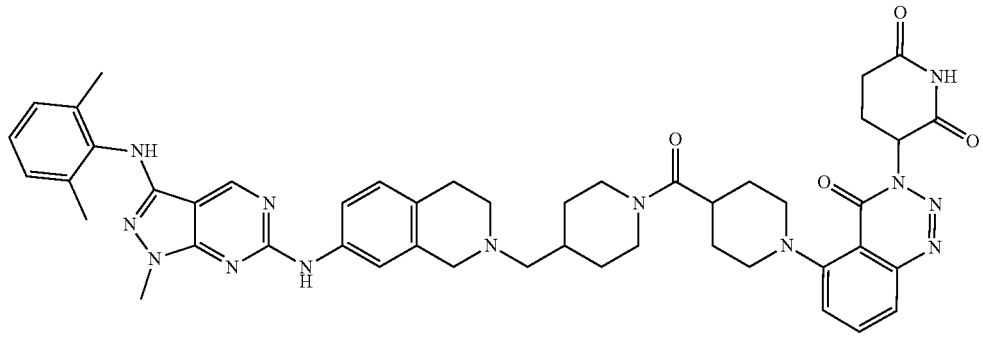

Compound 62

Step 1: Synthesis of tert-butyl 1-(3-(2,6-dioxopiperidin-3-yl)-4-oxo-3,4-dihydrobenzo[d][1,2,3]triazin-5-yl)piperidine-4-carboxylate (Compound 62-2-C)

A solution of Compound 62-2-A (WO 2020/162725) (1.0 g, 3.62 mmol) in DMSO (10 mL) was added with Compound 62-2-B (TCI, B3873) (tert-butylpiperidine-4-carboxylate; 1.06 g, 5.43 mmol) and DIPEA (1.9 mL, 10.8 mmol) and the resulting mixture was stirred at 90° C. for 2 hours. The reaction mixture was quenched with water, subjected to extraction with DCM (25 mL×2), and washed with a saturated brine solution. The pooled organic layer was dried over sodium sulfate to give a crude mixture which was then purified by column chromatography using MeOH/DCM to afford Compound 62-2-C as a yellow solid (1.1 g, 2.49 mmol, 69%).

Step 2: Synthesis of 1-(3-(2,6-dioxopiperidin-3-yl)-4-oxo-3,4-dihydrobenzo[d][1,2,3]triazin-5-yl)piperidine-4-carboxylic acid (Compound 62-2)

A solution of Compound 62-2-C (100 mg, 0.226 mmol) in DCM (1 mL) was added with 4 N HCl/1,4-dioxane (1.0 mL) and stirred at room temperature for 3 hours. After completion of the reaction, the solvent was evaporated. The residue was neutralized with NaHCO₃ (aq) before extraction with DCM to afford Compound 62-2 as a yellow solid (80.0 mg).

Step 3: Synthesis of 3-(5-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-one (Compound 62)

A solution of Compound 62-2 (8.4 mg, 0.022 mmol) in DMF (1 mL) was added at 30° C. with HATU (22 mg, 0.057 mmol), Compound 62-1 (identical to Compound 29-1) (10 mg, 0.020 mmol) and TEA (6.0 mg, 0.057 mmol) and the resulting mixture was stirred at 30° C. for 12 hours. The reaction mixture was added with water, followed by extraction with DCM. The organic layer was washed with water and brine and concentrated in a vacuum to give a crude material which was then purified by MPLC to afford Compound 62 as an off-white solid (5.0 mg).

Compound 63. 3-(7-((2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-4-oxobenzo[d][1,2,3]triazin-3 (4H)-yl)piperidin-2,6-one

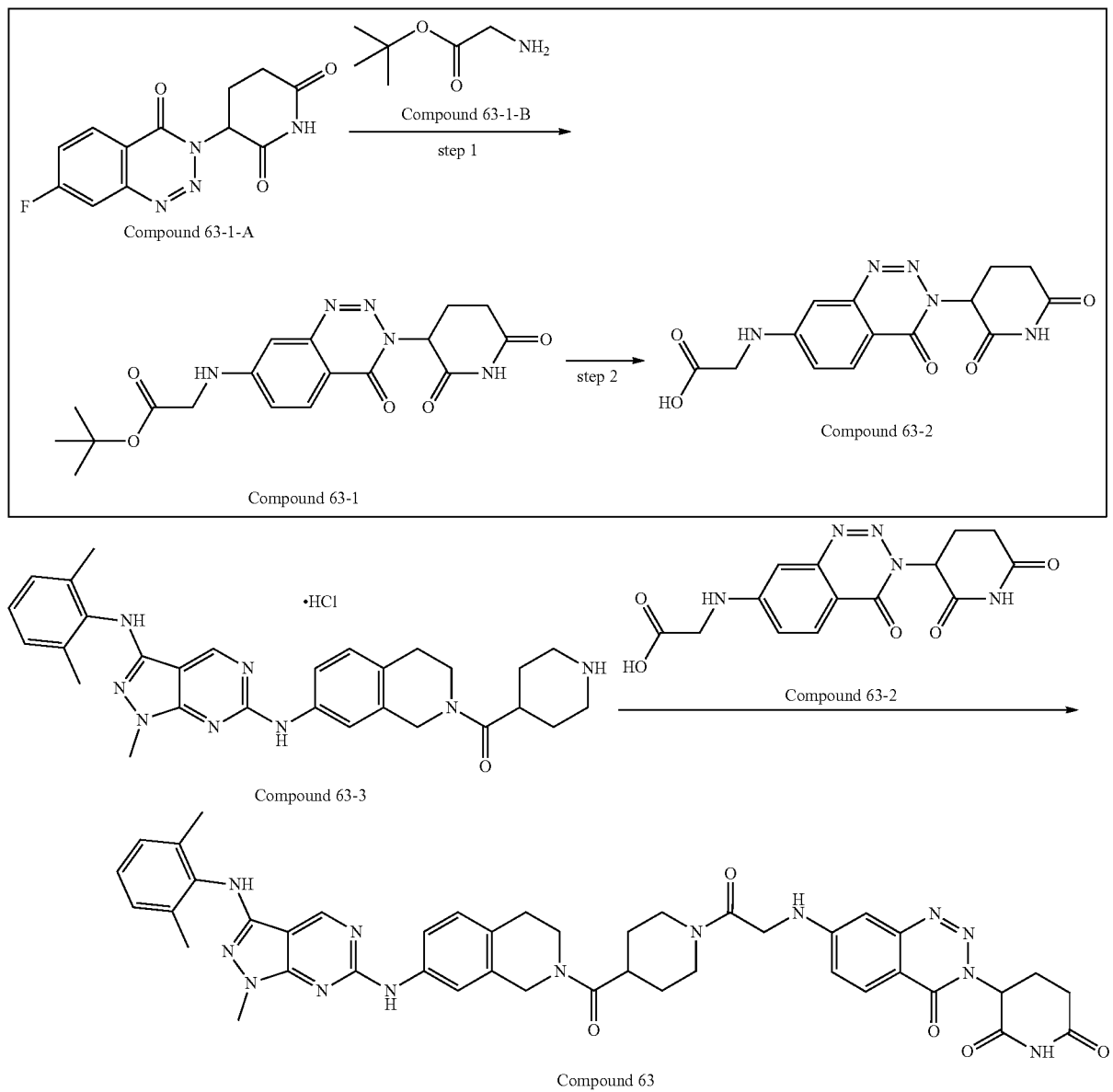

Step 1: Synthesis of tert-butyl (3-(2,6-dioxopiperidin-3-yl)-4-oxo-3,4-dihydrobenzo[d][1,2,3]triazin-7-yl)glycinate (Compound 63-1)

A solution of Compound 63-1-A (identical to Compound 53-2) (90 mg, 0.325 mmol) in DMSO (2 mL) was added with Compound 63-1-B (BLDPharm, BD22001) (tert-butyl glycinate; 64 mg, 0.487 mmol) and DIPEA (0.17 mL, 0.975 mmol). The resulting mixture was stirred at 90° C. for 2 hours. The reaction mixture was quenched with water before extraction with DCM (25 mL×2). The organic layer was washed with saturated brine. The pooled organic layer was concentrated in a vacuum to give a crude mixture which was then purified by column chromatography using MeOH/DCM to afford Compound 63-1 as a yellow solid (90 mg, 0.232 mmol, 71%).

Step 2: Synthesis of (3-(2,6-dioxopiperidin-3-yl)-4-oxo-3,4-dihydrobenzo[d][1,2,3]triazin-7-yl)glycine (Compound 63-2)

A solution of Compound 63-1 (50 mg, 120 mmol) in DCM (10 mL) was added with TFA/DCM (0.5 mL) and stirred at room temperature for 1 hour. After completion of the reaction, the solvent was evaporated. The residue was subjected to extraction with CHCl₃ and concentrated to afford Compound 63-2 as a yellow fluffy solid (38.0 mg).

Step 3: Synthesis of 3-(7-((2-(4-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-2-oxoethyl)amino)-4-oxobenzo[d][1,2,3]triazin-3 (4H)-yl)piperidin-2,6-one (Compound 63)

A solution of Compound 63-2 (7.2 mg, 0.022 mmol) in DMF (1 mL) was added at 30° C. with HATU (22 mg, 0.057 mmol), Compound 63-3 (identical to Compound 29-1) (10 mg, 0.019 mmol) and TEA (6.0 mg, 0.057 mmol) and the resulting mixture was stirred at room temperature for 12 hours. The reaction mixture was added with water before extraction with DCM. The organic layer was washed with water and brine and concentrated in a vacuum to give a crude material which was then purified by MPLC to afford Compound 63 as a brown solid (3.5 mg).

Compound 64. 3-(4-(3-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-3-oxopropyl)-1-oxoisoindolin-2-yl)piperidin-2,6-one

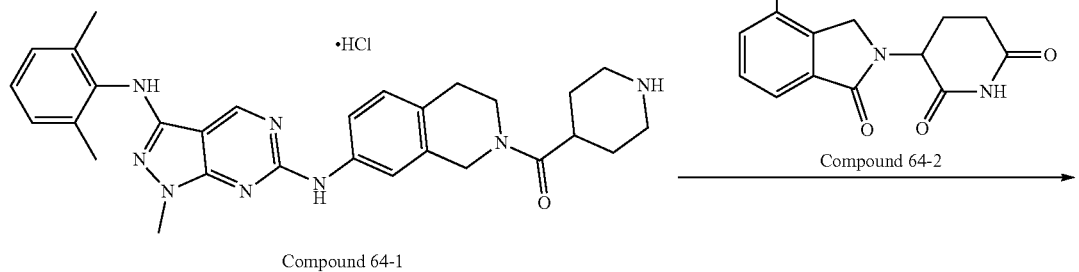

Compound 64-1

Compound 64-2

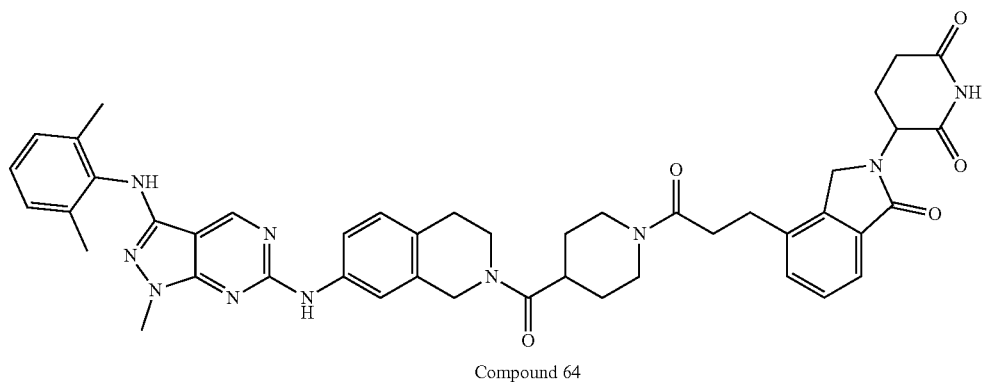

Compound 64

A solution of Compound 64-1 (identical to Compound 29-1) (10.0 mg, 0.020 mmol) in DMF (1 mL) was added with HATU (23.0 mg, 0.060 mmol), Compound 64-2 (WO 2020/051235) (6.3 mg, 0.020 mmol), and TEA (11.0 mg, 0.080 mmol) and the resulting mixture was stirred at room temperature for 12 hours. When the product was formed as analyzed by TLC, the reaction mixture was added with water, subjected to extraction with MC (30 mL×3), and washed with water (3×) and brine. The pooled organic layer was dried over sodium sulfate and purified by MPLC using 10% MeOH/MC to afford Compound 64 as a brown solid (7.0 mg, 0.0088 mmol, 44%).

Compound 65. 3-(4-(3-(7-((3-((2,6-Dimethylphenyl)amino)-1-methyl-1H-pyrazolo[3,4-d]pyrimidin-6-yl)amino)-3,4-dihydroisoquinolin-2(1H)-yl)-3-oxopropyl)-1-oxoisoindolin-2-yl)piperidin-2,6-one

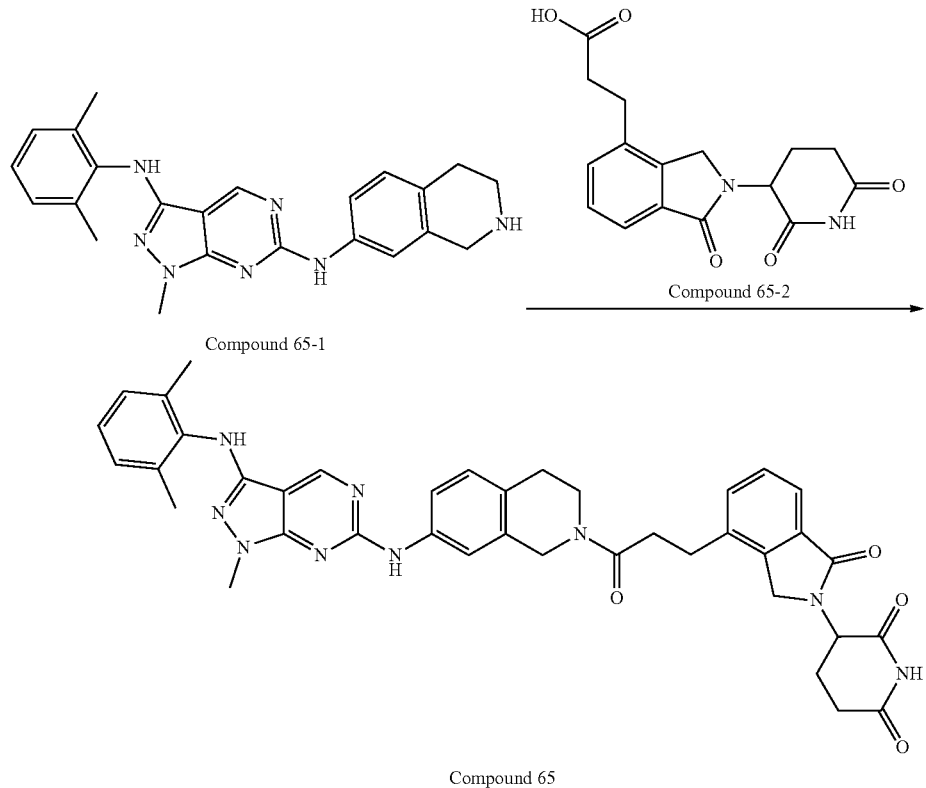

A solution of Compound 65-2 (WO 2020/051235) (10 mg, 0.032 mmol) in DMF (1 mL) was added with HATU (33 mg, 0.87 mmol), Compound 65-1 (Korean Patent No. 2128018) (10 mg, 0.029 mmol), and TEA (12 mg, 0.12 mmol) and the resulting mixture was stirred at room temperature for 12 hours. When the product was formed as analyzed by TLC, the reaction mixture was added with water, subjected to extraction with MC (30 mL×3), and washed with water (3×) and brine. The pooled organic layer was dried over sodium sulfate and purified by MPLC using 10% MeOH/MC to afford Compound 65 as a brown solid (9.0 mg, 0.012 mmol, 44%).

Compound 66. 5-(3-(7-((3-((2,6-Dimethylphenyl))amino)-1-methyl-1H-pyrazolo[3,4-d]pyrimidin-6-yl)amino)-1,2,3,4-tetrahydroisoquinoline-2-carbonyl)pyrrolidin-1-yl)-2-(2,6-dioxopiperidin-3-yl)isoindoline-1,3-dione

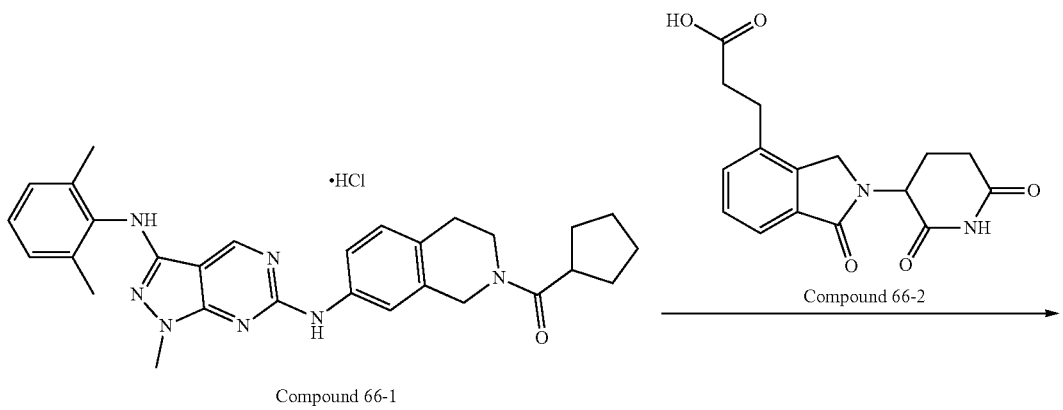

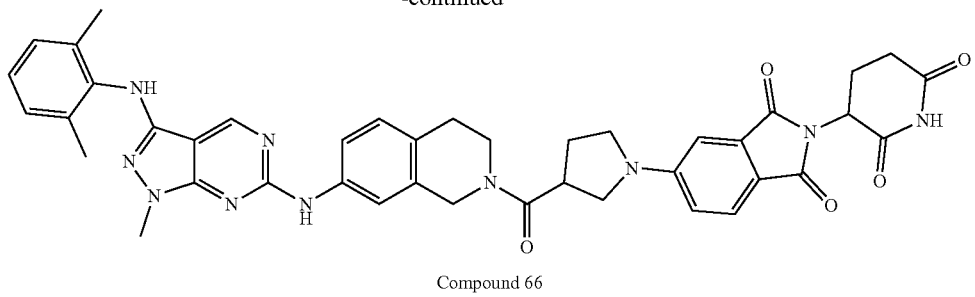

Compound 66

A solution of Compound 66-2 (Combi-Blocks, HD-3240) (7.73 mg, 0.028 mmol) in DMSO (1 mL) was added with Compound 66-1 (identical to Compound 67-4) (15.0 mg, 0.028 mmol) and DIPEA (14.5 mg, 0.11 mmol) and the resulting mixture was stirred at 90° C. for 6 hours. When the product was formed as analyzed by TLC, the reaction mixture was added with water, subjected to extraction with EA (50 mL×3), and washed with water (3×) and brine. The pooled organic layer was dried over sodium sulfate and purified by MPLC using 10% MeOH/MC to afford Compound 66 as a yellow solid (4.0 mg, 0.053 mmol, 18%).

Compound 67. 5-(4-(3-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl)isoindoline-1,3-dione

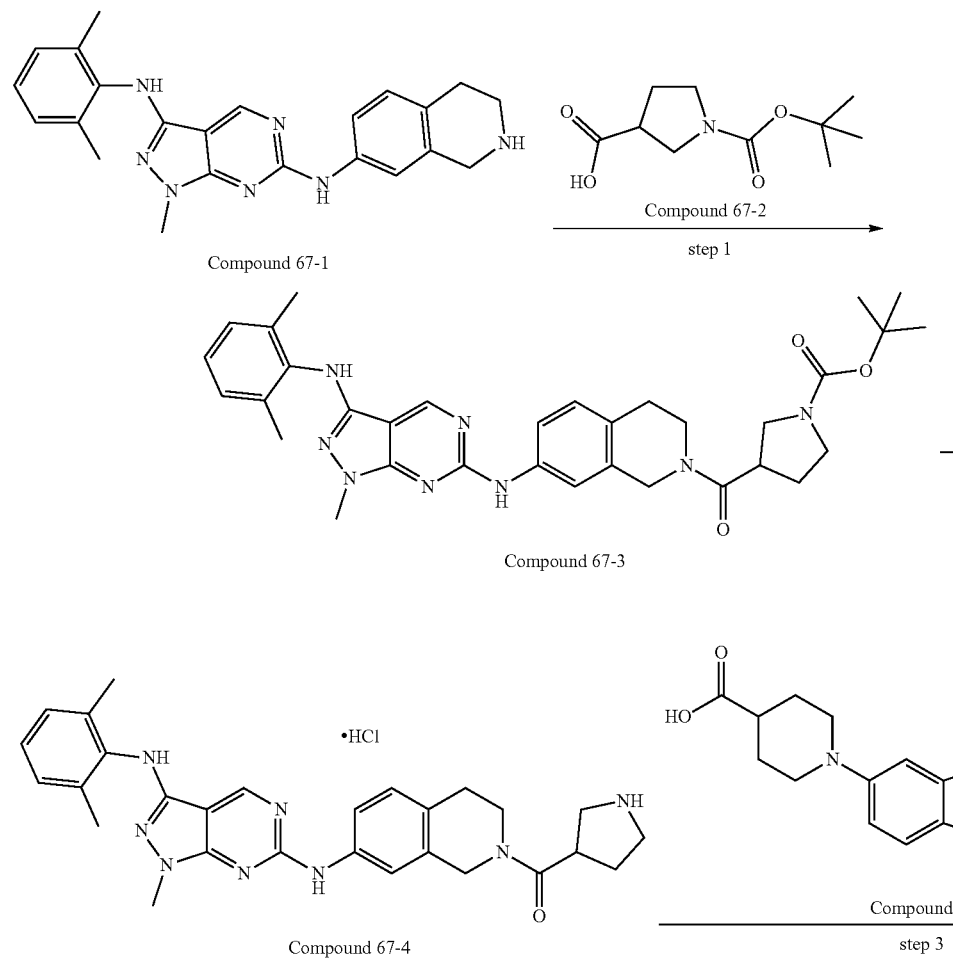

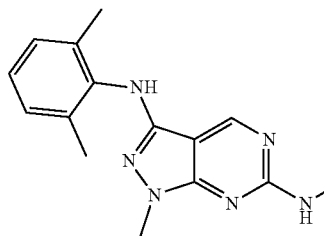

Compound 67

Step 1: Synthesis of tert-butyl 3-(7-((3-(2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carboxylate (Compound 67-3)

A solution of Compound 67-2 (Sigma Aldrich, 706590) (1-(tert-butoxycarbonyl)pyrrolidine-3-carboxylic acid; 30.0 mg, 0.137 mmol) in DMF (1 mL) was added with HATU (143 mg, 0.375 mmol), Compound 67-1 (Korean Patent No. 2128018) (50.0 mg, 0.125 mmol), and TEA (50.5 mg, 0.500 mmol) and the resulting mixture was stirred at room temperature for 12 hours. The reaction mixture was added with water, subjected to extraction with EA, and washed with water and brine. Then, the organic layer was concentrated in a vacuum to give a crude material which was then purified by MPLC to afford Compound 67-3 as a brown solid (71 mg).

Step 2: Synthesis of N3-(2,6-dimethylphenyl)-1-methyl-N6-(2-(piperidin-4-ylmethyl)-1,2,3,4-tetrahydroisoquinolin-7-yl)-1H-pyrazolo[3,4-d]pyrimidine-3,6-diamine hydrochloride (Compound 67-4)

A solution of Compound 67-3 (60.0 mg, 0.100 mmol) in DCM (1.0 mL) was added with 4 N—HCl/dioxane (0.5 mL) and stirred at room temperature for 1 hour. After completion of the reaction, the solvent was evaporated and the residual dioxane layer was subjected to extraction with CHCl$_3$. The reaction mixture was neutralized with an aqueous sodium bicarbonate solution before extraction with DCM. The organic layer was concentrated in a vacuum to afford Compound 67-4 as a yellow fluffy solid (45 mg).

Step 3: Synthesis of 5-(4-(3-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl)isoindoline-1,3-dione (Compound 67)

A solution of Compound 67-4 (10.7 mg, 0.0281 mmol) in DMF (1 mL) was added with HATU (31.9 mg, 0.0843 mmol), Compound 67-5 (WO 2020/162725) (15.0 mg, 0.0281 mmol), and TEA (14.5 mg, 0.112 mmol) and the resulting mixture was stirred at room temperature for 4 hours. The reaction mixture was added with water, subjected to extraction with EA, and washed with water and brine. Then, the organic layer was concentrated in a vacuum to give a crude material which was then purified by MPLC to afford Compound 67 as a white solid (6.0 mg).

Compound 68. 3-(7-((2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)amino)-4-oxobenzo[d][1,2,3]triazin-3 (4H)-yl)piperidin-2,6-one

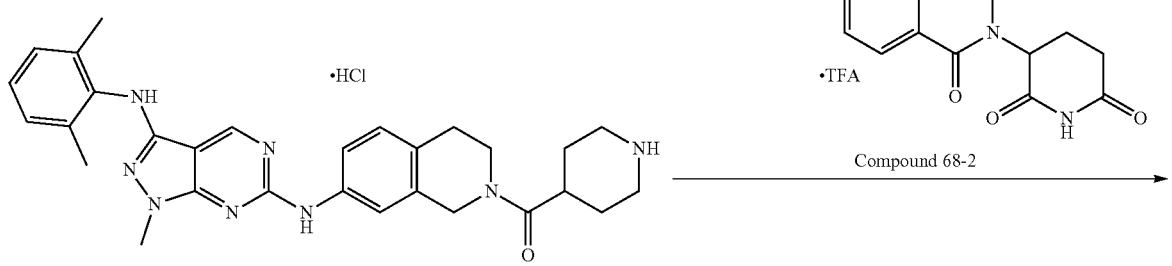

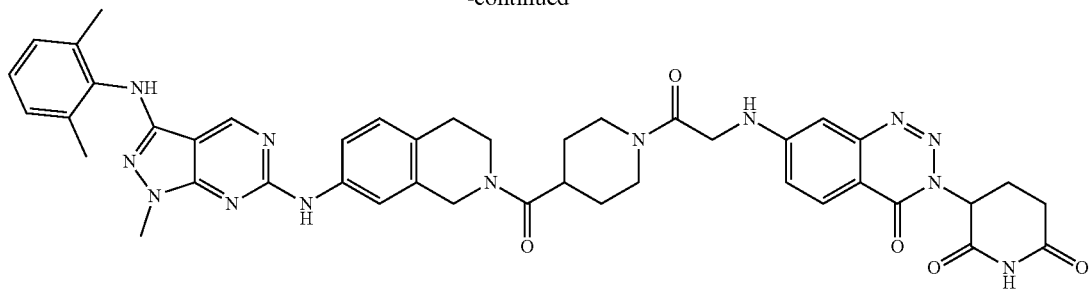

Compound 68

A solution of Compound 68-2 (identical to Compound 63-2) (9.3 mg, 0.021 mmol) in DMF (1 mL) was added at room temperature with HATU (22 mg, 0.057 mmol), Compound 68-1 (identical to Compound 43-4) (10 mg, 0.019 mmol), and TEA (6.0 mg, 0.057 mmol) and the resulting mixture was stirred at room temperature for 16 hours. The reaction mixture was added with water, subjected to extraction with EA, and washed with water and brine. Then, the organic layer was concentrated in a vacuum to give a crude material which was then purified by MPLC to afford Compound 68 as a yellow solid (10.8 mg).

Compound 69. 3-(7-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3 (4H)-yl)piperidin-2,6-one

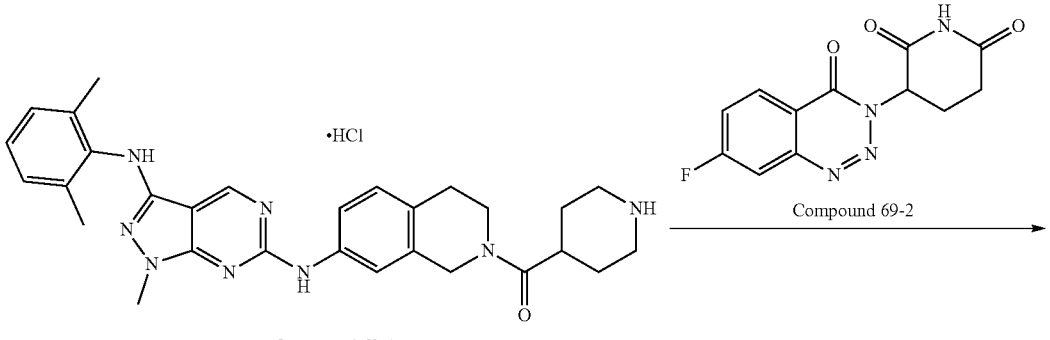

Compound 69-1

Compound 69-2

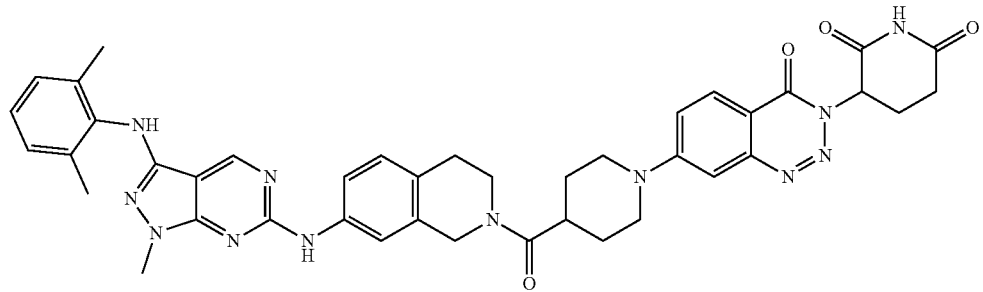

Compound 69

A solution of Compound 69-2 (identical to Compound 53-2) (5.8 mg, 0.019 mmol) in DMSO (1 mL) was added at room temperature with Compound 69-1 (identical to Compound 43-4) (10 mg, 0.019 mmol) and DIPEA (12 mg, 0.095 mmol) and the resulting mixture was stirred at 90° C. for 3 hours. The reaction mixture was added with water, subjected to extraction with EA, and washed with water and brine. Then, the organic layer was concentrated in a vacuum to give a crude material which was then purified by MPLC to afford Compound 69 as a yellow solid (4.5 mg).

Compound 70. 5-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-(2,6-dioxopiperidin-3-yl)isoindoline-1,3-dione

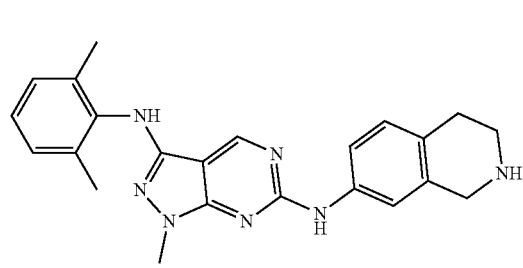

Compound 70-1

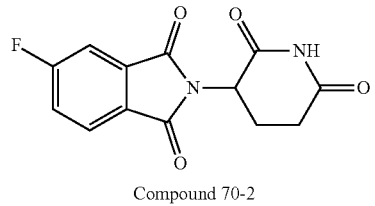

Compound 70-2

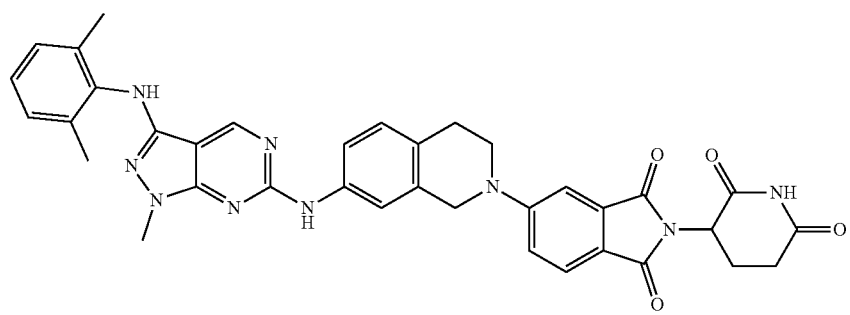

Compound 70

A solution of Compound 70-2 (Combi-Blocks, HD-3240) (11.1 mg, 0.0402 mmol) in DMSO (0.5 mL) was added at room temperature with Compound 70-1 (Korean Patent No. 2128018) (20.0 mg, 0.0402 mmol) and DIPEA (16.0 mg, 0.120 mmol) and the resulting mixture was stirred at 90° C. for 6 hours. When the product was formed as analyzed by TLC, the reaction mixture was added with water, subjected to extraction with EA (10 mL×3), and washed with water (3×) and brine. The pooled organic layer was dried over sodium sulfate and purified by MPLC using 10% MeOH/MC (elution at 4%) to afford Compound 70 as a fluorescent green solid (20.0 mg, 0.0305 mmol, 75%).

Compound 71. 3-(7-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-4-oxobenzo[d][1,2,3]triazin-3 (4H)-yl)piperidin-2,6-one

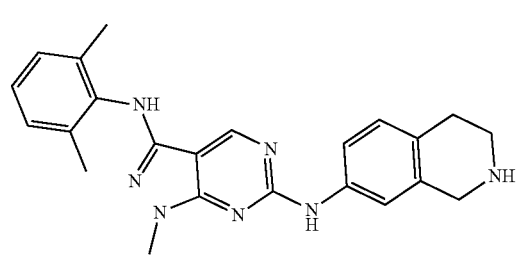

Compound 71-1

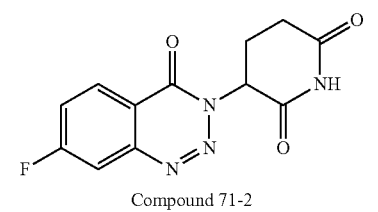

Compound 71-2

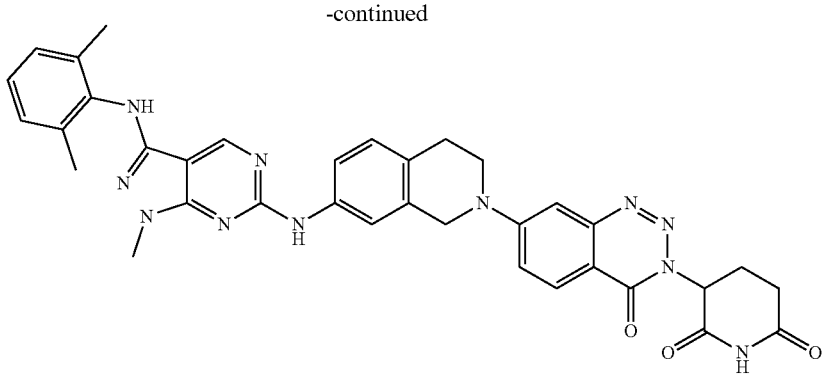

Compound 71

A solution of Compound 71-2 (identical to Compound 53-2) (11.1 mg, 0.0402 mmol) in DMSO (0.5 mL) was added at room temperature with Compound 71-1 (Korean Patent No. 2128018) (20.0 mg, 0.0402 mmol) and DIPEA (16.0 mg, 0.120 mmol) and the resulting mixture was stirred at 90° C. for 6 hours. When the product was formed as analyzed by TLC, the reaction mixture was added with water, subjected to extraction with EA (10 mL×3), and washed with water (3×) and brine. The pooled organic layer was dried over sodium sulfate and purified by MPLC using 5% MeOH/MC to afford Compound 71 as a fluorescent green solid (18.0 mg, 0.0274 mmol, 68%).

Compound 72. 5-((2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxo-ethyl)amino)-2-(2,6-dioxopiperidin-3-yl)isoindoline-1,3-dione A solution of Compound 72-1 (Korean Patent No. 2128018) (10.0 mg, 0.020 mmol) in DMF (1 mL) was added with HATU (23.0 mg, 0.060 mmol), Compound 72-2 (WO 2020/162725) (6.3 mg, 0.020 mmol), and TEA (11.0 mg, 0.080 mmol) and the resulting mixture was stirred at room temperature for 12 hours. When the product was formed as analyzed by TLC, the reaction mixture was added with water, subjected to extraction with EA (30 mL×3), and washed with water (3×) and brine. The pooled organic layer was dried over sodium sulfate and purified by MPLC using 10% MeOH/MC to afford Compound 72 as a neon green solid (30 mg, 0.042 mmol, 84%).

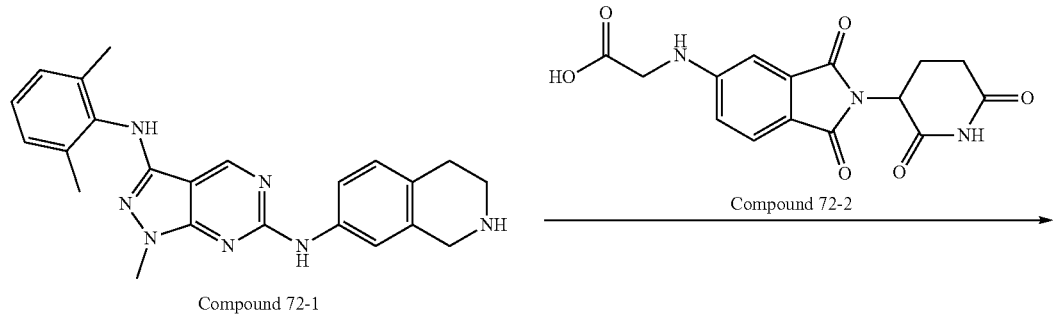

Compound 72-1

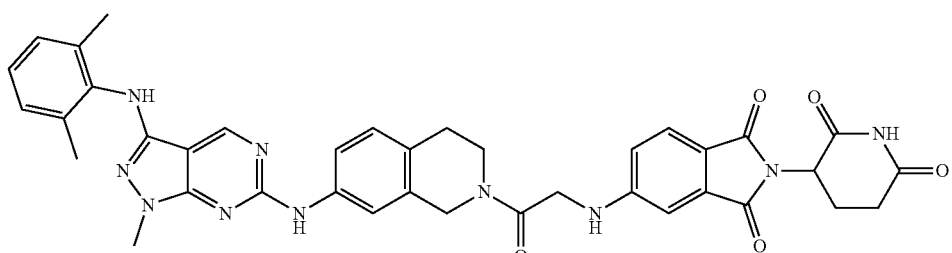

Compound 72

Compound 73. 5-(4-((5-((3-((2,6-Dimethylphenyl)amino)-1-methyl-1H-pyrazolo[3,4-d]pyrimidin-6-yl)amino)isoindolin-2-yl)methyl)piperidin-1-yl)-2-(2,6-dioxopiperidin-3-yl)isoindoline-1,3-dione

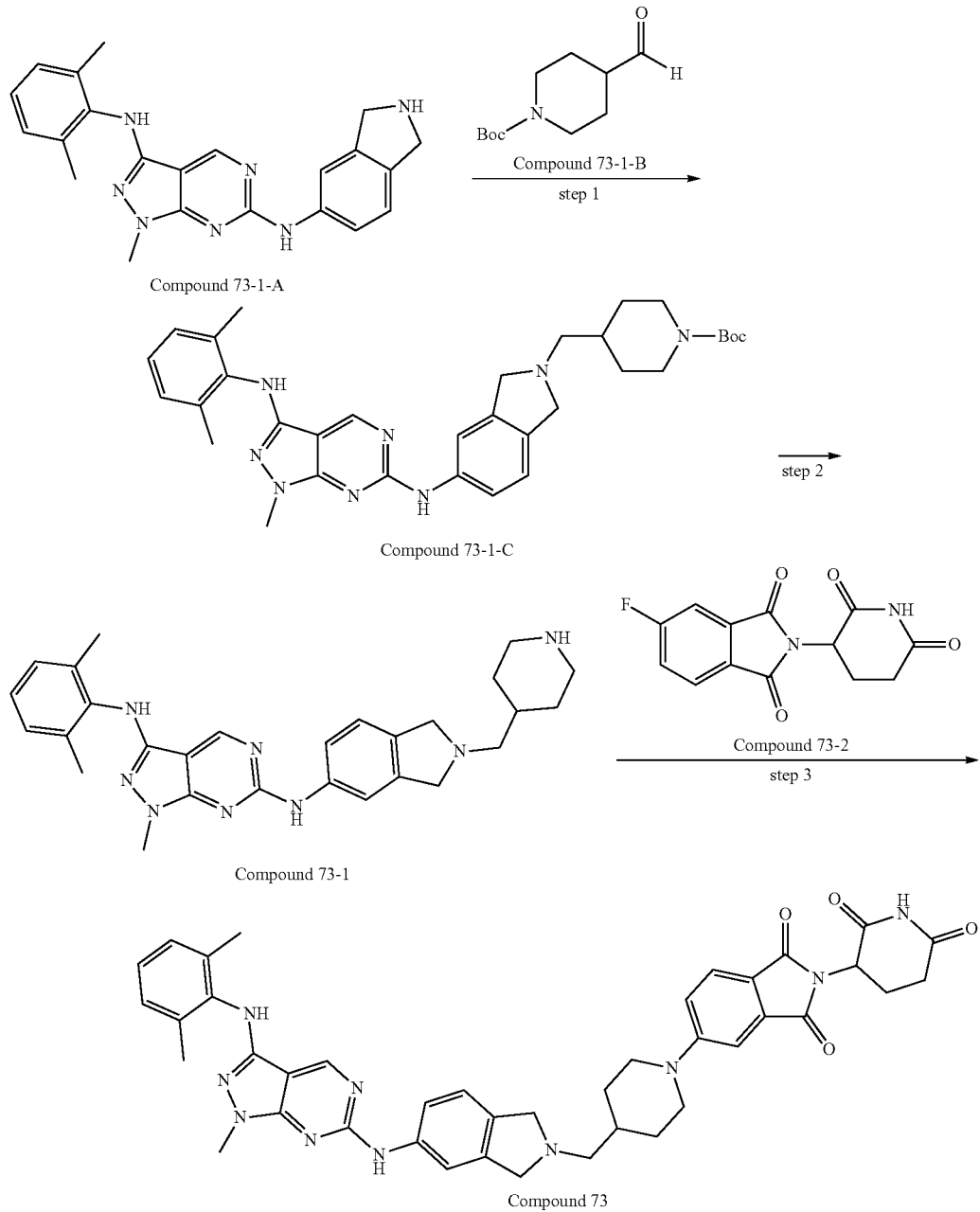

Step 1: Synthesis of tert-butyl 4-((5-((3-((2,6-dimethylphenyl)amino)-1-methyl-1H-pyrazolo[3,4-d]pyrimidin-6-yl)amino)isoindolin-2-yl)methyl)piperidine-1-carboxylate (Compound 73-1-C)

A solution of Compound 73-1-A (Korean Patent No. 2128018) (92.0 mg, 0.0239 mmol) in MeOH (1 mL) was added with Compound 73-1-B (TCI, B3873) (Boc-piperidine aldehyde; 56.0 mg, 0.263 mmol), and acetic acid (2.73 μl, 0.2 mmol) and stirred for 2 hours. To the mixture was added NaCNBH₃ (22.5 mg, 0.195 mmol) before additional 3 hours of stirring. When the reaction was completed as analyzed by TLC, the solvent was completely evaporated. The residue was dissolved in MC and washed with water and a saturated sodium bicarbonate. The organic layer was dried over sodium sulfate and the solvent was evaporated in a vacuum. The residue was dissolved in DCM and purified by MPLC using 5% MeOH to afford Compound 73-1-C as a black solid (70.0 mg, 0.120 mmol, 70%).

Step 2: Synthesis of N3-(2,6-dimethylphenyl)-1-methyl-N6-(2-(piperidin-4-ylmethyl)isoindolin-5-yl)-1H-pyrazolo[3,4-d]pyrimidine-3,6-diamine (Compound 73-1)

A solution of Compound 73-1-C (60 mg, 0.103 mmol) in DCM (5 mL) was added with 4 N HCl/1,4-dioxane (360 µl, 0.360 mmol) and stirred at room temperature for 3 hours. After completion of the reaction, the solvent was evaporated. Neutralization with NaHCO₃ (aq.) was followed by extraction with DCM (20 mL×3). The organic layer was evaporated in a vacuum to afford Compound 73-1 as a brown solid (26 mg, 0.140 mmol, 53%).

Step 3: Synthesis of 5-(4-((5-((3-((2,6-dimethylphenyl)amino)-1-methyl-1H-pyrazolo[3,4-d]pyrimidin-6-yl)amino)isoindolin-2-yl)methyl)piperidin-1-yl)-2-(2,6-dioxopiperidin-3-yl)isoindoline-1,3-dione (Compound 73)

A solution of Compound 73-2 (Combi-Blocks, HD-3240) (5.5 mg, 0.020 mmol) in DMSO (5 mL) was added at room temperature with Compound 73-1 (10.0 mg, 0.020 mmol) and DIPEA (8.0 mg, 0.062 mmol) and the resulting mixture was stirred at 90° C. for 3 hours. When the product was formed as analyzed by TLC, the reaction mixture was added with water, subjected to extraction with EA (50 mL×3), and washed with water (3×) and brine. The pooled organic layer was dried over sodium sulfate and purified by MPLC using 10% MeOH/MC to afford Compound 73 as a yellow solid (9.0 mg, 0.012399 mmol, 58%).

Compound 74. 3-(7-(4-((5-((3-((2,6-Dimethylphenyl)amino)-1-methyl-1H-pyrazolo[3,4-d]pyrimidin-6-yl)amino)isoindolin-2-yl)methyl)piperidin-1-yl)-4-oxobenzo[d][1,2,3]triazin-3 (4H)-yl)piperidin-2,6-one

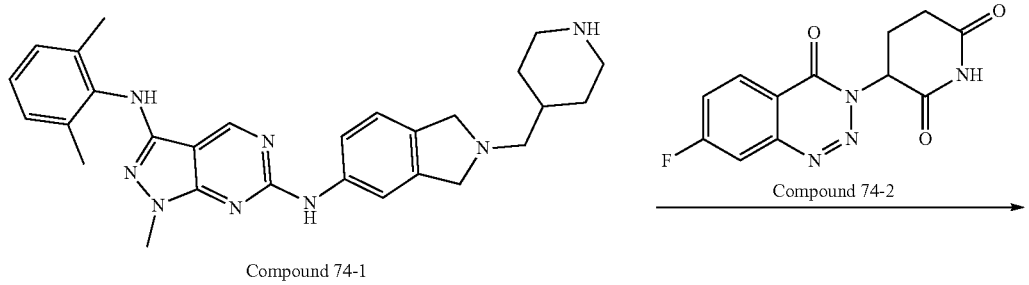

Compound 74-1

Compound 74-2

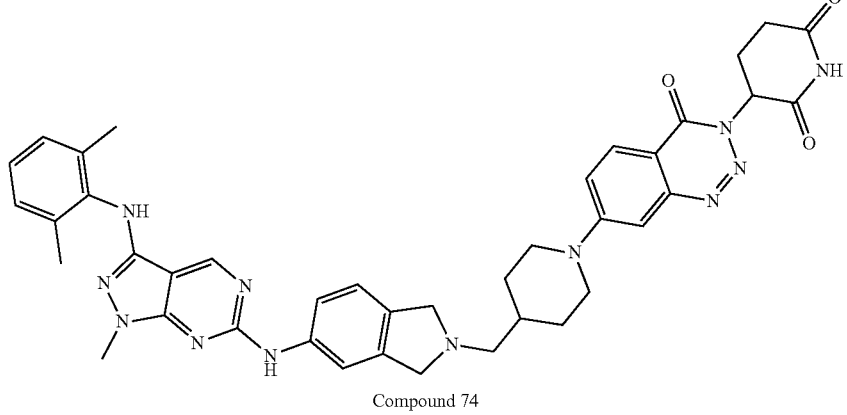

Compound 74

A solution of Compound 74-2 (identical to Compound 53-2) (6.8 mg, 0.024 mmol) in DMSO (0.5 mL) was added at room temperature with Compound 74-1 (identical to Compound 73-1) (12.0 mg, 0.024 mmol) and DIPEA (0.072 mg, 9.32 mmol) and the resulting mixture was stirred at 90° C. for 3 hours. When the product was formed as analyzed by TLC, the reaction mixture was added with water, subjected to extraction with EA (10 mL×3), and washed with water (3×) and brine. The pooled organic layer was dried over sodium sulfate and purified by MPLC using 10% MeOH/

MC (eluted at 4%) to afford Compound 74 as a yellow solid (1.6 mg, 0.0021 mmol, 10%).

Compound 75. 5-(4-((7-((3-((2,6-Dimethylphenyl)amino)-1-methyl-1H-pyrazolo[3,4-d]pyrimidin-6-yl)amino)-1-methyl-3,4-dihydroisoquinolin-2 (1H)-yl)methyl)piperidin-1-yl)-2-(2,6-dioxopiperidin-3-yl)isoindoline-1,3-dione temperature with Compound 75-2 (TCI, P1653) (200 mg, 1.73 mmol) and DIPEA (372 mg, 519 mmol) and the resulting mixture was stirred at 90° C. for 1 hour. The reaction mixture was added with water, subjected to extraction with EA, and washed with water and brine. Then, the organic layer was concentrated in a vacuum to give a crude material which was then purified by MPLC to afford Compound 75-3 as a yellow solid (440 mg).

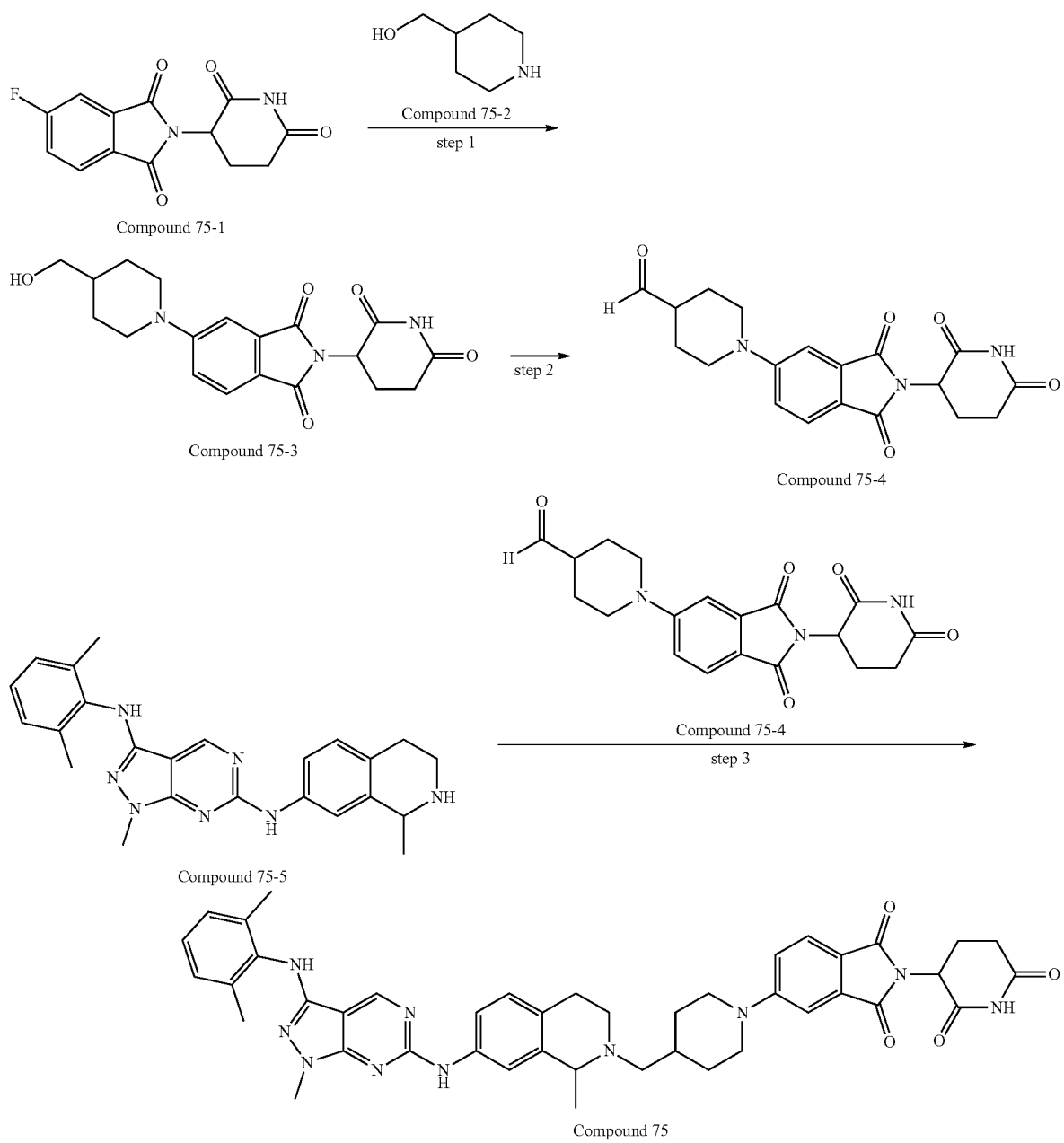

Step 1: Synthesis of 2-(2,6-dioxopiperidin-3-yl)-5-(4-(hydroxymethyl)piperidin-1-yl)isoindoline-1,3-dione (Compound 75-3)

A solution of Compound 75-1 (Combi-Blocks, HD-3240) (480 mg, 1.73 mmol) in DMSO (5 mL) was added at room Step 2: Synthesis of 1-(2-(2,6-dioxopiperidin-3-yl)-1,3-dioxoisoindolin-5-yl)piperidine-4-carbaldehyde (Compound 75-4)

At −78° C., a solution of DMSO (315 mg, 4.03 mmol) in DCM was added dropwise to a solution of oxalyl chloride (256 mg, 0.673 mmol) in DCM (25 mL). This mixture was added with drops of a solution of Compound 75-3 (250 mg, 0.673 mmol) in DCM (5 mL) and stirred for 10 minutes. After addition of TEA (612 mg, 6.05 mmol), stirring was conducted at room temperature for 1 hour until the reaction was completed. The reaction mixture was quenched with water and subjected to extraction with EA. Then, the organic layer was washed with water and brine and concentrated in a vacuum to give a crude material which was then purified by MPLC to afford Compound 75-4 as a yellow solid (110 mg).

Step 3: Synthesis of 5-(4-((7-((3-((2,6-dimethylphenyl)amino)-1-methyl-1H-pyrazolo[3,4-d]pyrimidin-6-yl)amino)-1-methyl-3,4-dihydroisoquinolin-2(1H)-yl)methyl)piperidin-1-yl)-2-(2,6-dioxopiperidin-3-yl)isoindoline-1,3-dione (Compound 75)

A solution of Compound 75-4 (20 mg, 0.053 mmol) in MeOH (0.5 mL) was added with Compound 75-5 (Korean Patent No. 2128018) (20 mg, 0.048 mmol) and acetic acid and stirred for 1 hour. After addition of NaCNBH₃ (4.5 mg, 0.072 mmol), stirring was conducted at room temperature for 12 hours. The solvent was completely evaporated from the reaction mixture and the residue was dissolved in MC and washed with water and an aqueous saturated sodium bicarbonate. The organic layer was concentrated in a vacuum to give a crude material which was then purified by MPLC to afford Compound 75 as a yellow solid (3.5 mg).

Compound 76. 2-(2,6-Dioxopiperidin-3-yl)-5-(4-((7-((3-((4-(2-methoxyethoxy)-2,6-dimethylphenyl)amino)-1-methyl-1H-pyrazolo[3,4-d]pyrimidin-6-yl)amino)-3,4-dihydroisoquinolin-2(1H)-yl)methyl)piperidin-1-yl)isoindoline-1,3-dione

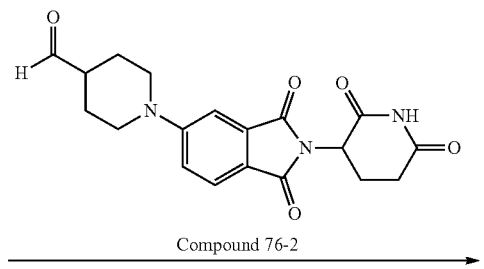

Compound 76-2

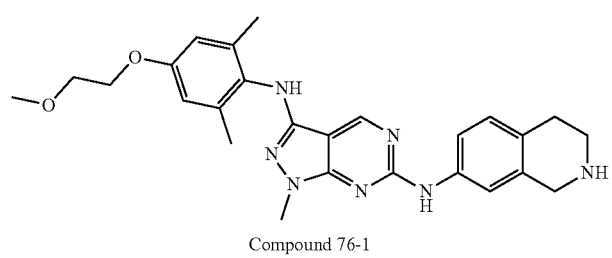

Compound 76-1

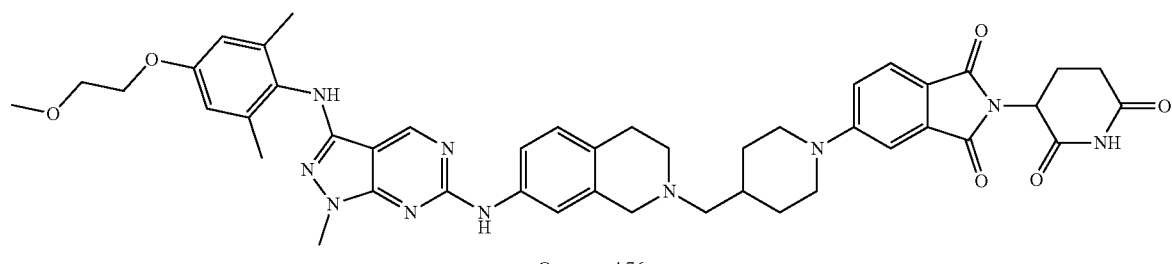

Compound 76

A solution of Compound 76-2 (WO 2020/162725) (8.5 mg, 0.23 mmol) in MeOH (0.5 mL) was added with Compound 76-1 (Korean Patent No. 2128018) (10 mg, 0.021 mmol) and drops of acetic acid and stirred for 1 hours. To the mixture was added NaCNBH₃ (2.0 mg, 0.031 mmol), followed by stirring for 12 hours. When the reaction was completed as analyzed by TLC, the solvent was completely evaporated. The residue was dissolved in MC and washed with water and a saturated sodium bicarbonate solution. The organic layer was dried over sodium sulfate and the solvent was evaporated in a vacuum. The residue was purified MPLC using 5% MeOH/MC to afford Compound 76 as a yellow solid (3.5 mg, 0.0012 mmol, 20%).

Compound 77. 5-((3-((2,6-Dimethylphenyl)amino)-1-methyl-1H-pyrazolo[3,4-d]pyrimidin-6-yl)amino)-2'-(2,6-dioxopiperidin-3-yl)-[2,5'-biisoindoline]-1',3'-dione

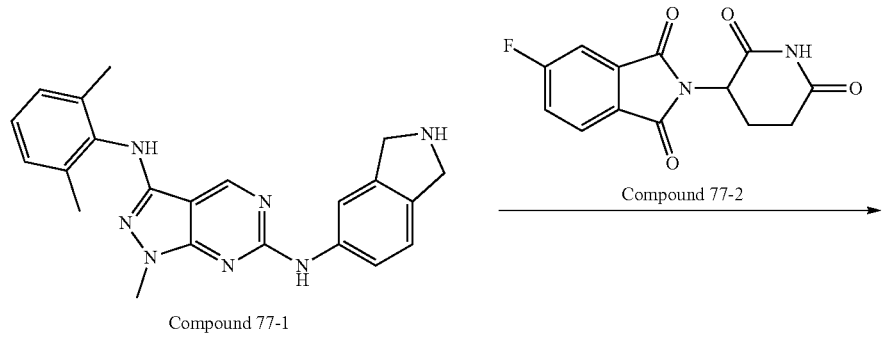

A solution of Compound 77-1 (Korean Patent No. 2128018) (20.0 mg, 0.0519 mmol) in DMSO (0.5 mL) was added at room temperature with Compound 77-2 (Combi-Blocks, HD-3240) (14.3 mg, 0.0519 mmol) and DIPEA (26.9 μL, 0.156 mmol) and the resulting mixture was stirred at 90° C. for 2 hours. The reaction mixture was subjected to extraction with water and DCM (80 mL×3) and then washed with brine (50 mL×2). Purification by MPLC (5% MeOH in MC, gradient) afforded Compound 77 as a yellow solid (9.9 mg, 0.0154 mmol, 30%).

Compound 78. 5-(4-((7-((3-((2,6-Dimethylphenyl)amino)-1-methyl-1H-pyrazolo[3,4-d]pyrimidin-6-yl)amino)-1-isopropyl-3,4-dihydroisoquinolin-2 (1H)-yl)methyl)piperidin-1-yl)-2-(2,6-dioxopiperidin-3-yl)isoindoline-1,3-dione

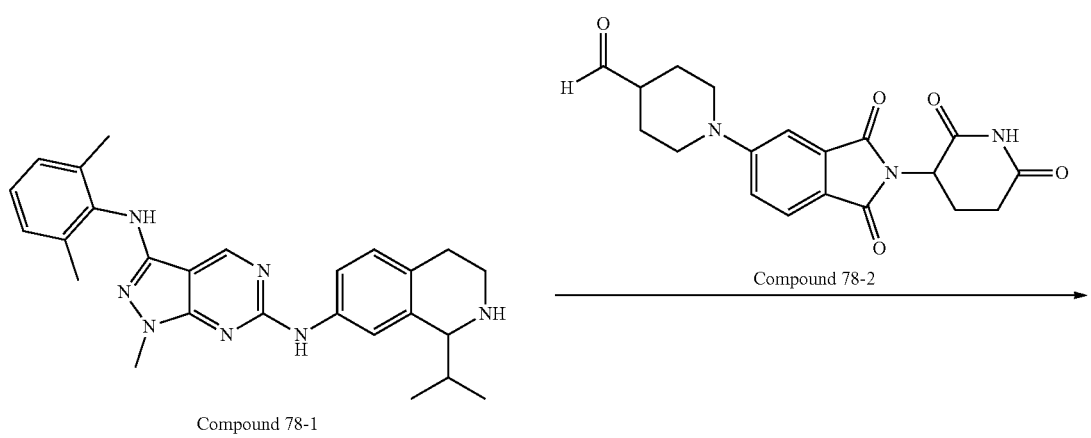

-continued

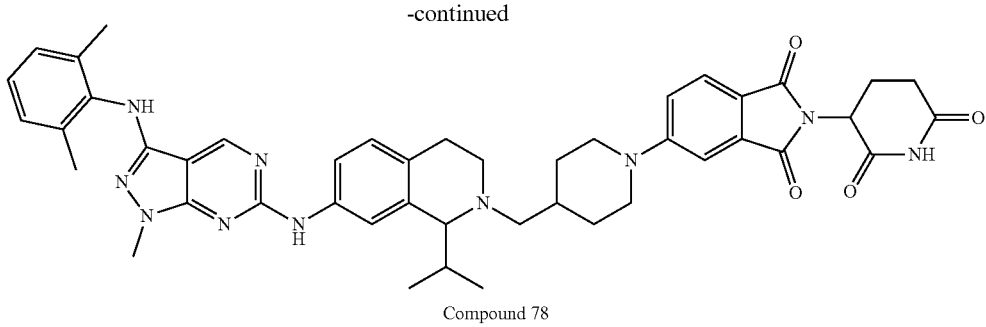

Compound 78

A solution of Compound 78-2 (WO 2020/051564) (9.0 mg, 0.024 mmol) in MeOH (10 mL) was added with Compound 78-1 (Korean Patent No. 2128018) (10 mg, 0.022 mmol) and drops of acetic acid and stirred for 1 hour. To this mixture was added $NaCNBH_3$ (2.0 mg, 0.033 mmol), followed by stirring at room temperature for 12 hours. The solvent was completely removed from the reaction mixture and the residue was dissolved in MC and washed with water and a saturated sodium bicarbonate solution. The organic layer was concentrated in a vacuum to give a crude material which was then purified by MPLC to afford Compound 78 as a yellow solid (7.0 mg).

Compound 79. 5-(4-((7-((3-((2,6-Dimethylphenyl) amino)-1-methyl-1H-pyrazolo[3,4-d]pyrimidin-6-yl) amino)-3,4-dihydroisoquinolin-2 (1H)-yl)methyl) piperidin-1-yl)-2-(1-methyl-2,6-dioxopiperidin-3-yl) isoindoline-1,3-dione

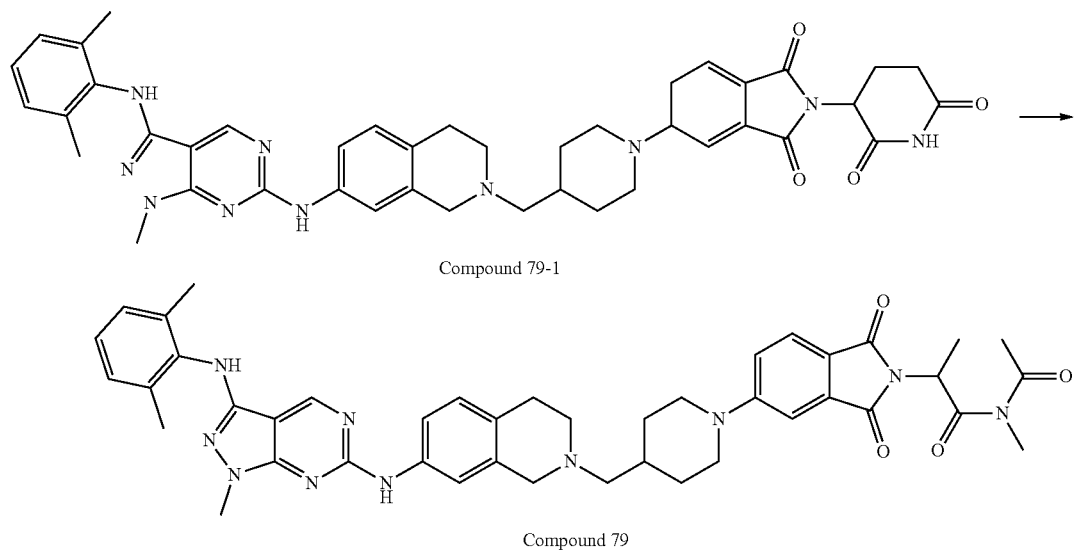

A solution of Compound 79-1 (identical to Compound 29) (25 mg, 0.0332 mmol) in DMF (1 mL) was added with iodomethane (4.24 mg, 0.0298 mmol) and then with cesium carbonate (21.6 mg, 0.0664 mmol). The solution was stirred at room temperature for 12 hours. When a new spot was detected in TLC, the reaction mixture was quenched with water. The aqueous layer was subjected to extraction with EtOAc (25 mL×2), and the pooled organic layer was washed with water and brine and dried over sodium sulfate. The solvent was evaporated in a vacuum. The crude mixture was purified by MPLC using 5% MeOH:DCM as an eluent to afford Compound 79 as a yellow crystalline solid (20.0 mg, 0.0260 mmol, 78%).

Compound 80. 3-(5-((2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-1-oxoisoindolin-2-yl)piperidin-2,6-one

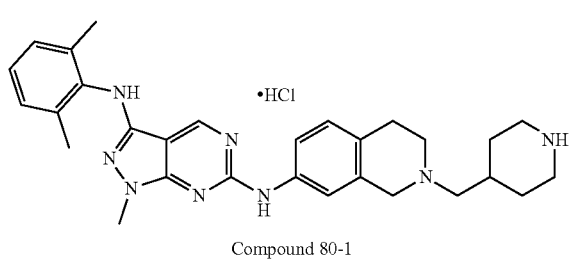
Compound 80-1

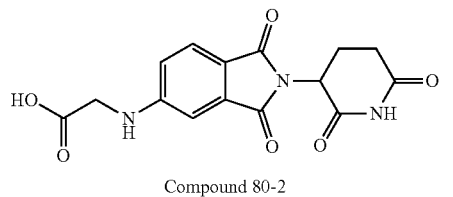
Compound 80-2

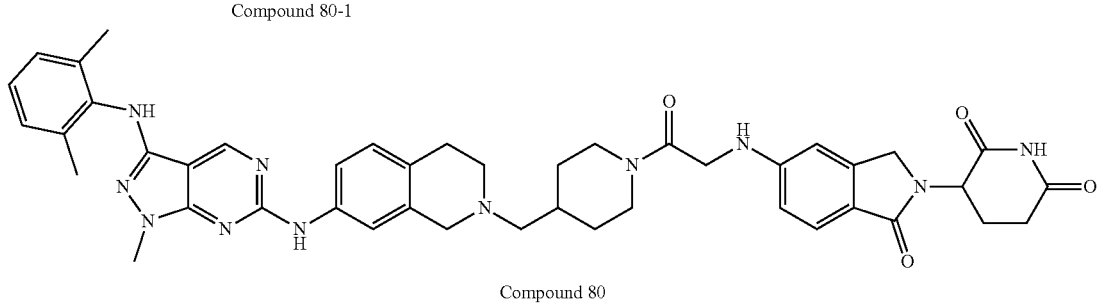
Compound 80

A solution of Compound 80-2 (WO 2020/162725) (14.0 mg, 0.044 mmol) in DMF (2 mL) was added at room temperature with HATU (45.6 mg, 0.120 mmol), Compound 80-1 (identical to Compound 29-1) (20.0 mg, 0.0402 mmol), and TEA (20.3 mg, 0.201 mmol) and the resulting mixture was stirred at room temperature for 12 hours until the reaction was completed. When the product was formed as analyzed by TLC, the reaction mixture was added with water, subjected to extraction with EA (30 mL×3), and washed with water (3×) and brine. The pooled organic layer was dried over sodium sulfate and purified by MPLC using 5% MeOH/MC to afford Compound 80 as a white solid (6.0 mg, 0.040 mmol, 19%).

Compound 81. 3-(5-((2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethyl)amino)-1-oxoisoindolin-2-yl)piperidin-2,6-one

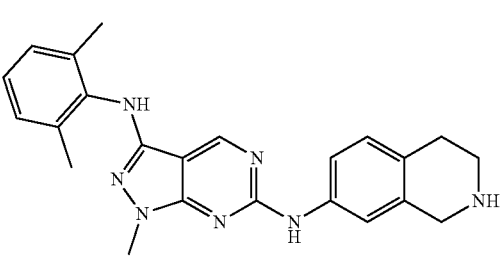
Compound 81-1

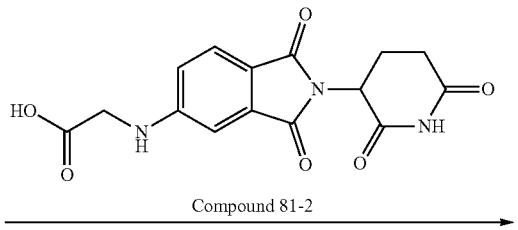
Compound 81-2

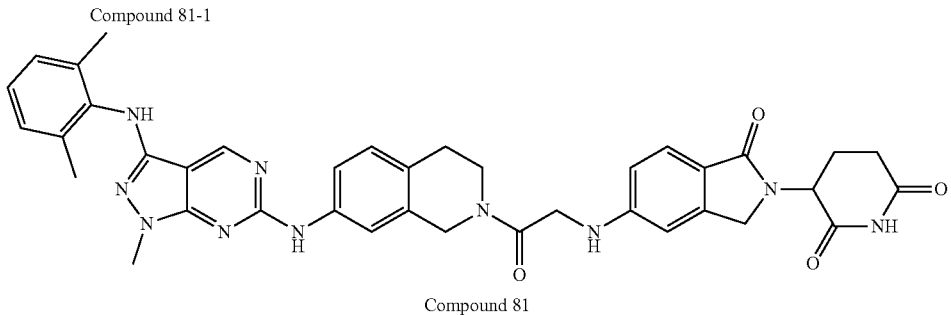
Compound 81

A solution of Compound 81-2 (WO 2020/162725) (17.5 mg, 0.0550 mmol) in DMF (2 mL) was added at room temperature with HATU (57.0 mg, 0.150 mmol), Compound 81-1 (Korean Patent No. 2128018) (20 mg, 0.0500 mmol), and TEA (25.2 mg, 0.250 mmol). The mixture was stirred at room temperature for 12 hours until the reaction was completed. When the product was formed as analyzed by TLC, the reaction mixture was added with water, subjected to extraction with EA (30 mL×3), and washed with water (3×) and brine. The pooled organic layer was dried over sodium sulfate and purified by MPLC using 5% MeOH/MC to afford Compound 81 as an off-white solid (11 mg, 0.0157 mmol, 31%).

Compound 82. 5-(4-((7-((3-((2,6-Dichlorophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione

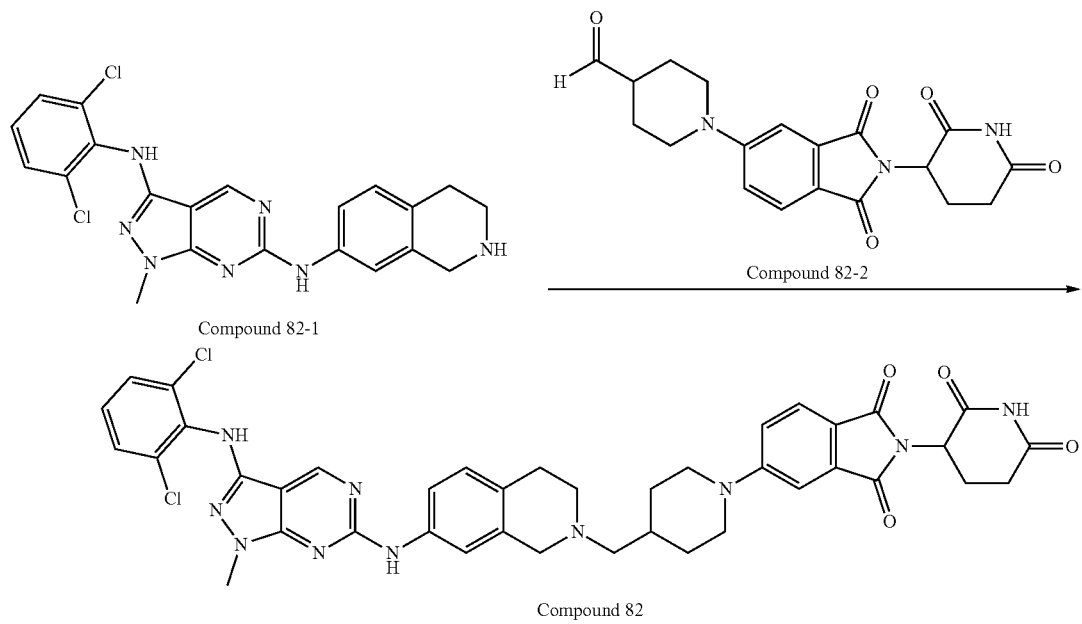

A solution of Compound 82-1 (Korean Patent No. 2128018) (20.0 mg, 0.0454 mmol) in MeOH (1 mL) was added with Compound 82-2 (WO 2020/051564) (18.5 mg, 0.0499 mmol), together with acetic acid (0.519 µl, 0.00908 mmol), and stirred for 1 hour. After addition of NaCNBH$_3$ (4.28 mg, 0.0681 mmol) to the mixture, stirring was conducted at room temperature for 2 days. The reaction mixture was added with water, subjected to extraction with MC, and washed with brine. The organic layer was dried over sodium sulfate, and the solvent was evaporated in a vacuum. The residue was purified by silica gel column chromatography using 5% MeOH in DCM to afford Compound 82 as a yellow solid (18.9 mg, 0.0455 mmol, 88%).

Compound 83. 5-(4-((7-((3-((2,4-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione

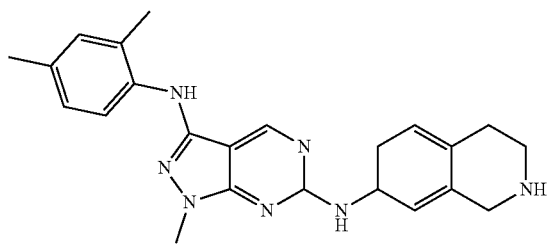
Compound 83-1

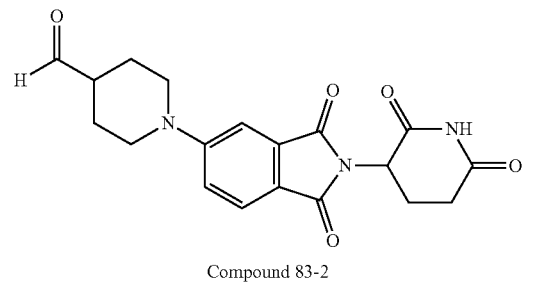
Compound 83-2

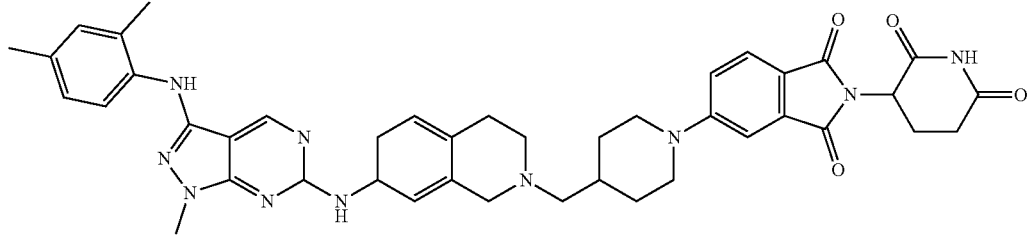
Compound 83

A solution of Compound 83-1 (Korean Patent No. 2128018) (23.0 mg, 0.0576 mmol) in MeOH (1 mL) was added with Compound 83-2 (WO 2020/051564) (23.4 mg, 0.0499 mmol), together with acetic acid (0.658 μl, 0.0115 mmol) and stirred for 12 hours. After addition of NaCNBH₃ (5.43 mg, 0.0864 mmol) to the mixture, stirring was conducted at room temperature for 2 hours. The reaction mixture was added with water, subjected to extraction with MC, and washed with brine. The organic layer was dried over sodium sulfate, and the solvent was evaporated in a vacuum. The residue was purified by silica gel column chromatography using 80% EA in hex to afford Compound 83 as a yellow solid (11.2 mg, 0.0149 mmol, 26%).

Compound 84. 2-(2,6-Dioxopiperidin-3-yl)-5-(4-((7-((1-methyl-3-(o-tolylamino)-1H-pyrazolo[3,4-d]pyrimidin-6-yl)amino)-3,4-dihydroisoquinolin-2 (1H)-yl)methyl)piperidin-1-yl)isoindoline-1,3-dione

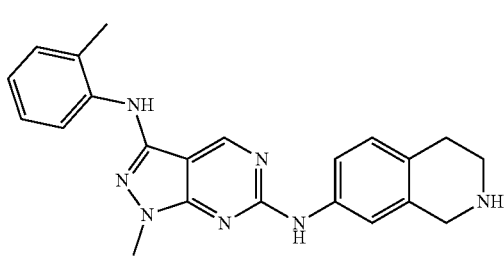
Compound 84-1

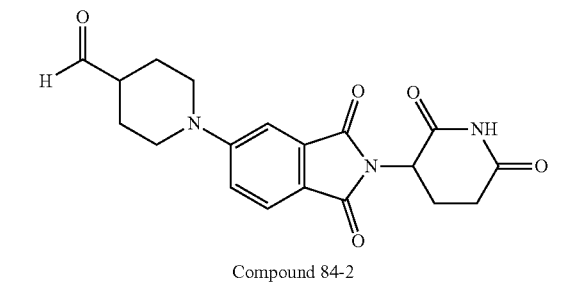
Compound 84-2

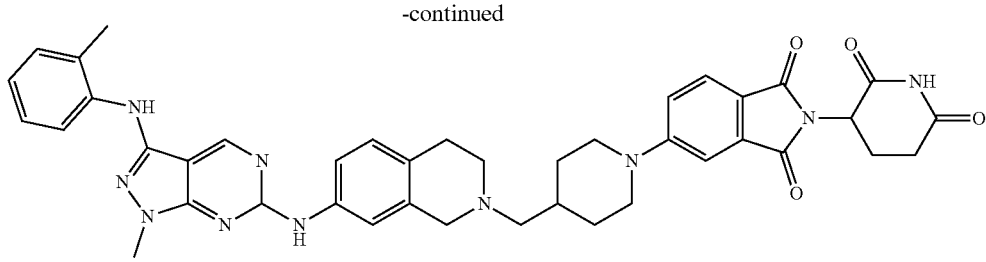

Compound 84

A solution of Compound 84-1 (Korean Patent No. 2128018) (20.0 mg, 0.0518 mmol) in MeOH (1 mL) was added with Compound 84-2 (WO 2020/051564) (21.1 mg, 0.0571 mmol), together with acetic acid (0.593 μl, 0.0104 mmol) and stirred for 12 hours. After addition of NaCNBH$_3$ (4.89 mg, 0.0778 mmol) to the mixture, stirring was conducted at room temperature for 6 hours. The reaction mixture was added with water, subjected to extraction with MC, and washed with brine. The organic layer was dried over sodium sulfate, and the solvent was evaporated in a vacuum. The residue was purified by silica gel column chromatography using 80% EA in hexane to afford Compound 84 as a yellow solid (33.6 mg, 0.0455 mmol, 88%).

Compound 85. 5-(4-((7-((3-((2-Chloro-6-methylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione A solution of compound 85-1 (Korean Patent No. 2128018) (11.0 mg, 0.0262 mmol) in MeOH (1 mL) was added with Compound 85-2 (WO 2020/051564) (10.6 mg, 0.0288 mmol), together with acetic acid (0.299 μl, 0.0104 mmol), and stirred for 2 hours. After addition of NaCNBH$_3$ (4.89 mg, 0.0393 mmol) to the mixture, stirring was conducted at room temperature for 6 hours. The reaction mixture was added with water, subjected to extraction with MC, and washed with brine. The organic layer was dried over sodium sulfate, and the solvent was evaporated in a vacuum. The residue was purified by silica gel column chromatography using 5% MeOH in DCM to afford Compound 85 as a yellow solid (4.10 mg, 0.00530 mmol, 20%).

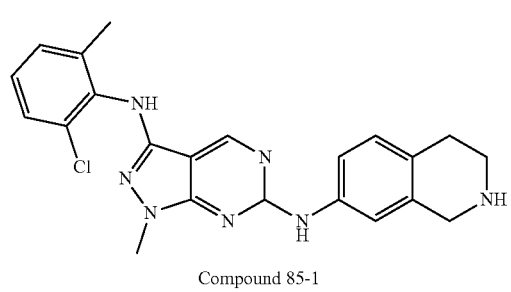

Compound 85-1

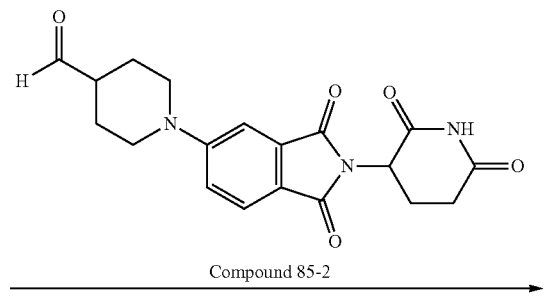

Compound 85-2

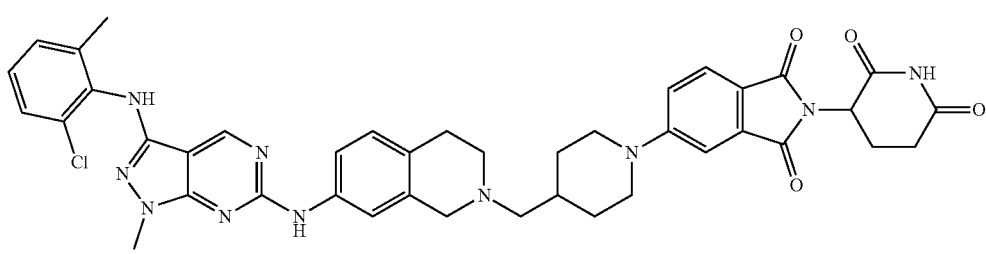

Compound 85

Compound 86. 5-(4-((7-((3-((2,6-Dimethylphenyl)amino)-1-isopropyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione

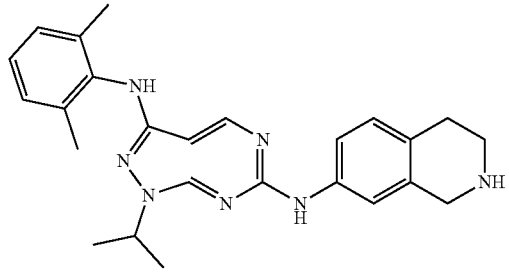

Compound 86-1

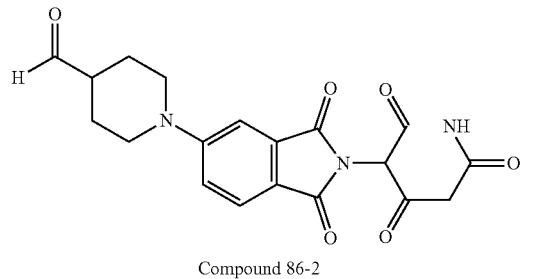

Compound 86-2

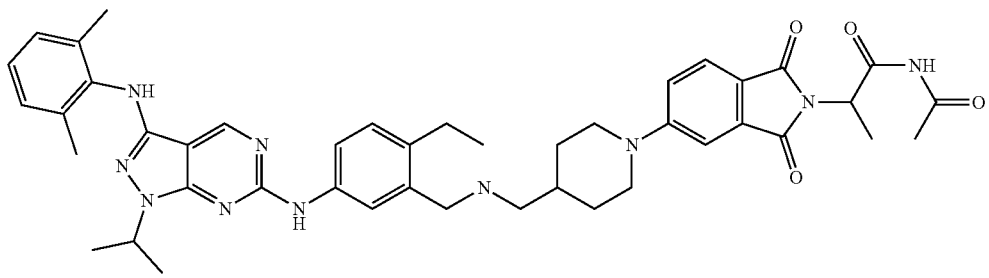

Compound 86

A solution of Compound 86-1 (Korean Patent No. 2128018) (23.0 mg, 0.0576 mmol) in MeOH (1 mL) was added with Compound 86-2 (WO 2020/051564) (23.4 mg, 0.0499 mmol), together with acetic acid (0.658 µl, 0.0115 mmol) and stirred for 12 hours. After addition of NaCNBH₃ (5.43 mg, 0.0864 mmol) to the mixture, stirring was conducted at room temperature for 2 hours. The reaction mixture was added with water, subjected to extraction with MC, and washed with brine. The organic layer was dried over sodium sulfate, and the solvent was evaporated in a vacuum. The residue was purified by silica gel column chromatography using 5% MeOH in DCM to afford Compound 86 as a yellow solid (2.00 mg, 0.00256 mmol, 10%).

Compound 87. 5-(3-(7-((3-((2,6-Dimethylphenyl)amino)-1-methyl-1H-pyrazolo[3,4-d]pyrimidin-6-yl)amino)-3,4-dihydroisoquinolin-2 (1H)-yl)azetidin-1-yl)-2-(2,6-dioxopiperidin-3-yl)isoindoline-1,3-dione

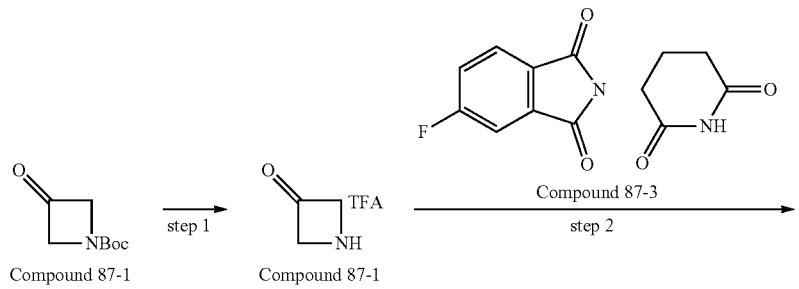

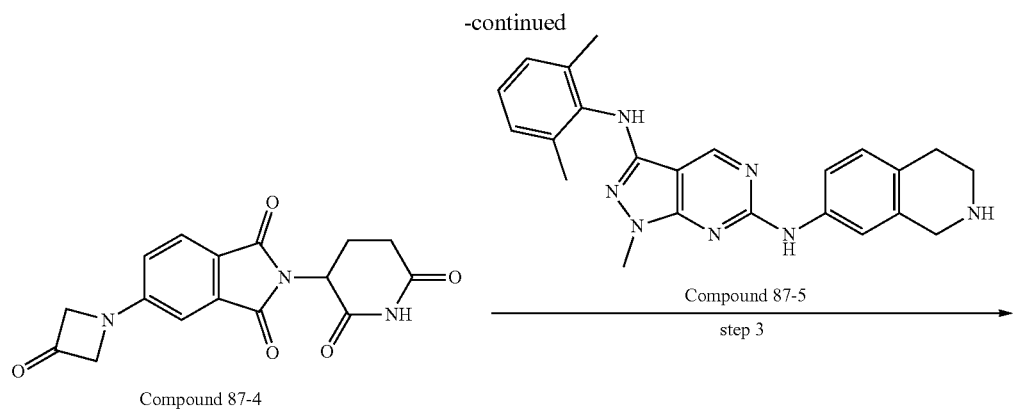

Compound 87-4

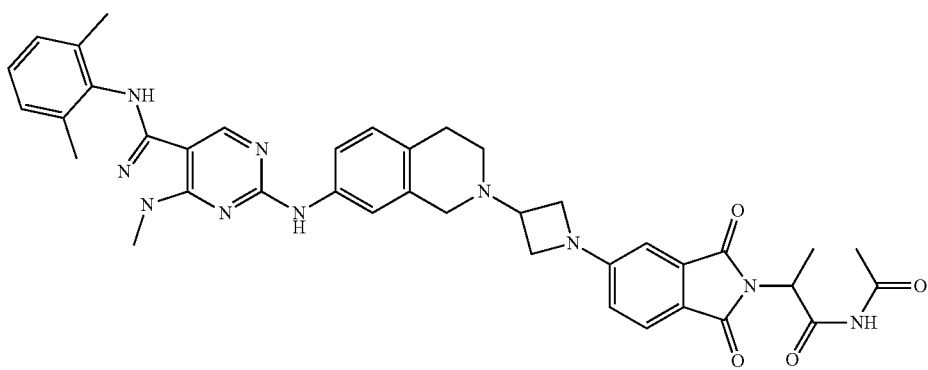

Compound 87

Step 1: Synthesis of 2,2,2-trifluoroacetaldhyde compound with azetidin-3-one (Compound 87-2)

To 40% TFA/DCM (6/9 mL) was added Compound 87-1 (TCI, B3988) (1-(tert-butoxycarbonyl)-3-azetidinone; 200 mg, 1.168 mmol), followed by stirring at room temperature for 2 hours. After completion of the reaction, the solvent was evaporated from the reaction mixture. The white precipitates thus formed were collected by filtration and washed with ether. In the case where impurities were not removed, the crude mixture was purified by MPLC using 70% EA/HEX to afford Compound 87-2 as an ivory oil (196 mg, 1.166 mmol, 99%).

Step 2: Synthesis of 2-(2,6-dioxopiperidin-3-yl)-5-(3-oxoazetidin-1-yl)isoindoline-1,3-dione (Compound 87-4)

To a solution of Compound 87-2 (196 mg, 1.166 mmol) in DMSO (2 mL) were added a solution of Compound 87-3 (Combi-Blocks, HD-3240) (2-(2,6-dioxopiperidin-3-yl)-5-fluoroisoindoline-1,3-dione; 258 mg, 0.934 mmol) in DMSO. Then, DIPEA (0.8 mL, 4.664 mmol) was added. The mixture was stirred at 90° C. for 12 hours. After completion of the reaction, the reaction mixture was quenched with water, subjected to extraction with EA (3×30 mL), and washed with water (3×) and brine. The pooled organic layer was dried over sodium sulfate and filtered, and the solvent was evaporated in a vacuum. Purification by MPLC using 60% EA/HEX afforded Compound 87-4 as a yellow solid (91 mg, 0.278 mmol, 44%).

Step 3: Synthesis of 5-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)-2-(2,6-dioxopiperidin-3-yl)isoindoline-1,3-dione (Compound 87)

A solution of Compound 87-4 (25 mg, 0.0764 mmol) in DMF (1 mL) was added with Compound 87-5 (Korean Patent No. 2128018) (30 mg, 0.0764 mmol) and AcOH (4.0 μl, 0.0764 mmol) and stirred at room temperature for 12 hours. Then, sodium triacetoxyborohydride (24 mg, 0.113 mmol) was added. The mixture was stirred at room temperature for 1 hour. After completion of the reaction, the reaction mixture was quenched with water, subjected to extraction with EA (3×15 mL), and washed with water (3×) and the brine solution NaHCO₃. The pooled organic layer was dried over sodium sulfate and filtered, and the solvent was evaporated in a vacuum. Purification by MPLC using 5% MeOH/MC afforded Compound 87 as an off-white solid (15 mg, 0.0021 mmol, 28%).

Compound 88. 5-(4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)-2-(2,6-dioxopiperidin-3-yl)isoindoline-1,3-dione

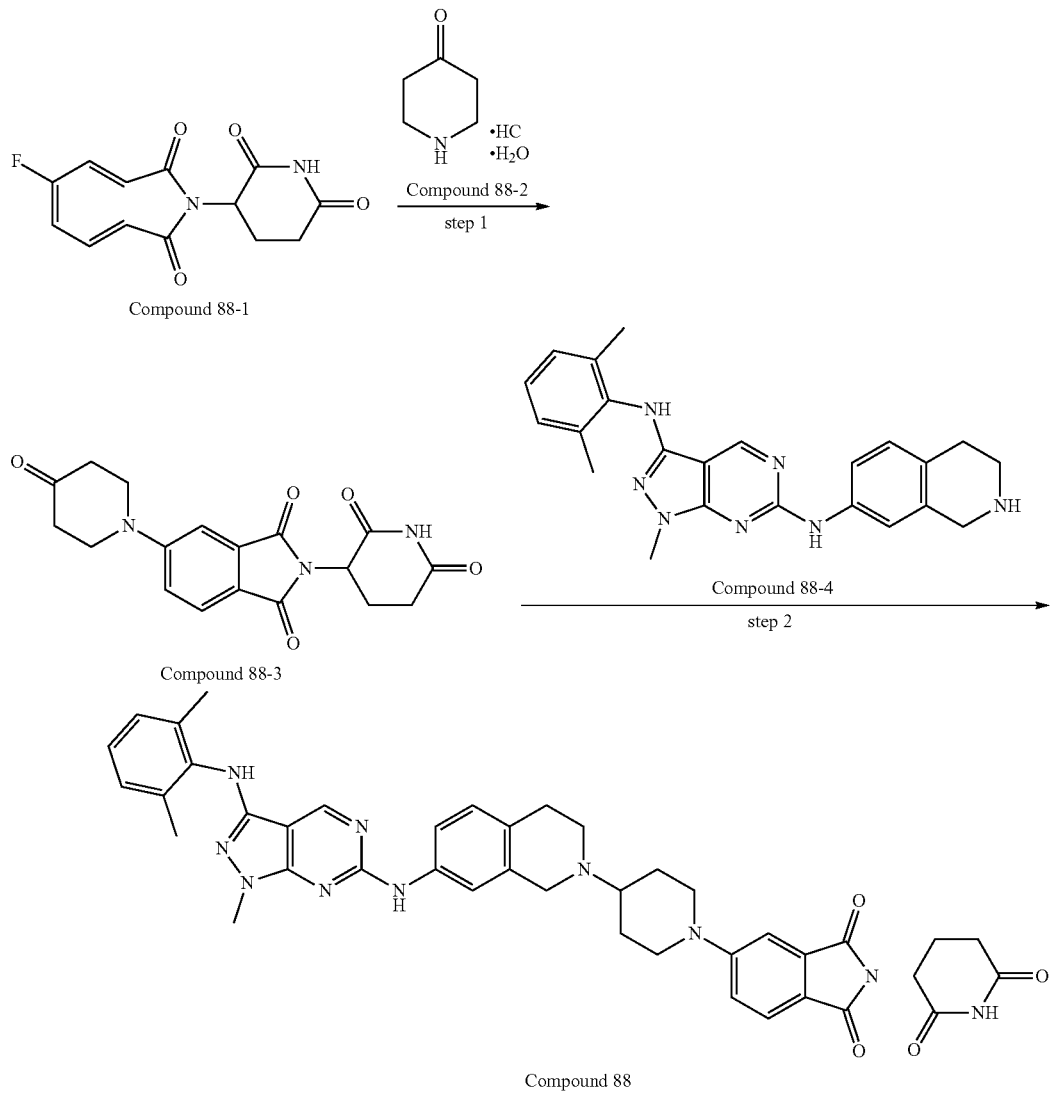

Step 1: Synthesis of 2-(2,6-dioxopiperidin-3-yl)-5-(4-oxopiperidin-1-yl)isoindoline-1,3-dione (Compound 88-3)

A solution of Compound 88-1 (Combi-Blocks, HD-3240) (2-(2,6-dioxopiperidin-3-yl)-5-fluoroisoindoline-1,3-dione; 300 mg, 1.09 mmol) in DMSO (5 mL) was added at room temperature with Compound 88-2 (Sigma Aldrich, 841672) (4-piperidone monohydrate hydrochloride; 167 mg, 1.09 mmol) and DIPEA (0.8 mL, 4.344 mmol). The reaction mixture was stirred at 90° C. for 12 hours, quenched with water, subjected to extraction with EtOAc (3×50 mL), and washed with water (3×) and brine. The pooled organic layer was dried over sodium sulfate and filtered, and the solvent was evaporated in a vacuum. Purification by MPLC using 5% MeOH/EtOAc afforded Compound 88-3 as a yellow solid (155 mg, 0.436 mmol, 40%).

Step 2: Synthesis of 5-(4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)-2-(2,6-dioxopiperidin-3-yl)isoindoline-1,3-dione (Compound 88)

To a solution of Compound 88-3 (50 mg, 0.141 mmol) in DMF (1 mL) was added a solution of Compound 88-4 (Korean Patent No. 2128018) (56 mg, 0.141 mmol) in DMF (141 μl, 0.141 mmol) and 1 M AcOH at room temperature. The mixture was stirred at room temperature for 12 hours and then added with sodium triacetoxyborohydride (45 mg, 0.21 mmol). After stirring at room temperature for 1 hour, the reaction mixture was quenched with water and NaHCO₃ (aq) and subjected to extraction with EtOAc (3×15 mL). The pooled organic layer was washed with water (3×) and brine, dried over sodium sulfate, and filtered. The solvent was evaporated in a vacuum. The crude mixture was purified by MPLC using 5% MeOH/MC to afford Compound 88 as a yellow solid (25.0 mg, 0.0338 mmol, 24%).

Compound 89. 5-(3-(7-((3-((2,6-Dimethylphenyl)amino)-1-methyl-1H-pyrazolo[3,4-d]pyrimidin-6-yl)amino)-3,4-dihydroisoquinolin-2 (1H)-yl)pyrrolidin-1-yl)-2-(2,6-dioxopiperidin-3-yl)isoindoline-1,3-dione organic layer was dried over sodium sulfate and filtered, and the solvent was evaporated in a vacuum. Purification by MPLC using 5% MeOH/EA afforded Compound 89-3 as a yellow solid (40 mg, crude).

Step 2: Synthesis of 5-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)pyrrolidin-1-yl)-2-(2,6-dioxopiperidin-3-yl)isoindoline-1,3-dione (Compound 89)

A solution of Compound 89-4 (Korean Patent No. 2128018) (14 mg, 0.035 mmol) in DMF (1 mL) was added with Compound 89-3 (18 mg, 0.053 mmol) and AcOH (2.0

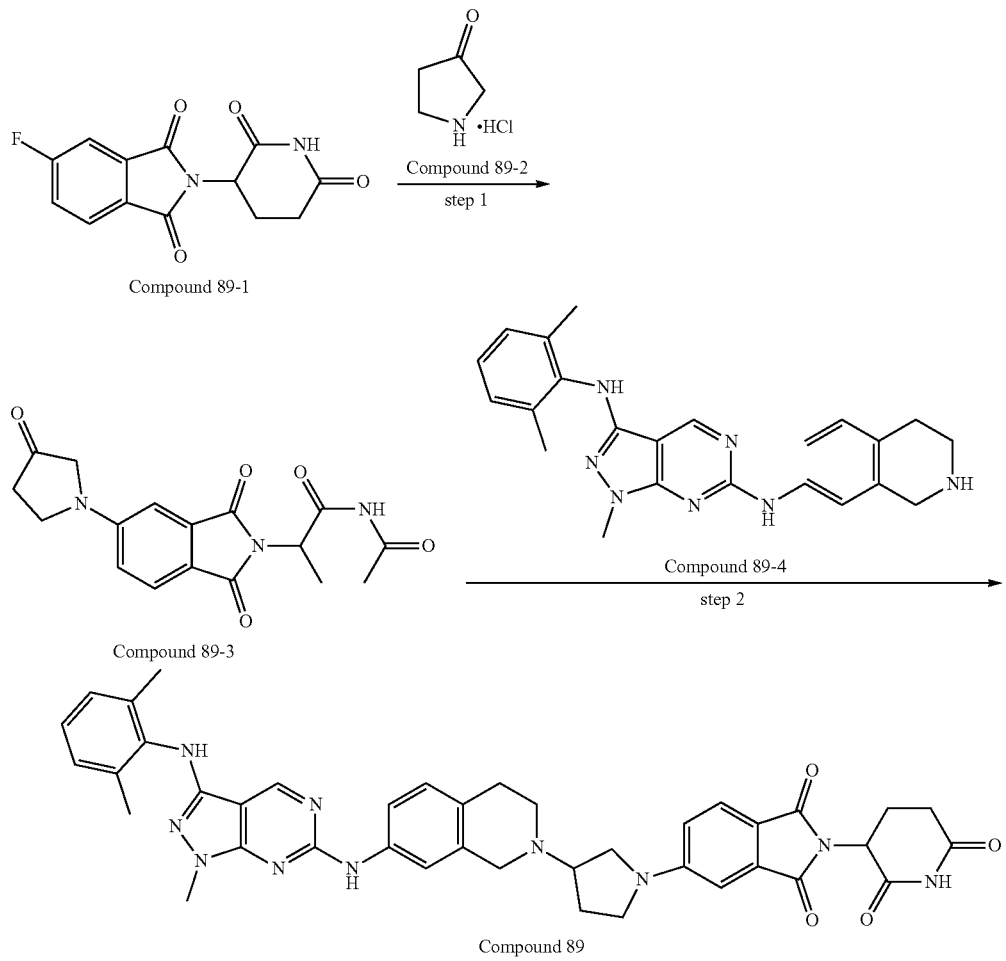

Step 1: Synthesis of 2-(2,6-dioxopiperidin-3-yl)-5-(3-oxopyrrolidin-1-yl)isoindoline-1,3-dione (Compound 89-3)

A solution of Compound 89-1 (Combi-Blocks, HD-3240) (2-(2,6-dioxopiperidin-3-yl)-5-fluoroisoindoline-1,3-dione; 127 mg, 0.461 mmol) in DMSO (2 mL) was added with Compound 89-2 (Combi blocks, OS-1284) (pyrrolidin-3-one HCl; 70 mg, 0.576 mmol) and then with DIPEA (0.4 mL, 2.304 mmol). The mixture was stirred at 90° C. for 12 hours. After completion of the reaction, the reaction mixture was quenched with water, subjected to extraction EA (3×50 mL), and washed with water (3×) and brine. The pooled μl, 0.035 mmol). The mixture was stirred at room temperature for 12 hours and added with sodium triacetoxyborohydride (11 mg, 0.053 mmol). The mixture was stirred for an additional 1 hours. After completion of the reaction, the reaction mixture was quenched with water, subjected to extraction EA (3×15 mL), and washed with water (3×) and the brine solution NaHCO₃. The pooled organic layer was dried over sodium sulfate and filtered, and the solvent was evaporated in a vacuum. Purification by MPLC using 5% MeOH/EA afforded Compound 89 as a yellow solid (9.6 mg, 0.0132 mmol, 24%).

Compound 90. 2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1,3-dioxoisoindolin-5-yl)acetamide

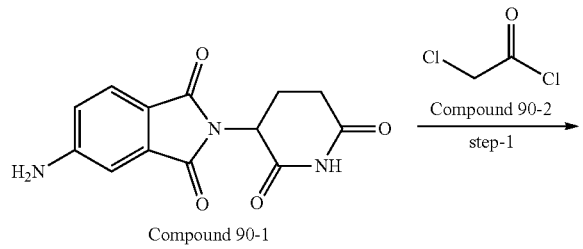

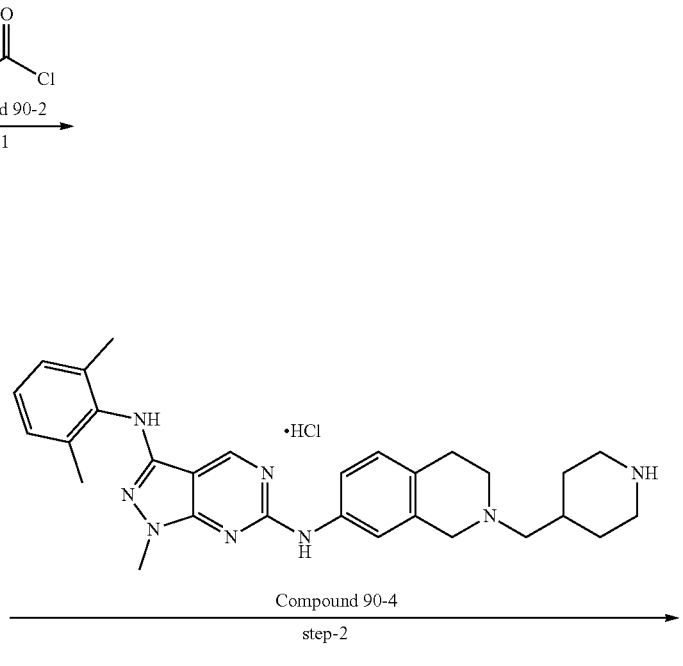

Step 1: Synthesis of 2-chloro-N-(2-(2,6-dioxopiperidin-3-yl)-1,3-dioxoisoindolin-5-yl)acetamide (Compound 90-3)

To a suspension of Compound 90-1 (WO 2019/148055) (100 mg, 0.367 mmol) in THF (2 mL) was added Compound 90-2 (Sigma, 104493) (chloroacetyl chloride; 124 mg, 1.10 mmol). The mixture was stirred at 70° C. for 12 hours. When a new spot was detected in TLC, the reaction mixture was quenched with water (10 mL) and subjected to extraction with EtOAc (25 mL×2), and the pooled organic layer was dried over sodium sulfate. The solvent was evaporated in a vacuum to afford Compound 90-3 as a slightly impure bright green solid (61.0 mg, 0.175 mmol, 48%).

Step 2: Synthesis of 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1,3-dioxoisoindolin-5-yl)acetamide (Compound 90)

To a solution of Compound 90-4 (identical to Compound 29-1) (20.0 mg, 0.040 mmol) in DMF (1 mL) were added Compound 90-3 (12.6 mg, 0.360 mmol) and DIPEA (15.6 mg, 0.121 mmol), and the mixture was stirred at 80° C. for 12 hours. When a new spot was detected in TLC, the reaction mixture was quenched with water (10 mL) and subjected to extraction with DCM (15 mL×2), and the pooled organic layer was washed with water (15 mL×2) and brine (15 mL×3). The crude product was purified by MPLC using DCM as an eluent to afford Compound 90 as a brown solid (11.0 mg, 0.014 mmol, 34%).

Compound 91. 2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1-oxoisoindolin-5-yl)acetamide

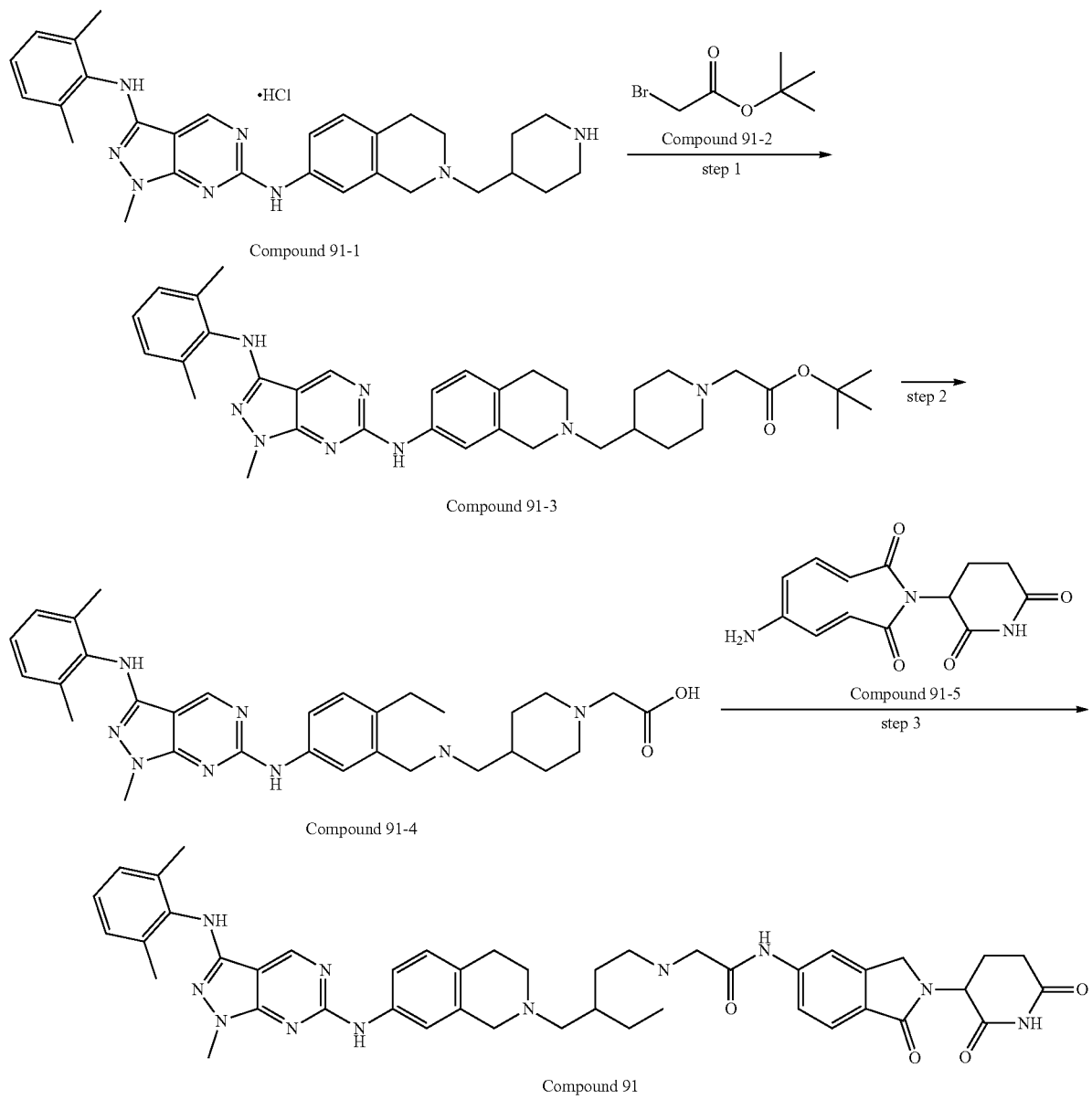

Step 1: Synthesis of tert-butyl 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)acetate (Compound 91-3)

A solution of Compound 91-1 (identical to Compound 29-1) (50.0 mg 0.100 mmol) in DCM (2 mL) was added with Compound 91-2 (TCI, B1473) (tert-butyl bromoacetate; 38.7 mg, 0.201 mmol) and 37% NaOH (2 mL) and then with TBAB (32.3 mg, 0.100 mmol), and the mixture was stirred at room temperature for 5 hours. When a new spot was detected in TLC, the reaction mixture was quenched with water (10 mL) and subjected to extraction with DCM (15 mL×2). The crude product was purified by MPLC using 5% MeOH:DCM as an eluent to afford Compound 91-3 as a brown solid (39 mg, 0.0640 mmol, 63%).

Step 2: Synthesis of 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)acetic acid (Compound 91-4)

A solution of Compound 91-3 (35.0 mg, 0.057 mmol) in 40% TFA/DCM (1 mL) was stirred for 12 hours. When the reaction was completed as analyzed by TLC, the solvent was completely evaporated to afford Compound 91-4 as a brown solid (18.0 mg, 0.032 mmol, 57%). The crude product was used in the next step without additional purification.

Step 3: Synthesis of 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1-oxoisoindolin-5-yl)acetamide (Compound 91)

A solution of Compound 91-4 (15.0 mg, 0.0270 mmol) in DMF (2 mL) was added at room temperature with HATU (20.5 mg, 0.0540 mmol), Compound 91-5 (WO 2019/148055) (7.01 mg, 0.0270 mmol), and TEA (10.9 mg, 0.108 mmol) and stirred at room temperature for 12 hours. The reaction mixture was quenched with water (10 mL) and subjected to extraction with DCM (15 mL×2), and the pooled organic layer was washed with water (15 mL×2) and brine (15 mL×3). The crude mixture was purified by chromatography using 5% MeOH/DCM as an eluent to afford Compound 91 as a brown solid (9.1 mg, 0.011 mmol, 42.3%).

Compound 92. 4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)-N-(2-(2,6-dioxopiperidin-3-yl)-1-oxoisoindolin-5-yl)piperidine-1-carboxamide

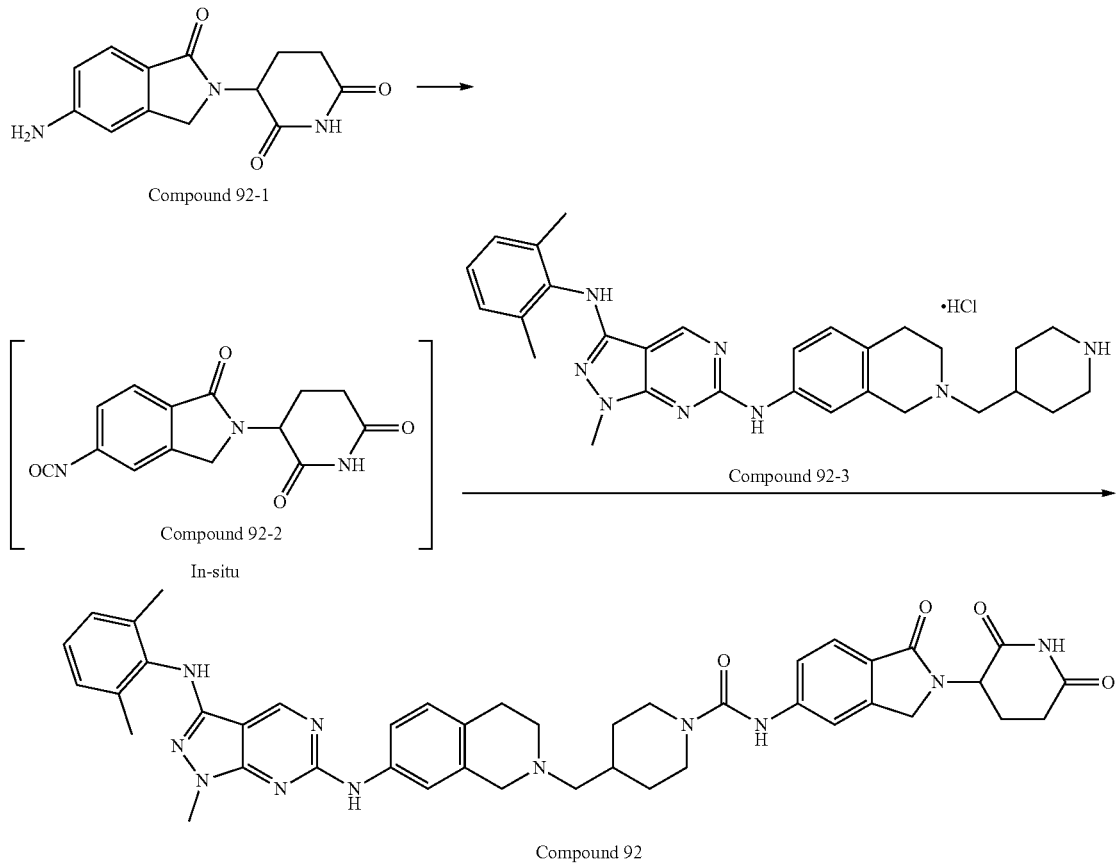

Compound 92

A suspension of Compound 92-1 (WO 2019/148055) (20.0 mg, 0.0771 mmol) in DCM (5 mL) was added with triphosgene (115 mg, 0.385 mmol) and TEA (39.0 mg, 0.385 mmol) and stirred at room temperature for 6 hours. The solvent was completely evaporated in a vacuum to give the isocyanate intermediate Compound 92-2. A solution of the intermediate Compound 92-2 in THF (5 mL) was added with Compound 92-3 (identical to Compound 29-1) (38.2 mg, 0.0771 mmol) and TEA (15.5 mg, 0.0154 mmol) and stirred at 40° C. for 1 hour. When the reaction was completed as analyzed by TLC, the reaction mixture was quenched with water and subjected to extraction with EA (25 mL×3). The pooled organic layer was dried over sodium sulfate and filtered, and the solvent was evaporated in a vacuum. The crude mixture was purified by MPLC using 10% MeOH:MC to afford Compound 92 as a white solid (17.0 mg, 0021 mmol 28%).

Compound 93. 5-(4-(2-(7-((3-((2,6-dimethylphenyl)amino)-1-methyl-1H-pyrazolo [3,4-d]pyrimidin-6-yl)amino)-3,4-dihydroisoquinolin-2 (1H)-yl)-2-oxo-ethyl)piperazin-1-yl)-2-(2,6-dioxopiperidin-3-yl)isoindoline-1,3-dione

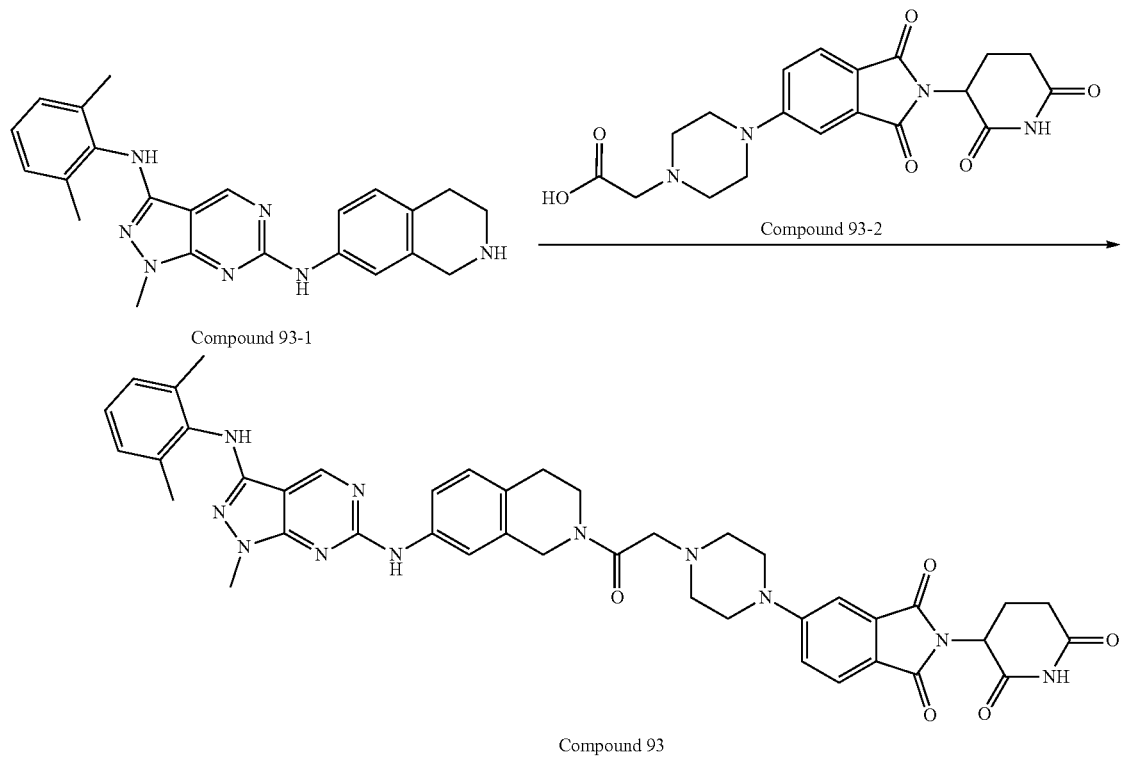

A solution of Compound 93-1 (Korean Patent No. 2128018) (20.0 mg, 0.0501 mmol) in DMF (2 mL) was added at room temperature with HATU (38.0 mg, 0.100 mmol), Compound 93-2 (WO 2020/160193) (20.0 mg, 0.0501 mmol), and TEA (10.9 mg, 0.108 mmol). The resulting mixture was stirred at room temperature for 12 hours. The reaction mixture was quenched with water (10 mL) and subjected to extraction with DCM (15 mL×2), and the pooled organic layer was washed with water (15 mL×2) and brine (15 mL×3). The crude mixture was purified by chromatography using 5% MeOH/DCM as an eluent to afford Compound 93 as a brown solid (17.0 mg, 0.011 mmol, 42.3%).

Compound 94. 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-((2-(2,6-dioxopiperidin-3-yl)-1-oxoisoindolin-5-yl)methyl)acetamide

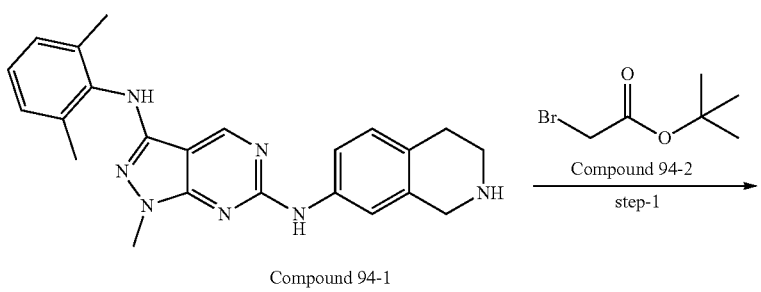

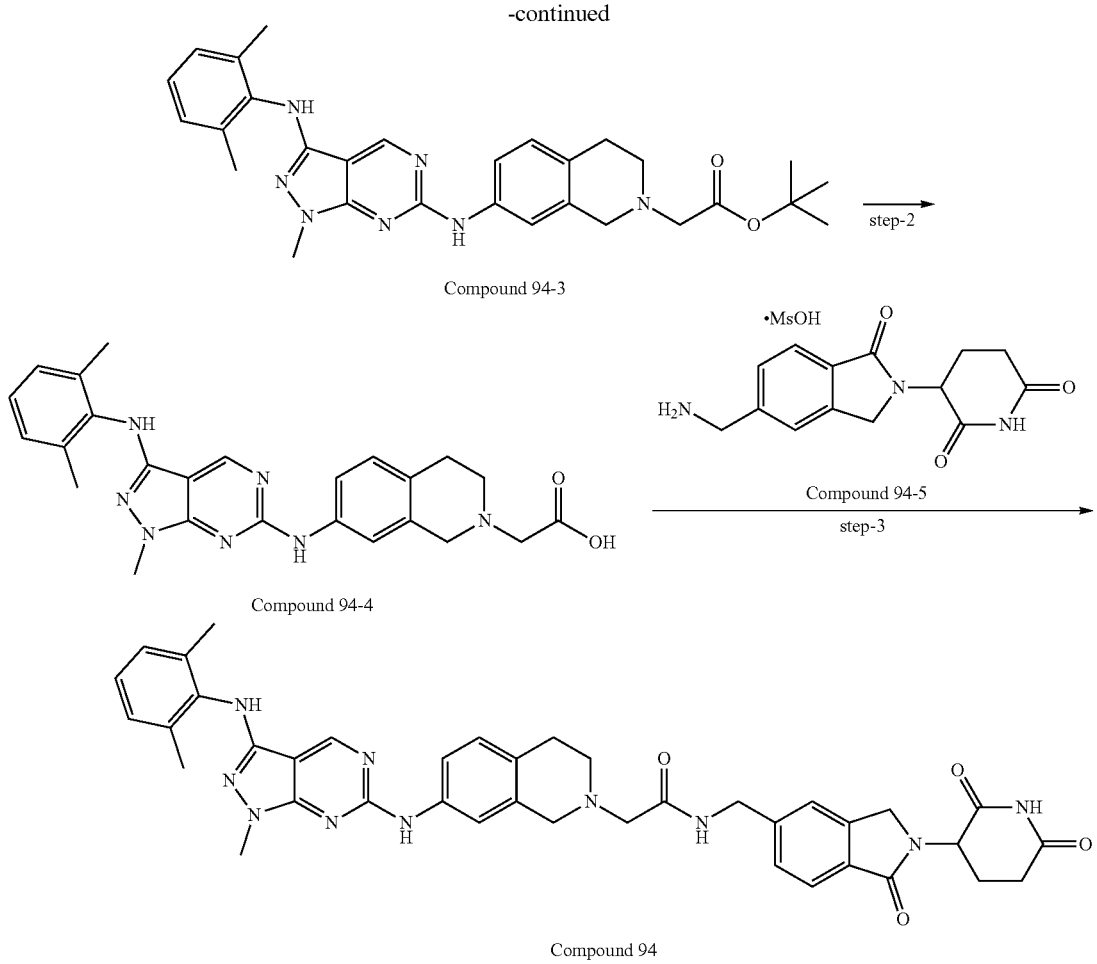

Compound 94

Step 1: Synthesis of tert-butyl 2-(7-((3-((2,6-dimethylphenyl)amino)-1-methyl-1H-pyrazolo[3,4-d]pyrimidin-6-yl)amino)-3,4-dihydroisoquinolin-2(1H)-yl)acetate (Compound 94-3)

At 0° C., a solution of Compound 94-1 (Korean Patent No. 2128018) (100 mg, 0.250 mmol) in THF (10 mL) was added with Compound 94-2 (TCI, B1473) (tert-butyl bromoacetate; 53.7 mg, 0.275 mmol) and then with TEA (50.6 mg, 0.50 mmol). The mixture was stirred at room temperature for 4 hours. When a new spot was detected in TLC, the reaction mixture was quenched with water (10 mL) and subjected to extraction with DCM (15 mL×2). The crude product was purified by MPLC using 5% MeOH/DCM as an eluent to afford Compound 94-3 as a brown solid (100 mg, 0.275 mmol, 78%).

Step 2: Synthesis of 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetic acid (Compound 94-4)

In a 7-mL vial, Compound 94-3 (95.0 mg, 0.184 mmol) was stirred together with 40% TFA/DCM (5 mL) for 16 hours. When the reaction was completed as analyzed by TLC, the solvent was completely evaporated in a vacuum, and the residue was washed with diethylether to afford Compound 94-4 as a yellow solid (78.0 mg, 0.170 mmol, 67%).

Step 3: Synthesis of 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-((2-(2,6-dioxopiperidin-3-yl)-1-oxoisoindolin-5-yl)methyl) acetamide (Compound 94)

A solution of Compound 94-4 (15.0 mg, 0.0330 mmol) in DMF (2 mL) was added at room temperature with HATU (24.9 mg, 0.100 mmol), Compound 94-5 (WO 2019/136016) (12.1 mg, 0.0330 mmol), and TEA (13.2 mg, 0.131 mmol). The resulting mixture was stirred at room temperature for 12 hours. TLC indicated that the reaction had proceeded and a new spot was formed. The reaction mixture was quenched with water (10 mL) and subjected to extraction with DCM (15 mL×2). The combined organic layer was washed with water (20 mL×2) and brine (20 mL×2). The pooled organic layer was dried over sodium sulfate and the solvent evaporated in a vacuum. The crude mixture was purified by MPLC using 5% MeOH/DCM as an eluent to afford Compound 94 as a white solid (7.0 mg, 0.00982 mmol, 30%).

Compound 95. 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-2-(2,6-dioxopiperidin-3-yl)isoindoline-1,3-dione

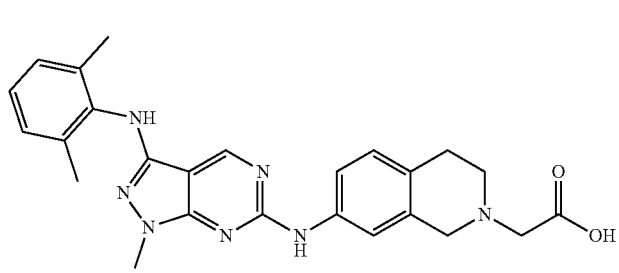

Compound 95-1

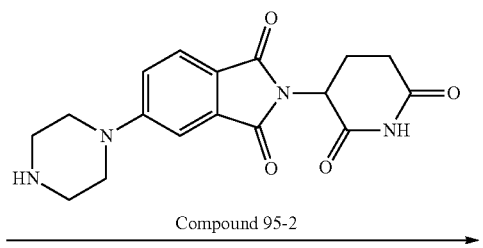

Compound 95-2

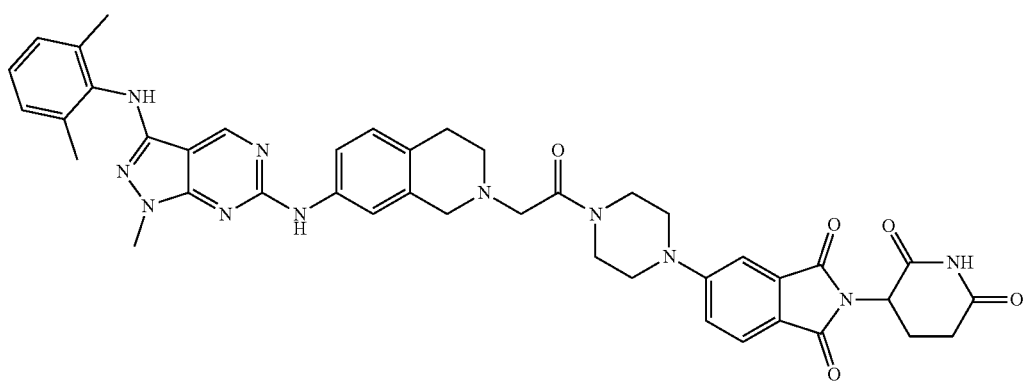

Compound 95

A solution of Compound 95-1 (identical to Compound 103-4) (15.0 mg, 0.0330 mmol) in DMF (2 mL) was added at room temperature with HATU (24.9 mg, 0.0660 mmol), Compound 95-2 (WO 2020/160192) (11.2 mg, 0.0330 mmol), and TEA (13.2 mg, 0.131 mmol) and stirred at room temperature for 12 hours. When a new spot was formed as analyzed by TLC, the reaction mixture was quenched with water (10 mL) before extraction with EA (15 mL×2). The combined organic layer was washed with water (20 mL×2) and brine (20 mL×2). The pooled organic layer was dried over sodium sulfate and the solvent was evaporated in a vacuum. The crude mixture was purified by MPLC using 5% MeOH/DCM as an eluent to afford Compound 95 as a white solid (7.0 mg, 0.00982 mmol, 30%).

Compound 96. 7-((3-((2,6-dimethylphenyl)amino)-1-methyl-1H-pyrazolo[3,4-d]pyrimidin-6-yl)amino)-N-(2-(2,6-dioxopiperidin-3-yl)-1-oxoisoindolin-5-yl)-3,4-dihydroisoquinoline-2 (1H)-carboxamide

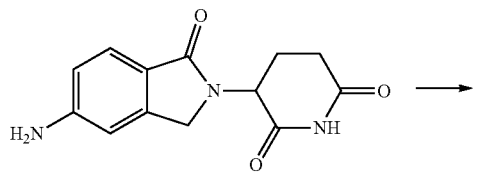

Compound 96-1

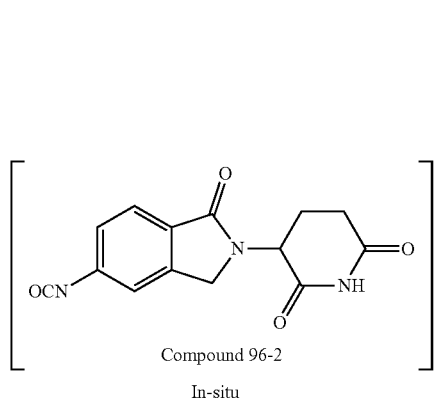

Compound 96-2

In-situ

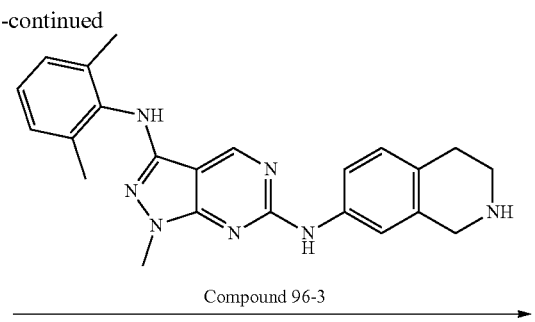

Compound 96-3

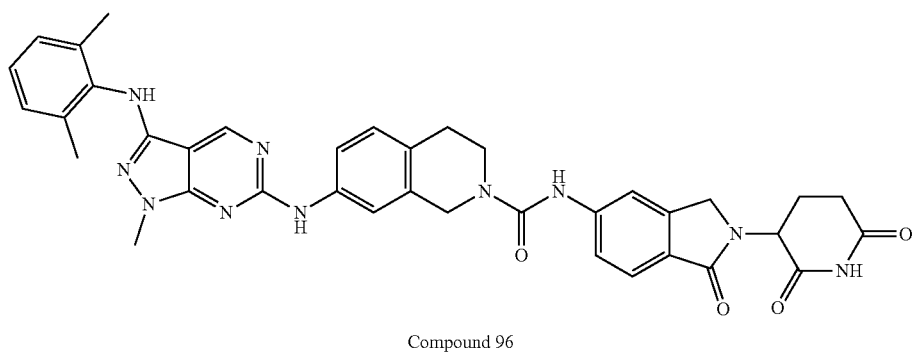

Compound 96

A suspension of Compound 96-1 (WO 2020/012337) (20.0 mg, 0.0771 mmol) in DCM (5 mL) was added with triphosgene (115 mg, 0.385 mmol) and TEA (15.5 mg, 0.0154 mmol) and stirred at room temperature for 6 hours. The solvent was completely evaporated in a vacuum to give the isocyanate intermediate Compound 96-2. A solution of the intermediate Compound 96-2 in THE (5 mL) was added with Compound 96-3 (Korean Patent No. 2128018) (30.8 mg, 0.0771 mmol) and TEA (15.5 mg, 0.0154 mmol) and stirred at 40° C. for 1 hour. When the reaction was completed as analyzed by TLC, the reaction mixture was quenched with water and subjected to extraction with EA (25 mL×3). The pooled organic layer was dried over sodium sulfate and filtered, and the solvent was evaporated in a vacuum. The crude mixture was purified by MPLC using 10% MeOH:MC, followed by recrystallization in a solvent mixture of MC and diethylether to afford Compound 96 as a white solid (16 mg, 0.0233 mmol, 30%).

Compound 97. 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-(1-(2-(2,6-dioxopiperidin-3-yl)-1,3-dioxoisoindolin-5-yl)piperidin-4-yl)acetamide

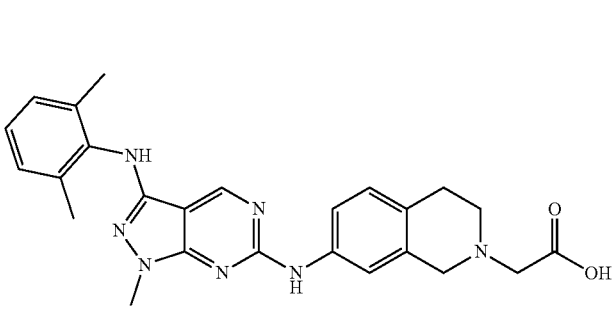

Compound 97-1

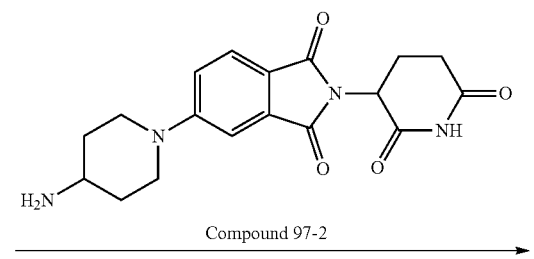

Compound 97-2

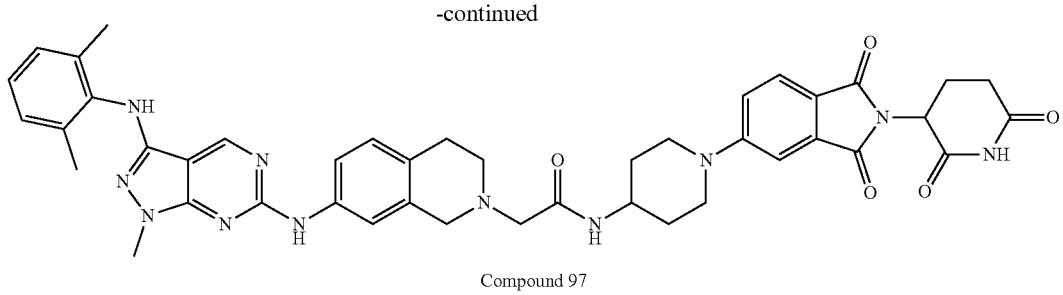

Compound 97

A solution of Compound 97-1 (identical to Compound 103-4) (10.0 mg, 0.0221 mmol) in DMF (2 mL) was added at room temperature with HATU (16.6 mg, 0.0442 mmol), Compound 97-2 (WO 2021/058017) (7.79 mg, 0.0221 mmol), and TEA (8.84 mg, 0.0870 mmol). The resulting mixture was stirred at room temperature for 12 hours. When a new spot was formed as analyzed by TLC, the reaction mixture was quenched with water (10 mL) and subjected to extraction with DCM (15 mL×2). The combined organic layer was washed with water (20 mL×2) and brine (20 mL×2). The pooled organic layer was dried over sodium sulfate and the solvent was evaporated in a vacuum. The crude mixture was purified by MPLC using 5% MeOH/DCM as an eluent to afford Compound 97 as a green solid (11.0 mg, 0.0142 mmol, 63%).

Compound 98. 3-(5-(((2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethyl)amino)methyl)-1-oxoisoindolin-2-yl)piperidin-2,6-one

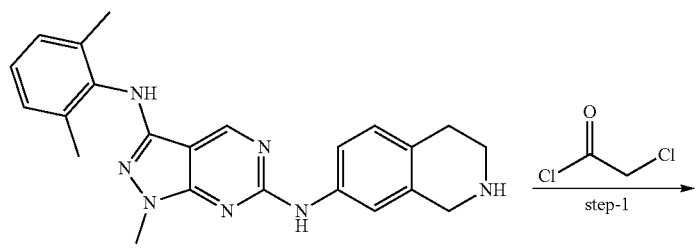

Compound 98-1

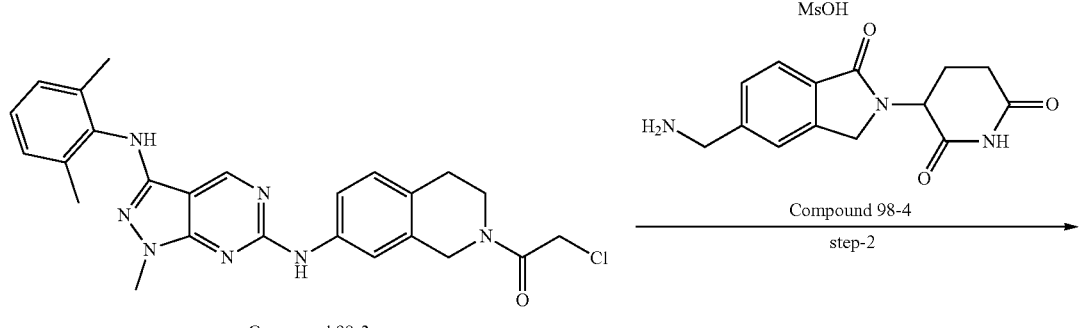

Compound 98-3

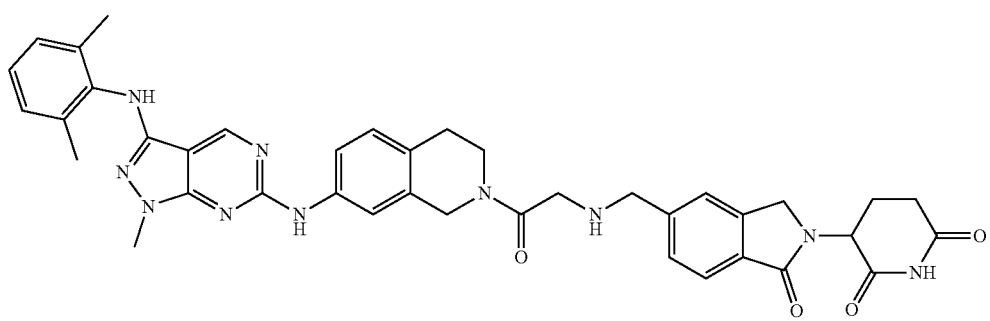

Compound 98

Step 1: Synthesis of 2-chloro-1-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethan-1-one (Compound 98-3)

A solution of Compound 98-1 (Korean Patent No. 2128018) (30.0 mg, 0.0751 mmol) in THE (5 mL) was added at room temperature with Compound 98-2 (Sigma, 104493) (chloroacetyl chloride; 53.7 mg, 0.0826 mmol) and the resulting mixture was stirred at room temperature for 4 hours. When a new spot was formed in TLC, the reaction mixture was quenched with water (10 mL) before extraction with DCM (15 mL×2). The crude mixture was purified by MPLC using 5% MeOH/DCM as an eluent to afford Compound 98-3 as a yellow solid (24.0 mg, 0.0505 mmol, 67%).

Step 2: Synthesis of 3-(5-(((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)amino)methyl)-1-oxoisoindolin-2-yl)piperidin-2,6-one (Compound 98)

A solution of Compound 98-3 (10.0 mg, 0.0210 mmol) in ACN (2 mL) was added at room temperature with sodium carbonate (5.80 mg, 0.0420 mmol), Compound 98-4 (WO 2019/136016) (7.80 mg, 0.0210 mmol), and KI (0.697 mg, 0.00420 mmol). The resulting mixture was stirred at 80° C. for 4 hours. When a new spot was formed in TLC, the reaction mixture was quenched with water (10 mL) before extraction with EA (15 mL×2). The pooled organic layer was dried over sodium sulfate and the solvent was evaporated in a vacuum. The crude mixture was purified by MPLC using 5% MeOH/DCM as an eluent to afford Compound 98 as a white solid (7.0 mg, 0.0142 mmol, 63%).

Compound 99. 7-((3-((2,6-dimethylphenyl)amino)-1-methyl-1H-pyrazolo[3,4-d]pyrimidin-6-yl)amino)-N-((2-(2,6-dioxopiperidin-3-yl)-1-oxoisoindolin-5-yl)methyl)-3,4-dihydroisoquinoline-2 (1H)-carboxamide

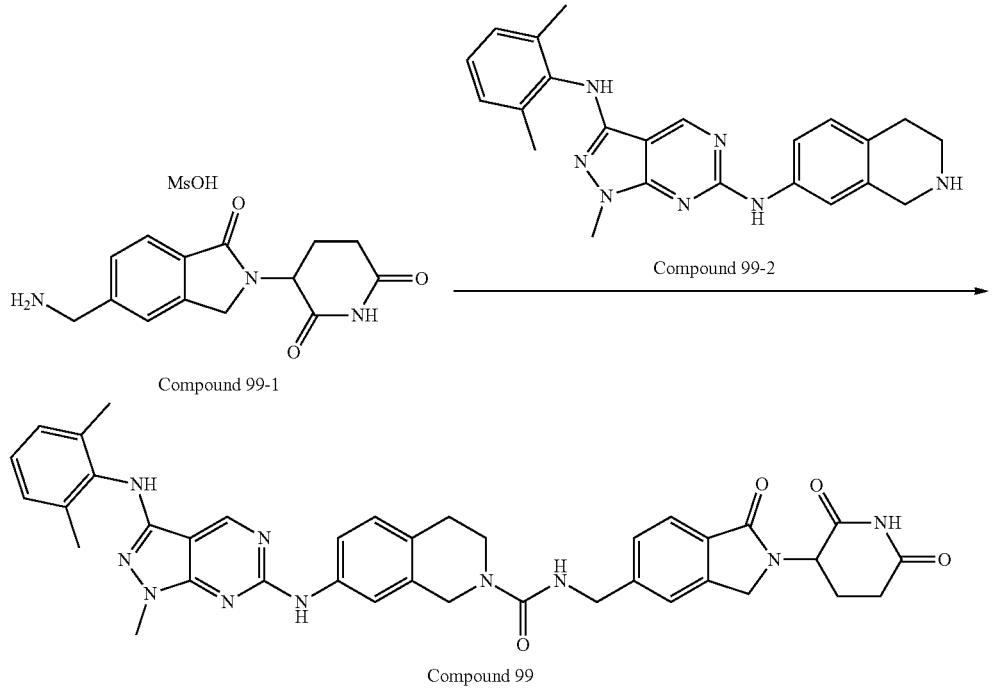

A suspension of Compound 99-1 (WO 2019/136016) (15.0 mg, 00410 mmol) in DMF (2 mL) was added with TEA (8.21 mg, 0.0820 mmol) and CDI (6.58 mg, 0.0490 mmol) and stirred at room temperature for 4 hours. After addition of Compound 99-2 (Korean Patent No. 2128018) (10.0 mg, 0.490 mmol), the resulting mixture was stirred at 80° C. for 12 hours. When a new spot was formed in TLC, the reaction mixture was quenched with water before extraction with EA (25 mL×2). The pooled organic layer was washed with water (20 mL×3) and brine (20 mL×3) and dried over sodium sulfate, and the solvent was evaporated in a vacuum. The crude mixture was purified by MPLC using a 9:1 mixture of MC:MeOH to afford Compound 99 as an off-white solid (11.0 mg, 0.0410 mmol, 39%).

Compound 100. N-(4-((3-((2,6-dimethylphenyl)amino)-1-methyl-1H-pyrazolo[3,4-d]pyrimidin-6-yl)amino)phenethyl)-1-(2-(2,6-dioxopiperidin-3-yl)-1,3-dioxoisoindolin-5-yl)piperidine-4-carboxamide

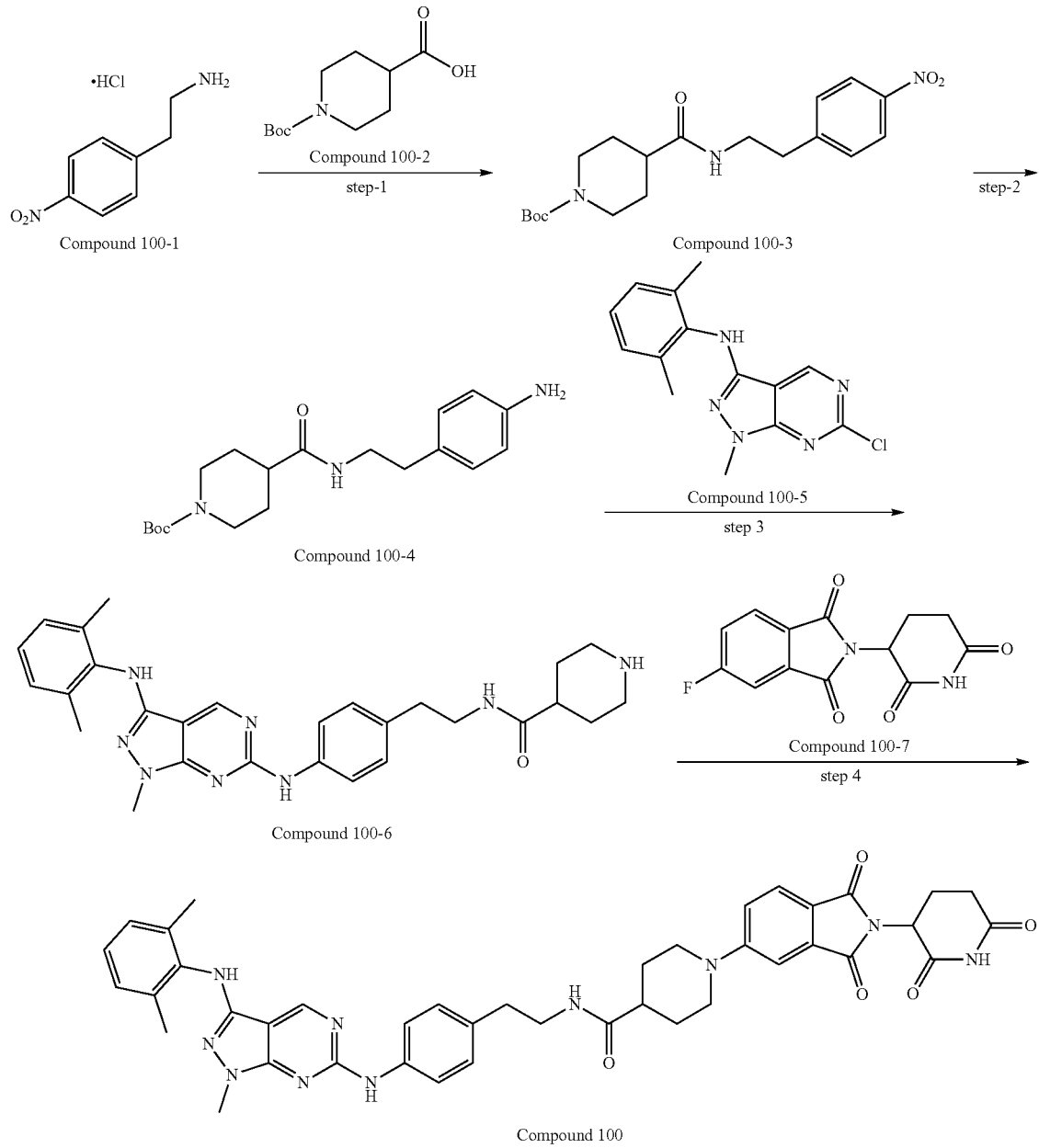

Step 1: Synthesis of tert-butyl 4-((4-nitrophenethyl)carbamoyl)piperidine-1-carboxylate (Compound 100-3)

A suspension of Compound 100-1 (Combi-blocks, OR-2197) (2-(4-nitrophenyl)ethane-1-amine hydrochloride; 500.0 mg, 2.46 mmol) in DMF (5 mL) was added with TEA (995.0 mg, 9.48 mmol) and then at room temperature with HATU (1.87 g, 4.92 mmol) and the resulting mixture was stirred for 15 minutes. After addition of Compound 100-2 (BLDPharm, BD00948389) (1-(tert-butoxycarbonyl)piperidine-4-carboxylic acid; 565.0 mg, 2.46 mmol), the mixture was stirred at room temperature for 2 hours. The crude reaction mixture was diluted with water (20 mL) before extraction with ethyl acetate (3×25 mL). The pooled organic layer was washed with water (2×10 mL) and brine (2×10 mL), dried over MgSO$_4$, and concentrated in a vacuum. The concentrate was purified by column chromatography using EA/Hex 50% to afford Compound 100-3 as a purple solid (565 mg, 1.49 mmol, 60%).

Step 2: Synthesis of tert-butyl 4-((4-aminophenethyl)carbamoyl)piperidine-1-carboxylate (Compound 100-4)

A solution of Compound 100-3 (200 mg, 0.529 mmol) in EtOAc (5 mL) was added with 10% Pd/C (20 mg). The resulting mixture was stirred at room temperature under a pressure of 35 psi for 12 hours in a $H_2$ (g) atmosphere in a Parr reactor. When the reaction was completed as analyzed by TLC, Pd/C was removed by filtration through a celite filter, and the combined filtrate was concentrated to afford Compound 100-4 as a white solid (160 mg, 0.460 mmol, 87%).

Step 3: Synthesis of N-(4-((3-((2,6-dimethylphenyl)amino)-1-methyl-1H-pyrazolo[3,4-d]pyrimidin-6-yl)amino)phenethyl)piperidine-4-carboxamide (Compound 100-6)

A suspension of Compound 100-4 (100 mg, 0.287 mmol) in IPA (5 mL) was added with Compound 100-5 (Korean Patent No. 2128018) (82.3 mg, 287 mmol) and PTSA-$H_2O$ (60.0 mg, 0.315 mmol), heated to 90° C., and stirred for 12 hours. When the reaction was completed as analyzed by TLC, the solvent was evaporated. The residue was diluted with water, acidified with 1 N HCl, and washed with DCM. The aqueous layer was basified with saturated $NaHCO_3$ (aq.) and subjected to extraction with DCM (50 mL×2). The pooled organic layer was dried over sodium sulfate and filtered. The solvent was evaporated in a vacuum to afford Compound 100-6 as a yellow solid (80.0 mg, 0.160 mmol, 55%).

Step 4: Synthesis of N-(4-((3-((2,6-dimethylphenyl)amino)-1-methyl-1H-pyrazolo[3,4-d]pyrimidin-6-yl)amino)phenethyl)-1-(2-(2,6-dioxopiperidin-3-yl)-1,3-dioxoisoindolin-5-yl)piperidine-4-carboxamide (Compound 100)

A suspension of Compound 100-6 (20.0 mg, 0.040 mmol) in DMSO (1 mL) was added with Compound 100-7 (Combi-Blocks, HD-3240) (11.0 mg, 0.040 mmol) and DIPEA (15.5 mg, 0.120 mmol), heated to 90° C., and stirred for 14 hours. When the reaction was completed as analyzed by TLC, the solvent was evaporated. The residue was diluted with water, followed by extraction with EA (20 mL×3). The pooled organic layer was dried over sodium sulfate and filtered. The solvent was evaporated in a vacuum and the crude mixture was purified by column chromatography using DCM/MeOH 5% to afford Compound 100 as a yellow solid (4.02 mg, 0.005 mmol, 13%).

Compound 101. N-(4-((3-((2,6-dimethylphenyl)amino)-1-methyl-1H-pyrazolo[3,4-d]pyrimidin-6-yl)amino)phenethyl)-1-(2-((2-(2,6-dioxopiperidin-3-yl)-1,3-dioxoisoindolin-5-yl)amino)-2-oxoethyl)piperidine-4-carboxamide

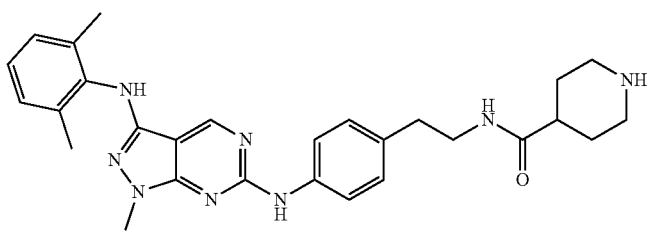

Compound 101-1

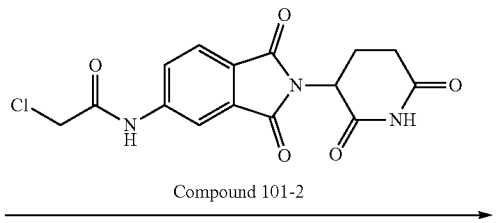

Compound 101-2

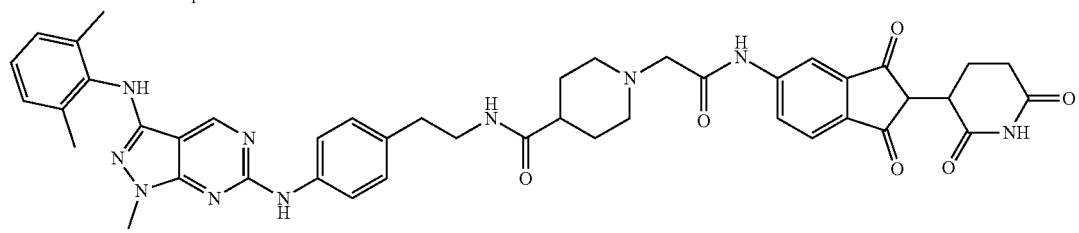

Compound 101

A suspension of Compound 101-1 (identical to Compound 100-6) (15.0 mg, 0.030 mmol) in DMSO (1 mL) was added with Compound 101-2 (WO 2020/038415) (10.50 mg, 0.030 mmol) and DIPEA (11.6 mg, 0.090 mmol), heated to 90° C., and stirred for 16 hours. When the reaction was completed as analyzed by TLC, the reaction mixture was quenched with water, and the aqueous layer was subjected to extraction with EA (20 mL×3). The pooled organic layer was dried over sodium sulfate and filtered, and the solvent was evaporated in a vacuum. The crude mixture was purified by column chromatography using DCM/MeOH 5% to afford Compound 101 as a purple solid (14.0 mg, 0.0172 mmol, 57%).

Compound 102. N4-(4-((3-((2,6-Dimethylphenyl)amino)-1-methyl-1H-pyrazolo[3,4-d]pyrimidin-6-yl)amino)phenethyl)-N1-(2-(2,6-dioxopiperidin-3-yl)-1-oxoisoindolin-5-yl)piperidine-1,4-dicarboxamide

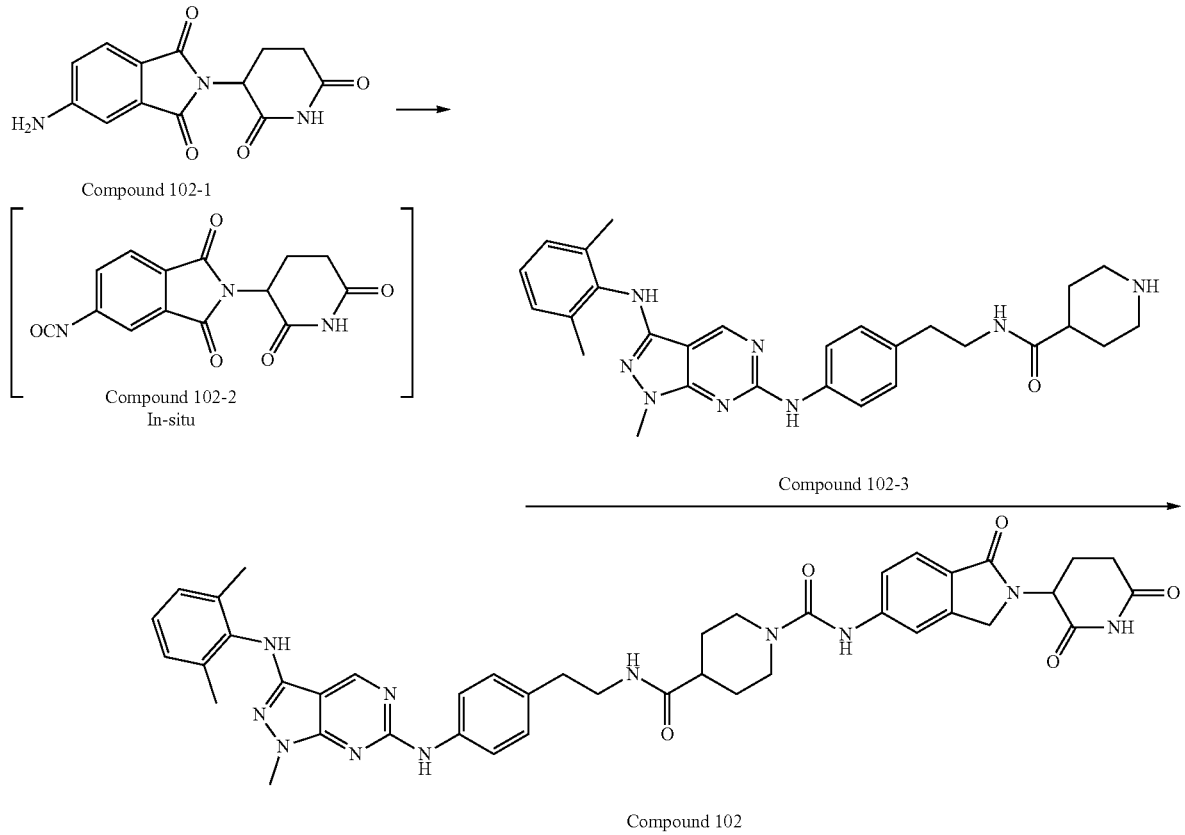

A suspension of Compound 102-1 (WO 2020/01233) (15.0 mg, 0.057 mmol) in DCM (5 mL) was added with triphosgene (85.74 mg, 0.289 mmol) and TEA (29.21 mg, 0.289 mmol) and stirred at room temperature for 6 hours. When the reaction was completed as analyzed by TLC, the reaction solvent was evaporated to give the intermediate Compound 102-2 which was then dissolved in THF and loaded, together with a solution of Compound 102-3 (identical to Compound 100-6) (28.42 mg, 0.057 mmol) in THF, and TEA (11.52 mg, 0.114 mmol), into an RB. The mixture was stirred at 40° C. for 1 hour. When TLC indicated the completion of the reaction, the reaction mixture was diluted with water and the aqueous layer was subjected to extraction with BA (20 mL×3). The pooled organic layer was dried over sodium sulfate and filtered, and the solvent was evaporated in a vacuum. The residue was purified by column chromatography using DCM/MeOH 5% to afford Compound 102 as a yellow solid (12 mg, 0.015 mmol, 26%).

Compound 103. 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-1-oxoisoindolin-2-yl)piperidin-2,6-one

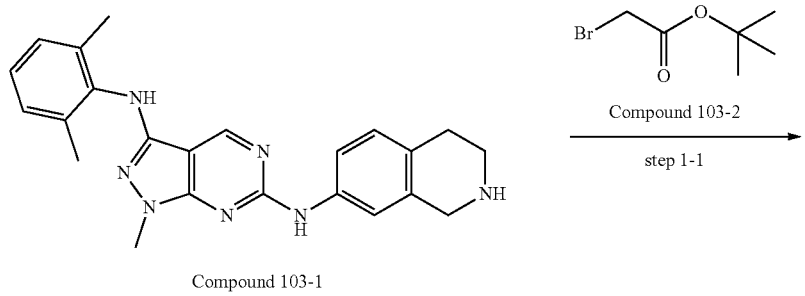

-continued
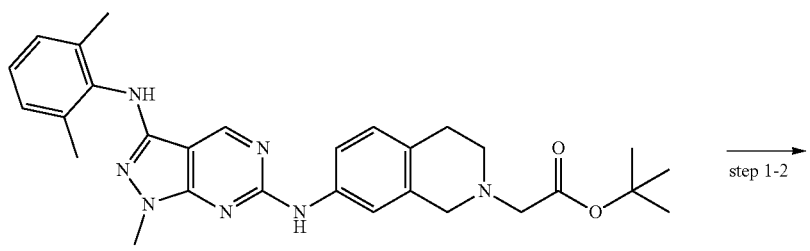
Compound 103-3
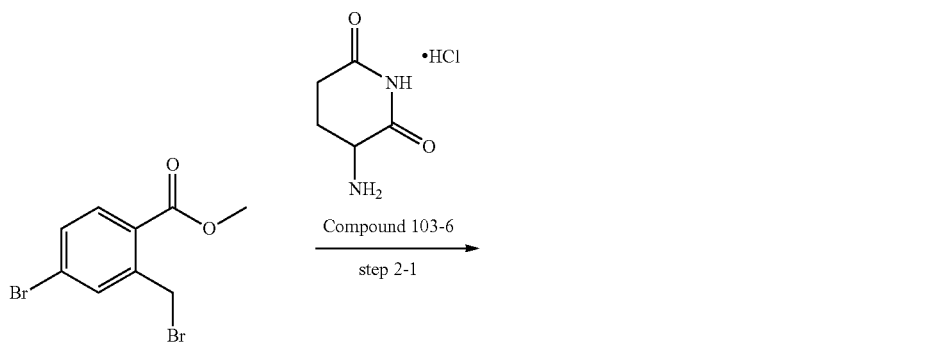
Compound 103-4
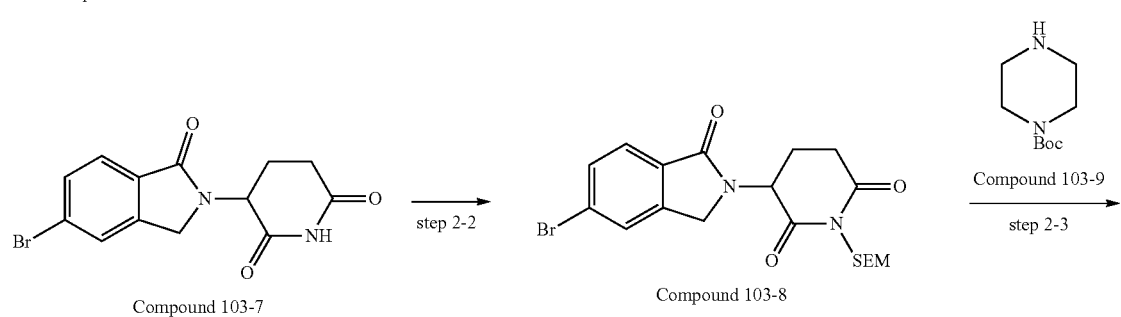
Compound 103-5   Compound 103-6
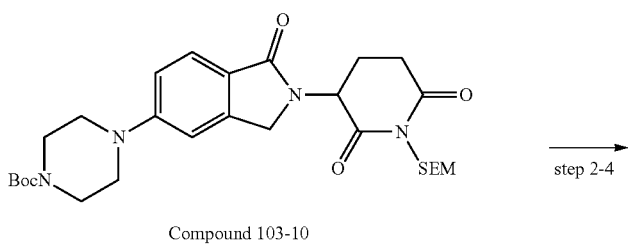
Compound 103-7   Compound 103-8   Compound 103-9
Compound 103-10

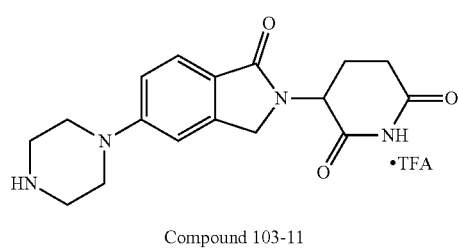

Compound 103-11

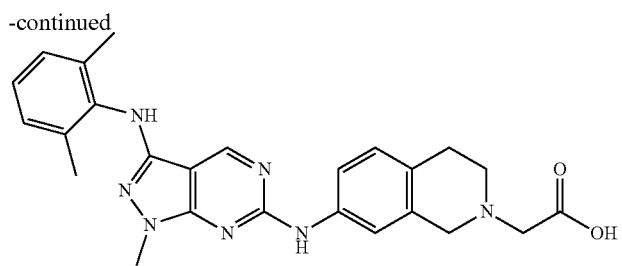

Compound 103-4 step 2-5

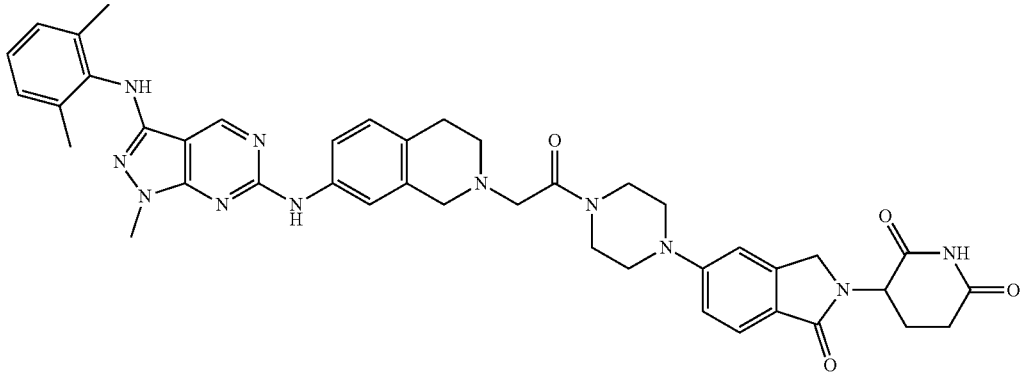

Compound 103

Step 1: Synthesis of 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetic acid (Compound 103-4)

Step 1-1. Synthesis of tert-butyl 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetate (Compound 103-3)

A solution of Compound 103-1 (Korean Patent No. 2128018) (30 mg, 0.075 mmol) in THF (1 mL) was added with Compound 103-2 (TCI, B1473) (tert-butyl bromoacetate; 12 μl, 0.083 mmol) and then at 0° C. with TEA (21 μl, 0.150 mmol). The resulting mixture was stirred at room temperature for 4 hours. After completion of the reaction, the reaction mixture was quenched with water, subjected to extraction with EA (3×10 mL), and washed with water (3×). The pooled organic layer was dried over sodium sulfate and filtered, and the solvent was evaporated in a vacuum. The residue was purified by MPLC using 5% MeOH/MC to afford Compound 103-3 as a pale yellow oil (26 mg, 0.051 mmol, 67%).

Step 1-2. Synthesis of 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetic acid (Compound 103-4)

A solution of Compound 103-3 (26 mg, 0.051 mmol) was added to 40% TFA/DCM (0.4/0.6 mL) and the resulting mixture was stirred at room temperature for 3 hours. After completion of the reaction, the solvent was evaporated from the reaction mixture in a vacuum, and the white precipitates thus formed were collected by filtration and washed with ether. The wetted product was dried in a vacuum to afford Compound 103-4 as a pale yellow solid (19 mg, 0.034 mmol, 68%).

Step 2: Synthesis of 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-1-oxoisoindolin-2-yl)piperidin-2,6-one (Compound 103)

Step 2-1. Synthesis of 3-(5-bromo-1-oxoisoindolin-2-yl)piperidin-2,6-one (Compound 103-7)

A solution of Compound 103-5 (TCI, M2941) (methyl 4-bromo-2-(bromomethyl)benzoate; 1 g, 3.25 mmol) in DMF (5 mL) was added at room temperature with Compound 103-6 (BLDPharm, BD170886) (3-aminopiperidin-2,6-one hydrochloride; 588 mg, 3.57 mmol) and potassium carbonate (1.3 g, 9.74 mmol). The resulting mixture was stirred at 110° C. for 3 hours. When the product was formed as analyzed by TLC, the reaction mixture was added with water and quenched to 0° C. The solid thus formed was filtered and washed with water. The wetted product was dried in a vacuum to afford Compound 103-7 as a gray solid (856 mg, 2.649 mmol, 82%).

Step 2-2. Synthesis of 3-(5-bromo-1-oxoisoindolin-2-yl)-1-((2-(trimethylsilyl)ethoxy)methyl)piperidin-2,6-one (Compound 103-8)

A solution of Compound 103-7 (200 mg, 0.62 mmol) in DMF (1 mL) was added with SEMCl (0.13 mL, 0.74 mmol) and DBU (0.14 mL, 0.93 mmol). The mixture was stirred at room temperature for 5 hours. After completion of the reaction, the reaction mixture was quenched with NH$_4$Cl, subjected to extraction with EA (3×15 mL), and washed with water (3×) and brine. The pooled organic layer was dried over sodium sulfate and filtered, and the solvent was evaporated in a vacuum. The residue was purified by MPLC using 50% EA/HEX to afford Compound 103-8 as an ivory solid (179 mg, 0.39 mmol, 64%).

Step 2-3. Synthesis of tert-butyl 4-(2-(2,6-dioxo-1-((2-(trimethylsilyl)ethoxy)methyl)piperidin-3-yl)-1-oxoisoindolin-5-yl)piperazine-1-carboxylate (Compound 103-10)

A solution of Compound 103-8 (100 mg, 0.221 mmol) in dioxane (5 mL) was added with Compound 103-9 (TCI, B2415) (1-Boc-piperazine; 49 mg, 0.265 mmol), cesium carbonate (223 mg, 0.684 mmol), RuPhos (21 mg, 0.044 mmol), and RuPhos Pd G2 (34 mg, 0.044 mmol). The mixture was stirred at 100° C. for 16 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 50% EA/HEX to afford Compound 103-10 as an ivory solid (56 mg, 0.100 mmol, 45%).

Step 2-4. Synthesis of 3-(1-oxo-5-(piperazin-1-yl)isoindolin-2-yl)piperidin-2,6-one and 2,2,2-trifluoroacetaldhyde compound (1:1) (Compound 103-11)

Compound 103-10 (56 mg, 0.100 mmol) was added to 40% TFA/DCM (1.6/2.4 mL) and stirred at room temperature for 3 hours. After completion of the reaction, the solvent was evaporated from the reaction mixture in a vacuum. The white precipitates thus formed were collected by filtration and washed with ether. The wetted product was dried in a vacuum to afford Compound 103-11 as a pale yellow solid (32 mg, 0.097 mmol, 97%).

Step 2-5. Synthesis of 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-1-oxoisoindolin-2-yl) piperidin-2,6-one (Compound 103)

A solution of Compound 103-4 (19 mg, 0.034 mmol) in DMF (1 mL) was added with Compound 103-11 (12 mg, 0.038 mmol), EDCl (16 mg, 0.085 mmol), HOBt (7 mg, 0.051 mmol), and DIPEA (24 μl, 0.137 mmol) and stirred at room temperature for 12 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/MC to afford Compound 103 as a pale yellow solid (6 mg, 0.008 mmol, 23%).

Compound 104. 3-(5-(4-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethyl)piperazin-1-yl)-1-oxoisoindolin-2-yl) piperidin-2,6-one

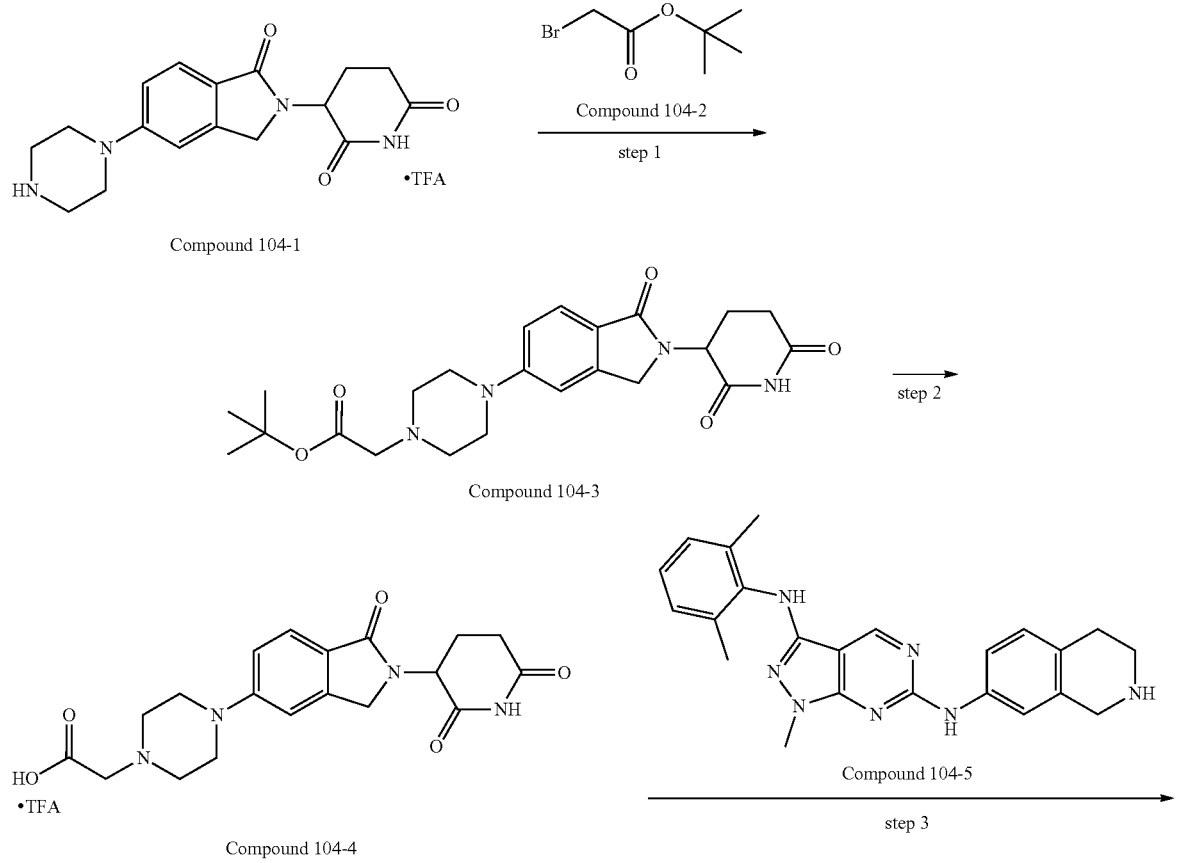

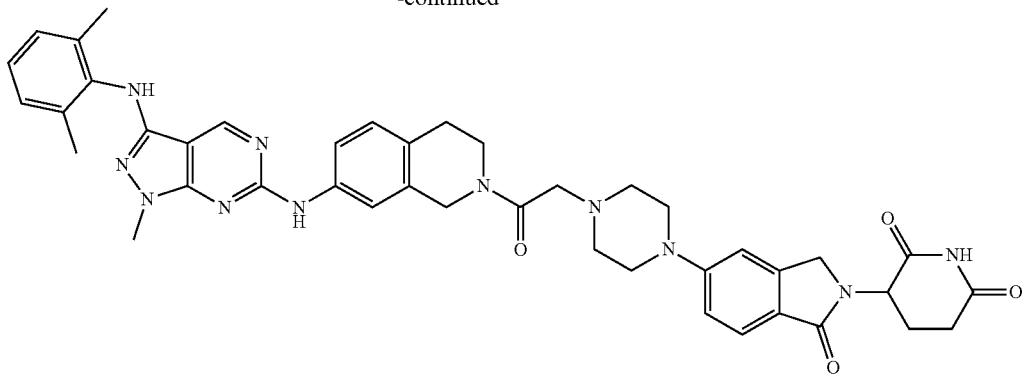

Compound 104

Step 1: Synthesis of tert-butyl 2-(4-(2-(2,6-dioxopiperidin-3-yl)-1-oxoisoindolin-5-yl)piperazin-1-yl)acetate (Compound 104-3)

A solution of Compound 104-1 (identical to Compound 103-11) (27 mg, 0.082 mmol) in THE (1 mL) was added with Compound 104-2 (TCI, B1473) (tert-butyl bromoacetate; 13 µl, 0.090 mmol) and then at 0° C. with TEA (23 µl, 0.164 mmol). The mixture was stirred at room temperature for 4 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/MC to afford Compound 104-3 as an ivory oil (11 mg, 0.025 mmol, 31%).

Step 2: Synthesis of 2-(4-(2-(2,6-dioxopiperidin-3-yl)-1-oxoisoindolin-5-yl)piperazin-1-yl)acetic acid and 2,2,2-trifluoroacetaldhyde compound (1:1) (Compound 104-4)

Compound 104-3 (11 mg, 0.025 mmol) was added to 40% TFA/DCM (0.4/0.6 mL) and stirred at room temperature for 3 hours. After completion of the reaction, the solvent was evaporated from the reaction mixture in a vacuum. The white precipitates thus formed were collected by filtration and washed with ether. The wetted product was dried in a vacuum to afford Compound 104-4 as an ivory solid (10 mg, 0.021 mmol, 83%).

Step 3: Synthesis of 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperazin-1-yl)-1-oxoisoindolin-2-yl)piperidin-2,6-one (Compound 104)

A solution of Compound 104-4 (10 mg, 0.021 mmol) in DMF (1 mL) was added with Compound 104-5 (Korean Patent No. 2128018) (8 mg, 0.021 mmol), HATU (16 mg, 0.041 mmol), and TEA (9 µl, 0.062 mmol). The mixture was stirred at room temperature for 4 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/MC to afford Compound 104 as an off-white solid (5 mg, 0.007 mmol, 32%).

Compound 105. 3-(5-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethoxy)-1-oxoisoindolin-2-yl)piperidin-2,6-one

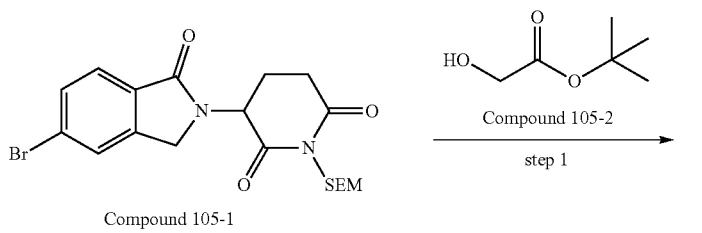

-continued

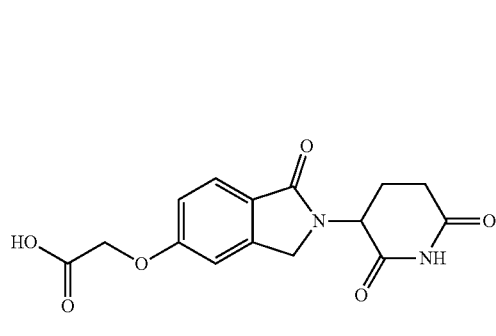

Compound 105-4

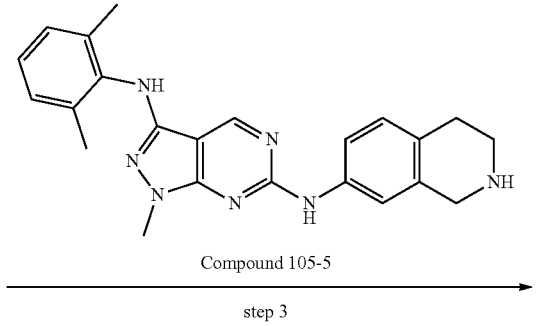

Compound 105-5 step 3

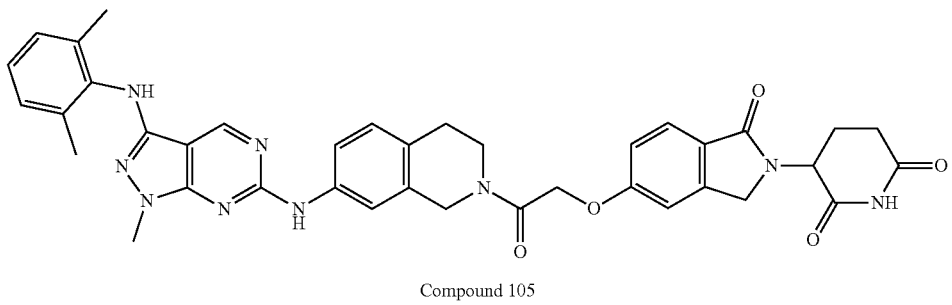

Compound 105

Step 1: Synthesis of tert-butyl 2-((2-(2,6-dioxo-1-((2-(trimethylsilyl)ethoxy)methyl)piperidin-3-yl)-1-oxoisoindolin-5-yl)oxy)acetate (Compound 105-3)

A stirred solution of Compound 105-1 (identical to Compound 103-8) (3-(5-bromo-1-oxoisoindolin-2-yl)-1-((2-(trimethylsilyl)ethoxy)methyl)piperidin-2,6-one; 100 mg, 0.22 mmol), Compound 105-2 (oakwood, 222563) (tert-butyl 2-hydroxyacetate; 29 mg, 0.22 mmol), (Ir[dF(CF$_3$)ppy]$_2$ (dtbpy))PF$_6$ (25 mg, 0.022 mmol), NiCl$_2$ (glyme) (24 mg, 0.11 mmol), dtbbpy (30 mg, 0.11 mmol) in MeCN (1 mL) degassed in a nitrogen atmosphere was added with 2,2,6,6-tetramethylpiperidine (38 µl, 0.22 mmol). While being exposed to blue LED light, the mixture was vigorously stirred overnight at room temperature. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 50% EA/HEX to afford Compound 105-3 as an off-white solid (61 mg, 0.121 mmol, 55%).

Step 2: Synthesis of 2-((2-(2,6-dioxopiperidin-3-yl)-1-oxoisoindolin-5-yl)oxy)acetic acid (Compound 105-4)

Compound 105-3 (60 mg, 0.12 mmol) was added to 40% TFA/DCM (3 mL) and stirred at room temperature for 3 hours. After completion of the reaction, the solvent was evaporated from the reaction mixture in a vacuum. The white precipitates thus formed were collected by filtration and washed with ether. The wetted product was dried in a vacuum to afford Compound 105-4 as an ivory solid (15 mg, 0.047 mmol, 79%).

Step 3: Synthesis of 3-(5-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)-1-oxoisoindolin-2-yl)piperidin-2,6-one (Compound 105)

A solution of Compound 105-5 (Korean Patent No. 2128018) (25 mg, 0.06 mmol) in DMF (1 mL) was added with Compound 105-4 (20 mg, 0.06 mmol), HATU (48 mg, 0.13 mmol), and TEA (36 µl, 0.19 mmol). The mixture was stirred at room temperature for 2 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/MC to afford Compound 105 as an off-white solid (7 mg, 0.010 mmol, 17%).

Compound 106. 3-(5-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)oxy)-1-oxoisoindolin-2-yl) piperidin-2,6-one

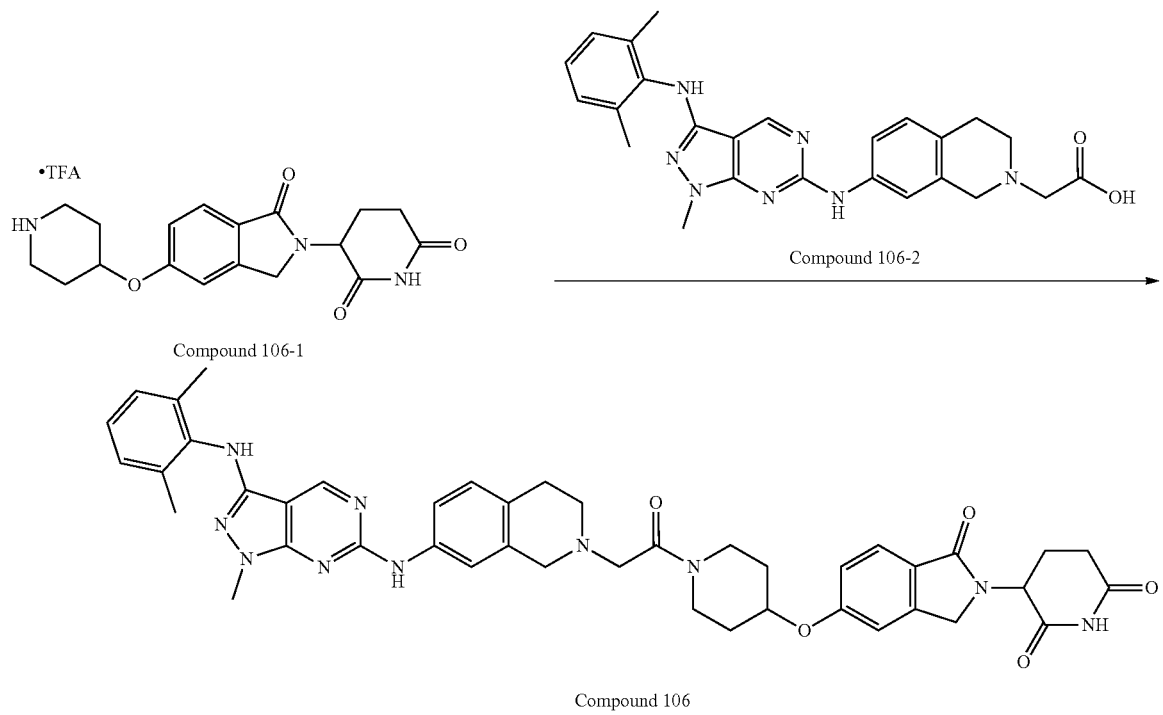

Compound 106-1

Compound 106-2

Compound 106

A solution of Compound 106-2 (identical to 103-4) (30 mg, 0.07 mmol) in DMF (1 mL) was added with Compound 106-1 (identical to Compound 116-5) (23 mg, 0.07 mmol), EDCI (14 mg, 0.07 mmol), HOBt (10 mg, 0.07 mmol), and DIPEA (37 uL, 0.210 mmol). The mixture was stirred at room temperature for 12 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 10% MeOH/MC to afford Compound 106 as an off-white solid (8 mg, 0.010 mmol, 15%).

Compound 107. (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl) methyl)piperidin-1-yl)-1,3-dioxoisoindolin-2-yl)-2, 6-dioxopiperidin-1-yl)methyl pivalate

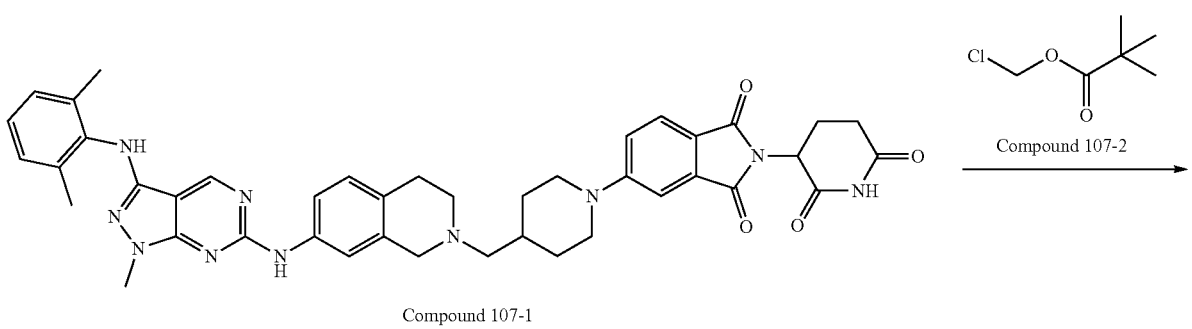

Compound 107-1

Compound 107-2

-continued

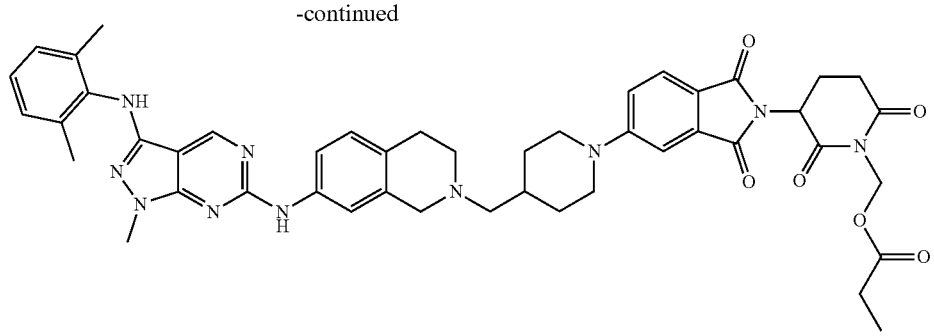

Compound 107

A solution of Compound 107-1 (identical to Compound 29) (25 mg, 0.0332 mmol) in DMF (1 mL) was added with Compound 107-2 (TCI, P1012) (chloromethylpivalate; 4.24 mg, 0.0298 mmol) and then with cesium carbonate (21.6 mg, 0.0664 mmol) and TBAI (2.45 mg, 0.0664 mmol). The mixture was stirred at room temperature for 1 hour. When a new spot was formed as analyzed by TLC, the reaction mixture was quenched with water and the aqueous layer was subjected to extraction with EtOAc (25 mL×2). The combined organic layer was washed with water and brine and dried over sodium sulfate. The solvent was evaporated in a vacuum. The crude mixture was purified by MPLC using 5% MeOH/DCM as an eluent to afford Compound 107 as a yellow crystalline solid (14.0 mg, 0.0161 mmol, 48%).

Compound 108. 2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-N-(2-(2,6-dioxopiperidin-3-yl)-1-oxoisoindolin-5-yl)acetamide

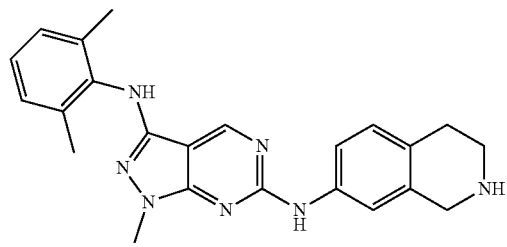
Compound 108-1

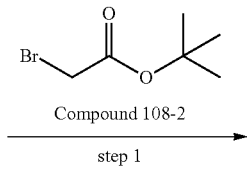
Compound 108-2 step 1

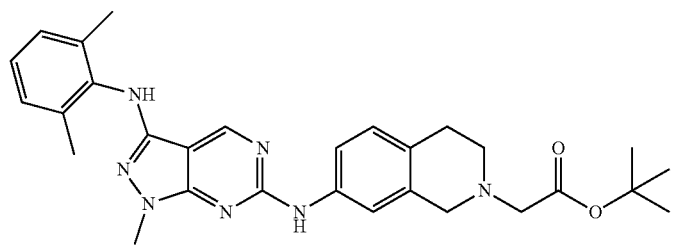
Compound 108-3 step 2

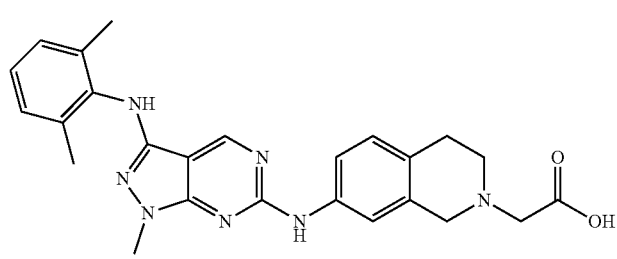
Compound 108-4

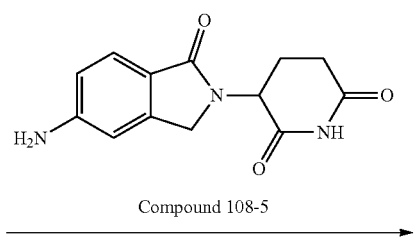
Compound 108-5 step 3

-continued

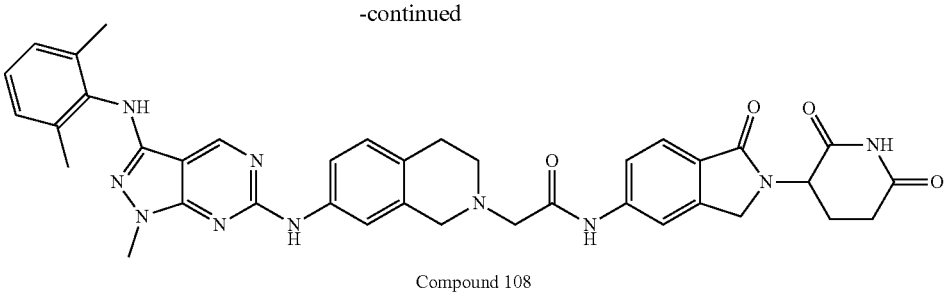

Compound 108

Step 1: Synthesis of tert-butyl 2-(7-((3-((2,6-dimethylphenyl)amino)-1-methyl-1H-pyrazolo[3,4-d]pyrimidin-6-yl)amino)-3,4-dihydroisoquinolin-2(1H)-yl)acetate (Compound 108-3)

A solution of Compound 108-1 (Korean Patent No. 2128018) (50.0 mg, 0.125 mmol) in THF (5.0 mL) was added at 0° C. with Compound 108-2 (TCI, B1473) (tert-butyl bromoacetate; 26.5 mg, 0.137 mmol) and then with TEA (25.2 mg, 0.25 mmol). The mixture was stirred at room temperature for 4 hours. When a new spot was formed as analyzed by TLC, the reaction mixture was quenched with water (10 mL) before extraction with DCM (15 mL×2). The crude mixture was purified by MPLC using a solvent mixture of 5% MeOH:DCM to afford Compound 108-3 as a brown solid.

Step 2: Synthesis of 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetic acid (Compound 108-4)

In a 7-mL vial, Compound 108-3 (40.0 mg, 0.0779 mmol) was added to 40% TFA/DCM (2 mL) and stirred for 16 hours. When the reaction was completed as analyzed by TLC, the solvent was completely evaporated in a vacuum. The residue was washed with diethylether to afford Compound 108-4 as a yellow solid (28.0 mg, 0.061 mmol, 78%).

Step 3: Synthesis of 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-(2-(2,6-dioxopiperidin-3-yl)-1-oxoisoindolin-5-yl)acetamide (Compound 108)

A solution of Compound 108-4 (10.0 mg, 0.0218 mmol) in DMF (2 mL) was added at room temperature with HATU (16.5 mg, 0.0436 mmol), Compound 108-5 (WO 2020/01233) (5.66 mg, 0.0218 mmol), and TEA. The mixture was stirred at room temperature for 12 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the solvent was evaporated in a vacuum. The crude mixture was purified by MPLC using a solvent mixture of 5% MeOH:DCM to afford Compound 108 as a white solid (7.0 mg, 0.0100 mmol, 45%).

Compound 109. 5-(4-((6-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione

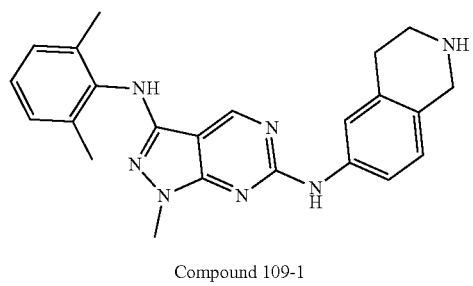

Compound 109-1

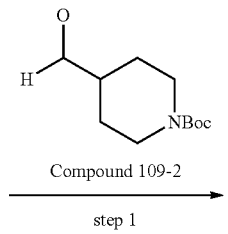

Compound 109-2 step 1

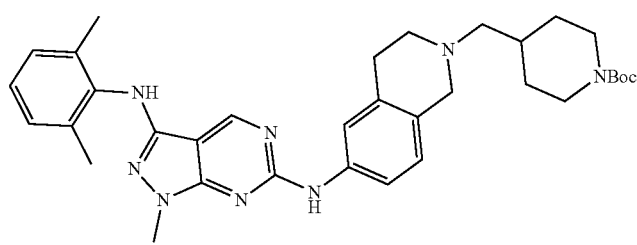

Compound 109-3 step 2

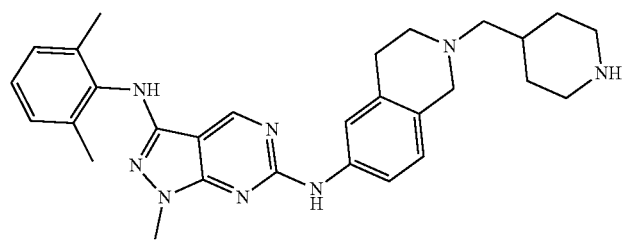

Compound 109-4

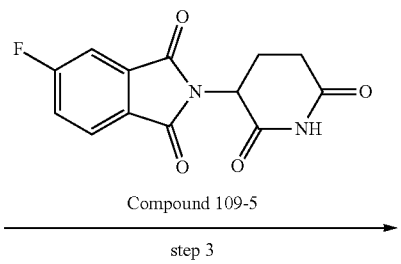

Compound 109-5 step 3

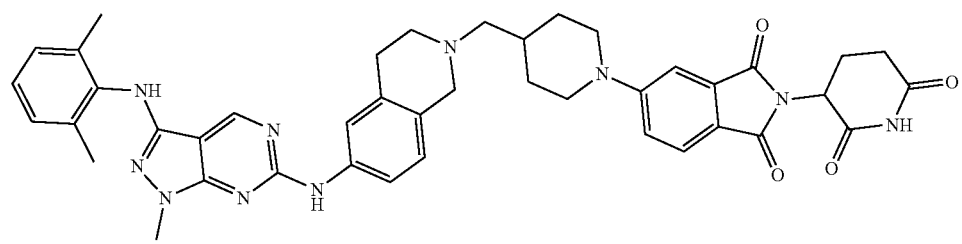

Compound 109

Step 1: Synthesis of tert-butyl 4-((6-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidine-1-carboxylate (Compound 109-3)

A solution of Compound 109-2 (TCI, B3873) (Boc-piperidine aldehyde; 46.9 mg, 0.200 mmol) in MeOH (5 mL) was added with Compound 109-1 (Korean Patent No. 2128018) (80.0 g, 0.200 mmol) and one drop of acetic acid and stirred for 1 hour. To this mixture was added NaCNBH$_3$ (24.0 mg, 0.400 mmol), followed by stirring at room temperature for 12 hours. When the reaction was completed as analyzed by TLC, the solvent was completely evaporated. The residue was dissolved in MC and washed with water and a saturated sodium bicarbonate solution. The organic layer was dried over sodium sulfate and the solvent was evaporated in a vacuum. The residue was purified MPLC using 10% MeOH/MC to afford Compound 109-3 as a yellow solid (80.0 mg, 0.134 mmol, 67%).

Step 2: Synthesis of N3-(2,6-dimethylphenyl)-1-methyl-N6-(2-(piperidin-4-ylmethyl)-1,2,3,4-tetrahydroisoquinolin-6-yl)-1H-pyrazolo[3,4-d]pyrimidine-3,6-diamine (Compound 109-4)

A solution of Compound 109-3 (80.0 mg, 0.134 mmol) in DCM (5 mL) was added at room temperature 4 N HCl/dioxane (0.083 mL, 0.335 mmol) and stirred for 1 hour. When the reaction was completed as analyzed by TLC, the solvent was completely evaporated in a vacuum. The residue was dissolved in water (15 mL) and washed with DCM (15 mL×2). The aqueous layer was basified with saturated sodium bicarbonate powder and subjected to extraction with DCM (20 mL×2). The pooled organic layer was dried over sodium sulfate. The solvent was evaporated in a vacuum to afford Compound 109-4 as an off-white solid (56.0 mg, 0.112 mmol, 84%).

Step 3: Synthesis of 5-(4-((6-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-2-(2,6-dioxopiperidin-3-yl)isoindoline-1,3-dione (Compound 109)

A solution of Compound 109-5 (Combi-Blocks, HD-3240) (5.56 mg, 0.0201 mmol) in DMSO (1 mL) was added at room temperature with Compound 109-4 (10.0 mg, 0.0201 mmol) and DIPEA (6.09 mg, 1.08 mmol). The mixture was stirred at 90° C. for 12 hours. When a new spot was formed as analyzed by TLC, the reaction mixture was quenched with water (10 mL), subjected to EA (30 mL×3), and washed with water (3×) and brine. The combined organic layer was dried over sodium sulfate and the solvent was evaporated in a vacuum to give a crude mixture. This crude mixture was purified by MPLC using a solvent mixture of 5% MeOH:MC to afford Compound 109 as a brown solid (3.0 mg, 0.00398 mmol, 19%)

Compound 110. 5-((2-(4-((6-((3-((2,6-Dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-2-oxoethyl)amino)-2-(2,6-dioxopiperidin-3-yl)isoindoline-1,3-dione

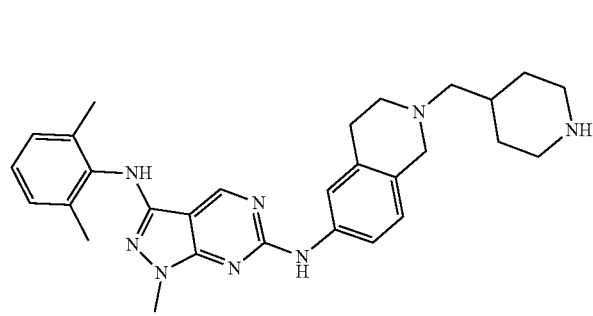

Compound 110-1

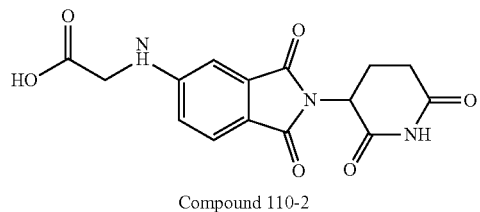

Compound 110-2

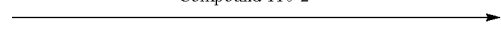

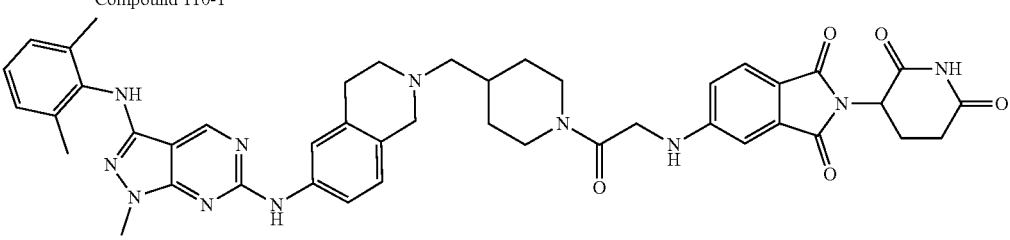

Compound 110

A solution of Compound 110-1 (identical to Compound 109-4) (10.0 mg, 0.0201 mmol) in DMF (2 mL) was added at room temperature with HATU (15.3 mg, 0.0402 mmol), Compound 110-2 (WO 2020/162725) (5.66 mg, 0.0218 mmol), and TEA (8.81 mg, 0.0872 mmol). The resulting mixture was stirred at room temperature for 12 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the solvent was evaporated in a vacuum. The crude mixture was purified by MPLC using a solvent mixture of 5% MeOH:DCM to afford Compound 110 as a white solid (8.0 mg, 0.00987 mmol, 49%).

Compound 111. 1-(5-(4-(2-(6-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethyl)piperidine-1-carbonyl)-2-methoxyphenyl)dihydropyrimidine-2,4 (1H,3H)-dione

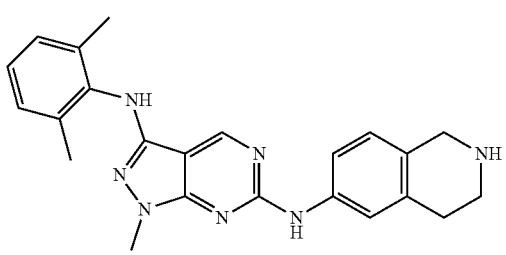

Compound 111-1

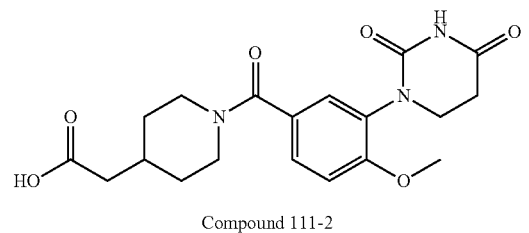

Compound 111-2

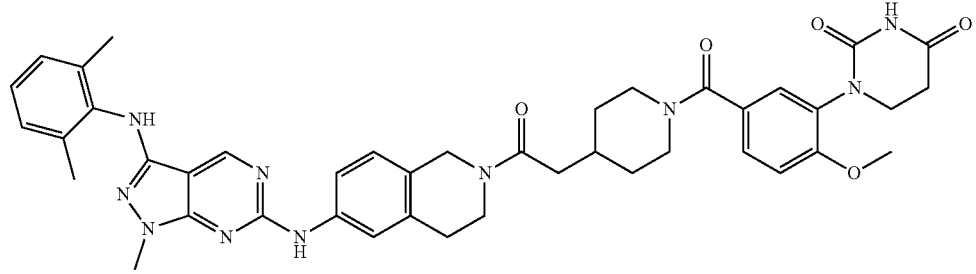

Compound 111

A solution of Compound 111-1 (Korean Patent No. 2128018) (10.0 mg, 0.0250 mmol) in DMF (2 mL) was added at room temperature with HATU (19.0 mg, 0.0500 mmol), Compound 111-2 (identical to Compound 112-4) (9.75 mg, 0.0250 mmol), and TEA (7.58 mg, 0.0750 mmol). The resulting mixture was stirred at room temperature for 12 hours. When a new spot was formed as analyzed by TLC, the reaction mixture was quenched with water (10 mL) before extraction with EA (15 mL×2). The pooled organic was washed with water (20 mL×2) and brine (20 mL×2) and dried over sodium sulfate and the solvent was evaporated in a vacuum. The crude mixture was purified by MPLC using a solvent mixture of 5% MeOH:DCM to afford Compound 111 as a brown solid (11.0 mg, 0.00142 mmol, 57%).

Compound 112. 1-(5-(4-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethyl)piperidine-1-carbonyl)-2-methoxyphenyl)dihydropyrimidine-2,4 (1H,3H)-dione

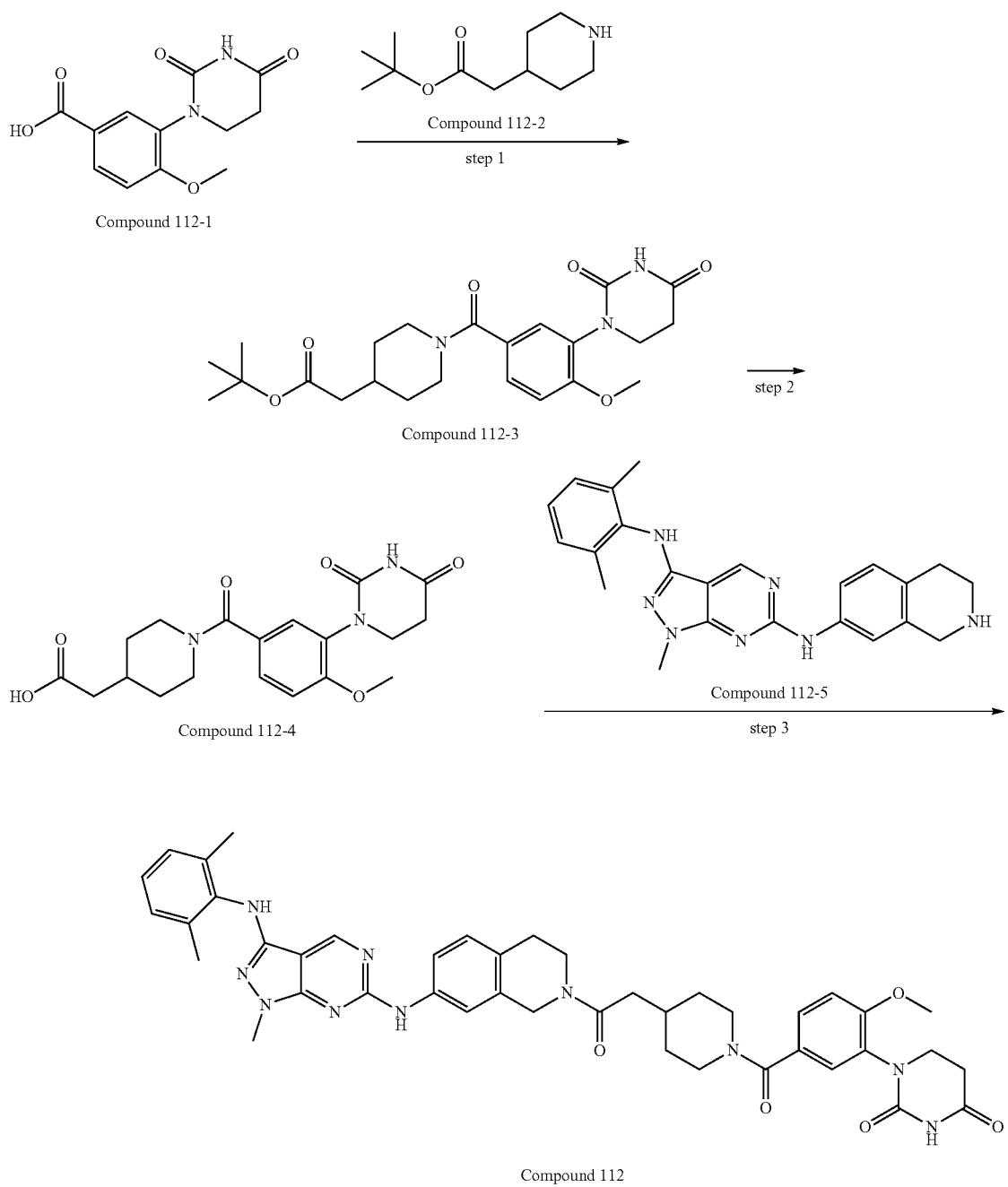

Step 1: Synthesis of tert-butyl 2-(1-(3-(2,4-dioxotetrahydropyrimidin-1 (2H)-yl)-4-methoxybenzoyl)piperidin-4-yl)acetate (Compound 112-3)

A solution of Compound 112-1 (WO 2019/186358) (300 mg, 1.14 mmol) in DMF (10 mL) was added with HATU (1.30 g, 3.52 mmol) and DIPEA (590 mg, 4.56 mmol) and stirred for 10 minutes. Finally, after addition of Compound 112-2 (BLDPharm, BD27827) (tert-butyl 2-(piperidin-4-yl)acetate; 300 mg, 1.14 mmol), stirring was conducted at 30° C. for 12 hours. The reaction mixture was quenched with water (10 mL) and ice. Thereafter, the compound was extracted with EA and washed with water. The compound was dried over sodium sulfate and the solvent was evaporated in a vacuum. The crude material was purified by silica gel column chromatography using a solvent mixture of 10% MeOH:DCM as an eluent to afford Compound 112-3 as an off-white solid (71 mg, 0.159 mmol, 14%).

Step 2: Synthesis of 2-(1-(3-(2,4-dioxotetrahydropyrimidin-1 (2H)-yl)-4-methoxybenzoyl)piperidin-4-yl)acetic acid (Compound 112-4)

A suspension of Compound 112-3 (4.41 g, 9.98 mmol) in DCM (24 mL) was added with TFA (16 mL) and stirred at 40° C. for 3 hours. When the reaction was completed as analyzed by TLC, the volatile material was evaporated in a vacuum, and the residual solvent was removed by a high-vacuum pump to afford Compound 112-4 as a yellow solid (60 mg, 9.90 mmol, 99%).

Step 3: Synthesis of 1-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidine-1-carbonyl)-2-methoxyphenyl)dihydropyrimidine-2,4 (1H,3H)-dione (Compound 112)

A solution of Compound 112-5 (Korean Patent No. 2128018) (10 mg, 0.0250 mmol) in DMF (1 mL) was added with HATU (28.5 mg, 0.0750 mmol) and DIPEA (16.2 mg, 0.125 mmol) and stirred for 10 minutes. Finally, after addition of Compound 112-4 (10.7 mg, 0.0275 mmol) at room temperature, stirring was conducted at 40° C. for 2 hours. Thereafter, the reaction mixture was quenched with water (10 mL) and ice. White precipitates were observed and filtered to afford Compound 112 as an off-white solid (17 mg, 0.0221 mmol, 88%).

Compound 113. N-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethyl)-3-(2,4-dioxotetrahydropyrimidin-1 (2H)-yl)-4-methoxybenzamide

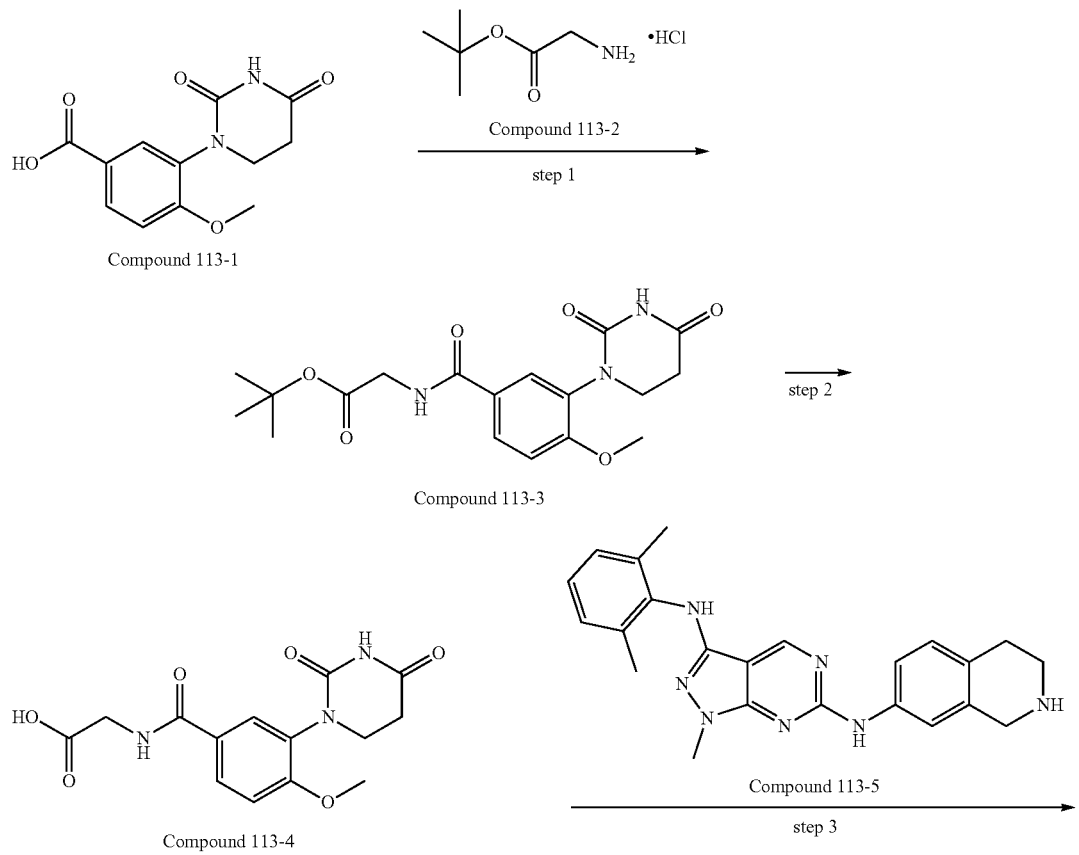

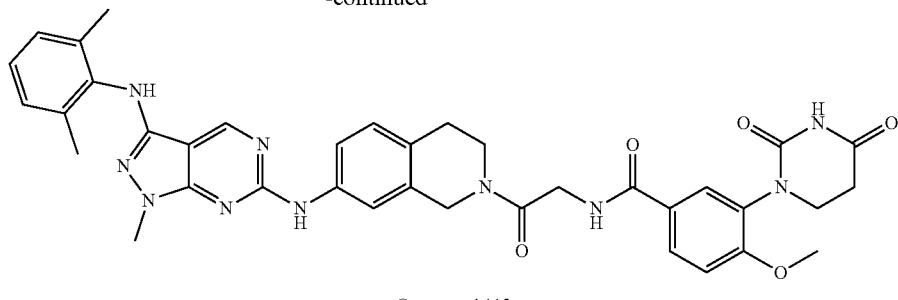

Compound 113

Step 1: Synthesis of tert-butyl (3-(2,4-dioxotetrahydropyrimidin-1 (2H)-yl)-4-methoxybenzoyl)glycinate (Compound 113-3)

A solution of Compound 113-1 (identical to Compound 112-1) (500 mg, 1.89 mmol) in DMF (10 mL) was added with Compound 113-2 (TCI, G0254) (tert-butyl glycinate-HCl; 248 mg, 1.89 mmol), HOBt (384 mg, 2.84 mmol), EDCI (544 mg, 2.84 mmol), and DIPEA (1.6 mL, 9.45 mmol), and the resulting mixture was stirred at room temperature for 13 hours. The reaction mixture was quenched with water before extraction with EA (3×30 mL). The combined organic layer was dried over sat. NaCl (aq.) solution and $Na_2SO_4$ and the solvent was removed in a vacuum. The crude mixture was purified by column chromatography using 5% MeOH in DCM to afford Compound 113-3 as a white solid (638 mg, 1.69 mmol, 89%).

Step 2: Synthesis of (3-(2,4-dioxotetrahydropyrimidin-1 (2H)-yl)-4-methoxybenzoyl)glycine (Compound 113-4)

A solution of Compound 113-3 (625 mg, 1.66 mmol) in DCM (2 mL) was added at room temperature with 40% TFA/DCM (10 mL). The resulting mixture was stirred at room temperature for 2 hours. The solvent was evaporated, followed by adding ether. The solid thus formed was filtered to afford Compound 113-4 as a white solid (532 mg, 1.41 mmol, 100%).

Step 3: Synthesis of N-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)-3-(2,4-dioxotetrahydropyrimidin-1 (2H)-yl)-4-methoxybenzamide (Compound 113)

A solution of Compound 113-4 (50.0 mg, 0.156 mmol) in DMF (3 mL) was added with Compound 113-5 (Korean Patent No. 2128018) (64.0 mg, 0.156 mmol), HOBt (32.5 mg, 0.240 mmol), EDCI (46.0 mg, 0.240 mmol), and DIPEA (138 μl, 0.801 mmol) and after the temperature was elevated from room temperature to 40° C., the resulting mixture was stirred for 17 hours. The reaction mixture was quenched with water before extraction with EA (3×30 mL). The combined organic layer was dried over sat. NaCl (aq) solution and $Na_2SO_4$ and the solvent was removed in a vacuum. The crude mixture was purified by column chromatography using 5% MeOH in DCM to afford Compound 113 as a white solid (110 mg, 98%).

Compound 114. N-(4-((3-((2,6-Dimethylphenyl)amino)-1-methyl-1H-pyrazolo[3,4-d]pyrimidin-6-yl)amino)phenethyl)-1-(2-((2-(2,6-dioxopiperidin-3-yl)-1,3-dioxoisoindolin-5-yl)amino)-2-oxoethyl)piperidine-4-carboxamide

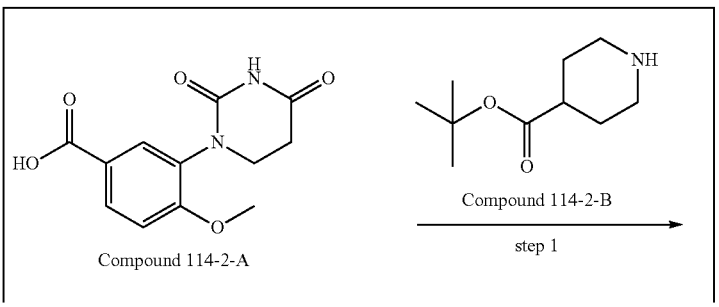

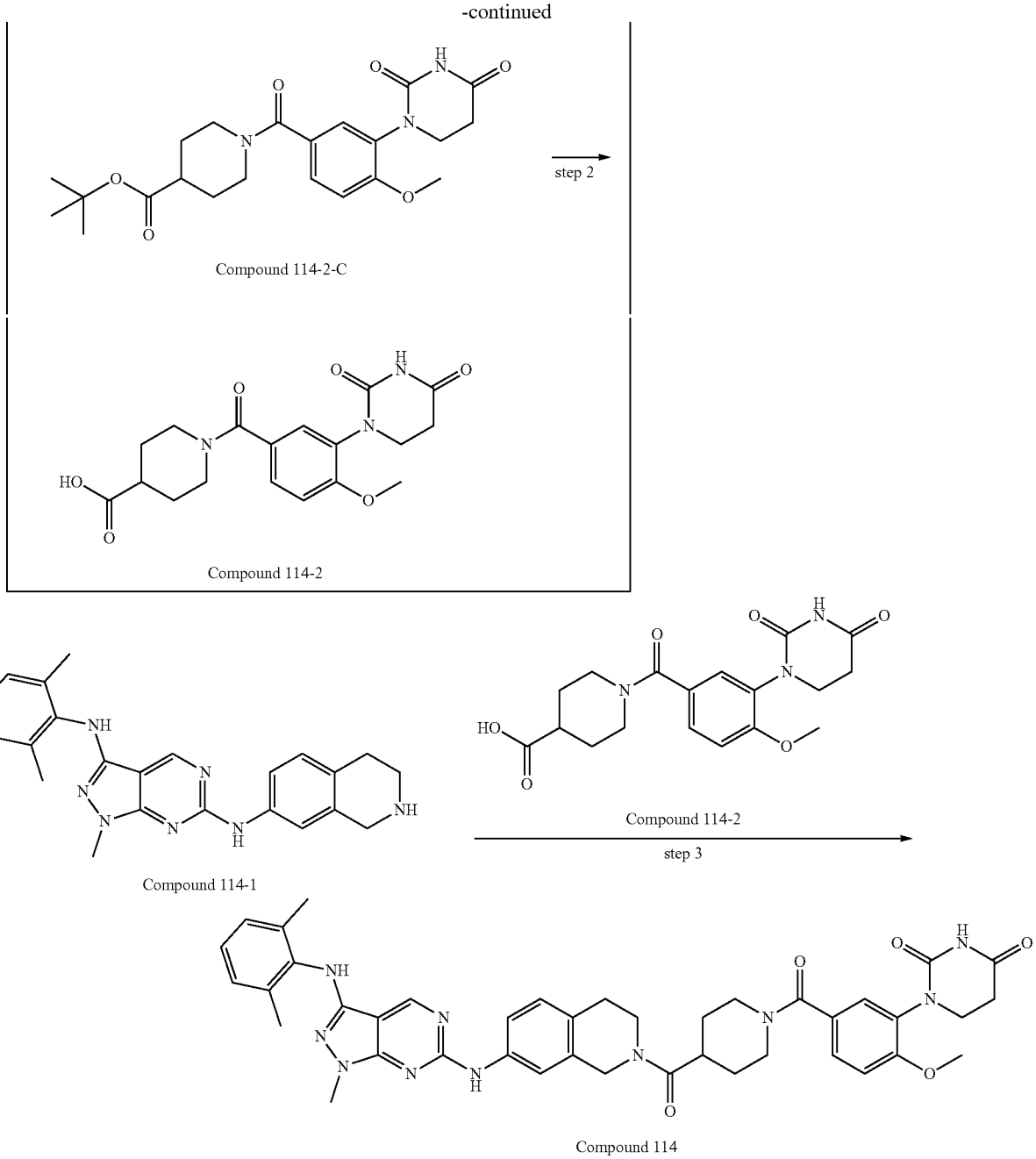

Step 1: Synthesis of tert-butyl 1-(3-(2,4-dioxotetrahydropyrimidin-1 (2H)-yl)-4-methoxybenzoyl)piperidine-4-carboxylate (Compound 114-2-C)

A suspension of Compound 114-2-B (Combi-Blocks, QK-3943) (tert-butyl piperidine-4-carboxylate; 126 mg, 0.681 mmol) in DMF (5 mL) was added with DIPEA (293 mg, 2.26 mmol) and then at room temperature with HATU (574 mg, 1.51 mmol) and the mixture was stirred at room temperature for 15 minutes. After addition of Compound 114-2-A (WO 2019/186358) (200 mg, 0.756 mmol), the resulting mixture was stirred at room temperature for 14 hours. The residual solvent was evaporated in a vacuum. The crude reaction mixture was diluted with water (10 mL) before extraction with ethylacetate (3×15 mL). The pooled organic layer was dried over MgSO₄ and concentrated in a vacuum to give a crude mixture which was then purified by column chromatography using MeOH/DCM 5% to afford Compound 114-2-C as a white solid (205 mg, 0.475 mmol, 69%).

Step 2: Synthesis of 1-(3-(2,4-dioxotetrahydropyrimidin-1 (2H)-yl)-4-methoxybenzoyl)piperidine-4-carboxylic acid (Compound 114-2)

Compound 114-2-C (200 mg, 0.463 mmol) was added to 40% TFA/DCM (10 mL). This mixture was stirred at room temperature for 3 hours. The solvent was completely evaporated. The crude product was triturated with ether and dried in a vacuum to afford Compound 114-2 as an ivory solid (102 mg, 0.271 mmol, 58%).

Step 3: Synthesis of N-(4-((3-((2,6-dimethylphenyl)amino)-1-methyl-1H-pyrazolo[3,4-d]pyrimidin-6-yl)amino)phenethyl)-1-(2-((2-(2,6-dioxopiperidin-3-yl)-1,3-dioxoisoindolin-5-yl)amino)-2-oxoethyl)piperidine-4-carboxamide (Compound 114)

A suspension of Compound 114-2 (16.0 mg, 0.0413 mmol) in DMF (2 mL) was added with DIPEA (15.0 mg, 0.112 mmol) and then at room temperature with HATU (29.0 mg, 0.0750 mmol) and the mixture was stirred at room temperature for 15 minutes. After addition of Compound 114-1 (Korean Patent No. 2128018) (15.0 mg, 0.0375 mmol), and the resulting mixture was stirred at room temperature for 14 hours. The crude reaction mixture was diluted with water (10 mL) before extraction with ethyl acetate (3×15 mL). The combined organic layer was dried over MgSO₄ and concentrated in a vacuum to give a crude mixture which was then purified by column chromatography using MeOH/DCM 5% to afford Compound 114 as a beige solid (7.70 mg, 0.0101 mmol, 28%).

Compound 115. 3-(5-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperazin-1-yl)-1-oxoisoindolin-2-yl)piperidin-2,6-one

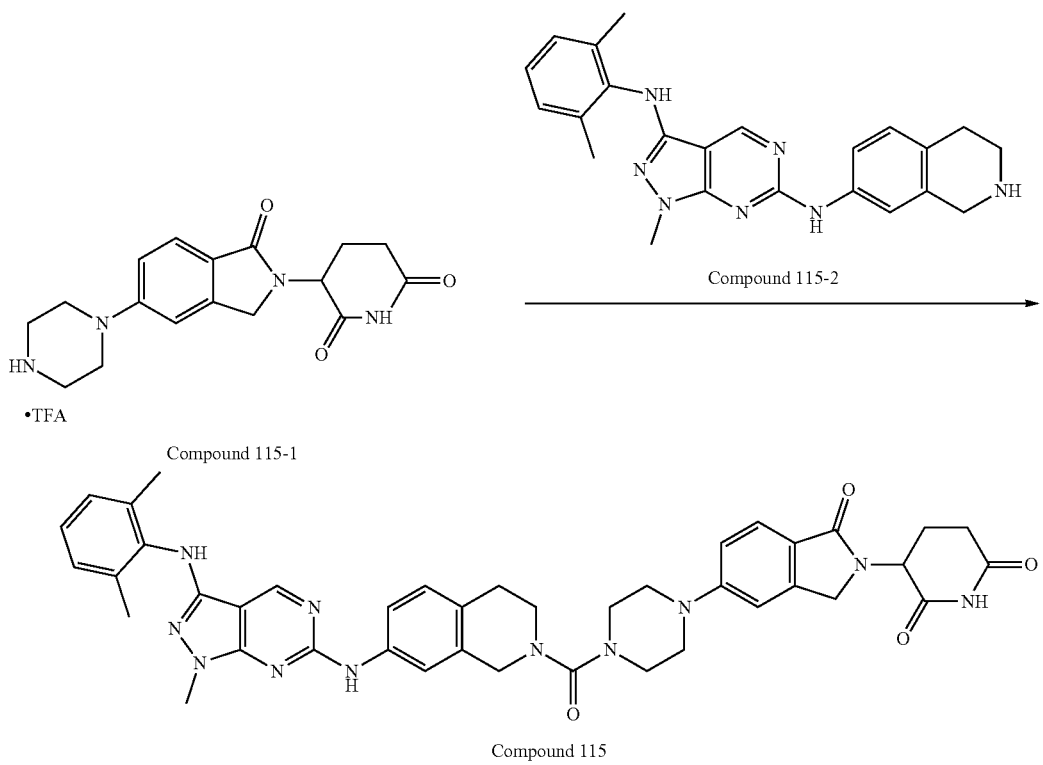

A solution of Compound 115-1 (identical to 103-11) (20 mg, 0.047 mmol) in DCM (5 mL) was added with triphosgene (70 mg, 0.235 mmol) and Et₃N (33 µl, 0.235 mmol). The resulting mixture was stirred at room temperature for 6 hours. After completion of the reaction, the solvent was completely evaporated in a vacuum to give an isocyanate intermediate. This intermediate was added with THF (5 mL) and then with Compound 115-2 (Korean Patent No. 2128018) (19 mg, 0.047 mmol) and Et₃N (13 µl, 0.094 mmol). The resulting mixture was stirred at 40° C. for 1 hour. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/MC to afford Compound 115 as a white solid (3 mg, 0.004 mmol, 9%).

Compound 116. 3-(6-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)oxy)-1-oxoisoindolin-2-yl)piperidin-2,6-one

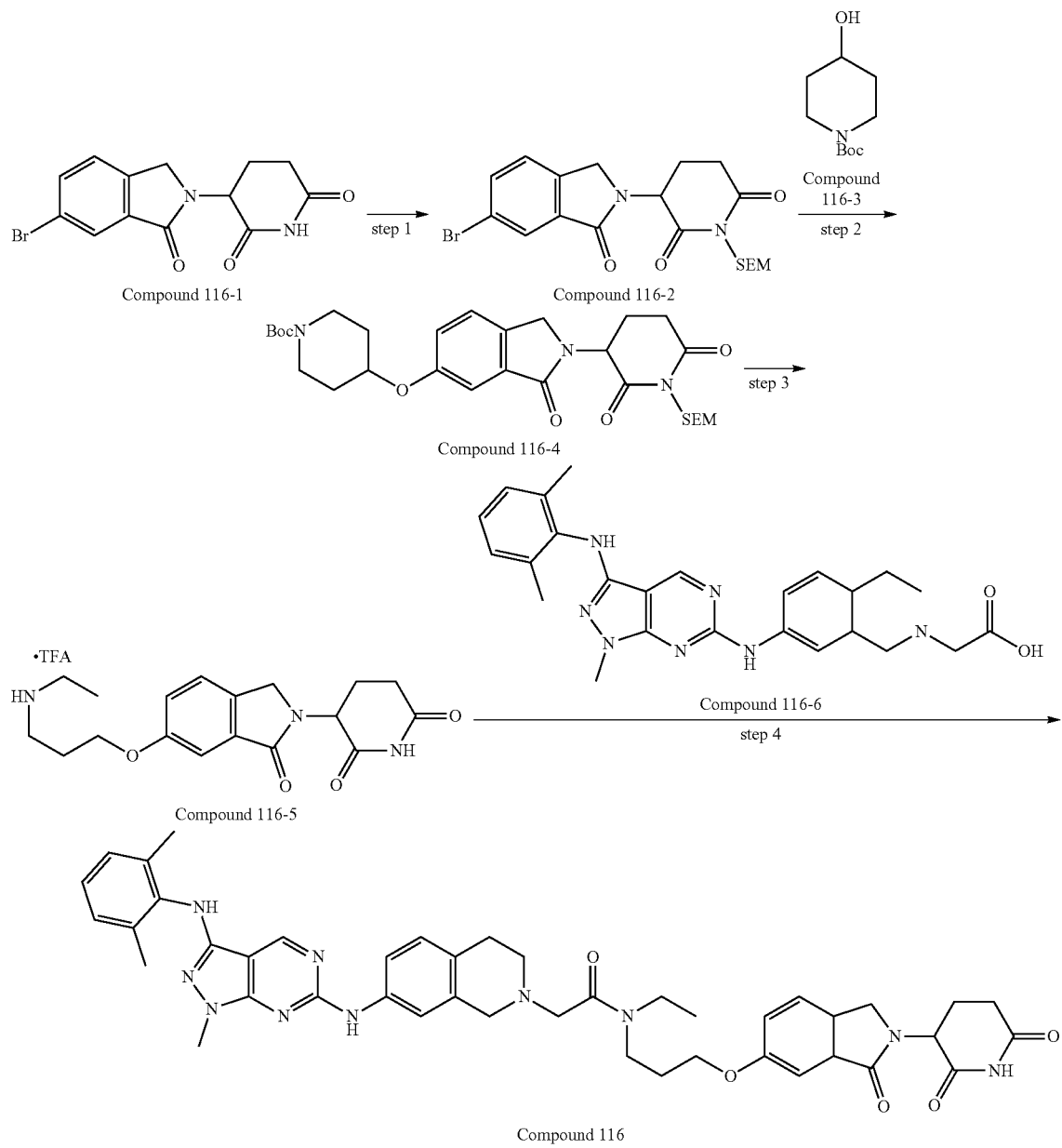

Step 1: Synthesis of 3-(6-bromo-1-oxoisoindolin-2-yl)-1-((2-(trimethylsilyl)ethoxy)methyl)piperidin-2,6-one (Compound 116-2)

A solution of Compound 116-1 (WO 2020/160192) (1 g, 3.095 mmol) in DMF (6 mL) was added with 2-(trimethylsilyl)ethoxymethyl chloride (SEMCl; 1 mL, 5.570 mmol) and 1,8-diazabicyclo (5,4,0)undec-7-ene (DBU; 1 mL, 6.808 mmol). The resulting mixture was stirred at room temperature for 5 hours. After completion of the reaction, the reaction mixture was quenched with NH$_4$Cl, subjected to extraction with EA (3×30 mL), and washed with water (3×) and brine. The pooled organic layer was dried over sodium sulfate and filtered, and the solvent was evaporated in a vacuum. The residue was purified by MPLC using 50% EA/HEX to afford Compound 116-2 as an off-white solid (556 mg, 1.226 mmol, 40%).

Step 2: Synthesis of tert-butyl 4-((2-(2,6-dioxo-1-((2-(trimethylsilyl)ethoxy)methyl)piperidin-3-yl)-3-oxoisoindolin-5-yl)oxy)piperidine-1-carboxylate (Compound 116-4)

A solution of Compound 116-2 (100 mg, 0.221 mmol) in MeCN (3 mL) was added with Compound 116-3 (TCI, B2671) (tert-butyl 4-hydroxypiperidine-1-carboxylate; 44 mg, 0.221 mmol), (Ir[dF(CF$_3$)ppy]$_2$(dtbpy))PF$_6$ (25 mg, 0.022 mmol), NiCl$_2$ (glyme) (24 mg, 0.110 mmol), dtbbpy (30 mg, 0.110 mmol), and 2,2,6,6-tetramethylpiperidine (38 μl, 0.221 mmol) and purged with nitrogen gas. The mixture was stirred at room temperature for 16 hours under blue LED light. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 50% EA/HEX to afford Compound 116-4 as a yellow oil (44 mg, 0.077 mmol, 35%).

Step 3: Synthesis of 3-(1-oxo-6-(piperidin-4-yloxy)isoindolin-2-yl)piperidin-2,6-one and 2,2,2-trifluoroacetaldhyde Compound (1:1) (Compound 116-5)

Compound 116-4 (58 mg, 0.101 mmol) was added to 40% TFA/DCM (1.6/2.4 mL). The resulting mixture was stirred at room temperature for 3 hours. The volatile material was evaporated to give a beige solid which was then washed with diethylether and concentrated in a vacuum to afford Compound 116-5 as a beige solid (45 mg, 0.102 mmol, quant.).

Step 4: Synthesis of 3-(6-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)oxy)-1-oxoisoindolin-2-yl)piperidin-2,6-one (Compound 116)

A solution of Compound 116-5 (10 mg, 0.022 mmol) in DMF (1 mL) was added with Compound 116-6 (identical to Compound 103-4) (10 mg, 0.022 mmol), HATU (17 mg, 0.044 mmol), and Et$_3$N (9 μl, 0.066 mmol). The resulting mixture was stirred at room temperature for 12 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/MC to afford Compound 116 as a yellow solid (9 mg, 0.011 mmol, 53%).

Compound 117. 3-(6-((1-(2-(7-((3-((2,6-dimethylphenyl)amino)-1-methyl-TH-pyrazolo[3,4-d]pyrimidin-6-yl)amino)-3,4-dihydroisoquinolin-2 (1H)-yl)-2-oxoethyl)piperidin-4-yl)oxy)-1-oxoisoindolin-2-yl)piperidin-2,6-one

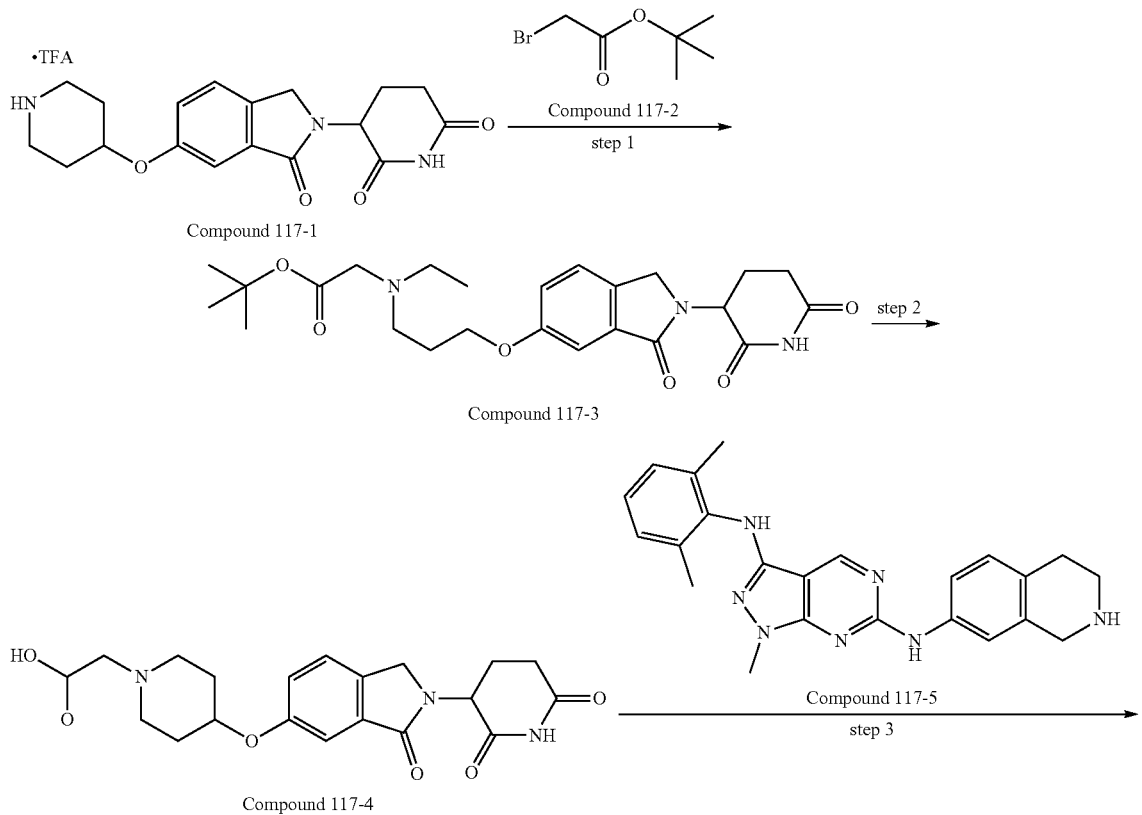

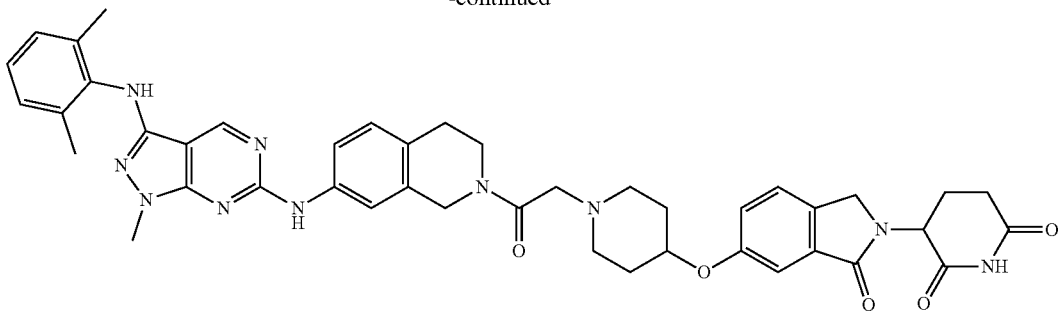

Compound 117

Step 1: Synthesis of tert-butyl 2-(4-((2-(2,6-dioxopiperidin-3-yl)-3-oxoisoindolin-5-yl)oxy)piperidin-1-yl)acetate (Compound 117-3)

A solution of Compound 117-1 (identical to Compound 116-5) (35 mg, 0.079 mmol) in THF (1 mL) was added with Compound 117-2 (TCI, B1473) (tert-butyl bromoacetate; 13 μl, 0.087 mmol) and then at 0° C. with Et₃N (22 μl, 0.159 mmol). The resulting mixture was stirred at room temperature for 4 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/MC to afford Compound 117-3 as an off-white solid (8 mg, 0.017 mmol, 22%).

Step 2: Synthesis of 2-(4-((2-(2,6-dioxopiperidin-3-yl)-3-oxoisoindolin-5-yl)oxy)piperidin-1-yl)acetic acid (Compound 117-4)

Compound 117-3 (8 mg, 0.017 mmol) was added to 40% TFA/DCM (0.4/0.6 mL). The resulting mixture was stirred at room temperature for 3 hours. The volatile material was evaporated to given an ivory solid which was then washed with diethylether and concentrated in a vacuum to afford Compound 117-4 as an ivory solid (5 mg, 0.012 mmol, 71%).

Step 3: Synthesis of 3-(6-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidin-4-yl)oxy)-1-oxoisoindolin-2-yl)piperidin-2,6-one (Compound 117)

A solution of Compound 117-4 (5 mg, 0.012 mmol) in DMF (1 mL) was added with Compound 117-5 (Korean Patent No. 2128018) (5 mg, 0.012 mmol), HATU (9 mg, 0.025 mmol), and Et₃N (5 μl, 0.037 mmol). The resulting mixture was stirred at room temperature for 12 hours. After completion of the reaction, the reaction mixture was quenched with water, subjected to extraction with EA (3×15 mL), and washed with water (3×) and brine. The pooled organic layer was dried over sodium sulfate and filtered, and the solvent was evaporated in a vacuum. The residue was purified by MPLC using 5% MeOH/DCM to afford Compound 117 as a yellow solid (7 mg, 0.009 mmol, 72%).

Compound 118. 2-(2,6-Dioxopiperidin-3-yl)-5-(4-((7-((3-((4-methoxy-2-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione

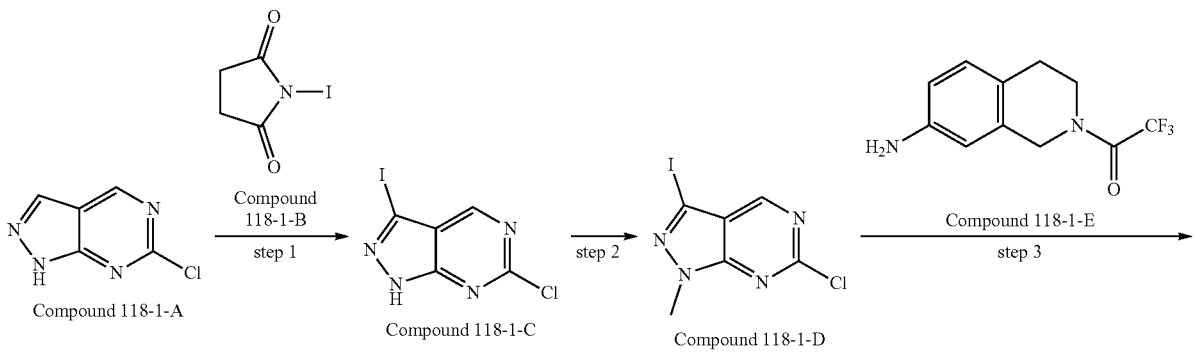

-continued

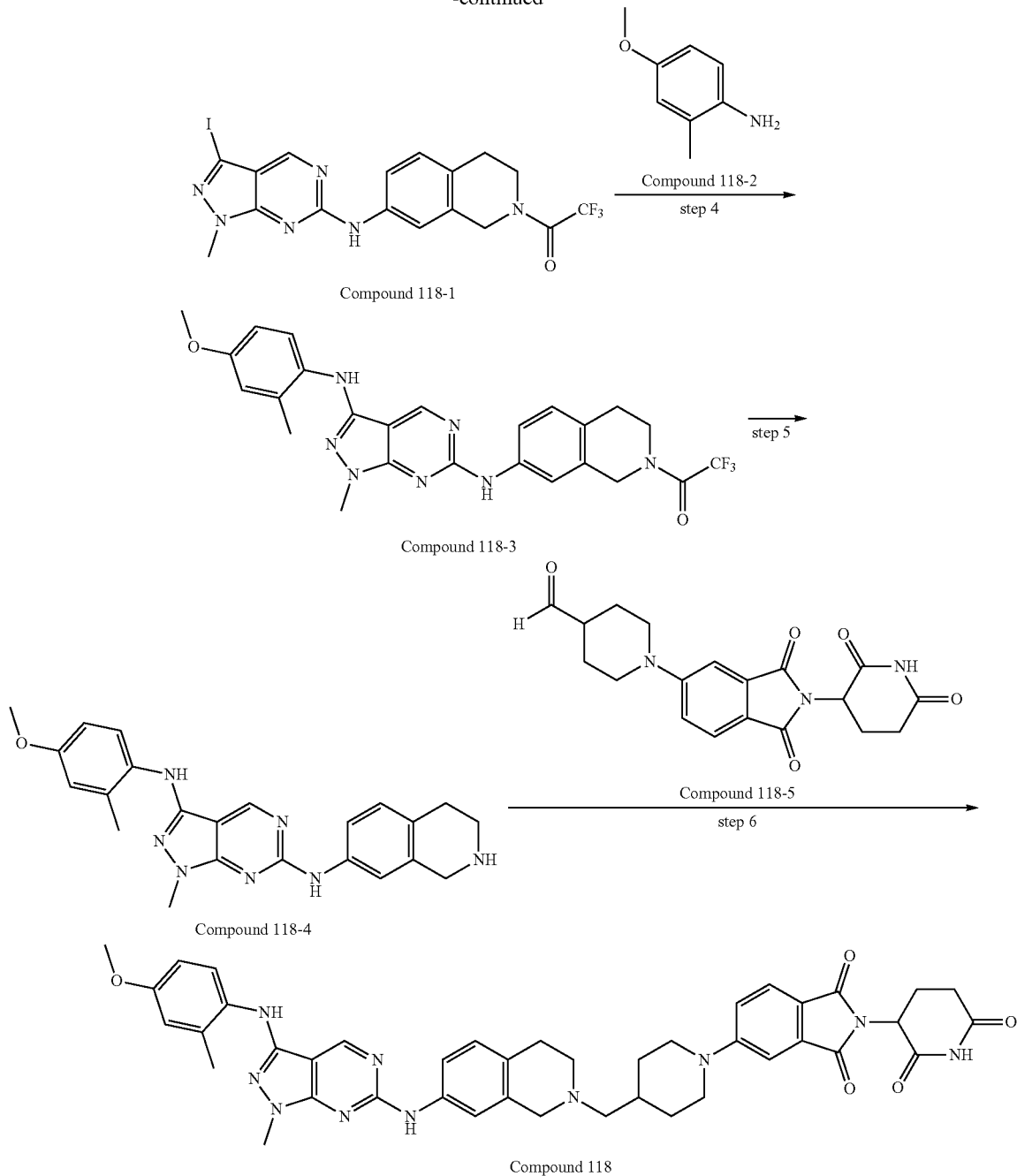

Step 1: Synthesis of 6-chloro-3-iodo-1H-pyrazolo[3,4-d]pyrimidine (Compound 118-1-C)

To a solution of Compound 118-1-A (Combi-block, QA-6971) (6-chloro-1H-pyrazolo[3,4-d]pyrimidine; 2 g, 12.94 mmol, 1.0 eq.) in DMF (30 mL) was added Compound 118-1-B (TCI, 10074) (4.4 g, 19.41 mmol, 1.5 eq.) at room temperature. The mixture was stirred at 80° C. for 3 hours. After the temperature was decreased to ambient temperature, the solvent was evaporated in a vacuum. Subsequently, the residue was dissolved in water before extraction with ethyl acetate, and the solution was washed with a saturated ammonium chloride solution. The organic layer was dried over anhydrous sodium sulfate. The solvent was evaporated to give a solid which was then filtered, washed with ether, and dried to afford Compound 118-1-C as an ivory solid (2.6 g, 72%).

Step 2: Synthesis of 6-chloro-3-iodo-1-methyl-1H-pyrazolo[3,4-d]pyrimidine (Compound 118-1-D)

A solution of Compound 118-1-C (2.6 g, 9.27 mmol, 1.0 eq.) in DMF (10 mL) was added at 0° C. with NaH (449 mg, 11.12 mmol, 1.2 eq.). The mixture was stirred at 0° C. for 15 minutes. Methyl iodide (1.15 mL, 18.54 mmol, 2.0 eq.) was added at 0° C. to the mixture which was then warmed to room temperature and stirred for 3 hours. The reaction mixture was quenched with iced water before extraction with ethyl acetate. The organic layer was dried over anhydrous sodium sulfate and concentrated in a vacuum. The residue was purified by silica gel column chromatography using 30% EA/HEX as an eluent to afford Compound 118-1-D as an ivory solid (2.5 g, 91%).

Step 3: Synthesis of 2,2,2-trifluoro-1-(7-((3-iodo-1-methyl-1H-pyrazolo[3,4-d]pyrimidin-6-yl)amino)-3,4-dihydroisoquinolin-2 (1H)-yl)ethan-1-one (Compound 118-1)

To Compound 118-1-D (1 g, 3.4 mmol, 1.0 eq.) was added a solution of Compound 118-1-E (Korean Patent No. 2128018) (830 mg, 3.4 mmol, 1.0 eq.) in 0.08 M HCl/ethoxyethanol at room temperature. The mixture was stirred at 90° C. for 12 hours. The reaction mixture was quenched with iced water before extraction with ethyl acetate. The organic layer was dried over anhydrous sodium sulfate and concentrated in a vacuum. The residue was purified by silica gel column chromatography using 30% EA/HEX as an eluent to afford Compound 118-1 as an ivory solid (1.05 g, 61%).

Step 4: Synthesis of 2,2,2-trifluoro-1-(7-((3-((4-methoxy-2-methylphenyl)amino)-1-methyl-1H-pyrazolo[3,4-d]pyrimidin-6-yl)amino)-3,4-dihydroisoquinolin-2 (1H)-yl)ethan-1-one (Compound 118-3)

A solution of Compound 118-1 (50 mg, 0.1 mmol, 1.0 eq.) in toluene (2 mL) was added with $Cs_2CO_3$ (326 mg, 1.0 mmol, 10 eq.), $Pd_2(dba)_3$ (4.6 mg, 0.005 mmol, 0.05 eq.), Xantphos (9.3 mg, 0.016 mmol, 0.16 eq.), and Compound 118-2 (TCI, M1474) (4-methoxy-2-methylaniline; 13 μl, 0.1 mmol, 1.0 eq.) in a nitrogen atmosphere. The resulting mixture was stirred at 110° C. for 12 hours. The reaction mixture was quenched with water before extraction with ethyl acetate. The organic layer was dried over sodium sulfate and concentrated in a vacuum. The crude mixture was purified by silica gel column chromatography using 30% EA/HEX as an eluent to afford Compound 118-3 as a brown solid (38 mg, 71%).

Step 5: Synthesis of N3-(4-methoxy-2-methylphenyl)-1-methyl-N6-(1,2,3,4-tetrahydroisoquinolin-7-yl)-1H-pyrazolo[3,4-d]pyrimidine-3,6-diamine (Compound 118-4)

A solution of Compound 118-3 (30 mg, 0.059 mmol, 1 eq) in THF (1 mL)/MeOH (0.5 mL)/$H_2O$ (0.5 mL) was added with LiOH·$H_2O$ (6.2 mg, 0.147 mmol, 2.5 eq) and stirred at room temperature for 2 hours. After progression of the reaction was confirmed by TLC, the reaction mixture was quenched with water and subjected to extraction with EA. The pooled organic layer was dried over $Na_2SO_4$ and the solvent was removed in a vacuum to afford Compound 118-4 as a brown solid (27 mg, quant.).

Step 6: Synthesis of 2-(2,6-dioxopiperidin-3-yl)-5-(4-((7-((3-((4-methoxy-2-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 118)

A solution of Compound 118-4 (15 mg, 0.036 mmol, 1.0 eq.) in MeOH (1 mL) was added with Compound 118-5 (WO 2020/051564) (15 mg, 0.040 mmol) and 1 M AcOH in MeOH (36 μl) and stirred at room temperature for 12 hours. The mixture was added with $NaCNBH_3$ (3.4 mg, 0.054 mmol, 1.5 eq.), stirred at room temperature for 2 hours, and then quenched with water. Extraction with MC was followed by washing the reaction mixture with brine. The organic layer was dried over sodium sulfate and the solvent was evaporated in a vacuum. The crude mixture was purified by silica gel column chromatography using 5% MeOH/MC as an eluent to afford Compound 118 as a yellow solid (13 mg, 47%).

Compound 119. 5-(4-((7-((3-((2,3-Dihydro-1H-inden-4-yl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione

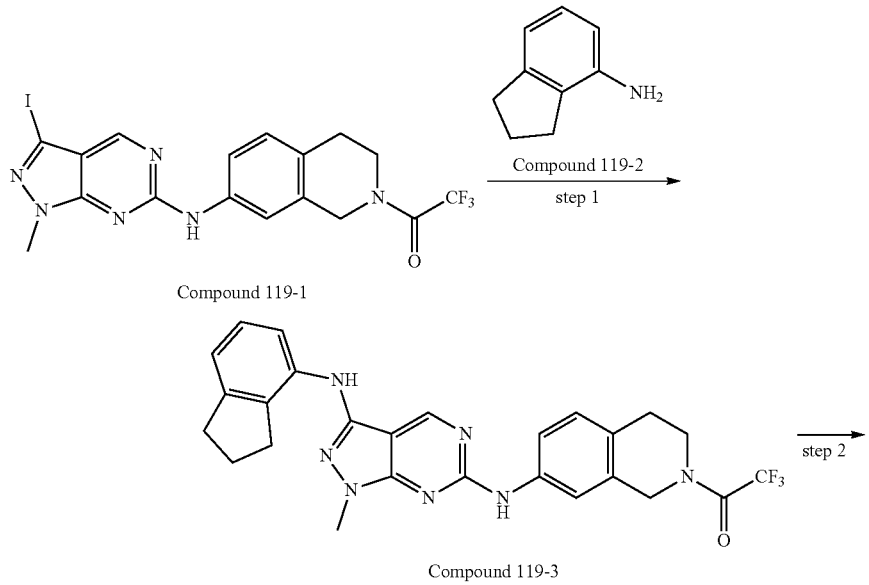

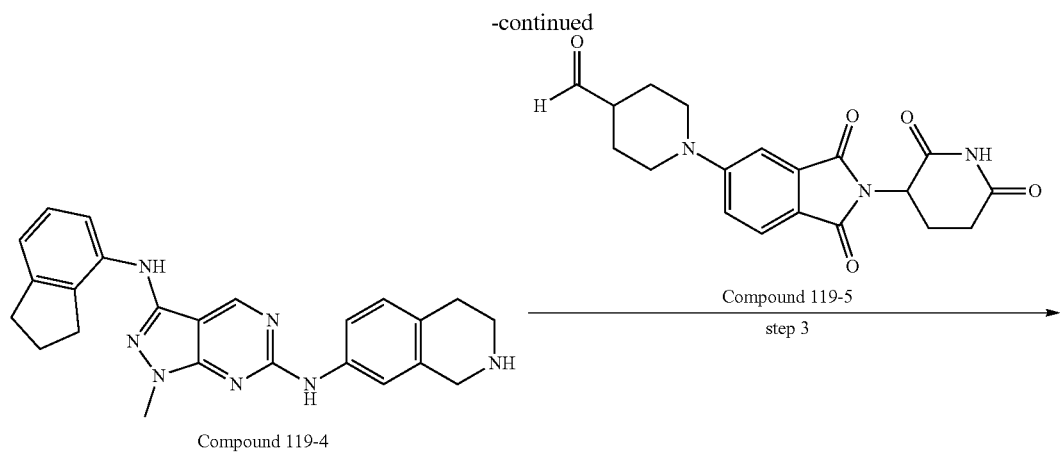

Compound 119-4

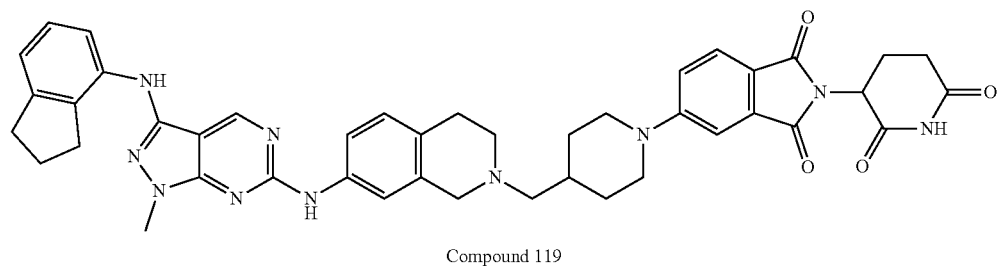

Compound 119

Step 1: Synthesis of 1-(7-((3-((2,3-dihydro-1H-inden-4-yl)amino)-1-methyl-TH-pyrazolo[3,4-d]pyrimidin-6-yl)amino)-3,4-dihydroisoquinolin-2 (1H)-yl)-2,2,2-trifluoroethan-1-one (Compound 119-3)

A solution of Compound 119-1 (identical to Compound 118-1) (50 mg, 0.1 mmol, 1.0 eq.) in toluene (2 mL) was added with $Cs_2CO_3$ (326 mg, 1.0 mmol, 10 eq.), $Pd_2(dba)_3$ (4.6 mg, 0.005 mmol, 0.05 eq.), Xantphos (9.3 mg, 0.016 mmol, 0.16 eq.), and Compound 119-2 (Sigma, 162108) (4-aminoindane; 12 µl, 0.1 mmol, 1.0 eq.) in a nitrogen atmosphere. The mixture was stirred at 110° C. for 12 hours. The reaction mixture was quenched with water before extraction with ethyl acetate. The organic layer was dried over sodium sulfate and concentrated in a vacuum. The crude mixture was purified by silica gel column chromatography using 30% EA/HEX as an eluent to afford Compound 119-3 as a yellow solid (35 mg, 69%).

Step 2: Synthesis of N3-(2,3-dihydro-1H-inden-4-yl)-1-methyl-N6-(1,2,3,4-tetrahydroisoquinolin-7-yl)-1H-pyrazolo[3,4-d]pyrimidine-3,6-diamine (Compound 119-4)

A solution of Compound 119-3 (30 mg, 0.0591 mmol, 1.0 eq.) and $LiOH \cdot H_2O$ (6.2 mg, 0.148 mmol, 2.5 eq.) in THF (1 mL)/MeOH (0.5 mL)/$H_2O$ (0.5 mL) was stirred at room temperature for 2 hours. The progression of the reaction was monitored by TLC, and the reaction mixture was quenched with water before extraction with EA. The pooled organic layer was dried over $Na_2SO_4$ and the solvent was removed in a vacuum to afford Compound 119-4 as a yellow solid (15 mg, 63%).

Step 3: Synthesis of 5-(4-((7-((3-((2,3-dihydro-1H-inden-4-yl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 119)

A solution of Compound 119-4 (15 mg, 0.0365 mmol, 1.0 eq.) in MeOH (1 mL) was added with Compound 119-5 (WO 2020/051564) (15 mg, 0.0402 mmol), and 1M AcOH in MeOH (36.5 µl) and stirred for 12 hours. The mixture was added with $NaCNBH_3$ (3.4 mg, 0.054 mmol, 1.5 eq.) and stirred at room temperature for 2 hours. The reaction mixture was quenched with water, subjected to extraction with MC, and washed with brine. The organic layer was dried over sodium sulfate and the solvent was evaporated in a vacuum. The crude mixture was purified by silica gel column chromatography using 5% MeOH/MC as an eluent to afford Compound 119 as a yellow solid (3.3 mg, 12%).

Compound 120. 2-(2,6-Dioxopiperidin-3-yl)-5-(4-((7-((3-((2-fluoro-4-methylphenyl)amino)-1-methyl-1H-pyrazolo[3,4-d]pyrimidin-6-yl)amino)-3,4-dihydroisoquinolin-2 (1H)-yl)methyl)piperidin-1-yl) isoindoline-1,3-dione

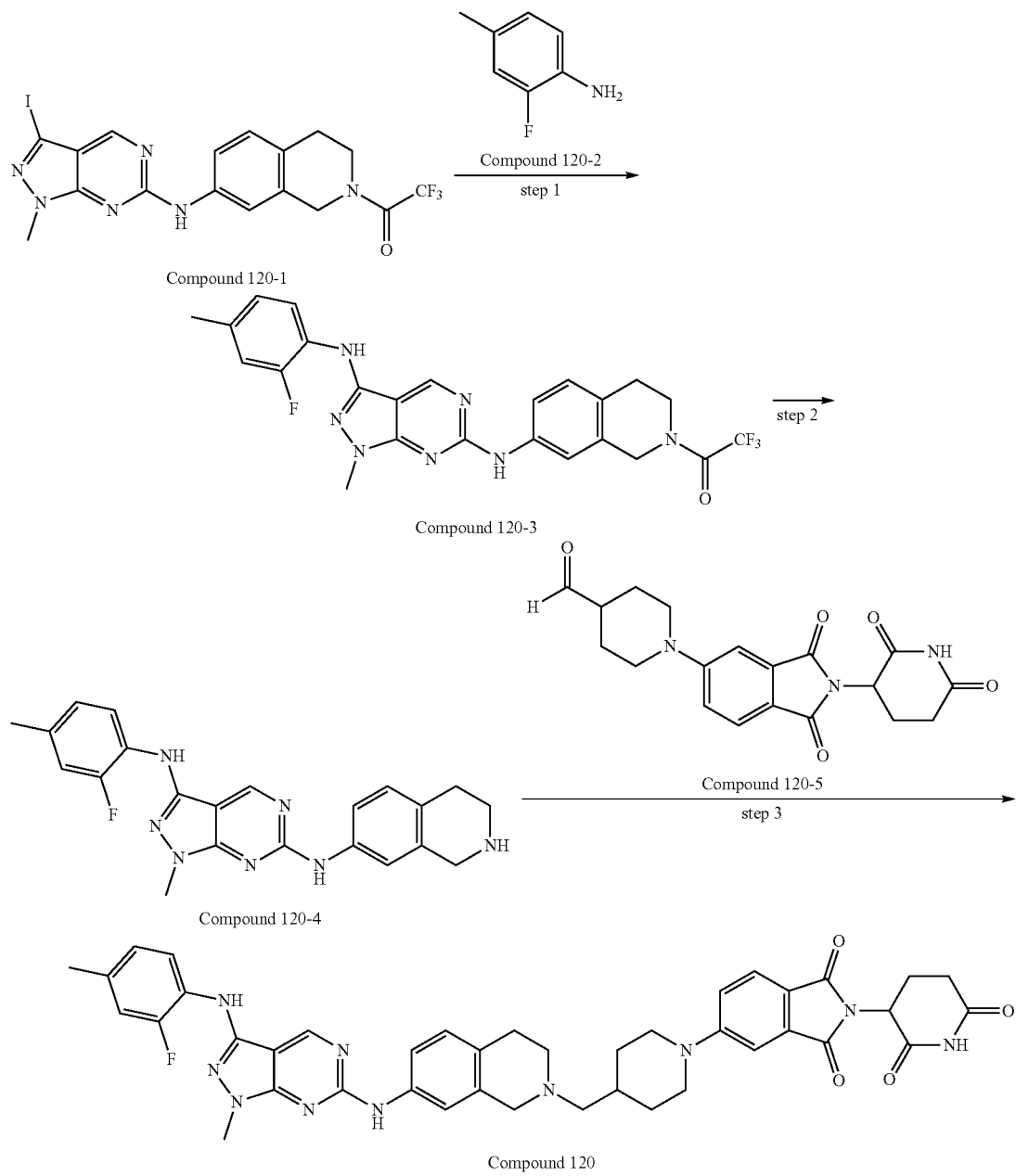

Step 1: Synthesis of 2,2,2-trifluoro-1-(7-((3-((2-fluoro-4-methylphenyl)amino)-1-methyl-1H-pyrazolo[3,4-d]pyrimidin-6-yl)amino)-3,4-dihydroisoquinolin-2 (1H)-yl)ethan-1-one (Compound 120-3)

A solution of Compound 120-1 (identical to Compound 118-1) (50 mg, 0.1 mmol, 1.0 eq.) in toluene (2 mL) was added with $Cs_2CO_3$ (326 mg, 1.0 mmol, 10 eq.), $Pd_2(dba)_3$ (4.6 mg, 0.005 mmol, 0.05 eq.), Xantphos (9.3 mg, 0.016 mmol, 0.16 eq.), and Compound 120-2 (TCI, F0529) (2-fluoro-4-methylaniline; 11 μl, 0.1 mmol, 1.0 eq.) in a nitrogen atmosphere. The mixture was stirred at 110° C. for 12 hours. The reaction mixture was quenched with water before extraction with ethyl acetate. The organic layer was dried over sodium sulfate and concentrated in a vacuum. The crude mixture was purified by silica gel column chromatography using 30% EA/HEX as an eluent to afford Compound 120-3 as a yellow solid (18 mg, 36%).

Step 2: Synthesis of N3-(2-fluoro-4-methylphenyl)-1-methyl-N6-(1,2,3,4-tetrahydroisoquinolin-7-yl)-1H-pyrazolo[3,4-d]pyrimidine-3,6-diamine (Compound 120-4)

A solution of Compound 120-3 (18 mg, 0.036 mmol, 1.0 eq.) and LiOH·H$_2$O (4 mg, 0.090 mmol, 2.5 eq.) in THE (1 mL)/MeOH (0.5 mL)/H$_2$O (0.5 mL) was stirred at room temperature for 2 hours. The progression of the reaction was monitored by TLC, and the reaction mixture was quenched with water before extraction with EA. The pooled organic layer was dried over Na$_2$SO$_4$ and the solvent was removed in a vacuum to afford Compound 120-4 as a yellow solid (14 mg, quant.).

Step 3: Synthesis of 2-(2,6-dioxopiperidin-3-yl)-5-(4-((7-((3-((2-fluoro-4-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 120)

A solution of Compound 120-4 (14 mg, 0.035 mmol, 1.0 eq.) in MeOH (1 mL) was added with Compound 120-5 (WO 2020/051564) (14 mg, 0.039 mmol) and 1 M AcOH in MeOH (35 µl) and stirred for 12 hours. The mixture was added with NaCNBH$_3$ (3.3 mg, 0.053 mmol, 1.5 eq.) and stirred at room temperature for 2 hours. The reaction mixture was quenched with water, subjected to extraction with MC, and washed with brine. The organic layer was dried over sodium sulfate and the solvent was evaporated in a vacuum. The crude mixture was purified by silica gel column chromatography using 5% MeOH/MC as an eluent to afford Compound 120 as a yellow solid (14 mg, 53%).

Compound 121. 2-(2,6-Dioxopiperidin-3-yl)-5-(4-((7-((3-((4-fluoro-2-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione

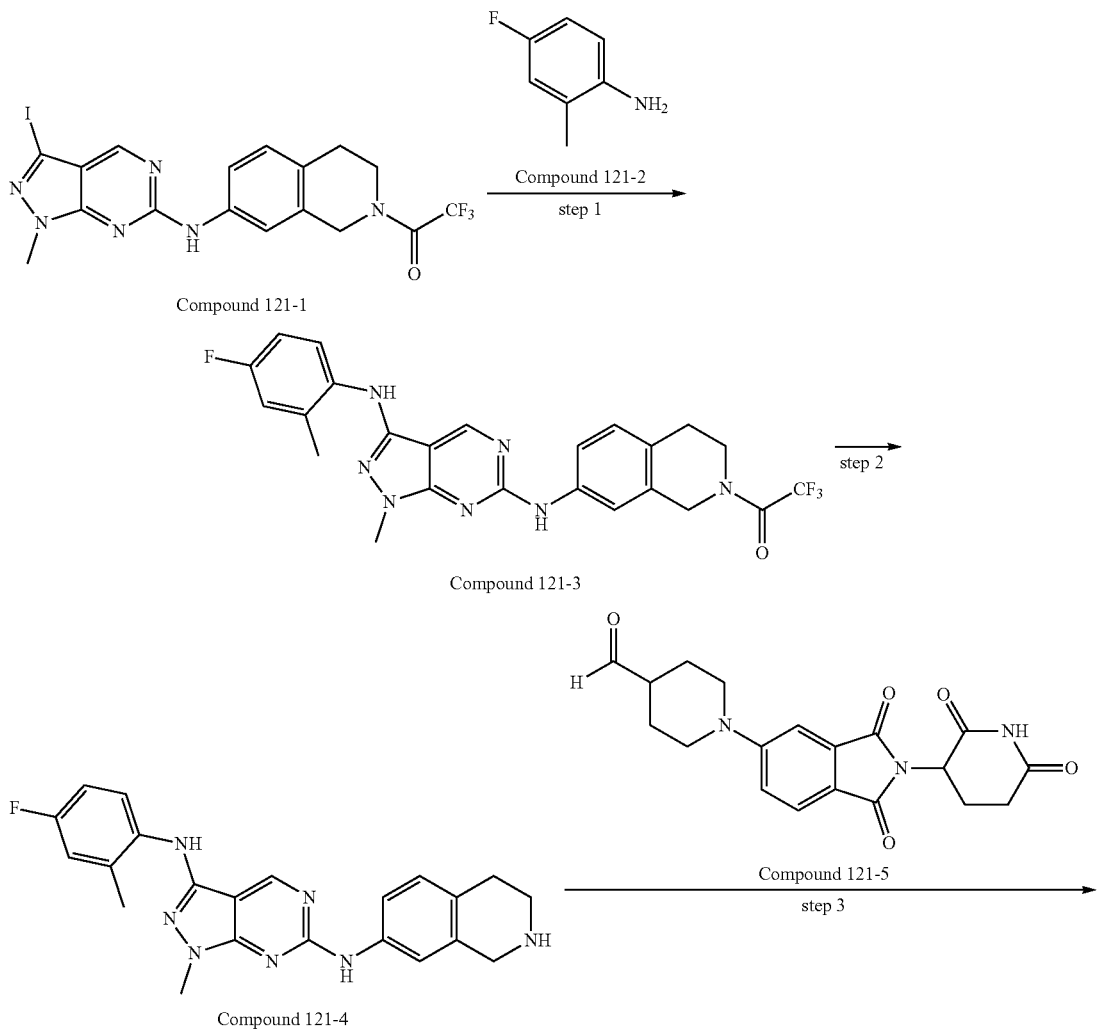

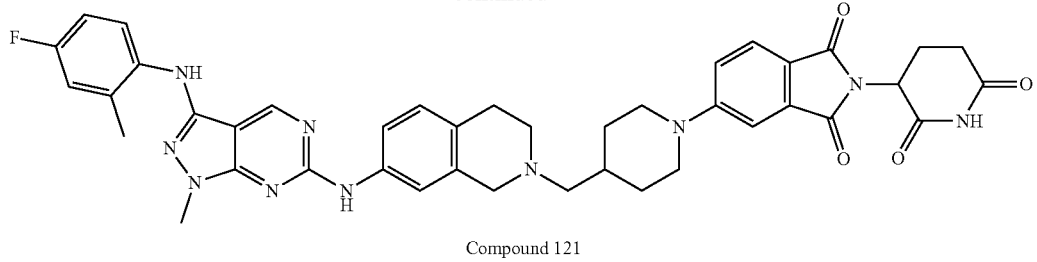

Compound 121

Step 1: Synthesis of 2,2,2-trifluoro-1-(7-((3-((4-fluoro-2-methylphenyl)amino)-1-methyl-1H-pyrazolo[3,4-d]pyrimidin-6-yl)amino)-3,4-dihydroisoquinolin-2 (1H)-yl)ethan-1-one (Compound 121-3)

A solution of Compound 121-1 (identical to Compound 118-1) (50 mg, 0.1 mmol, 1.0 eq.) in toluene (2 mL) was added with $Cs_2CO_3$ (326 mg, 1.0 mmol, 10 eq.), $Pd_2(dba)_3$ (4.6 mg, 0.005 mmol, 0.05 eq.), Xantphos (9.3 mg, 0.016 mmol, 0.16 eq.), and Compound 121-2 (TCI, F0398) (4-fluoro-2-methylaniline; 11 μl, 0.1 mmol, 1.0 eq.) in a nitrogen atmosphere. The mixture was stirred at 110° C. for 12 hours. The reaction mixture was quenched with water before extraction with ethyl acetate. The organic layer was dried over sodium sulfate and concentrated in a vacuum. The crude mixture was purified by silica gel column chromatography using 30% EA/HEX as an eluent to afford Compound 121-3 as a yellow solid (14 mg, 28%).

Step 2: Synthesis of N3-(4-fluoro-2-methylphenyl)-1-methyl-N6-(1,2,3,4-tetrahydroisoquinolin-7-yl)-1H-pyrazolo[3,4-d]pyrimidine-3,6-diamine (Compound 121-4)

A solution of Compound 121-3 (14 mg, 0.028 mmol, 1.0 eq.) and LiOH·H$_2$O (3 mg, 0.070 mmol, 2.5 eq.) in THF (1 mL)/MeOH (0.5 mL)/H$_2$O (0.5 mL) was stirred at room temperature for 2 hours. The progression of the reaction was monitored by TLC, and the reaction mixture was quenched with water before extraction with EA. The pooled organic layer was dried over $Na_2SO_4$ and the solvent was removed in a vacuum to afford Compound 121-4 as a yellow solid (11.8 mg, quant.).

Step 3: Synthesis of 2-(2,6-dioxopiperidin-3-yl)-5-(4-((7-((3-((4-fluoro-2-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 121)

A solution of Compound 121-4 (11.6 mg, 0.029 mmol, 1.0 eq.) in MeOH (1 mL) was added with Compound 121-5 (WO 2020/051564) (12 mg, 0.032 mmol), and 1 M AcOH in MeOH (29 μl) and stirred for 12 hours. The mixture was added with NaCNBH$_3$ (2.8 mg, 0.044 mmol, 1.5 eq.) and stirred at room temperature for 2 hours. The reaction mixture was quenched with water, subjected to extraction with MC, and washed with brine. The organic layer was dried over sodium sulfate and the solvent was evaporated in a vacuum. The crude mixture was purified by silica gel column chromatography using 5% MeOH/MC as an eluent to afford Compound 121 as a yellow solid (5 mg, 23%).

Compound 122. N-(4-((6-((2-((1-(2-(2,6-Dioxopiperidin-3-yl)-1,3-dioxoisoindolin-5-yl)piperidin-4-yl)methyl)-1,2,3,4-tetrahydroisoquinolin-7-yl)amino)-1-methyl-1H-pyrazolo[3,4-d]pyrimidin-3-yl)amino)-3-methylphenyl)-3-(trifluoromethyl)benzamide

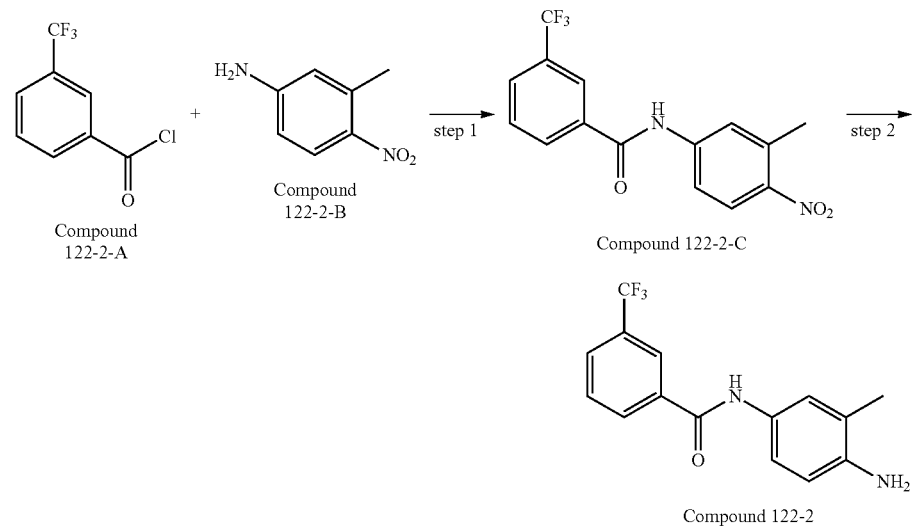

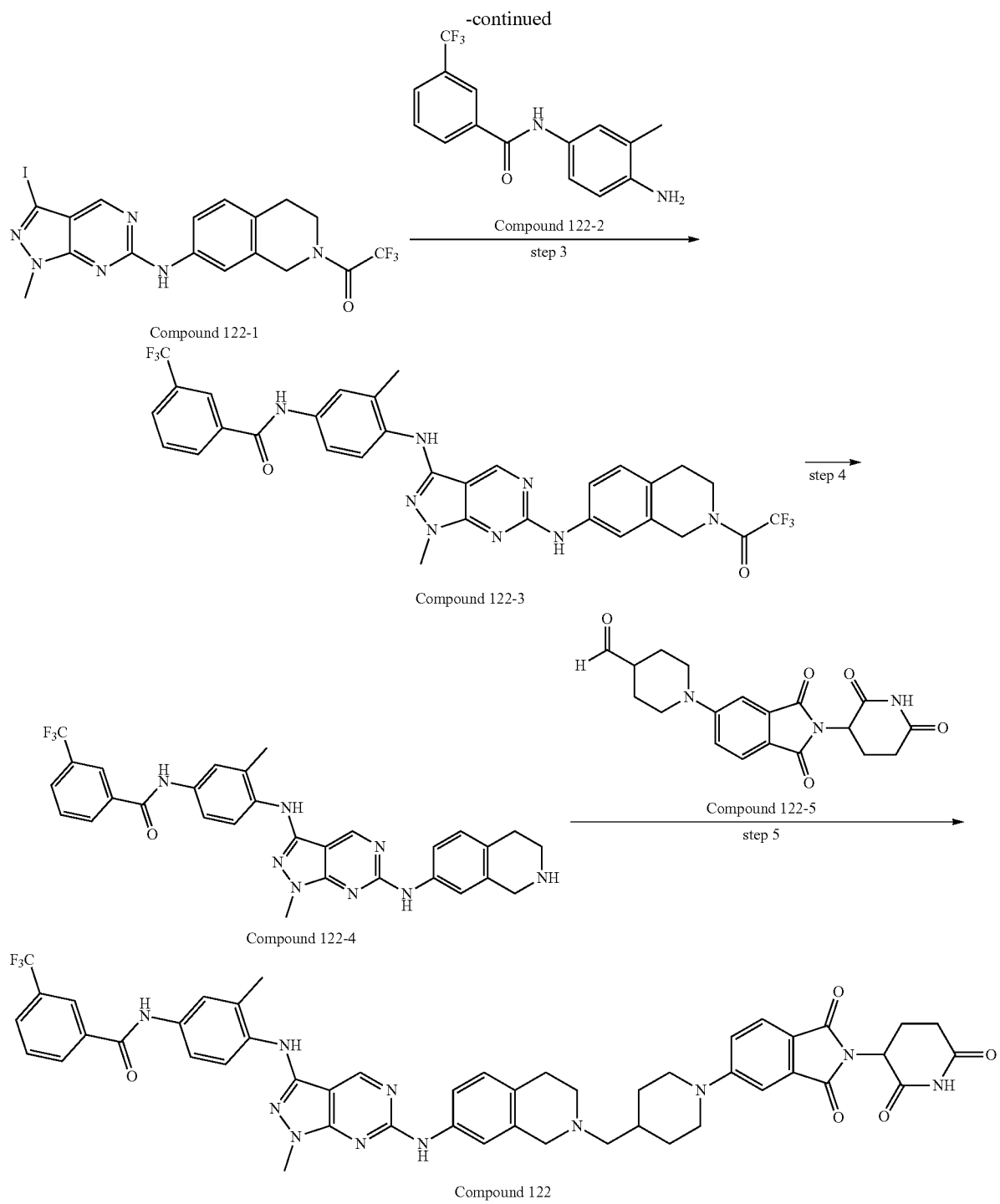

Step 1: Synthesis of N-(3-methyl-4-nitrophenyl)-3-(trifluoromethyl)benzamide (Compound 122-2-C)

At 0° C., Compound 122-2-A (SIGMA, 250279) (3-(trifluoromethyl)benzoylchloride; 362 μl, 2.4 mmol, 1.0 eq.) and TEA (665 μl, 4.8 mmol, 1.2 eq.) were dissolved in DCM (15 mL). To this solution were added drops of Compound 122-2-B (TCI, M1677) (3-methyl-4-nitroaniline; 441 mg, 2.9 mmol, 2.0 eq.) at 0° C., followed by stirring at room temperature for 12 hours. The reaction mixture was quenched with water before extraction with ethylacetate. The organic layer was dried over sodium sulfate and concentrated in a vacuum. The residue was purified by silica gel column chromatography using 30% EA/HEX as an eluent to afford Compound 122-2-C as an ivory solid.

Step 2: Synthesis of N-(4-amino-3-methylphenyl)-3-(trifluoromethyl)benzamide (Compound 122-2)

Compound 122-2-C (800 mg, 2.467 mmol, 1.0 eq) was added with iron powder (689 mg, 12.335 mmol, 5.0 eq.), ethyl alcohol/water (8:1 15 mL), and HCl (17 μl, 35% aqueous solution), heated to 90° C. under protection with nitrogen, and stirred for 12 hours. After completion of the reaction, the reaction mixture was filtered and the filtrate was concentrated in a vacuum and subjected to extraction with water and ethylacetate. The organic layer was dried over sodium sulfate and concentrated in a vacuum. The residue was purified by silica gel column chromatography using 30% EA/HEX as an eluent to afford Compound 122-2 as a yellow solid (684 mg, 94%).

Step 3: Synthesis of N-(3-methyl-4-((1-methyl-6-((2-(2,2,2-trifluoroacetyl)-1,2,3,4-tetrahydroisoquinolin-7-yl)amino)-1H-pyrazolo[3,4-d]pyrimidin-3-yl)amino)phenyl)-3-(trifluoromethyl)benzamide (Compound 122-3)

A solution of Compound 122-1 (identical to Compound 118-1) (50 mg, 0.1 mmol, 1.0 eq.) in toluene (2 mL) was added with $Cs_2CO_3$ (326 mg, 1.0 mmol, 10 eq.), $Pd_2(dba)_3$ (4.6 mg, 0.005 mmol, 0.05 eq.), Xantphos (9.3 mg, 0.016 mmol, 0.16 eq.), and Compound 122-2 (29 mg, 0.1 mmol, 1.0 eq.) in a nitrogen atmosphere. The mixture was stirred at 110° C. for 12 hours. The reaction mixture was quenched with water before extraction with ethyl acetate. The organic layer was dried over sodium sulfate and concentrated in a vacuum. The crude mixture was purified by silica gel column chromatography using 50% EA/HEX as an eluent to afford Compound 122-3 as a yellow solid (40 mg, 60%).

Step 4: Synthesis of N-(3-methyl-4-((1-methyl-6-((1,2,3,4-tetrahydroisoquinolin-7-yl)amino)-1H-pyrazolo[3,4-d]pyrimidin-3-yl)amino)phenyl)-3-(trifluoromethyl)benzamide (Compound 122-4)

A solution of Compound 122-3 (40 mg, 0.060 mmol, 1.0 eq.) and $LiOH \cdot H_2O$ (6.3 mg, 0.15 mmol, 2.5 eq.) in THF (1 mL)/MeOH (0.5 mL)/$H_2O$ (0.5 mL) was stirred at room temperature for 2 hours. The progression of the reaction was monitored by TLC, and the reaction mixture was quenched with water before extraction with EA. The pooled organic layer was dried over $Na_2SO_4$ and the solvent was removed in a vacuum to afford Compound 122-4 as a yellow solid (28 mg, 82%).

Step 5: N-(4-((6-((2-((1-(2-(2,6-dioxopiperidin-3-yl)-1,3-dioxoisoindolin-5-yl)piperidin-4-yl)methyl)-1,2,3,4-tetrahydroisoquinolin-7-yl)amino)-1-methyl-1H-pyrazolo[3,4-d]pyrimidin-3-yl)amino)-3-methylphenyl)-3-(trifluoromethyl)benzamide (Compound 122)

A solution of Compound 122-4 (20 mg, 0.035 mmol, 1.0 eq.) in MeOH (1 mL) was added with Compound 122-5 (WO 2020/051564) (14 mg, 0.039 mmol) and 1 M AcOH in MeOH (35 µl) and stirred for 12 hours. The mixture was added with $NaCNBH_3$ (3.3 mg, 0.053 mmol, 1.5 eq.) and stirred at room temperature for 2 hours. The reaction mixture was quenched with water, subjected to extraction with MC, and washed with brine. The organic layer was dried over sodium sulfate and the solvent was evaporated in a vacuum. The crude mixture was purified by silica gel column chromatography using 5% MeOH/MC as an eluent to afford Compound 122 as a yellow solid (10 mg, 31%).

Compound 123. 5-((2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)ethyl)amino)-2-(2,6-dioxopiperidin-3-yl)isoindoline-1,3-dione

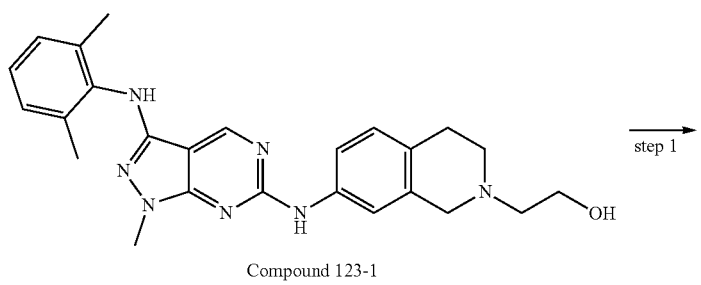

Compound 123-1

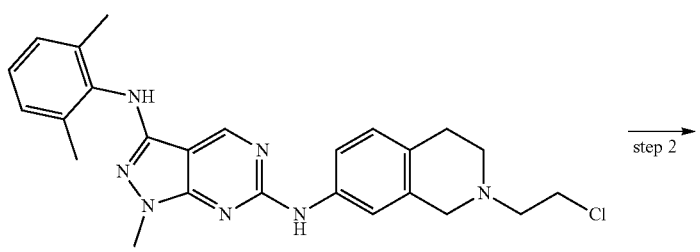

Compound 123-2

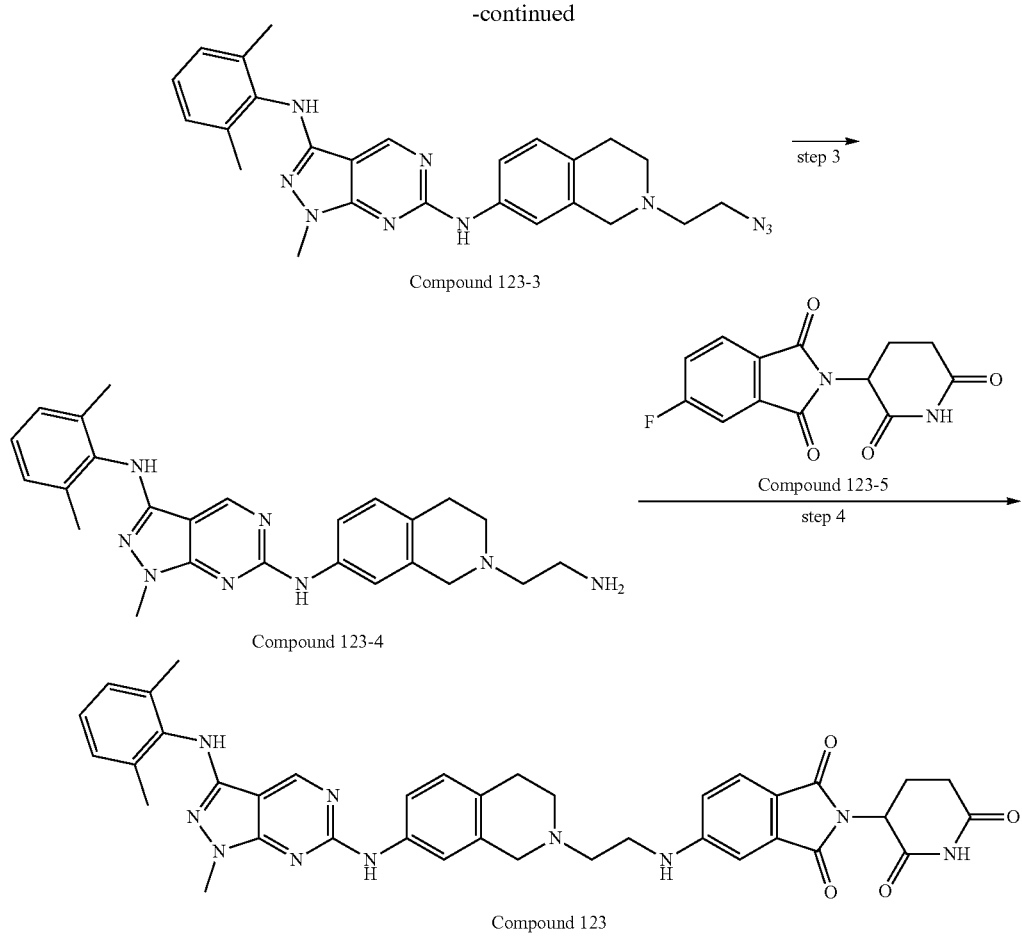

Compound 123-3

Compound 123-4

Compound 123-5

Compound 123

Step 1: Synthesis of N6-(2-(2-chloroethyl)-1,2,3,4-tetrahydroisoquinolin-7-yl)-N3-(2,6-dimethylphenyl)-1-methyl-H-pyrazolo[3,4-d]pyrimidine-3,6-diamine (Compound 123-2)

A stirred solution of Compound 123-1 (Korean Patent No. 2128018) (200 mg, 0.450 mmol) in DCM (15 mL) was cooled to 0° C. and added with TEA (410 mg, 4.05 mmol) and DMAP (30.0 mg, 0.225 mmol) and then slowly with p-toluene sulfonylchloride (130 mg, 0.676 mmol), followed by stirring at room temperature for 12 hours. After completion of the reaction, the reaction mixture was diluted with DCM (20 mL) and washed with water. The aqueous layer was subjected to extraction with DCM (25 mL×2), and the pooled organic layer was washed with 1 N HCl and brine. The organic layer was dried over sodium sulfate and the solvent was evaporated in a vacuum. The crude material was purified by silica gel column chromatography using a solvent mixture of 5% MeOH/DCM as an eluent to afford the chloro-compound Compound 123-2 as a yellow solid (156 mg, 0.337 mmol, 75%).

Step 2: Synthesis of N6-(2-(2-azidoethyl)-1,2,3,4-tetrahydroisoquinolin-7-yl)-N3-(2,6-dimethylphenyl)-1-methyl-H-pyrazolo[3,4-d]pyrimidine-3,6-diamine (Compound 123-3)

A solution of Compound 123-2 (50.0 mg, 0.108 mmol) in DMF (0.5 mL) was added with sodium azide (42.2 mg, 0.649 mmol) and stirred at room temperature for 12 hours. When the starting material was completely consumed as analyzed by TLC, the reaction mixture was added with water before two rounds of extraction with EA. The organic layer was washed with water and then with brine. The pooled organic layer was dried over sodium sulfate and the solvent was evaporated in a vacuum to afford Compound 123-3 as a yellow oil (51.0 mg, 0.108 mmol, 100%).

Step 3: Synthesis of N6-(2-(2-aminoethyl)-1,2,3,4-tetrahydroisoquinolin-7-yl)-N3-(2,6-dimethylphenyl)-1-methyl-H-pyrazolo[3,4-d]pyrimidine-3,6-diamine (Compound 123-4)

A solution of Compound 123-3 (50.0 mg, 0.192 mmol) in MeOH (10 mL) was added at room temperature with Pd/C (10%, 5.0 mg) and stirred at room temperature for 16 hours under a hydrogen balloon. When the reaction was completed as analyzed by TLC, the reaction mixture was filtered through a celite pad and the solvent was evaporated in a vacuum. The residue was washed to afford Compound 123-4 as a yellow solid (40.0 mg, 0.0903 mmol, 85%).

Step 4: Synthesis of 5-((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)amino)-2-(2,6-dioxopiperidin-3-yl)isoindoline-1,3-dione (Compound 123)

A stirred solution of Compound 123-4 (15.0 mg, 0.0338 mmol) in DMSO (2 mL) was added with Compound 123-5

(Combi-Blocks, HD-3240) (9.33 mg, 0.0338 mmol), filled with DIPEA (13.1 mg, 0.101 mmol), and stirred at 90° C. for 2 hours. After completion of the reaction, the reaction mixture was diluted with DCM (20 mL) and washed with water. The aqueous layer was subjected to extraction with EA (25 mL×2), and the pooled organic layer was washed with water (20 mL×2) and brine (20 mL×2). The organic layer was dried over sodium sulfate and the solvent was evaporated in a vacuum. The crude material was purified by silica gel column chromatography using a solvent mixture of 5% MeOH/DCM as an eluent to afford the chloro-compound Compound 123 as a yellow solid (6.0 mg, 0.00858 mmol, 25%).

Compound 124. 5-(2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-7-azaspiro[3.5]nonan-7-yl)-2-(2,6-dioxopiperidin-3-yl)isoindoline-1,3-dione dione (Combi-Blocks, HD-3240) (810 mg, 3.90 mmol), and DIPEA (2.3 mL, 11.7 mmol) in DMSO (6.5 mL) was stirred at 120° C. for 1 hour in a microwave oven. The reaction mixture was added with distilled water (10 mL) before extraction with EtOAc (15 mL×2). The organic layer was washed with brine (15 mL×2), dried over anhydrous magnesium sulfate, filtered, and concentrated in a vacuum. Crystallization in (EtOAc/hexane) afforded a yellow solid (800 mg, 50%).

Step 2: Synthesis of 5-(2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-7-azaspiro[3.5]nonan-7-yl)-2-(2,6-dioxopiperidin-3-yl)isoindoline-1,3-dione (Compound 124)

A suspension of 7-(2-(2,6-dioxopiperidin-3-yl)-1,3-dioxoisoindolin-5-yl)-7-azaspiro[3.5]nonane-2-carboxylic acid (34.0 mg, 0.08 mmol), N3-(2,6-dimethylphenyl)-1-methyl-N6-(1,2,3,4-tetrahydroisoquinolin-7-yl)-1H-pyra

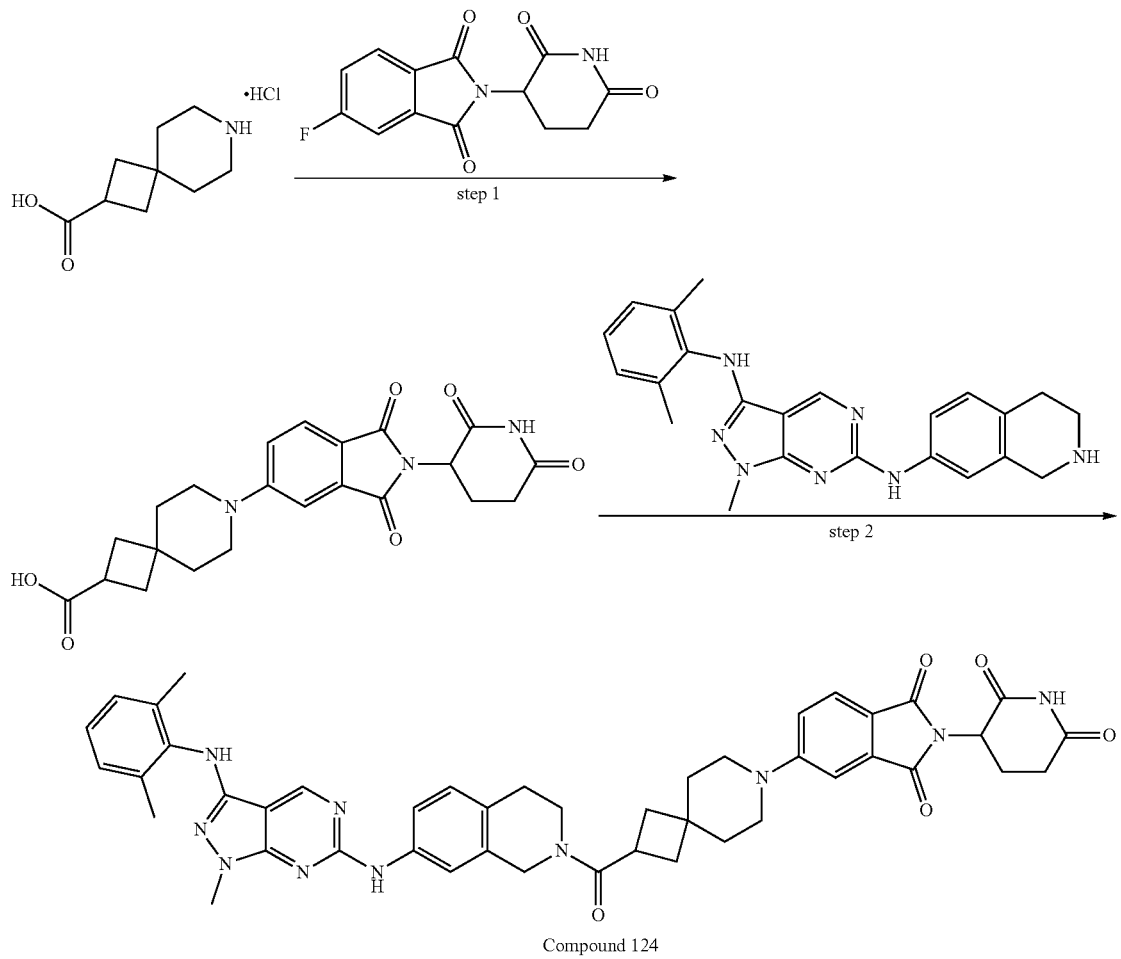

Compound 124

Step 1: Synthesis of 7-(2-(2,6-dioxopiperidin-3-yl)-1,3-dioxoisoindolin-5-yl)-7-azaspiro[3.5]nonane-2-carboxylic acid A suspension of 7-azaspiro[3,5]nonane-2-carboxylic acid hydrochloride (Combi-Blocks, ST-6386) (1.07 g, 3.90 mmol), 2-(2,6-dioxopiperidin-3-yl)-5-fluoroisoindoline-1,3- zolo[3,4-d]pyrimidine-3,6-diamine (Korean Patent No. 2128018) (33.4 mg, 0.08 mmol), HATU (45 mg, 0.12 mmol), and DIPEA (0.04 mL, 0.24 mmol) in DMF (1.5 mL) was stirred at room temperature for 16 hours. The reaction mixture was added with distilled water (5 mL) and filtered. The solid thus obtained was washed with distilled water and dried to afford a yellow solid (17 mg, 26%).

Compound 125. 5-(4-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethyl)piperidin-1-yl)-2-(2,6-dioxopiperidin-3-yl)isoindoline-1,3-dione

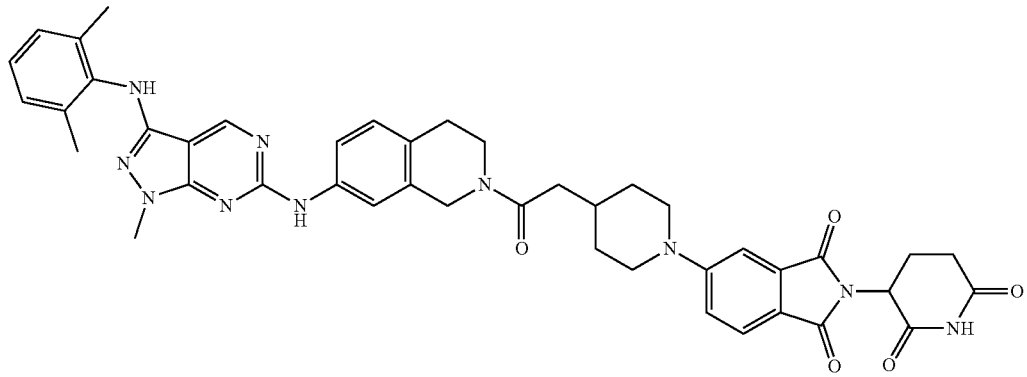

Compound 125

Compound 125 was synthesized in the same manner as in the synthesis procedure for Compound 124, with the exception of using 2-(piperidin-4-yl)acetic acid hydrochloride (Combi-Blocks, OR-5687) instead of 7-azaspiro[3,5]nonane-2-carboxylic acid hydrochloride (Combi-Blocks, ST-6386).

Compound 126. 5-(4-(3-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-3-oxopropyl)piperidin-1-yl)-2-(2,6-dioxopiperidin-3-yl)isoindoline-1,3-dione

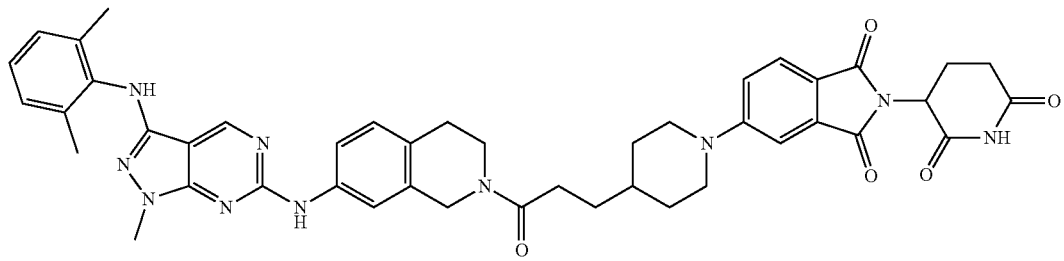

Compound 126

Compound 126 was synthesized in the same manner as in the synthesis procedure for Compound 124, with the exception of using 3-(piperidin-4-yl)propanoic acid hydrochloride (Combi-Blocks, QE-3962) instead of 7-azaspiro[3,5]nonane-2-carboxylic acid hydrochloride (Combi-Blocks, ST-6386).-

Compound 127. 5-(4-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethoxy)piperidin-1-yl)-2-(2,6-dioxopiperidin-3-yl)isoindoline-1,3-dione

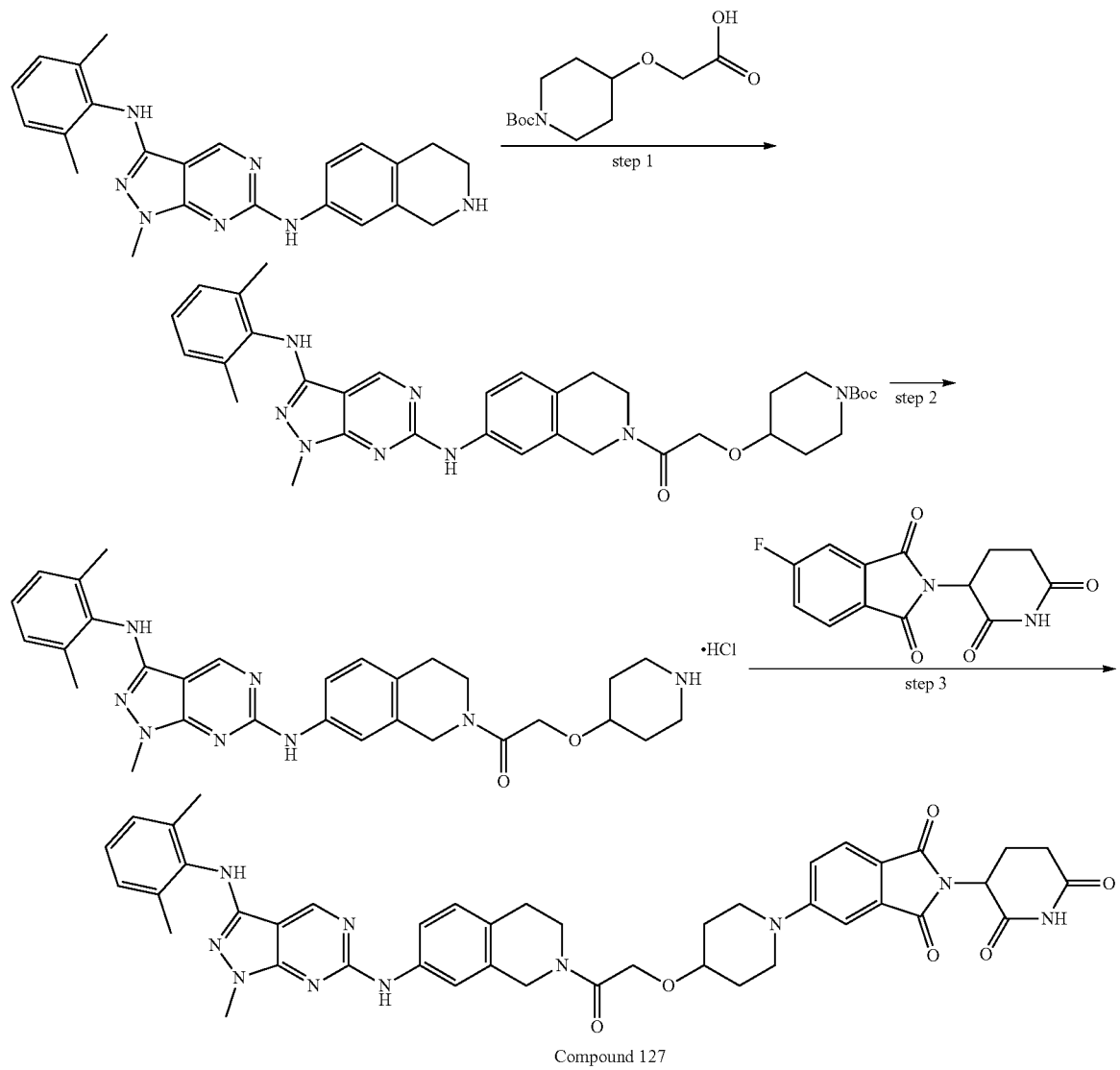

Compound 127

Step 1: Synthesis of tert-butyl 4-(2-(7-((3-((2,6-dimethylphenyl) amino)-1-methyl-1H-pyrazolo[3,4-d]pyrimidin-6-yl)amino)-3,4-dihydroisoquinolin-2 (1H)-yl)-2-oxoethoxy)piperidine-1-carboxylate A suspension of N3-(2,6-dimethylphenyl)-1-methyl-N6-(1,2,3,4-tetrahydroisoquinolin-7-yl)-1H-pyrazolo[3,4-d]pyrimidine-3,6-diamine (Korean Patent No. 2128018) (20.8 mg, 0.05 mmol), 2-((1-(tert-butoxycarbonyl)piperidin-4-yl)oxy)acetic acid (Combi-Blocks, SS-3318) (13.5 mg, 0.05 mmol), HATU (30 mg, 0.80 mmol), and DIPEA (0.03 mL, 0.16 mmol) in DMF (1.5 mL) was stirred at room temperature for 2 hours. The reaction mixture was added with distilled water (5 mL) before extraction with EtOAc (10 mL×2). The organic layer was dried over anhydrous magnesium, filtered, and concentrated in a vacuum. The residue thus obtained was purified by MPLC (5% MeOH/DCM) to afford a white solid 21 mg (63%).

Step 2: Synthesis of 1-(7-((3-((2,6-dimethylphenyl) amino)-1-methyl-1H-pyrazolo[3,4-d]pyrimidin-6-yl) amino)-3,4-dihydroisoquinolin-2 (1H)-yl)-2-(piperidin-4-yloxy)ethan-1-one hydrochloride A suspension of tert-butyl 4-(2-(7-((3-((2,6-dimethylphenyl)amino)-1-methyl-1H-pyrazolo[3,4-d]pyrimidin-6-yl) amino)-3,4-dihydroisoquinolin-2 (1H)-yl)-2-oxoethoxy)piperidine-1-carboxylate (21 mg, 0.032 mmol) in DCM (1 mL) was added with 4 N HCl/dioxane (0.01 mL, 0.26 mmol)

and stirred at room temperature for 0.5 hours. the reaction mixture was concentrated to afford a white solid (16 mg, 86%).

Step 3: Synthesis of 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)piperidin-1-yl)-2-(2,6-dioxopiperidin-3-yl)isoindoline-1,3-dione (Compound 127)

A suspension of 1-(7-((3-((2,6-dimethylphenyl)amino)-1-methyl-H-pyrazolo[3,4-d]pyrimidin-6-yl)amino)-3,4-dihydroisoquinolin-2 (1H)-yl)-2-(piperidin-4-yloxy)ethan-1-one hydrochloride (16 mg, 0.03 mmol) in DMSO (1.5 mL) was added with 2-(2,6-dioxopiperidin-3-yl)-5-fluoroisoindoline-1,3-dione (Combi-Blocks, HD-3240) (7.45 mg, 0.03 mmol) and DIPEA (0.01 mL, 0.08 mmol) and stirred at 120° C. for 1 hour in a microwave oven. The reaction mixture was added with distilled water (7 mL) before extraction with EtOAc (10 mL×2). The organic layer was washed with brine (10 mL×2), dried over anhydrous magnesium, filtered, and concentrated in a vacuum. The residue thus obtained was purified by PTLC (2.5% MeOH/DCM) to afford a yellow solid (4 mg, 18%).

Compound 128. 5-(4-(((1r,4r)-4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)cyclohexyl)oxy)piperidin-1-yl)-2-(2,6-dioxopiperidin-3-yl)isoindoline-1,3-dione Compound 128

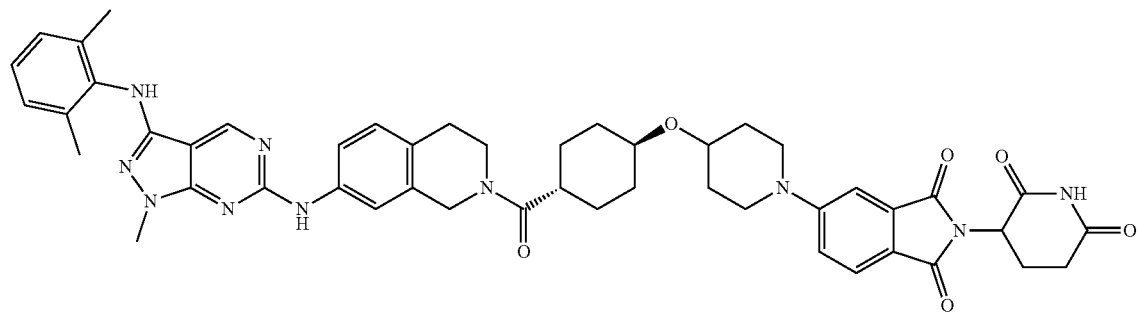

Compound 128 was synthesized in the same manner as in the synthesis procedure for Compound 124, with the exception of using (1r,4r)-4-(piperidin-4-yloxy)cyclohexane-1-carboxylic acid (eNovation chemicals, K08283) instead of 7-azaspiro[3,5]nonane-2-carboxylic acid hydrochloride (Combi-Blocks, ST-6386).

Compound 129. 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)-4-hydroxypiperidin-1-yl)-2-(2,6-dioxopiperidin-3-yl)isoindoline-1,3-dione Compound 129

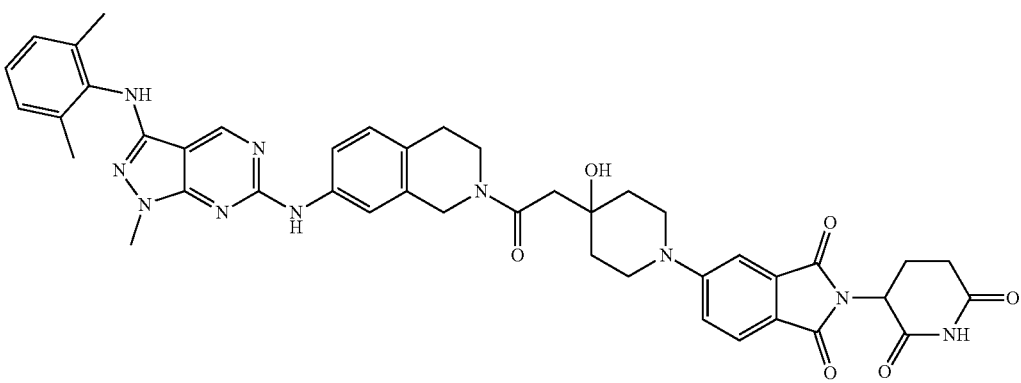

Compound 129 was synthesized in the same manner as in the synthesis procedure for Compound 127, with the exception of using 2-(1-(tert-butoxycarbonyl)-4-hydroxypiperidin-4-yl)acetic acid (Combi-Blocks, QK-2527) instead of 2-((1-(tert-butoxycarbonyl)piperidin-4-yl)oxy)acetic acid (Combi-Blocks, SS-3318).

Compound 130. 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidin-1-yl)-2-(2,6-dioxopiperidin-3-yl)isoindoline-1,3-dione 0.13 mmol) and tert-butyl 1-oxa-6-azaspiro[2.5]octane-6-carboxylate (TCI, B5501) (27 mg, 0.13 mmol) in EtOH (2 mL) was added with TEA (0.03 mL, 0.19 mmol) and stirred at 120° C. for 1 hour in a microwave oven. The reaction mixture was added with distilled water (5 mL) before extraction with EtOAc (10 mL×2). The organic layer was dried over anhydrous magnesium, filtered, and concentrated in a vacuum. The residue thus obtained was purified by MPLC (5% MeOH/DCM) to afford a white solid (60 mg, 78%).

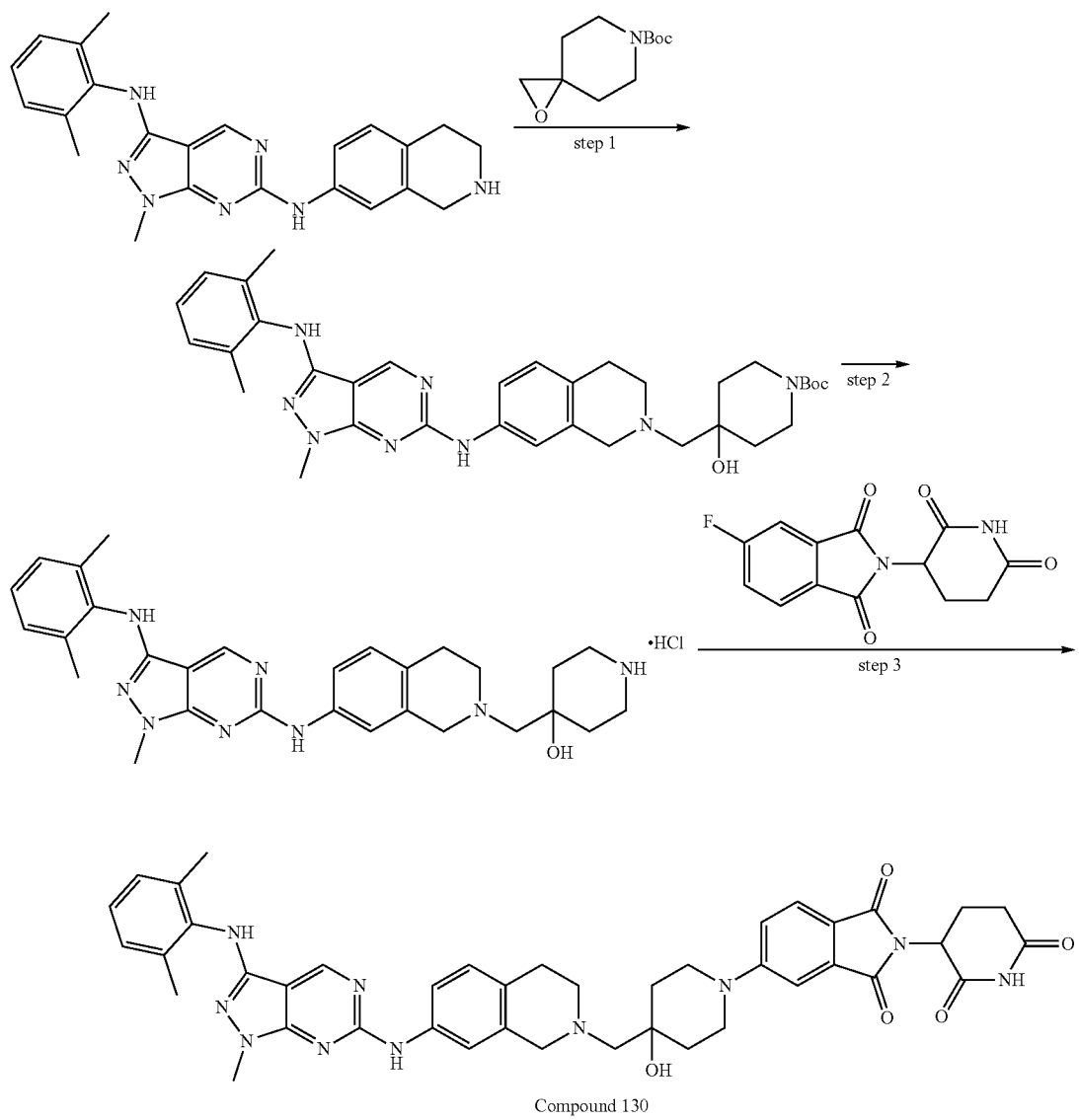

Compound 130

Step 1: Synthesis of tert-butyl 4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidine-1-carboxylate A suspension of N3-(2,6-dimethylphenyl)-1-methyl-N6-(1,2,3,4-tetrahydroisoquinolin-7-yl)-1H-pyrazolo[3,4-d]pyrimidine-3,6-diamine (Korean Patent No. 2128018) (50 mg, Step 2: Synthesis of 4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl) piperidin-4-ol hydrochloride A suspension of tert-butyl 4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidine-1-carboxylate (60 mg, 0.09 mmol) in DCM (1 mL) was added with 4 N HCl/dioxane (0.03 mL, 0.9 mmol) and stirred at room temperature for 0.5 hours. The reaction mixture was concentrated to afford a yellow solid (48 mg, 97%).

Step 3: Synthesis of 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl) methyl)-4-hydroxypiperidin-1-yl)-2-(2,6-dioxopiperidin-3-yl)isoindoline-1,3-dione (Compound 130)

A suspension of 4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidin-4-ol hydrochloride (31.30 mg, 0.06 mmol) in DMSO (1.5 mL) was added with 2-(2,6-dioxopiperidin-3-yl)-5-fluoroisoindoline-1,3-dione (Combi-Blocks, HD-3240) (16.0 mg, 0.06 mmol), and DIPEA (0.04 mL, 0.23 mmol) and stirred at 120° C. for 1 hour in a microwave oven. The reaction mixture was added with distilled water (7 mL) before extraction with EtOAc (10 mL×2). The organic layer was washed with brine (10 mL×2), dried over anhydrous magnesium, filtered, and concentrated in a vacuum. The residue thus obtained was purified by PTLC (5% MeOH/DCM) to afford a yellow solid (7.2 mg, 16%).

Compound 131. 5-(4-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl) ethyl)-4-hydroxypiperidin-1-yl)-2-(2,6-dioxopiperidin-3-yl)isoindoline-1,3-dione

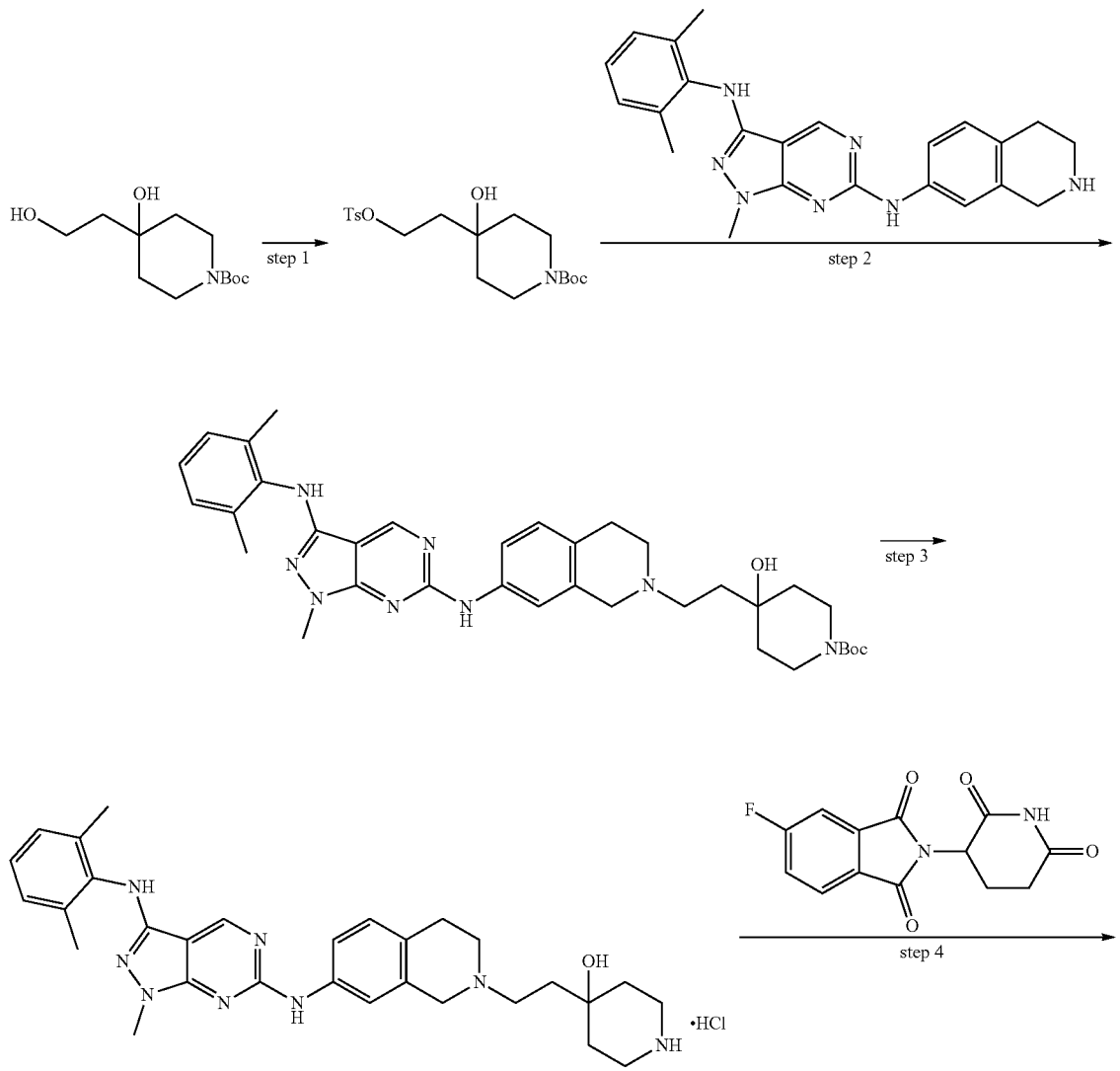

-continued

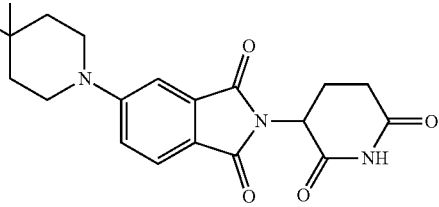

Compound 131

Step 1: Synthesis of tert-butyl 4-hydroxy-4-(2-(tosyloxy)ethyl)piperidine-1-carboxylate A suspension of t-butyl 4-hydroxy-4-(2-hydroxyethyl) piperidine-1-carboxylate (Achemblocks, Q61169) (100 mg, 0.40 mmol) in DCM (2 mL) was added at 0° C. with p-toluenesulfonyl chloride (76.3 mg, 0.40 mmol), and TEA (0.11 mL, 0.80 mmol) and stirred at room temperature for 3 hours. The reaction mixture was added with 1 N HCl solution (10 mL) before extraction with EtOAc (15 mL×2). The organic layer was dried over anhydrous magnesium, filtered, and concentrated in a vacuum. The residue thus obtained was purified by MPLC (25% EtOAc/Hex) to afford a white oil (110 mg, 69%).

Step 2: Synthesis of tert-butyl 4-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)ethyl)-4-hydroxypiperidine-1-carboxylate A suspension of t-butyl 4-hydroxy-4-(2-(tosyloxy)ethyl) piperidine-1-carboxylate (53.2 mg, 0.33 mmol), N3-(2,6-dimethylphenyl)-1-methyl-N6-(1,2,3,4-tetrahydroisoquinolin-7-yl)-1H-pyrazolo[3,4-d]pyrimidine-3,6-diamine (Korean Patent No. 2128018) (53.2 mg, 0.33 mmol), and K$_2$CO$_3$ (55.0 mg, 0.4 mmol) in DMF (2 mL) was stirred at 70° C. for 4 hours. The reaction mixture was added with distilled water (10 mL) before extraction with EtOAc (15 mL×2). The organic layer was washed with brine (5 mL×2), dried over anhydrous magnesium, filtered, and concentrated in a vacuum. The residue thus obtained was purified by MPLC (6% MeOH/DCM) to afford a white solid (39 mg, 46%).

Step 3: Synthesis of 4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)piperidin-4-ol hydrochloride A suspension of t-butyl 4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)-4-hydroxypiperidine-1-carboxylate (39 mg, 0.06 mmol) in DCM (1 mL) was added with 4 N HCl/dioxane (0.02 mL, 0.6 mmol) and stirred at room temperature for 0.5 hours. The reaction mixture was concentrated to afford a yellow solid (34 mg, 97%).

Step 4: Synthesis of 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)-4-hydroxypiperidin-1-yl)-2-(2,6-dioxopiperidin-3-yl)isoindoline-1,3-dione (Compound 131)

A suspension of 4-(2-(7-((3-((2,6-dimethylphenyl)amino)-1-methyl-1H-pyrazolo[3,4-d]pyrimidin-6-yl) amino)-3,4-dihydroisoquinolin-2 (1H)-yl)ethyl)piperidin-4-ol hydrochloride (34 mg, 0.06 mmol) in DMSO (1.0 mL) was added with 2-(2,6-dioxopiperidin-3-yl)-5-fluoroisoindoline-1,3-dione (Combi-Blocks, HD-3240) (16.0 mg, 0.06 mmol) and DIPEA (0.04 mL, 0.23 mmol) and stirred at 120° C. for 1 hour in a microwave oven. The reaction mixture was added with distilled water (7 mL) before extraction with EtOAc (10 mL×2). The organic layer was washed with brine (10 mL×2), dried over anhydrous magnesium, filtered, and concentrated in a vacuum. The residue thus obtained was purified by PTLC (5% MeOH/DCM) to afford a yellow solid (8.0 mg, 17%).

Compound 132. 3-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-5-oxo-5,7-dihydro-6H-pyrrolo[3,4-b]pyridin-6-yl)piperidin-2,6-one Compound 132

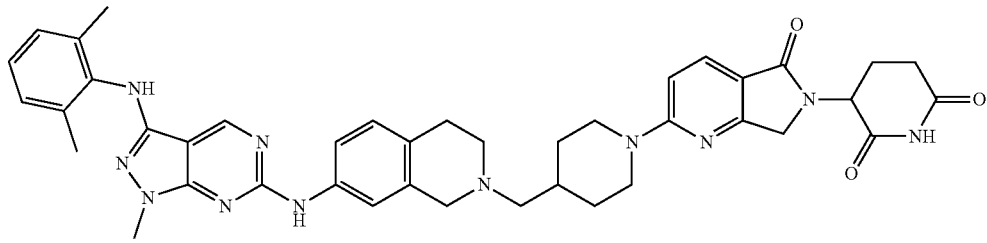

Compound 132 was synthesized in the same manner as in the synthesis procedure for Compound 131, with the exception of using tert-butyl 4-(hydroxymethyl)piperidine-1-carboxylate (Combi-Blocks, AM-1024) and 3-(2-chloro-5-oxo-5,7-dihydro-6H-pyrrolo[3,4-b]pyridin-6-yl)piperidin-2,6-one (WO2018/140809) instead of t-butyl 4-hydroxy-4-(2-hydroxyethyl)piperidine-1-carboxylate (Achemblocks, Q61169) and 2-(2,6-dioxopiperidin-3-yl)-5-fluoroisoindoline-1,3-dione (Combi-Blocks, HD-3240), respectively.

Compound 133. 3-(2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidin-1-yl)-5-oxo-5,7-dihydro-6H-pyrrolo[3,4-b]pyridin-6-yl)piperidin-2,6-one

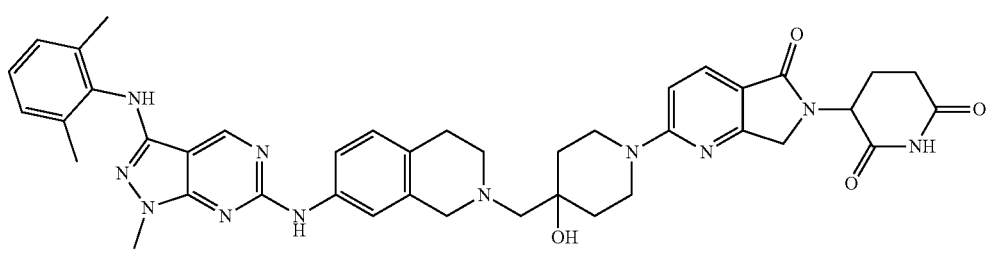

Compound 133

Compound 133 was synthesized in the same manner as in the synthesis procedure for Compound 130, with the exception of using 3-(2-chloro-5-oxo-5,7-dihydro-6H-pyrrolo[3,4-b]pyridin-6-yl)piperidin-2,6-one (WO2018/140809) instead of 2-(2,6-dioxopiperidin-3-yl)-5-fluoroisoindoline-1,3-dione (Combi-Blocks, HD-3240).

Compound 134. 5-(4-((4-(5-((3-((2,6-Dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione

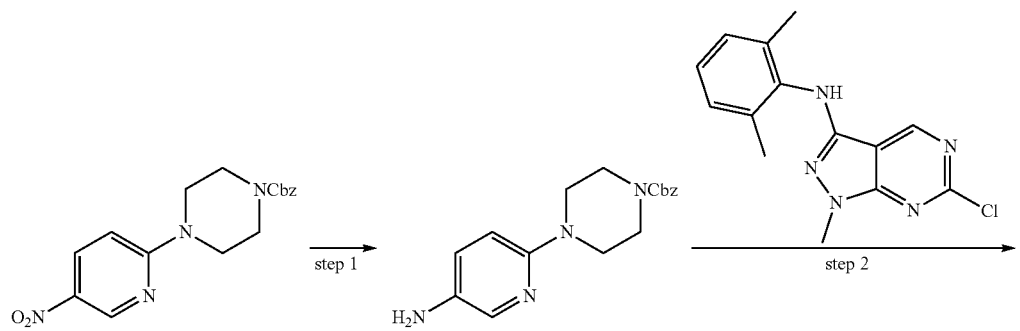

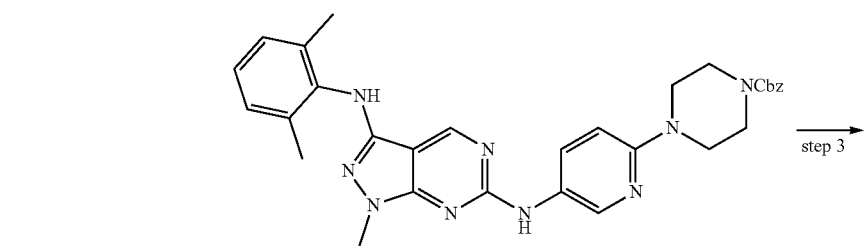

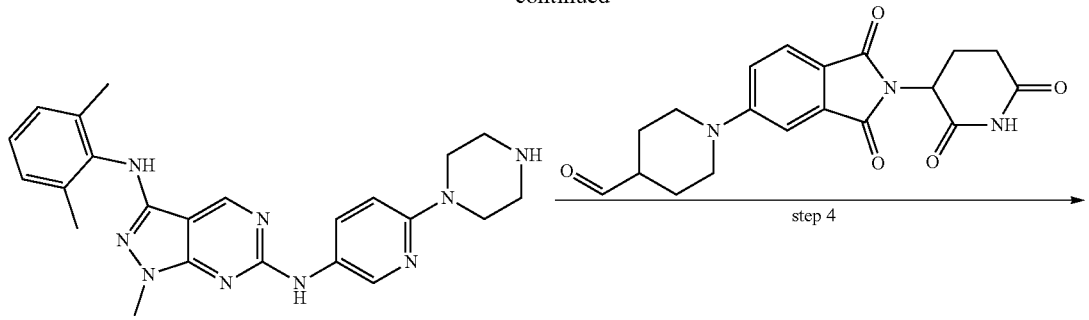

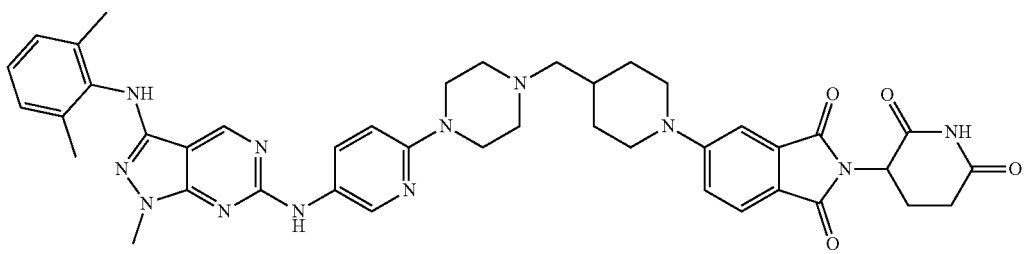

Compound 134

Step 1: Synthesis of benzyl 4-(5-aminopyridin-2-yl)piperazine-1-carboxylate

A solution of benzyl 4-(5-nitropyridin-2-yl)piperazine-1-carboxylate (WO2008/147831) (300 mg, 0.86 mmol) in a mixture of EtOH (2 mL) and THF (2 mL) was added with SnCl2 (830 mg, 4.40 mmol) and stirred at 80° C. for 2 hours. The mixture was concentrated in a vacuum and added with 2 N NaOH to form a pH of 14. After extraction with DCM (20 mL), the organic was dried over anhydrous magnesium sulfate, filtered, and concentrated in a vacuum. The residue thus obtained was purified by MPLC (60% EtOAc/hexane) to afford a brown oil (140 mg, 52%).

Step 2: Synthesis of benzyl 4-(5-((3-((2,6-dimethylphenyl)amino)-1-methyl-1H-pyrazolo[3,4-d]pyrimidin-6-yl)amino)pyridin-2-yl)piperazine-1-carboxylate A suspension of benzyl 4-(5-aminopyridin-2-yl)piperazine-1-carboxylate (80 mg, 0.28 mmol) in IPA (3.2 mL) was added with 6-chloro-N-(2,6-dimethylphenyl)-1-methyl-1H-pyrazolo[3,4-d]pyrimidine-3-amine (Korean Patent No. 2128018) (87 mg, 0.28 mmol) and pTSA (53 mg, 0.28 mmol) and stirred at 90° C. for 12 hours. The reaction mixture was added with distilled water (10 mL) before extraction with EtOAc (15 mL×2). The organic layer was dried over anhydrous magnesium, filtered, and concentrated in a vacuum. The residue thus obtained was purified by MPLC (5% MeOH/DCM) to afford a yellow solid (100 mg, 64%).

Step 3: Synthesis of N3-(2,6-dimethylphenyl)-1-methyl-N6-(6-(piperazin-1-yl)pyridin-3-yl)-1H-pyrazolo[3,4-d]pyrimidine-3,6-diamine A suspension of benzyl 4-(5-((3-((2,6-dimethylphenyl)amino)-1-methyl-1H-pyrazolo[3,4-d]pyrimidin-6-yl)amino)pyridin-2-yl)piperazine-1-carboxylate (90 mg, 0.16 mmol) in MeOH (3 mL) was added with Pd/C (10 wt % Pd, 10 mg) and stirred at room temperature for 4 hours under a hydrogen stream. The reaction mixture was filtered and concentrated to afford a yellow solid (66 mg, 96%).

Step 4: Synthesis of 5-(4-((4-(5-((3-((2,6-dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione (Compound 134)

A suspension of N3-(2,6-dimethylphenyl)-1-methyl-N6-(6-(piperazin-1-yl)pyridin-3-yl)-1H-pyrazolo[3,4-d]pyrimidine-3,6-diamine (31.0 mg, 0.07 mmol) and 1-(2-(2,6-dioxopiperidin-3-yl)-1,3-dioxoisoindolin-5-yl)piperidine-4-carbaldehyde (WO2018/140809) (26.6 mg, 0.07 mmol) in MeOH (1.5 mL) was added with NaBH(OAc)3 (30.5 mg, 0.14 mmol) and stirred at room temperature for 1 hour. The reaction mixture was added with an aqueous NaHCO3 solution (15 mL) before extraction with EtOAc (15 mL×2). The organic layer was dried over anhydrous magnesium, filtered, and concentrated in a vacuum. The residue thus obtained was purified by PTLC (5% MeOH/DCM) to afford a yellow solid (27 mg, 50%).

Compound 135. 5-(4-((1-(5-((3-((2,6-Dimethylphenyl)amino)-1-methyl-1H-pyrazolo[3,4-d]pyrimidin-6-yl)amino)pyridin-2-yl)piperidin-4-yl)methyl)piperazin-1-yl)-2-(2,6-dioxopiperidin-3-yl)isoindoline-1,3-dione

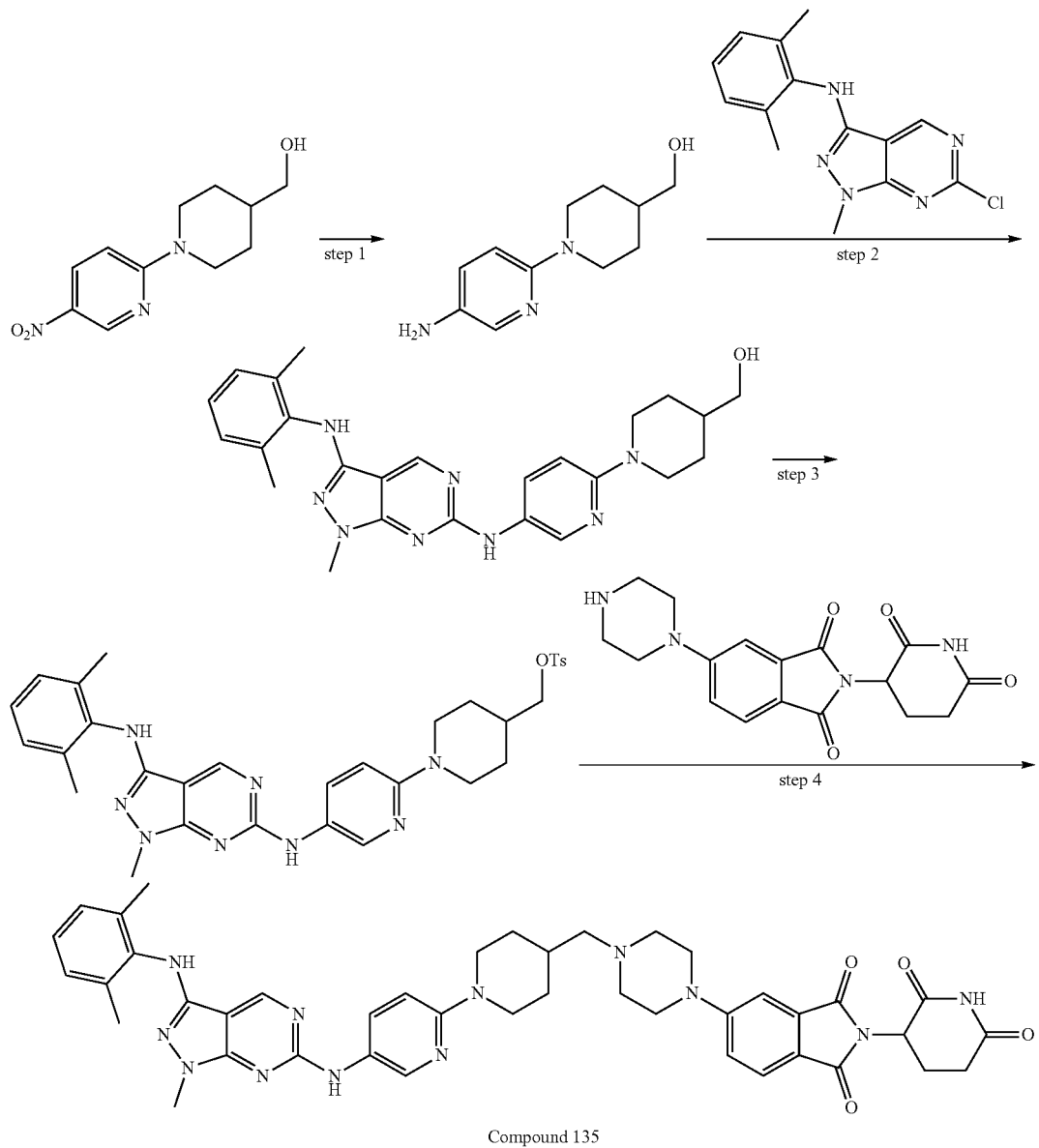

Compound 135

Step 1: Synthesis of (1-(5-aminopyridin-2-yl)piperidin-4-yl)methanol

A solution of (1-(5-nitropyridin-2-yl)piperidin-4-yl)methanol (Combi-Blocks, JK-5095) (340 mg, 1.43 mmol) in MeOH (7 mL) was added with Pd/C (10 wt % Pd, 34 mg) and stirred at room temperature for 2 hours under a hydrogen atmosphere. The mixture was filtered and concentrated. The residue thus obtained purified by MPLC (50% EtOAc/hexane) to afford a brown oil (250 mg, 84%).

Step 2: Synthesis of (1-(5-((3-((2,6-dimethylphenyl)amino)-1-methyl-1H-pyrazolo[3,4-d]pyrimidin-6-yl)amino)pyridin-2-yl)piperidin-4-yl)methanol A suspension of (1-(5-aminopyridin-2-yl)piperidin-4-yl)methanol (60 mg, 0.21 mmol) in IPA (2.5 mL) was added with 6-chloro-N-(2,6-dimethylphenyl)-1-methyl-1H-pyrazolo[3,4-d]pyrimidine-3-amine (Korean Patent No. 2128018) (43.2 mg, 0.21 mmol) and pTSA (40 mg, 0.21 mmol) and stirred at 90° C. for 12 hours. The reaction mixture was added with distilled water (10 mL) before extraction with EtOAc (15 mL×2). The organic layer was dried over anhydrous magnesium, filtered, and concentrated in a vacuum. The residue thus obtained was purified by MPLC (5% MeOH/DCM) to afford a yellow solid (92 mg, 95%).

Step 3: Synthesis of (1-(5-((3-((2,6-dimethylphenyl)amino)-1-methyl-1H-pyrazolo[3,4-d]pyrimidin-6-yl)amino)pyridin-2-yl)piperidin-4-yl)methyl 4-methylbenzenesulfonate A suspension of (1-(5-((3-((2,6-dimethylphenyl)amino)-1-methyl-1H-pyrazolo[3,4-d]pyrimidin-6-yl)amino)pyridin-2-yl)piperidin-4-yl)methanol (56 mg, 0.12 mmol) in DCM (2 mL) was added at 0° C. with P-toluenesulfonyl chloride (46.5 mg, 0.24 mmol) and TEA (0.05 mL, 0.36 mmol) and stirred at room temperature for 4 hours. The reaction mixture was added with 1 N HCl (10 mL) before extraction with EtOAc (15 mL×2). The organic layer was dried over anhydrous magnesium, filtered, and concentrated in a vacuum. The residue thus obtained was purified by MPLC (5% MeOH/DCM) to afford a yellow solid (58 mg, 77%).

Step 4: Synthesis of 5-(4-((1-(5-((3-((2,6-dimethylphenyl)amino)-1-methyl-1H-pyrazolo[3,4-d]pyrimidin-6-yl)amino)pyridin-2-yl)piperidin-4-yl)methyl)piperazin-1-yl)-2-(2,6-dioxopiperidin-3-yl)isoindoline-1,3-dione (Compound 135)

A suspension of (1-(5-((3-((2,6-dimethylphenyl)amino)-1-methyl-1H-pyrazolo[3,4-d]pyrimidin-6-yl)amino)pyridin-2-yl)piperidin-4-yl)methyl 4-methylbenzenesulfonate (30 mg, 0.05 mmol), 2-(2,6-dioxopiperidin-3-yl)-5-(piperazin-1-yl)isoindoline-1,3-dione (WO2018/119441) (16.4 mg, 0.05 mmol), and K$_2$CO$_3$ (20.3 mg, 0.15 mmol) in DMF (1.5 mL) was stirred at 70° C. for 4 hours. The reaction mixture was added with distilled water (10 mL) before extraction with EtOAc (15 mL×2). The organic layer was washed with brine (5 mL×2), dried over anhydrous magnesium, filtered, and concentrated in a vacuum. The residue thus obtained was purified by MPLC (8% MeOH/DCM) to afford a yellow solid (6.0 mg, 16%).

Compound 136. 5-(4-((4-(3-((3-((2,6-dimethylphenyl)amino)-1-methyl-1H-pyrazolo[3,4-d]pyrimidin-6-yl)amino)phenyl)piperazin-1-yl)methyl)piperidin-1-yl)-2-(2,6-dioxopiperidin-3-yl)isoindoline-1,3-dione Compound 136

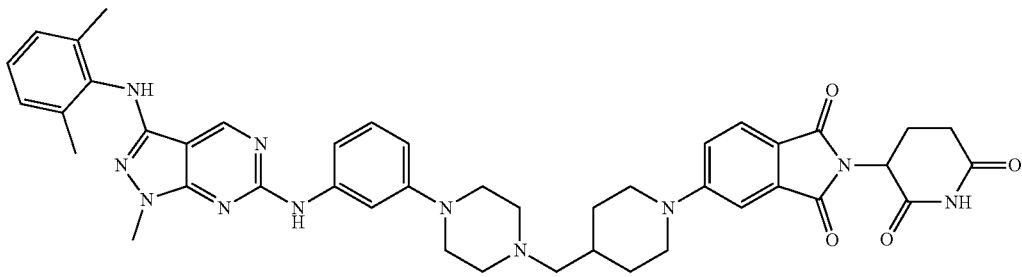

Compound 136 was synthesized in the same manner as in the synthesis procedure for Compound 134, with the exception of using benzyl 4-(3-aminophenyl)piperazine-1-carboxylate (Tetrahedron, 2014, 70, 459-464) instead of benzyl 4-(5-aminopyridin-2-yl)piperazine-1-carboxylate (Step 1 for synthesis of Compound 134).

Compound 137. 5-(4-((7-((3-((2,6-Dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-N-(2,6-dioxopiperidin-3-yl)picolinamide

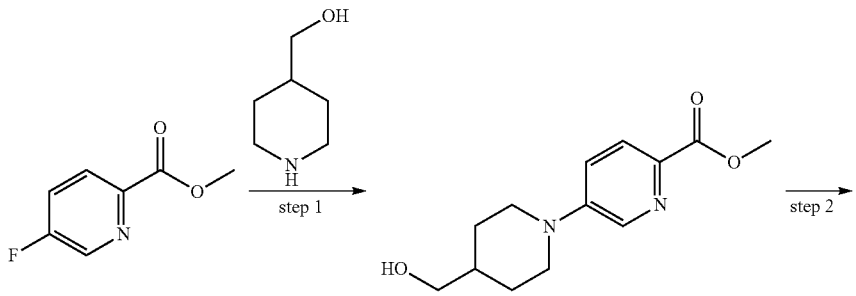

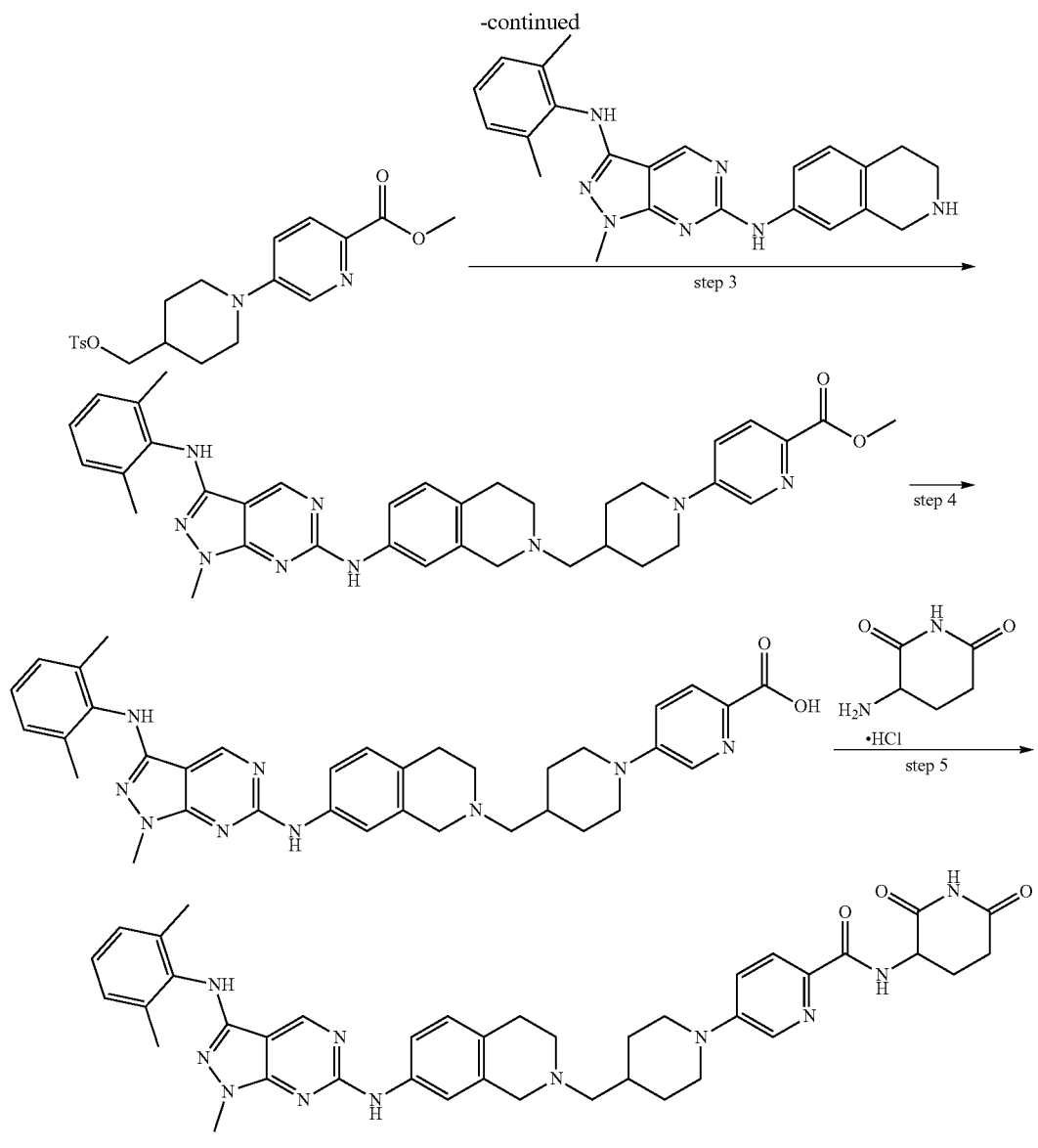

Compound 137

Step 1: Synthesis of methyl 5-(4-(hydroxymethyl)piperidin-1-yl)picolinate

A suspension of methyl 5-fluoropicolinate (Combi-Blocks, PY-1211) (300 mg, 1.93 mmol), piperidin-4-yl-methanol (Combi-Blocks, OS-7789) (444.6 mg, 3.86 mmol), and $K_2CO_3$ (1.33 g, 9.67 mmol) in DMSO (9.6 mL) was stirred at 120° C. for 1 hour in a microwave oven. The reaction mixture was added with distilled water (20 mL) before extraction with EtOAc (10 mL×2). The organic layer was washed with brine (20 mL×2), dried over anhydrous magnesium, filtered, and concentrated in a vacuum. The residue thus obtained was purified by MPLC (50% EtOAc/HEX) to afford a white solid (240 mg, 50%).

Step 2: Synthesis of methyl 5-(4-((tosyloxy)methyl)piperidin-1-yl)picolinate A suspension of methyl 5-(4-(hydroxymethyl)piperidin-1-yl)picolinate (97 mg, 0.39 mmol) in DCM (2 mL) was added at 0° C. with p-toluenesulfonyl chloride (147.0 mg, 0.77 mmol) and TEA (0.16 mL, 1.16 mmol) and stirred at room temperature for 3 hours. The reaction mixture was added with 1 N HCl (10 mL) before extraction with EtOAc (15 mL×2). The organic layer was dried over anhydrous magnesium, filtered, and concentrated in a vacuum. The residue thus obtained was purified by MPLC (5% MeOH/DCM) to afford a white solid (107 mg, 68%).

Step 3: Synthesis of methyl 5-(4-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)piperidin-1-yl)picolinate A suspension of N3-(2,6-dimethylphenyl)-1-methyl-N6-(1,2,3,4-tetrahydroisoquinolin-7-yl)-1H-pyrazolo[3,4-d]pyrimidine-3,6-diamine (Korean Patent No. 2128018) (32.0 mg, 0.08 mmol), methyl 5-(4-((tosyloxy)methyl)piperidin-1-yl)picolinate (32.4 mg, 0.08 mmol), and $K_2CO_3$ (33.0 mg, 0.24 mmol) in DMF (1 mL) was stirred at 70° C. for 16 hours. The reaction mixture was added with distilled water (10 mL) before extraction with EtOAc (15 mL×2). The organic layer was washed with brine (5 mL×2), dried over anhydrous magnesium, filtered, and concentrated in a vacuum. The residue thus obtained was purified by MPLC (5% MeOH/DCM) to afford a white solid (35.4 mg, 70%).

Step 4: Synthesis of 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)picolinic acid A suspension of methyl 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)picolinate (49.0 mg, 0.08 mmol) in THF/H$_2$O=3/1 (1.0 mL) was added with lithium hydroxide monohydrate (6.5 mg, 0.16 mmol) and stirred at room temperature for 4 hours. The reaction mixture was added with distilled water (10 mL) before extraction with EtOAc (15 mL×2). The aqueous layer was added with 1 N HCl to adjust the pH into 2, followed by extraction with EtOAc (25 mL×2). The organic layer was dried over anhydrous sodium sulfate, filtered, concentrated in a vacuum to afford a white solid (40 mg, 80%).

Step 5: Synthesis of 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2,6-dioxopiperidin-3-yl) picolinamide (Compound 137)

A suspension of 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)picolinic acid (50.0 mg, 0.08 mmol), 3-aminopiperidin-2,6-one hydrochloride (Combi-Blocks, QA-9228) (9.8 mg, 0.06 mmol), HATU (45.6 mg, 0.12 mmol), and DIPEA (0.04 mL, 0.24 mmol) in DMF (1.0 mL) was stirred at room temperature for 16 hours. The reaction mixture was added with distilled water (15 mL) before extraction with EtOAc (15 mL×2). The organic layer was dried over anhydrous magnesium, filtered, and concentrated in a vacuum. The residue thus obtained was purified by MPLC (5% MeOH/DCM) to afford a white solid (6 mg, 10%).

Compound 138. 5-(3-((4-(7-((3-((2,6-Dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)azetidin-1-yl)-2-(2,6-dioxopiperidin-3-yl)isoindoline-1,3-dione

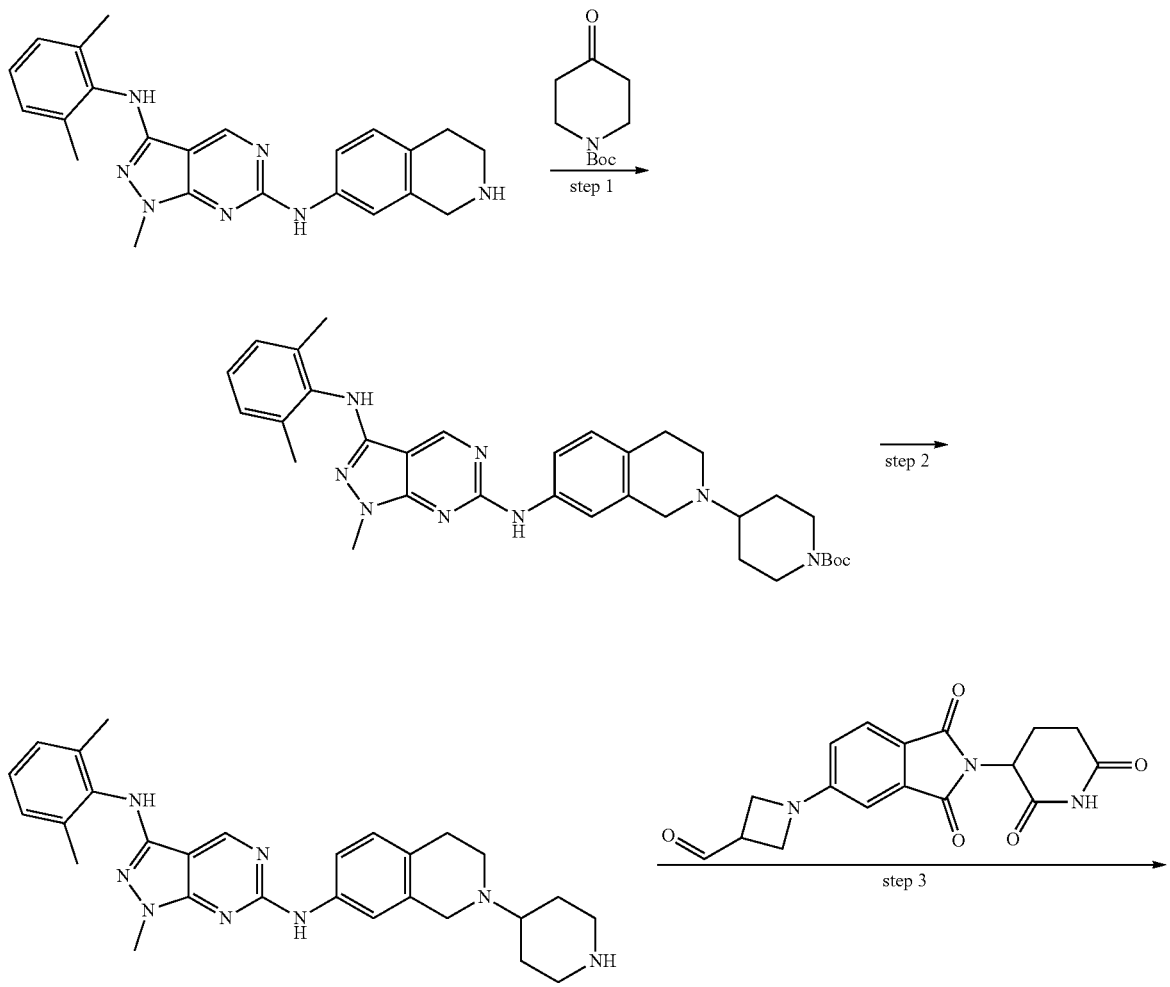

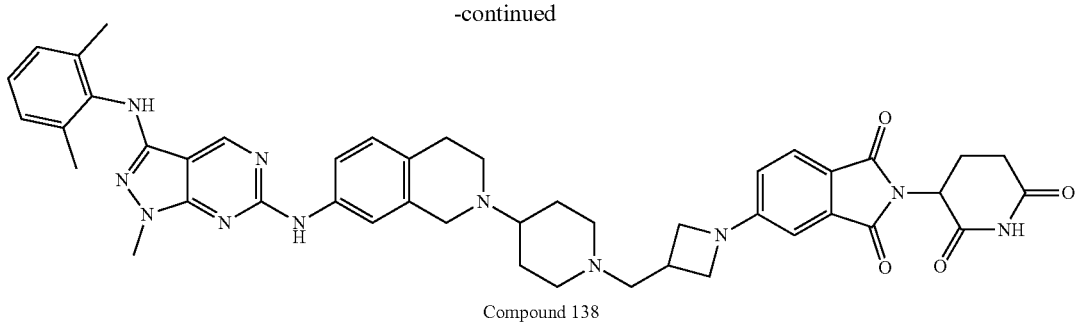

Compound 138

Step 1: Synthesis of tert-butyl 4-(7-((3-((2,6-dimethylphenyl)amino)-1-methyl-1H-pyrazolo[3,4-d]pyrimidin-6-yl)amino)-3,4-dihydroisoquinolin-2(1H)-yl)piperidine-1-carboxylate A suspension of N3-(2,6-dimethylphenyl)-1-methyl-N6-(1,2,3,4-tetrahydroisoquinolin-7-yl)-1H-pyrazolo[3,4-d]pyrimidine-3,6-diamine (Korean Patent No. 2128018) (32 mg, 0.08 mmol) and tert-butyl 4-oxopiperidine-1-carboxylate (Sigma Aldrich, 461350) (24 mg, 0.12 mmol) in MeCN (3 mL) was added with NaBH(OAc)$_3$ (51 mg, 0.24 mmol) and stirred at room temperature for 4 hours. The reaction mixture was added with an aqueous NaHCO$_3$ solution (30 mL) before extraction with DCM (15 mL×2). The organic layer was dried over anhydrous magnesium, filtered, and concentrated in a vacuum. The residue thus obtained was purified by MPLC (2% MeOH/DCM) to afford a bright yellow solid (10 mg, 21%).

Step 2: Synthesis of N3-(2,6-dimethylphenyl)-1-methyl-N6-(2-(piperidin-4-yl)-1,2,3,4-tetrahydroisoquinolin-7-yl)-1H-pyrazolo[3,4-d]pyrimidine-3,6-diamine A suspension of tert-butyl 4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidine-1-carboxylate (13 mg, 0.02 mmol) in DCM (0.5 mL) was added with 4 N HCl/dioxane (0.5 mL) and stirred at room temperature for 1 hour. The reaction mixture was added with an aqueous NaHCO$_3$ solution (30 mL) before extraction with DCM (15 mL×3). The organic layer was dried over anhydrous magnesium, filtered, and concentrated in a vacuum to afford Compound as a yellow solid (10 mg, 93%).

Step 3: Synthesis of 5-(3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)azetidin-1-yl)-2-(2,6-dioxopiperidin-3-yl)isoindoline-1,3-dione (Compound 138)

A suspension of N3-(2,6-dimethylphenyl)-1-methyl-N6-(2-(piperidin-4-yl)-1,2,3,4-tetrahydroisoquinolin-7-yl)-1H-pyrazolo[3,4-d]pyrimidine-3,6-diamine (7 mg, 0.02 mmol) and 1-(2-(2,6-dioxopiperidin-3-yl)-1,3-dioxoisoindolin-5-yl)azetidine-3-carbaldehyde (WO2020/167518) (7.4 mg, 0.02 mmol) in MeCN (2 mL) was added with NaBH(OAc)$_3$ (9 mg, 0.04 mmol) and stirred at room temperature for 2 hours. The reaction mixture was added with an aqueous NaHCO$_3$ solution (20 mL) before extraction with DCM (10 mL×3). The organic layer was dried over anhydrous magnesium, filtered, and concentrated in a vacuum. The residue thus obtained was purified by PTLC (10% MeOH/DCM) to afford a bright yellow solid (4.3 mg, 37%).

Compound 139. 5-(4-((4-(7-((3-((2,6-Dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)piperidin-1-yl)-2-(2,6-dioxopiperidin-3-yl)isoindoline-1,3-dione Compound 139

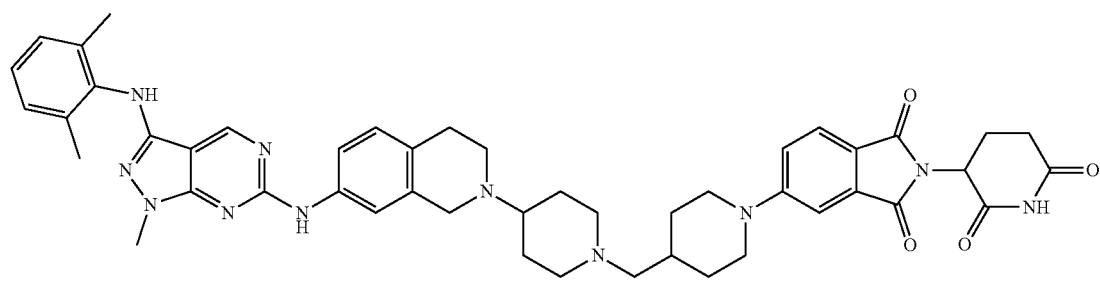

Compound 139 was synthesized in the same manner as in the synthesis procedure for Compound 138, with the exception of using 1-(2-(2,6-dioxopiperidin-3-yl)-1,3-dioxoisoindolin-5-yl)piperidine-4-carbaldehyde (WO2018/140809) instead of 1-(2-(2,6-dioxopiperidin-3-yl)-1,3-dioxoisoindolin-5-yl)azetidine-3-carbaldehyde (WO2020/167518).

Compound 140. 5-((R)-3-((4-(7-((3-((2,6-dimethylphenyl)amino)-1-methyl-1H-pyrazolo[3,4-d]pyrimidin-6-yl)amino)-3,4-dihydroisoquinolin-2(1H)-yl)piperidin-1-yl)methyl)piperidin-1-yl)-2-(2,6-dioxopiperidin-3-yl)isoindoline-1,3-dione Compound 140

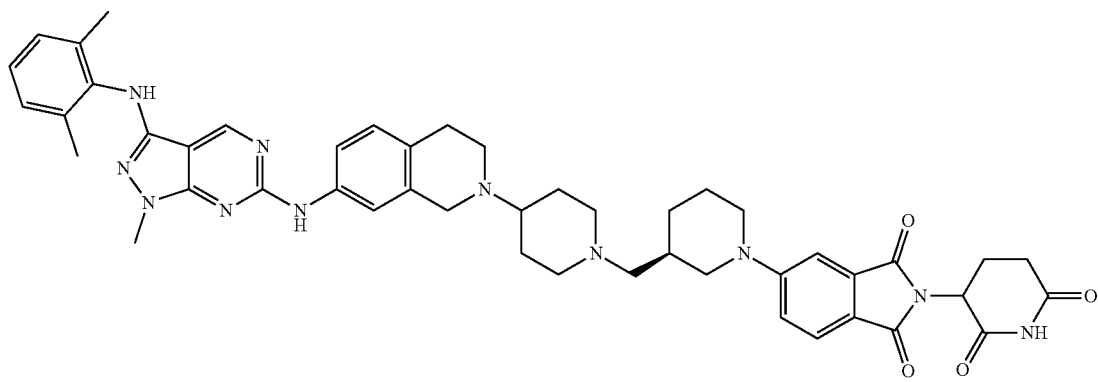

Compound 140

Compound 140 was synthesized in the same manner as in the synthesis procedure for Compound 138, with the exception of using (3S)-1-(2-(2,6-dioxopiperidin-3-yl)-1,3-dioxoisoindolin-5-yl)piperidine-3-carbaldehyde (WO2020/081450) instead of 1-(2-(2,6-dioxopiperidin-3-yl)-1,3-dioxoisoindolin-5-yl)azetidine-3-carbaldehyde (WO2020/167518).

Compound 141. 5-((S)-3-((4-(7-((3-((2,6-dimethylphenyl)amino)-1-methyl-1H-pyrazolo[3,4-d]pyrimidin-6-yl)amino)-3,4-dihydroisoquinolin-2(1H)-yl)piperidin-1-yl)methyl)piperidin-1-yl)-2-(2,6-dioxopiperidin-3-yl)isoindoline-1,3-dione

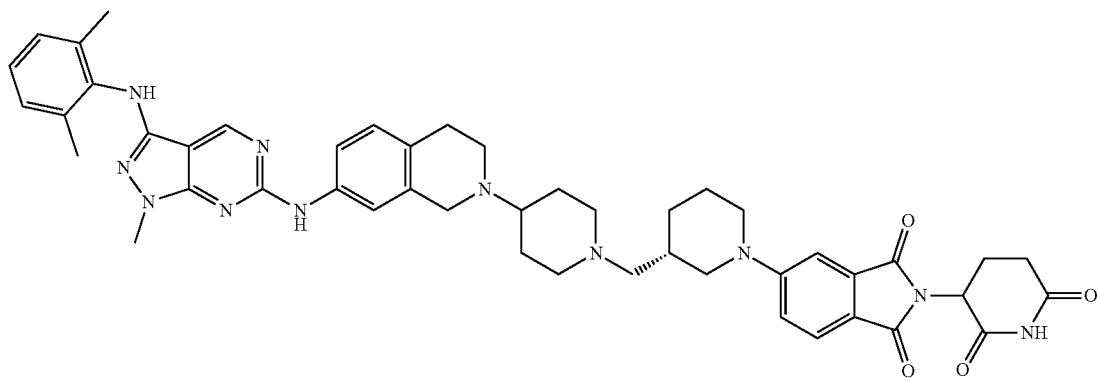

Compound 141

Compound 141 was synthesized in the same manner as in the synthesis procedure for Compound 138, with the exception of using (3R)-1-(2-(2,6-dioxopiperidin-3-yl)-1,3-dioxoisoindolin-5-yl)piperidine-3-carbaldehyde (WO2020/081450) instead of 1-(2-(2,6-dioxopiperidin-3-yl)-1,3-dioxoisoindolin-5-yl)azetidine-3-carbaldehyde (WO2020/167518).

Compound 142. 5-((R)-3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)pyrrolidin-1-yl)-2-(2,6-dioxopiperidin-3-yl)isoindoline-1,3-dione Compound 142

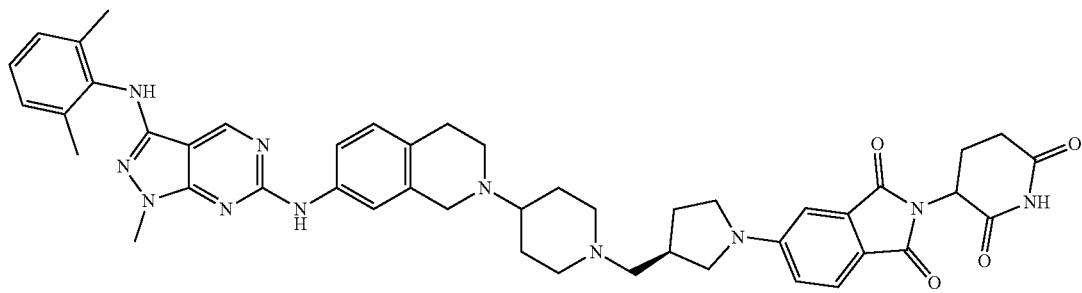

Compound 142 was synthesized in the same manner as in the synthesis procedure for Compound 138, with the exception of using (3S)-1-(2-(2,6-dioxopiperidin-3-yl)-1,3-dioxoisoindolin-5-yl)pyrrolidine-3-carbaldehyde (WO2020/081450) instead of 1-(2-(2,6-dioxopiperidin-3-yl)-1,3-dioxoisoindolin-5-yl)azetidine-3-carbaldehyde (WO2020/167518).

Compound 143. 5-((S)-3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)pyrrolidin-1-yl)-2-(2,6-dioxopiperidin-3-yl)isoindoline-1,3-dione Compound 143

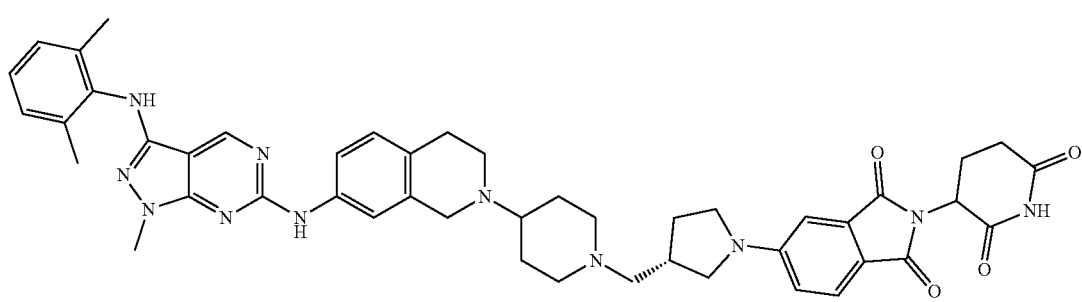

Compound 143 was synthesized in the same manner as in the synthesis procedure for Compound 138, with the exception of using (3R)-1-(2-(2,6-dioxopiperidin-3-yl)-1,3-dioxoisoindolin-5-yl)pyrrolidine-3-carbaldehyde (WO2020/081450) instead of 1-(2-(2,6-dioxopiperidin-3-yl)-1,3-dioxoisoindolin-5-yl)azetidine-3-carbaldehyde (WO2020/167518).-

Compound 144. 5-((R)-3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione Compound 144

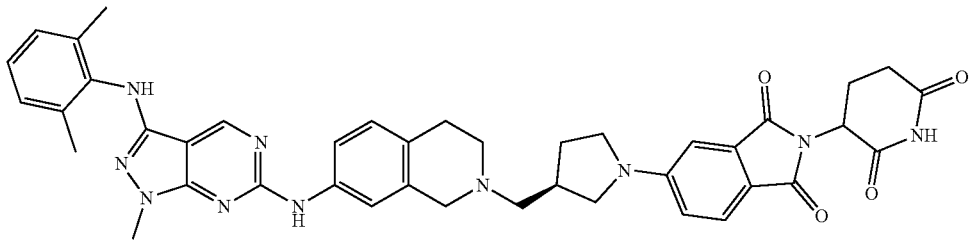

Compound 144 was synthesized in the same manner as in the synthesis procedure for Compound 87, with the exception of using (3S)-1-(2-(2,6-dioxopiperidin-3-yl)-1,3-dioxoisoindolin-5-yl)pyrrolidine-3-carbaldehyde (WO2020/081450) instead of 2-(2,6-dioxopiperidin-3-yl)-5-(3-oxoazetidin-1-yl)isoindoline-1,3-dione (Compound 87-4).

Compound 145. 5-((S)-3-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione Compound 145

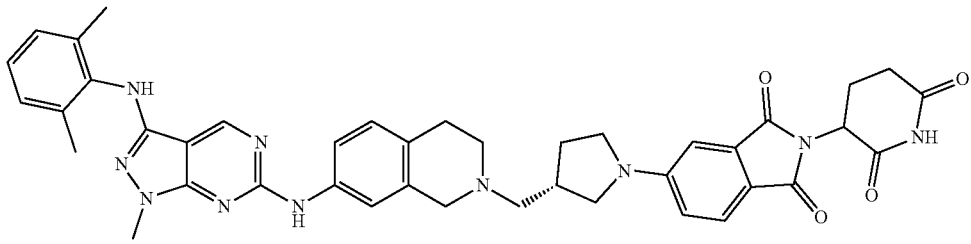

Compound 145 was synthesized in the same manner as in the synthesis procedure for Compound 87, with the exception of using (3R)-1-(2-(2,6-dioxopiperidin-3-yl)-1,3-dioxoisoindolin-5-yl)pyrrolidine-3-carbaldehyde (WO2020/081450) instead of 2-(2,6-dioxopiperidin-3-yl)-5-(3-oxoazetidin-1-yl)isoindoline-1,3-dione (Compound 87-4).-

Compound 146. 5-(4-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)ethyl) piperidin-1-yl)-2-(2,6-dioxopiperidin-3-yl) isoindoline-1,3-dione

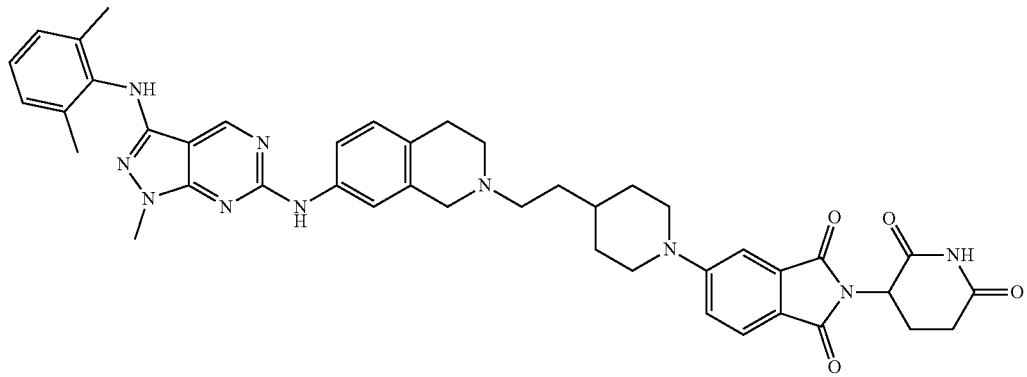

Compound 146

Compound 146 was synthesized in the same manner as in the synthesis procedure for Compound 87, with the exception of using 2-(1-(2-(2,6-dioxopiperidin-3-yl)-1,3-dioxoisoindolin-5-yl)piperidin-4-yl)acetaldehyde (WO2018/071606) instead of 2-(2,6-dioxopiperidin-3-yl)-5-(3-oxoazetidin-1-yl)isoindoline-1,3-dione (Compound 87-4).

Compound 147. 5-(3-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl) methyl)piperidin-1-yl)azetidin-1-yl)-2-(2,6-dioxopiperidin-3-yl)isoindoline-1,3-dione

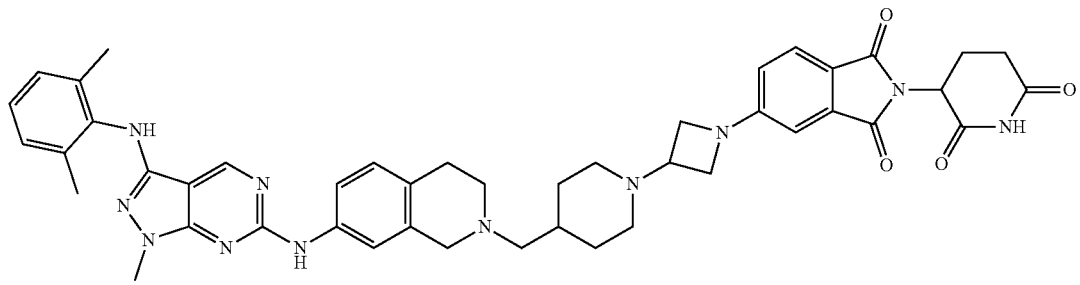

Compound 147

Compound 147 was synthesized in the same manner as in the synthesis procedure for Compound 138, with the exception of using tert-butyl 4-formylpiperidine-1-carboxylate (Sigma Aldrich, 722022) and 2-(2,6-dioxopiperidin-3-yl)-5-(3-oxoazetidin-1-yl)isoindoline-1,3-dione (Compound 87-4) instead of tert-butyl 4-oxopiperidine-1-carboxylate (Sigma Aldrich, 461350) and 1-(2-(2,6-dioxopiperidin-3-yl)-1,3-dioxoisoindolin-5-yl)azetidine-3-carbaldehyde (WO2020/167518), respectively.

Compound 148. 5-((1R,5S,6S)-6-((7-((3-((2,6-Dimethylphenyl)amino)-1-methyl-1H-pyrazolo[3,4-d]pyrimidin-6-yl)amino)-3,4-dihydroisoquinolin-2(1H)-yl)methyl)-3-azabicyclo[3.1.0]hexan-3-yl)-2-(2,6-dioxopiperidin-3-yl)isoindoline-1,3-dione

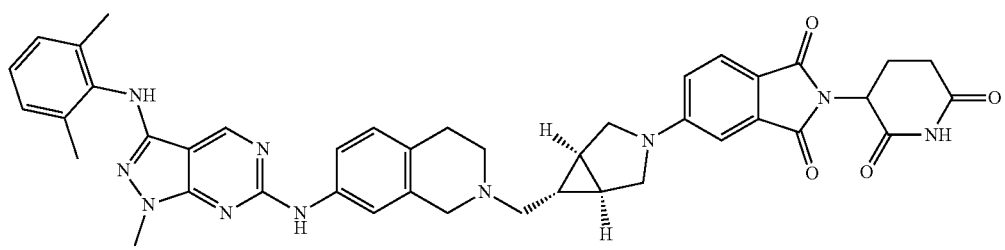

Compound 148

Compound 148 was synthesized in the same manner as in the synthesis procedure for Compound 87, with the exception of using (1R,5S,6r)-3-(2-(2,6-dioxopiperidin-3-yl)-1,3-dioxoisoindolin-5-yl)-3-azabicyclo[3.1.0]hexane-6-carbaldehyde (WO2020/081450) instead of 2-(2,6-dioxopiperidin-3-yl)-5-(3-oxoazetidin-1-yl)isoindoline-1,3-dione (Compound 87-4).

Compound 149. 5-(4-((3-(7-((3-((2,6-Dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)piperidin-1-yl)-2-(2,6-dioxopiperidin-3-yl)isoindoline-1,3-dione

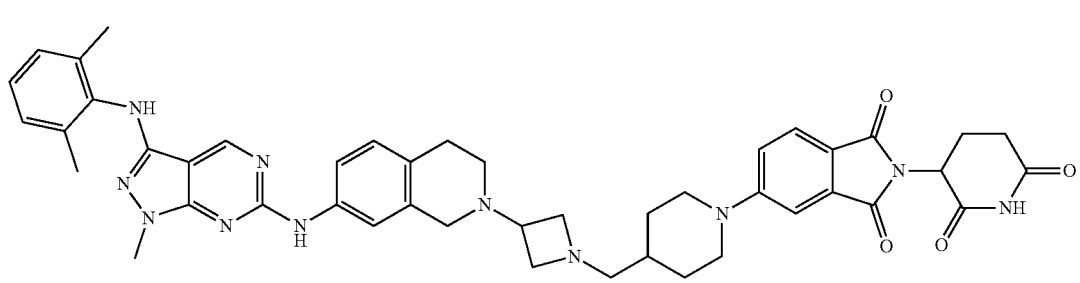

Compound 149

Compound 149 was synthesized in the same manner as in the synthesis procedure for Compound 138, with the exception of using tert-butyl 3-oxoazetidine-1-carboxylate (Sigma Aldrich, 696315) and 1-(2-(2,6-dioxopiperidin-3-yl)-1,3-dioxoisoindolin-5-yl)piperidine-4-carbaldehyde (WO2018/140809) instead of tert-butyl 4-oxopiperidine-1-carboxylate (Sigma Aldrich, 461350) and 1-(2-(2,6-dioxopiperidin-3-yl)-1,3-dioxoisoindolin-5-yl)azetidine-3-carbaldehyde (WO2020/167518), respectively.

Compound 150. 5-((R)-3-((3-(7-((3-((2,6-Dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)pyrrolidin-1-yl)-2-(2,6-dioxopiperidin-3-yl)isoindoline-1,3-dione

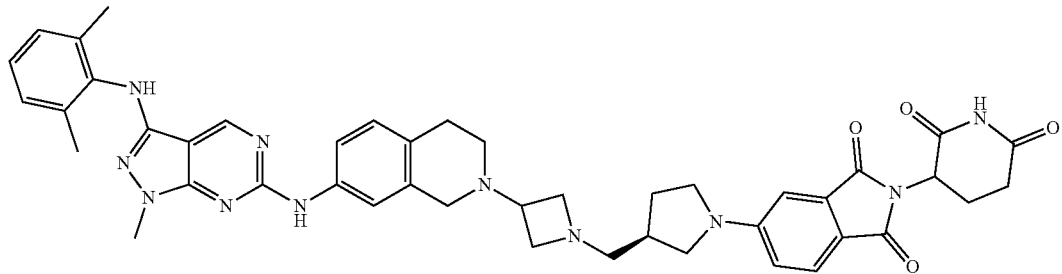

Compound 150

Compound 150 was synthesized in the same manner as in the synthesis procedure for Compound 138, with the exception of using tert-butyl 3-oxoazetidine-1-carboxylate (Sigma Aldrich, 696315) and (3S)-1-(2-(2,6-dioxopiperidin-3-yl)-1,3-dioxoisoindolin-5-yl)pyrrolidine-3-carbaldehyde (WO2020/081450) instead of tert-butyl 4-oxopiperidine-1-carboxylate (Sigma Aldrich, 461350) and 1-(2-(2,6-dioxopiperidin-3-yl)-1,3-dioxoisoindolin-5-yl)azetidine-3-carbaldehyde (WO2020/167518), respectively.

Compound 151. 5-((S)-3-((3-(7-((3-((2,6-Dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)pyrrolidin-1-yl)-2-(2,6-dioxopiperidin-3-yl)isoindoline-1,3-dione

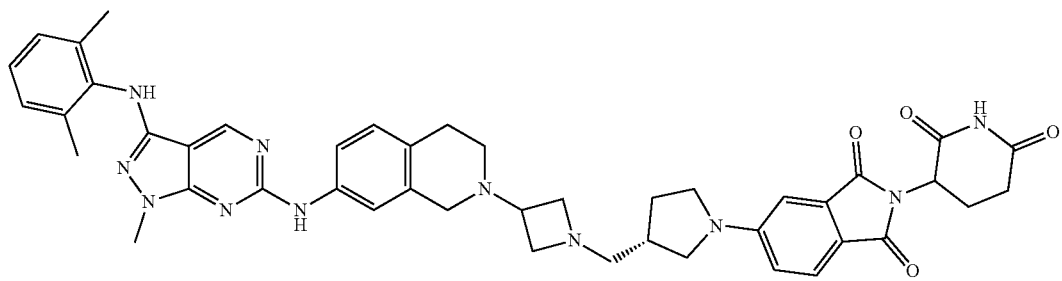

Compound 151

Compound 151 was synthesized in the same manner as in the synthesis procedure for Compound 138, with the exception of using tert-butyl 3-oxoazetidine-1-carboxylate (Sigma Aldrich, 696315) and (3R)-1-(2-(2,6-dioxopiperidin-3-yl)-1,3-dioxoisoindolin-5-yl)pyrrolidine-3-carbaldehyde (WO2020/081450) instead of tert-butyl 4-oxopiperidine-1-carboxylate (Sigma Aldrich, 461350) and 1-(2-(2,6-dioxopiperidin-3-yl)-1,3-dioxoisoindolin-5-yl)azetidine-3-carbaldehyde (WO2020/167518), respectively.-

Compound 152. 5-(3-((3-(7-((3-((2,6-Dimethylphenyl)amino)-1-methyl-TH-pyrazolo[3,4-d]pyrimidin-6-yl)amino)-3,4-dihydroisoquinolin-2 (1H)-yl)azetidin-1-yl)methyl)azetidin-1-yl)-2-(2,6-dioxopiperidin-3-yl)isoindoline-1,3-dione

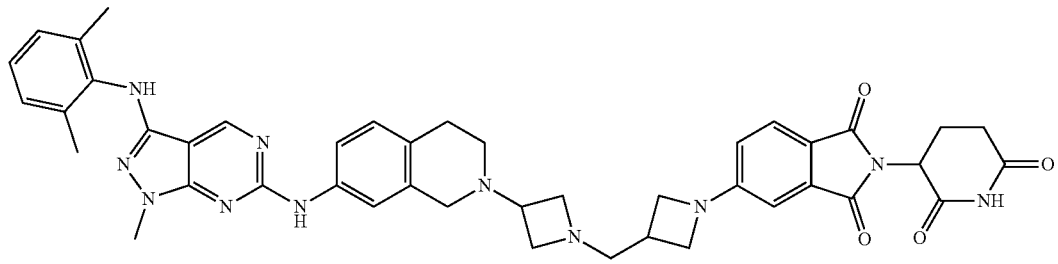

Compound 152

Compound 152 was synthesized in the same manner as in the synthesis procedure for Compound 138, with the exception of using tert-butyl 3-oxoazetidine-1-carboxylate (Sigma Aldrich, 696315) instead of tert-butyl 4-oxopiperidine-1-carboxylate (Sigma Aldrich, 461350).

Compound 153. 5-((1R,5S,6S)-6-((3-(7-((3-((2,6-Dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)-3-azabicyclo[3.1.0]hexan-3-yl)-2-(2,6-dioxopiperidin-3-yl)isoindoline-1,3-dione

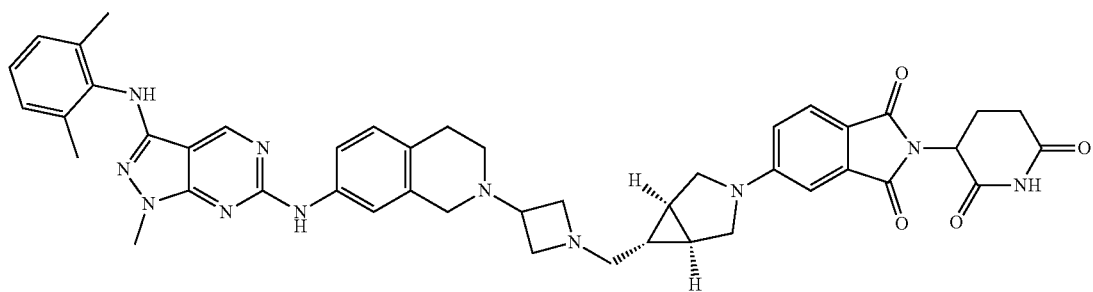

Compound 153

Compound 153 was synthesized in the same manner as in the synthesis procedure for Compound 138, with the exception of using tert-butyl 3-oxoazetidine-1-carboxylate (Sigma Aldrich, 696315) and (1R,5S,6r)-3-(2-(2,6-dioxopiperidin-3-yl)-1,3-dioxoisoindolin-5-yl)-3-azabicyclo[3.1.0]hexane-6-carbaldehyde (WO2020/081450) instead of tert-butyl 4-oxopiperidine-1-carboxylate (Sigma Aldrich, 461350) and 1-(2-(2,6-dioxopiperidin-3-yl)-1,3-dioxoisoindolin-5-yl)azetidine-3-carbaldehyde (WO2020/167518), respectively.-

Compound 154. 5-((R)-3-((4-(5-((3-((2,6-Dimethylphenyl)amino)-1-methyl-1H-pyrazolo[3,4-d]pyrimidin-6-yl)amino)pyridin-2-yl)piperazin-1-yl)methyl)pyrrolidin-1-yl)-2-(2,6-dioxopiperidin-3-yl)isoindoline-1,3-dione

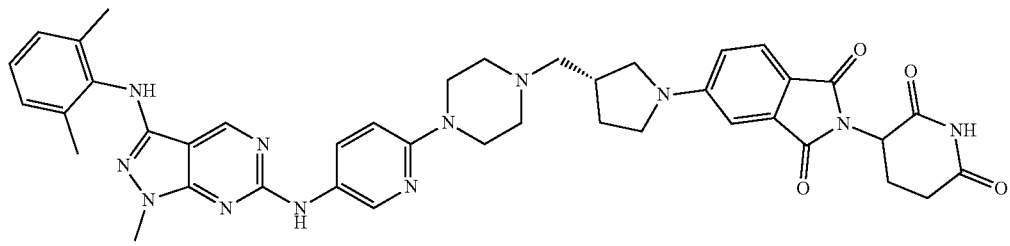

Compound 154

Compound 154 was synthesized in the same manner as in the synthesis procedure for Compound 135, with the exception of using (3S)-1-(2-(2,6-dioxopiperidin-3-yl)-1,3-dioxoisoindolin-5-yl)pyrrolidine-3-carbaldehyde (WO2020/081450) instead of 1-(2-(2,6-dioxopiperidin-3-yl)-1,3-dioxoisoindolin-5-yl)piperidine-4-carbaldehyde (WO2018/140809).

Compound 155. 5-((S)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)pyrrolidin-1-yl)-2-(2,6-dioxopiperidin-3-yl)isoindoline-1,3-dione

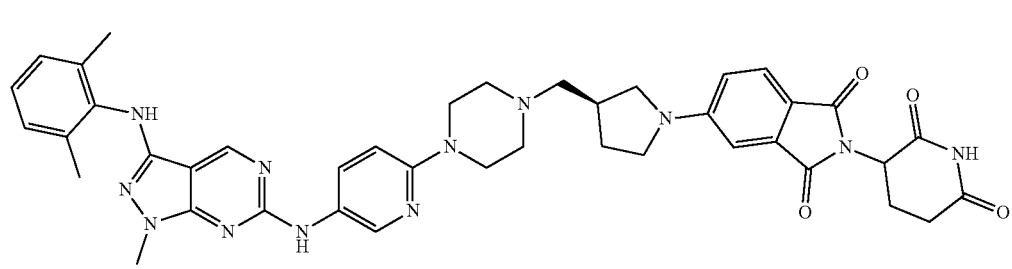

Compound 155

Compound 155 was synthesized in the same manner as in the synthesis procedure for Compound 134, with the exception of using (3R)-1-(2-(2,6-dioxopiperidin-3-yl)-1,3-dioxoisoindolin-5-yl)pyrrolidine-3-carbaldehyde (WO2020/081450) instead of 1-(2-(2,6-dioxopiperidin-3-yl)-1,3-dioxoisoindolin-5-yl)piperidine-4-carbaldehyde (WO2018/140809).-

Compound 156. 5-(4-(4-(5-((3-((2,6-dimethylphenyl)amino)-1-methyl-1H-pyrazolo[3,4-d]pyrimidin-6-yl)amino)pyridin-2-yl)piperazin-1-yl)piperidin-1-yl)-2-(2,6-dioxopiperidin-3-yl)isoindoline-1,3-dione

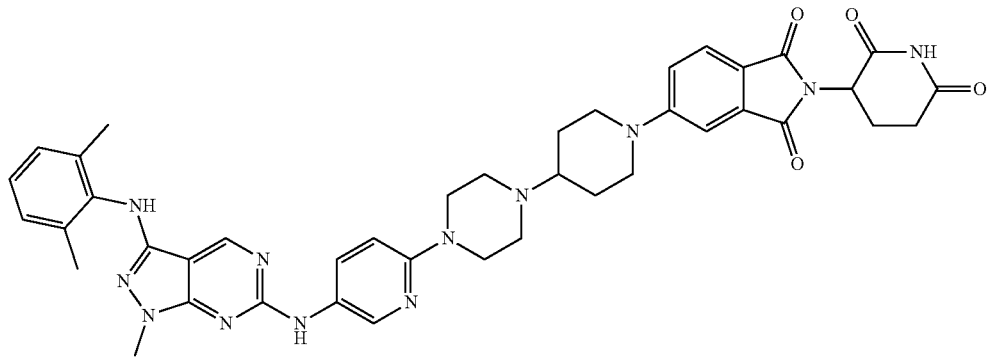

Compound 156

Compound 156 was synthesized in the same manner as in the synthesis procedure for Compound 134, with the exception of using 2-(2,6-dioxopiperidin-3-yl)-5-(4-oxopiperidin-1-yl)isoindoline-1,3-dione (Compound 88-3) instead of 1-(2-(2,6-dioxopiperidin-3-yl)-1,3-dioxoisoindolin-5-yl)piperidine-4-carbaldehyde (WO2018/140809).

Compound 157. 5-(4-(2-(4-(5-((3-((2,6-dimethylphenyl)amino)-1-methyl-1H-pyrazolo[3,4-d]pyrimidin-6-yl)amino)pyridin-2-yl)piperazin-1-yl)ethyl)piperidin-1-yl)-2-(2,6-dioxopiperidin-3-yl)isoindoline-1,3-dione

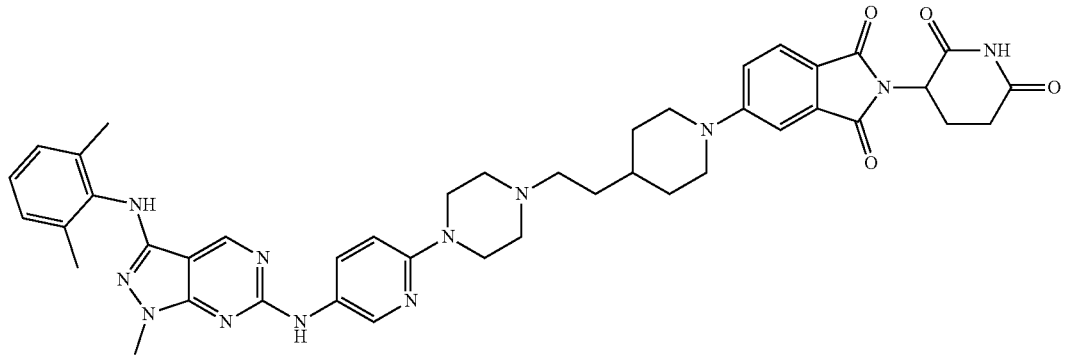

Compound 157

Compound 157 was synthesized in the same manner as in the synthesis procedure for Compound 134, with the exception of using 2-(1-(2-(2,6-dioxopiperidin-3-yl)-1,3-dioxoisoindolin-5-yl)piperidin-4-yl)acetaldehyde (WO2018/071606) instead of 1-(2-(2,6-dioxopiperidin-3-yl)-1,3-dioxoisoindolin-5-yl)piperidine-4-carbaldehyde (WO2018/140809).-

Compound 158. 5-(3-(4-(5-((3-((2,6-Dimethylphenyl)amino)-1-methyl-1H-pyrazolo[3,4-d]pyrimidin-6-yl)amino)pyridin-2-yl)piperazin-1-yl)azetidin-1-yl)-2-(2,6-dioxopiperidin-3-yl)isoindoline-1,3-dione

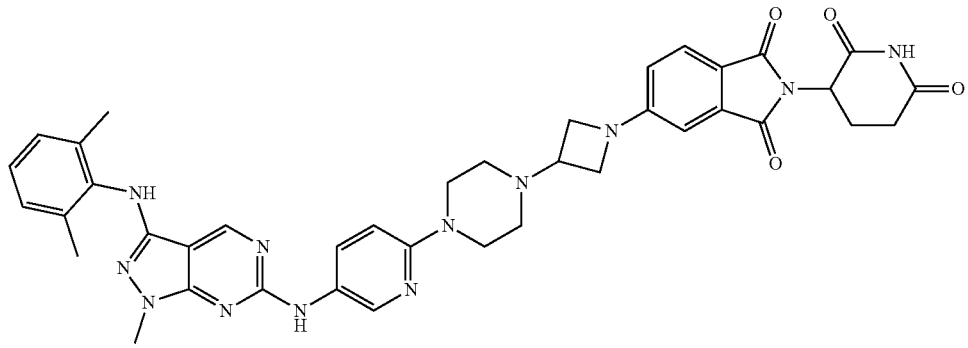

Compound 158

Compound 158 was synthesized in the same manner as in the synthesis procedure for Compound 134, with the exception of using 2-(2,6-dioxopiperidin-3-yl)-5-(3-oxoazetidin-1-yl)isoindoline-1,3-dione (Compound 87-4) instead of 1-(2-(2,6-dioxopiperidin-3-yl)-1,3-dioxoisoindolin-5-yl)piperidine-4-carbaldehyde (WO2018/140809).

Compound 159. 5-(3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)azetidin-1-yl)-2-(2,6-dioxopiperidin-3-yl)isoindoline-1,3-dione

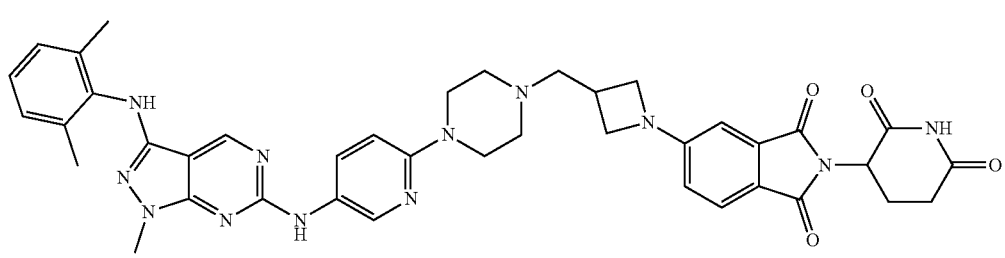

Compound 159

Compound 159 was synthesized in the same manner as in the synthesis procedure for Compound 134, with the exception of using 1-(2-(2,6-dioxopiperidin-3-yl)-1,3-dioxoisoindolin-5-yl)azetidine-3-carbaldehyde (WO2020/167518) instead of 1-(2-(2,6-dioxopiperidin-3-yl)-1,3-dioxoisoindolin-5-yl)piperidine-4-carbaldehyde (WO2018/140809).-

Compound 160. 5-((R)-3-((4-(5-((3-((2,6-Dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione

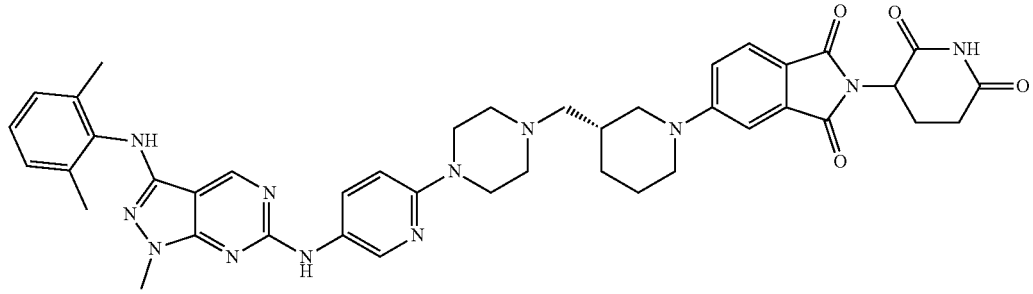

Compound 160

Compound 160 was synthesized in the same manner as in the synthesis procedure for Compound 134, with the exception of using (3S)-1-(2-(2,6-dioxopiperidin-3-yl)-1,3-dioxoisoindolin-5-yl)piperidine-3-carbaldehyde (WO2020/081450) instead of 1-(2-(2,6-dioxopiperidin-3-yl)-1,3-dioxoisoindolin-5-yl)piperidine-4-carbaldehyde (WO2018/140809).

Compound 161. 5-((S)-3-((4-(5-((3-((2,6-Dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione

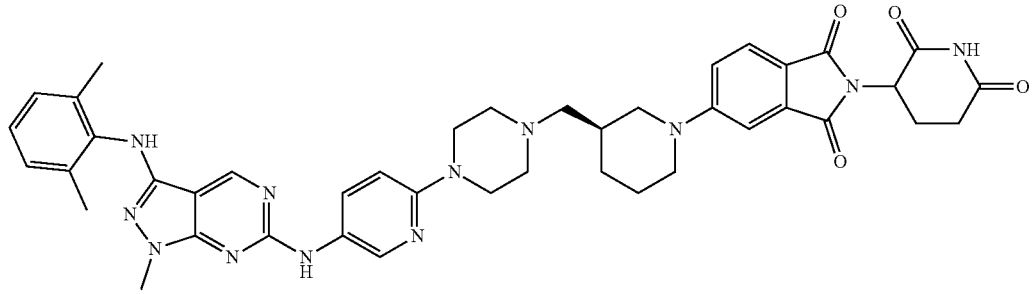

Compound 161

Compound 161 was synthesized in the same manner as in the synthesis procedure for Compound 134, with the exception of using (3R)-1-(2-(2,6-dioxopiperidin-3-yl)-1,3-dioxoisoindolin-5-yl)piperidine-3-carbaldehyde (WO2020/081450) instead of 1-(2-(2,6-dioxopiperidin-3-yl)-1,3-dioxoisoindolin-5-yl)piperidine-4-carbaldehyde (WO2018/140809).-

Compound 162. 5-(4-((4-(6-((3-((2,6-Dimethylphenyl)amino)-1-methyl-1H-pyrazolo[3,4-d]pyrimidin-6-yl)amino)pyridin-3-yl)piperazin-1-yl)methyl)piperidin-1-yl)-2-(2,6-dioxopiperidin-3-yl)isoindoline-1,3-dione

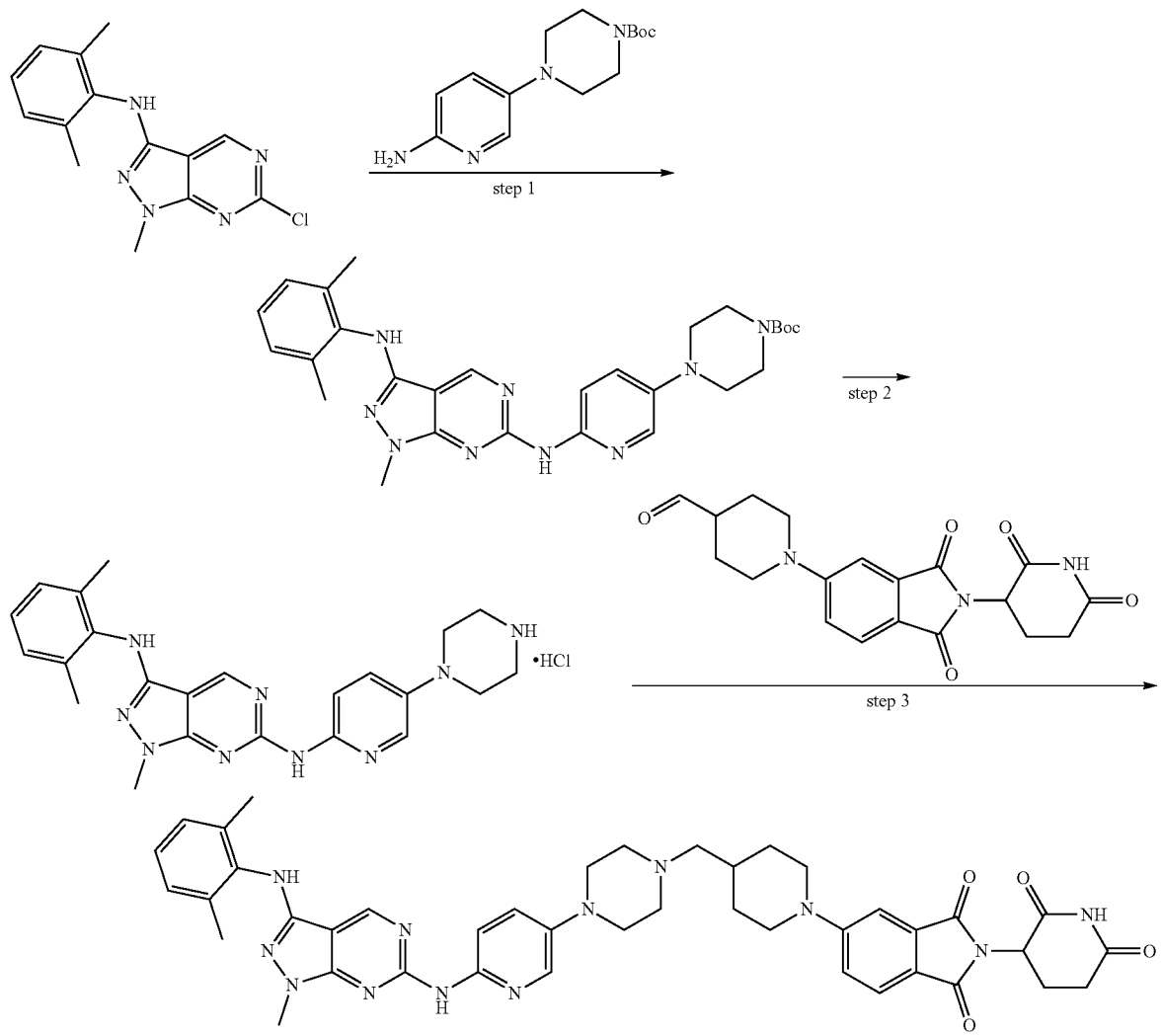

Compound 162

Step 1: Synthesis of tert-butyl 4-(6-((3-((2,6-dimethylphenyl)amino)-1-methyl-1H-pyrazolo[3,4-d]pyrimidin-6-yl)amino)pyridin-3-yl)piperazine-1-carboxylate A suspension of 6-chloro-N-(2,6-dimethylphenyl)-1-methyl-1H-pyrazolo[3,4-d]pyrimidine-3-amine (Korean Patent No. 2128018) (60.0 mg, 0.2 mmol), tert-butyl 4-(6-aminopyridin-3-yl)piperazine-1-carboxylate (Combi-Blocks, QE-9781) (61.0 mg, 0.22), Pd$_2$(dba)$_3$ (18.2 mg, 0.02 mmol), xantphos (23 mg, 0.04 mmol), and tBuOK (35.0 mg, 0.31 mmol) in dioxane (2 mL) was stirred at 120° C. for 2 hours in a microwave oven. The reaction mixture was added with distilled water (10 mL) before extraction with EtOAc (15 mL×2). The organic layer was dried over anhydrous magnesium, filtered, and concentrated in a vacuum. The residue thus obtained was purified by MPLC (5% MeOH/DCM) to afford a yellow solid (40 mg, 38%).

Step 2: Synthesis of N3-(2,6-dimethylphenyl)-1-methyl-N6-(5-(piperazin-1-yl)pyridin-2-yl)-1H-pyrazolo[3,4-d]pyrimidine-3,6-diamine hydrochloride A suspension of tert-butyl 4-(6-((3-((2,6-dimethylphenyl)amino)-1-methyl-1H-pyrazolo[3,4-d]pyrimidin-6-yl)amino)pyridin-3-yl)piperazine-1-carboxylate (40.0 mg, 0.08 mmol) in DCM (2 mL) was added with 4 N HCl/dioxane (0.2 mL) and stirred at room temperature for 1 hour. The reaction mixture was concentrated to afford a yellow solid (32 mg, 98%).

Step 3: Synthesis of 5-(4-((4-(6-((3-((2,6-dimethylphenyl)amino)-1-methyl-1H-pyrazolo[3,4-d]pyrimidin-6-yl)amino)pyridin-3-yl)piperazin-1-yl)methyl)piperidin-1-yl)-2-(2,6-dioxopiperidin-3-yl)isoindoline-1,3-dione (Compound 162)

A suspension of N3-(2,6-dimethylphenyl)-1-methyl-N6-(5-(piperazin-1-yl)pyridin-2-yl)-1H-pyrazolo[3,4-d]pyrimidine-3,6-diamine hydrochloride (43.0 mg, 0.1 mmol), 1-(2-(2,6-dioxopiperidin-3-yl)-1,3-dioxoisoindolin-5-yl)piperidine-4-carbaldehyde (WO2018/140809) (40.8 mg, 0.11 mmol) in MeOH/DCM=1/1 (1.5 mL) was added with NaBH(OAc)₃ (43 mg, 0.2 mmol) and stirred at room temperature for 3 hours. The reaction mixture was added with an aqueous NaHCO₃ solution (15 mL), followed by extraction with DCM (15 mL×2). The organic layer was dried over anhydrous magnesium sulfate, filtered, and concentrated in a vacuum. The residue thus obtained was purified by MPLC (5% MeOH/DCM) to afford a yellow solid (18 mg, 23%).

Compound 163. 5-(4-((4-(4-((3-((2,6-Dimethylphenyl)amino)-1-methyl-1H-pyrazolo[3,4-d]pyrimidin-6-yl)amino)phenyl)piperazin-1-yl)methyl)piperidin-1-yl)-2-(2,6-dioxopiperidin-3-yl)isoindoline-1,3-dione Compound 163

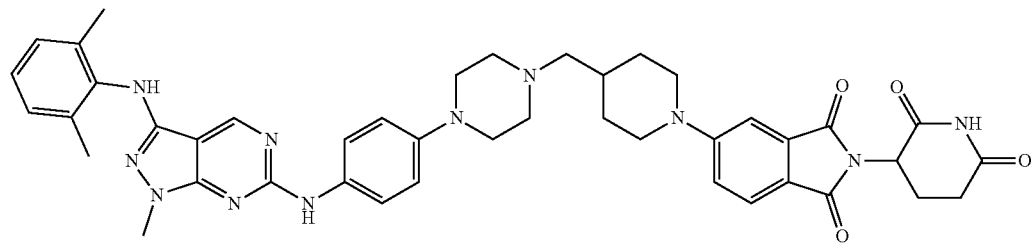

Compound 163 was synthesized in the same manner as in the synthesis procedure for Compound 162, with the exception of using tert-butyl 4-(4-aminophenyl)piperazine-1-carboxylate (Combi-Blocks, AN-1426) instead of tert-butyl 4-(6-aminopyridin-3-yl)piperazine-1-carboxylate (Combi-Blocks, QE-9781).

Compound 164. 5-(4-((4-(5-((3-((2,6-Dimethylphenyl)amino)-1-methyl-1H-pyrazolo[3,4-d]pyrimidin-6-yl)amino)pyridin-2-yl)piperidin-1-yl)methyl)piperidin-1-yl)-2-(2,6-dioxopiperidin-3-yl)isoindoline-1,3-dione Compound 164

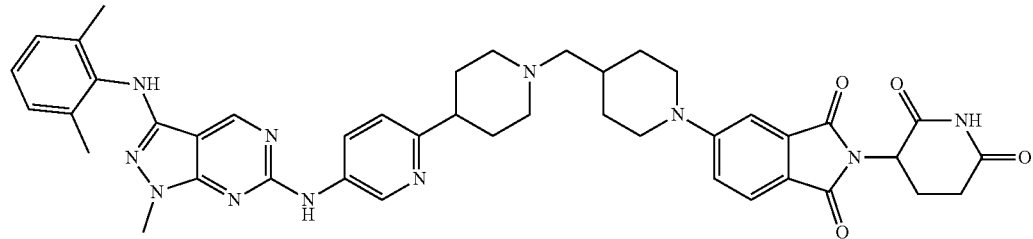

Compound 164 was synthesized in the same manner as in the synthesis procedure for Compound 162, with the exception of using tert-butyl 4-(5-aminopyridin-2-yl)piperidine-1-carboxylate (Combi-Blocks, QK-5999) instead of tert-butyl 4-(6-aminopyridin-3-yl)piperazine-1-carboxylate (Combi-Blocks, QE-9781).

Compound 165. 5-(4-((4-(4-((3-((2,6-Dimethylphenyl)amino)-1-methyl-1H-pyrazolo[3,4-d]pyrimidin-6-yl)amino)phenyl)piperidin-1-yl)methyl)piperidin-1-yl)-2-(2,6-dioxopiperidin-3-yl)isoindoline-1,3-dione Compound 165

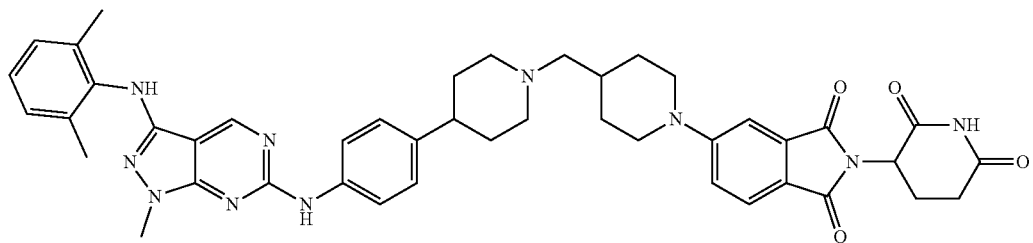

Compound 165 was synthesized in the same manner as in the synthesis procedure for Compound 162, with the exception of using tert-butyl 4-(4-aminophenyl)piperidine-1-carboxylate (TCI, B5832) instead of tert-butyl 4-(6-aminopyridin-3-yl)piperazine-1-carboxylate (Combi-Blocks, QE-9781).

Compound 166. 5-((R)-3-((4-(4-((3-((2,6-Dimethylphenyl)amino)-1-methyl-1H-pyrazolo[3,4-d]pyrimidin-6-yl)amino)phenyl)piperidin-1-yl)methyl)pyrrolidin-1-yl)-2-(2,6-dioxopiperidin-3-yl)isoindoline-1,3-dione Compound 166

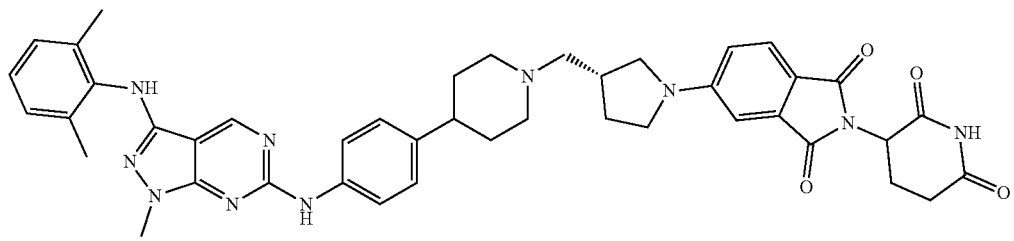

Compound 166 was synthesized in the same manner as in the synthesis procedure for Compound 162, with the exception of using tert-butyl 4-(4-aminophenyl)piperidine-1-carboxylate (TCI, B5832) and (3S)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.-

Compound 167. 5-((S)-3-((4-(4-((3-((2,6-Dimethylphenyl)amino)-1-methyl-1H-pyrazolo[3,4-d]pyrimidin-6-yl)amino)phenyl)piperidin-1-yl)methyl)pyrrolidin-1-yl)-2-(2,6-dioxopiperidin-3-yl)isoindoline-1,3-dione

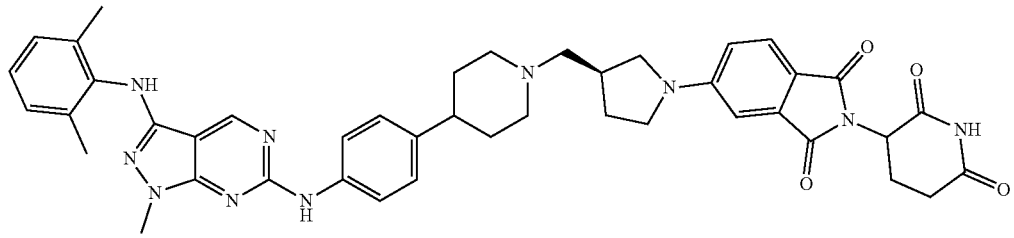

Compound 167

Compound 167 was synthesized in the same manner as in the synthesis procedure for Compound 162, with the exception of using tert-butyl 4-(4-aminophenyl)piperidine-1-carboxylate (TCI, B5832) and (3R)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 168. 5-(4-(4-((3-((2,6-Dimethylphenyl)amino)-1-methyl-1H-pyrazolo[3,4-d]pyrimidin-6-yl)amino)phenyl)-[1,4'-bipyridin]-1'-yl)-2-(2,6-dioxopiperidin-3-yl)isoindoline-1,3-dione

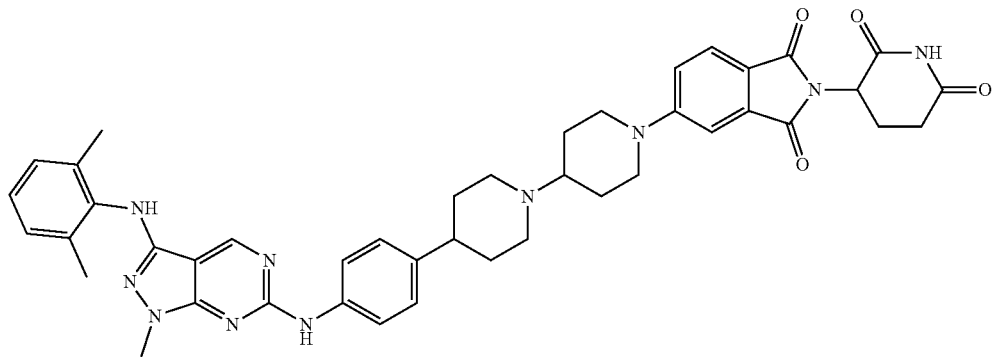

Compound 168

Compound 168 was synthesized in the same manner as in the synthesis procedure for Compound 162, with the exception of using tert-butyl 4-(4-aminophenyl)piperidine-1-carboxylate (TCI, B5832) and 2-(2,6-dioxopiperidin-3-yl)-5-(4-oxopiperidin-1-yl)isoindoline-1,3-dione (Compound 88-3) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 169. 5-(3-((4-(4-((3-((2,6-Dimethylphenyl)amino)-1-methyl-1H-pyrazolo[3,4-d]pyrimidin-6-yl)amino)phenyl)piperidin-1-yl)methyl)azetidin-1-yl)-2-(2,6-dioxopiperidin-3-yl)isoindoline-1,3-dione

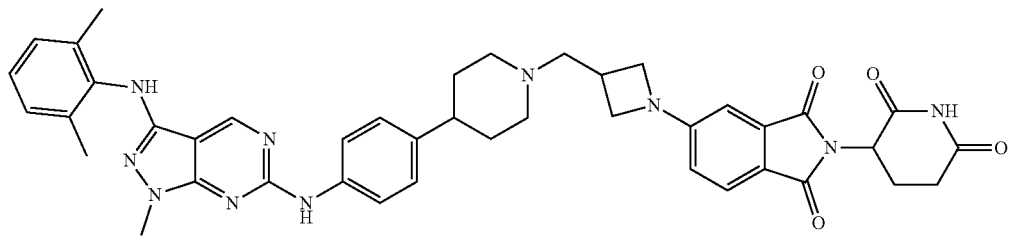

Compound 169

Compound 169 was synthesized in the same manner as in the synthesis procedure for Compound 162, with the exception of using tert-butyl 4-(4-aminophenyl)piperidine-1-carboxylate (TCI, B5832) and 1-(2-(2,6-dioxopiperidin-3-yl)-1,3-dioxoisoindolin-5-yl)azetidine-3-carbaldehyde (WO2020/167518) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 170. 3-(2-(4-((4-(4-((3-((2,6-Dimethylphenyl)amino)-1-methyl-1H-pyrazolo[3,4-d]pyrimidin-6-yl)amino)phenyl)piperidin-1-yl)methyl)piperidin-1-yl)-5-oxo-5,7-dihydro-6H-pyrrolo[3,4-b]pyridin-6-yl)piperidin-2,6-one

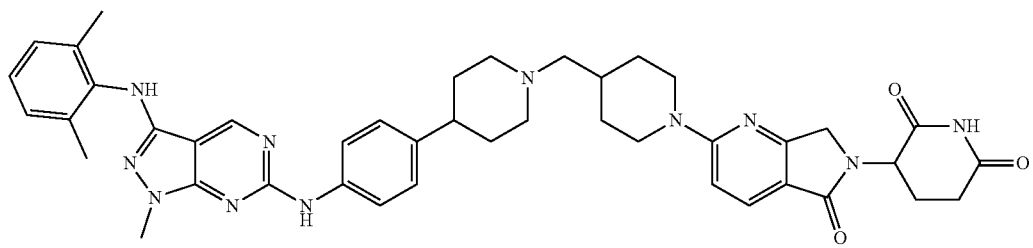

Compound 170

Compound 170 was synthesized in the same manner as in the synthesis procedure for Compound 162, with the exception of using tert-butyl 4-(4-aminophenyl)piperidine-1-carboxylate (TCI, B5832) and 1-(6-(2,6-dioxopiperidin-3-yl)-5-oxo-6,7-dihydro-5H-pyrrolo[3,4-b]pyridin-2-yl)piperidine-4-carbaldehyde instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809).

Compound 171. 5-(4-((4-(5-((3-((2,6-Dimethylphenyl)amino)-1-methyl-1H-pyrazolo[3,4-d]pyrimidin-6-yl)amino)pyrimidin-2-yl)piperazin-1-yl)methyl)piperidin-1-yl)-2-(2,6-dioxopiperidin-3-yl)isoindoline-1,3-dione

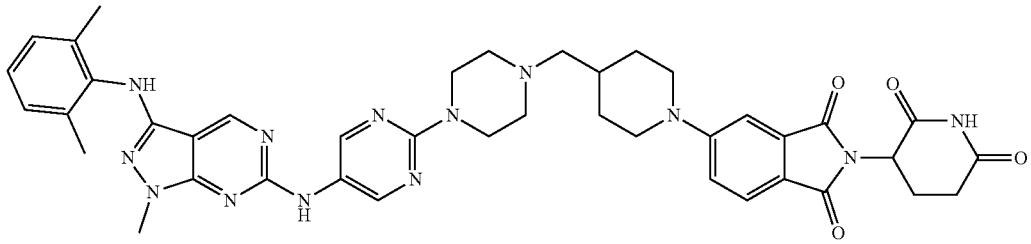

Compound 171

Compound 171 was synthesized in the same manner as in the synthesis procedure for Compound 162, with the exception of using tert-butyl 4-(5-aminopyrimidin-2-yl)piperazine-1-carboxylate (WO2008/141976) instead of tert-butyl 4-(6-aminopyridin-3-yl)piperazine-1-carboxylate (Combi-Blocks, QE-9781).

Compound 172. 5-(4-((6-((3-((2,6-Dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-2-(2,6-dioxopiperidin-3-yl)isoindoline-1,3-dione

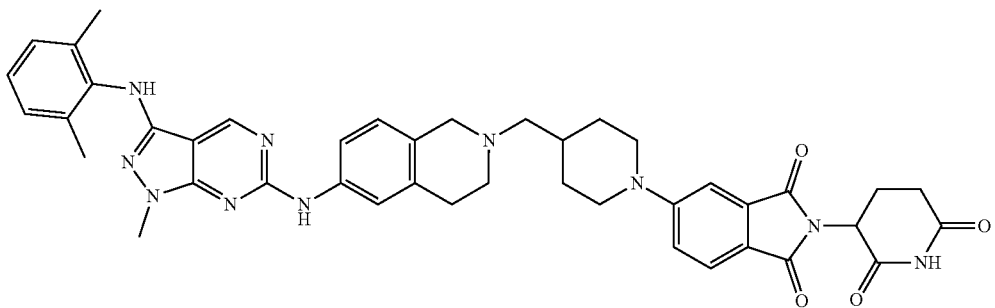

Compound 172

Compound 172 was synthesized in the same manner as in the synthesis procedure for Compound 162, with the exception of using tert-butyl 6-amino-3,4-dihydroisoquinoline-2(1H)-carboxylate (Combi-Blocks, ST-5411) instead of tert-butyl 4-(6-aminopyridin-3-yl)piperazine-1-carboxylate (Combi-Blocks, QE-9781).

Compound 173. 5-((R)-3-((6-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione

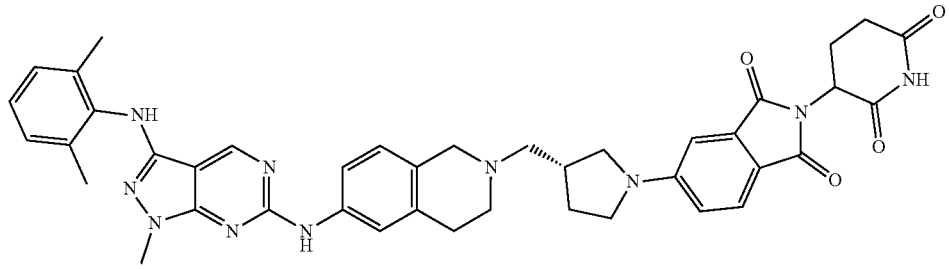

Compound 173

Compound 173 was synthesized in the same manner as in the synthesis procedure for Compound 162, with the exception of using tert-butyl 6-amino-3,4-dihydroisoquinoline-2 (1H)-carboxylate (Combi-Blocks, ST-5411) and (3R)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 174. 5-((S)-3-((6-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione

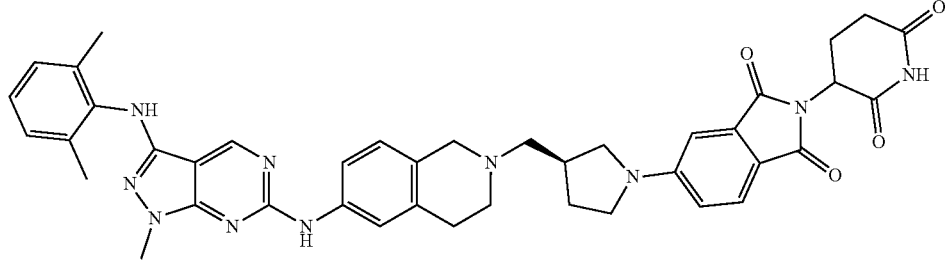

Compound 174

Compound 174 was synthesized in the same manner as in the synthesis procedure for Compound 162, with the exception of using tert-butyl 6-amino-3,4-dihydroisoquinoline-2 (1H)-carboxylate (Combi-Blocks, ST-5411) and (3S)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 175. 5-(4-((3-(4-((3-((2,6-Dimethylphenyl)amino)-1-methyl-1H-pyrazolo[3,4-d]pyrimidin-6-yl)amino)phenyl)azetidin-1-yl)methyl)piperidin-1-yl)-2-(2,6-dioxopiperidin-3-yl)isoindoline-1,3-dione

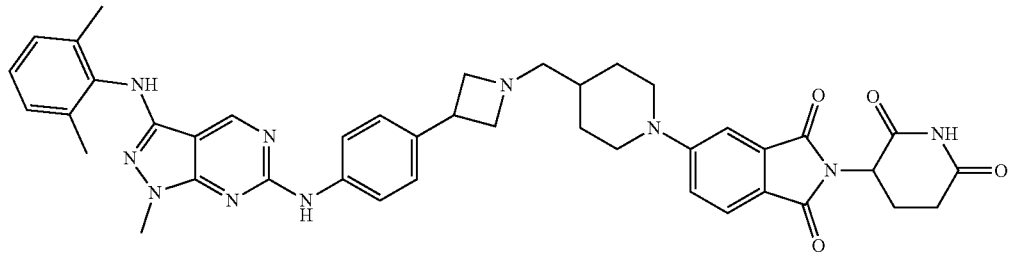

Compound 175

Compound 175 was synthesized in the same manner as in the synthesis procedure for Compound 162, with the exception of using tert-butyl 3-(4-aminophenyl)azetidine-1-carboxylate (Combi-Blocks, HA-2714) instead of tert-butyl 4-(6-aminopyridin-3-yl)piperazine-1-carboxylate (Combi-Blocks, QE-9781).

Compound 176. 5-((R)-3-((3-(4-((3-((2,6-dimethylphenyl)amino)-1-methyl-1H-pyrazolo[3,4-d]pyrimidin-6-yl)amino)phenyl)azetidin-1-yl)methyl)pyrrolidin-1-yl)-2-(2,6-dioxopiperidin-3-yl)isoindoline-1,3-dione

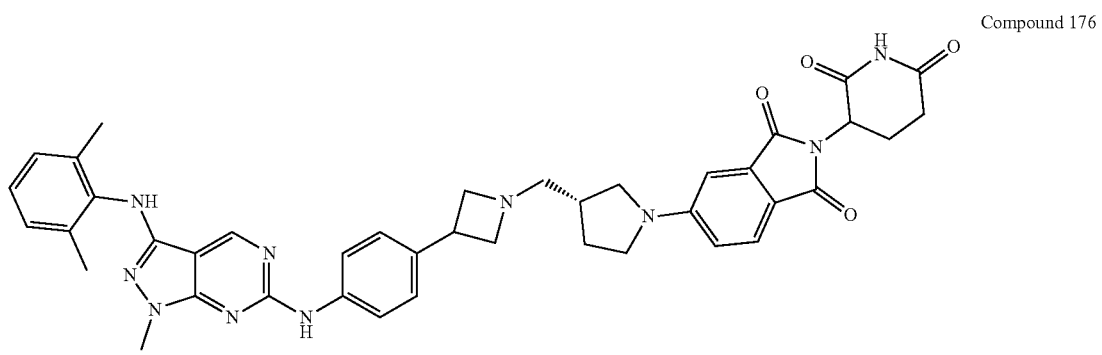 [SMILES: Cc1cccc(C)c1Nc1nn(C)c2nc(Nc3ccc(C4CN(C[C@H]5CCN(c6ccc7c(c6)C(=O)N(C6CCC(=O)NC6=O)C7=O)C5)C4)cc3)ncc12]

Compound 176

Compound 176 was synthesized in the same manner as in the synthesis procedure for Compound 162, with the exception of using tert-butyl 3-(4-aminophenyl)azetidine-1-carboxylate (Combi-Blocks, HA-2714) and (3R)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 177. 5-((S)-3-((3-(4-((3-((2,6-Dimethylphenyl)amino)-1-methyl-1H-pyrazolo[3,4-d]pyrimidin-6-yl)amino)phenyl)azetidin-1-yl)methyl)pyrrolidin-1-yl)-2-(2,6-dioxopiperidin-3-yl)isoindoline-1,3-dione

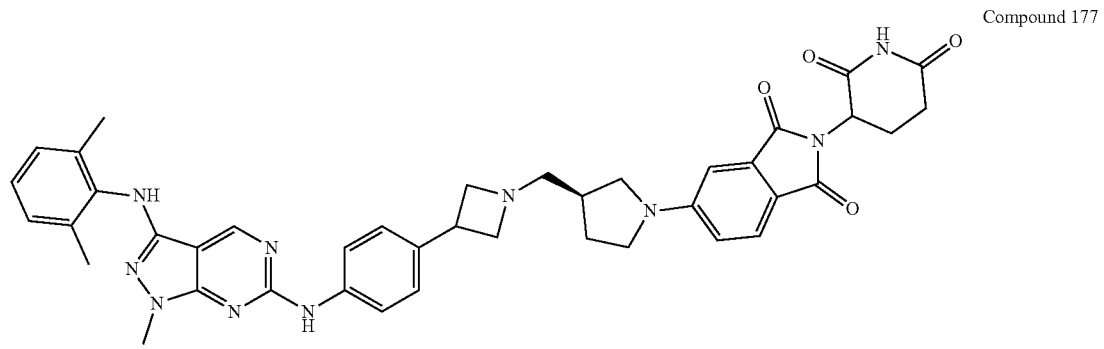 [SMILES: Cc1cccc(C)c1Nc1nn(C)c2nc(Nc3ccc(C4CN(C[C@@H]5CCN(c6ccc7c(c6)C(=O)N(C6CCC(=O)NC6=O)C7=O)C5)C4)cc3)ncc12]

Compound 177

Compound 177 was synthesized in the same manner as in the synthesis procedure for Compound 162, with the exception of using tert-butyl 3-(4-aminophenyl)azetidine-1-carboxylate (Combi-Blocks, HA-2714) and (3S)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 178. 5-(4-(3-(7-((3-((2,6-Dimethylphenyl)amino)-1-methyl-1H-pyrazolo[3,4-d]pyrimidin-6-yl)amino)-3,4-dihydroisoquinolin-2(1H)-yl)-2-hydroxypropyl)piperazin-1-yl)-2-(2,6-dioxopiperidin-3-yl)isoindoline-1,3-dione

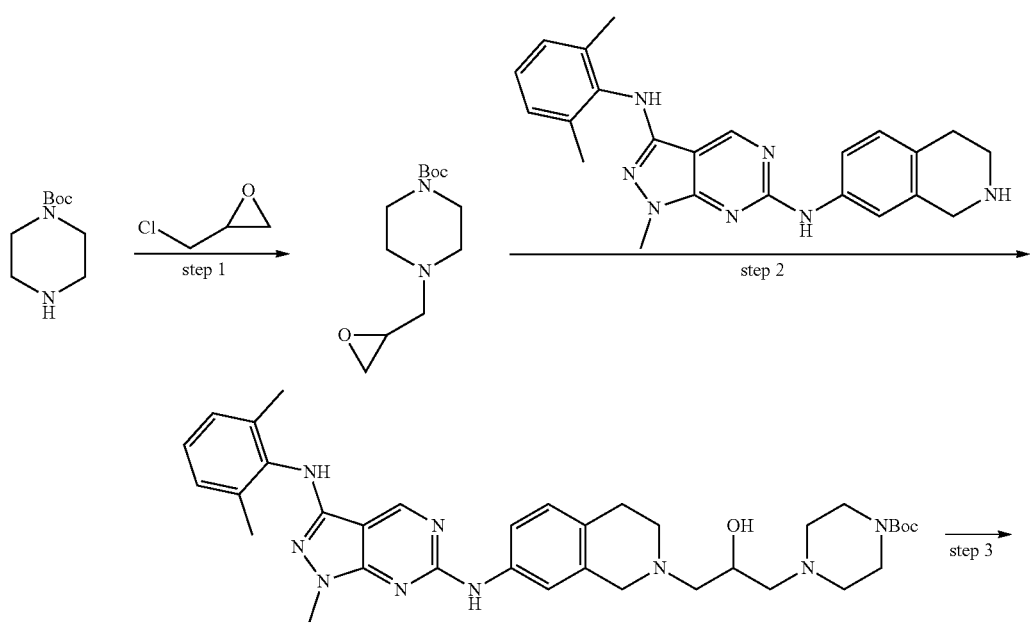

-continued

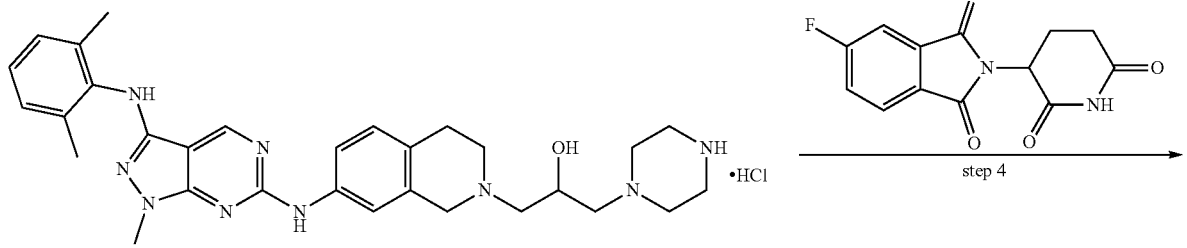

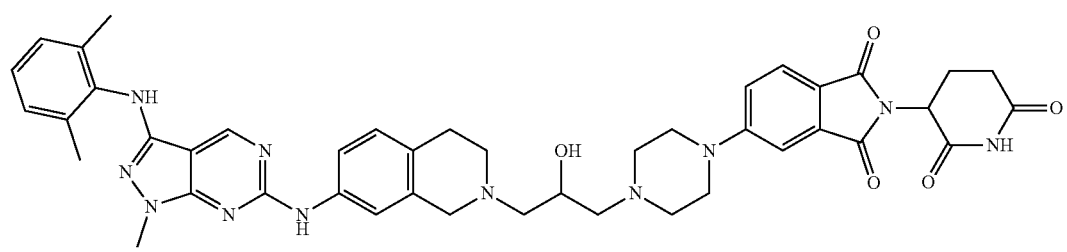

Compound 178

Step 1: Synthesis of tert-butyl 4-(oxiran-2-ylmethyl)piperazine-1-carboxylate A suspension of tert-butyl piperazine-1-carboxylate (Sigma Aldrich, 343536) (225 mg, 1.2 mmol) and 2-(chloromethyl)oxirane (TCI, E0012) (0.1 mL, 1.2 mmol) in EtOH (2 mL) was stirred at room temperature for 5 hours. The reaction mixture was concentrated in a vacuum. The residue thus obtained was purified by MPLC (50% EtOAc/HEX) to afford a white oil (242 mg, 83%).

Step 2: Synthesis of tert-butyl 4-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-hydroxypropyl)piperazine-1-carboxylate A suspension of N3-(2,6-dimethylphenyl)-1-methyl-N6-(1,2,3,4-tetrahydroisoquinolin-7-yl)-1H-pyrazolo[3,4-d]pyrimidine-3,6-diamine (Korean Patent No. 2128018) (46 mg, 0.11 mmol), and tert-butyl 4-(oxiran-2-ylmethyl)piperazine-1-carboxylate (27 mg, 0.11 mmol) in EtOH (2 mL) was added with TEA (0.02 mL, 0.17 mmol) and stirred at 120° C. for 1 hour in a microwave oven. The reaction mixture was concentrated in a vacuum. The residue thus obtained was purified by MPLC (5% MeOH/DCM) to afford a yellow solid (74 mg, 77%).

Step 3: Synthesis of 1-(7-((3-((2,6-dimethylphenyl)amino)-1-methyl-1H-pyrazolo[3,4-d]pyrimidin-6-yl)amino)-3,4-dihydroisoquinolin-2 (1H)-yl)-3-(piperazin-1-yl)propan-2-ol hydrochloride A suspension of tert-butyl 4-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-hydroxypropyl)piperazine-1-carboxylate (74 mg, 0.11 mmol) in DCM (4 mL) was added with 4N HCl/dioxane (0.4 mL) and stirred at room temperature for 1 hour. The reaction mixture was concentrated to afford a yellow solid (73 mg, 105%).

Step 4: Synthesis of 5-(4-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-hydroxypropyl)piperazin-1-yl)-2-(2,6-dioxopiperidin-3-yl)isoindoline-1,3-dione (Compound 178)

A suspension of 1-(7-((3-((2,6-dimethylphenyl)amino)-1-methyl-1H-pyrazolo[3,4-d]pyrimidin-6-yl)amino)-3,4-dihydroisoquinolin-2 (1H)-yl)-3-(piperazin-1-yl)propan-2-ol hydrochloride (44 mg, 0.07 mmol) in DMSO (1 mL) was added with 2-(2,6-dioxopiperidin-3-yl)-5-fluoroisoindoline-1,3-dione (Combi-Blocks, HD-3240) (21 mg, 0.07 mmol) and DIPEA (0.06 mL, 0.38 mmol) and stirred at 110° C. for 16 hours. The reaction mixture was added with distilled water (20 mL) before extraction with EtOAc (15 mL×2). The organic layer was washed with brine (15 mL×2), dried over anhydrous magnesium, filtered, and concentrated in a vacuum. The residue thus obtained was purified by PTLC (5% MeOH/DCM) to afford a yellow solid (5 mg, 5%).

Compound 179. 5-((R)-3-((4-(4-((3-((2,6-Dimethylphenyl)amino)-1-methyl-1H-pyrazolo[3,4-d]pyrimidin-6-yl)amino)phenyl)piperazin-1-yl)methyl)pyrrolidin-1-yl)-2-(2,6-dioxopiperidin-3-yl)isoindoline-1,3-dione

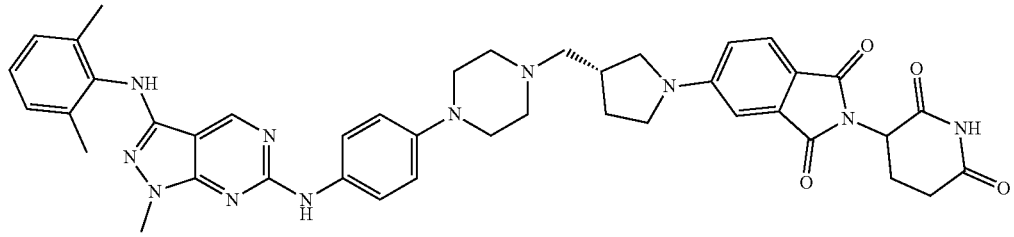

Compound 179

Compound 179 was synthesized in the same manner as in the synthesis procedure for Compound 162, with the exception of using tert-butyl 4-(4-aminophenyl)piperazine-1-carboxylate (Combi-Blocks, AN-1426) and (3S)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 180. 5-((S)-3-((4-(4-((3-((2,6-Dimethylphenyl)amino)-1-methyl-1H-pyrazolo[3,4-d]pyrimidin-6-yl)amino)phenyl)piperazin-1-yl)methyl)pyrrolidin-1-yl)-2-(2,6-dioxopiperidin-3-yl)isoindoline-1,3-dione

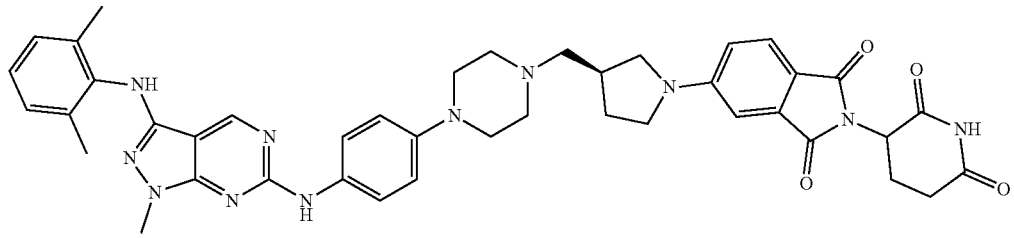

Compound 180

Compound 180 was synthesized in the same manner as in the synthesis procedure for Compound 162, with the exception of using tert-butyl 4-(4-aminophenyl)piperazine-1-carboxylate (Combi-Blocks, AN-1426) and (3R)-1-(2-(2,6-dioxopiperidin-3-yl)-1,3-dioxoisoindolin-5-yl)pyrrolidine-3-carbaldehyde (WO2020/081450) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.-

Compound 181. 5-(3-((4-(4-((3-((2,6-Dimethylphenyl)amino)-1-methyl-1H-pyrazolo[3,4-d]pyrimidin-6-yl)amino)phenyl)piperazin-1-yl)methyl)azetidin-1-yl)-2-(2,6-dioxopiperidin-3-yl)isoindoline-1,3-dione

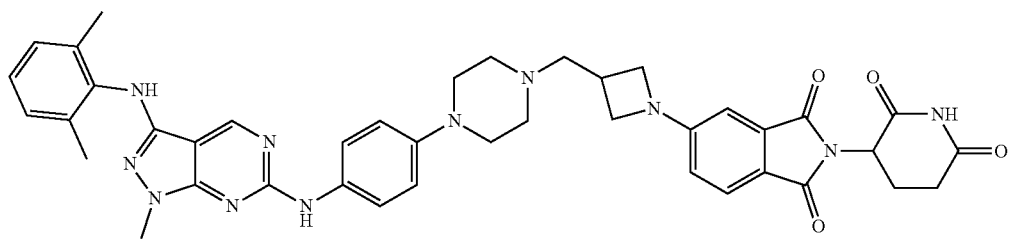

Compound 181

Compound 181 was synthesized in the same manner as in the synthesis procedure for Compound 162, with the exception of using tert-butyl 4-(4-aminophenyl)piperazine-1-carboxylate (Combi-Blocks, AN-1426) and 1-(2-(2,6-dioxopiperidin-3-yl)-1,3-dioxoisoindolin-5-yl)azetidine-3-carbaldehyde (WO2020/167518) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 182. 5-(3-((3-(4-((3-((2,6-Dimethylphenyl)amino)-1-methyl-1H-pyrazolo[3,4-d]pyrimidin-6-yl)amino)phenyl)azetidin-1-yl)methyl)azetidin-1-yl)-2-(2,6-dioxopiperidin-3-yl)isoindoline-1,3-dione

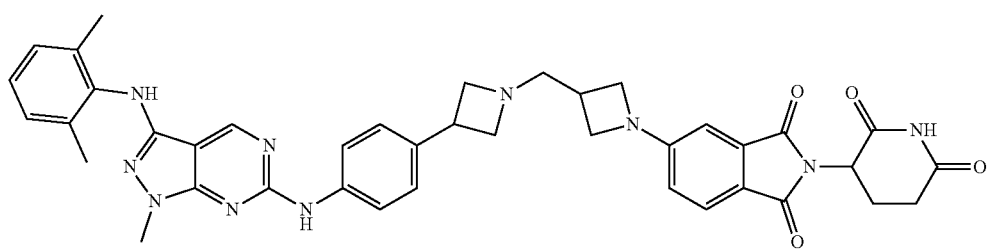

Compound 182

Compound 182 was synthesized in the same manner as in the synthesis procedure for Compound 162, with the exception of using tert-butyl 3-(4-aminophenyl)azetidine-1-carboxylate (Combi-Blocks, HA-2714) and 1-(2-(2,6-dioxopiperidin-3-yl)-1,3-dioxoisoindolin-5-yl)azetidine-3-carbaldehyde (WO2020/167518) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.-

Compound 183. 5-(3-(((S)-4-(4-((3-((2,6-Dimethylphenyl)amino)-1-methyl-1H-pyrazolo[3,4-d]pyrimidin-6-yl)amino)phenyl)-3-methylpiperazin-1-yl)methyl)azetidin-1-yl)-2-(2,6-dioxopiperidin-3-yl)isoindoline-1,3-dione

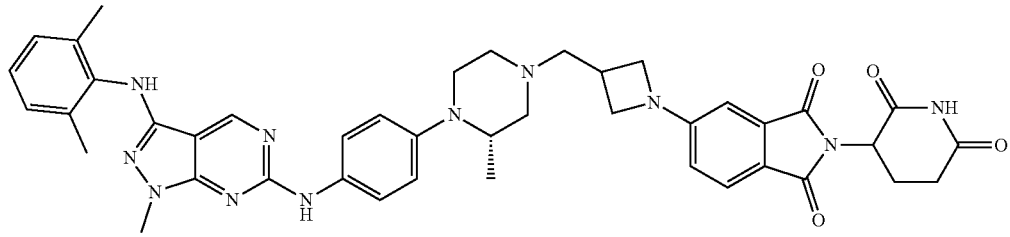

Compound 183

Compound 183 was synthesized in the same manner as in the synthesis procedure for Compound 162, with the exception of using tert-butyl (S)-4-(4-aminophenyl)-3-methylpiperazine-1-carboxylate (WO2014/189466) and 1-(2-(2,6-dioxopiperidin-3-yl)-1,3-dioxoisoindolin-5-yl)azetidine-3-carbaldehyde (WO2020/167518) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 184. 5-(3-(((R)-4-(4-((3-((2,6-Dimethylphenyl)amino)-1-methyl-1H-pyrazolo[3,4-d]pyrimidin-6-yl)amino)phenyl)-3-methylpiperazin-1-yl)methyl)azetidin-1-yl)-2-(2,6-dioxopiperidin-3-yl)isoindoline-1,3-dione

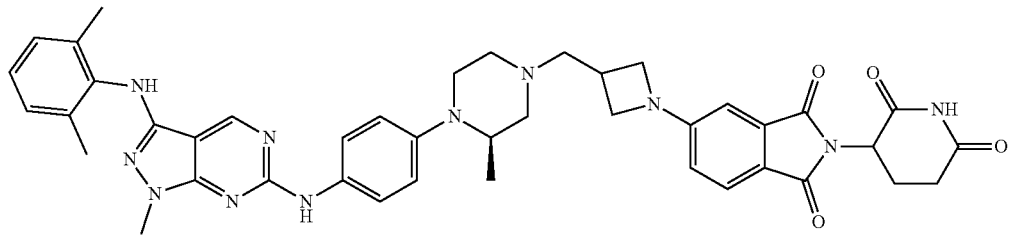

Compound 184

Compound 184 was synthesized in the same manner as in the synthesis procedure for Compound 162, with the exception of using tert-butyl (R)-4-(4-aminophenyl)-3-methylpiperazine-1-carboxylate (WO2014/189466) and 1-(2-(2,6-dioxopiperidin-3-yl)-1,3-dioxoisoindolin-5-yl)azetidine-3-carbaldehyde (WO2020/167518) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 185. 5-(3-(((S)-4-(4-((3-((2,6-Dimethylphenyl)amino)-1-methyl-1H-pyrazolo[3,4-d]pyrimidin-6-yl)amino)phenyl)-2-methylpiperazin-1-yl)methyl)azetidin-1-yl)-2-(2,6-dioxopiperidin-3-yl)isoindoline-1,3-dione

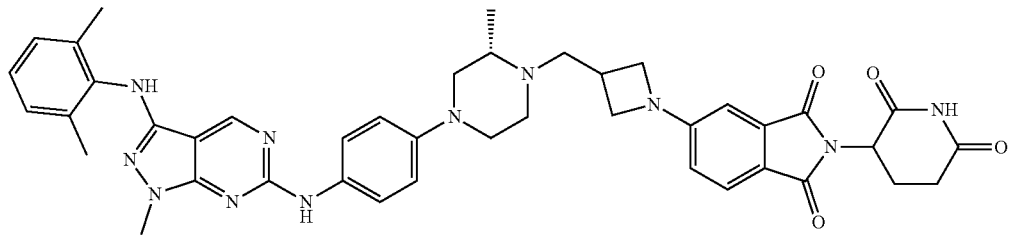

Compound 185

Compound 185 was synthesized in the same manner as in the synthesis procedure for Compound 162, with the exception of using tert-butyl (S)-4-(4-aminophenyl)-2-methylpiperazine-1-carboxylate (WO2015/092431) and 1-(2-(2,6-dioxopiperidin-3-yl)-1,3-dioxoisoindolin-5-yl)azetidine-3-carbaldehyde (WO2020/167518) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.

Compound 186. 5-(3-(((R)-4-(4-((3-((2,6-Dimethylphenyl)amino)-1-methyl-1H-pyrazolo[3,4-d]pyrimidin-6-yl)amino)phenyl)-2-methylpiperazin-1-yl)methyl)azetidin-1-yl)-2-(2,6-dioxopiperidin-3-yl)isoindoline-1,3-dione

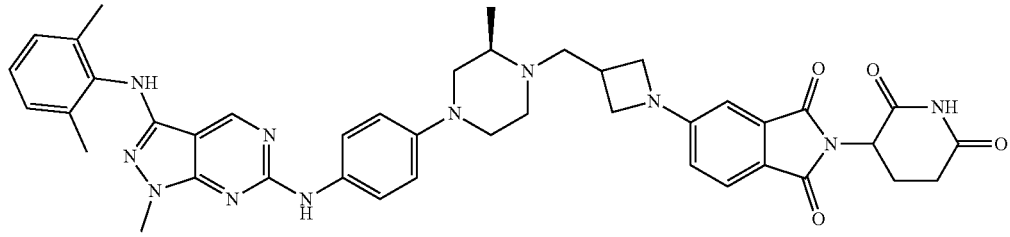

Compound 186

Compound 186 was synthesized in the same manner as in the synthesis procedure for Compound 162, with the exception of using tert-butyl (R)-4-(4-aminophenyl)-2-methylpiperazine-1-carboxylate (WO2015/092431) and 1-(2-(2,6-dioxopiperidin-3-yl)-1,3-dioxoisoindolin-5-yl)azetidine-3-carbaldehyde (WO2020/167518) instead of tert-butyl 4-(6-aminopyridin-3-yl)piperazine-1-carboxylate (Combi-Blocks, QE-9781) and 1-(2-(2,6-dioxopiperidin-3-yl)-1,3-dioxoisoindolin-5-yl)piperidine-4-carbaldehyde (WO2018/140809), respectively.-

Compound 187. 3-(2-(3-((4-(4-((3-((2,6-Dimethylphenyl)amino)-1-methyl-1H-pyrazolo[3,4-d]pyrimidin-6-yl)amino)phenyl)piperazin-1-yl)methyl)azetidin-1-yl)-5-oxo-5,7-dihydro-6H-pyrrolo[3,4-b]pyridin-6-yl)piperidin-2,6-one

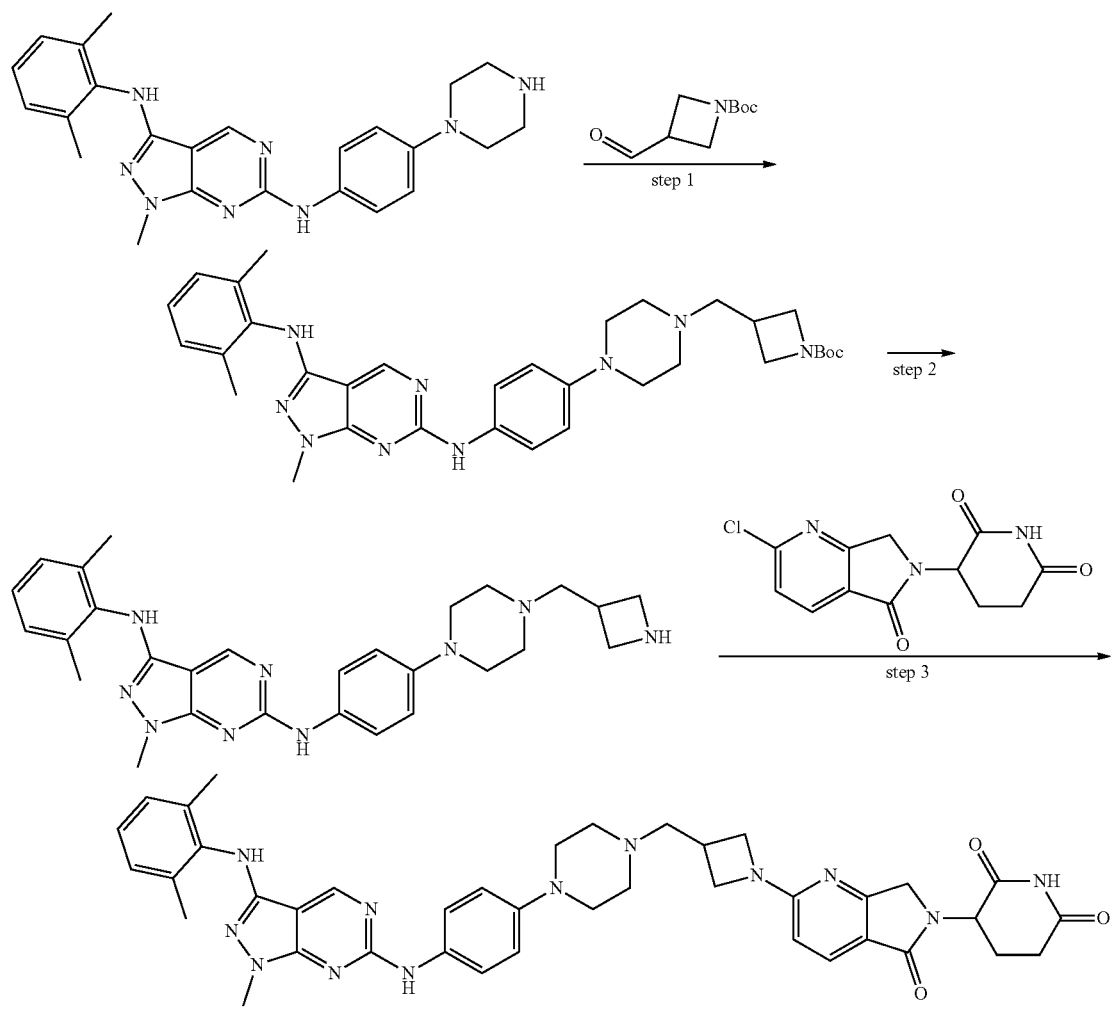

Compound 187

Step 1: Synthesis of tert-butyl 3-((4-(4-((3-((2,6-dimethylphenyl)amino)-1-methyl-1H-pyrazolo[3,4-d]pyrimidin-6-yl)amino)phenyl)piperazin-1-yl)methyl)azetidine-1-carboxylate A suspension of N3-(2,6-dimethylphenyl)-1-methyl-N6-(4-(piperazin-1-yl)phenyl)-1H-pyrazolo[3,4-d]pyrimidine-3,6-diamine (Korean Patent No. 2128018) (73.0 mg, 0.17 mmol), tert-butyl 3-formylazetidine-1-carboxylate (TCI, B5160) (31.5 mg, 0.17 mmol) in ACN (1.0 mL) was added with NaBH(OAc)₃ (72.0 mg, 0.34 mmol) and stirred at room temperature for 1 hour. The reaction mixture was added with an aqueous NaHCO₃ solution (15 mL), followed by extraction with DCM (15 mL×2). The organic layer was dried over anhydrous magnesium sulfate, filtered, and concentrated in a vacuum. The residue thus obtained was purified by MPLC (50% EA/Hex) to afford a yellow solid (70 mg, 69%).

Step 2: Synthesis of N6-(4-(4-(azetidin-3-ylmethyl)piperazin-1-yl)phenyl)-N3-(2,6-dimethylphenyl)-1-methyl-1H-pyrazolo[3,4-d]pyrimidine-3,6-diamine A suspension of tert-butyl 3-((4-(4-((3-((2,6-dimethylphenyl)amino)-1-methyl-1H-pyrazolo[3,4-d]pyrimidin-6-yl)amino)phenyl)piperazin-1-yl)methyl)azetidine-1-carboxylate (40.0 mg, 0.07 mmol) in DCM (4 mL) was added with 4 N HCl/dioxane (0.3 mL) and stirred at room temperature for 1 hour. The reaction mixture was neutralized with an aqueous NaHCO₃ solution, followed by extraction with DCM (10 mL×2). The organic layer was dried over anhydrous magnesium sulfate, filtered, and concentrated in a vacuum to afford a yellow solid (26 mg, 78%).

Step 3: Synthesis of 3-(2-(3-((4-(4-((3-((2,6-dimethylphenyl)amino)-1-methyl-1H-pyrazolo[3,4-d]pyrimidin-6-yl)amino)phenyl)piperazin-1-yl)methyl)azetidin-1-yl)-5-oxo-5,7-dihydro-6H-pyrrolo[3,4-b]pyridin-6-yl)piperidin-2,6-one (Compound 187)

A suspension of N6-(4-(4-(azetidin-3-ylmethyl)piperazin-1-yl)phenyl)-N3-(2,6-dimethylphenyl)-1-methyl-1H-pyrazolo[3,4-d]pyrimidine-3,6-diamine (26 mg, 0.05 mmol) in DMSO (1 mL) was added with 3-(2-chloro-5-oxo-5,7-dihydro-6H-pyrrolo[3,4-b]pyridin-6-yl)piperidin-2,6-one (WO2018/140809) (15 mg, 0.05 mmol) and DIPEA (0.02 mL, 0.10 mmol) and stirred at 100° C. for 16 hours. The reaction mixture was added with distilled water (20 mL) before extraction with EtOAc (15 mL×2). The organic layer was washed with brine (15 mL×2), dried over anhydrous magnesium, filtered, and concentrated in a vacuum. The residue thus obtained was purified by PTLC (5% MeOH/DCM) to afford a yellow solid (7 mg, 20%).

Compound 188. 3-(2-(4-((4-(4-((3-((2,6-Dimethylphenyl)amino)-1-methyl-1H-pyrazolo[3,4-d]pyrimidin-6-yl)amino)phenyl)piperazin-1-yl)methyl)piperidin-1-yl)-5-oxo-5,7-dihydro-6H-pyrrolo[3,4-b]pyridin-6-yl)piperidin-2,6-one Compound 188

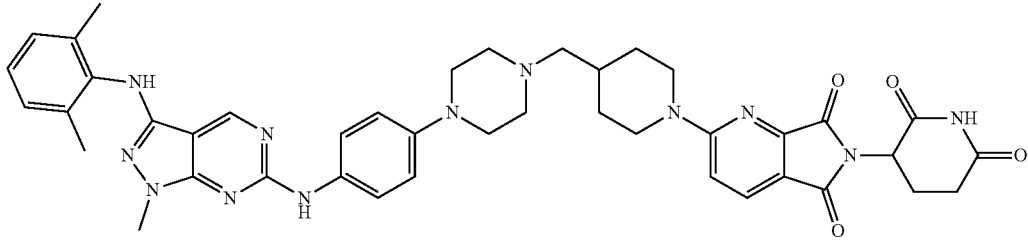

Compound 188 was synthesized in the same manner as in the synthesis procedure for Compound 187, with the exception of using tert-butyl 4-formylpiperidine-1-carboxylate (TCI, B3873) instead of tert-butyl 3-formylazetidine-1-carboxylate (TCI, B5160).

Compound 189. 2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(3-(N-(2,6-dioxopiperidin-3-yl)sulfamoyl)-4-methylphenyl)acetamide

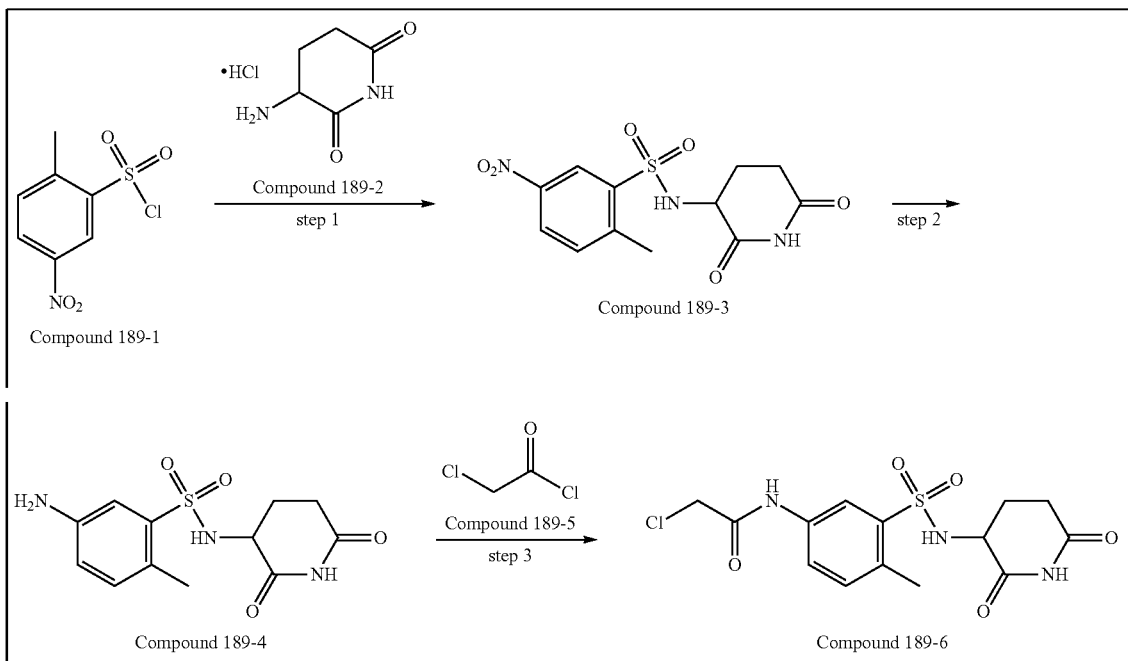

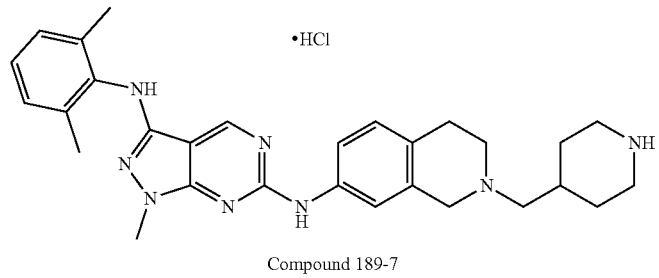

Compound 189-7

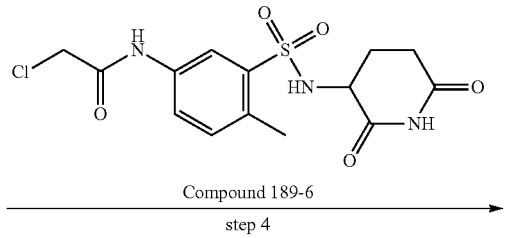

Compound 189-6 step 4

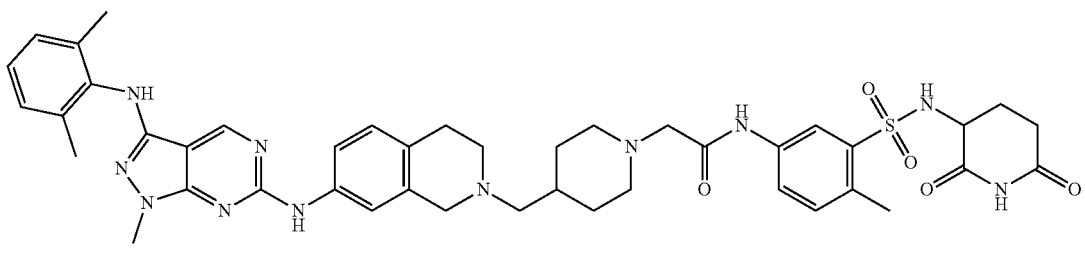

Compound 189

Step 1: Synthesis of N-(2,6-dioxopiperidin-3-yl)-2-methyl-5-nitrobenzenesulfonamide A solution of Compound 189-1 (TCI, M2178) (2-methyl-5-nitrobenzenesulfonyl chloride; 500 mg, 2.12 mmol) in THF (5 mL) was added at room temperature with Compound 189-2 (Combi-Blocks, QA-9228) (3-aminopiperidin-2,6-one hydrochloride; 698 mg, 4.24 mmol) and $K_2CO_3$ (1.47 g, 10.6 mmol). The resulting mixture was stirred overnight at room temperature. When a new spot was formed as analyzed by TLC, the solvent was completely evaporated. The residue was directly purified under MPLC using 5% MeOH/MC (dry column) to afford Compound 189-3 as an off-white solid (300 mg, 0.917 mmol, 43%).

Step 2: Synthesis of 5-amino-N-(2,6-dioxopiperidin-3-yl)-2-methylbenzenesulfonamide A solution of Compound 189-3 (200 mg, 0.611 mmol) in MeOH (10 mL) was added at room temperature with 10% Pd/C (40 mg). The resulting mixture was stirred at room temperature for 2 hours. When a new spot was formed as analyzed by TLC, the crude mixture was filtered through a celite filter and evaporated in a vacuum to afford Compound 189-4 as a beige solid (125 mg, 0.420 mmol, 69%).

Step 3: Synthesis of 2-chloro-N-(3-(N-(2,6-dioxopiperidin-3-yl)sulfamoyl)-4-methylphenyl)acetamide A suspension of Compound 189-4 (50 mg, 0.168 mmol) in THF (1 mL) was added with Compound 189-5 (sigma, 104493) (chloroacetyl chloride; 56.4 mg, 0.505 mmol) and TEA (46 uL, 0.336 mmol). The resulting mixture was stirred at room temperature for 3 hours. When a new spot was formed as analyzed by TLC, the reaction mixture was quenched with water (10 mL) before extraction with EA (25 mL×2). The pooled organic layer was dried over sodium sulfate and the solvent was evaporated in a vacuum to obtain the title compound. The crude product was purified by MPLC using a solvent mixture of 10% MeOH:DCM to afford Compound 189-6 as a white solid (50 mg, 0.134 mmol, 80%).

Step 4: Synthesis of 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl) methyl)piperidin-1-yl)-N-(3-(N-(2,6-dioxopiperidin-3-yl)sulfamoyl)-4-methylphenyl)acetamide (Compound 189)

A suspension of Compound 189-7 (identical to Compound 28-4) (15 mg, 0.281 mmol) in DMF (1 mL) was added with Compound 189-6 (12.6 mg, 0.0338 mmol). The mixture was stirred at 70° C. for 14 hours. When a new spot was formed as analyzed by TLC, the reaction mixture was quenched with water (10 mL) before extraction with EA (25 mL×2). The pooled organic layer was dried over sodium sulfate and the solvent was evaporated in a vacuum. The crude product was purified by column chromatography using DCM/MeOH 5% to afford Compound 189 as a white solid (11.9 mg, 0.0143 mmol, 51%).

Compound 190. 7-((3-((2,6-Dimethylphenyl)amino)-1-methyl-1H-pyrazolo[3,4-d]pyrimidin-6-yl)amino)-N-(3-(N-(2,6-dioxopiperidin-3-yl)sulfamoyl)-4-methylphenyl)-3,4-dihydroisoquinoline-2(1H)-carboxamide

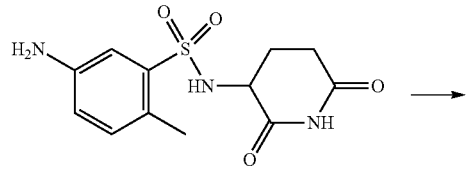

Compound 190-1

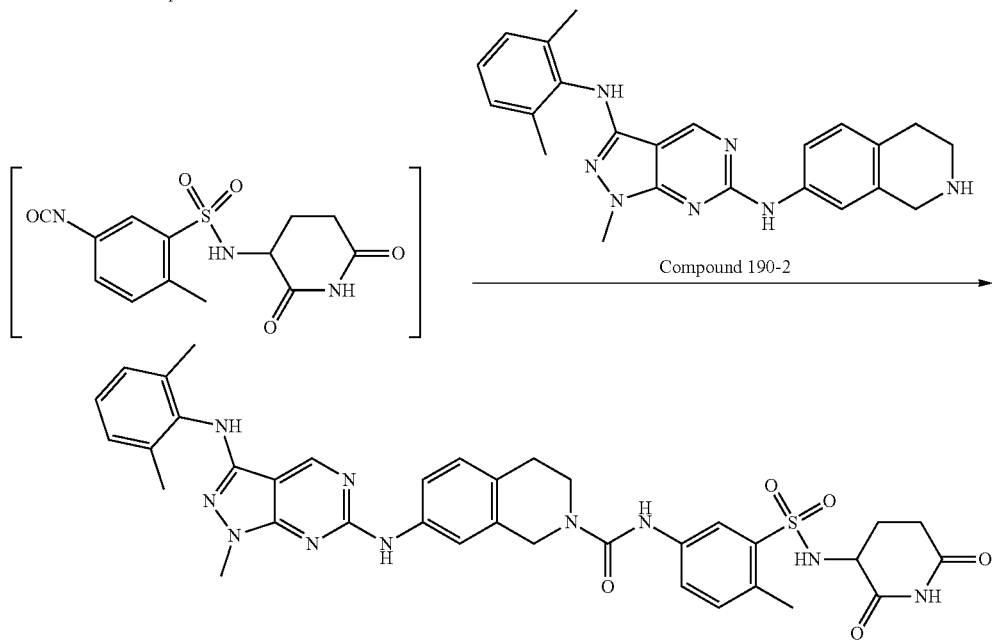

Compound 190

A solution of Compound 190-1 (identical to Compound 189-4) (27.9 g, 0.0939 mmol) in DCM (1 mL) was added at room temperature with triphosgene (139 mg, 0.470 mmol). The mixture was stirred at room temperature for 2 hours. After completion of the reaction, the reaction mixture was concentrated in a vacuum. The mixture in THF (1 mL) was added with Compound 190-2 (Korean Patent No. 2128018) (30 mg, 0.0751 mmol) and TEA (26.2 uL, 0.188 mmol) and stirred overnight at room temperature. When a product was formed as analyzed by TLC, the reaction mixture was concentrated in a vacuum. The residue was purified by column chromatography using MeOH/DCM (10%) to afford Compound 190 as a white solid (6 mg, 0.00830 mmol 11%).

Compound 192. 3-(3-((3-(2-(7-((3-((2,6-Dimethylphenyl)amino)-1-methyl-1H-pyrazolo[3,4-d]pyrimidin-6-yl)amino)-3,4-dihydroisoquinolin-2(1H)-yl)-2-oxoethyl)phenyl)amino)-2,5-dioxo-2,5-dihydro-1H-pyrrol-1-yl)piperidin-2,6-one

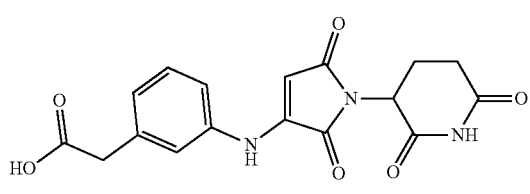

Compound 192-1

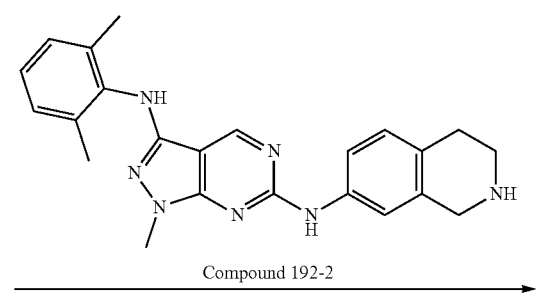

Compound 192-2

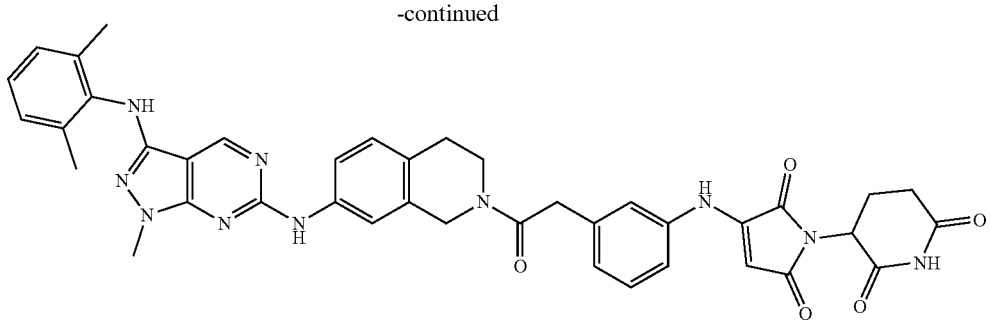

Compound 192

A solution of Compound 192-1 (WO2022/065962A1) (15 mg, 0.042 mmol) in DMF (1 mL) was added with Compound 192-2 (Korean Patent No. 2128018) (17 mg, 0.042 mmol), EDCI (20 mg, 0.105 mmol), HOBt (9 mg, 0.063 mmol), and DIPEA (29 µl, 0.168 mmol). The resulting mixture was stirred at room temperature for 12 hours. After completion of the reaction, the reaction mixture was quenched with water, subjected to extraction with EA (15 mL×3), and washed with water (3×) and brine. The pooled organic layer was dried over sodium sulfate and filtered, and the solvent was evaporated in a vacuum. The residue was purified by MPLC using 5% MeOH/MC to afford Compound 192 as a grayish yellow solid (17 mg, 0.023 mmol, 55%).

Compound 193. 3-(3-((3-(2-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)phenyl)amino)-2,5-dioxo-2,5-dihydro-1H-pyrrol-1-yl)piperidin-2,6-one

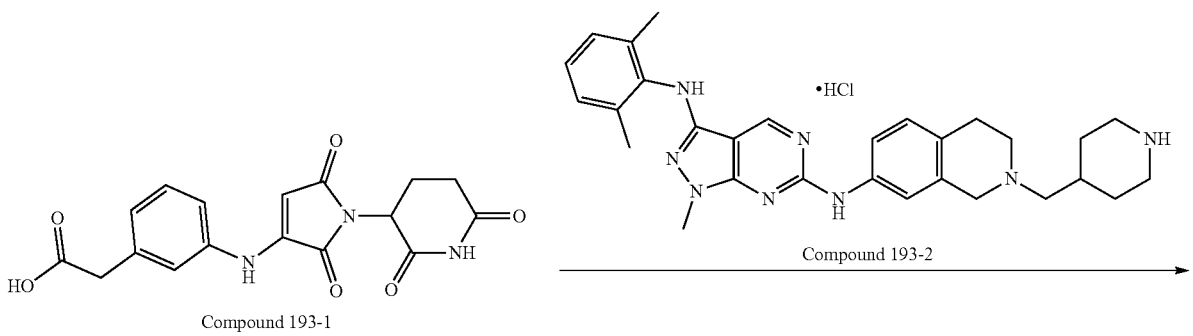

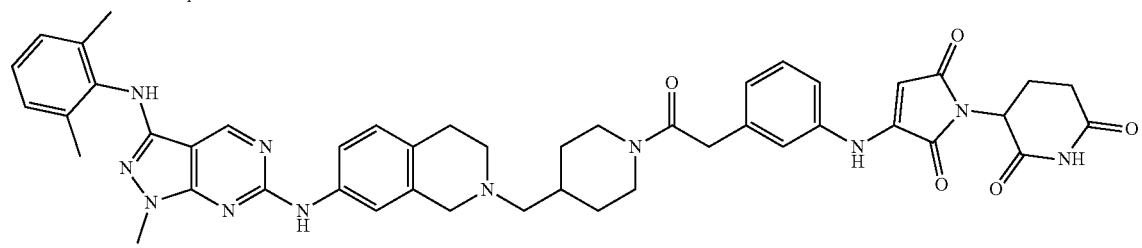

Compound 193

A solution of Compound 193-1 (WO2022/065962A1) (15 mg, 0.042 mmol) in DMF (1 mL) was added with Compound 193-2 (identical to Compound 28-4) (21 mg, 0.042 mmol), EDCI (20 mg, 0.105 mmol), HOBt (9 mg, 0.063 mmol), and DIPEA (29 µp, 0.168 mmol). The resulting mixture was stirred at room temperature for 12 hours. After completion of the reaction, the reaction mixture was quenched with water, subjected to extraction with EA (15 mL×3), and washed with water (3×) and brine. The pooled organic layer was dried over sodium sulfate and filtered, and the solvent was evaporated in a vacuum. The residue was purified by MPLC using 5% MeOH/MC to afford Compound 193 as a grayish yellow solid (19 mg, 0.023 mmol, 54%).

Compound 194. 5-(2-(7-((3-((2,6-Dimethylphenyl)amino)-1-methyl-1H-pyrazolo[3,4-d]pyrimidin-6-yl)amino)-3,4-dihydroisoquinolin-2 (1H)-yl)-2-oxoethoxy)-2-(2,6-dioxopiperidin-3-yl)isoindoline-1,3-dione

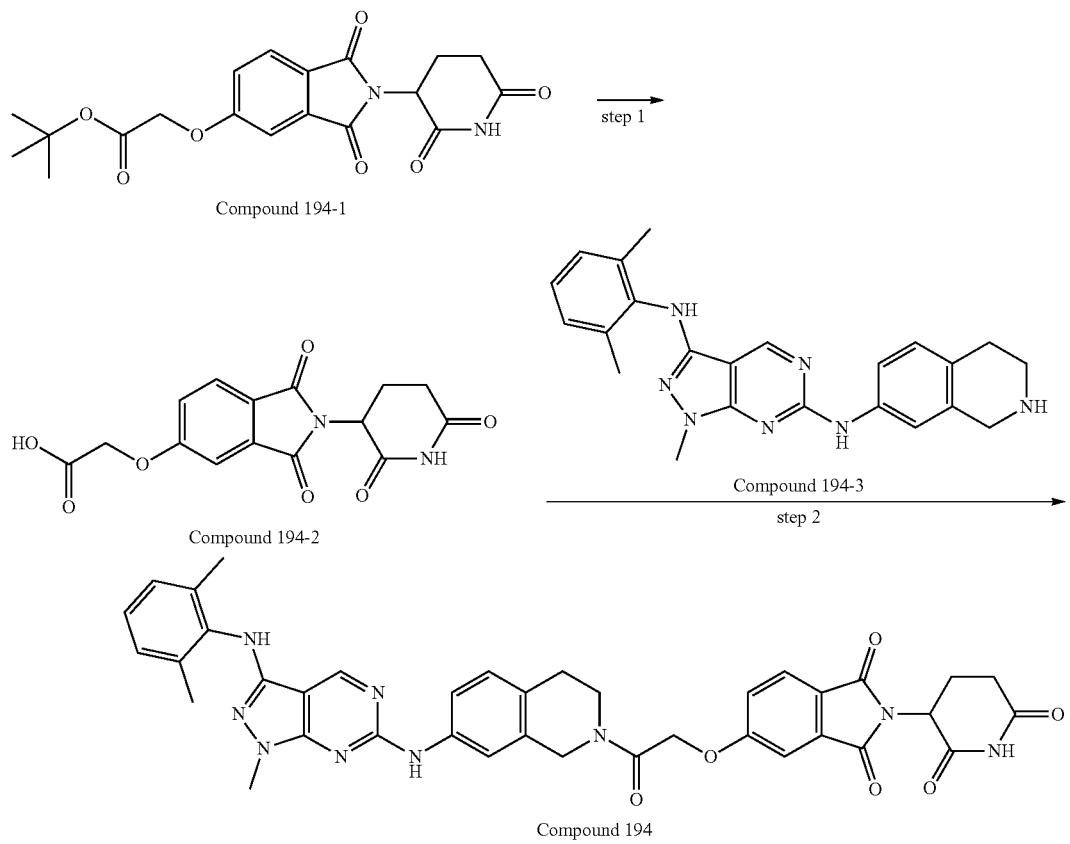

Step 1: Synthesis of 2-((2-(2,6-dioxopiperidin-3-yl)-1,3-dioxoisoindolin-5-yl)oxy)acetic acid To Compound 194-1 (WO2021/155321A1) (119 mg, 0.306 mmol) was added 40% TFA/DCM (1.6/2.4 mL). The resulting mixture was stirred at room temperature for 3 hours. The volatile material was evaporated to give a beige solid which was then washed with diethyl ether and concentrated in a vacuum to afford Compound 194-2 as an ivory solid (70 mg, 0.211 mmol, 69%).

Step 2: Synthesis of 5-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)-2-(2,6-dioxopiperidin-3-yl)isoindoline-1,3-dione (Compound 194)

A solution of Compound 194-2 (15 mg, 0.045 mmol) in DMF (1 mL) was added with Compound 194-3 (Korean Patent No. 2128018) (18 mg, 0.045 mmol), HATU (34 mg, 0.090 mmol), and Et$_3$N (19 μl, 0.135 mmol). The resulting mixture was stirred at room temperature for 12 hours. After completion of the reaction, the reaction mixture was quenched with water, subjected to extraction with EA (15 mL×3), and washed with water (3×) and brine. The pooled organic layer was dried over sodium sulfate and filtered, and the solvent was evaporated in a vacuum. The residue was purified by MPLC using 5% MeOH/DCM to afford Compound 194 as a grayish solid (14 mg, 0.020 mmol, 43%).

Compound 195. 5-(4-((7-((3-((2-Bromo-6-methylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione
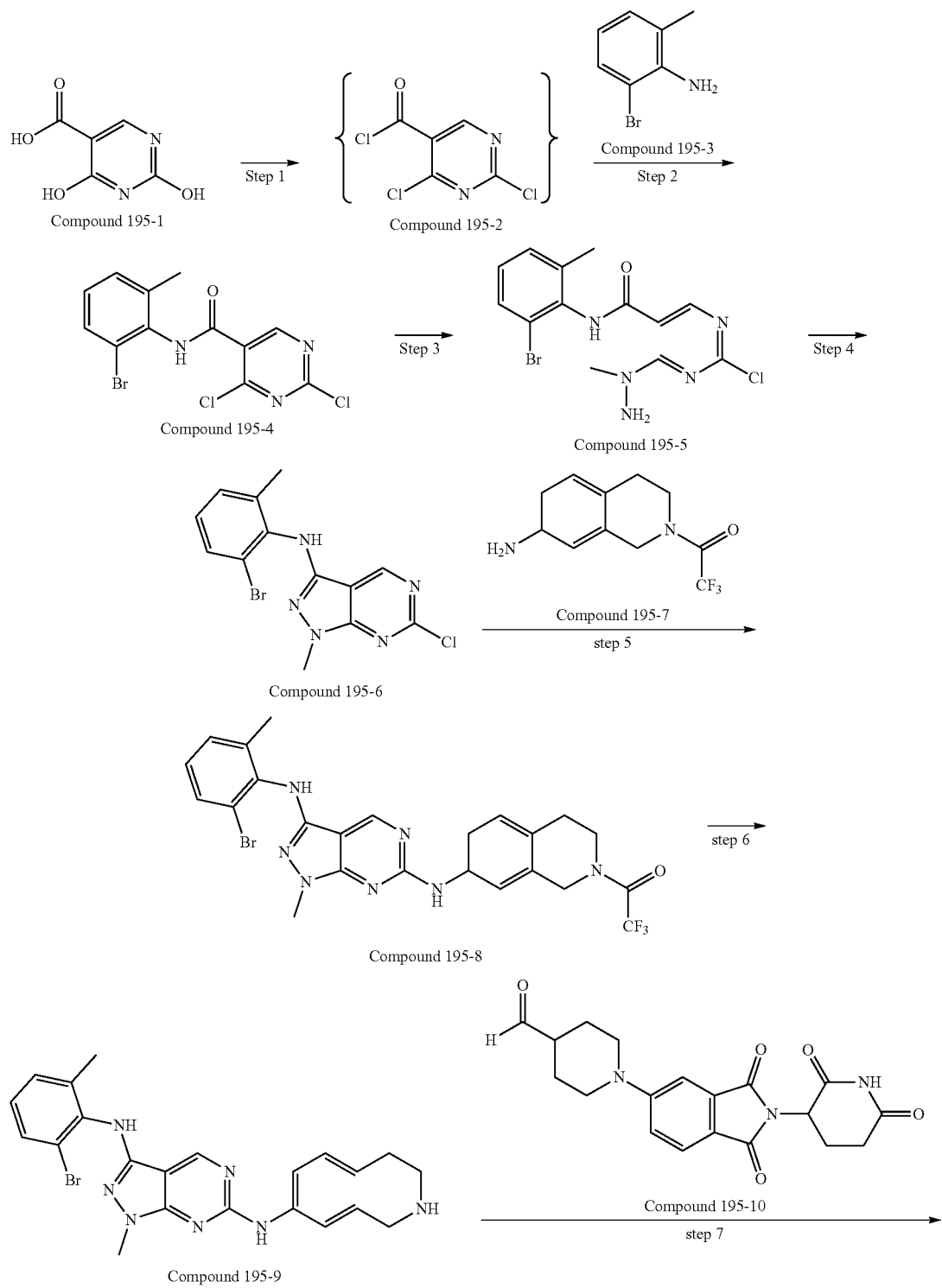

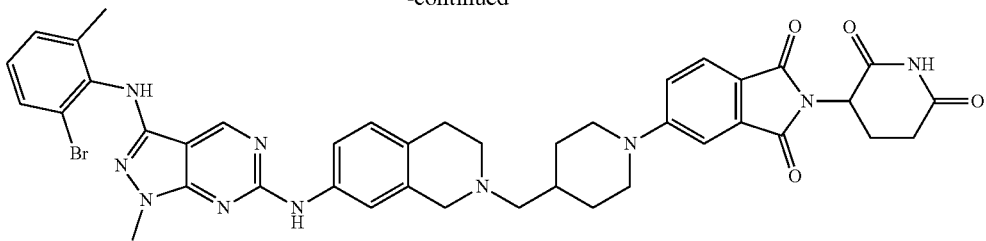

Compound 195

Step 1: Synthesis of 2,4-dichloropyrimidine-5-carbonyl chloride

In a round-bottom flask, Compound 195-1 (Sigma, 126268) (2,4-dihydroxypyrimidine-5-carboxylic acid; 1.00 g, 6.41 mmol) was added little by little at 0° C. to $POCl_3$ (2.40 mL, 25.6 mmol), followed by slow addition of $PCl_5$ (4.67 g, 22.4 mmol). The mixture was heated at 120° C. for 12 hours under reflux, concentrated, dried, and then slurried with DCM (50 mL). The solid thus precipitated was filtered and washed with Hex and DCM. The solvent was evaporated in a vacuum to afford Compound 195-2 as a reddish yellow liquid (1.56 g, 7.38 mmol, >100%).

Step 2: Synthesis of N-(2-bromo-6-methylphenyl)-2,4-dichloropyrimidine-5-carboxamide A solution of Compound 195-2 (Korean Patent No. 2128018) (1.35 g, 6.39 mmol) in THF (50 mL) was added at room temperature with Compound 195-3 (Alfa, A11884) (2-bromo-6-methylaniline; 1.19 g, 6.39 mmol). The resulting mixture was stirred at room temperature for 13 hours. After the formation of a solid was observed, the solid was filtered and washed with water (3×50 mL). The solid was purified using Hex and EA (trituration) to afford Compound 195-4 as an ivory solid (1.84 g, 6.39 mmol, 94%).

Step 3: Synthesis of N-(2-bromo-6-methylphenyl)-2-chloro-4-(1-methylhydrazineyl)pyrimidine-5-carboxamide A solution of Compound 195-4 (1.70 g, 4.71 mmol) in THF (30 mL) was added with methyl hydrazine sulfate (TCI, M0341) (746 mg, 5.18 mmol) and then at room temperature with 2 N NaOH (8.24 mL). The resulting mixture was stirred at room temperature for 6 hours and concentrated to remove THF. The reaction mixture was washed with water and the organic layer was dried over sodium sulfate and concentrated in a vacuum. The residue was purified by MPLC using 50% EA in Hex to afford Compound 195-5 as a white solid (580 mg, 1.90 mmol, 41%).

Step 4: Synthesis of N-(2-bromo-6-methylphenyl)-6-chloro-1-methyl-1H-pyrazolo[3,4-d]pyrimidin-3-amine To a solution of Compound 195-5 (515 mg, 1.39 mmol) in toluene was added $PCl_5$ (318 mg, 1.53 mmol) at room temperature. The mixture was stirred at 120° C. for 13 hours and then concentrated to remove toluene. Subsequently, water (20 mL) and sodium bicarbonate were added to basify the aqueous layer (pH 8-9). After being isolated, the organic layer was dried over sodium sulfate and the filtrate was concentrated in a vacuum to afford Compound 195-6 as a yellow solid (198 mg, 0.561 mmol, 40%).

Step 5: 1-(7-((3-((2-bromo-6-methylphenyl)amino)-1-methyl-1H-pyrazolo[3,4-d]pyrimidin-6-yl)amino)-3,4-dihydroisoquinolin-2 (1H)-yl)-2,2,2-trifluoroethan-1-one Into a 50-mL RB was loaded Compound 195-6 (198 mg, 0.562 mmol), followed by Compound 195-7 (Korean Patent No. 2128018) (151 mg, 0.618 mmol), PTSA (116 mg, 0.674 mmol), and IPA (10 mL). The mixture was heated at 90° C. for 11 hours. The reaction mixture was concentrated and basified with $K_2CO_3$ before extraction with DCM (50 mL×2). The organic layer was dried over sodium sulfate and the organic solvent evaporated in a vacuum. The residue was purified by MPLC using 5% MeOH in DCM to afford Compound 195-8 as a yellow solid (260 mg, 0.464 mmol, 83%).

Step 6: Synthesis of N3-(2-bromo-6-methylphenyl)-1-methyl-N6-(1,2,3,4-tetrahydroisoquinolin-7-yl)-1H-pyrazolo[3,4-d]pyrimidine-3,6-diamine A solution of Compound 195-8 (146 mg, 0.261 mmol) in THF/MeOH/water (2:1:0.5) (1 mL) was added with $LiOH·H_2O$ (38.3 mg, 0.912 mmol) and stirred at room temperature for 2 hours. The reaction solvent was evaporated using a rotary evaporator. The concentrate was subjected to acid/base work-up with 1 N HCl and $NaHCO_3$ to afford Compound 195-9 as a white solid (58.0 mg, 0.125 mmol, 48%).

Step 7: Synthesis of 5-(4-((7-((3-((2-bromo-6-methylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 195)

A solution of Compound 195-9 (45.7 mg, 0.0984 mmol) in DMF (1 mL) was added with Compound 195-10 (WO 2020/162725) (40.0 mg, 0.108 mmol) and acetic acid (2 drops) and stirred for 1 hour. To this mixture was added $NaBH_3CN$ (9.28 mg, 0.148 mmol), followed by stirring at room temperature for 2 hours. After completion of the reaction, the reaction mixture was quenched with water and subjected to extraction with DCM (3×50 mL). the organic layer was washed with brine and dried over $MgSO_4$. The crude product was purified by MPLC (5% MeOH in DCM) to afford Compound 195 as a yellow solid (42.7 mg, 0.0522 mmol).

Compound 199. 5-(4-(((1-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)cyclopropyl)amino)methyl)piperidin-1-yl)-2-(2,6-dioxopiperidin-3-yl)isoindoline-1,3-dione

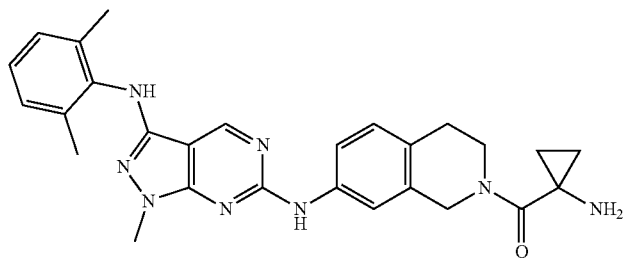

Compound 199-1

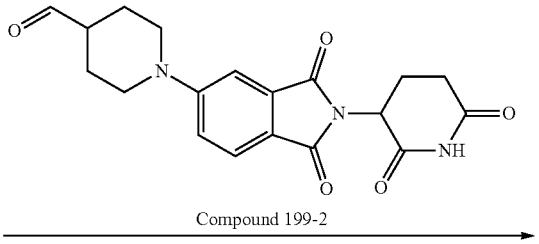

Compound 199-2

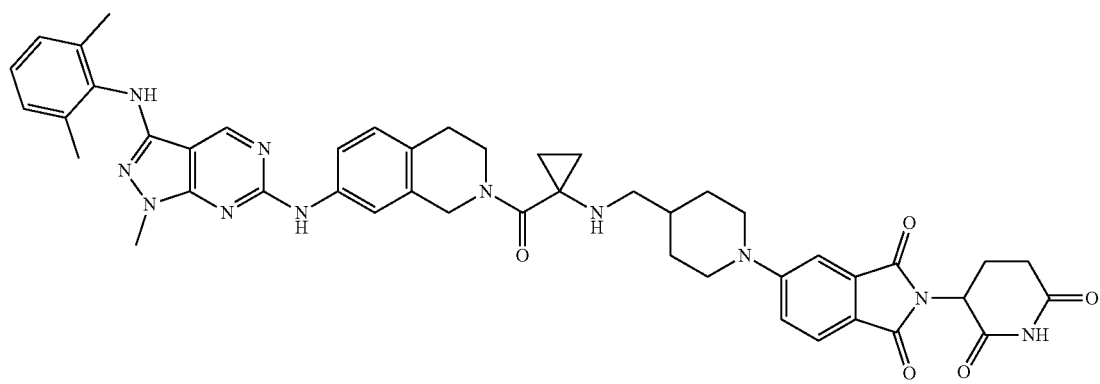

Compound 199

A solution of Compound 199-1 (15.0 mg, 0.0310 mmol) in MeOH 1 mL was added with Compound 199-2 (WO 2020/162725) (11.5 g, 0.0310 mmol) and then with acetic acid (drops) and stirred at room temperature for 2 hours. The mixture was added with NaCNBH$_3$ (4.87 mg, 0.0775 mmol) and stirred at room temperature for 2 hours. When the reaction was completed as analyzed by TLC, the solvent was completely evaporated. The residue was dissolved in MC and washed with saturated sodium bicarbonate. The organic layer was dried over sodium sulfate and the organic solvent evaporated in a vacuum. The residue was purified by MPLC using 5% MeOH/MC to afford Compound 199 as a yellow solid (6.00 mg, 0.0717 mmol, 23%).

Compound 201. 3-(3-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2,5-dioxo-2,5-dihydro-1H-pyrrol-1-yl)piperidin-2,6-one

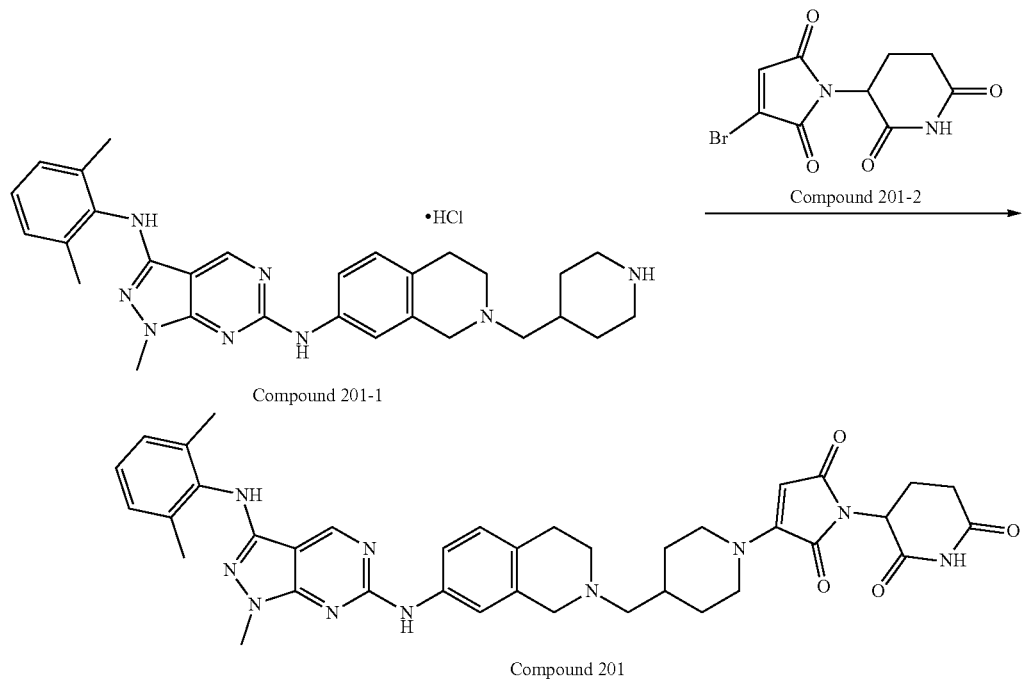

A solution of Compound 200-1 (identical to Compound 28-4) (20.0 mg 0.0375 mmol) in dioxane (1.0 mL) was added with Compound 200-2 (WO2021/236885) (10.8 mg, 0.0375 mmol) and then with TEA (9.47 mg, 0.0937 mmol). The mixture was stirred at 65° C. for 12 hours. When a new spot was formed as analyzed by TLC, the reaction mixture was quenched with water (10 mL) before extraction with DCM (50 mL×2). The crude product was purified by MPLC using a solvent mixture of 5% MeOH:DCM to afford Compound 201 as a brown solid (19.0 mg, 0.0270 mmol, 72%).

Compound 204. N-(1-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)cyclopropyl)-1-(2-(2,6-dioxopiperidin-3-yl)-1,3-dioxoisoindolin-5-yl)piperidine-4-carboxamide

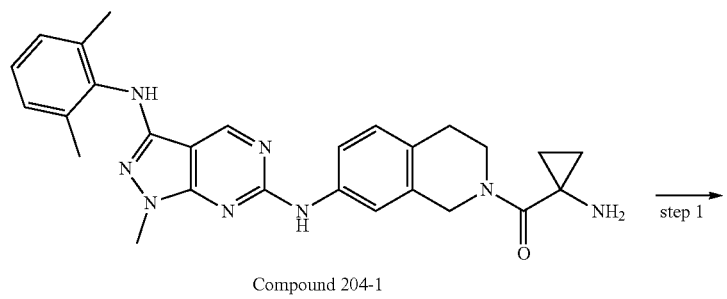

-continued

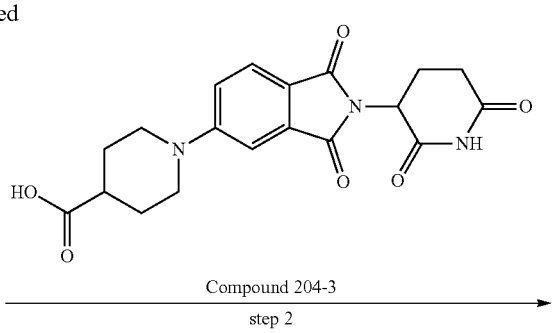

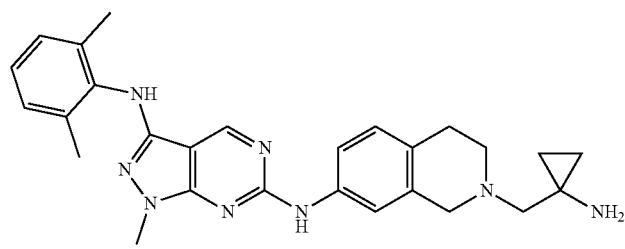

Compound 204-2

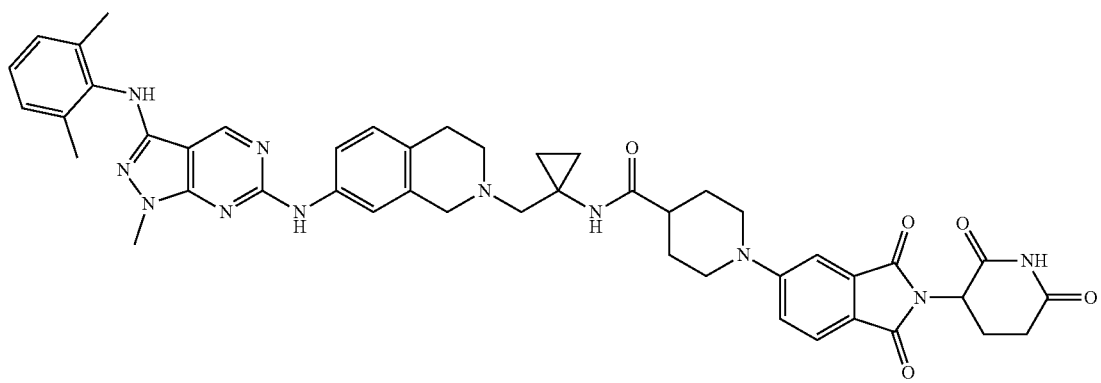

Compound 204

Step 1: Synthesis of N6-(2-((1-aminocyclopropyl)methyl)-1,2,3,4-tetrahydroisoquinolin-7-yl)-N3-(2,6-dimethylphenyl)-1-methyl-1H-pyrazolo[3,4-d]pyrimidine-3,6-diamine A solution of Compound 204-1 (identical to Compound 199-1) (200 mg, 0.414 mmol) in anhydrous THF (50 mL) was added with BH₃·THF (2.07 mL, 2.07 mmol) and stirred at room temperature for 12 hours. The reaction mixture was quenched with MeOH (5 mL) and concentrated in a vacuum to give a crude material. This crude material was dissolved in a mixture of MeOH:dimethylaminoethanol (DMAE) (5:1) (20 mL) and fluxed for 3 hours. The solvent was evaporated in a vacuum, followed by quenching with water. The aqueous layer was subjected to extraction with EA (15 mL×2). The pooled organic layer was dried over sodium sulfate and filtered, and the solvent was evaporated in a vacuum to afford Compound 204-2 as a white solid (163.0 mg, 0.347 mmol, 94%, crude) which was then identified by LC/MC without further purification.

Step 2: Synthesis of N-(1-((7-((3-((2,6-dimethylphenyl)amino)-1-methyl-1H-pyrazolo[3,4-d]pyrimidin-6-yl)amino)-3,4-dihydroisoquinolin-2(1H)-yl)methyl)cyclopropyl)-1-(2-(2,6-dioxopiperidin-3-yl)-1,3-dioxoisoindolin-5-yl)piperidine-4-carboxamide (Compound 204)

A solution of Compound 204-2 (20.0 mg, 0.0426 mmol) in DMF (1 mL) was added at room temperature with HATU (32.4 mg, 0.0852 mmol), Compound 204-3 (WO2021/083949A1) (19.7 mg, 0.0512 mmol), and TEA (12.9 mg, 0.127 mmol). The resulting mixture was stirred at room temperature for 12 hours. When a new spot was formed as analyzed by TLC, the reaction mixture was quenched with water (10 mL) before extraction with EA (15 mL×2). The combined organic layer was washed with water (20 mL×2) and brine (20 mL×2) and then with saturated aqueous NaHCO₃ and dried. The solvent was evaporated over sodium sulfate in a vacuum. The crude product was purified by MPLC using a solvent mixture of 10% MeOH:DCM to afford Compound 204 as a yellow solid (11.0 mg, 0.0131 mmol, 30%).

Compound 205. N-(1-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)cyclopropyl)-2-((2-(2,6-dioxopiperidin-3-yl)-1,3-dioxoisoindolin-5-yl)oxy)acetamide

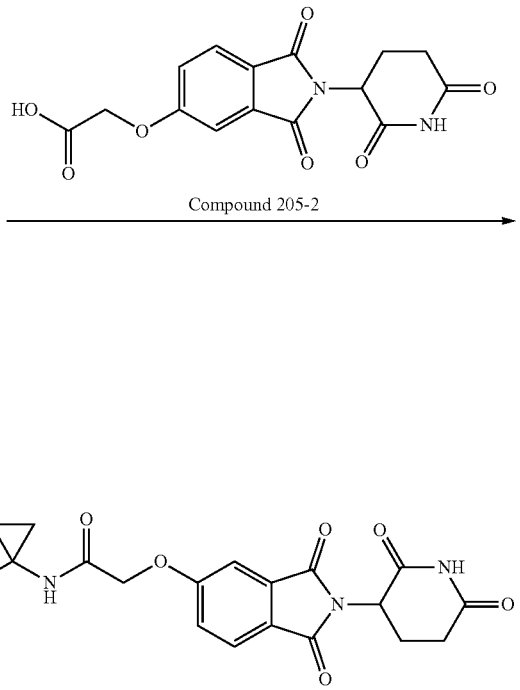

Compound 205-2

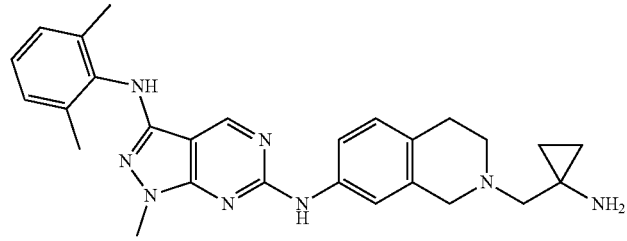

Compound 205-1

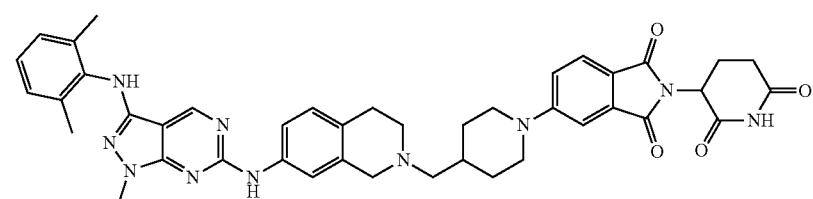

Compound 205

A solution of Compound 205-1 (identical to Compound 204-2) (20.0 mg, 0.0426 mmol) in DMF (1 mL) was added at room temperature with HATU (32.4 mg, 0.0852 mmol), Compound 205-2 (identical to Compound 194-2) (17.0 mg, 0.0512 mmol), and TEA (12.9 mg, 0.127 mmol). The resulting mixture was stirred at room temperature for 12 hours. When a new spot was formed as analyzed by TLC, the reaction mixture was quenched with water (10 mL) before extraction with EA (15 mL×2). The combined organic layer was washed with water (20 mL×2) and brine (20 mL×2) and with saturated aqueous NaHCO₃ and dried. The solvent was evaporated over sodium sulfate in a vacuum. The crude product was purified by HPLC using a solvent mixture of 10% MeOH:DCM to afford Compound 205 as a yellow solid (8.0 mg, 0.0102 mmol, 23%).

Compound 206. (3-(5-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methylpiperidine-4-carboxylate bistrifluoroacetic acid

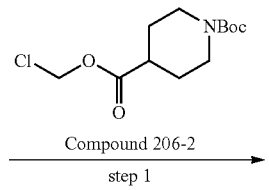

Compound 206-2 step 1

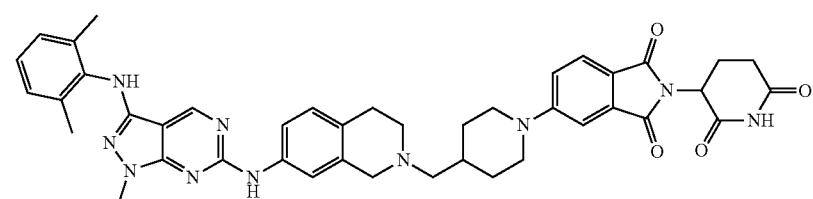

Compound 206-1

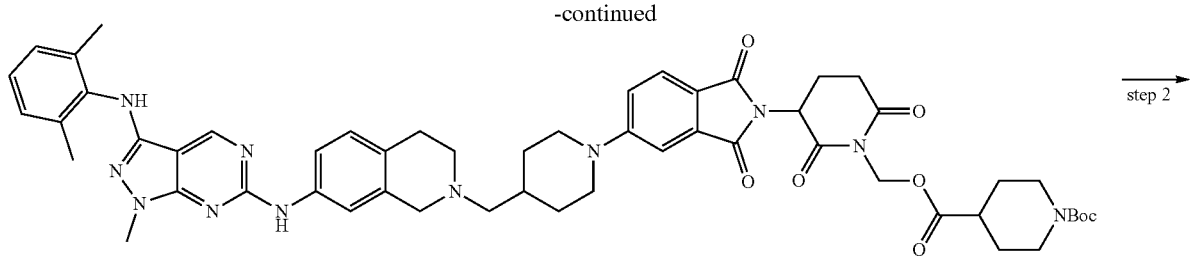

Compound 206-3

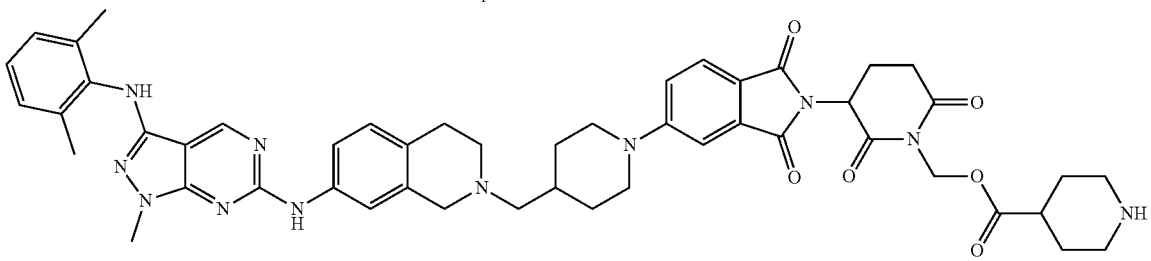

Compound 206

Step 1: Synthesis of 1-(tert-butyl)4-((3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl) methyl) piperidine-1,4-dicarboxylate A solution of Compound 206-1 (identical to Compound 29) (75.0 mg, 0.0996 mmol) in DMF (1 mL) was added with cesium carbonate (97.3 mg, 0.298 mmol) and TBAI (18.4 mg, 0.0498 mmol) and stirred for 20 minutes. After addition of Compound 206-2 (WO2010/053732 A1) (55.3 mg, 0.199 mmol), stirring was conducted at room temperature for 1 hour. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 206-3 as a fluorescent green solid (48.0 mg, 0.0482 mmol, 48%).

Step 2: Synthesis of (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methylpiperidine-4-carboxylate bistrifluoroacetic acid (Compound 206)

A solution of Compound 206-3 (30.0 mg, 0.0301 mmol) in DCM (2 mL) was added with 40% TFA/DCM (2 mL) and stirred at room temperature for 1 hour. When the starting material was consumed as analyzed by TLC, the solvent was evaporated. The residue was washed with diethyl ether (5 mL). The product was dried in a vacuum to afford Compound 206 as a yellow solid (30.0 mg, 0.0267 mmol, 88%).

Compound 207. (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methyl 4-methylpentanoate

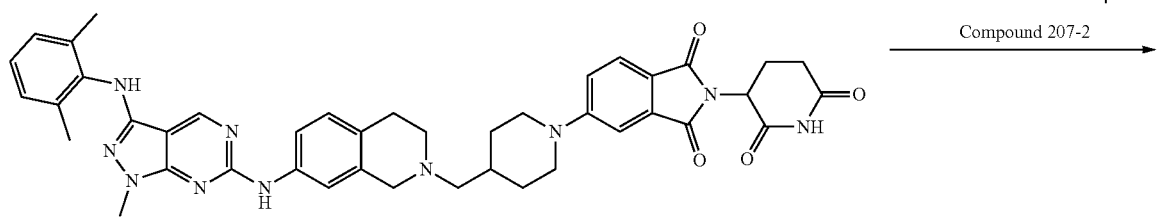

Compound 207-1

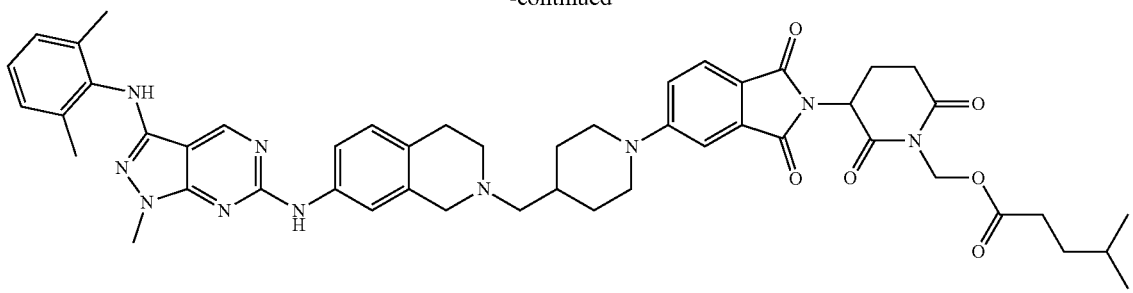

Compound 207

A solution of Compound 207-1 (identical to Compound 29) (25 mg, 0.0332 mmol) in DMF (1 mL) was added with cesium carbonate (21.6 mg, 0.0664 mmol) and TBAI (2.45 mg, 0.0664 mmol) and stirred for 20 minutes. After addition of Compound 207-2 (Journal of Antibiotics (1986), 39 (9), 1329-42) (10.9 mg, 0.0664 mmol), stirring was conducted at room temperature for 1 hour. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 207 as a fluorescent green solid (10.0 mg, 0.0113 mmol, 34%).

Compound 208. 5-(4-((7-((3-((2,6-Dimethylphenyl) amino)-1-methyl-1H-pyrazolo[3,4-d]pyrimidin-6-yl) amino)-3,4-dihydroisoquinolin-2 (1H)-yl)methyl) piperidin-1-yl)-2-(2,6-dioxopiperidin-3-yl)-6-fluoroisoindoline-1,3-dione

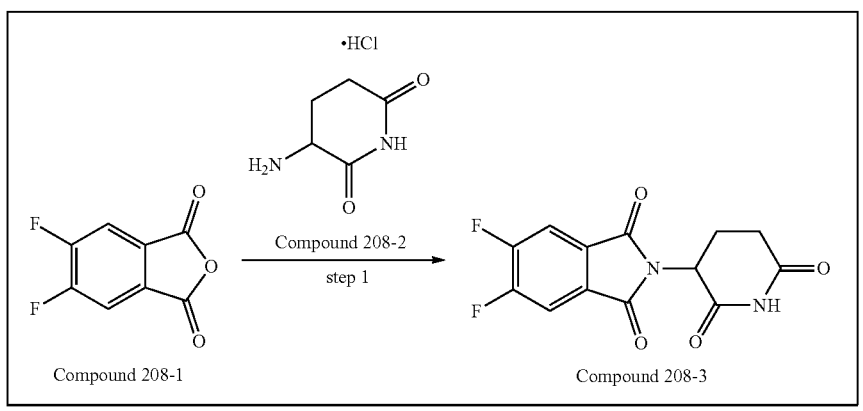

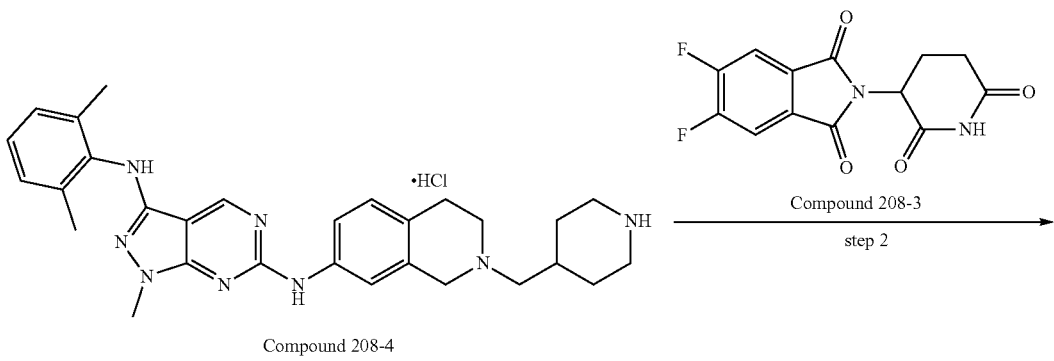

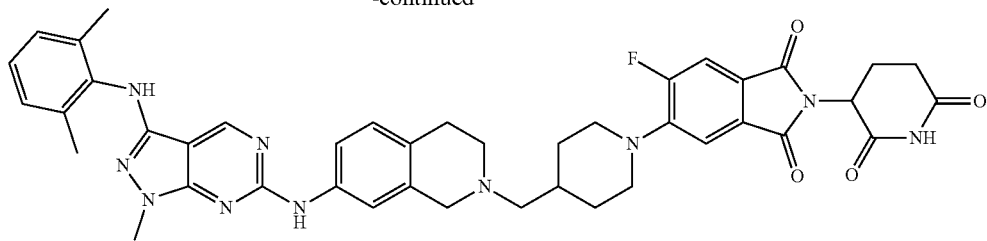

Compound 208

Step 1: Synthesis of 2-(2,6-dioxopiperidin-3-yl)-5,6-difluoroisoindoline-1,3-dione A mixture of Compound 208-1 (BLD, BD10776) (5,6-difluoroisobenzofurane-1,3-dione) (500 mg, 3.621 mmol), Compound 208-2 (Combi-Blocks, QA-9228) (3-aminopiperidin-2,6-one hydrochloride) (596 g, 3.62 mmol), and potassium acetate (710 mg, 7.24 mmol) was added with acetic acid (50 mL) and fluxed at 120° C. for 6 hours. The reaction mixture was quenched and the solvent was evaporated in a vacuum. The residue was added with water (150 mL) and stirred for 1 hour. The solid thus formed was filtered under suction and dried in a high vacuum to afford Compound 208-3 as a purple solid (825 mg, 2.80 mmol, 77%).

Step 2: Synthesis of 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)-6-fluoroisoindoline-1,3-dione (Compound 208)

A solution of Compound 208-4 (identical to Compound 28-4) (20.0 mg, 0.0375 mmol) in DMSO (1 mL) was added with Compound 208-3 (13.2 mg, 0.0450 mmol) and DIPEA (19.4 mg, 0.150 mmol) and stirred at 90° C. for 12 hours. When the reaction was completed as analyzed by TLC, the reaction mixture was quenched with water before extraction with EtOAc (25 mL×2) for the aqueous solution. The combined organic layer was washed with water (20 mL×2) and brine (20 mL×2). The organic layer was dried over sodium sulfate and the organic solvent evaporated in a vacuum. The crude product was purified by MPLC using a solvent mixture of 10% MeOH:DCM as an eluent to afford Compound 208 as a fluorescent green solid (14.0 mg, 0.0181 mmol, 48%).

Compound 209. 3-(5-(1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)-1-oxoisoindolin-2-yl)piperidin-2,6-one

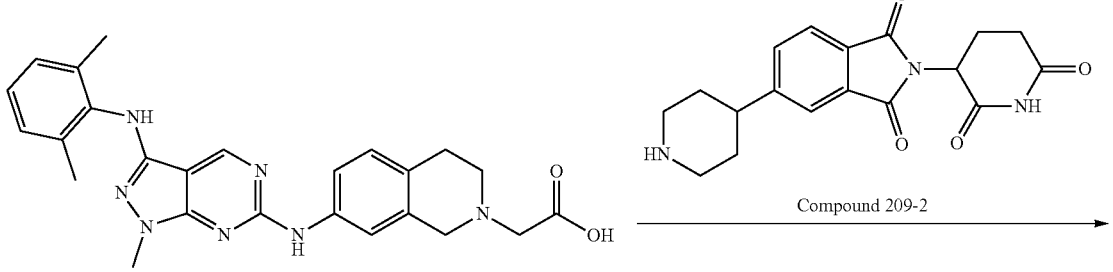

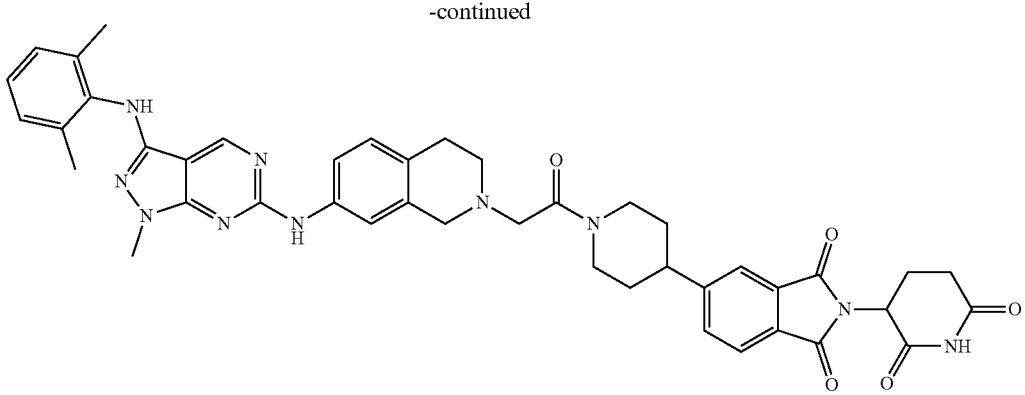

Compound 209

A solution of Compound 209-1 (identical to Compound 103-4) (10.0 mg, 0.0218 mmol) in DMF (2 mL) was added at room temperature with HATU (16.5 mg, 0.0436 mmol), Compound 209-2 (WO2022/081976A1) (7.15 mg, 0.0218 mmol), and TEA (8.81 mg, 0.0872 mmol). The resulting mixture was stirred at room temperature for 12 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the solvent was evaporated in a vacuum. The crude product was purified by MPLC using a solvent mixture of 5% MeOH: DCM to afford Compound 209 as a yellow solid (11.0 mg, 0.0143 mmol, 65%).

Compound 210. 5-(4-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl) methyl)piperidine-1-carbonyl)piperidin-1-yl)-2-(2,6-dioxopiperidin-3-yl)-6-fluoroisoindoline-1,3-dione

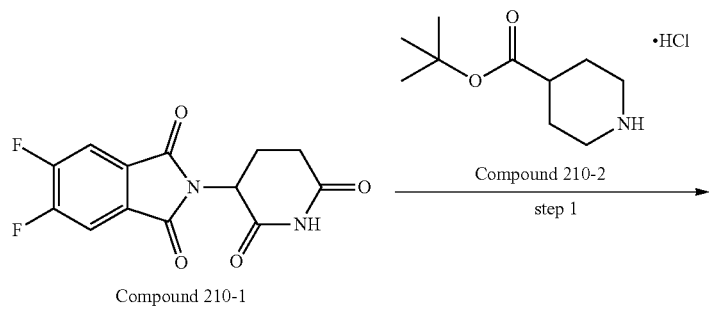

Compound 210-1

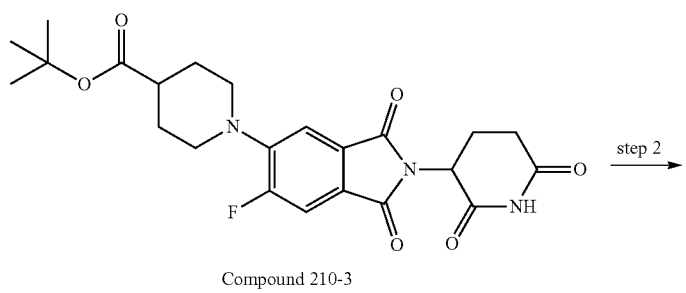

Compound 210-3

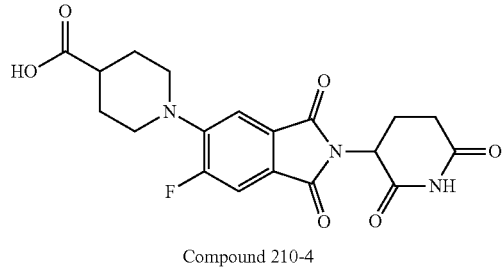

Compound 210-4

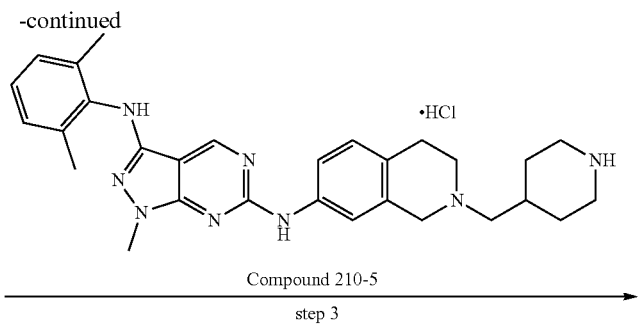

Compound 210-5 step 3

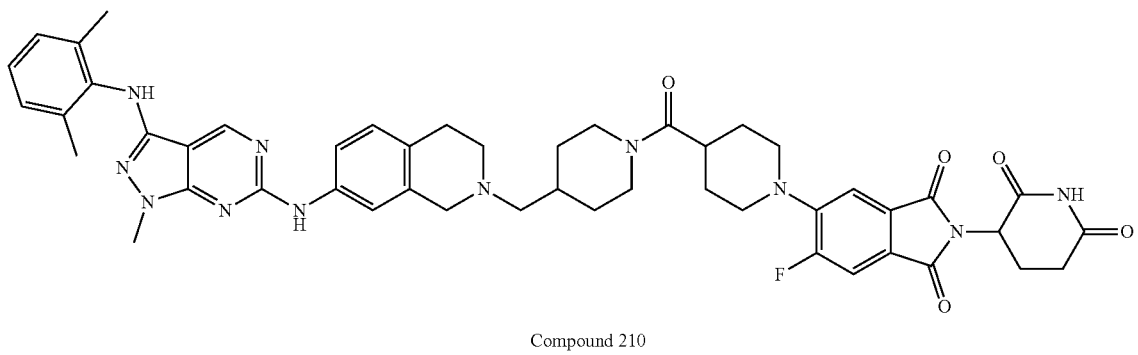

Compound 210

Step 1: Synthesis of tert-butyl 1-(2-(2,6-dioxopiperidin-3-yl)-6-fluoro-1,3-dioxoisoindolin-5-yl)piperidine-4-carboxylate A solution of Compound 210-2 (Combi-Blocks, QK-3943) (tert-butyl piperidine-4-carboxylate chloride) (31.4 mg, 0.169 mmol) in DMSO (2 mL) was added with Compound 210-1 (identical to Compound 208-3) (50.0 mg, 0.169 mmol) and DIPEA (87.5 mg, 0.676 mmol) and stirred at 90° C. for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 210-3 as a green solid (61.0 mg, 0.132 mmol, 78%).

Step 2: Synthesis of 1-(2-(2,6-dioxopiperidin-3-yl)-6-fluoro-1,3-dioxoisoindolin-5-yl)piperidine-4-carboxylic acid A solution of Compound 210-3 (61.0 mg, 0.132 mmol) in DCM (5 mL) was added with 40% TFA/DCM (2 mL) and stirred at room temperature for 2 hours. When the starting material was consumed as analyzed by TLC, the solvent was evaporated. The residue was washed with diethyl ether (5 mL). The product was dried in a vacuum to afford Compound 210-4 as a yellow solid (38.0 mg, 0.0942 mmol, 71%).

Step 3: Synthesis of 5-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-2-(2,6-dioxopiperidin-3-yl)-6-fluoroisoindoline-1,3-dione (Compound 210)

A solution of Compound 210-5 (identical to Compound 28-4) (15.0 mg, 0.0281 mmol) in DMF (2 mL) was added at room temperature with HATU (21.4 mg, 0.0562 mmol), Compound 210-4 (11.3 mg, 0.0281 mmol), and TEA (11.4 mg, 0.112 mmol). The resulting mixture was stirred at room temperature for 4 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the organic solvent evaporated in a vacuum. The crude product was purified by MPLC using a solvent mixture of 5% MeOH:DCM to afford Compound 210 as a yellow crystal (9.00 mg, 0.0102 mmol, 36%).

Compound 211. 5-((2-(4-((7-((3-((2,6-Dimethylphenyl)amino)-1-methyl-1H-pyrazolo[3,4-d]pyrimidin-6-yl)amino)-3,4-dihydroisoquinolin-2(1H)-yl)methyl)piperidin-1-yl)-2-oxoethyl)amino)-2-(2,6-dioxopiperidin-3-yl)-6-fluoroisoindoline-1,3-dione

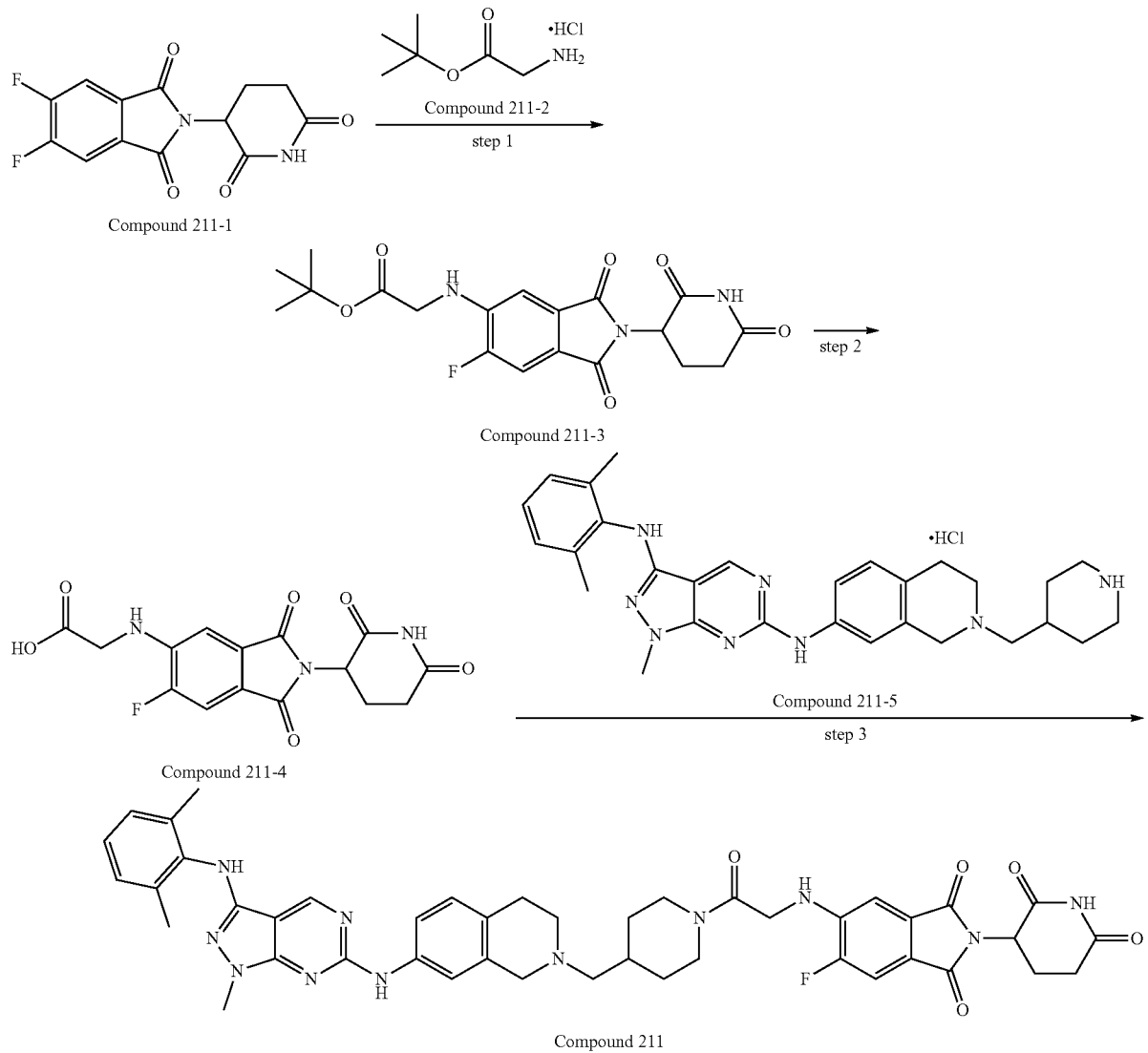

Step 1: Synthesis of tert-butyl (2-(2,6-dioxopiperidin-3-yl)-6-fluoro-1,3-dioxoisoindolin-5-yl)glycinate A solution of Compound 211-2 (TCI, G0254) (tert-butyl glycinate chloride) (28.3 mg, 0.169 mmol) in DMSO (2 mL) was added with Compound 211-1 (identical to Compound 208-3) (50.0 mg, 0.169 mmol) and DIPEA (87.5 mg, 0.676 mmol) and stirred at 90° C. for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 211-3 as a fluorescent green solid (32.0 mg, 0.0789 mmol, 46%).

Step 2: Synthesis of (2-(2,6-dioxopiperidin-3-yl)-6-fluoro-1,3-dioxoisoindolin-5-yl)glycine Compound 211-3 (30.0 mg, 0.0740 mmol) was added with 40% TFA/DCM (2 mL) and stirred at room temperature for 2 hours. When the starting material was consumed as analyzed by TLC, the solvent was evaporated. The residue was washed with diethyl ether (5 mL). The product was dried in a vacuum to afford Compound 211-4 as a brownish green solid (21.0 mg, 0.0601 mmol, 81%). The crude material was used in the next step without further purification.

Step 3: Synthesis of 5-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-2-(2,6-dioxopiperidin-3-yl)-6-fluoroisoindoline-1,3-dione (Compound 211)

A solution of Compound 211-5 (identical to Compound 28-4) (15.0 mg, 0.0281 mmol) in DMF (2 mL) was added at room temperature with HATU (21.4 mg, 0.0562 mmol), Compound 211-4 (9.81 mg, 0.0281 mmol), and TEA (11.4 mg, 0.112 mmol). The resulting mixture was stirred at room temperature for 4 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the organic solvent evaporated in a vacuum. The crude product was purified by MPLC using a solvent mixture of 5% MeOH:DCM to afford Compound 211 as a greenish brown solid (7.00 mg, 0.00845 mmol, 30%).

Compound 217. 5-(4-((7-((3-((2,6-Dibromophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione Compound 217

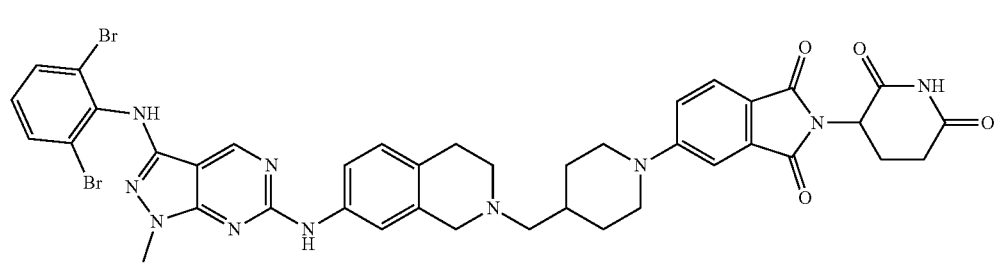

Compound 217 was synthesized in the same manner as in the synthesis procedure for Compound 195, with the exception of using 2,6-dibromoaniline instead of 2-bromo-6-methylaniline.

Compound 218. 5-(4-((7-((3-((2-Bromo-6-chlorophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione Compound 218

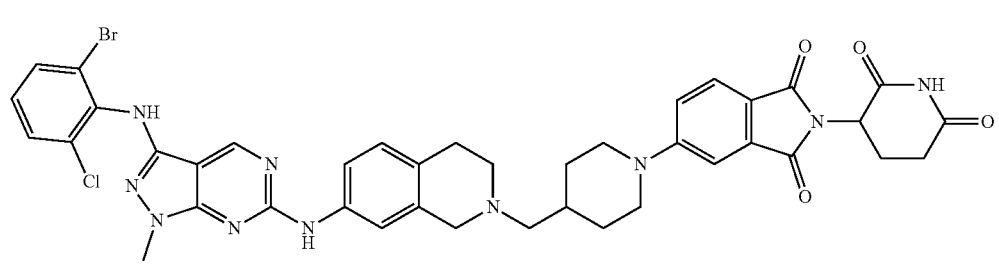

Compound 218 was synthesized in the same manner as in the synthesis procedure for Compound 195, with the exception of using 2-bromo-6-chloroaniline instead of 2-bromo-6-methylaniline.

Compound 219. 5-(4-((7-((3-((2-chloro-6-iodophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione

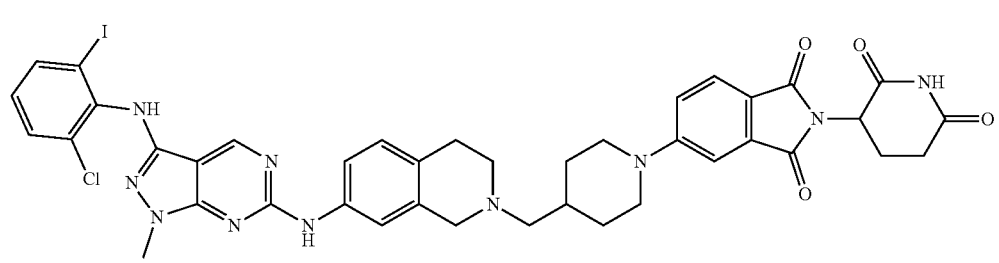

Compound 219

Compound 219 was synthesized in the same manner as in the synthesis procedure for Compound 195, with the exception of using 2-chloro-6-iodoaniline instead of 2-bromo-6-methylaniline.

Compound 220. 3-(5-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-6-fluoro-1-oxoisoindolin-2-yl)piperidin-2,6-one

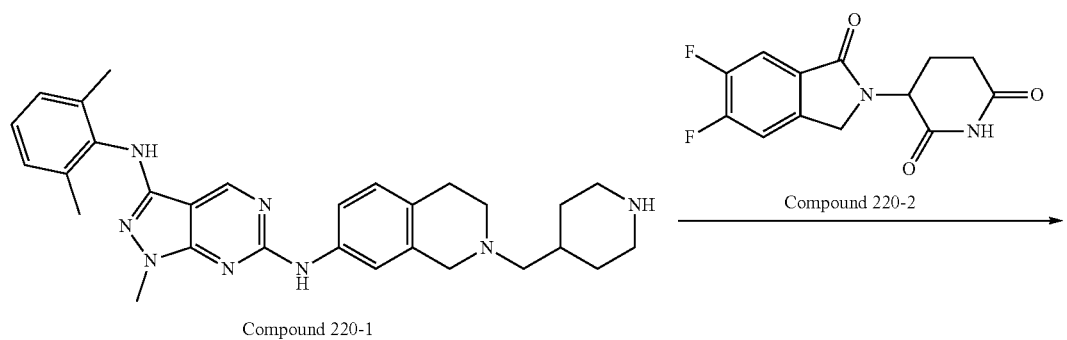

Compound 220-1

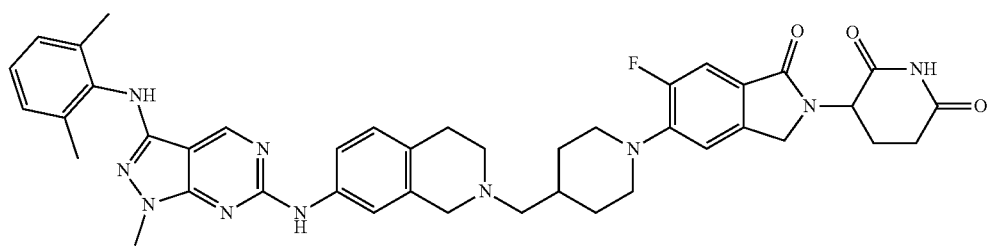

Compound 220

A solution of Compound 220-1 (identical to Compound 28-4) (20.0 mg, 0.0402 mmol) in DMSO (2 mL) was added at room temperature with Compound 220-2 (WO2020/118098) (10.2 mg, 0.0362 mmol) and DIPEA (26.0 mg, 0.201 mmol). The resulting mixture was stirred at 140° C. for 18 hours. When the product was formed as analyzed by TLC, the reaction mixture was added with water, subjected to extraction with EA (100 mL×3), and washed with water (3×) and brine. The organic layer was dried over sodium sulfate and purified by MPLC using MeOH/DCM (5%) to afford Compound 220 (2.5 mg, 0.0033 mmol, 9%).

Compound 221. 2-(2,6-dioxopiperidin-3-yl)-5-(4-((7-((3-((4-fluoro-2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione Compound 221

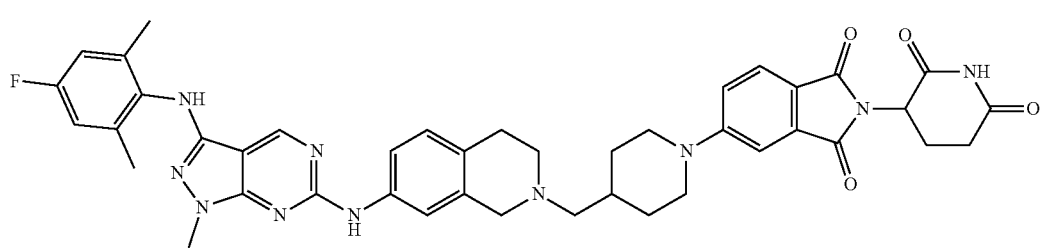

Compound 221 was synthesized in the same manner as in the synthesis procedure for Compound 195, with the exception of using 4-fluoro-2,6-dimethylaniline instead of 2-bromo-6-methylaniline.

Compound 222. 5-(4-(2-(4-(4-((3-((2,6-Dimethylphenyl)amino)-1-methyl-1H-pyrazolo[3,4-d]pyrimidin-6-yl)amino)phenyl)piperidin-1-yl)-2-oxoethyl)piperidin-1-yl)-2-(2,6-dioxopiperidin-3-yl)isoindoline-1,3-dione

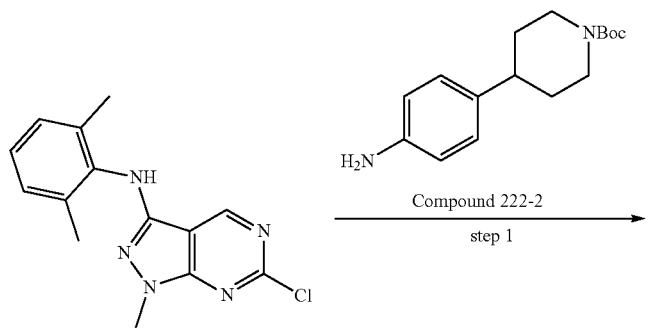

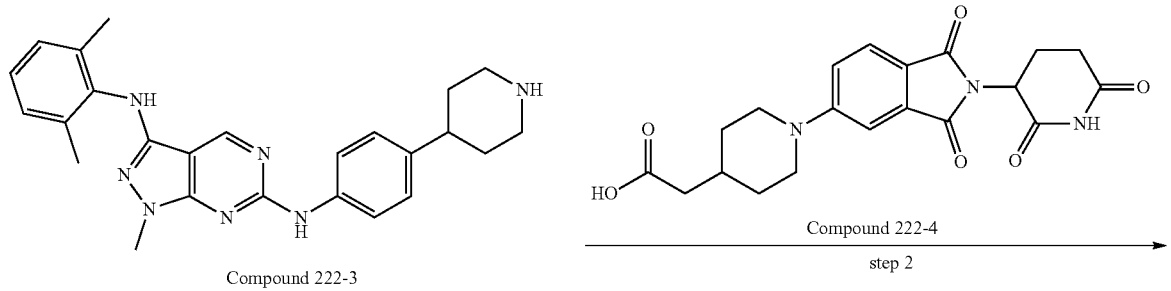

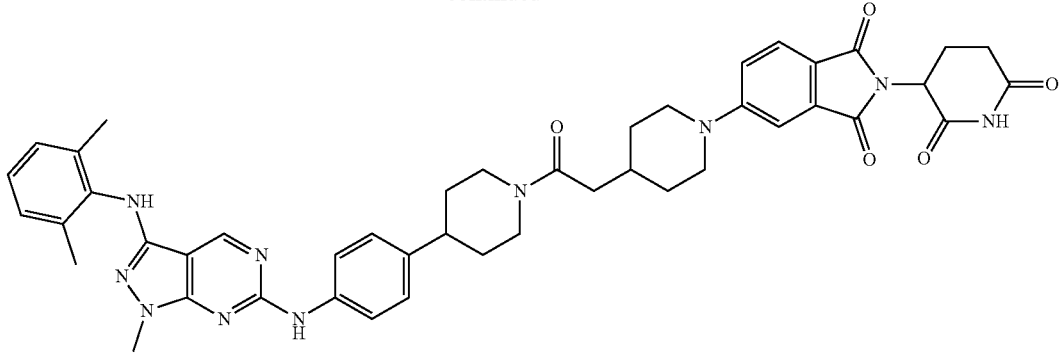

Compound 222

Step 1: Synthesis of N3-(2,6-dimethylphenyl)-1-methyl-N6-(4-(piperidin-4-yl)phenyl)-1H-pyrazolo[3,4-d]pyrimidine-3,6-diamine A solution of Compound 222-1 (WO2018/208132A1) (200 mg, 0.609 mmol) in IPA (3 mL) was added with tert-butyl 4-(4-aminophenyl)piperidine-1-carboxylate (Compound 222-2) (BLD Pharm, BD24501-25 g) (211 mg, 0.765 mmol), and PTSA (144 mg, 0.834 mmol). The resulting mixture was stirred at 90° C. for 12 hours and the solvent was removed in a vacuum. After addition of 4 M HCl in dioxane, the mixture was stirred at room temperature for 2 hours. The reaction mixture was concentrated and basified with sodium bicarbonate before extraction with EtOAc (3×15 mL). The white precipitates thus formed were dried in a vacuum to afford Compound 222-3 as a grayish yellow solid (197 mg, 0.461 mmol, 66%).

Step 2: Synthesis of 5-(4-(2-(4-(4-(4-((3-((2,6-dimethylphenyl)amino)-1-methyl-1H-pyrazolo[3,4-d]pyrimidin-6-yl)amino)phenyl)piperidin-1-yl)-2-oxoethyl)piperidin-1-yl)-2-(2,6-dioxopiperidin-3-yl)isoindoline-1,3-dione (Compound 222)

A solution of Compound 222-3 (15 mg, 0.035 mmol) in DMF (1 mL) was added with Compound 222-4 (WO2021/083949) (14 mg, 0.035 mmol), EDCI (17 mg, 0.088 mmol), HOBt (7 mg, 0.053 mmol), and DIPEA (37 μL, 0.210 mmol). The resulting mixture was stirred at room temperature for 12 hours. After completion of the reaction, the reaction mixture was quenched with water, extracted with EtOAc (3×15 mL), and washed with water (3×) and brine. The pooled organic layer was dried over sodium sulfate and filtered, and the solvent was evaporated in a vacuum. The residue was purified by MPLC using 5% MeOH/DCM to afford Compound 222 as a grayish yellow solid (10 mg, 0.012 mmol, 35%).

Compound 225. 5-(4-(2-(4-(4-(4-((3-((2,6-dimethylphenyl)amino)-1-methyl-1H-pyrazolo[3,4-d]pyrimidin-6-yl)amino)phenyl)piperidin-1-yl)-2-oxoethyl)piperazin-1-yl)-2-(2,6-dioxopiperidin-3-yl)isoindoline-1,3-dione

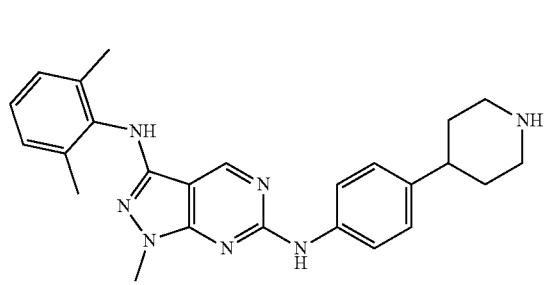

Compound 225-1

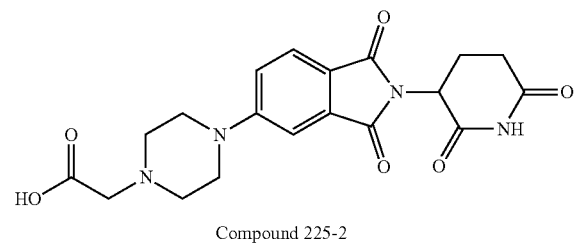

Compound 225-2

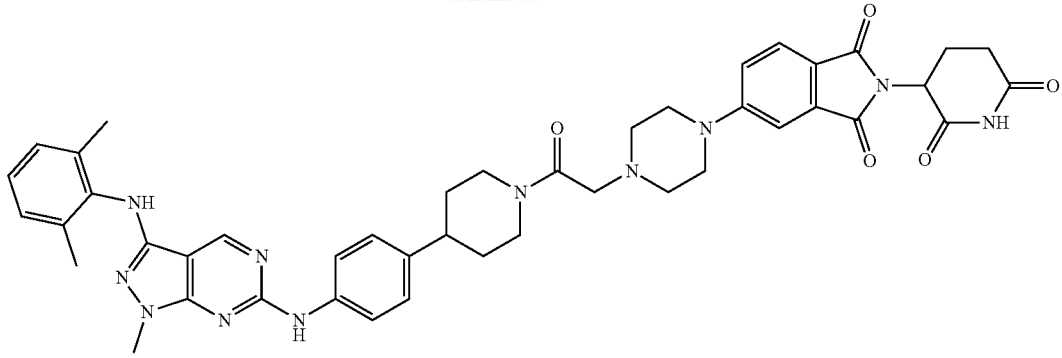

Compound 225

A solution of Compound 225-1 (identical to Compound 222-3) (15 mg, 0.035 mmol) in DMF (1 mL) was added with Compound 225-2 (identical to Compound 18-2) (14 mg, 0.035 mmol), HATU (27 mg, 0.070 mmol), and Et₃N (15 µL, 0.105 mmol). The resulting mixture was stirred at room temperature for 12 hours. After completion of the reaction, the reaction mixture was quenched with water, extracted with EtOAc (3×15 mL), and washed with water (3×) and brine. The pooled organic layer was dried over sodium sulfate and filtered, and the solvent was evaporated in a vacuum. The residue was purified by MPLC using 5% MeOH/DCM to afford Compound 225 as a grayish yellow solid (15 mg, 0.019 mmol, 53%).

Compound 226. 5-(4-(2-(4-(4-(4-((3-((2,6-Dimethylphenyl)amino)-1-methyl-1H-pyrazolo[3,4-d]pyrimidin-6-yl)amino)-2-fluorophenyl)piperidin-1-yl)-2-oxoethyl)piperazin-1-yl)-2-(2,6-dioxopiperidin-3-yl)isoindoline-1,3-dione

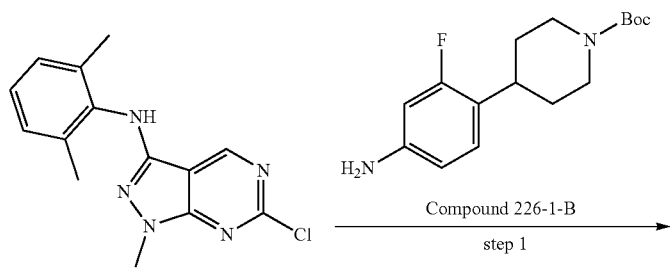

Compound 226-1-A

Compound 226-1-B step 1

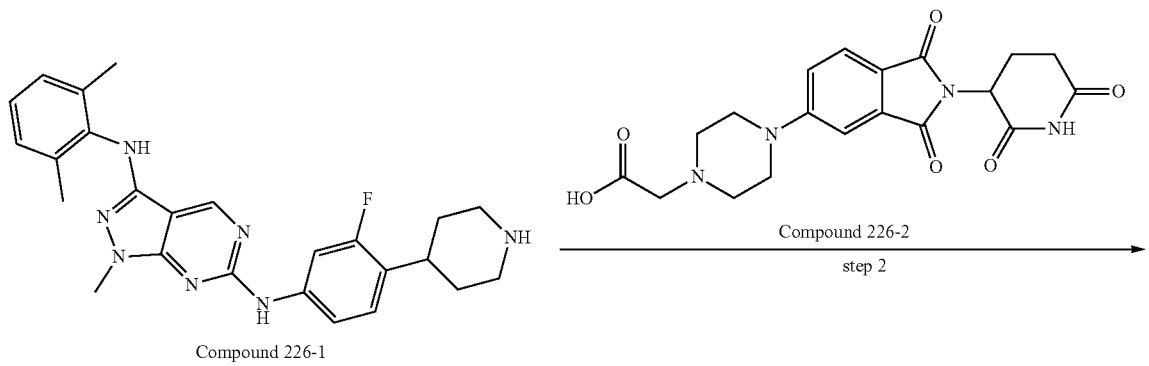

Compound 226-1

Compound 226-2 step 2

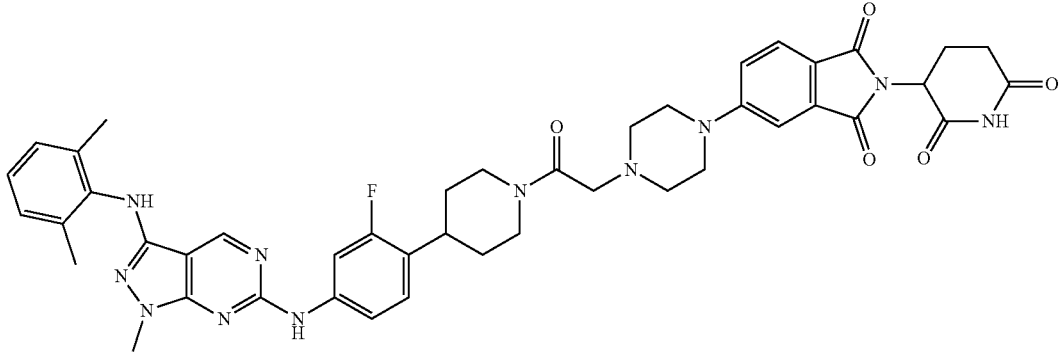

Compound 226

Step 1: Synthesis of N3-(2,6-dimethylphenyl)-N6-(3-fluoro-4-(piperidin-4-yl)phenyl)-1-methyl-1H-pyrazolo[3,4-d]pyrimidine-3,6-diamine A solution of Compound 226-1-A (Korean Patent No. 2128018) (70 mg, 0.24 mmol), pTSA (42 mg, 0.24 mmol) in IPA (1 mL) was added with Compound 226-1-B (Combi-blocks, QY-7014) (tert-butyl 4-(4-amino-2-fluorophenyl)piperidine-1-carboxylate) (71 mg, 0.24 mmol), and the resulting mixture was stirred at 95° C. for 16 hours. The reaction mixture was concentrated and triturated with ether to afford Compound 226-1 (92 mg, 85%).

Step 2: Synthesis of 5-(4-(2-(4-(4-((3-((2,6-dimethylphenyl)amino)-1-methyl-1H-pyrazolo[3,4-d]pyrimidin-6-yl)amino)-2-fluorophenyl)piperidin-1-yl)-2-oxoethyl)piperazin-1-yl)-2-(2,6-dioxopiperidin-3-yl)isoindoline-1,3-dione (Compound 226)

A solution of Compound 226-1 (15 mg, 0.034 mmol) in DMF (1 mL) was added with Compound 226-2 (identical to Compound 225-2) (13 mg, 0.034 mmol), HATU (26 mg, 0.067 mmol), and Et$_3$N (14 μL, 0.101 mmol). The resulting mixture was stirred at room temperature for 12 hours. After completion of the reaction, the reaction mixture was quenched with water, extracted with EtOAc (3×15 mL), and washed with water (3×) and brine. The pooled organic layer was dried over sodium sulfate and filtered, and the solvent was evaporated in a vacuum. The residue was purified by MPLC using 5% MeOH/DCM to afford Compound 226 as a grayish yellow (14 mg, 0.017 mmol, 50%).

Compound 227. 5-(4-(2-(4-(4-((3-((2,6-dimethylphenyl)amino)-1-methyl-1H-pyrazolo[3,4-d]pyrimidin-6-yl)amino)-2-fluorophenyl)piperidin-1-yl)-2-oxoethyl)piperidin-1-yl)-2-(2,6-dioxopiperidin-3-yl)isoindoline-1,3-dione

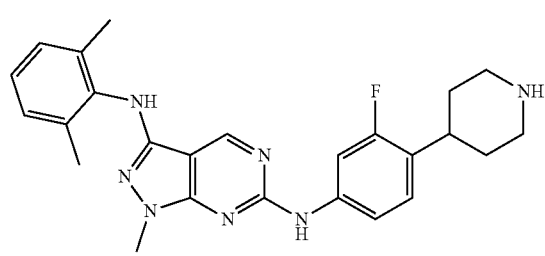

Compound 227-1

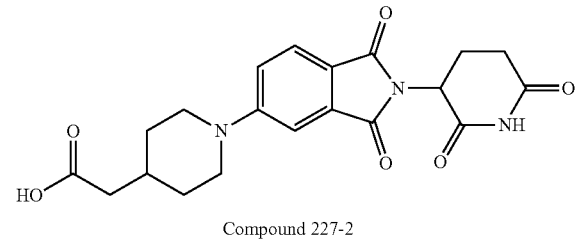

Compound 227-2

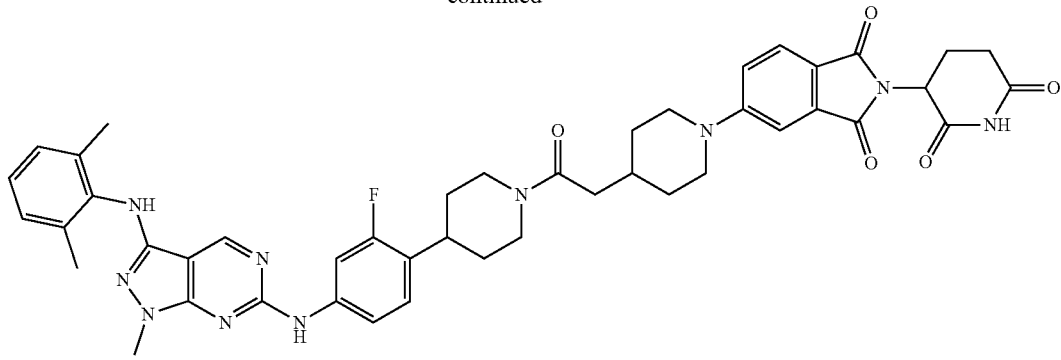

Compound 227

A solution of Compound 227-1 (identical to Compound 226-1) (10 mg, 0.022 mmol) in DMF (1 mL) was added with Compound 227-2 (identical to Compound 222-4) (9 mg, 0.022 mmol), HATU (17 mg, 0.045 mmol), and Et₃N (9 µL, 0.067 mmol). The resulting mixture was stirred at room temperature for 12 hours. After completion of the reaction, the reaction mixture was quenched with water, extracted with EtOAc (3×15 mL), and washed with water (3×) and brine. The pooled organic layer was dried over sodium sulfate and filtered, and the solvent was evaporated in a vacuum. The residue was purified by MPLC using 5% MeOH/DCM to afford Compound 227 as a grayish yellow (7 mg, 0.008 mmol, 38%).

Compound 228. 5-(3-(4-(4-((3-((2,6-dimethylphenyl)amino)-1-methyl-1H-pyrazolo[3,4-d]pyrimidin-6-yl)amino)phenyl)piperidine-1-carbonyl)azetidin-1-yl)-2-(2,6-dioxopiperidin-3-yl)isoindoline-1,3-dione

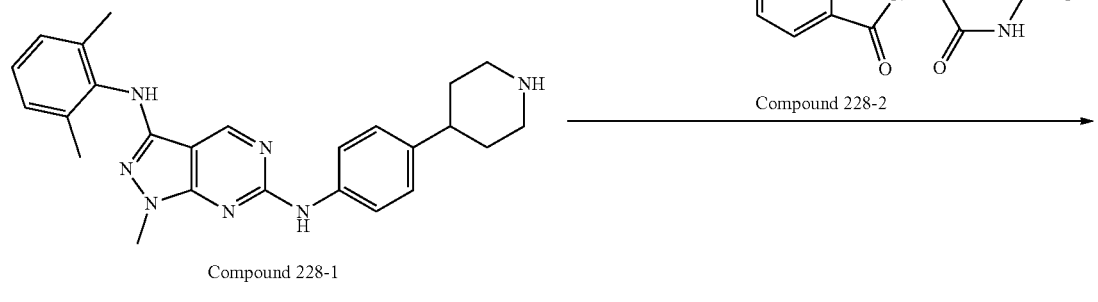

Compound 228-1

Compound 228-2

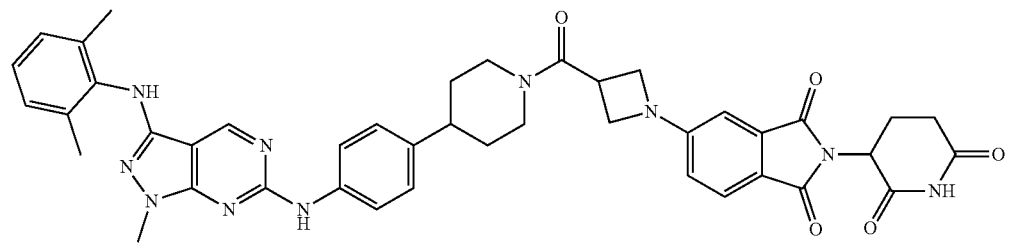

Compound 228

A solution of Compound 228-1 (identical to Compound 222-3) (15 mg, 0.035 mmol) in DMF (1 mL) was added with Compound 228-2 (identical to Compound 27-2) (13 mg, 0.035 mmol), HATU (27 mg, 0.070 mmol), and Et$_3$N (15 μL, 0.105 mmol). The resulting mixture was stirred at room temperature for 12 hours. After completion of the reaction, the reaction mixture was quenched with water, extracted with EtOAc (3×15 mL), and washed with water (3×) and brine. The pooled organic layer was dried over sodium sulfate and filtered, and the solvent was evaporated in a vacuum. The residue was purified by MPLC using 5% MeOH/DCM to afford Compound 228 as a grayish yellow (6 mg, 0.008 mmol, 22%).

Compound 229. 5-(3-(4-(4-((3-((2,6-dimethylphenyl)amino)-1-methyl-1H-pyrazolo[3,4-d]pyrimidin-6-yl)amino)-2-fluorophenyl)piperidine-1-carbonyl)azetidin-1-yl)-2-(2,6-dioxopiperidin-3-yl)isoindoline-1,3-dione

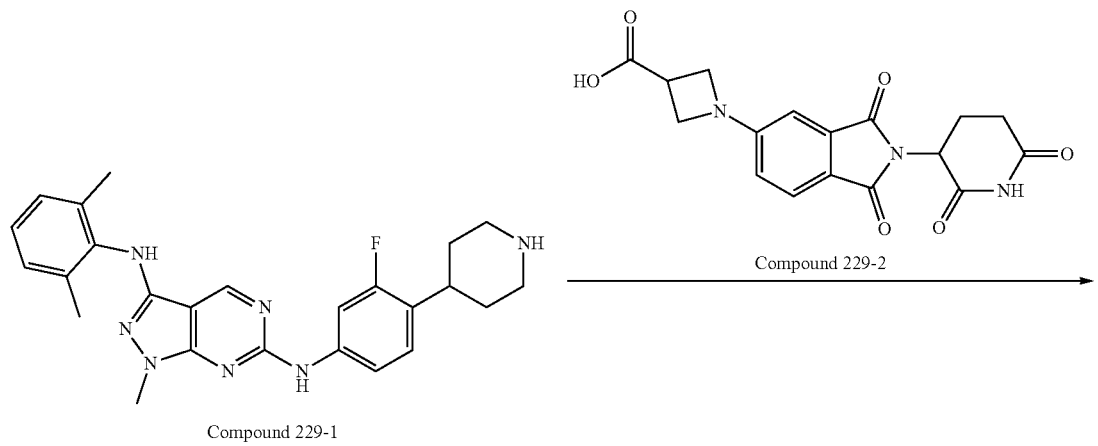

Compound 229-1

Compound 229-2

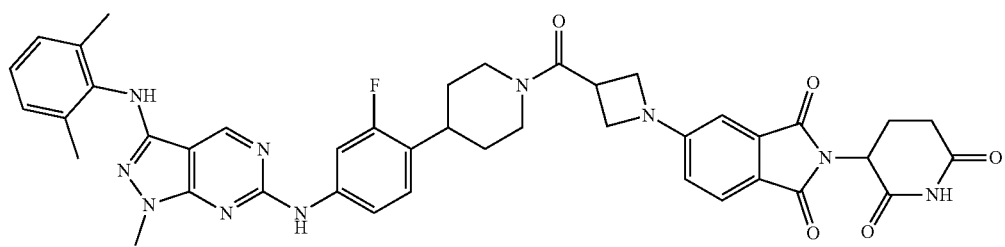

Compound 229

A solution of Compound 229-1 (identical to Compound 226-1) (10 mg, 0.022 mmol) in DMF (1 mL) was added with Compound 229-2 (identical to Compound 228-2) (8 mg, 0.022 mmol), HATU (17 mg, 0.045 mmol), and Et$_3$N (9 μL, 0.067 mmol). The resulting mixture was stirred at room temperature for 12 hours. After completion of the reaction, the reaction mixture was quenched with water, extracted with EtOAc (3×15 mL), and washed with water (3×) and brine. The pooled organic layer was dried over sodium sulfate and filtered, and the solvent was evaporated in a vacuum. The residue was purified by MPLC using 5% MeOH/DCM to afford Compound 229 as a grayish yellow solid (4 mg, 0.005 mmol, 23%).

Compound 230. 5-(4-((4-(4-((3-((2,6-Dimethylphenyl)amino)-1-methyl-1H-pyrazolo[3,4-d]pyrimidin-6-yl)amino)phenyl)-3,6-dihydropyridin-1 (2H)-yl) methyl)piperidin-1-yl)-2-(2,6-dioxopiperidin-3-yl) isoindoline-1,3-dione

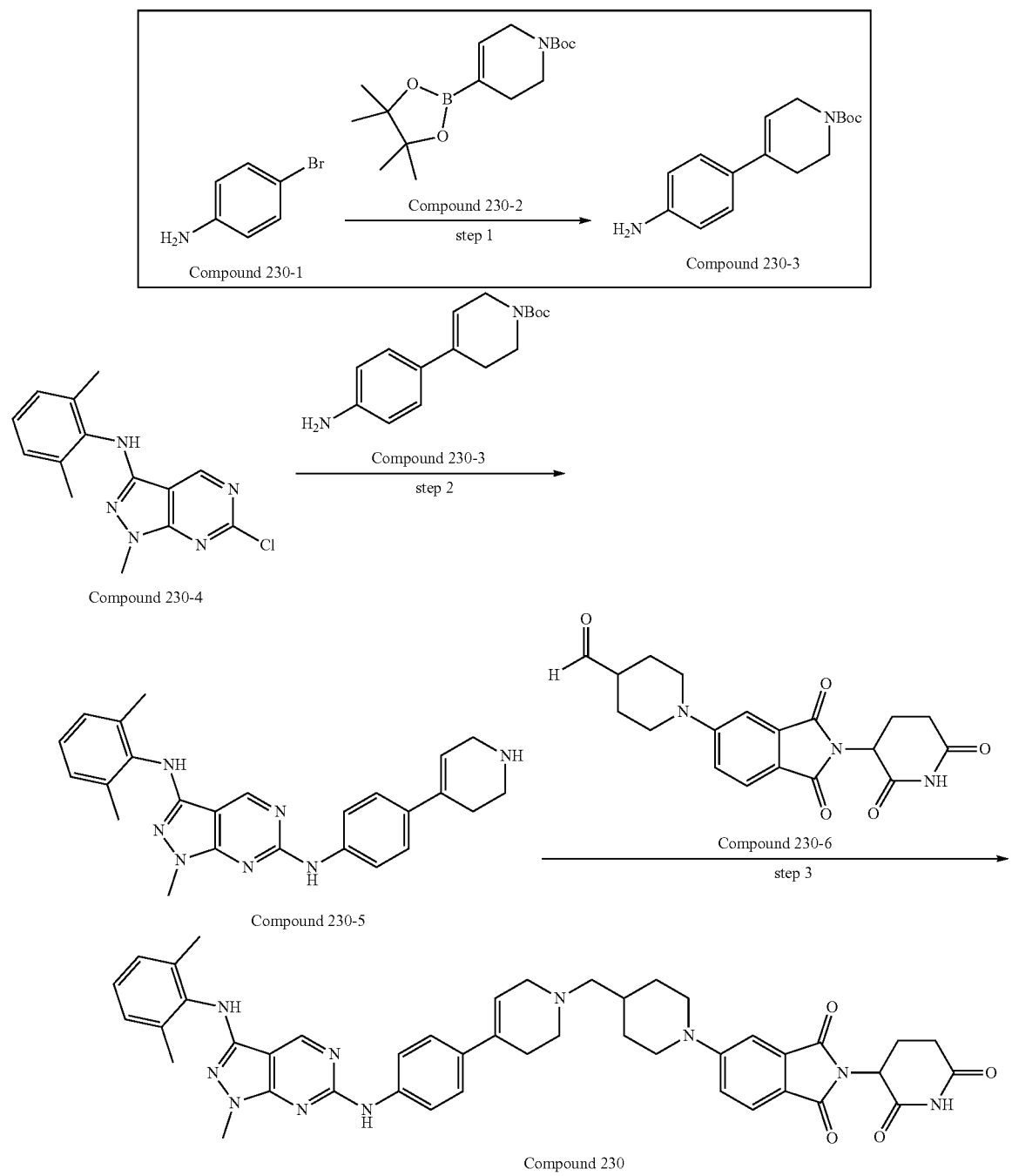

Step 1: Synthesis of tert-butyl 4-(4-aminophenyl)-3, 6-dihydropyridine-1 (2H)-carboxylate A solution of 4-bromoaniline (Compound 230-1) (TCI, B1393) (200 mg, 1.17 mmol) in dioxane/water (2/2 mL) was added with tert-butyl 4-(4,4,5,5-tetramethyl-1,3,2-dioxaborolan-2-yl)-3,6-dihydropyridine-1 (2H)-carboxylate (Compound 230-2) (BLD Pharm, BD33046) (397 mg, 1.29 mmol), Na$_2$CO$_3$ (372 mg, 3.51 mmol), Pd(dppf)$_2$Cl$_2$·DCM (47 mg, 0.0059 mmol), and DPPF (33 mg, 0.059 mmol). The mixture was stirred at 80° C. for 15 hours in a nitrogen atmosphere. After completion of the reaction, the reaction mixture was quenched with water, subjected to extraction with EtOAc (3×30 mL), and washed with water (3×). The pooled organic layer was dried over sodium sulfate and filtered, and the solvent was evaporated in a vacuum. The residue was purified by MPLC using 50% EtOAc/HEX to afford Compound 230-3 as an off-white solid (265 mg, 0.966 mmol, 82%).

Step 2: Synthesis of N3-(2,6-dimethylphenyl)-1-methyl-N6-(4-(1,2,3,6-tetrahydropyridin-4-yl)phenyl)-1H-pyrazolo[3,4-d]pyrimidine-3,6-diamine A solution of Compound 230-4 (identical to Compound 222-1) (70 mg, 0.243 mmol), Compound 230-3 (67 mg, 0.243 mmol) in i-PrOH (1 mL) was added with MeSO₃H (42 mg, 0.243 mmol). The mixture was heated to 95° C. and stirred at the same temperature for 15 hours. After completion of the reaction, the reaction mixture was concentrated and subjected to extraction with EtOAc (3×20 mL) and saturated NaHCO₃ (10 mL). The white precipitates thus formed were dried in a vacuum to afford Compound 230-5 as a grayish yellow solid (27 mg, 0.063 mmol, 26%).

Step 3: Synthesis of 5-(4-((4-(4-((3-((2,6-dimethylphenyl)amino)-1-methyl-1H-pyrazolo[3,4-d]pyrimidin-6-yl)amino)phenyl)-3,6-dihydropyridin-1(2H)-yl)methyl)piperidin-1-yl)-2-(2,6-dioxopiperidin-3-yl)isoindoline-1,3-dione (Compound 230)

A solution of Compound 230-5 (20 mg, 0.047 mmol) in MeOH (1 mL) was added with Compound 230-6 (identical to Compound 195-10) (17 mg, 0.047 mmol) and AcOH (3 μL, 0.047 mmol). The resulting mixture was stirred at room temperature for 12 hours. Addition of NaBH₃CN (4 mg, 0.070 mmol) was followed by stirring at room temperature for 1 hour. After completion of the reaction, the reaction mixture was quenched with water, extracted with EtOAc (3×15 mL), and washed with water (3×) and NaHCO₃. The pooled organic layer was dried over sodium sulfate and filtered, and the solvent was evaporated in a vacuum. The residue was purified by MPLC using 5% MeOH/DCM to afford Compound 230 as a grayish yellow solid (11 mg, 0.014 mmol, 30%).

Compound 231. 5-(4-((4-(4-((3-((2,6-Dimethylphenyl)amino)-1-methyl-1H-pyrazolo[3,4-d]pyrimidin-6-yl)amino)-3-fluorophenyl)piperidin-1-yl)methyl)piperidin-1-yl)-2-(2,6-dioxopiperidin-3-yl)isoindoline-1,3-dione

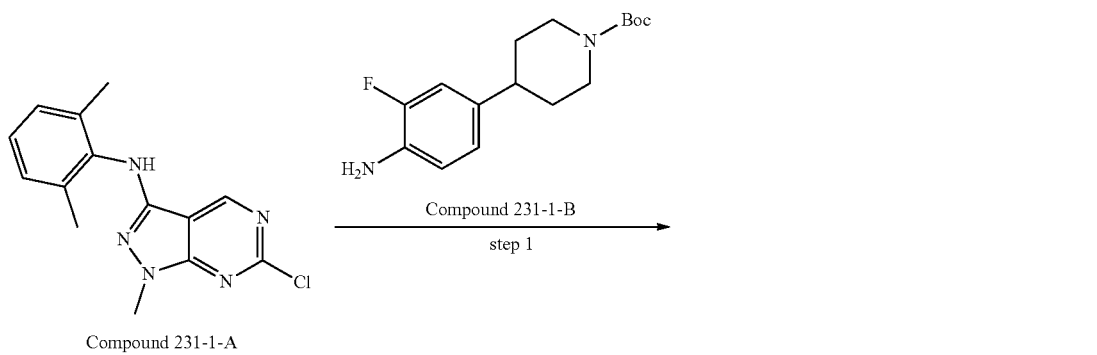

Compound 231-1-A

Compound 231-1-B step 1

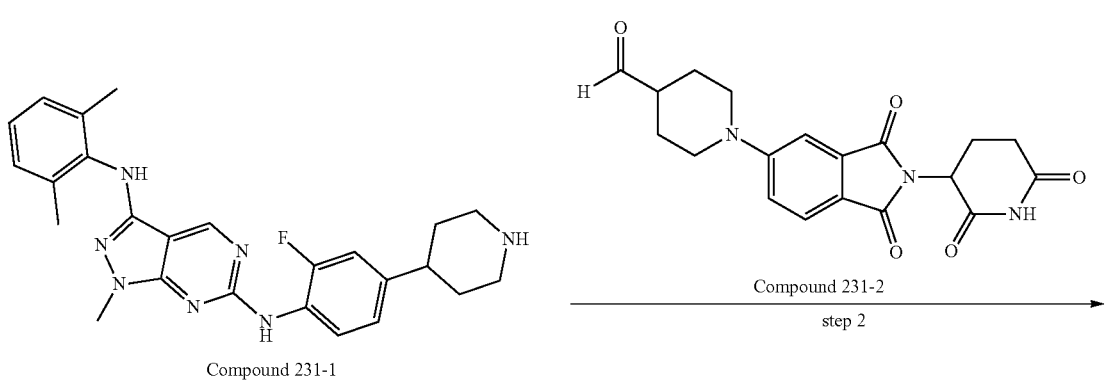

Compound 231-1

Compound 231-2 step 2

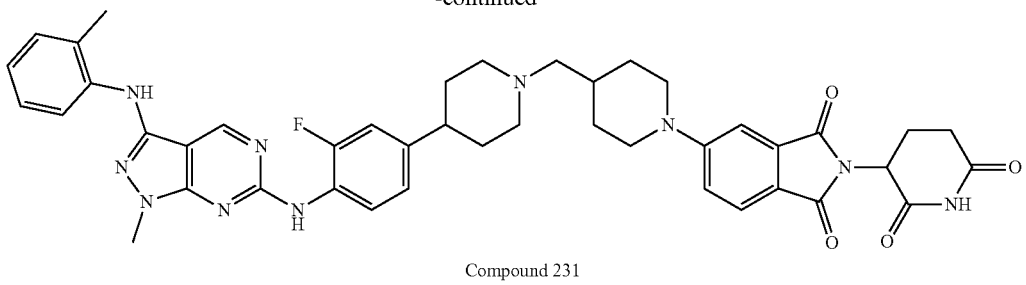

Compound 231

Step 1: Synthesis of N3-(2,6-dimethylphenyl)-N6-(2-fluoro-4-(piperidin-4-yl)phenyl)-1-methyl-1H-pyrazolo[3,4-d]pyrimidine-3,6-diamine A solution of Compound 231-1-A (Korean Patent No. 2128018) (70 mg, 0.24 mmol) and pTSA (42 mg, 0.24 mmol) in IPA (1 mL) was added with Compound 231-1-B (Chemscene, CS-0096060) (tert-butyl 4-(4-amino-2-fluorophenyl)piperidine-1-carboxylate) (71 mg, 0.24 mmol). The resulting mixture was stirred at 95° C. for 16 hours. The reaction mixture was concentrated and triturated with ether to afford Compound 231-1 (91 mg, 85%).

Step 2: Synthesis of 5-(4-((4-(4-(3-((2,6-dimethylphenyl)amino)-1-methyl-1H-pyrazolo[3,4-d]pyrimidin-6-yl)amino)-3-fluorophenyl)piperidin-1-yl)methyl)piperidin-1-yl)-2-(2,6-dioxopiperidin-3-yl)isoindoline-1,3-dione (Compound 231)

A solution of Compound 231-1 (20 mg, 0.045 mmol) in MeOH (1 mL) was added with Compound 231-2 (identical to Compound 230-6) (17 mg, 0.045 mmol) and AcOH (3 μL, 0.045 mmol). The resulting mixture was stirred at room temperature for 12 hours. Addition of NaBH$_3$CN (4 mg, 0.067 mmol) was followed by stirring at room temperature for 1 hour. After completion of the reaction, the reaction mixture was quenched with water, extracted with DCM (3×15 mL), and washed with water (3×) and NaHCO$_3$. The pooled organic layer was dried over sodium sulfate and filtered, and the solvent was evaporated in a vacuum. The residue was purified by MPLC using 5% MeOH/DCM to afford Compound 231 as a grayish yellow solid (11 mg, 0.014 mmol, 31%).

Compound 232. 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-(2,6-dioxopiperidin-3-yl)isoindoline-1,3-dione Compound 232-1

Compound 232-2

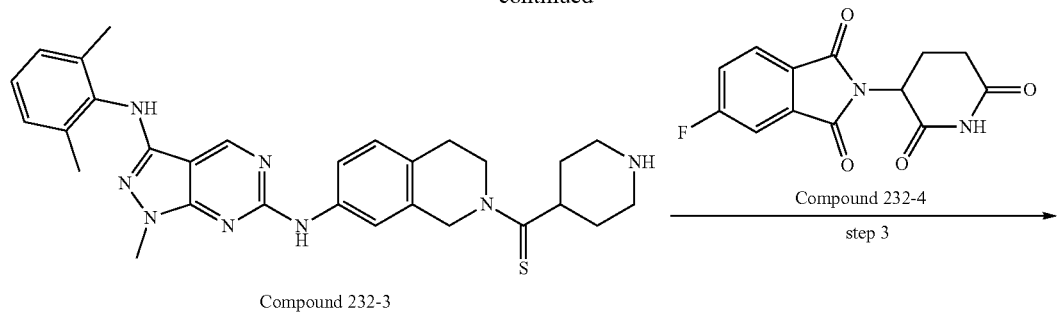

Compound 232-3

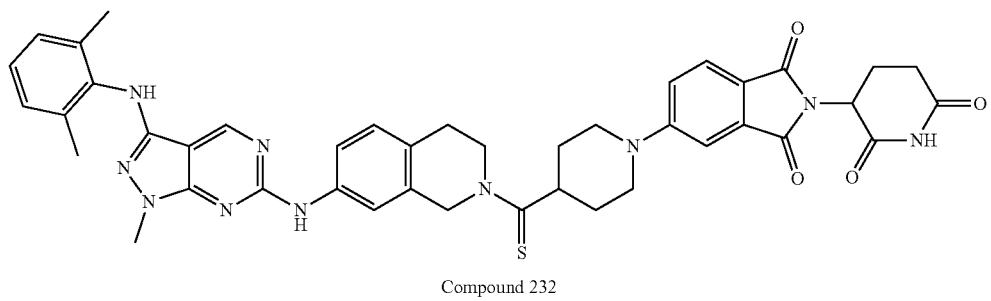

Compound 232

Step 1: Synthesis of tert-butyl 4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidine-1-carboxylate A solution of Compound 232-1 (identical to Compound 43-3) (300 mg, 0.491 mmol) in toluene was added at room temperature with a Lawesson reagent (298 mg, 0.737 mmol) and heated at 120° C. for 16 hours. When a new spot was formed as analyzed by TLC, the reaction mixture was cooled and quenched with water. The aqueous was subjected to extraction with EA (15 mL×2), and the pooled organic layer was dried over sodium sulfate and filtered, and the solvent was evaporated in a vacuum. The residue was purified by MPLC using a solvent mixture of 5% MeOH:MC to afford Compound 232-2 as a slightly impure yellow oil (260 mg, 0.415 mmol, 84%).

Step 2: Synthesis of (7-((3-((2,6-dimethylphenyl)amino)-1-methyl-1H-pyrazolo[3,4-d]pyrimidin-6-yl)amino)-3,4-dihydroisoquinolin-2 (1H)-yl) (piperidin-4-yl)methanethione A solution of Compound 232-2 (150 mg, 0.239 mmol) in DCM (25 mL) was added with 4N HCl/dioxane (0.150 mL, 0.598 mmol) and stirred for 1 hour. After completion of the reaction, the solvent was evaporated and the residual dioxane was traced with chloroform (20 ml). The residue was neutralized with a sodium bicarbonate solution before extraction with DCM (2×100 mL). The solvent was evaporated in a vacuum to afford the free base Compound 232-3 as an off-white solid (150 mg, 0.239 mg, 86%).

Step 3: Synthesis of 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-(2,6-dioxopiperidin-3-yl)isoindoline-1,3-dione (Compound 232)

A solution of Compound 232-3 (6.0 mg, 0.011 mmol) in DMSO (1 mL) was added at room temperature with Compound 232-4 (identical to Compound 2-1) (3.15 mg, 0.011 mmol) and DIPEA (5.90 mg, 0.046 mmol). The mixture was stirred at 90° C. for 12 hours. The resulting mixture was stirred at 90° C. for 12 hours. When the product was formed as analyzed by TLC, the reaction mixture was added with water, subjected to extraction with EA (50 mL×3), and washed with water (3×) and brine. The pooled organic layer was dried over sodium sulfate and purified by MPLC using 10% MeOH/MC (eluted at 4%) to afford Compound 232 as a yellow solid (2.50 mg, 0.0110 mmol, 28%).

Compound 233. 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-(2,6-dioxopiperidin-3-yl)-6-fluoroisoindoline-1,3-dione

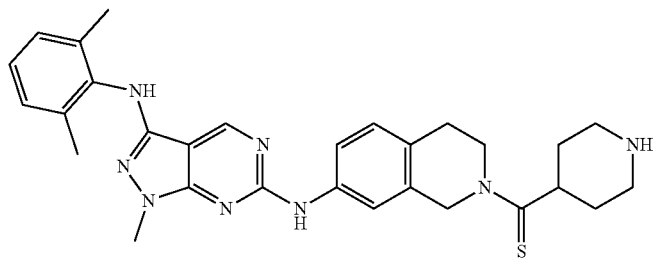

Compound 233-1

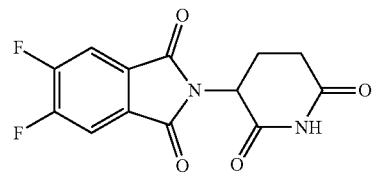

Compound 233-2

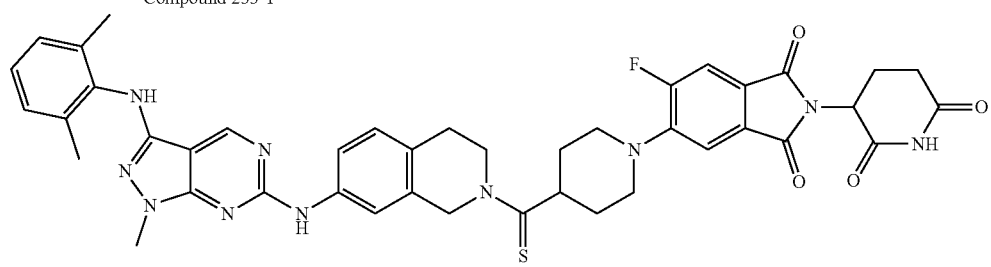

Compound 233

A solution of Compound 233-1 (identical to Compound 232-3) (10 mg, 0.019 mmol) in DMSO (1 mL) was added with Compound 233-2 (identical to Compound 208-3) (5.59 mg, 0.019 mmol) and DIPEA (9.83 µl, 0.057 mmol) and stirred at 90° C. for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 233 as a yellow solid (9.0 mg, 0.019 mmol, 60%).

Compound 234. 5-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidine-1-carbonyl)piperidin-1-yl)-2-(2,6-dioxopiperidin-3-yl)isoindoline-1,3-dione

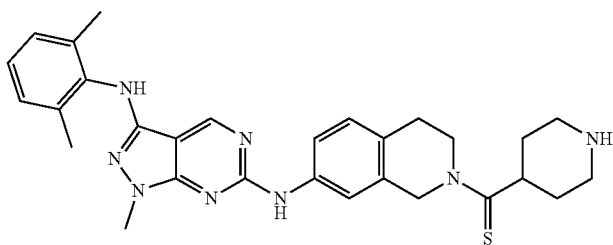

Compound 234-1

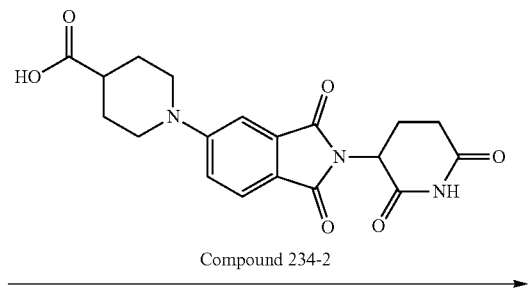

Compound 234-2

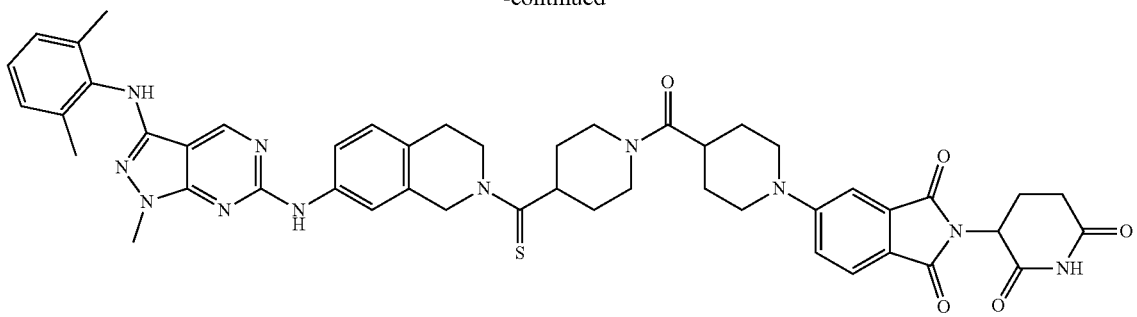

Compound 234

A solution of Compound 234-1 (identical to Compound 233-1) (10 mg, 0.019 mmol) in DMF (2 mL) was added at room temperature with HATU (14.4 mg, 0.0380 mmol), Compound 234-2 (identical to Compound 230-6) (8.05 mg, 0.021 mmol), and TEA (7.68 μl, 0.057 mmol)). The resulting mixture was stirred at room temperature for 12 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the solvent was evaporated in a vacuum. The crude product was purified by MPLC using a solvent mixture of 5% MeOH: DCM to afford Compound 234 as a yellow solid (8.0 mg, 0.019 mmol, 47%).

Compound 235. 5-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-oxoethyl)amino)-2-(2,6-dioxopiperidin-3-yl)isoindoline-1,3-dione

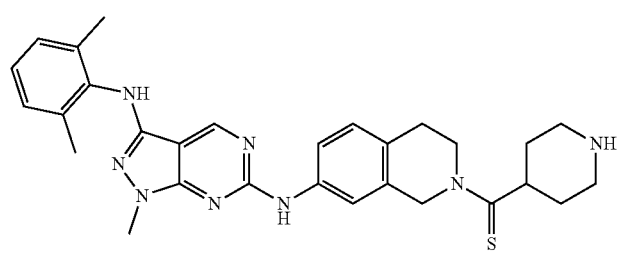

Compound 235-1

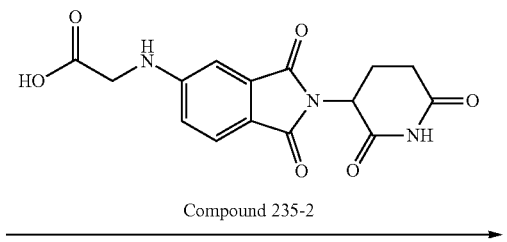

Compound 235-2

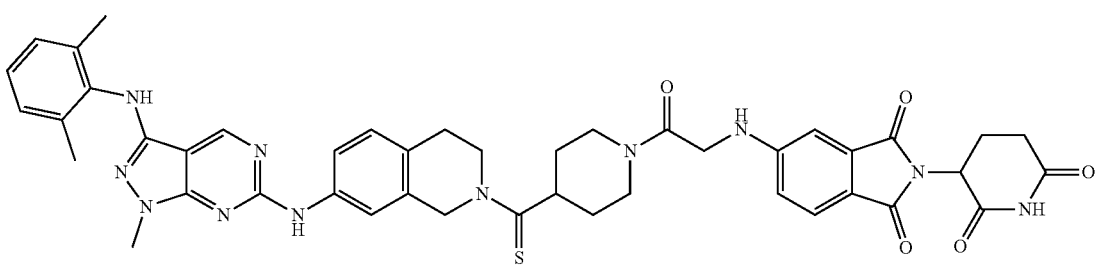

Compound 235

A solution of Compound 235-1 (identical to Compound 233-1) (10 mg, 0.019 mmol) in DMF (2 mL) was added at room temperature with HATU (14.4 mg, 0.038 mmol), Compound 235-2 (identical to Compound 12-1) (6.92 mg, 0.021 mmol), and TEA (7.68 µl, 0.057 mmol). The resulting mixture was stirred at room temperature for 12 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the solvent was evaporated in a vacuum. The crude product was purified by MPLC using a solvent mixture of 5% MeOH: DCM to afford Compound 235 as a yellow solid (11.0 mg, 0.0190 mmol 70%).

Compound 236. 5-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-oxoethoxy)-2-(2,6-dioxopiperidin-3-yl)isoindoline-1,3-dione

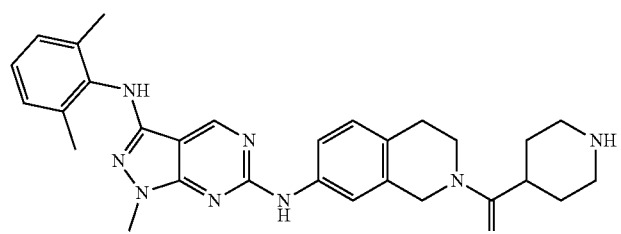

Compound 236-1

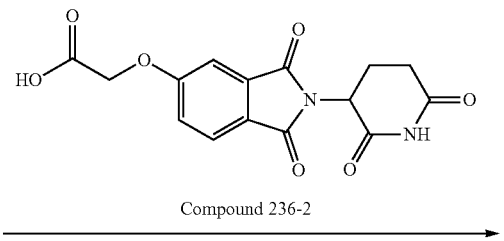

Compound 236-2

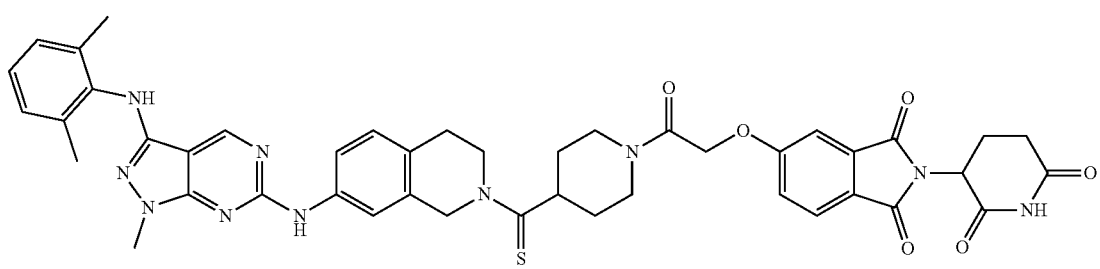

Compound 236

A solution of Compound 236-1 (identical to Compound 233-1) (20 mg, 0.038 mmol) in DMF (2 mL) was added at room temperature with HATU (28.9 mg, 0.076 mmol), Compound 236-2 (identical to Compound 205-2) (13.88 mg, 0.042 mmol), and TEA (0.015 ml, 0.114 mmol). The resulting mixture was stirred at room temperature for 12 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the solvent was evaporated in a vacuum. The crude product was purified by MPLC using a solvent mixture of 5% MeOH:DCM to afford Compound 236 as a yellow solid (11.0 mg, 0.0380 mmol, 35%).

Compound 237. 3-(5-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl) methyl)piperidin-1-yl)-1-oxoisoindolin-2-yl) piperidin-2,6-one
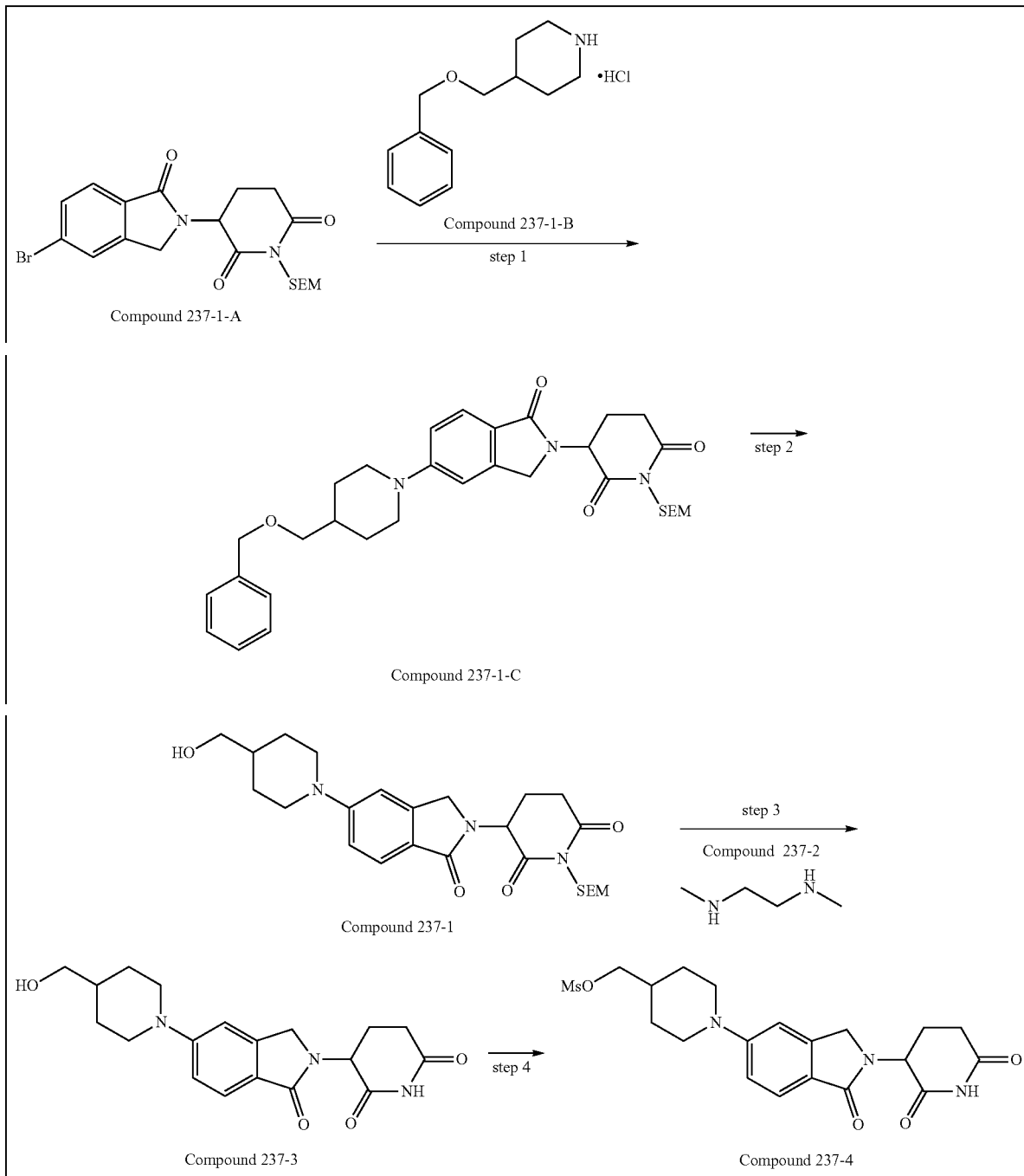

439

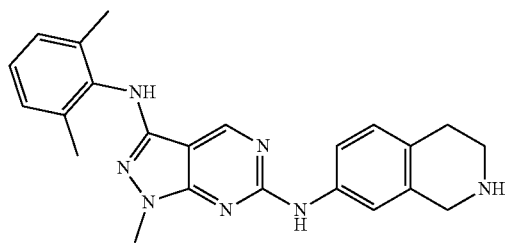

Compound 237-5

-continued

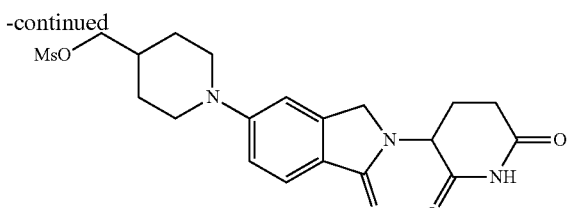

Compound 237-4 step 5

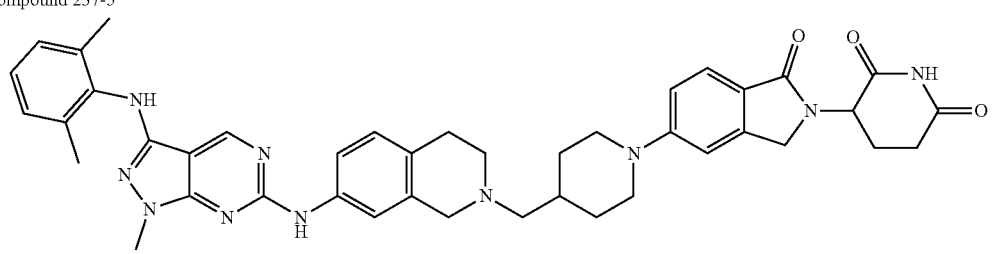

Compound 237

Step 1: Synthesis of 3-(5-(4-((benzyloxy)methyl)piperidin-1-yl)-1-oxoisoindolin-2-yl)-1-((2-(trimethylsilyl)ethoxy)methyl)piperidin-2,6-one A solution of Compound 237-1-A (identical to Compound 103-8) (280 mg, 0.618 mmol) in dioxane (3 mL) was added with Compound 237-1-B (BLD, BD00805044) (4-((benzyloxy)methyl)piperidine chloride) (179 mg, 0.741 mmol), Cs₂CO₃ (6241 mg, 0.7) mmol), RuPhos (58 mg, 0.124 mmol), and RuPhos Pd G2 (96 mg, 0.124 mmol). The resulting mixture was stirred at 100° C. for 16 hours in a nitrogen atmosphere. The progression of the reaction was monitored by TLC. Thereafter, the reaction mixture was quenched with water and separated into EA and water layers through Büchner funnel. The pooled organic layer was dried over Na₂SO₄ and the solvent was removed. The crude mixture was purified by silica gel column chromatography using EA/HEX as an eluent to afford Compound 237-1-C as an ivory solid (152 mg, 0.263 mmol).

Step 2: Synthesis of 3-(5-(4-(hydroxymethyl)piperidin-1-yl)-1-oxoisoindolin-2-yl)-1-((2-(trimethylsilyl)ethoxy)methyl)piperidin-2,6-one A solution of Compound 237-1-C (152 mg, 0.263 mmol) in MeOH was added at room temperature with 10% Pd/C (25 mg) and the resulting mixture was stirred at room temperature for 16 hours under a hydrogen balloon pressure. When the starting material was completely consumed as analyzed by TLC, the reaction mixture was filtered through a celite bed. Removal of MeOH by concentration afforded Compound 237-1 as a white oil (105 mg, 0.215 mmol, 82%).

Step 3: Synthesis of 3-(5-(4-(hydroxymethyl)piperidin-1-yl)-1-oxoisoindolin-2-yl)piperidine-2,6-dione A solution of Compound 237-1 (50 mg, 0.103 mmol) in MeCN (5 mL) was added at 0° C. with methane sulfonic acid (26.6 μl, 0.410 mmol) and stirred at room temperature for 12 hours. The mixture was cooled to 0° C. and added slowly with a half amount of Compound 237-2 (Sigma Aldrich D157805) (N1,N2-dimethylethane-1,2-diamine; 18.08 mg, 0.205 mmol) and then with TEA (111 μl, 0.820 mmol), followed by stirring for 2 hours. Then, the other half amount of Compound 237-2 (Sigma Aldrich D157805) (N1,N2-dimethylethane-1,2-diamine; 18.08 mg, 0.205 mmol) was added, followed by stirring for 2 hours. The reaction mixture was quenched with before extraction with DCM (20 mL×2). The pooled organic layer was dried over sodium sulfate and filtered, and the solvent was evaporated in a vacuum to afford Compound 237-3 as a crude brown solid (36.0 mg, 0.103 mmol).

Step 4: Synthesis of (1-(2-(2,6-dioxopiperidin-3-yl)-1-oxoisoindolin-5-yl)piperidin-4-yl)methyl methanesulfonate At 0° C., a solution of crude Compound 237-3 (36 mg, 0.101 mmol) in DCM (1 mL) was added with MsCl (15.70 μl, 0.201 mmol) and TEA (40.7 μl, 0.302 mmol). The mixture was stirred at 0° C. for 1 hour. When the reaction was completed as analyzed by TLC, the reaction mixture was quenched with water before extraction with EA (20 mL×2). The pooled organic layer was dried over sodium sulfate and filtered, and the solvent was evaporated in a vacuum. The crude product was purified by MPLC using 5% MeOH:MC to afford the title compound Compound 237-4 as a white solid (9.0 mg, 0.101 mmol, 21%).

Step 5: 3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1-oxoisoindolin-2-yl)piperidine-2,6-dione (Compound 237)

A solution of Compound 237-5 (7.34 mg, 0.018 mmol) in ACN (2 mL) was added at room temperature with Compound 237-4 (Korean Patent No. 2128018) (8.0 mg, 0.018 mmol), KI (1.525 mg, 9.18 μmol) and DIPEA (9.52 μl, 0.055 mmol). The mixture was stirred at 80° C. for 12 hours. When the product was formed as analyzed by TLC, the reaction mixture was added with water, subjected to extraction with EA (50 mL×3), and washed with water (3×) and brine. The pooled organic layer was dried over sodium sulfate and purified by MPLC using 10% MeOH/MC (eluted at 6%) to afford Compound 237 as a yellow solid (2.60 mg, 0.0180 mmol, 20%).

Compound 238. 5-(4-(4-((3-((2,6-dimethylphenyl)amino)-1-methyl-1H-pyrazolo[3,4-d]pyrimidin-6-yl)amino)phenyl)piperazin-1-yl)-2-(2,6-dioxopiperidin-3-yl)isoindoline-1,3-dione

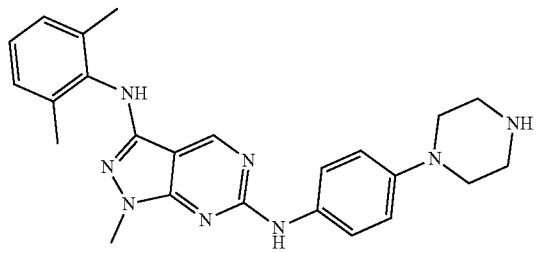

Compound 238-1

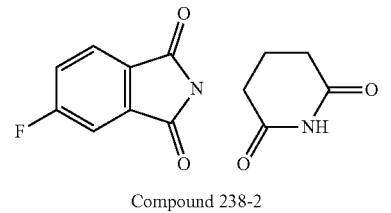

Compound 238-2

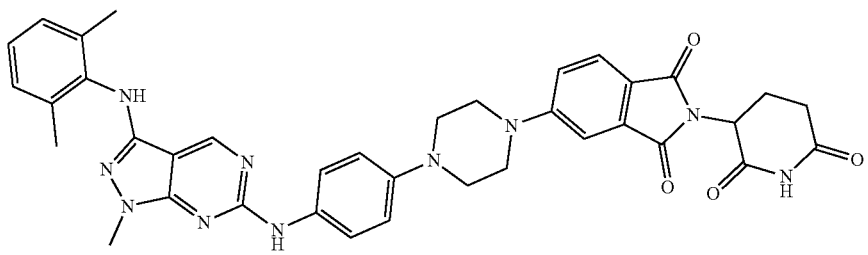

Compound 238

A solution of Compound 238-1 (identical to Compound 245-1-C) (20 mg, 0.047 mmol) in DMSO (1 mL) was added with Compound 238-2 (identical to Compound 2-1) (12.9 mg, 0.047 mmol) and DIPEA (0.040 ml, 0.233 mol) and heated from room temperature to 90° C. at which stirring was conducted for 16 hours to complete the reaction. When a new spot was formed as analyzed by TLC, the reaction mixture was quenched with water (5 mL) before extraction with EA. The combined organic layer was washed with water and brine. The pooled organic layer was dried over sodium sulfate and filtered, and the solvent was evaporated in a vacuum. The crude product was purified by MPLC using a solvent mixture of 10% MeOH:DCM to afford Compound 238 as a yellow solid (9 mg, 0.013 mmol, 28%).

Compound 239. 5-(4-(4-((3-((2,6-Dimethylphenyl)amino)-1-methyl-1H-pyrazolo[3,4-d]pyrimidin-6-yl)amino)phenyl)piperazin-1-yl)-2-(2,6-dioxopiperidin-3-yl)-6-fluoroisoindoline-1,3-dione

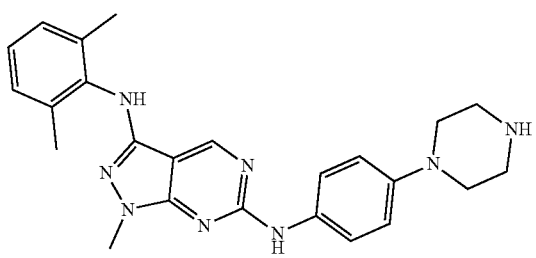

Compound 239-1

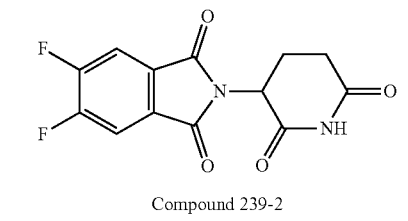

Compound 239-2

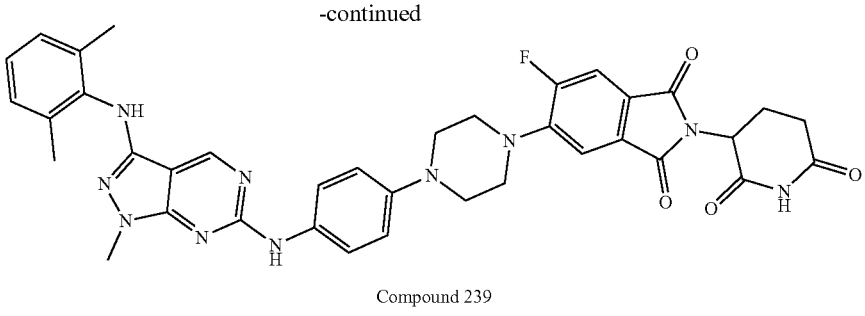

Compound 239

A solution of Compound 239-1 (identical to Compound 238-1) (20 mg, 0.047 mmol) in DMSO (1 mL) was added with Compound 239-2 (identical to Compound 233-2) (13.7 mg, 0.047 mmol) and DIPEA (0.040 ml, 0.233 mol) and heated from room temperature to 90° C. at which stirring was conducted for 16 hours to complete the reaction. When a new spot was formed as analyzed by TLC, the reaction mixture was quenched with water (5 mL) before extraction with EA. The combined organic layer was washed with water and brine. The pooled organic layer was dried over sodium sulfate and filtered, and the solvent was evaporated in a vacuum. The crude product was purified by MPLC using a solvent mixture of 10% MeOH:DCM to afford Compound 239 as a yellow solid (21.7 mg, 0.031 mmol, 66%).

Compound 240. (E)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)-3-(1-(1-(2-(2,6-dioxopiperidin-3-yl)-1,3-dioxoisoindolin-5-yl)piperidine-4-carbonyl)piperidin-4-yl)acrylonitrile

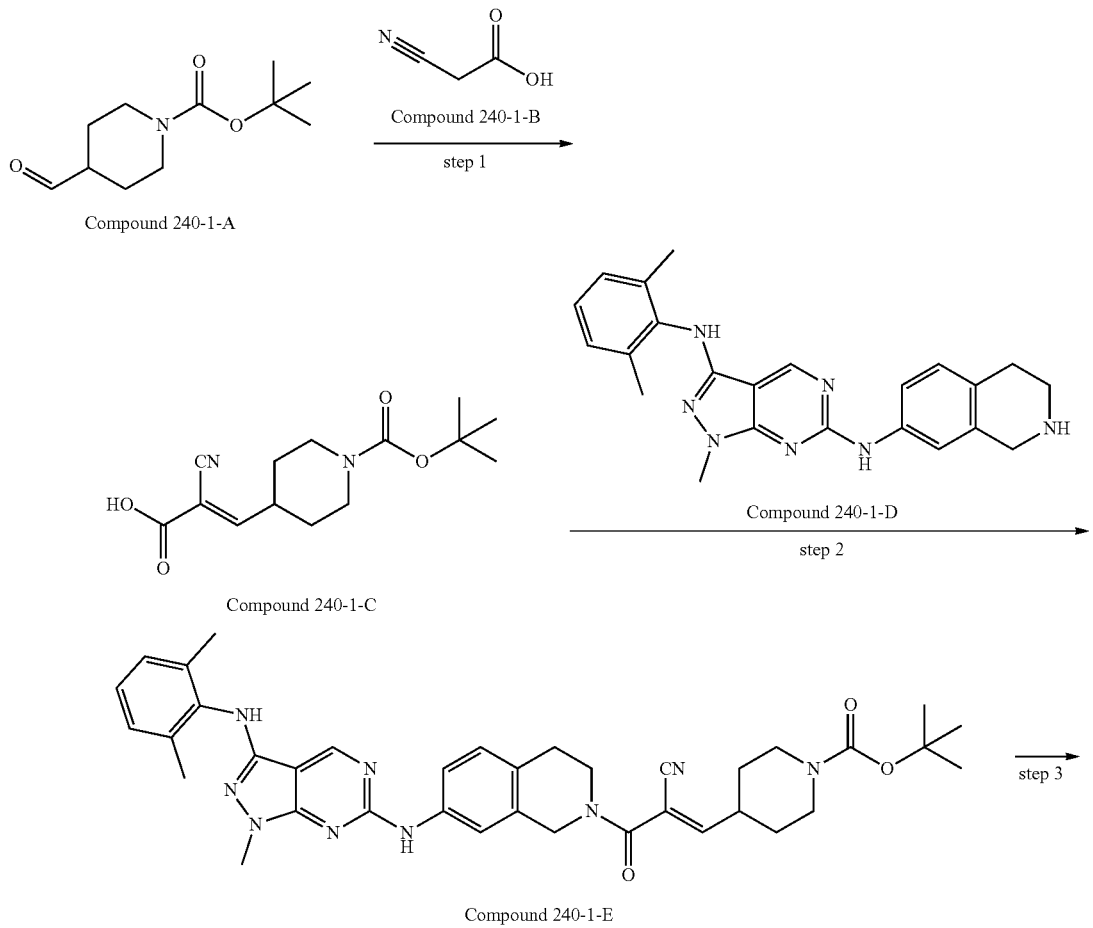

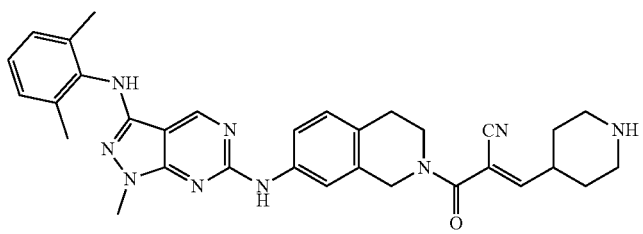

Compound 240-1

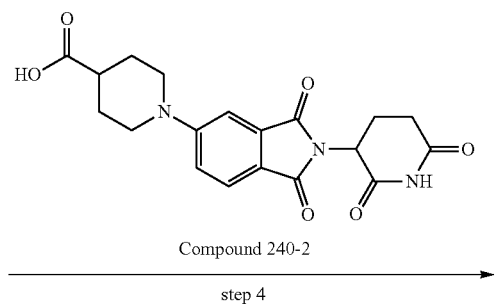

Compound 240-2 step 4

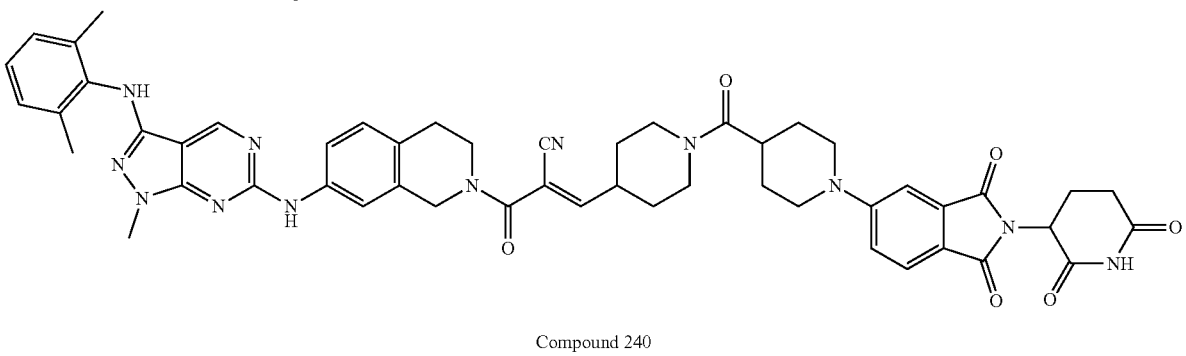

Compound 240

Step 1: Synthesis of (E)-3-(1-(tert-butoxycarbonyl)piperidin-4-yl)-2-cyanoacrylic acid A mixture of Compound 240-1-A (sigma, 722022) (tert-butyl 4-formylpiperidine-1-carboxylate) (500 mg, 2.34 mmol), Compound 240-1-B (sigma, C88505) (cyanoacetic acid) (300 mg, 3.51 mmol), and piperidine (sigma, 104094) (100 mg, 1.17 mmol) was stirred in ethanol (20 mL) and heated at 85° C. for 3 hours. The reaction mixture was cooled to room temperature and diluted with ethyl acetate (15 mL). After layer separation, the aqueous layer was subjected to extraction with EtOAc (25 mL). The pooled organic layer was washed with 1 M sodium hydroxide (25 mL×1), dried over MgSO$_4$, filtered, and concentrated in a vacuum. The residue was loaded into a silica column using 15% EtOAc/hexane to afford the desired Compound 240-1-C, as a sticky oil (92.0 mg, 0.328 mmol, 14%).

Step 2: Synthesis of tert-butyl (E)-4-(2-cyano-3-(7-((3-((2,6-dimethylphenyl)amino)-1-methyl-1H-pyrazolo[3,4-d] pyrimidin-6-yl)amino)-3,4-dihydroisoquinolin-2 (1H)-yl)-3-oxoprop-1-en-1-yl)piperidine-1-carboxylate A suspension of Compound 240-1-C (105 mg, 0.375 mmol) in DMF (10 mL) was added with DIPEA (97.0 mg, 0.751 mmol) and then at room temperature with HATU (190 mg, 0.501 mmol) and the mixture was stirred at room temperature for 15 minutes. After addition of Compound 240-1-D (identical to Compound 1-1) (100 mg, 0.250 mmol), the resulting mixture was stirred at room temperature for 14 hours. The crude reaction mixture was diluted with water (10 mL) before extraction with ethyl acetate (3×15 mL). The pooled organic layer was dried over MgSO$_4$ and concentrated in a vacuum to give a crude product which was then purified by column chromatography using MeOH/DCM 5% to afford Compound 240-1-E as a yellow solid (137 mg, 0.0207 mmol, 83%).

Step 3: Synthesis of (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(piperidin-4-yl)acrylonitrile A solution of Compound 240-1-E (95.0 mg, 0.144 mmol) in DCM (5 ml) was added with 4 N HCl (11.0 mg, 0.287 mmol) in dioxane. The resulting mixture was stirred at room temperature for 4 hours. After concentration in a vacuum, the crude product thus obtained was washed with ether and dried in a vacuum to afford Compound 240-1 as a white solid (51 mg, 0.0910 mmol, 64%).

Step 4: Synthesis of (E)-2-(7-((3-((2,6-dimethylphenyl)amino)-1-methyl-1H-pyrazolo [3,4-d]pyrimidin-6-yl)amino)-1,2,3,4-tetrahydroisoquinoline-2-carbonyl)-3-(1-(1-(2-(2,6-dioxopiperidin-3-yl)-1,3-dioxoisoindolin-5-yl)piperidine-4-carbonyl)piperidin-4-yl)acrylonitrile (Compound 240)

A suspension of Compound 240-1 (10 mg, 0.018 mmol) in DMF (2 mL) was added with DIPEA (6.92 mg, 0.053 mmol) and then at room temperature with HATU (13.54 mg, 0.036 mmol) and the mixture was stirred at room temperature for 15 minutes. After addition of Compound 240-2 (identical to Compound 230-6) (7.55 mg, 0.020 mmol), the resulting mixture was stirred at room temperature for 14 hours. The crude reaction mixture was diluted with water (10 mL) before extraction with ethyl acetate (3×15 mL). The pooled organic layer was dried over MgSO$_4$ and concentrated in a vacuum to give a crude product which was then purified by column chromatography using MeOH/DCM 5% to afford Compound 240 as a yellow solid (10.0 mg, 0.0107 mmol, 60.5%).

Compound 241. (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(1-(2-((2-(2,6-dioxopiperidin-3-yl)-1,3-dioxoisoindolin-5-yl)oxy)acetyl)piperidin-4-yl)acrylonitrile

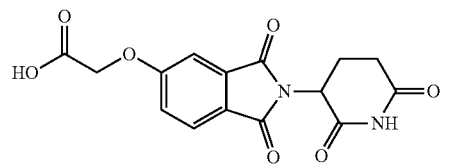

Compound 241-2

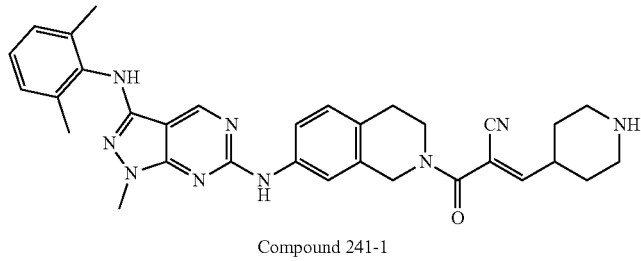

Compound 241-1

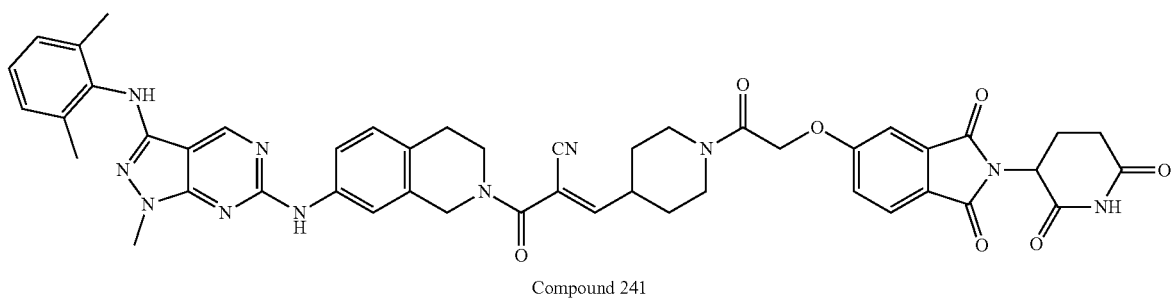

Compound 241

A suspension of Compound 241-1 (identical to Compound 240-1) (10 mg, 0.018 mmol) in DMF (2 mL) was added with DIPEA (6.92 mg, 0.053 mmol) and then at room temperature with HATU (13.54 mg, 0.036 mmol) and the mixture was stirred at room temperature for 15 minutes. After addition of Compound 241-2 (identical to Compound 236-2) (6.51 mg, 0.020 mmol), the resulting mixture was stirred at room temperature for 14 hours. The crude reaction mixture was diluted with water (10 mL) before extraction with ethyl acetate (3×15 mL). The pooled organic layer was dried over MgSO$_4$ and concentrated in a vacuum to give a crude product which was then purified by column chromatography using MeOH/DCM 5% to afford Compound 241 as a yellow solid (10.8 mg, 0.012 mmol, 69.3%).

Compound 243. 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-(2,6-dioxopiperidin-3-yl)isoindoline-1,3-dione

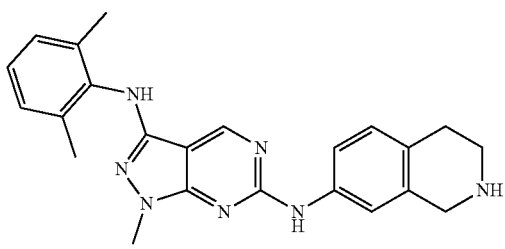

Compound 243-1

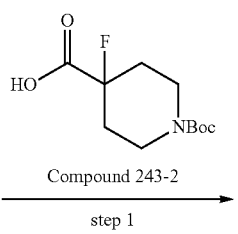

Compound 243-2 step 1

-continued

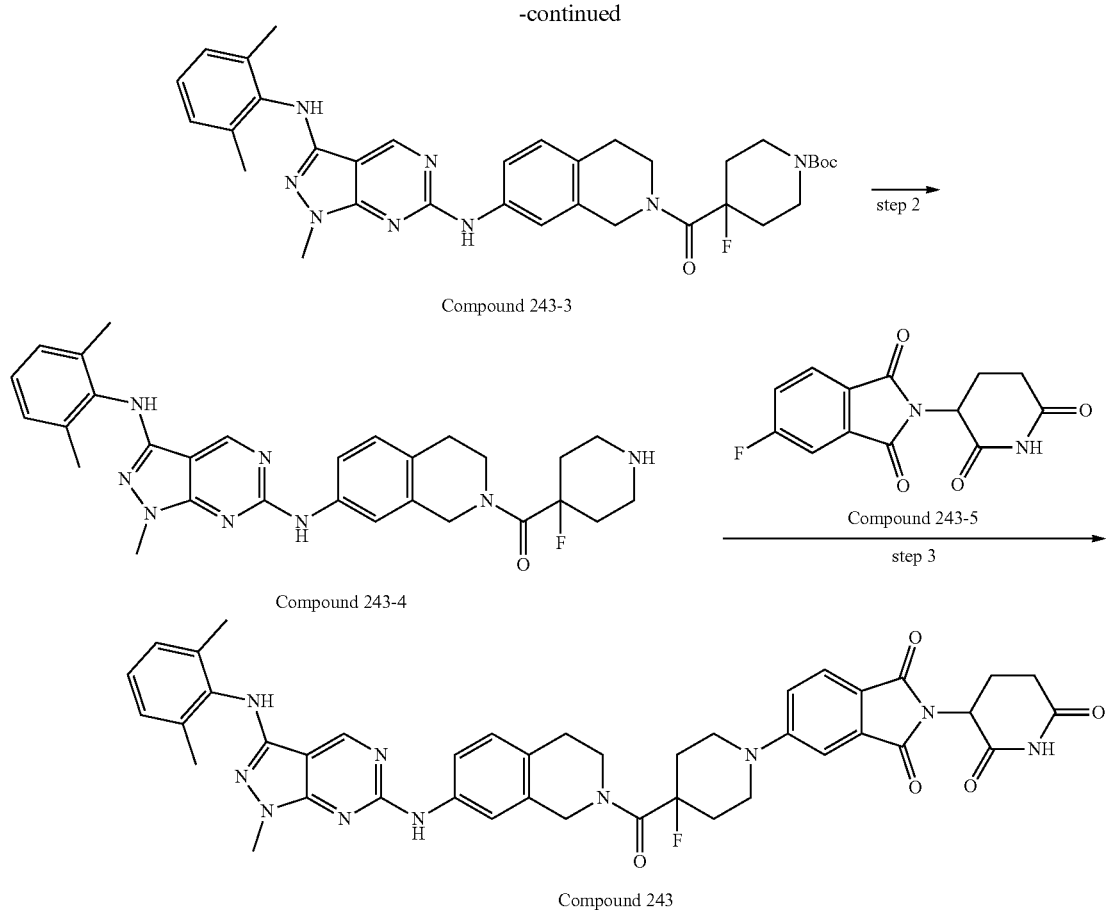

Compound 243-3

Compound 243-4

Compound 243-5

Compound 243

Step 1: Synthesis of tert-butyl 4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidine-1-carboxylate A solution of Compound 243-1 (Korean Patent No. 2128018) (250 mg, 0.626 mmol) in DMF (2 mL) was added at room temperature with HATU (476 mg, 1.252 mmol), Compound 243-2 (BLD Pharm BD57158 98%) (1-(tert-butoxycarbonyl)-4-fluoropiperidine-4-carboxylic acid; 155 mg, 0.626 mmol), and TEA (190 mg, 1.877 mmol). The resulting mixture was stirred at room temperature for 4 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the solvent was evaporated in a vacuum. The crude product was purified by MPLC using a solvent mixture of 5% MeOH:DCM to afford Compound 243-3 as a yellow crystal (351 mg, 0.558 mmol, 89%).

Step 2: Synthesis of (7-((3-((2,6-dimethylphenyl)amino)-1-methyl-1H-pyrazolo[3,4-d]pyrimidin-6-yl)amino)-3,4-dihydroisoquinolin-2 (1H)-yl) (4-fluoropiperidin-4-yl)methanone 2,2,2-trifluoroacetate In a 50-mL rb, Compound 243-3 (351 mg, 0.558 mmol) was added with 40% TFA/DCM and stirred together at room temperature for 2 hours. When the reaction was completed as analyzed by TLC, the solvent was completely evaporated and the residue was washed with diethyl ether. The product was dried in a high vacuum to afford Compound 243-4 as a yellow solid (324 mg, 0.558 mmol, 90%).

Step 3: Synthesis of 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-(2,6-dioxopiperidin-3-yl)isoindoline-1,3-dione (Compound 243)

A solution of Compound 243-4 (20 mg, 0.032 mmol) in DMSO (2 mL) was added with Compound 243-5 (identical to Compound 232-4) (9.39 mg, 0.032 mmol), and DIPEA (0.017 ml, 0.096 mmol) and stirred at 90° C. for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 243 as a yellow solid (7.0 mg, 0.032 mmol, 28%).

Compound 244. 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-(2,6-dioxopiperidin-3-yl)-6-fluoroisoindoline-1,3-dione

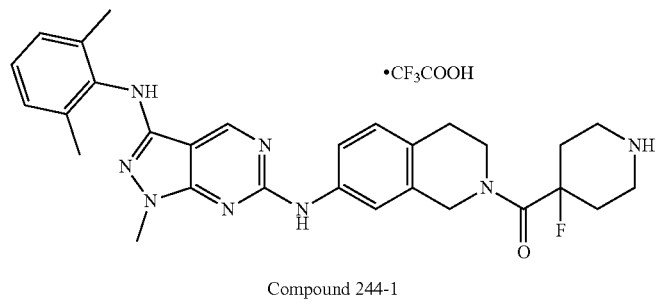

Compound 244-1

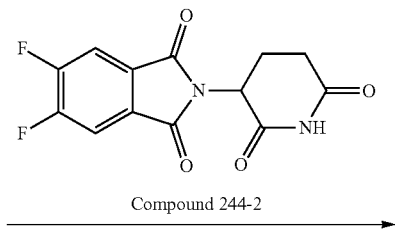

Compound 244-2

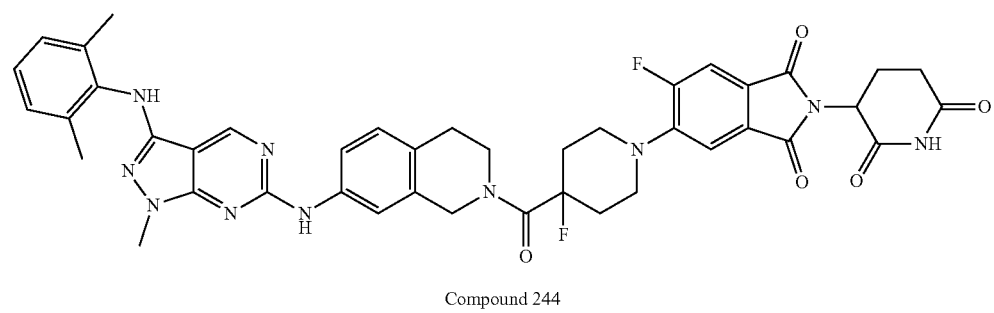

Compound 244

A solution of Compound 244-1 (identical to Compound 243-4) (20 mg, 0.032 mmol) in DMSO (1 mL) was added with Compound 244-2 (identical to Compound 208-3) (8.82 mg, 0.032 mmol) and DIPEA (0.017 ml, 0.096 mmol) and stirred at 90° C. for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 244 as a yellow solid (11.0 mg, 0.032 mmol, 43%).

Compound 245. 3-(5-(4-((4-(4-((3-((2,6-Dimethylphenyl)amino)-1-methyl-1H-pyrazolo[3,4-d]pyrimidin-6-yl)amino)phenyl)piperazin-1-yl)methyl)piperidin-1-yl)-6-fluoro-1-oxoisoindolin-2-yl)piperidin-2,6-one

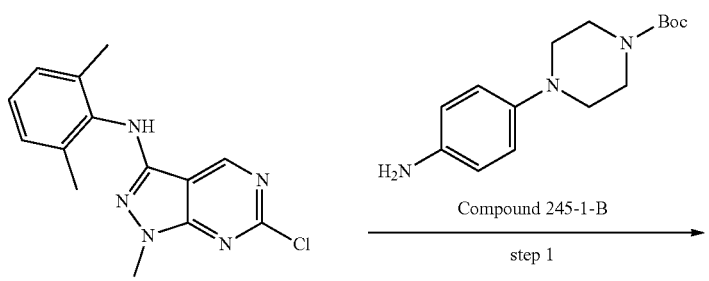

Compound 245-1-A

Compound 245-1-B step 1

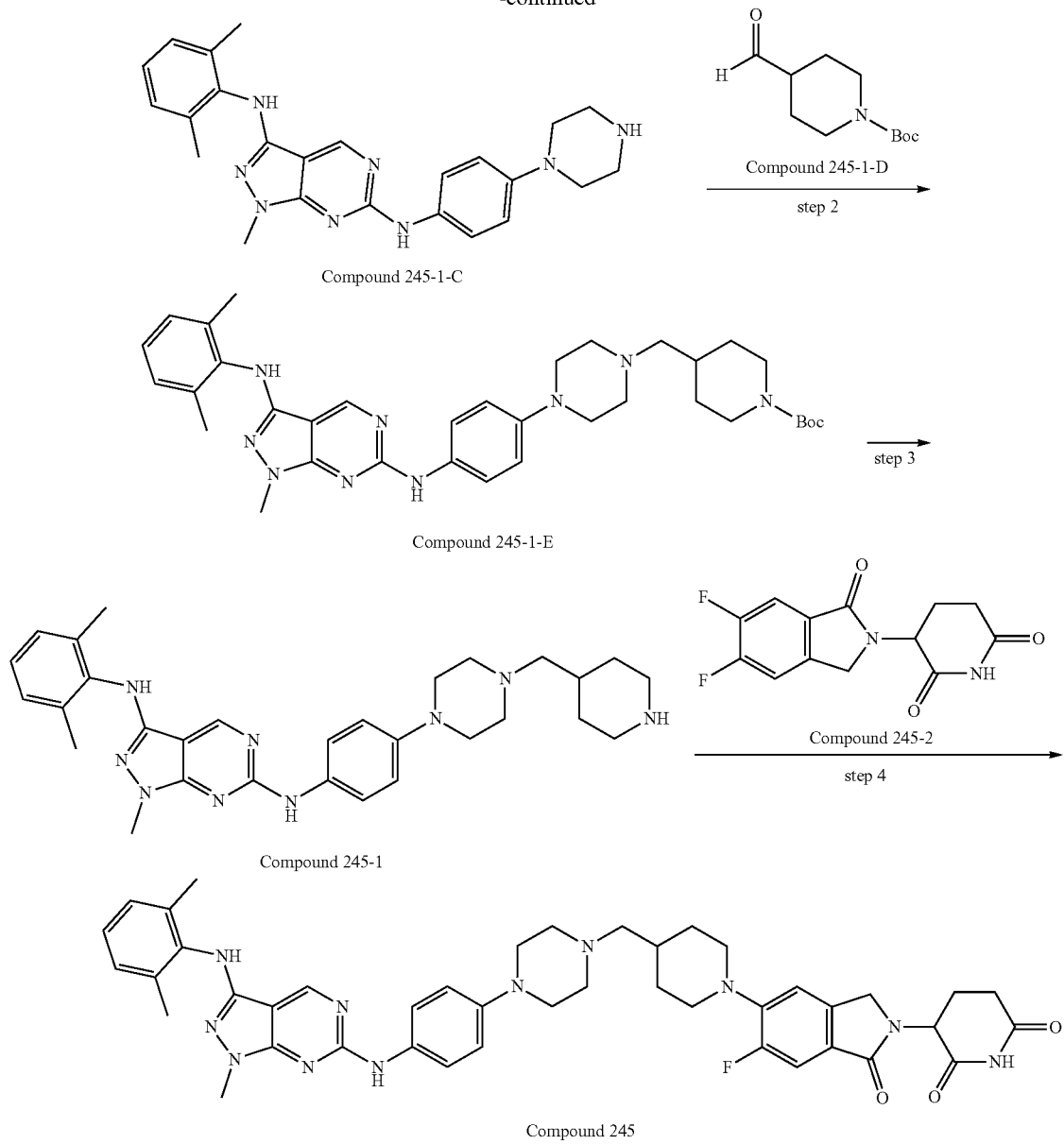

Compound 245-1-C

Compound 245-1-D step 2

Compound 245-1-E step 3

Compound 245-1

Compound 245-2 step 4

Compound 245

Step 1: Synthesis of N3-(2,6-dimethylphenyl)-1-methyl-N6-(4-(piperazin-1-yl)phenyl)-1H-pyrazolo[3,4-d]pyrimidine-3,6-diamine A solution of Compound 245-1-A (Korean Patent No. 2128018) (450 mg, 1.564 mmol) in IPA was added at room temperature with Compound 245-1-B (Combi-blocks, AN-1426) (tert-butyl 4-(4-aminophenyl)piperazine-1-carboxylate) (521 mg, 1.877 mmol) and pTSA (595 mg, 3.13 mmol). The mixture was stirred overnight at 90° C. After completion of the reaction, the solvent was evaporated in a vacuum before addition of water and DCM. The aqueous layer was isolated using a Büchner funnel and added with a saturated NaHCO₃ solution and DCM for basic post-treatment. The DCM layer was collected and evaporated in a vacuum to afford Compound 245-1-C as a yellow solid (350 mg).

Step 2: Synthesis of tert-butyl 4-((4-(4-((3-((2,6-dimethylphenyl)amino)-1-methyl-1H-pyrazolo[3,4-d]pyrimidin-6-yl)amino)phenyl)piperazin-1-yl)methyl)piperidine-1-carboxylate A solution of Compound 245-1-C (100 mg, 0.233 mmol) in MeOH (1 mL) was added with Compound 245-1-D (sigma, 722022) (Boc-piperidine aldehyde) (54.7 mg, 0.257 mmol) and acetic acid (1 drop, catalytic amount) and stirred overnight at room temperature. The mixture was added with NaCNBH₃ (22 mg, 0.350 mmol) and stirred for 1 hour. When the reaction was completed as analyzed by TLC, the solvent was completely evaporated. The residue was dissolved in MC and washed with saturated sodium bicarbonate. The organic layer was dried over sodium sulfate and the organic solvent evaporated in a vacuum. The residue was purified by MPLC using 10% MeOH/MC to afford Compound 245-1-E as a yellow solid (66.4 g, 0.106 mmol, 45.5%).

Step 3: Synthesis of N3-(2,6-dimethylphenyl)-1-methyl-N6-(4-(4-(piperidin-4-ylmethyl)piperazin-1-yl)phenyl)-1H-pyrazolo[3,4-d]pyrimidine-3,6-diamine A solution of Compound 245-1-E (60 mg, 0.096 mmol) in DCM (1.0 mL) was added with 4 N HCl/dioxane (0.5 ml, excess). The mixture was stirred overnight at room temperature. When the starting material disappeared as monitored by TLC, the solvent was evaporated in a vacuum and basic post-treatment with a saturated NaHCO₃ solution was provided. After the basic post-treatment, the organic layer was recrystallized in chloroform/Hex to afford Compound 245-1 as an off-white solid (42.7 mg, 0.081 mmol, 85%).

Step 4: Synthesis of 3-(5-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidin-1-yl)-6-fluoro-1-oxoisoindolin-2-yl)piperidin-2,6-one (Compound 245)

A solution of Compound 245-1 (20 mg, 0.038 mmol) in DMSO (1 mL) was added with Compound 245-2 (identical to Compound 220-2) (10.6 mg, 0.038 mmol) and DIPEA (0.033 ml, 0.190 mol) and heated from room temperature to 90° C. at which stirring was conducted for 16 hours to complete the reaction. When a new spot was formed as analyzed by TLC, the reaction mixture was quenched with water (5 mL) before extraction with EA. The combined organic layer was washed with water and brine. The pooled organic layer was dried over sodium sulfate and filtered, and the solvent was evaporated in a vacuum. The crude product was purified by MPLC using a solvent mixture of 10% MeOH:DCM to afford Compound 245 as a yellow solid (3.5 mg, 0.0045 mmol, 11.7%).

Compound 246. 5-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidine-1-carbonyl)piperidin-1-yl)-2-(2,6-dioxopiperidin-3-yl)isoindoline-1,3-dione

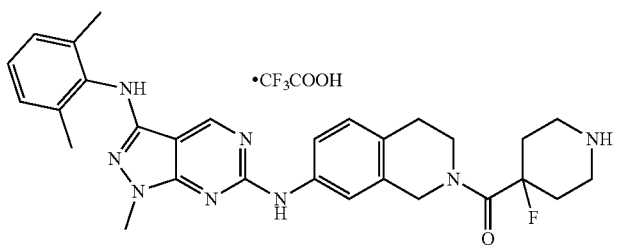

Compound 246-1

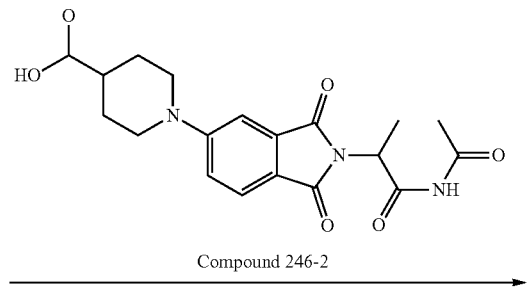

Compound 246-2

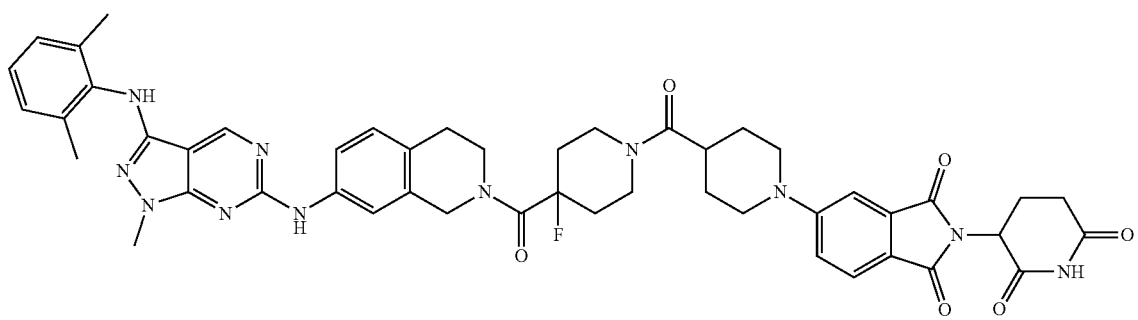

Compound 246

A solution of Compound 246-1 (identical to Compound 244-1) (20 mg, 0.031 mmol) in DMF (2 mL) was added with 2-(3H-[1,2,3]triazolo[4,5-b]pyridin-3-yl)-1,1,3,3-tetramethylisouronium hexafluorophosphate (V) (HATU; 23.6 mg, 0.0620 mmol), Compound 246-2 (identical to Compound 230-6) (11.9 mg, 0.0310 mmol), and TEA (0.013 ml, 0.093 mmol) and stirred at room temperature for 4 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 246 as a yellow solid (16.0 mg, 0.0310 mmol, 57%).

Compound 247. 5-((2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-oxoethyl)amino)-2-(2,6-dioxopiperidin-3-yl)isoindoline-1,3-dione

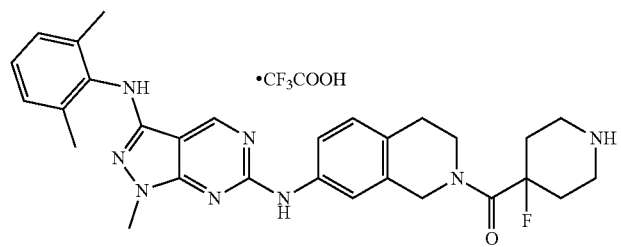

Compound 247-1

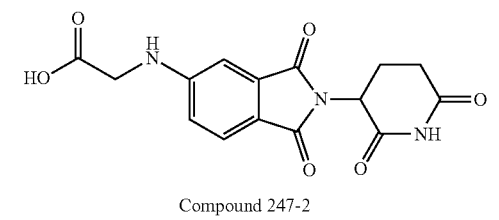

Compound 247-2

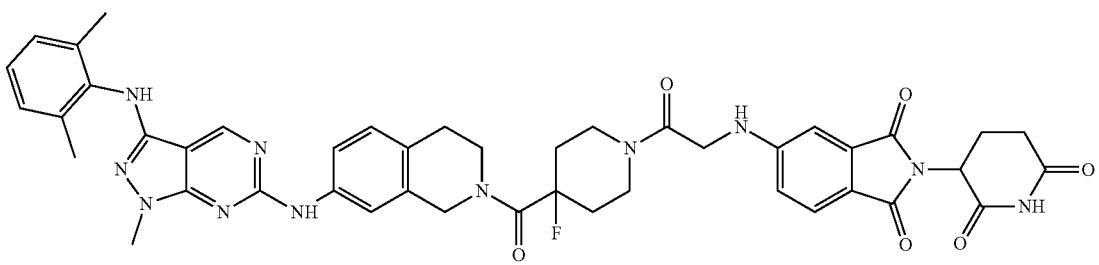

Compound 247

A solution of Compound 247-1 (identical to Compound 244-1) (20 mg, 0.031 mmol) in DMF (2 mL) was added with HATU (23.6 mg, 0.0620 mmol), Compound 247-2 (identical to Compound 235-2) (10.3 mg, 0.0310 mmol), and TEA (0.013 ml, 0.093 mmol) and stirred at room temperature for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 247 as a yellow solid (18.0 mg, 0.0310 mmol, 69%).

Compound 248. 5-(2-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-oxoethoxy)-2-(2,6-dioxopiperidin-3-yl)isoindoline-1,3-dione

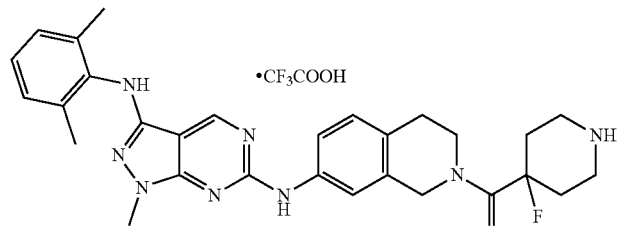

Compound 248-1

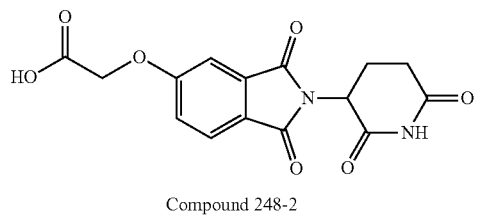

Compound 248-2

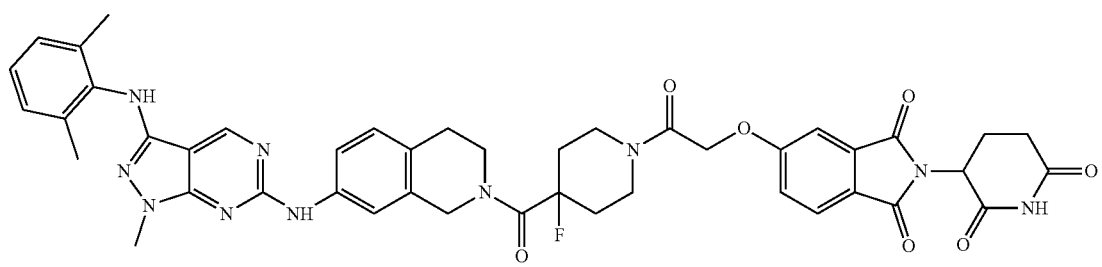

Compound 248

A solution of Compound 248-1 (identical to Compound 244-1) (20 mg, 0.031 mmol) in DMF (2 mL) was added with HATU (23.6 mg, 0.0620 mmol), Compound 248-2 (identical to Compound 236-2) (10.3 mg, 0.0310 mmol), and TEA (0.013 ml, 0.093 mmol) and stirred at room temperature for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using a solvent mixture of 5% MeOH:DCM to afford Compound 248 as a yellow solid (16.0 mg, 0.0310 mmol, 61%).

Compound 250. 5-(4-((4-(5-((3-((2,6-Dimethylphenyl)amino)-1-methyl-1H-pyrazolo[3,4-d]pyrimidin-6-yl)amino)-2-fluorophenyl)-3,6-dihydropyridin-1(2H)-yl)methyl)piperidin-1-yl)-2-(2,6-dioxopiperidin-3-yl)isoindoline-1,3-dione

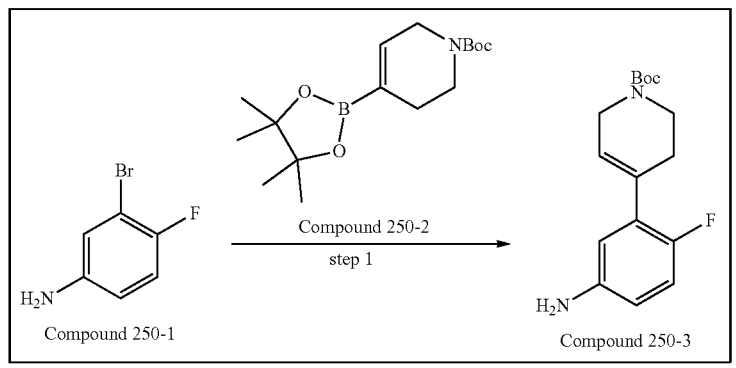

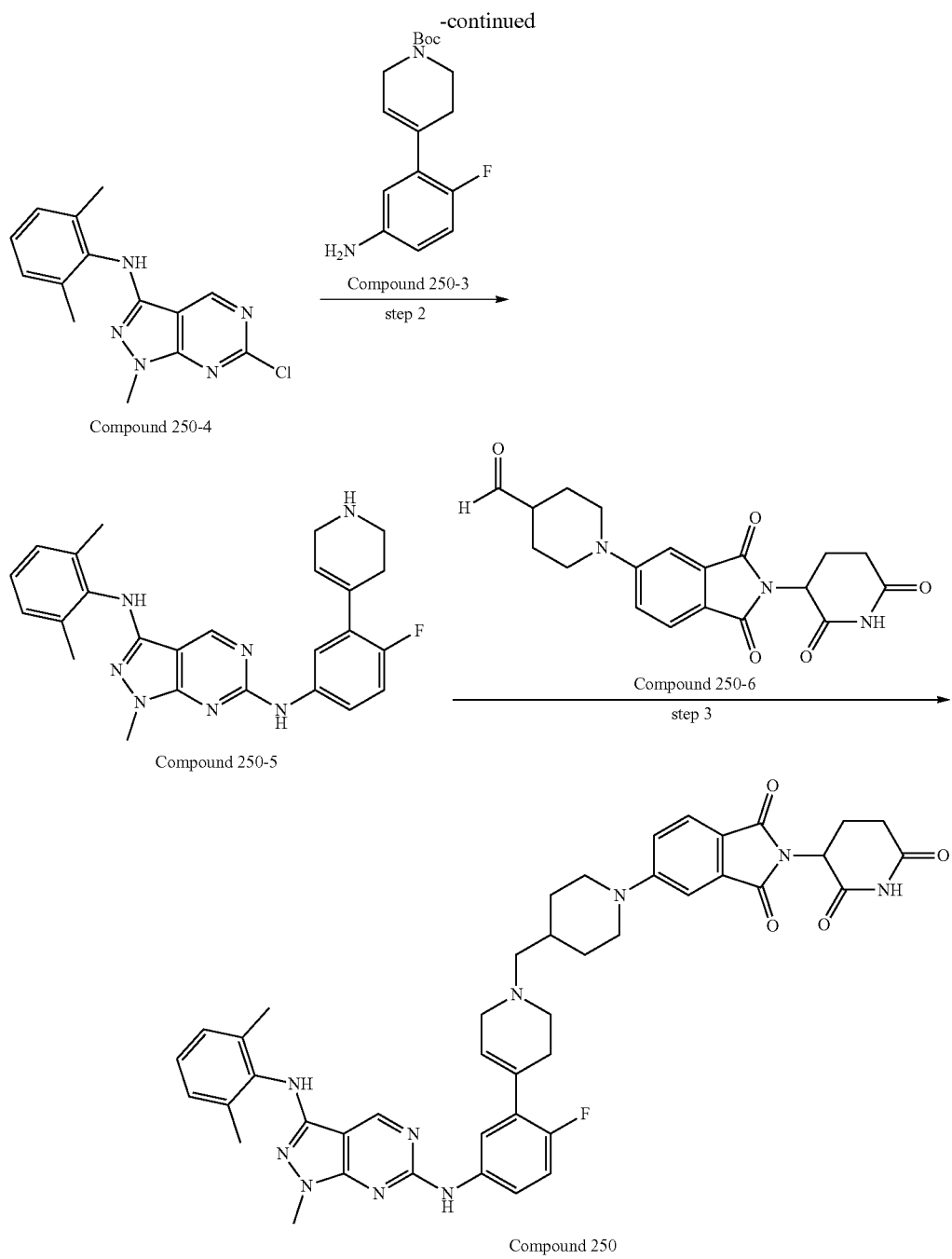

Step 1: Synthesis of tert-butyl 4-(5-amino-2-fluorophenyl)-3,6-dihydropyridine-1 (2H)-carboxylate In a sealed tube, 3-bromo-4-fluoroaniline (Compound 250-1) (Alfa Aesar, B25610) (219 mg, 1.17 mmol), and tert-butyl 4-(4,4,5,5-tetramethyl-1,3,2-dioxaborolan-2-yl)-3,6-dihydropyridine-1 (2H)-carboxylate (Compound 250-2) (BLD Pharm, BD33046) (397 mg, 1.29 mmol) were added with Pd(dppf)$_2$Cl$_2$·CH$_2$Cl$_2$ complex (47 mg, 0.059 mmol) in dioxane (2 mL)/water (2 mL), DPPF (33 mg, 0.059 mmol), and Na$_2$CO$_3$ (372 mg, 3.51 mmol) and the mixture was stirred at 80° C. for 15 hours. After completion of the reaction, the reaction mixture was subjected to extraction with EtOAc (3×20 mL) and water (10 mL), and the organic extract was dried (Na$_2$SO$_4$), filtered, and concentrated in a vacuum. The concentrate was purified by column chromatography using 5% MeOH/DCM to afford Compound 250-3 as a grayish yellow solid (149 mg, 0.51 mmol, 44%).

Step 2: Synthesis of N3-(2,6-dimethylphenyl)-N6-(4-fluoro-3-(1,2,3,6-tetrahydropyridin-4-yl)phenyl)-1-methyl-1H-pyrazolo[3,4-d]pyrimidine-3,6-diamine To a solution of 6-chloro-N-(2,6-dimethylphenyl)-1-methyl-1H-pyrazolo[3,4-d]pyrimidine-3-amine (Compound 250-4) (identical to Compound 230-4) (70 mg, 0.24 mmol) and tert-butyl 4-(5-amino-2-fluorophenyl)-3,6-dihydropyridine-1 (2H)-carboxylate (Compound 250-3) (67 mg, 0.24 mmol) in 2-propanol (1 mL) was added p-toluenesulfonic acid (42 mg, 0.24 mmol), and the mixture was heated to 95° C. and stirred for 15 hours. After completion of the reaction, the reaction mixture was concentrated and used immediately in the next step. (Compound 250-5; 61 mg, 0.137 mmol, 57%)

Step 3: Synthesis of 5-(4-((4-(5-((3-((2,6-dimethylphenyl)amino)-1-methyl-1H-pyrazolo[3,4-d]pyrimidin-6-yl)amino)-2-fluorophenyl)-3,6-dihydropyridin-1 (2H)-yl)methyl)piperidin-1-yl)-2-(2,6-dioxopiperidin-3-yl)isoindoline-1,3-dione (Compound 250)

A solution of N3-(2,6-dimethylphenyl)-N6-(4-fluoro-3-(1,2,3,6-tetrahydropyridin-4-yl)phenyl)-1-methyl-1H-pyrazolo[3,4-d]pyrimidine-3,6-diamine (Compound 250-5) (15 mg, 0.03 mmol) in MeOH (1 mL) was added with 1-(2-(2,6-dioxopiperidin-3-yl)-1,3-dioxoisoindolin-5-yl)piperidine-4-carbaldehyde (Compound 250-6) (identical to Compound 230-6) (13 mg, 0.03 mmol) and acetic acid (2 µL, 0.03 mmol). The resulting mixture was stirred at room temperature for 2 hours. Addition of NaBH$_3$CN (3 mg, 0.05 mmol) was followed by stirring at room temperature for 2 hours. After completion of the reaction, the reaction mixture was quenched with water and subjected to extraction with DCM (3×15 mL). The pooled organic layer was dried over Na$_2$SO$_4$ and filtered, and the solvent was evaporated in a vacuum. The crude product was purified by column chromatography using MeOH/DCM 5% to afford Compound 250 as a grayish yellow solid (9 mg, 0.01 mmol, 33%).

Compound 253. 5-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidin-1-yl)-2-(2,6-dioxopiperidin-3-yl)isoindoline-1,3-dione

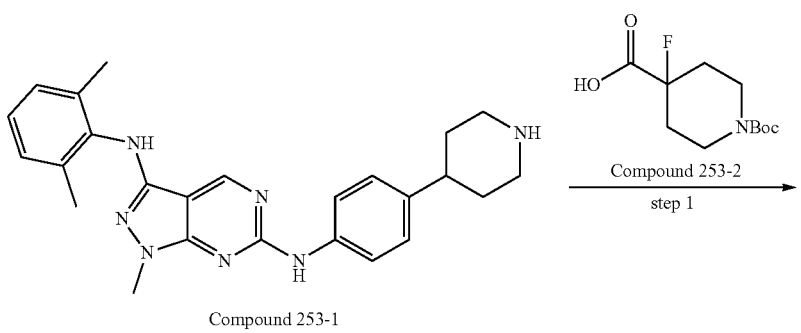

Compound 253-1

Compound 253-2
step 1

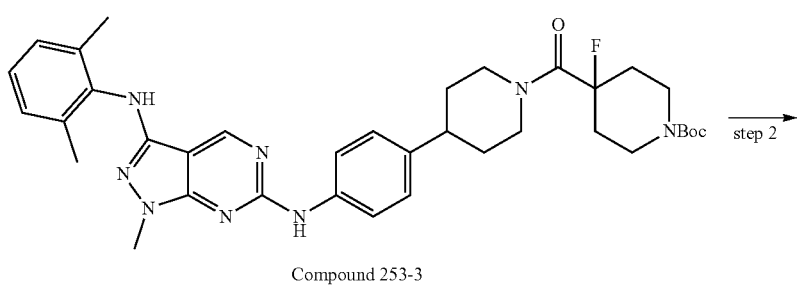

Compound 253-3
step 2

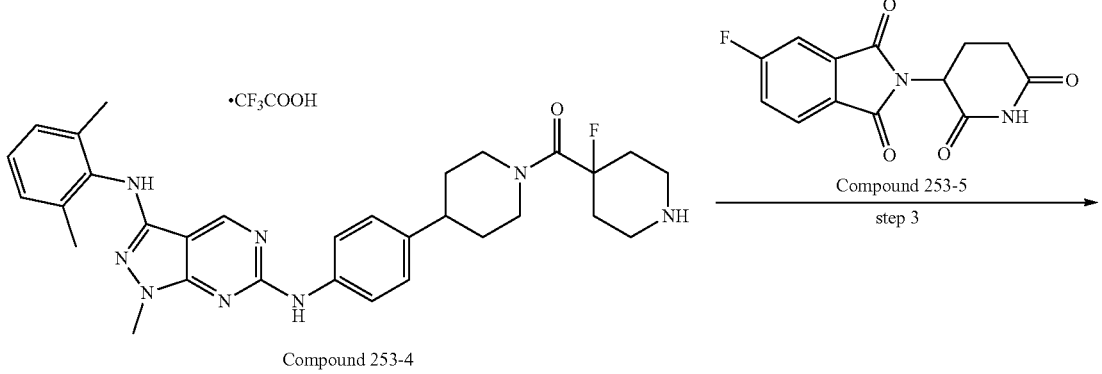

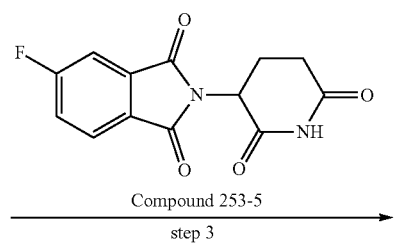

Compound 253-4

Compound 253-5
step 3

-continued

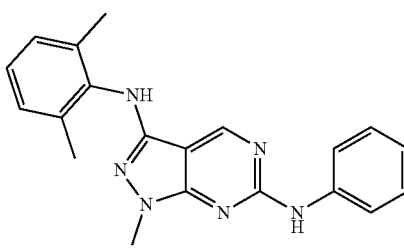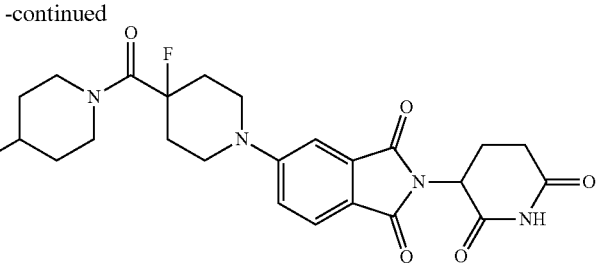

Compound 253

Step 1: Synthesis of tert-butyl 4-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidine-1-carboxylate A solution of Compound 253-1 (identical to Compound 228-1) (60.0 mg, 0.140 mmol) in tetrahydrofuran (5 ml) was added with Compound 253-2 (identical to Compound 243-2) (1-(tert-butoxycarbonyl)-4-fluoropiperidine-4-carboxylic acid) (34.7 mg, 0.140 mmol), HATU (80 mg, 0.210 mmol), and TEA (0.0470 ml, 0.351 mmol) and stirred at room temperature for 4 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 253-3 as a yellow solid (50.0 mg, 0.140 mmol, 54%).

Step 2: Synthesis of (4-(4-(4-((3-((2,6-dimethylphenyl)amino)-1-methyl-1H-pyrazolo[3,4-d]pyrimidin-6-yl)amino)phenyl)piperidin-1-yl) (4-fluoropiperidin-4-yl)methanone 2,2,2-trifluoroacetate In a 50-mL rb, 40% TFA/DCM (1 mL) was added to Compound 253-3 (49 mg, 0.075 mmol) and stirred together at room temperature for 2 hours. When the reaction was completed as analyzed by TLC, the solvent was completely evaporated and the residue was washed with diethyl ether. The product was dried in a high vacuum to afford Compound 253-4 as a yellow solid (46 mg, 0.075 mmol, 92%).

Step 3: Synthesis of 5-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidin-1-yl)-2-(2,6-dioxopiperidin-3-yl)isoindoline-1,3-dione (Compound 253)

A solution of Compound 253-4 (15 mg, 0.022 mmol) in DMSO (2 mL) was added at room temperature with Compound 253-5 (identical to Compound 232-4) (6.18 mg, 0.022 mmol) and DIPEA (8.69 mg, 0.067 mmol). The mixture was stirred at 90° C. for 12 hours. When a new spot was formed as analyzed by TLC, the reaction mixture was quenched with water (10 mL) before extraction with DCM (15 mL×2). The combined organic layer was washed with water (20 mL×2) and brine (20 mL×2). The pooled organic layer was dried over sodium sulfate and the organic solvent evaporated in a vacuum. The crude product was purified by MPLC using a solvent mixture of 5% MeOH:DCM to afford Compound 253 as a yellow solid (3.0 mg, 0.022 mmol, 18%).

Compound 254. 5-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidin-1-yl)-2-(2,6-dioxopiperidin-3-yl)-6-fluoroisoindoline-1,3-dione

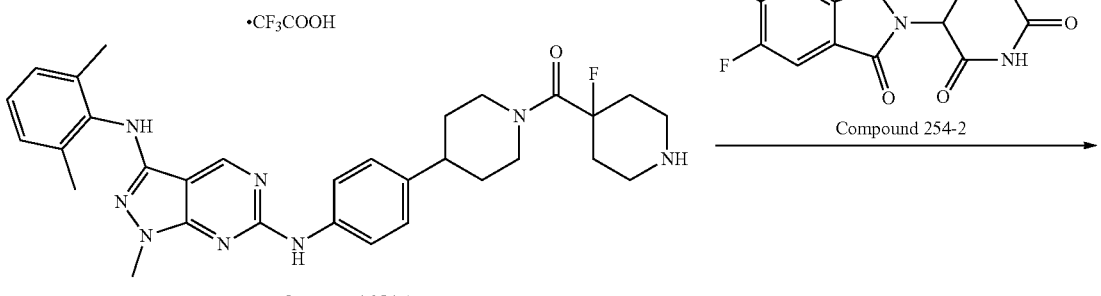

Compound 254-1

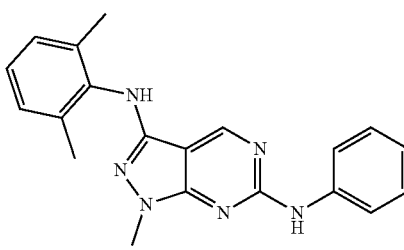
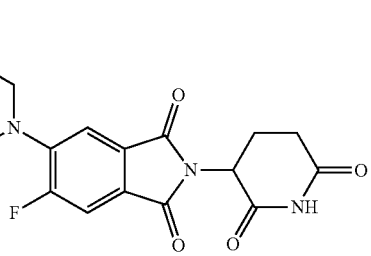

Compound 254

A solution of Compound 254-1 (identical to Compound 253-4) (15 mg, 0.022 mmol) in DMSO (2 mL) was added at room temperature with Compound 254-2 (identical to Compound 208-3) (6.58 mg, 0.022 mmol) and DIPEA (8.69 mg, 0.067 mmol). The mixture was stirred at 90° C. for 12 hours. When a new spot was formed as analyzed by TLC, the reaction mixture was quenched with water (10 mL) before extraction with EA (15 mL×2). The combined organic layer was washed with water (20 mL×2) and brine (20 mL×2). The pooled organic layer was dried over sodium sulfate and the solvent was evaporated in a vacuum. The crude product was purified by MPLC using a solvent mixture of 5% MeOH:DCM to afford Compound 254 as a yellow solid (11 mg, 0.022 mmol, 59%).

Compound 255. 3-(5-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidine-1-carbonyl)-1-oxoisoindolin-2-yl)piperidin-2,6-one

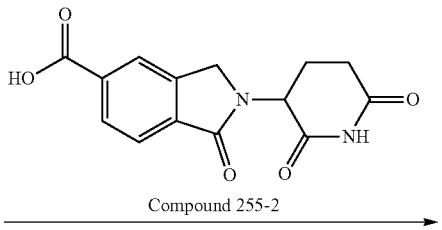

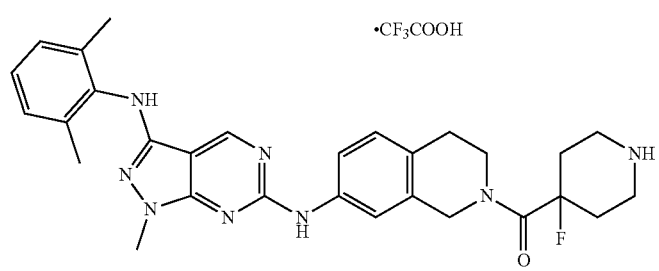

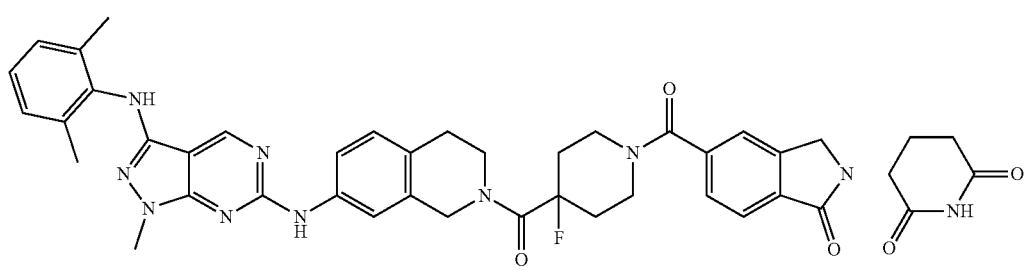

Compound 255

A solution of Compound 255-1 (identical to Compound 244-1) (20 mg, 0.031 mmol) in DMF (5 ml) was added with Compound 255-2 (identical to Compound 256-2) (8.97 mg, 0.031 mmol), HATU (11.83 mg, 0.031 mmol) and TEA (4.20 µl, 0.031 mmol) and stirred at room temperature for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 255 as a yellow solid (12.0 mg, 0.0310 mmol, 48%).

Compound 256. 3-(5-(4-((4-(4-((3-((2,6-Dimethylphenyl)amino)-1-methyl-1H-pyrazolo[3,4-d]pyrimidin-6-yl)amino)phenyl)piperazin-1-yl)methyl)piperidine-1-carbonyl)-1-oxoisoindolin-2-yl)piperidin-2,6-one

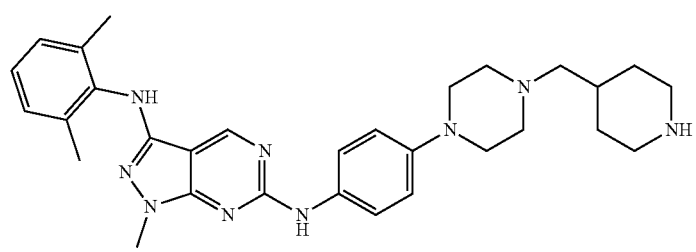

Compound 256-1

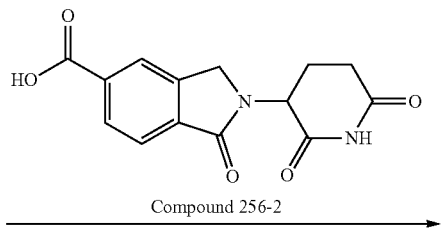

Compound 256-2

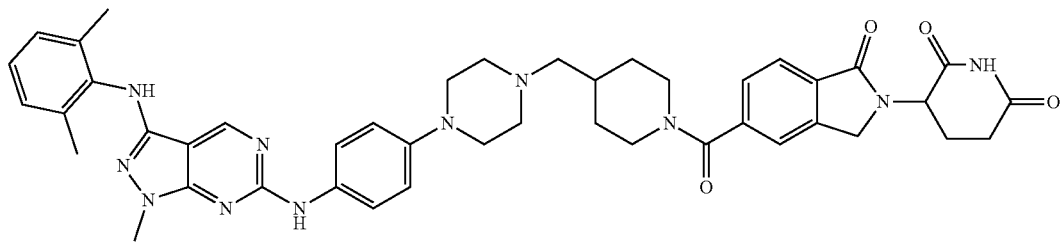

Compound 256

A solution of Compound 256-1 (identical to Compound 245-1) (15 mg, 0.029 mmol) in DMF (5 ml) was added with Compound 256-2 (BLD, BD01396745) (8.22 mg, 0.029 mmol), HATU (21.70 mg, 0.057 mmol), and TEA (15.39 µl, 0.114 mmol) and stirred at room temperature for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 256 as a yellow solid (8.0 mg, 0.029 mmol, 35%).

Compound 257. 3-(5-(4-(4-((3-((2,6-Dimethylphenyl)amino)-1-methyl-1H-pyrazolo[3,4-d]pyrimidin-6-yl)amino)phenyl)piperidine-1-carbonyl)-1-oxoisoindolin-2-yl)piperidin-2,6-one

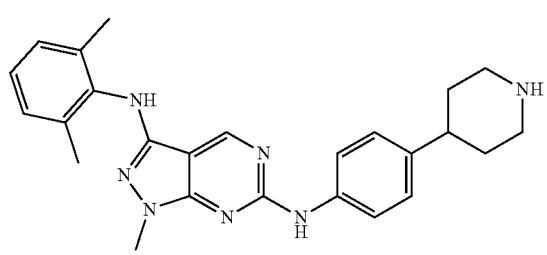

Compound 257-1

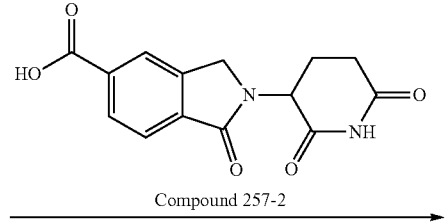

Compound 257-2

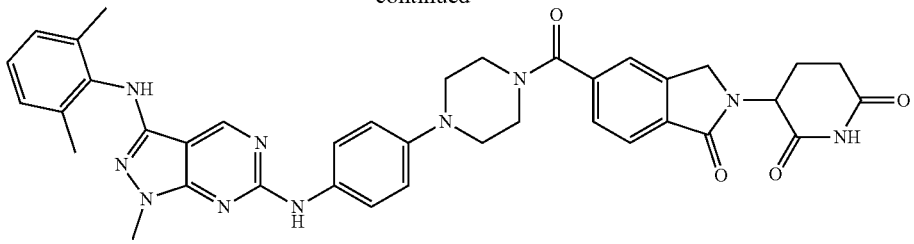

Compound 257

A solution of Compound 257-1 (identical to Compound 253-1) (15 mg, 0.035 mmol) in DMF (2 mL) was added with Compound 257-2 (identical to Compound 256-2) (10.11 mg, 0.035 mmol), HATU (26.7 mg, 0.070 mmol), and TEA (18.92 μl, 0.140 mmol) and stirred at room temperature for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 257 as a yellow solid (12.0 mg, 0.0350 mmol, 49%).

Compound 258. 3-(5-(4-((7-((3-((2,6-Dimethylphenyl)amino)-1-methyl-1H-pyrazolo[3,4-d]pyrimidin-6-yl)amino)-3,4-dihydroisoquinolin-2 (1H)-yl) methyl)piperidine-1-carbonyl)-1-oxoisoindolin-2-yl) piperidin-2,6-one

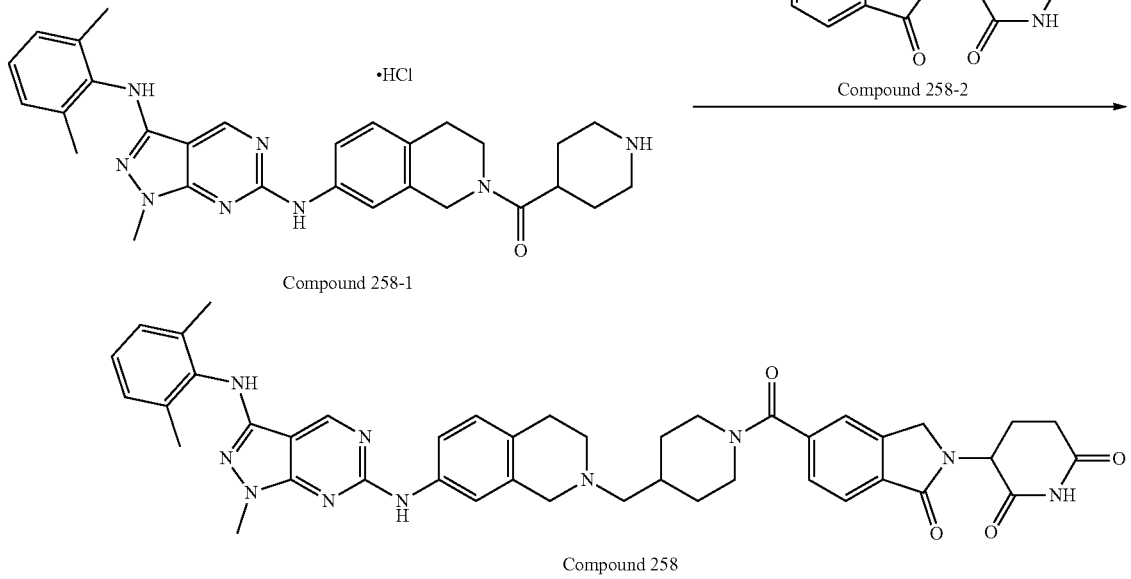

A solution of Compound 258-1 (identical to Compound 201-1) (15 mg, 0.030 mmol) in DMF (1 ml) was added with Compound 258-2 (identical to Compound 256-2) (8.71 mg, 0.030 mmol), HATU (22.97 mg, 0.060 mmol), and TEA (0.012 ml, 0.091 mmol) and stirred at room temperature for 12 hours. When the reaction was completed as analyzed by TLC, the reaction mixture was quenched with water before extraction with EtOAc (25 mL×2) for the aqueous layer. The combined organic layer was washed with water (20 mL×2) and brine (20 mL×2). The organic layer was dried over sodium sulfate and the organic solvent evaporated in a vacuum. The crude product was purified by MPLC using 5% MeOH:DCM as an eluent to afford Compound 258 as a yellow solid (7.00 mg, 0.0300 mmol, 30%).

Compound 259. (E)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)-3-(1-(2-(2,6-dioxopiperidin-3-yl)-1-oxoisoindoline-5-carbonyl)piperidin-4-yl)acrylonitrile

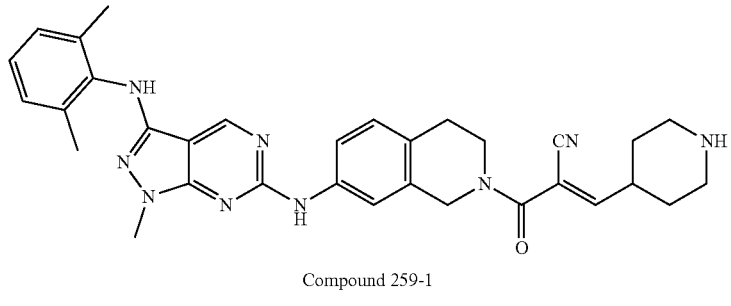

Compound 259-1

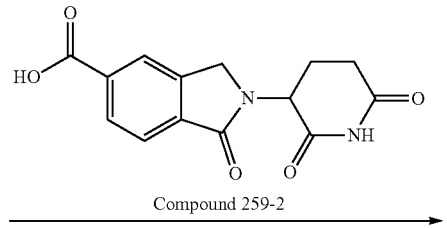

Compound 259-2

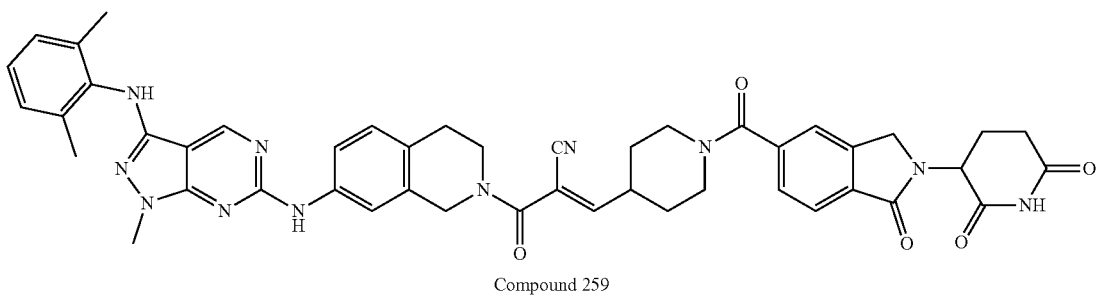

Compound 259

A suspension of Compound 259-1 (identical to Compound 260-1) (15.0 mg, 0.027 mmol) in DMF (2 mL) was added with DIPEA (10.3 mg, 0.080 mmol) and then at room temperature with HATU (20.3 mg, 0.053 mmol) and the mixture was stirred at room temperature for 15 minutes. After addition of Compound 259-2 (identical to Compound 256-2) (8.47 mg, 0.029 mmol), the resulting mixture was stirred at room temperature for 14 hours. The crude reaction mixture was diluted with water (10 mL) before extraction with ethyl acetate (3×15 mL). The pooled organic layer was dried over MgSO$_4$ and concentrated in a vacuum to give a crude product which was then purified by column chromatography using MeOH/DCM 5% to afford Compound 259 as a yellow solid (8.2 mg, 9.86 μmol, 36.9%).

Compound 260. (E)-2-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)-3-(1-((2-(2,6-dioxopiperidin-3-yl)-1,3-dioxoisoindolin-5-yl)glycyl)piperidin-4-yl)acrylonitrile

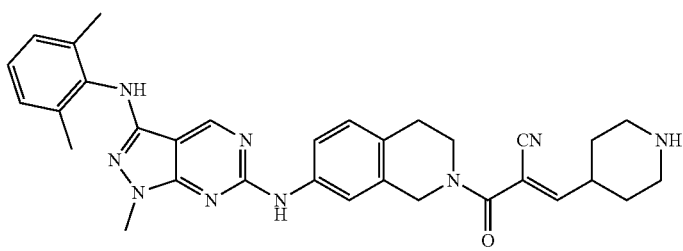

Compound 260-1

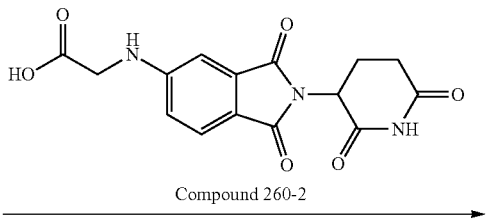

Compound 260-2

-continued

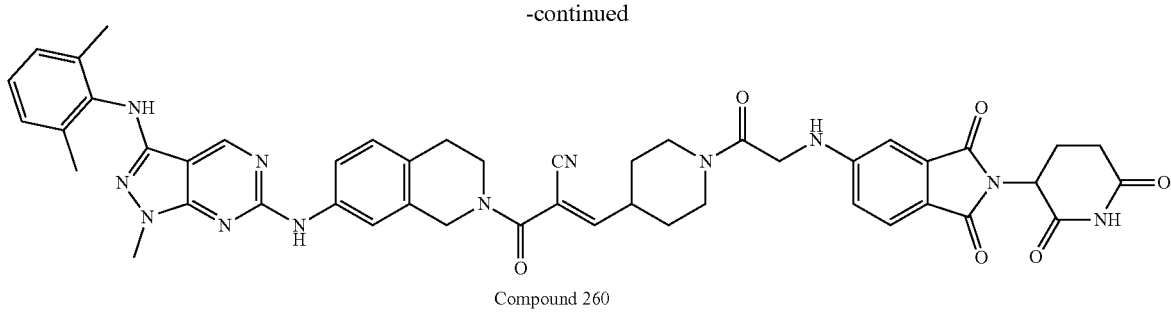

Compound 260

A suspension of Compound 260-1 (identical to Compound 240-1) (15 mg, 0.027 mmol) in DMF (2 mL) was added with DIPEA and then at room temperature with HATU (20 mg, 0.053 mmol) and the mixture was stirred at room temperature for 15 minutes. After addition of Compound 260-2 (identical to Compound 235-2) (9.7 mg, 0.029 mmol), the resulting mixture was stirred at room temperature for 14 hours. The crude reaction mixture was diluted with water (10 mL) before extraction with ethyl acetate (3×15 mL). The pooled organic layer was dried over MgSO$_4$ and concentrated in a vacuum to give a crude product which was then purified by column chromatography using MeOH/DCM 5% to afford Compound 260 as a yellow solid (12.2 mg, 0.014 mmol, 52.2%).

Compound 261. (E)-2-(4-(4-((3-((2,6-Dimethylphenyl)amino)-1-methyl-1H-pyrazolo[3,4-d]pyrimidin-6-yl)amino)phenyl)piperidine-1-carbonyl)-3-(1-((2-(2,6-dioxopiperidin-3-yl)-1,3-dioxoisoindolin-5-yl)glycyl)piperidin-4-yl)acrylonitrile

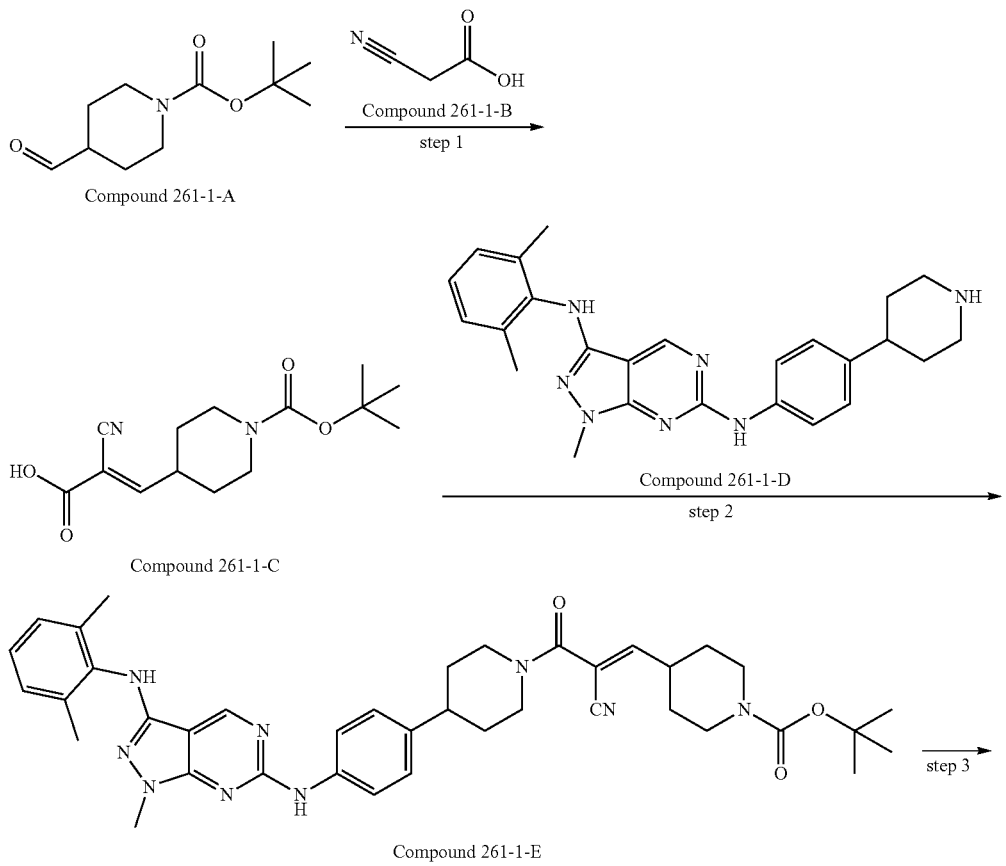

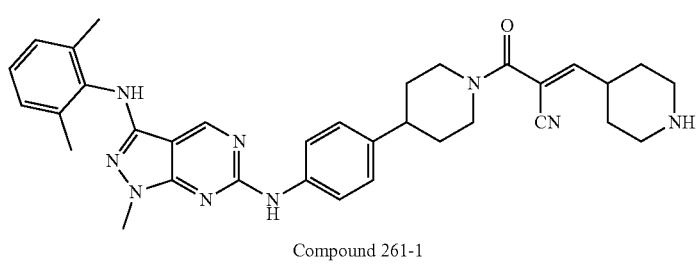

Compound 261-1

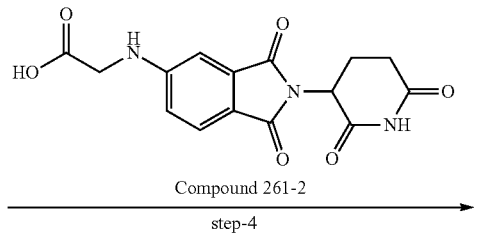

Compound 261-2 step-4

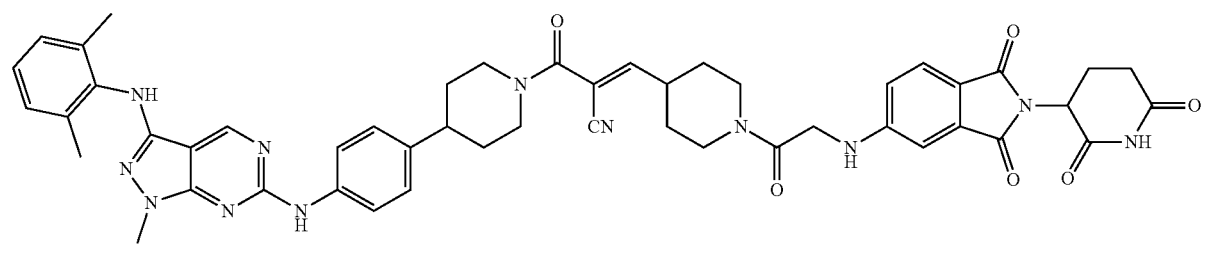

Compound 261

Step 1: Synthesis of (E)-3-(1-(tert-butoxycarbonyl)piperidin-4-yl)-2-cyanoacrylic acid A mixture of Compound 261-1-A (sigma, 722022) (tert-butyl 4-formylpiperidine-1-carboxylate (1.0 g, 4.6 mmol), Compound 261-1-B (sigma, C88505) (cyanoacetic acid) (479 mg, 5.6 mmol), glacial acetic acid (296 mg, 4.9 mmol), and ammonium acetate (181 mg, 2.3 mmol) was stirred in toluene (20 mL) and heated at 85° C. for 3 hours. The reaction mixture was cooled to the room temperature and diluted with ethyl acetate (15 mL). After separation of layers, extraction with EtOAc (25 mL×1) was applied to the aqueous layer. The pooled organic layer was washed with 1 M sodium hydroxide solution (25 mL×1), dried over MgSO₄, filtered, and concentrated in a vacuum. The residue was loaded into a silica column using 15% EtOAc/hexane to afford the desired Compound 261-1-C as a beige solid (632 mg, 2.255 mmol, 48.1%).

Step 2: Synthesis of tert-butyl (E)-4-(2-cyano-3-(4-(4-((3-((2,6-dimethylphenyl)amino)-1-methyl-H-pyrazolo[3,4])-d]pyrimidin-6-yl)amino)phenyl)piperidin-1-yl)-3-oxoprop-1-en-1-yl)piperidine-1-carboxylate A suspension of Compound 261-1-C (19 mg, 0.067 mmol) in DMF (3 mL) was added with DIPEA (22 mg, 0.16 mmol) and then at room temperature with HATU (43 mg, 0.11 mmol) and the mixture was stirred at room temperature for 15 minutes. After addition of Compound 261-1-D (identical to Compound 225-1) (24 mg, 0.056 mmol), the resulting mixture was stirred at room temperature for 14 hours. The crude reaction mixture was diluted with water (10 mL) before extraction with ethyl acetate (3×15 mL). The pooled organic layer was dried over MgSO₄ and concentrated in a vacuum to give a crude product which was then purified by column chromatography using MeOH/DCM 5% to afford Compound 261-1-E as a beige solid (25 mg, 0.036 mmol, 64.6%).

Step 3: Synthesis of (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(piperidin-4-yl)acrylonitrile A solution of Compound 261-1-E (24 mg, 0.035 mmol) in DCM (5 ml) was added with 4 N HCl (3.0 mg, 0.070 mmol) in dioxane. The mixture was stirred overnight at room temperature. The crude material was concentrated in a vacuum and the concentrate was dissolved in water and washed with EA (3×). Subsequently, the aqueous layer was neutralized with saturated NaHCO₃ before extraction with EA (3×). The solvent was evaporated from the organic layer which was then dried in a vacuum to afford Compound 261-1 as a yellow solid (12 mg, 0.020 mmol, 58.5%).

Step 4: Synthesis of (E)-2-(4-(4-((3-((2,6-dimethylphenyl)amino)-1-methyl-1H-pyrazolo[3,4-d]pyrimidin-6-yl)amino)phenyl)piperidine-1-carbonyl)-3-(1-((2-(2,6-dioxopiperidin-3-yl)-1,3-dioxoisoindolin-5-yl)glycyl)piperidin-4-yl)acrylonitrile (Compound 261)

A suspension of Compound 261-1 (11 mg, 0.019 mmol) in DMF (2 mL) was added with DIPEA and then at room temperature with HATU (15 mg, 0.037 mmol) and the mixture was stirred at room temperature for 15 minutes. After addition of Compound 261-2 (identical to Compound 235-2) (7.0 mg, 0.019 mmol), the resulting mixture was stirred at room temperature for 14 hours. The crude reaction mixture was diluted with water (10 mL) before extraction with ethyl acetate (3×15 mL). The pooled organic layer was dried over MgSO₄ and concentrated in a vacuum to give a crude product which was then purified by column chromatography using MeOH/DCM 5% to afford Compound 261 as a yellow solid (9.2 mg, 10.19 μmol, 54.6%).

Compound 262. 3-(5-(4-(4-(4-((3-((2,6-Dimethylphenyl)amino)-1-methyl-1H-pyrazolo[3,4-d]pyrimidin-6-yl)amino)phenyl)piperidine-1-carbonyl)piperidin-1-yl)-3-methyl-2-oxo-2,3-dihydro-1H-benzo[d]imidazol-1-yl)piperidin-2,6-one
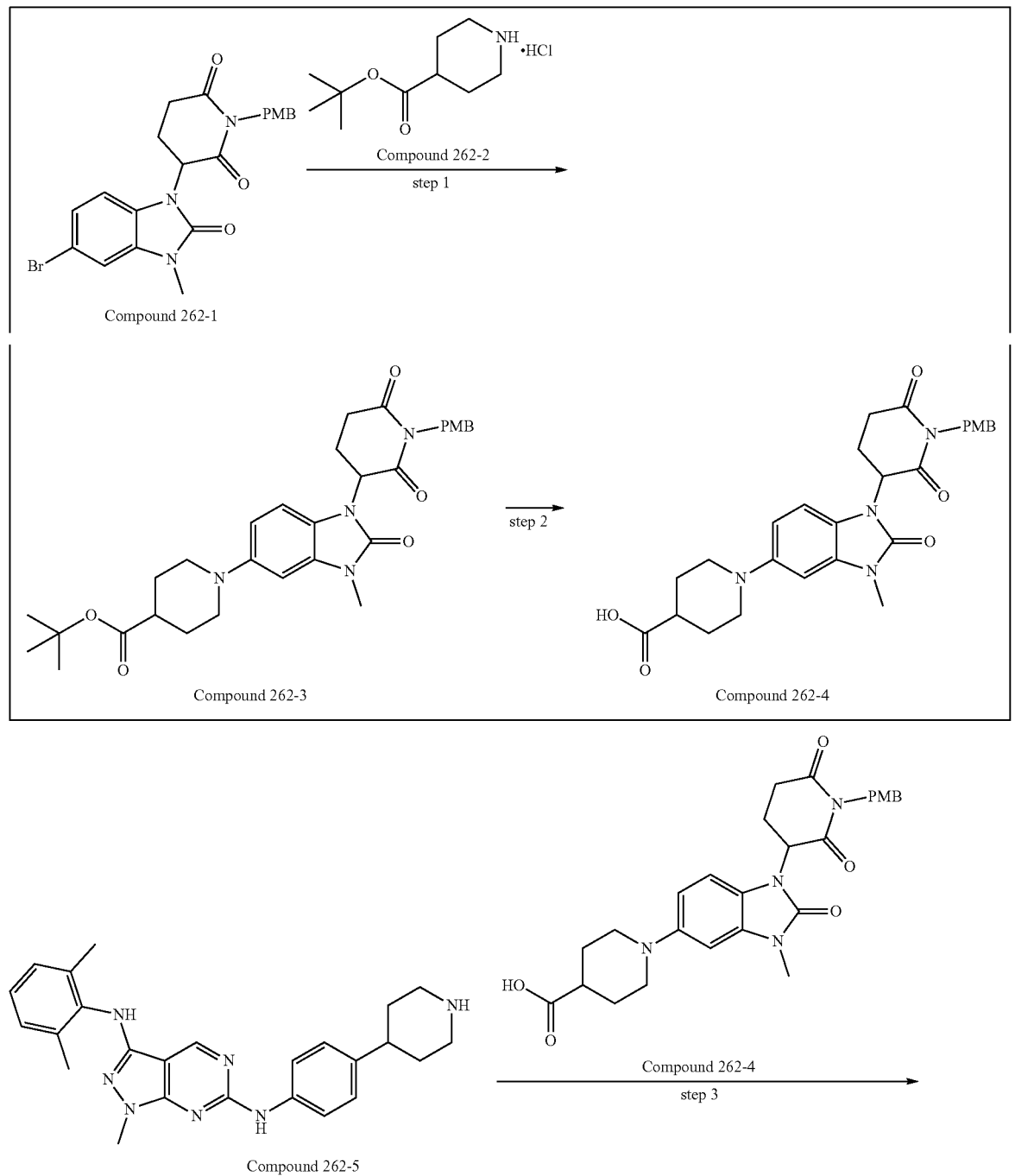

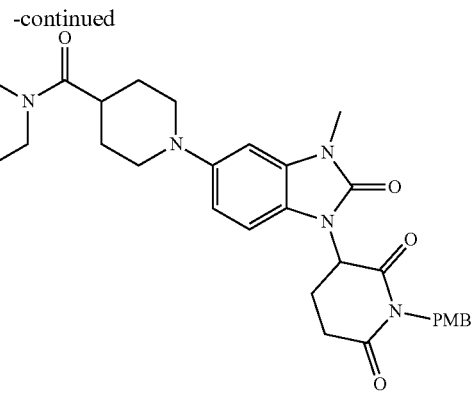

Compound 262-6

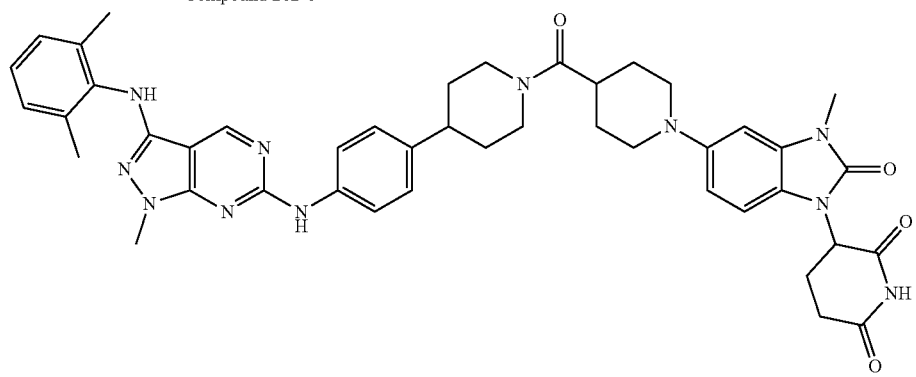

Compound 262

Step 1: Synthesis of tert-butyl 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylate A solution of Compound 262-1 (WO2020/113233) (100 mg, 0.22 mmol) in 1,4-dioxane (3 mL) was added with tert-butyl piperidine-4-carboxylate hydrochloride (Compound 262-2) (Acadechem, 20190523AP-1X, 50 g) (58 mg, 0.26 mmol), cesium carbonate (220 mg, 0.68 mmol), RuPhos (20 mg, 0.04 mmol), and RuPhos Pd G2 (34 mg, 0.04 mmol). The mixture was bubbled for 5 minutes with nitrogen gas and then stirred at 100° C. for 16 hours. After completion of the reaction, the reaction mixture was quenched with water and subjected to extraction with EtOAc (3×30 mL). The pooled organic layer was dried over Na₂SO₄ and filtered, and the solvent was evaporated in a vacuum. The crude product was purified by column chromatography using 50% EtOAc/HEX to afford Compound 262-3 as an off-white solid (51 mg, 0.07 mmol, 42%).

Step 2: Synthesis of 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylic acid To trifluoroacetic acid (1 mL) was added a solution of tert-butyl 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylate (Compound 262-3) (51 mg, 0.09 mmol) in DCM (1.5 mL). The resulting mixture was stirred at room temperature for 3 hours. After completion of the reaction, the solvent was removed in a vacuum. The ivory solid thus formed was washed with diethyl ether and concentrated in a vacuum to afford Compound 262-4 as an ivory solid (46 mg, 0.09 mmol, quant.).

Step 3: Synthesis of 3-(5-(4-(4-(4-((3-((2,6-dimethylphenyl)amino)-1-methyl-1H-pyrazolo[3,4-d]pyrimidin-6-yl)amino)phenyl)piperidine-1-carbonyl)piperidin-1-yl)-3-methyl-2-oxo-2,3-dihydro-1H-benzo[d]imidazol-1-yl)-1-(4-methoxybenzyl)piperidine-2,6-dione A solution of N3-(2,6-dimethylphenyl)-1-methyl-N6-(4-(piperidin-4-yl)phenyl)-1H-pyrazolo[3,4-d]pyrimidine-3,6-diamine (Compound 262-5) (identical to Compound 228-1) (20 mg, 0.05 mmol) in DMF (1 mL) was added with 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylic acid (Compound 262-4) (24 mg, 0.05 mmol), 1-[bis(dimethylamino)methylene]-1H-1,2,3-triazolo[4,5-b]pyridinium 3-oxide hexafluorophosphate (HATU; 36 mg, 0.09 mmol), and triethylamine (20 µL, 0.14 mmol). The resulting mixture was stirred at room temperature for 12 hours. After completion of the reaction, the reaction mixture was quenched with water, subjected to extraction with EtOAc (3×30 mL), and washed with water (3×5 mL) and brine. The pooled organic layer was dried over Na₂SO₄ and filtered, and the solvent was evaporated in a vacuum. The crude product was purified by column chromatography using 5% MeOH/DCM to afford Compound 262-6 as a grayish brown solid (33 mg, 0.04 mmol, 77%).

Step 4: Synthesis of 3-(5-(4-(4-(4-((3-((2,6-dimethylphenyl)amino)-1-methyl-1H-pyrazolo[3,4-d]pyrimidin-6-yl)amino)phenyl)piperidine-1-carbonyl)piperidin-1-yl)-3-methyl-2-oxo-2,3-dihydro-1H-benzo[d]imidazol-1-yl)piperidine-2,6-dione (Compound 262)

A solution of 3-(5-(4-(4-(4-((3-((2,6-dimethylphenyl)amino)-1-methyl-1H-pyrazolo[3,4-d]pyrimidin-6-yl)amino)phenyl)piperidine-1-carbonyl)piperidin-1-yl)-3-methyl-2-oxo-2,3-dihydro-1H-benzo[d]imidazol-1-yl)-1-(4-methoxybenzyl) piperidin-2,6-one (Compound 262-6) (70 mg, 0.24 mmol) in toluene (1 mL) was added with methanesulfonic acid (47 µL, 0.72 mmol). The mixture was heated to 100° C. and then stirred at the same temperature for 2 hours. After completion of the reaction, the reaction mixture was quenched with water, subjected to extraction with EtOAc (3×15 mL), and washed with water (3×5 mL). The pooled organic layer was dried over Na₂SO₄ and filtered, and the solvent was evaporated in a vacuum. The crude product was purified by column chromatography using 10% MeOH/DCM to afford Compound 262 as an off-white solid (5 mg, 0.01 mmol, 17%).

Compound 263. 5-(3-(4-(5-((3-((2,6-Dimethylphenyl)amino)-1-methyl-1H-pyrazolo[3,4-d]pyrimidin-6-yl)amino)-2-fluorophenyl)-1,2,3,6-tetrahydropyridine-1-carbonyl)azetidin-1-yl)-2-(2,6-dioxopiperidin-3-yl)isoindoline-1,3-dione

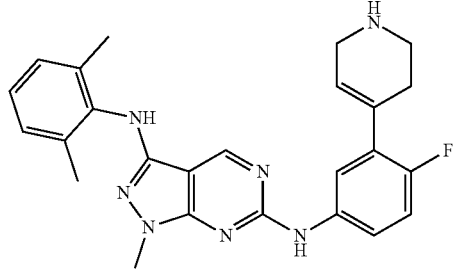

Compound 263-1

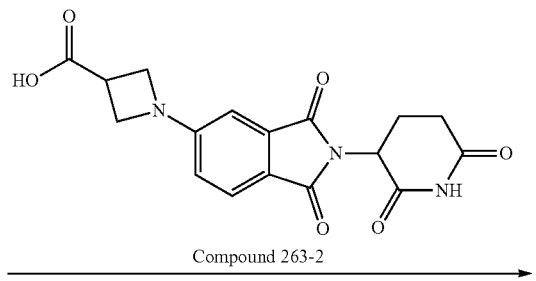

Compound 263-2

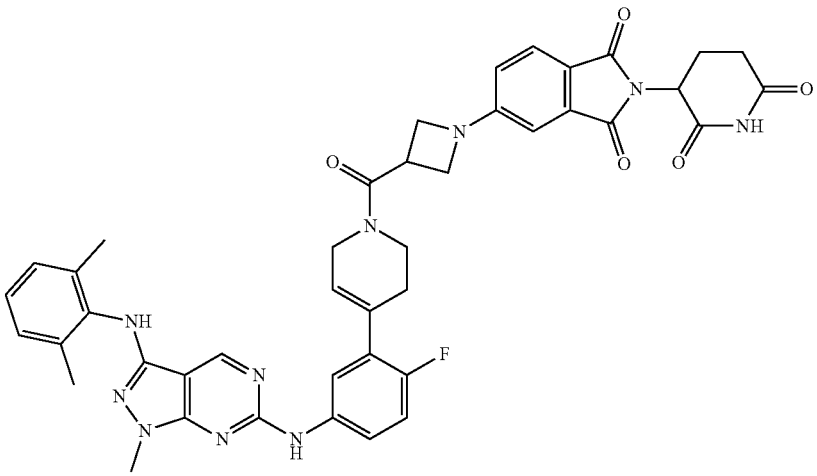

Compound 263

A solution of N3-(2,6-dimethylphenyl)-N6-(4-fluoro-3-(1,2,3,6-tetrahydropyridin-4-yl)phenyl)-1-methyl-H-pyrazolo[3,4-d]pyrimidine-3,6-diamine (Compound 263-1) (identical to Compound 250-5) (15 mg, 0.03 mmol) in DMF (1 mL) was added with 1-(2-(2,6-dioxopiperidin-3-yl)-1,3-dioxoisoindolin-5-yl)azetidine-3-carboxylic acid (Compound 263-2) (identical to Compound 228-2) (12 mg, 0.03 mmol), 1-[bis(dimethylamino)methylene]-1H-1,2,3-triazolo[4,5-b]pyridinium 3-oxide hexafluorophosphate (HATU; 26 mg, 0.07 mmol), and triethylamine (14 µL, 0.10 mmol). The resulting mixture was stirred at room temperature for 12 hours. After completion of the reaction, the reaction mixture was quenched with water, subjected to extraction with EtOAc (3×15 mL), and washed with water (3×5 mL) and brine. The pooled organic layer was dried over Na₂SO₄ and filtered, and the solvent was evaporated in a vacuum. The crude product was purified by column chromatography using 5% MeOH/DCM to afford Compound 263 as a grayish yellow solid (10 mg, 0.01 mmol, 38%).

Compound 264. 3-(5-(4-(7-((3-((2,6-Dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-3-methyl-2-oxo-2,3-dihydro-1H-benzo[d]imidazol-1-yl)piperidin-2,6-one
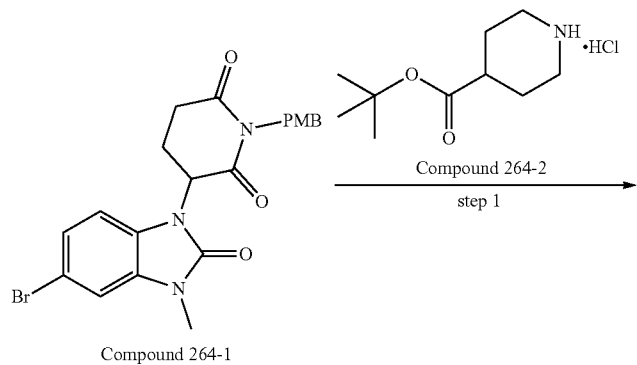
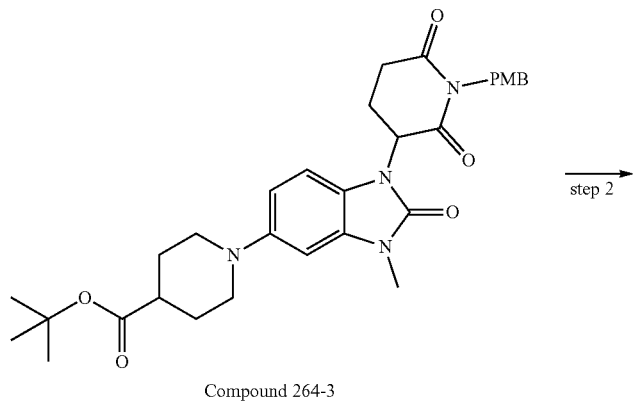
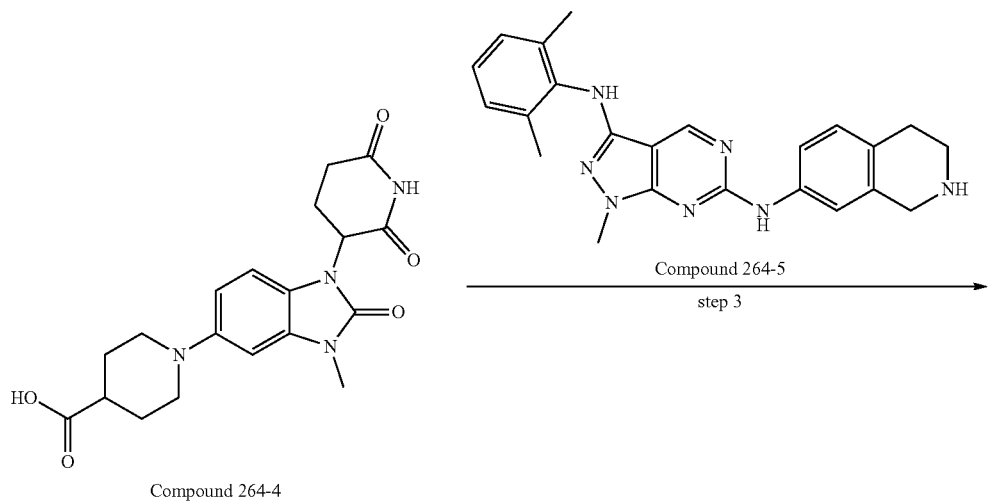

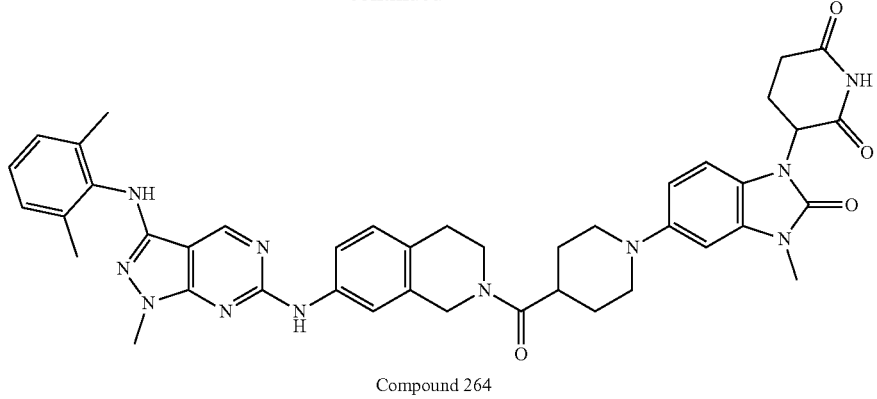

Compound 264

Step 1: Synthesis of tert-butyl 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylate A solution of Compound 264-1 (identical to Compound 262-1) (70 mg, 0.15 mmol) in 1,4-dioxane (3 mL) was added with tert-butyl piperidine-4-carboxylate hydrochloride (Compound 264-2) (Acadechem, 20190523AP-1X, 50 g) (41 mg, 0.18 mmol), cesium carbonate (154 mg, 0.47 mmol), RuPhos (14 mg, 0.03 mmol), and RuPhos Pd G2 (24 mg, 0.03 mmol). The mixture was bubbled for 5 minutes with nitrogen gas and then stirred at 100° C. for 16 hours. After completion of the reaction, the reaction mixture was quenched with water and subjected to extraction with EtOAc (3×30 mL). The pooled organic layer was dried over Na$_2$SO$_4$ and filtered, and the solvent was evaporated in a vacuum. The crude product was purified by column chromatography using 50% EtOAc/HEX to afford Compound 264-3 as an off-white solid (35 mg, 0.06 mmol, 41%).

Step 2: Synthesis of 1-(1-(2,6-dioxopiperidin-3-yl)-3-methyl-2-oxo-2,3-dihydro-1H-benzo[d]imidazol-5-yl)piperidine-4-carboxylic acid A solution of tert-butyl 1-(1-(1-(4-methoxybenzyl)-2,6-dioxopiperidin-3-yl)-3-methyl-2-oxo-2,3-dihydro-1H-benzo[d]imidazol-5-yl)piperidine-4-carboxylate (Compound 264-3) (35 mg, 0.06 mmol) in toluene (1 mL) was added with methanesulfonic acid (81 μL, 1.24 mmol). The mixture was heated to 100° C. and then stirred at the same temperature for 2 hours. After completion of the reaction, the reaction mixture was quenched with water, subjected to extraction with EtOAc (3×15 mL), and washed with water (3×5 mL). The pooled organic layer was dried over Na$_2$SO$_4$ and filtered, and the solvent was evaporated in a vacuum. The white precipitates thus formed were dried in a vacuum to afford Compound 264-4 as an off-white solid (18 mg, 0.05 mmol, 75%).

Step 3: Synthesis of 3-(5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-3-methyl-2-oxo-2,3-dihydro-1H-benzo[d]imidazol-1-yl)piperidine-2,6-dione (Compound 264)

A solution of 1-(1-(2,6-dioxopiperidin-3-yl)-3-methyl-2-oxo-2,3-dihydro-1H-benzo[d]imidazol-5-yl)piperidine-4-carboxylic acid (Compound 264-4) (15 mg, 0.04 mmol) in DMF (1 mL) was added with N3-(2,6-dimethylphenyl)-1-methyl-N6-(1,2,3,4-tetrahydroisoquinolin-7-yl)-1H-pyrazolo[3,4-d]pyrimidine-3,6-diamine (Compound 264-5) (Korean Patent No. 2128018) (15 mg, 0.04 mmol), 1-[bis(dimethylamino)methylene]-1H-1,2,3-triazolo[4,5-b]pyridinium 3-oxide hexafluorophosphate (HATU; 29 mg, 0.08 mmol), and triethylamine (16 μL, 0.11 mmol). The resulting mixture was stirred at room temperature for 12 hours. After completion of the reaction, the reaction mixture was quenched with water, subjected to extraction with EtOAc (3×15 mL), and washed with water (3×5 mL) and brine. The pooled organic layer was dried over Na$_2$SO$_4$ and filtered, and the solvent was evaporated in a vacuum. The crude product was purified by column chromatography using 5% MeOH/DCM to afford Compound 264 as an off-white solid (7 mg, 0.01 mmol, 24%).

Compound 268. 5-(4-((4-(6-((3-((2,6-dimethylphenyl)amino)-1-methyl-1H-pyrazolo[3,4-d]pyrimidin-6-yl)amino)pyridazin-3-yl)piperazin-1-yl)methyl)piperidin-1-yl)-2-(2,6-dioxopiperidin-3-yl)isoindoline-1,3-dione

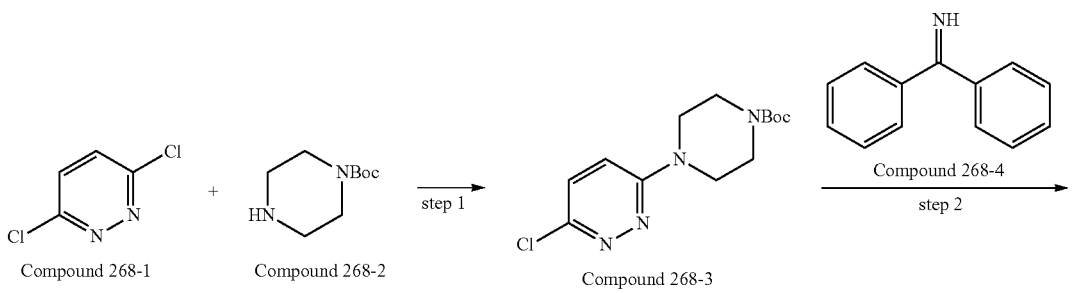

-continued
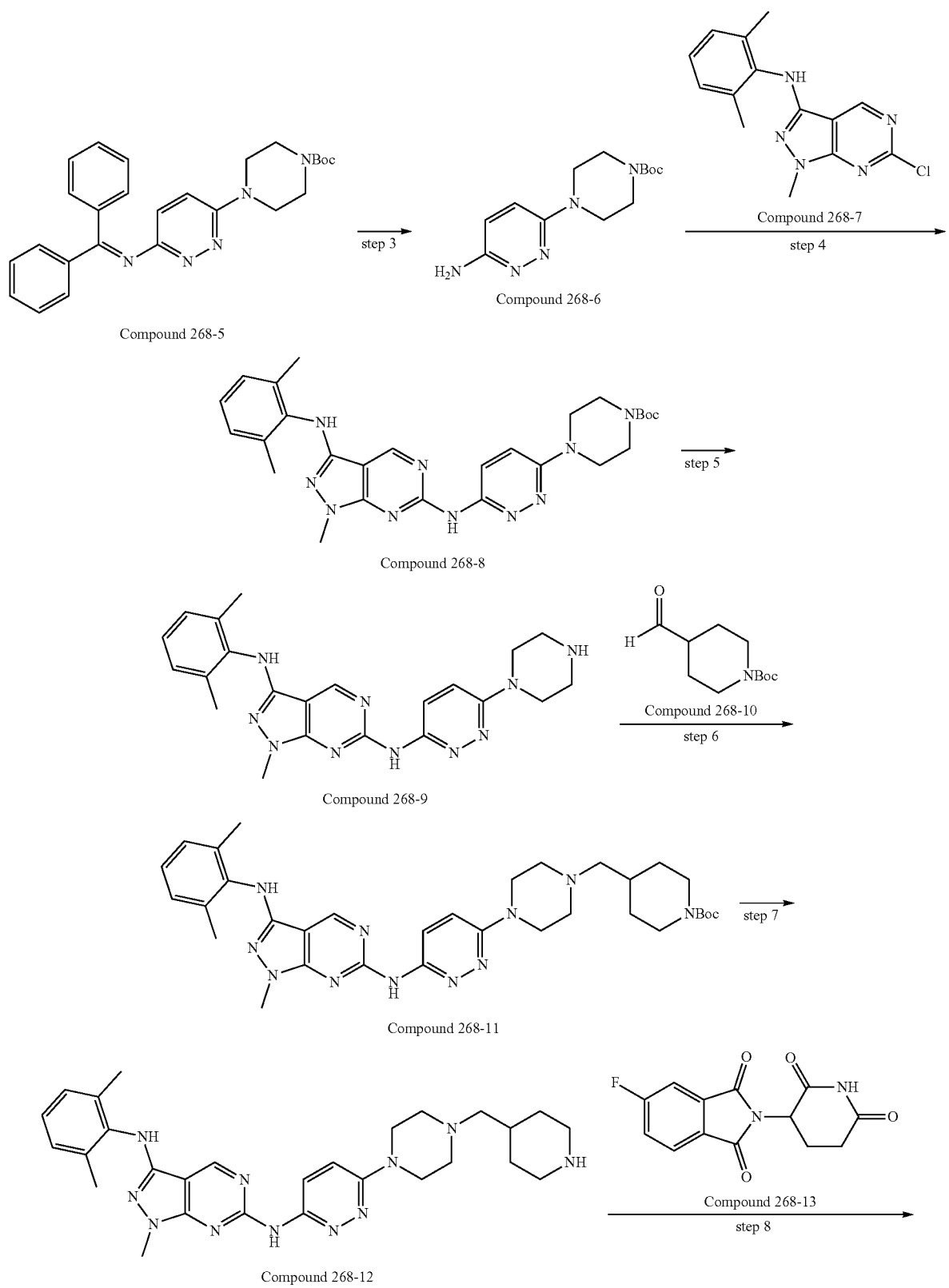

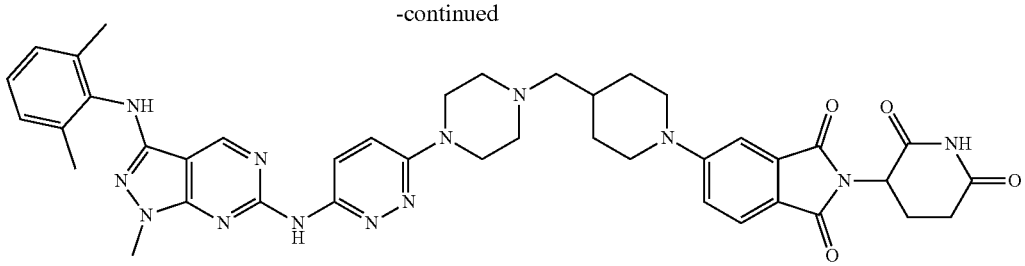

Compound 268

Step 1: Synthesis of tert-butyl 4-(6-chloropyridazin-3-yl)piperazine-1-carboxylate A solution of 3,6-dichloropyridazine (SIGMA, D73200) (Compound 268-1; 1.0 g, 6.7 mmol) and tert-butyl piperazine-1-carboxylate (SIGMA, 15502) (Compound 268-2; 1.3 g, 6.7 mmol) in DMF (5.0 mL) was added at room temperature with DIPEA (1.8 mL, 10.1 mmol). The mixture was stirred at 80° C. for 12 hours. After completion of the reaction, the reaction mixture was quenched with water and subjected to extraction with EtOAc (3×30 mL). The pooled organic layer was dried over $Na_2SO_4$ and filtered, and the solvent was evaporated in a vacuum. The crude product was purified by column chromatography using 30% EtOAc/Hx to afford Compound 268-3 as an off-white solid (1.7 g, 5.77 mmol, 86%).

Step 2: Synthesis of tert-butyl 4-(6-((diphenylmethylene)amino)pyridazin-3-yl)piperazine-1-carboxylate A solution of tert-butyl 4-(6-chloropyridazin-3-yl)piperazine-1-carboxylate (Compound 268-3; 420.0 mg, 1.4 mmol) in toluene (5.0 mL) was added with $Cs_2CO_3$ (916 mg, 2.81 mmol), $Pd_2(dba)_3$ (64 mg, 0.070 mmol), BINAP (88 mg, 0.141 mmol), and diphenylmethanimine (SIGMA, 293733) (Compound 268-4; 364 µl, 2.11 mmol). The mixture was stirred 100° C. for 12 hours in a nitrogen atmosphere. After completion of the reaction, the reaction mixture was quenched with water and subjected to extraction with EtOAc (3×30 mL). The pooled organic layer was dried over $Na_2SO_4$ and filtered, and the solvent was evaporated in a vacuum. The crude product was purified by column chromatography using 50% EtOAc/Hx to afford Compound 268-5 as an off-white solid (382 mg, 0.860 mmol, 61%).

Step 3: Synthesis of tert-butyl 4-(6-aminopyridazin-3-yl)piperazine-1-carboxylate In THF (5.0 mL) was dissolved tert-butyl 4-(6-((diphenylmethylene)amino)pyridazin-3-yl)piperazine-1-carboxylate (Compound 268-5) (380 mg, 0.857 mmol), followed by adding an aqueous 2 M citric acid solution (2.6 ml, 5.14 mmol), and the resulting mixture was stirred at room temperature for 12 hours. The reaction mixture was neutralized with an aqueous saturated sodium hydrogen carbonate solution and quenched with water before extraction with EtOAc (3×30 mL). The pooled organic layer was dried over $Na_2SO_4$ and filtered, and the solvent was evaporated in a vacuum. The crude product was washed with ether to afford Compound 268-6 as an off-white solid (180 mg, 0.643 mmol, 75%).

Step 4: Synthesis of tert-butyl-4-(6-((3-((2,6-dimethylphenyl)amino)-1-methyl-1H-pyrazolo[3,4-d]pyrimidin-6-yl)amino)pyridazin-3-yl)piperazine-1-carboxylate A solution of 6-chloro-N-(2,6-dimethylphenyl)-1-methyl-1H-pyrazolo[3,4-d]pyrimidine-3-amine (Compound 268-7) (identical to Compound 230-4) (50 mg, 0.17 mmol) in toluene/$H_2O$ (1.0 mL/4 µL) was added with $K_3PO_4$ (55 mg, 0.26 mmol), $Pd_2(dba)_3$ (8 mg, 0.0087 mmol), xantphos (10 mg, 0.017 mmol), and tert-butyl 4-(6-aminopyridazin-3-yl)piperazine-1-carboxylate (Compound 268-6) (58 mg, 0.21 mmol). The mixture was stirred at 100° C. for 12 hours in a nitrogen atmosphere. After completion of the reaction, the reaction mixture was quenched with water and subjected to extraction with EtOAc (3×15 mL). The pooled organic layer was dried over $Na_2SO_4$ and filtered, and the solvent was evaporated in a vacuum. The crude product was purified by column chromatography using 5% MeOH/DCM to afford Compound 268-8 as a grayish yellow solid (56 mg, 0.104 mmol, 61%).

Step 5: Synthesis of N3-(2,6-dimethylphenyl)-1-methyl-N6-(6-(piperazin-1-yl)pyridazin-3-yl)-1H-pyrazolo[3,4-d]pyrimidine-3,6-diamine A solution of tert-butyl-4-(6-((3-((2,6-dimethylphenyl)amino)-1-methyl-1H-pyrazolo[3,4-d]pyrimidin-6-yl)amino)pyridazin-3-yl)piperazine-1-carboxylate (Compound 268-8) (55 mg, 0.104 mmol) in DCM (1.0 mL) was added at 0° C. with drops of 4 M HCl/1,4-dioxane (0.26 mL, 1.04 mmol). The resulting mixture was stirred at room temperature for 3 hours. After completion of the reaction, the reaction mixture was quenched with water and subjected to extraction with EtOAc (3×10 mL). The pooled organic layer was dried over $Na_2SO_4$ and filtered, and the solvent was evaporated in a vacuum to afford Compound 268-9 as a grayish yellow solid (50 mg, 0.116 mmol, quant.).

Step 6: Synthesis of tert-butyl-4-((4-(6-((3-((2,6-dimethylphenyl)amino)-1-methyl-1H-pyrazolo[3,4-d]pyrimidin-6-yl)amino)pyridazin-3-yl)piperazin-1-yl)methyl)piperidine-1-carboxylate A solution of N3-(2,6-dimethylphenyl)-1-methyl-N6-(6-(piperazin-1-yl)pyridazin-3-yl)-1H-pyrazolo[3,4-d]pyrimidine-3,6-diamine (Compound 268-9) (65 mg, 0.151 mmol) in MeOH (3.0 mL) was added with tert-butyl 4-formylpiperidine-1-carboxylate (SIGMA, 722022) (Compound 268-10) (35 mg, 0.166 mmol) and 1M AcOH/MeOH (151 µL). The resulting mixture was stirred at room temperature for 12 hours. Addition of $NaBH_3CN$ (14 mg, 0.226 mmol) was followed by stirring the mixture at room temperature for 1 hour. After completion of the reaction, the reaction mixture was quenched with water and subjected to extraction with DCM (3×10 mL). The pooled organic layer was dried over Na₂SO₄ and filtered, and the solvent was evaporated in a vacuum. The crude product was purified by column chromatography using 5% MeOH/DCM to afford Compound 268-11 as a grayish yellow solid (73 mg, 0.116 mmol, 77%).

Step 7: Synthesis of N3-(2,6-dimethylphenyl)-1-methyl-N6-(6-(4-(piperidin-4-ylmethyl)piperazin-1-yl)pyridazin-3-yl)-1H-pyrazolo[3,4-d]pyrimidine-3,6-diamine A solution of tert-butyl-4-((4-(6-((3-((2,6-dimethylphenyl)amino)-1-methyl-1H-pyrazolo[3,4-d]pyrimidin-6-yl)amino)pyridazin-3-yl)piperazin-1-yl)methyl)piperidine-1-carboxylate (Compound 268-11) (70 mg, 0.112 mmol) in DCM (1.5 mL) was added at 0° C. with drops of 4 M HCl/1,4-dioxane (0.278 mL, 1.12 mmol). The resulting mixture was stirred at room temperature for 3 hours. After completion of the reaction, the reaction mixture was quenched with water and subjected to extraction with DCM (3×10 mL). The pooled organic layer was dried over Na₂SO₄ and filtered, and the solvent was evaporated in a vacuum to afford Compound 268-12 as a grayish yellow solid (63 mg, 0.119 mmol, quant.).

Step 8: Synthesis of 5-(4-((4-(6-((3-((2,6-dimethylphenyl)amino)-1-methyl-1H-pyrazolo[3,4-d]pyrimidin-6-yl)amino)pyridazin-3-yl)piperazin-1-yl)methyl)piperidin-1-yl)-2-(2,6-dioxopiperidin-3-yl)isoindoline-1,3-dione (Compound 268)

A mixture of N3-(2,6-dimethylphenyl)-1-methyl-N6-(6-(4-(piperidin-4-ylmethyl)piperazin-1-yl)pyridazin-3-yl)-1H-pyrazolo[3,4-d]pyrimidine-3,6-diamine (Compound 268-12) (15 mg, 0.028 mmol), Compound 268-13 (identical to Compound 232-4) (7.9 mg, 0.028 mmol), and DIPEA (25 µL, 0.142 mmol) in DMSO (1 mL) was stirred at 90° C. for 12 hours. After completion of the reaction, the reaction mixture was quenched with water and subjected to extraction with EtOAc (3×15 mL). The pooled organic layer was dried over Na₂SO₄ and filtered, and the solvent was evaporated in a vacuum. The crude product was purified by column chromatography using 5% MeOH/DCM to afford Compound 268 as a grayish yellow solid (18 mg, 0.023 mmol, 81%).

Compound 272. 3-(5-(4-((4-(4-((3-((2,6-dimethylphenyl)amino)-1-methyl-1H-pyrazolo[3,4-d]pyrimidin-6-yl)amino)phenyl)piperidin-1-yl)methyl)piperidin-1-yl)-6-fluoro-1-oxoisoindolin-2-yl)piperidin-2,6-one

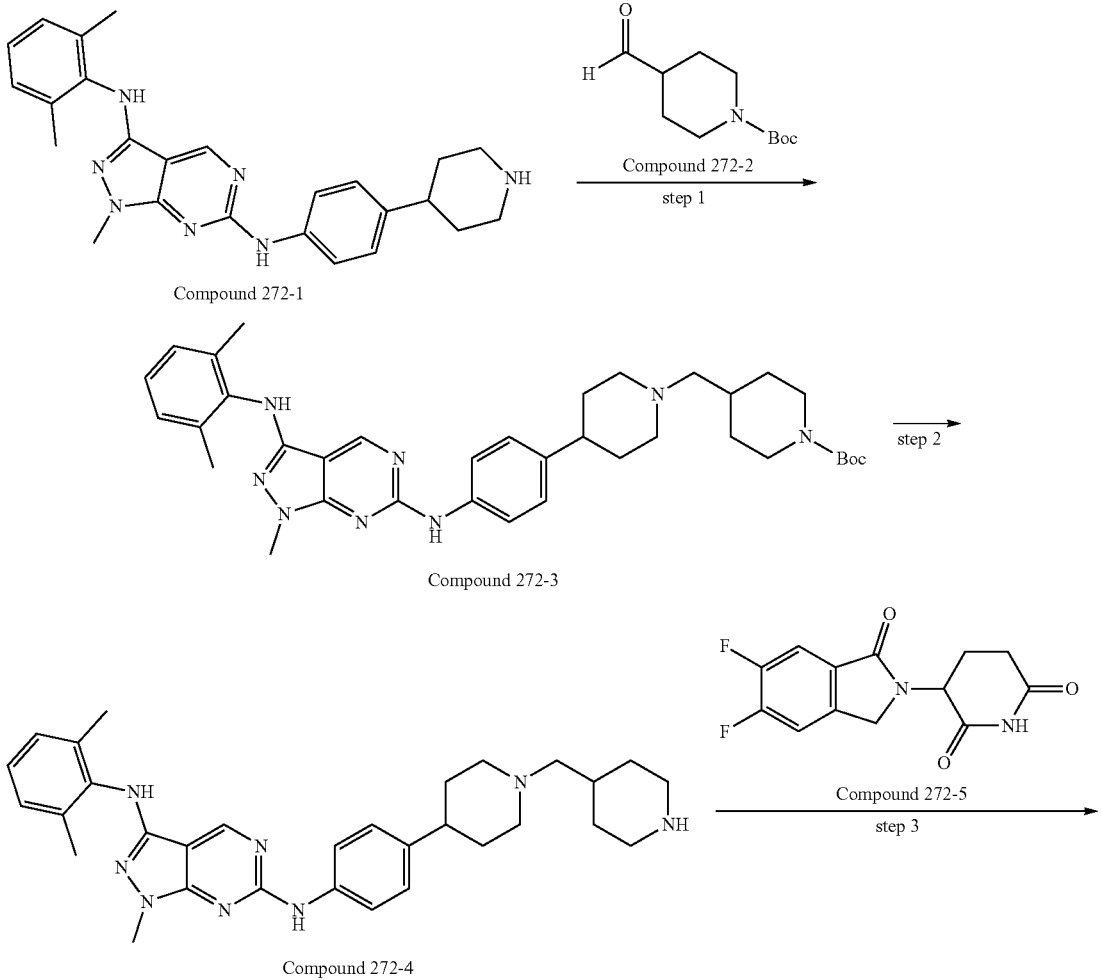

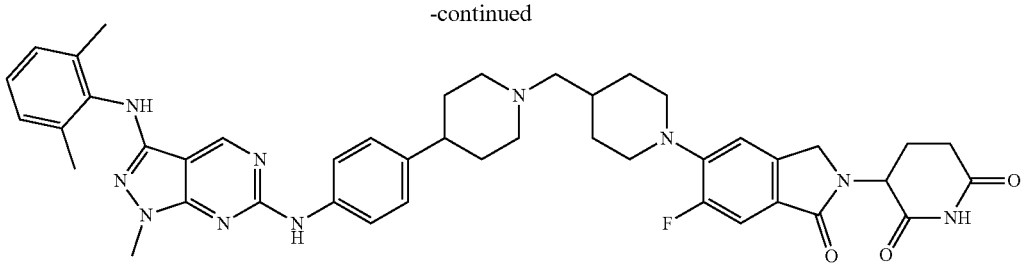

Compound 272

Step 1: Synthesis of tert-butyl 4-((4-(4-((3-((2,6-dimethylphenyl)amino)-1-methyl-1H-pyrazolo[3,4-d]pyrimidin-6-yl)amino)phenyl)piperazin-1-yl)methyl)piperidine-1-carboxylate A solution of Compound 272-1 (identical to Compound 222-3) (100 mg, 0.234 mmol) in MeOH (1 mL) was added with Compound 272-2 (TCI B3873) (54.9 mg, 0.257 mmol) and acetic acid (1 drop, catalytic amount) and stirred for 15 hours. After addition of NaBH₃CN (22 mg, 0.350 mmol), stirring was conducted for 1 hour. When the reaction was completed as analyzed by TLC, the solvent was completely evaporated. The residue was dissolved in MC and washed with saturated sodium bicarbonate. The organic layer was dried over sodium sulfate and the organic solvent evaporated in a vacuum. The residue was purified by MPLC using 10% MeOH/MC to afford Compound 272-3 (56.1 mg, 0.090 mmol, 38.4%).

Step 2: Synthesis of N3-(2,6-dimethylphenyl)-1-methyl-N6-(4-(1-(piperidin-4-ylmethyl)piperidin-4-yl)phenyl)-1H-pyrazolo[3,4-d]pyrimidine-3,6-diamine A solution of Compound 272-3 (50 mg, 0.080 mmol) in DCM (1.0 mL) was added with 4 N HCl/dioxane (0.5 ml, excess). The mixture was stirred at room temperature for 12 hours. When the starting material disappeared as monitored by TLC, the solvent was evaporated in a vacuum and basic post-treatment with a saturated NaHCO₃ solution was provided. After the basic post-treatment, the organic layer was recrystallized in chloroform/Hex to afford Compound 272-4 as an off-white solid (17 mg, 0.032 mmol, 41%).

Step 3: Synthesis of 3-(5-(4-((4-(4-((3-((2,6-dimethylphenyl)amino)-1-methyl-1H-pyrazolo[3,4-d]pyrimidin-6-yl)amino)phenyl)piperidin-1-yl)methyl)piperidin-1-yl)-6-fluoro-1-oxoisoindolin-2-yl)piperidine-2,6-dione (Compound 272)

A solution of Compound 272-4 (15 mg, 0.029 mmol) in DMSO (1 mL) was added with Compound 272-5 (identical to Compound 220-2) (8.01 mg, 0.029 mmol) and DIPEA (0.025 ml, 0.143 mol) and heated from room temperature to 90° C. at which stirring was conducted for 13 hours to complete the reaction. When a new spot was formed as analyzed by TLC, the reaction mixture was quenched with water (5 mL) before extraction with EA. The combined organic layer was washed with water and brine. The pooled organic layer was dried over sodium sulfate and filtered, and the solvent was evaporated in a vacuum. The crude product was purified by MPLC using a solvent mixture of 10% MeOH:DCM to afford Compound 272 as a yellow solid (3.5 mg, 0.00045 mmol, 16%).

Physical Data of Illustrative Compounds in Example 1

1H NMR spectrum and mass spectrometry (LCMS) data were obtained for the illustrative compounds reported in Example 1. The experimental data are summarized in Table 1, below.

TABLE 1

| Cpd. No. | 1H NMR/Mass Spec(LCMS) |
|---|---|
| Cpd. 1 | LC/MS 385 [M/2], 769 [M + H], 791 [M + Na], 1H NMR (500 MHz, Chloroform-d) δ 10.95 (s, 1H), 9.08 (s, 1H), 8.10 (s, 1H), 7.64-7.56 (m, 1H), 7.54-7.47 (m, 1H), 7.48-7.39 (m, 1H), 7.19 (d, J = 9.5 Hz, 3H), 7.14-7.08 (m, 2H), 6.92 (dd, J = 12.6, 8.5 Hz, 1H), 6.28 (dt, J = 25.1, 5.9 Hz, 1H), 6.14 (s, 0.5H), 6.00 (d, J = 9.3 Hz, 0.5H), 4.94 (td, J = 11.5, 5.2 Hz, 1H), 4.76 (d, J = 6.0 Hz, 1H), 4.54 (s, 2 = 1H), 3.82 (d, J = 4.6 Hz, 4H), 3.70-3.64 (m, 1H), 3.39-3.26 (m, 2H), 2.91-2.69 (m, 5H), 2.49-2.35 (m, 2H), 2.30 (d, J = 4.7 Hz, 6H), 2.19z-2.12 (m, 1H), 1.80-1.68 (m, 3H), 1.67 (s, 2H), 1.56-1.45 (m, 2H). |
| Cpd. 2 | LC/MS: 801[M + H]+ 1H NMR (400 MHz, DMSO-d6) δ 11.05 (s, 1H), 9.62 (d, J = 8.3 Hz, 1H), 8.33 (d, J = 3.0 Hz, 1H), 8.09 (s, 1H), 7.74-7.59 (m, 2H), 7.53 (dd, J = 19.5, 8.3 Hz, 1H), 7.21-6.98 (m, 6H), 6.87 (dd, J = 22.4, 8.2 Hz, 1H), 5.02 (dd, J = 12.9, 5.3 Hz, 1H), 4.58 (d, J = 5.3 Hz, 2H), 4.26 (d, J = 13.9 Hz, 2H), 3.69-3.64 (m, 1H), 3.63-3.55(m, 8H), 2.98-2.64 (m, 6H), 2.58 (s, 2H), 2.20 (s, 6H), 1.94 (s, 2H) |

TABLE 1-continued

| Cpd. No. | 1H NMR/Mass Spec(LCMS) |
|---|---|
| Cpd. 3 | LC/MS: 801.2 [M + H]+<br>1H NMR (500 MHz, DMSO-d6) δ 10.88 (s, 1H), 9.34 (s, 1H), 8.26 (d, J = 4.9 Hz, 2H), 7.91 (d, J = 10.5 Hz, 1H), 7.71-7.51 (m, 3H). 7.18-6.99 (m, 6H), 6.55 (s, 1H), 5.01 (dd, J = 12.3, 4.0 Hz, 1H), 4.59 (s, 2H), 4.25 (s, 2H), 3.63 (s, 11H), 3.47 (s, 2H), 2.99-2.70 (m, 6H), 2.22 (s, 6H), 2.10-1.91 (m, 2H). |
| Cpd. 4 | LC/MS: 912.4[M + H]+.<br>1H NMR (400 MHz, DMSO-d6) δ 11.08 (s, 1H), 9.63 (d, J = 12.4 Hz, 1H), 8.33 (d, J = 7.2 Hz, 1H), 8.09 (s, 1H), 7.88 (s, 1H), 7.73-7.56 (m, 3H), 7.29 (d, J = 9.2 Hz, 2H), 7.10-7.07 (m, 4H), 5.09 (dd, J = 12.8, 5.4 Hz, 1H), 4.59 (d, J = 5.4 Hz, 2H), 4.27 (d, J = 9.3 Hz, 2H), 3.79-3.49 (m, 9H), 3.48-3.36 (m, 3H), 3.22 (d, J = 7.0 Hz, 2H), 2.93-2.60 (m, 5H), 2.33 (s, 2H), 2.20 (s, 5H), 2.08-1.95 (m, 2H), 1.76 (s, 4H). |
| Cpd. 5 | LC/MS 1000 [M + H]+ 1023.0[M + Na]+.<br>1H NMR (400 MHz, DMSO-d6) δ 11.08 (s, 1H), 9.63 (d, J = 10.3 Hz, 1H), 8.37-8.28 (m, 1H), 8.09 (s, 1H), 7.90-7.82 (m, 1H), 7.74-7.58 (m, 3H), 7.32 (d, J = 7.7 Hz, 2H), 7.16-7.02 (m, 4H), 5.09 (dd, J = 12.9, 5.4 Hz, 1H),4.59 (d, J = 10.0 Hz, 2H), 4.25 (d, J = 9.3 Hz, 2H), 3.75-3.44 (m, 18H), 3.43-3.35 (m, 3H)), 3.24-3.15 (m, 2H), 2.97-2.64 (m, 6H), 2.37-2.28 (m, 2H), 2.20 (s, 6H), 2.10-1.96 (m, 2H), 1.77 (s, 4H). |
| Cpd. 6 | LC/MS: 1124.2 [M + H]+<br>1H NMR (400 MHz, DMSO-d6) δ 11.09 (s, 1H), 9.78 (s, 1H), 9.55 (s, 1H), 8.23 (s, 1H), 8.03 (s, 1H), 7.90 (s, 1H), 7.57 (t, J = 7.8 Hz, 1H), 7.48 (d, J = 8.6 Hz, 3H), 7.13 (d, J = 8.6 Hz, 1H), 7.03 (d, J = 6.5 Hz, 1H), 6.85 (d, J = 8.6 Hz, 2H), 6.72 (s, 2H), 6.60 (t, J = 5.8 Hz, 1H), 5.05 (dd, J = 12.9, 5.4 Hz, 1H), 4.12-4.05 (m, 2H), 4.01 (t, J = 4.7 Hz, 2H), 3.74-3.50 (m, 18H), 3.48-3.40 (m, 2H), 2.93-2.72 (m, 5H), 2.70-2.57 (m, 2H), 2.16 (s, 6H), 2.07-95 (m, 2H), 1.75 (s, 6H), 1.24 (s, 2H). |
| Cpd. 7 | LC/MS 853.2 [M + H]+.<br>1H NMR (400 MHz, DMSO-d6) δ 11.09 (s, 1H), 9.63 (d, J = 8.6 Hz, 1H), 8.34 (s, 1H), 8.09 (s, 1H), 7.68 (s, 1H), 7.64-7.53 (m, 2H), 7.16 7.05 (m, 4H), 7.02 (d, J = 7.1 Hz, 1H), 6.52 (s, 1H), 5.05 (dd, J = 13.0, 5.4 Hz, 1H), 4.66-4.54 (m, 2H), 3.69-3.59 (m, 4H), 3.28 (t, J = 6.7 Hz, 2H), 2.94-2.56 (m, 5H), 2.46-2.32 (m, 3H), 2.20 (s, 5H), 2.10-1.95 (m, 2H), 1.62-1.45 (m, 4H), 1.38-1.16 (m, 14H). |
| Cpd. 8 | LC/MS ESI 889.4 [M + H]+, 912.5[M + Na]+<br>1H NMR (500 MHz, DMSO-d6) δ 11.07 (s, 1H), 9.69-9.60 (m, 1H), 8.35 (s, 1H), 8.11 (s, 1H), 7.72-7.60 (m, 2H), 7.55 (d, J = 8.4 Hz, 1H), 7.19-7.06 (m, 5H), 7.00 (s, 1H), 6.89 (d, J = 8.0 Hz, 1H), 5.03 (dd, J = 12.5, 5.4 Hz, 1H), 4.59 (d, J = 13.2 Hz, 2H), 4.25 (d, J = 13.2 Hz, 2H), 3.71-3.42 (m, 22H), 2.92-2.63 (m, 4H), 2.20 (s, 6H), 2.04-1.95 (m, 1H). |
| Cpd. 9 | LC/MS 947.4 [M + H]+, 969.4[M + Na]+.<br>1H NMR (400 MHz, Chloroform-d) δ 10.49 (s, 1H), 8.33 (s, 1H), 7.87-7.34 (m, 5H), 7.30 (dd, J = 8.3, 2.3 Hz, 1H), 7.24-6.99 (m, 5H), 6.06 (d, J = 55.5 Hz, 1H), 4.97 (dd, J = 12.2, 5.3 Hz, 1H), 4.76-4.45 (m, 4H), 4.26 (d, J = 28.6 Hz, 2H), 3.86-3.51 (m, 19H), 2.95-2.66 (m, 5H), 2.28 (s, 6H), 2.20-1.96 (m, 2H). |
| Cpd. 10 | LC/MS 947.2 [M + H]+.<br>1H NMR (500 MHz, DMSO-d6) δ 11.11 (s, 1H), 9.65 (d, J = 13.1 Hz, 1H), 8.36 (s, 1H), 8.21-8.14 (m, 1H), 8.11 (s, 1H), 7.73-7.55 (m, 3H), 7.16-7.05 (m, 4H), 6.95 (d, J = 5.6 Hz, 1H), 6.86 (d, J = 8.5 Hz, 1H), 5.08 (dd, J = 12.5, 5.4 Hz, 1H), 4.59 (d, J = 12.1 Hz, 2H), 4.25 (d, J = 12.9 Hz, 2H), 3.94 (d, J = 5.6 Hz, 2H), 3.66-3.38 (m, 17H), 3.26 (d, J = 8.1 Hz, 2H), 3.13-3.07 (m, 4H), 2.94-2.59 (m, 4H), 2.20 (s, 5H), 2.07-1.99 (m, 1H). |
| Cpd. 11 | LC/MS (ESI) 925.4 [M + H]+, 947.8 [M + Na]+<br>1H NMR (400 MHz, Methanol-d4) δ 8.00-7.91 (m, 2H), 7.48-7.33 (m, 3H), 7.04-6.99 (m, 3H), 6.95 (d, J = 7.6 Hz, 2H), 6.72 (d, J = 8.5 Hz, 1H), 4.92 (dd, J = 12.4, 5.5 Hz, 1H), 4.49 (dt, J = 22.4, 5.0 Hz, 3 fH), 3.92-3.64 (m, 8H), 3.56 (d, J = 7.3 Hz, 3H), 3.45-3.30 (m, 6H), 2.82 (s, 4H), 2.76-2.49 (m, 3H), 2.16 (s, 6H), 2.02-1.85 (m, 2H). |
| Cpd. 12 | LC/MS (ESI) 926.0 [M + H]+, 949.1 [M + Na]+<br>1H NMR (400 MHz, Chloroform-d) δ 10.44-9.85 (m, 2H), 8.05-7.67 (m, 3H), 7.62 (d, J = 8.3 Hz, 1H), 7.54 (s, 1H), 7.24-7.06 (m, 5H), 6.99 (s, 1H), 6.79 (d, J = 8.3 Hz, 1H), 6.17 (s, 1H), 5.97 (s, 1H), 4.96 (dd, J = 12.0, 5.2 Hz, 1H), 4.56 (t, J = 4.9 Hz, 2H), 3.85 (d, J = 43.9 Hz, 10H), 3.67-3.40 (m, 7H), 3.21-2.57 (m, 8H), 2.29 (s, 6H), 2.17-2.00 (m, 2H). |
| Cpd. 13 | LC/MS (ESI) 890.2 [M + H]+.<br>1H NMR (400 MHz, DMSO-d6) δ 11.08 (s, 1H), 9.62 (d, J = 10.2 Hz, 1H), 8.33 (d, J = 8.5 Hz, 1H), 8.09 (s, 1H), 7.70-7.53 (m, 3H), 7.16-7.05 (m, 5H), 7.02 (d, J = 7.1 Hz, 1H), 6.63-6.50 (m, 1H), 5.05 (dd, J = 12.8, 5.4 Hz, 1H), 4.58 (d, J = 11.4 Hz, 2H), 4.24 (d, J = 10.0 Hz, 2H), 3.68-3.37 (m, 21H), 2.94-2.63 (m, 4H), 2.20 (s, 6H), 2.07-1.91 (m, 2H). |
| Cpd. 14 | LC/MS 904.2 [M + H]+, 926.2[M + Na]+<br>1H NMR (400 MHz, Methanol-d4) δ 7.96 (s, 1H), 7.80 (s, 1H), 7.58-7.32 (m, 3H), 7.04 (s, 4H), 6.94-6.84 (m, 2H), 4.96-4.87 (m, 1H), 4.61 (d, J = 23.3 Hz, 2H), 3.73-3.26 (m, 22H), 2.85-2.47 (m, 7H), 2.16 (s, 6H), 2.04-1.87 (m, 2H). |

TABLE 1-continued

| Cpd. No. | 1H NMR/Mass Spec(LCMS) |
|---|---|
| Cpd. 15 | LC/MS 904.0 [M + H]+, 926.1[M + Na]+<br>1H NMR (400 MHz, Methanol-d4) δ 8.09 (s, 1H), 7.92 (s, 1H), 7.67-7.48 (m, 3H), 7.21-7.08 (m, 4H), 6.99 (dd, J = 7.2, 2.2 Hz, 1H), 6.88-6.78 (m, 1H), 5.03 (dd, J = 12.3, 5.4 Hz, 1H), 4.73 (d, J = 21.1 Hz, 1H), 3.92-3.42 (m, 22H), 2.92-2.65 (m, 7H), 2.28 (s, 6H), 2.06 (t, J = 12.0 Hz, 2H). |
| Cpd. 16 | LC/MS 962.3 [M + H]+, 984.3 [M + Na]+<br>1H NMR (400 MHz, Methanol-d4) δ 7.97 (s, 1H), 7.80 (s, 1H), 7.67 (dd, J = 8.3, 3.9 Hz, 1H), 7.50 (s, 1H), 7.48-7.40 (m, 1H), 7.29 (dd, J = 7.0, 2.3 Hz, 1H), 7.22 (td, J = 8.2, 2.3 Hz, 1H), 7.07-6.94 (m, 4H), 3.73-3.62 (m, 3H), 3.57 (s, 3H), 3.52-3.30 (m, 16H), 2.83-2.48 (m, 7H)), 2.16 (s, 6H), 2.04-1.83 (m, 2H). |
| Cpd. 17 | LC/MS 962.3 [M + H]+, 984.3 [M + Na]+<br>1H NMR (400 MHz, DMSO-d6) δ 11.11 (s, 1H), 9.62 (d, J = 9.2 Hz, 1H), 8.33 (d, J = 8.6 Hz, 1H), 8.09 (s, 1H), 8.00 (t, J = 5.7 Hz, 1H), 7.81 (t, J = 7.8 Hz, 1H), 7.70-7.66 (m, 1H), 7.62 (d, J = 7.7 Hz, 1H), 7.49 (d, J = 7.3 Hz, 1H), 7.39 (d, J = 8.2 Hz, 1H), 7.17-7.04 (m, 4H), 5.11 (dd, J = 13.0, 5.4 Hz, 1H), 4.78 (s, 2H), 4.61 (d, J = 28.7 Hz, 2H), 3.73-3.56 (m, 7H), 3.56-3.41 (m, 13H), 2.96-2.55 (m, 8H), 2.20 (s, 6H), 2.0-1.89 (m, 2H). |
| Cpd. 18 | LC/MS 1030.3 [M + H]+, 1052.4 [M + Na]+<br>1H NMR (400 MHz, DMSO-d6) δ 11.08 (s, 1H), 9.62 (d, J = 10.0 Hz, 1H), 8.33 (d, J = 8.5 Hz, 1H), 8.09 (s, 1H), 7.78 (s, 1H), 7.72-7.58 (m, 3H), 7.35 (s, 1H), 7.25 (d, J = 8.2 Hz, 1H), 7.16-7.05 (m, 4H), 5.07 (dd, J = 12.8, 5.4 Hz, 1H), 4.61 (d, J = 27.4 Hz, 2H), 3.71-3.58 (m, 7H), 3.55-3.38 (m, 17H), 3.26 (d, J = 6.0 Hz, 2H), 3.03-2.54 (m, 13H), 2.20 (s, 6H), 2.04-1.91 (m, 2H). |
| Cpd. 19 | LC/MS 981.0 [M − H]−<br>1H NMR (500 MHz, Methanol-d4) δ 8.34 (s, 1H), 7.98 (d, J = 9.4 Hz, 1H), 7.47 (d, J = 8.2 Hz, 1H), 7.37 (t, J = 8.1 Hz, 1H), 7.04 (s, 4H), 6.93 (t, J = 6.3 Hz, 1H), 6.75-6.66 (m, 1H), 5.17 (s, 1H), 4.68-4.60 (m, 1H), 4.55 (s, 2H), 4.16 (s, 1H), 3.83 (d, J = 11.7 Hz, 4H), 3.65-3.24 (m, 17H), 2.90-2.79 (m, 2H), 2.37 (d, J = 7.9 Hz, 1H), 2.27-2.22 (m, 1H), 2.17 (s, 6H), 1.93 (d, J = 11.8 Hz, 2H). |
| Cpd. 20 | LC/MS: 869.7 [M + H]+<br>1H NMR (300 MHz, Chloroform-d) δ 11.05 (s, 1H), 8.36 (s, 1H), 7.88 (d, J = 8.3 Hz, 1H), 7.71 (d, J = 8.5 Hz, 2H), 7.64 (s, 1H), 7.18 (s, 3H), 7.12-6.97 (m, 3H), 5.92 (s, 1H), 4.97 (dd, J = 12.3, 5.1 Hz, 1H), 3.88-3.56 (m, 10H), 3.38 (t, J = 6.4, 4H), 3.11 (d, J = 7.4 Hz, 2H), 3.00-2.61 (m, 12H), 2.28 (s, 6H), 2.18-2.10 (m, 1H), 2.03 (d, J = 5.7 Hz, 2H). |
| Cpd. 21 | LC/MS 854.3 [M + H]+<br>1H NMR (300 MHz, Chloroform-d) δ 8.41-7.99 (m, 1H), 7.68-7.53 (m, 2H), 7.43 (d, J = 8.4 Hz, 1H), 7.21-6.91 (m, 6H), 6.82 (d, J = 8.5 Hz, 1H), 6.07 (s, 1H), 5.15-5.03 (m, 1H), 3.96-3.74 (m, 4H), 3.73 (s, 3H), 3.64 (s, 4H), 3.47 (s, 1H), 2.96 (s, 9H), 2.24 (s, 6H), 2.09-2.01 (m, 2H). |
| Cpd. 22 | LC/MS 960.2 [M + H]+<br>1H NMR (400 MHz, Chloroform-d) δ 10.48 (s, br 1H), 8.15 (s, 1H), 7.83-7.54 (m, 3H), 7.45 (s, 1H), 7.24-7.02 (m, 5H), 6.95-6.85 (m, 1H), 6.44 (s, 1H), 5.95 (s, 1H), 5.00-4.90 (m, 1H), 4.81-4.55 (m, 2H), 3.93-3.40 (m, 24H), 3.01-2.67 (m, 6H), 2.56-2.49 (m, 1H), 2.30 (s, 5H), 2.10-2.00 (m, 2H) |
| Cpd. 23 | LC/MS: 801.2 [M + H]+<br>1H NMR (400 MHz, DMSO-d6) δ 11.11 (s, 1H), 10.33 (s, 1H), 9.50 (s, 1H), 8.31 (s, 1H), 8.27 (s, 1H), 8.07 (s, 1H), 8.02 (d, J = 8.6 Hz, 1H), 7.85 (d, J = 8.2 Hz, 1H), 7.61-7.45 (m, 2H), 7.16-7.04 (m, 3H), 6.97 (d, J = 8.3 Hz, 1H), 5.11 (dd, J = 12.8, 5.4 Hz, 1H), 4.19 (s, 2H), 3.74-3.50 (m, 10H), 2.95-2.55 (m, 9H), 2.19 (s, 6H), 2.09-1.93 (m, 2H). |
| Cpd. 24 | LC/MS: 854.2 [M + H]+<br>1H NMR (400 MHz, DMSO-d6) δ 11.08 (s, 1H), 9.54 (s, 1H), 8.32 (s, 2H), 8.08 (s, 1H), 7.88 (t, J = 5.2 Hz 2H), 7.64-7.52 (m, 3H), 7.29 (d, J = 7.2 Hz, 1H), 7.22 (d, J = 8.6 Hz, 1H), 7.17-7.05 (m, 3H), 7.02 (s, 1H), 5.08 (dd, J = 12.9, 5.5 Hz, 1H), 3.60 (s, 8H), 3.52-3.44 (m, 3H), 3.28-3.21 (m, 2H), 2.96-2.58 (m, 11H), 2.20 (s, 6H), 2.01 (d, J = 16.5 Hz, 2H), 1.73 (s, 4H). |
| Cpd. 25 | LC/MS: 801.1 [M + H]+<br>1H NMR (500 MHz, Methanol-d4) δ 8.06 (s, 1H), 7.93 (s, 1H), 7.65 (d, J = 8.3 Hz, 1H), 7.54 (s, 1H), 7.45 (d, J = 8.3 Hz, 1H), 7.27 (t, J = 2.2 Hz, 1H), 7.21 (dt, J = 8.5, 2.0 Hz, 1H), 7.18-7.13 (m, 3H), 7.02 (d, J = 8.3 Hz, 1H), 5.10 (dd, J = 12.8, 5.3 Hz, 1H), 4.59 (s, 2H), 3.88-3.80 (m, 2H), 3.75 (t, J = 5.4 Hz, 2H), 3.68 (s, 3H), 3.63 (t, J = 5.3 Hz, 2H), 3.57-3.51 (m, 2H), 3.03-2.80 (m, 7H), 2.78-2.63 (m, 2H), 2.30 (s, 6H), 2.16-2.07 (m, 2H). |

TABLE 1-continued

| Cpd. No. | 1H NMR/Mass Spec(LCMS) |
|---|---|
| Cpd. 26 | LC/MS: 865.0 [M + H]+<br>1H NMR (400 MHz, DMSO-d6) δ 11.07 (s, 1H), 9.63 (d, J = 9.1 Hz, 1H), 8.34 (s, 1H), 8.09 (s, 1H), 7.80-7.52 (m, 3H), 7.33 (s, 1H), 7.24 (d, J = 9.7 Hz, 1H), 7.17-7.02 (m, 4H), 5.06 (dd, J = 13.0, 5.7 Hz, 1H), 4.97-4.59 (m, 4H), 4.54-4.42 (m, 1H), 4.07 (d, J = 13.1 Hz, 2H), 3.62 (s, 2H), 3.16-2.99 (m, 2H), 2.94-2.65 (m, 6H), 2.20 (s, 6H), 1.96 (q, J = 12.9, 11.7 Hz, 5H), 1.76 (s, 3H), 1.47 (s, 3H). |
| Cpd. 27 | LC/MS: 843.2 [M + H3O]+<br>1H NMR (400 MHz, Methanol-d4) δ 8.11 (s, 1H), 7.75 (s, 1H), 7.67 (d, J = 8.5 Hz, 1H), 7.53 (dd, J = 8.5, 2.2 Hz, 1H), 7.29-7.09 (m, 4H), 6.99 (s, 1H), 6.85 (d, J = 8.4 Hz, 1H), 5.05 (dd, J = 12.5, 5.4 Hz, 1H), 4.46 (s, 2H), 3.86 (s, 2H), 3.80-3.67 (m, 5H), 3.63-3.55 (m, 2H), 3.54-3.39 (m, 5H), 3.24 (q, J = 7.3 Hz, 4H), 2.91-2.64 (m, 4H), 2.29 (s, 6H), 2.15-2.01 (m, 2H). |
| Cpd. 28 | LC/MS: 864.2 [M + H]+<br>1H NMR (400 MHz, Acetone-d6) δ 9.76 (s, 1H), 8.41 (s, 1H), 8.04-7.82 (m, 2H), 7.68-7.43 (m, 3H), 7.18 (s, 1H), 7.12 (dd, J = 8.5, 2.4 Hz, 1H), 7.06-6.96 (m, 3H), 6.92 (d, J = 8.3 Hz, 1H), 4.93 (dd, J = 12.7, 5.3 Hz, 1H), 4.42 (d, J = 13.4 Hz, 1H), 4.07-3.92 (m, 3H), 3.54 (s, 3H), 3.07-2.96 (m, 3H), 2.94-2.56 (m, 14H), 2.52-2.28 (m, 3H), 2.13 (s, 6H), 2.09-2.00 (m, 1H), 1.70 (s, 5H). |
| Cpd. 29 | LC/MS 753.4 [M + H]+<br>1H NMR (400 MHz, Chloroform-d) δ 9.06 (s, 1H), 7.70 (dd, J = 8.3, 2.3 Hz, 1H), 7.47 (dd, J = 9.3, 4.9 Hz, 2H), 7.37 (d, J = 7.4 Hz, 2H), 7.31 (s, 1H), 7.17 (s, 3H), 7.08 (t, J = 7.0 Hz, 2H), 6.05 (s, 1H), 5.01-4.91 (m, 1H), 3.98 (d, J = 12.9 Hz, 2H), 3.82 (d, J = 2.3 Hz, 3H), 3.64 (s, 2H), 3.02 (t, J = 12.5 Hz, 2H), 2.96-2.82 (m, 4H), 2.82-2.69 (m, 3H), 2.42 (d, J = 6.6 Hz, 2H), 2.29 (s, 6H), 2.21-2.10 (m, 1H), 2.04-1.87 (m, 3H), 1.44-1.29 (m, 2H). |
| Cpd. 30 | LC/MS: 812.0 [M + H]+<br>1H NMR (500 MHz, DMSO-d6) δ 11.13 (s, 1H), 9.57 (s, 1H), 8.35 (d, J = 11.2 Hz, 1H), 8.10 (s, 1H), 7.84 (d, J = 8.3 Hz, 1H), 7.65-7.52 (m, 2H), 7.42 (s, 1H), 7.34 (d, J = 8.3 Hz, 1H), 7.16-7.05 (m, 3H), 7.02 (d, J = 8.3 Hz, 1H), 5.36-5.02 (m, 3H), 4.31 (d, J = 12.8 Hz, 1H), 3.81 (d, J = 13.4 Hz, 1H), 3.62 (s, 3H), 3.54 (s, 2H), 3.46-3.40 (m, 2H), 3.13-3.03 (m, 1H), 2.95-2.82 (m, 1H), 2.75 (s, 2H), 2.71-2.56 (m, 5H), 2.41-2.29 (m, 3H), 2.21 (s, 6H), 2.15-1.65 (m, 6H). |
| Cpd. 31 | 1H NMR(400 MHz, DMSO-d6) δ 11.08 (s, 1H), 9.54 (s, 1H), 8.32 (d, J = 2.0 Hz, 2H), 8.08 (s, 1H), 7.68 (d, J = 8.4 Hz, 1H), 7.61-7.50 (m, 2H), 7.35 (s, 1H), 7.25 (d, J = 8.6 Hz, 1H), 7.15-7.05 (m, 3H), 7.01 (d, J = 8.4 Hz, 1H), 5.07 (dd, 1H), 4.35 (d, J = 12.7 Hz, 1H), 4.05 (d, J = 12.9 Hz, 1H), 3.61 (s, 3H), 3.48 (d, J = 28.1 Hz, 6H), 3.17-2.80 (m, 5H), 2.78-2.59 (m, 7H), 2.31 (d, J = 8.9 Hz, 2H), 2.20 (s, 6H), 2.07-1.84 (m, 4H), 1.84-1.70 (m, 2H). |
| Cpd. 32 | 1H NMR (400 MHz, DMSO-d6) δ 11.06 (d, J = 8.2 Hz, 1H), 9.64 (d, J = 8.6 Hz, 1H), 8.40-8.18 (m, 2H), 8.12-8.01 (m, 1H), 7.76-7.42 (m, 3H), 7.35 (s, 1H), 7.29-7.16 (m, 1H), 7.15-7.05 (m, 3H), 5.20-4.24 (m, 7H), 3.91-3.53 (m, 7H), 3.2-3.0 (m, 3H), 2.95-2.74 (m, 3H), 2.72-2.65 (m, 2H), 2.34 (d, J = 9.0 Hz, 2H), 2.27-2.17 (m, 6H), 2.07-1.66 (m, 6H), 1.55-1.42 (m, 1H). |
| Cpd. 33 | LC/MS: 879.2 [M + H]+<br>1H NMR (500 MHz, DMSO-d6) δ 10.85 (s, 1H), 9.34 (s, 1H), 8.29-8.20 (m, 2H), 7.89 (d, J = 13.1 Hz, 1H), 7.68 (d, J = 9.3 Hz, 1H), 7.61 (s, 1H), 7.34 (s, 1H), 7.26 (d, J = 8.5 Hz, 1H), 7.11 (d, J = 11.0 Hz, 5H), 5.09-4.64 (m, 6H), 3.88-3.37 (m, 18H), 2.81-2.57 (m, 4H), 2.22 (d, J = 2.7 Hz, 6H), 2.12-1.89 (m, 2H). |
| Cpd. 34 | LC/MS: 811.2 [M + H]+<br>1H NMR (500 MHz, DMSO-d6, 60° C.) δ 10.88 (s, 1H), 9.32 (s, 1H), 8.25 (s, 1H), 7.89 (s, 1H), 7.81 (s, 1H), 7.71-7.57 (m, 2H), 7.38 (d, J = 33.3 Hz, 1H), 7.11 (s, 4H), 5.03 (d, J = 52.3 Hz, 3H), 4.73-4.49 (m, 2H), 3.67 (dd, J = 27.7, 8.4 Hz, 5H), 2.96-2.62 (m, 7H), 2.23 (d, J = 8.1 Hz, 7H), 1.90 (d, J = 92.1 Hz, 5H). |
| Cpd. 35 | LC/MS: 810.2 [M + H]+<br>1H NMR (500 MHz, DMSO-d6) δ 10.82 (s, 1H), 9.31 (s, 1H), 8.25 (d, J = 3.0 Hz, 1H), 7.88 (s, 1H), 7.75-7.48 (m, 3H), 7.17-7.08 (m, 4H), 7.03-6.72 (m, 3H), 5.07-4.94 (m, 2H), 4.71 (d, J = 15.5 Hz, 1H), 4.16 (d, J = 17.1 Hz, 1H), 4.02 (d, J = 17.2 Hz, 1H), 3.76-3.48 (m, 7H), 2.93-2.71 (m, 3H), 2.70-2.57 (m, 2H), 2.22 (s, 6H), 2.09-1.91 (m, 4H), 1.82 (s, 2H). |
| Cpd. 36 | LC/MS: 810.2 [M + H]+<br>1H NMR (400 MHz, Acetone-d6) δ 9.88 (s, 1H), 8.53 (s, 1H), 8.03 (s, 1H), 7.67 (d, J = 9.5 Hz, 2H), 7.61 (d, J = 8.3 Hz, 1H), 7.32 (s, 1H), 7.21-7.10 (m, 5H), 7.06 (d, J = 8.2 Hz, 1H), 6.41-6.36 (m, 1H), 5.06 (dd, J = 12.7, 5.4 Hz, 1H), 4.57 (d, J = 13.1 Hz, 1H), 4.27-4.03 (m, 4H), 3.74-3.60 (m, 5H), 3.18 (t, J = 12.8 Hz, 2H), 2.74 (d, J = 11.7 Hz, 3H), 2.42 (s, 2H), 2.29 (s, 6H), 2.24-2.15 (m, 3H), 2.01 (d, J = 12.7 Hz, 3H), 1.58 (s, 3H). |

TABLE 1-continued

| Cpd. No. | 1H NMR/Mass Spec(LCMS) |
|---|---|
| Cpd. 37 | 1H NMR (400 MHz, Methanol-d4) δ 8.08 (s, 1H), 8.01 (d, J = 9.2 Hz, 1H), 7.92 (s, 2H), 7.69 (dd, J = 9.3, 2.8 Hz, 1H), 7.55 (d, J = 5.9 Hz, 3H), 7.16 (s, 3H), 7.10 (d, J = 8.8 Hz, 1H), 5.90 (dd, J = 11.4, 5.5 Hz, 1H), 4.58 (d, J = 18.9 Hz, 2H), 4.17 (d, J = 13.3 Hz, 3H), 3.72 (d, J = 18.5 Hz, 5H), 3.28-3.02 (m, 5H), 3.01-2.80 (m, 7H), 2.78-2.64 (m, 2H), 2.59-2.48 (m, 2H), 2.36 (dd, J = 13.2, 6.9 Hz, 1H), 2.28 (s, 6H), 2.10-1.96 (m, 4H), 1.97-1.79 (m, 7H). |
| Cpd. 38 | 1H NMR (400 MHz, Chloroform-d) δ 7.77 (s, 1H), 7.50-7.34 (m, 5H), 7.23-7.12 (m, 4H), 7.08 (d, J = 8.4 Hz, 1H), 7.01 (d, J = 8.4 Hz, 1H), 5.90 (s, 1H), 3.92 (s, 3H), 3.82 (s, 3H), 3.78-3.69 (m, 2H), 3.64 (s, 2H), 2.91-2.80 (m, 4H), 2.79-2.69 (m, 2H), 2.41 (dd, J = 13.1, 6.8 Hz, 2H), 2.29 (s, 6H), 2.11 (s, 1H), 2.08-2.00 (m, 2H), 1.99-1.77 (m, 5H). |
| Cpd. 39 | 1H NMR (300 MHz, Chloroform-d) δ 8.75 (d, J = 22.3 Hz, 1H), 7.69 (d, J = 8.5 Hz, 1H), 7.49-7.39 (m, 2H), 7.35 (s, 1H), 7.15 (s, 3H), 7.09-7.01 (m, 2H), 5.95 (d, J = 3.3 Hz, 1H), 4.94 (dd, J = 12.0, 5.1 Hz, 1H), 4.34 (t, J = 8.5 Hz, 1H), 4.18 (t, J = 9.1 Hz, 1H), 4.04-3.92 (m, 1H), 3.82-3.72 (m, 4H), 3.66 (s, 2H), 3.50-3.40 (m, 3H), 3.08 (s, 2H), 3.01-2.91 (m, 2H), 2.90-2.83 (m, 3H), 2.83-2.74 (m, 4H), 2.72-2.63 (m, 4H), 2.27 (s, 6H), 2.19-1.98 (m, 3H). |
| Cpd. 40 | 1H NMR (300 MHz, Chloroform-d) δ 8.70 (d, J = 7.9 Hz, 1H), 7.70 (d, J = 8.5 Hz, 1H), 7.52-7.43 (m, 1H), 7.38 (s, 1H), 7.32 (s, 1H), 7.18 (s, 3H), 7.12-7.03 (m, 2H), 5.97 (s, 1H), 4.96 (dd, J = 11.9, 5.1 Hz, 1H), 4.35 (t, J = 8.2 Hz, 1H), 4.16 (t, J = 9.1 Hz, 1H), 4.06-3.92 (m, 3H), 3.81 (s, 3H), 3.73 (d, J = 13.8 Hz, 2H), 3.04 (q, J = 11.0 Hz, 3H), 2.96-2.69 (m, 8H), 2.47 (dd, J = 10.3, 5.7 Hz, 1H), 2.29 (s, 6H), 2.22-2.10 (m, 1H), 2.09-1.80 (m, 6H). |
| Cpd. 41 | 1H NMR (400 MHz, Chloroform-d) δ 7.79 (d, J = 8.2 Hz, 1H), 7.66 (d, J = 8.5 Hz, 1H), 7.61 (s, 1H), 7.56 (d, J = 10.3 Hz, 1H), 7.50 (s, 1H), 7.33 (t, J = 7.9 Hz, 1H), 7.25 (d, J = 2.3 Hz, 1H), 7.18 (s, 3H), 7.11- 6.99 (m, 2H), 6.02 (d, J = 13.4 Hz, 1H), 4.96 (dd, J = 12.2, 5.4 Hz, 1H), 4.00-3.87 (m, 3H), 3.82 (s, 3H), 3.05-2.70 (m, 5H), 2.63 (d, J = 6.0 Hz, 2H), 2.29 (s, 6H), 2.19-2.00 (m, 3H), 1.99-1.83 (m, 4H). |
| Cpd. 42 | 1H NMR (400 MHz, Chloroform-d) δ 7.76 (d, J = 8.4 Hz, 1H), 7.69 (d, J = 8.6 Hz, 1H), 7.61 (s, 1H), 7.56-7.41 (m, 2H), 7.34 (d, J = 7.9 Hz, 1H), 7.18 (s, 3H), 7.06 (t, J = 8.1 Hz, 1H), 5.99 (d, J = 14.0 Hz, 1H), 4.96 (dd, J = 12.2, 5.4 Hz, 1H), 4.64 (d, J = 13.7 Hz, 2H), 4.03-3.73 (m, 7H), 3.06 (t, J = 12.3 Hz, 2H), 2.98-2.69 (m, 5H), 2.66-2.52 (m, 2H), 2.29 (s, 6H), 2.22-2.11 (m, 1H), 2.11-2.01 (m, 2H), 1.99-1.79 (m, 8H). |
| Cpd. 43 | LC/MS: 825.2 [M + H]+<br>1H NMR (400 MHz, DMSO-d6) δ 11.11 (s, 1H), 9.64 (d, J = 10.0 Hz, 1H), 8.35 (s, 1H), 8.32 (s, 1H), 8.10 (s, 1H), 7.84 (d, J = 8.4 Hz, 1H), 7.69 (s, 1H), 7.63 (d, J = 8.4 Hz, 1H), 7.44 (s, 1H), 7.35 (d, J = 8.6 Hz, 1H), 7.11 (d, J = 5.6 Hz, 4H), 5.13 (dt, J = 13.6, 6.8 Hz, 3H), 4.75 (s, 1H), 4.60 (s, 1H), 4.32 (s, 1H), 3.79 (s, 3H), 3.63 (d, J = 3.0 Hz, 4H), 3.26-2.55 (m, 6H), 2.20 (s, 6H), 2.11-1.91 (m, 2H), 1.70 (m, 3H), 1.43 (s, 1H). |
| Cpd. 44 | 1H NMR (400 MHz, Methanol-d4) δ 8.09 (s, 1H), 7.92 (s, 3H), 7.69 (t, J = 9.9 Hz, 2H), 7.58 (t, J = 8.2 Hz, 1H), 7.39 (s, 1H), 7.26 (d, J = 8.6 Hz, 1H), 7.15 (d, J = 11.4 Hz, 4H), 5.09 (dd, J = 12.5, 5.4 Hz, 2H), 4.72 (s, 1H), 4.62-4.52 (m, 1H), 4.35-4.16 (m, 1H), 3.88 (t, J = 6.1 Hz, 1H), 3.71 (d, J = 4.3 Hz, 4H), 3.52 (s, 6H), 2.95 (s, 1H), 2.90-2.76 (m, 4H), 2.71 (d, J = 5.1 Hz, 4H), 2.29 (s, 6H), 2.05 (d, J = 9.4 Hz, 1H), 1.83 (d, J = 14.8 Hz, 4H), 1.70-1.58 (m, 3H). |
| Cpd. 45 | 1H NMR (400 MHz, Methanol-d4) δ 8.09 (s, 1H), 7.68 (d, J = 9.7 Hz, 1H), 7.60 (q, J = 8.6 Hz, 2H), 7.17 (s, 4H), 7.09 (s, 1H), 6.95 (s, 1H), 5.07 (dd, J = 12.4, 5.4 Hz, 2H), 4.73 (s, 1H), 4.58 (d, J = 14.3 Hz, 2H), 4.19 (t, J = 7.2 Hz, 2H), 4.05 (s, 1H), 3.95-3.85 (m, 2H), 3.71 (d, J = 3.9 Hz, 4H), 3.01-2.68 (m, 9H), 2.29 (s, 6H), 2.18 (s, 1H), 2.05 (d, J = 9.6 Hz, 2H), 1.91-1.78 (m, 3H). |
| Cpd. 46 | 1H NMR (400 MHz, Methanol-d4) δ 8.12-8.08 (m, 1H), 8.02 (d, J = 9.0 Hz, 1H), 7.92 (s, 1H), 7.77 (s, 1H), 7.72-7.61 (m, 2H), 7.56 (s, 1H), 7.24 (dd, J = 22.2, 8.5 Hz, 1H), 7.16 (s, 3H), 5.95-5.85 (m, 1H), 4.35 (s, 1H), 4.20 (d, J = 13.7 Hz, 1H), 4.16-4.08 (m, 1H), 3.84-3.75 (m, 1H), 3.73 (s, 1H), 3.71 (s, 2H), 3.66 (s, 1H), 3.55-3.48 (m, 1H), 3.19-3.06 (m, 3H), 3.02-2.92 (m, 2H), 2.89-2.80 (m, 2H), 2.68 (s, 2H), 2.29 (s, 6H), 2.06 (s, 2H), 1.94-1.72 (m, 3H), 1.65-1.40 (m, 5H). |
| Cpd. 47 | 1H NMR (300 MHz, Chloroform-d) δ 8.59 (s, 1H), 7.64 (d, J = 8.3 Hz, 1H), 7.51-7.36 (m, 3H), 7.16 (s, 3H), 7.09 (d, J = 8.3 Hz, 1H), 6.79 (d, J = 2.1 Hz, 1H), 6.52 (dd, J = 8.3, 2.1 Hz, 1H), 5.94-5.89 (m, 1H), 4.93 (dd, J = 12.1, 5.3 Hz, 1H), 4.19 (t, J = 8.0 Hz, 2H), 3.87-3.69 (m, 5H), 3.27-3.11 (m, 1H), 3.04-2.66 (m, 7H), 2.62 (s, 1H), 2.27 (s, 6H), 2.19-2.08 (m, 1H), 2.03 (d, J = 5.9 Hz, 2H). |
| Cpd. 48 | 1H NMR (300 MHz, Chloroform-d) δ 9.28 (s, 1H), 8.19-8.13 (m, 1H), 7.70-7.60 (m, 2H), 7.52-7.40 (m, 3H), 7.38 (s, 1H), 7.22-7.13 (m, 3H), 7.09 (d, J = 8.3 Hz, 1H), 6.04 (s, 1H), 5.85-5.74 (m, 1H), 5.00-4.85 (m, 2H), 4.58 (d, J = 13.3 Hz, 1H), 3.94-3.61 (m, 6H), 3.15 (t, J = 12.6 Hz, 1H), 3.06-2.62 (m, 8H), 2.56-2.34 (m, 3H), 2.29 (s, 6H), 2.15-1.80 (m, 5H). |

TABLE 1-continued

| Cpd. No. | 1H NMR/Mass Spec(LCMS) |
|---|---|
| Cpd. 49 | LC/MS 783.3[M + H]+<br>1H NMR (300 MHz, Chloroform-d), rotamer pattern observed. δ 10.96 (s, 0.5H), 10.23 (s, 0.5H), 8.41 (s, 1H), 8.01-7.75 (m, 2H), 7.68-7.57 (m, 2H), 7.44-7.38 (m, 1H), 7.25-7.14 (m, 3H), 7.13-6.95 (m, 2H), 5.94-5.88 (m, 3H), 4.99 (dd, 1H), 4.90-4.65 (m, 2H), 4.46 (t, J = 8.6 Hz, 1H), 4.32-4.16 (m, 1H), 4.10-4.00 (m, 1H), 3.93-3.73 (m, 4H), 3.66 (dd, J = 10.3, 4.9 Hz, 1H), 3.60-3.36 (m, 2H), 3.03-2.54 (m, 9H), 2.30 (s, 6H), 2.23-2.14 (m, 1H), 2.09-1.98 (m, 1H). |
| Cpd. 50 | 1H NMR (300 MHz, Chloroform-d) δ 8.40 (s, 1H), 7.67 (d, J = 8.1 Hz, 1H), 7.42 (d, J = 10.7 Hz, 2H), 7.26-7.04 (m, 5H), 6.79 (s, 1H), 6.53 (d, J = 8.3 Hz, 1H), 5.93 (s, 1H), 5.36 (s, 1H), 5.02-4.86 (m, 1H), 4.23 (td, 2H), 3.92-3.54 (m, 6H), 3.41-3.01 (m, 3H), 3.00-2.66 (m, 7H), 2.64 (s, 1H), 2.60-2.41 (m, 2H), 2.29 (s, 6H), 2.22-1.78 (m, 10H). |
| Cpd. 51 | 1H NMR (300 MHz, Chloroform-d) rotamer pattern observed. δ 8.93 (s, 0.5H), 8.68 (s, 0.5H), 8.08 (d, J = 23.7 Hz, 1H), 7.73-7.39 (m, 4H), 7.18 (s, 4H), 7.09 (d, J = 8.5 Hz, 1H), 6.95 (d, J = 12.5 Hz, 1H), 6.84 (d, J = 8.4 Hz, 1H), 5.90 (s, 1H), 5.01-4.89 (m, 1H), 4.29 (dd, J = 15.2, 9.1 Hz, 2H), 3.81 (s, 5H), 3.62 (s, 2H), 2.98 (s, 1H), 2.94-2.70 (m, 8H), 2.29 (s, 6H), 2.25-2.10 (m, 2H), 2.05 (d, J = 6.0 Hz, 2H). |
| Cpd. 52 | 1H NMR (300 MHz, Chloroform-d) δ 8.94 (d, J = 28.0 Hz, 1H), 7.96 (d, J = 8.8 Hz, 1H), 7.52-7.32 (m, 3H), 7.24 (d, J = 2.6 Hz, 1H), 7.16 (d, J = 3.9 Hz, 4H), 7.09 (d, J = 8.3 Hz, 1H), 6.09-5.95 (m, 2H), 5.78 (dd, J = 11.3, 5.7 Hz, 1H), 4.66 (d, J = 13.3 Hz, 1H), 4.01 (d, J = 3.8 Hz, 2H), 3.86-3.73 (m, 4H), 3.67 (s, 2H), 3.24-2.66 (m, 10H), 2.55-2.34 (m, 3H), 2.29 (s, 6H), 2.12-1.86 (m, 4H). |
| Cpd. 53 | 1H NMR (300 MHz, Chloroform-d) δ 8.25 (s, 1H), 8.14 (d, J = 8.9 Hz, 1H), 7.48-7.29 (m, 5H), 7.18 (s, 3H), 7.10 (d, J = 8.9 Hz, 2H), 5.87 (s, 1H), 5.84-5.75 (m, 1H), 4.05 (d, J = 13.0 Hz, 2H), 3.82 (d, J = 1.1 Hz, 3H), 3.70-3.64 (m, 1H), 3.14-2.99 (m, 3H), 3.01-2.85 (m, 5H), 2.81 (d, J = 17.5 Hz, 3H), 2.44 (s, 3H), 2.29 (s, 6H), 2.02 (d, J = 13.3 Hz, 4H). |
| Cpd. 54 | 1H NMR (400 MHz, Chloroform-d) δ 8.58 (d, J = 15.3 Hz, 1H), 7.69 (d, J = 8.5 Hz, 1H), 7.62 (s, 1H), 7.55 (d, J = 8.9 Hz, 1H), 7.41 (s, 2H), 7.29 (s, 1H), 7.16 (s, 3H), 7.11 (d, J = 9.1 Hz, 1H), 7.06 (d, J = 8.8 Hz, 1H), 6.07-5.95 (m, 1H), 4.94 (dd, J = 12.2, 5.3 Hz, 1H), 4.74 (d, J = 9.8 Hz, 1H), 4.67 (s, 1H), 4.61 (s, 1H), 4.07-3.88 (m, 3H), 3.88-3.67 (m, 5H), 3.19 (t, J = 11.8 Hz, 1H), 3.06 (t, J = 12.2 Hz, 2H), 2.96-2.63 (m, 8H), 2.27 (s, 6H), 2.19-2.08 (m, 1H), 2.06-1.64 (m, 8H). |
| Cpd. 55 | 1H NMR (400 MHz, Chloroform-d) δ 9.17 (s, 0.2H), 8.87 (s, 0.2H), 8.39 (s, 0.5H), 8.15 (d, J = 8.8 Hz, 1H), 7.64 (d, J = 12.1 Hz, 3H), 7.57-7.35 (m, 3H), 7.17 (s, 3H), 7.11 (t, J = 8.2 Hz, 1H), 6.08-5.87 (m, 1H), 5.79 (s, 1H), 4.91 (s, 2H), 4.78-4.61 (m, 2H), 4.51 (d, J = 12.7 Hz, 1H), 3.77 (d, J = 23.5 Hz, 6H), 3.26 (d, J = 12.2 Hz, 1H), 3.04-2.77 (m, 7H), 2.40 (s, 1H), 2.27 (s, 6H), 2.17 (s, 2H), 2.03 (d, J = 7.9 Hz, 1H), 1.88-1.73 (m, 4H). |
| Cpd. 56 | 1H NMR (400 MHz, DMSO-d6) δ 11.08 (s, 1H), 9.65 (d, J = 13.2 Hz, 1H), 8.33 (d, J = 11.1 Hz, 1H), 8.10 (s, 1H), 7.72-7.58 (m, 3H), 7.34 (s, 1H), 7.25 (s, 1H), 7.16-7.04 (m, 4H), 5.12-5.01 (m, 1H), 4.76 (, 1H), 4.59 (s, 1H), 4.08 (s, 2H), 3.80 (s, 1H), 3.72-3.59 (m, 4H), 3.39 (s, 5H), 3.10 (t, J = 12.7 Hz, 2H), 2.92-2.78 (m, 2H), 2.68 (d, J = 10.1 Hz, 1H), 2.20 (s, 6H), 1.80-1.57 (m, 4H). |
| Cpd. 57 | 1H NMR (400 MHz, Chloroform-d) δ 9.10-8.83 (m, 1H), 7.94 (d, J = 8.9 Hz, 1H), 7.72-7.52 (m, 2H), 7.43 (s, 2H), 7.16-7.10 (m, J = 10.5 Hz, 5H), 6.16-5.96 (m, 2H), 5.78 (s, 1H), 4.80-4.64 (m, 2H), 4.57 (t, J = 14.7 Hz, 1H), 4.00 (s, 2H), 3.92-3.67 (m, 6H), 3.20 (s, 1H), 3.06-2.70 (m, 7H), 2.45-2.32 (m, 1H), 2.26 (s, 6H), 2.06-1.73 (m, 5H). |
| Cpd. 58 | 1H NMR (400 MHz, DMSO-d6) δ 11.15 (s, 1H), 9.68-9.63 (m, 1H), 8.35 (s, 1H), 8.11 (s, 1H), 8.06-7.96 (m, 1H), 7.79-7.66 (m, 2H), 7.63 (d, J = 8.3 Hz, 1H), 7.38 (s, 1H), 7.22-6.97 (m, 4H), 5.89 (dd, J = 12.2, 5.4 Hz, 1H), 4.77 (s, 1H), 4.59 (s, 1H), 4.21-3.99 (m, 2H), 3.81 (t, J = 5.9 Hz, 1H), 3.72-3.56 (m, 3H), 3.29-3.21 (m, 1H), 3.21-2.88 (m, 4H), 2.84 (s, 1H), 2.77-2.59 (m, 3H), 2.20 (s, 6H), 2.02-1.88 (m, 1H), 1.85-1.72 (m, 2H), 1.72-1.56 (m, 2H). |
| Cpd. 59 | 1H NMR (400 MHz, Chloroform-d)ROTOMER PATTERN δ 9.63 (s, 0.4H), 9.33 (s, 0.6H), 7.86-7.76 (m, 1H), 7.76-7.60 (m, 3H), 7.58-7.38 (m, 2H), 7.28-7.22 (m, 1H), 7.22-7.06 (m, 4H), 6.25-6.05 (m, 1H), 5.76 (t, J = 13.9 Hz, 1H), 4.76 (s, 1H), 4.69 (s, 1H), 3.82 (s, 4H), 3.79-3.70 (m, 1H), 3.65-3.50 (m, 2H), 3.07-2.74 (m, 8H), 2.36 (t, J = 7.7 Hz, 1H), 2.28 (s, 6H), 2.23-2.14 (m, 1H), 1.88 (s, 3H). |
| Cpd. 60 | 1H NMR (300 MHz, Chloroform-d:acetone (98:2)) Rotamers δ 9.09-8.86 (m, 1H), 8.18-8.07 (m, 0.25H), 7.81 (d, J = 8.5 Hz, 0.65H), 7.68-7.29 (m, 4H), 7.22-7.06 (m, 4H), 6.89-6.73 (m, 2H), 6.10-5.98 (m, 1H), 4.83-4.71 (m, 2H), 4.71-4.53 (m, 2H), 4.09-3.96 (m, 1H), 3.90-3.71 (m, 6H), 3.25-2.65 (m, 11H), 2.27 (s, 6H), 2.05-1.59 (m, 10H). |
| Cpd. 61 | 1H NMR (300 MHz, Chloroform-d) δ 8.62 (s, 1H), 7.81 (d, J = 8.5 Hz, 1H), 7.49 (d, J = 5.5 Hz, 1H), 7.47-7.39 (m, 2H), 7.35 (s, 1H), 7.16 (s, 3H), 7.07 (d, J = 8.3 Hz, 1H), 6.87-6.76 (m, 2H), 5.93 (s, 1H), 4.78 (dd, J = 12.7, 5.8 Hz, 1H), 4.64 (d, J = 13.0 Hz, 1H), 3.97-3.84 (m, 2H), 3.80 (s, 3H), 3.68-3.54 (m, 2H), 3.07 (t, J = 12.2 Hz, 1H), 2.98-2.77 (m, 6H), |

TABLE 1-continued

| Cpd. No. | 1H NMR/Mass Spec(LCMS) |
|---|---|
| | 2.75-2.53 (m, 4H), 2.43-2.32 (m, 2H), 2.27 (s, 6H), 2.06-1.76 (m, 7H), 1.19-1.07 (m, 2H). |
| Cpd. 62 | 1H NMR (300 MHz, Chloroform-d)Rotamers δ 9.42 (s, 0.5H), 9.25 (s, 0.5H), 7.78 (t, J = 8.0 Hz, 1H), 7.65 (d, J = 7.7 Hz, 1H), 7.47-7.34 (m, 4H), 7.24 (s, 1H), 7.14 (s, 3H), 7.05 (d, J = 8.3 Hz, 1H), 6.24-6.11 (m, 1H), 5.75 (dd, J = 11.4, 5.3 Hz, 1H), 4.65 (d, J = 13.2 Hz, 1H), 3.93 (d, J = 13.6 Hz, 1H), 3.80 (s, 3H), 3.68-3.47 (m, 4H), 3.11-2.51 (m, 13H), 2.43-2.29 (m, 3H), 2.26 (s, 6H), 2.21-2.08 (m, 2H), 1.95 (s, 1H), 1.82 (d, J = 13.7 Hz, 4H), 1.22-1.04 (m, 2H). |
| Cpd. 63 | 1H NMR (400 MHz, Chloroform-d) δ 8.38 (s, 1H), 8.10 (s, 1H), 7.78 (d, J = 8.9 Hz, 1H), 7.46 (s, 1H), 7.43 (s, 1H), 7.34 (s, 1H), 7.24-7.18 (m, 1H), 7.16 (s, 3H), 7.07 (d, J = 8.4 Hz, 1H), 6.56 (s, 2H), 5.88 (s, 1H), 5.50 (s, 1H), 4.81-4.72 (m, 1H), 4.63 (d, J = 13.3 Hz, 1H), 4.31-4.20 (m, 1H), 3.87 (s, 2H), 3.80 (s, 3H), 3.62 (s, 2H), 3.10 (t, J = 12.7 Hz, 1H), 3.04-2.92 (m, 1H), 2.90-2.80 (m, 3H), 2.79-2.66 (m, 4H), 2.39 (s, 2H), 2.27 (s, 6H), 2.07-1.96 (m, 2H), 1.96-1.83 (m, 3H). |
| Cpd. 64 | 1H NMR (500 MHz, Chloroform-d) δ 9.17 (d, J = 23.8 Hz, 1H), 7.75 (d, J = 7.2 Hz, 1H), 7.48-7.30 (m, 6H), 7.14 (s, H), 7.04 (d, J = 8.2 Hz, 1H), 6.09 (s, 1H), 5.22 (d, J = 13.2 Hz, 1H), 4.58 (d, J = 13.3 Hz, 1H), 4.52-4.35 (m, 2H), 3.79 (s, 4H), 3.66-3.51 (m, 2H), 3.06-2.95 (m, 2H), 2.96-2.87 (m, 2H), 2.87-2.76 (m, 3H), 2.76-2.62 (m, 4H), 2.56 (t, J = 14.6 Hz, 1H), 2.42-2.29 (m, 3H), 2.26 (s, 6H), 2.24-2.16 (m, 2H), 1.89-1.72 (m, 4H). |
| Cpd. 65 | 1H NMR (500 MHz, Chloroform-d) δ 10.47 (s, 1H), 9.01 (s, 1H), 8.09 (s, 1H), 7.89 (d, J = 8.3 Hz, 1H), 7.80-7.70 (m, 2H), 7.55 (d, J = 13.4 Hz, 2H), 7.48-7.38 (m, 6H), 7.19-7.11 (m, 8H), 7.05 (d, J = 7.9 Hz, 1H), 6.03 (s, 2H), 5.30 (dd, J = 13.0, 5.4 Hz, 1H), 5.20 (dd, J = 13.4, 5.1 Hz, 1H), 4.77-4.59 (m, 3H), 4.55-4.26 (m, 6H), 3.89 (dt, J = 13.0, 6.7 Hz, 1H), 3.80 (d, J = 7.9 Hz, 6H), 3.67 (dt, J = 12.6, 6.0 Hz, 1H), 3.59 (q, J = 5.8 Hz, 2H), 3.06 (dt, J = 23.7, 6.9 Hz, 4H), 2.93-2.69 (m, 13H), 2.27 (d, J = 7.7 Hz, 12H). |
| Cpd. 66 | 1H NMR (500 MHz, Chloroform-d) δ 8.23-8.11 (m, 1H), 7.66 (dd, J = 15.0, 9.2 Hz, 2H), 7.53-7.38 (m, 3H), 7.19-7.15 (m, 3H), 7.15-7.10 (m, 1H), 6.96 (d, J = 6.1 Hz, 1H), 6.70 (t, J = 7.9 Hz, 1H), 5.89 (d, J = 11.6 Hz, 1H), 4.98-4.89 (m, 1H), 4.78 (d, J = 5.2 Hz, 1H), 4.74 (d, J = 5.7 Hz, 1H), 3.84-3.72 (m, 6H), 3.71-3.45 (m, 2H), 2.98-2.67 (m, 6H), 2.34 (d, J = 8.1 Hz, 1H), 2.27 (s, 8H), 2.15-1.97 (m, 1H). |
| Cpd. 67 | 1H NMR (400 MHz, Chloroform-d) δ 9.28-9.11 (m, 1H), 7.73-7.63 (m, 1H), 7.63-7.56 (m, 1H), 7.54-7.39 (m, 3H), 7.28 (d, J = 2.4 Hz, 1H), 7.15 (s, 3H), 7.13-6.98 (m, 2H), 6.14-5.99 (m, 1H), 4.94 (dd, J = 12.1, 5.4 Hz, 1H), 4.85-4.60 (m, 2H), 4.05-3.88 (m, 3H), 3.89-3.53 (m, 8H), 3.54-3.26 (m, 2H), 3.11-2.98 (m, 2H), 2.99-2.95 (m, 1H), 2.95-2.79 (m, 4H), 2.79-2.70 (m, 1H), 2.70-2.58 (m, 1H), 2.44 (dq, J = 14.5, 8.6, 7.8 Hz, 1H), 2.27 (s, 6H), 2.21-1.99 (m, 3H), 1.99-1.78 (m, 4H). |
| Cpd. 68 | 1H NMR (300 MHz, Chloroform-d) δ 8.86 (d, J = 71.7 Hz, 1H), 7.76 (d, J = 8.5 Hz, 1H), 7.64 (d, J = 18.4 Hz, 1H), 7.46 (d, J = 12.7 Hz, 2H), 7.39 (d, J = 2.6 Hz, 1H), 7.21-7.06 (m, 4H), 6.56 (d, J = 6.4 Hz, 1H), 6.22 (d, J = 27.2 Hz, 1H), 6.07 (d, J = 21.1 Hz, 1H), 5.48 (s, 1H), 4.70 (d, J = 20.5 Hz, 2H), 4.56 (s, 1H), 4.00 (s, 1H), 3.92-3.83 (m, 2H), 3.79 (s, 3H), 3.75 (s, 1H), 3.18 (s, 1H), 3.04 (d, J = 6.8 Hz, 1H), 2.90 (d, J = 9.6 Hz, 3H), 2.80 (t, J = 7.7 Hz, 4H), 2.26 (s, 6H), 1.94 (m, J = 11.7 Hz, 3H), 1.77 (m, J = 11.8, 7.8 Hz, 3H). |
| Cpd. 69 | 1H NMR (400 MHz, Chloroform-d) δ 8.89-8.38 (m, 1H), 8.10 (d, J = 45.2 Hz, 1H), 7.87 (d, J = 8.5 Hz, 1H), 7.50 (dd, J = 98.5, 32.3 Hz, 6H), 6.12 (s, 1H), 5.83 (s, 1H), 5.45 (d, J = 62.7 Hz, 2H), 5.01-4.58 (m, 3H), 4.28-3.98 (m, 3H), 3.82 (s, 4H), 3.56 (s, 1H), 3.11 (dq, J = 38.6, 14.4, 13.4 Hz, 2H), 3.00-2.67 (m, 10H), 2.40 (s, 1H), 2.29 (d, J = 2.6 Hz, 7H). |
| Cpd. 70 | LC/MS: 656.2 [M + H]+<br>1H NMR (400 MHz, DMSO-d6) δ 11.07 (s, 1H), 9.67 (s, 1H), 8.35 (s, 1H), 8.10 (s, 1H), 7.81 (d, J = 2.2 Hz, 1H), 7.71 (d, J = 8.5 Hz, 1H), 7.63 (dd, J = 8.3, 2.2 Hz, 1H), 7.40 (d, J = 2.3 Hz, 1H), 7.30 (d, J = 2.4 Hz, 1H), 7.19-7.04 (m, 4H), 5.08 (dd, J = 12.8, 5.4 Hz, 1H), 4.65 (s, 2H), 3.75 (t, J = 5.9 Hz, 2H), 3.64 (s, 3H), 2.96-2.83 (m, 3H), 2.64-2.54 (m, 2H), 2.21 (s, 6H), 2.07-1.96 (m, 1H). |
| Cpd. 71 | LC/MS: 656.4 [M + H]+<br>1H NMR (500 MHz, DMSO-d6) δ 11.15 (s, 1H), 9.69 (s, 1H), 8.35 (s, 1H), 8.10 (s, 1H), 8.04 (d, J = 9.0 Hz, 1H), 7.83 (d, J = 2.2 Hz, 1H), 7.67-7.58 (m, 2H), 7.51 (d, J = 2.5 Hz, 1H), 7.21-7.04 (m, 4H), 5.90 (dd, J = 12.4, 5.5 Hz, 1H), 4.69 (s, 2H), 3.80 (t, J = 5.9 Hz, 2H), 3.65 (s, 3H), 3.00-2.89 (m, 3H), 2.73-2.61 (m, 2H), 2.29-2.22 (m, 1H), 2.20 (s, 6H). |
| Cpd. 72 | LC/MS : 713 [M + H]+.<br>1H NMR (300 MHz, DMSO-d6) δ 11.07 (s, 1H), 9.68 (d, J = 17.9 Hz, 1H), 8.36 (s, 1H), 8.11 (d, J = 2.8 Hz, 1H), 7.72 (d, J = 5.4 Hz, 1H), 7.66 (d, J = 8.4 Hz, 1H), 7.58 (d, J = 8.3 Hz, 1H), 7.14 (d, J = 12.0 Hz, 6H), 7.05 (d, J = 8.5 Hz, 1H), 5.05 (dd, J = 12.6, 5.3 Hz, 1H), 4.75 (s, 1H), 4.65 (s, 1H), 4.33-4.21 (m, 2H), 3.75 (q, J = 6.2 Hz, 2H), 3.64 (d, J = 6.8 Hz, 3H), 2.93-2.81 (m, 2H), 2.79-2.71 (m, 1H), 2.58 (d, J = 16.4 Hz, 2H), 2.21 (d, J = 1.8 Hz, 6H), 2.07-1.94 (m, 1H). |

TABLE 1-continued

| Cpd. No. | 1H NMR/Mass Spec(LCMS) |
| --- | --- |
| Cpd. 73 | 1H NMR (400 MHz, Chloroform-d) δ 8.84 (s, 1H), 7.70 (d, J = 8.6 Hz, 1H), 7.63 (s, 1H), 7.54 (s, 1H), 7.51-7.43 (m, 2H), 7.40 (s, 1H), 7.20-7.14 (m, 4H), 7.08 (dd, J = 8.6, 2.4 Hz, 1H), 7.02 (s, 1H), 6.00 (s, 1H), 4.96 (dd, J = 12.2, 5.4 Hz, 1H), 3.98 (t, J = 14.1 Hz, 5H), 3.87-3.76 (m, 3H), 3.03 (t, J = 12.0 Hz, 2H), 2.96-2.62 (m, 5H), 2.29 (s, 6H), 2.20-1.97 (m, 4H), 1.86 (d, J = 12.1 Hz, 2H), 1.43-1.32 (m, 2H). |
| Cpd. 74 | 1H NMR (400 MHz, Chloroform-d) δ 8.39-8.30 (m, 1H), 8.15 (dd, J = 9.0, 0.9 Hz, 1H), 8.05 (d, J = 7.2 Hz, 1H), 7.83-7.76 (m, 1H), 7.65-7.57 (m, 1H), 7.53-7.46 (m, 1H), 7.45-7.36 (m, 2H), 7.32 (dd, J = 9.1, 2.6 Hz, 1H), 7.22-7.14 (m, 3H), 5.94 (d, J = 11.7 Hz, 1H), 5.81 (dd, J = 11.5, 5.4 Hz, 1H), 4.44 (d, J = 7.0 Hz, 1H), 4.05 (d, J = 13.0 Hz, 2H), 3.86 (s, 3H), 3.58 (t, J = 6.6 Hz, 1H), 3.11-2.78 (m, 9H), 2.46-2.35 (m, 1H), 2.30 (d, J = 1.2 Hz, 6H), 2.19-1.97 (m, 3H), 1.89 (d, J = 13.1 Hz, 2H). |
| Cpd. 75 | LC/MS 767.4 [M + H]+<br>1H NMR (500 MHz, Chloroform-d) δ 8.53 (s, 1H), 7.69 (d, J = 8.6 Hz, 1H), 7.47 (s, 1H), 7.45 (d, J = 2.8 Hz, 1H), 7.40 (d, J = 9.0 Hz, 2H), 7.35 (s, 1H), 7.30 (d, J = 2.4 Hz, 1H), 7.21-7.15 (m, 3H), 7.07 (d, J = 8.7 Hz, 2H), 5.96 (d, J = 7.2 Hz, 1H), 4.96 (dd, J = 12.4, 5.3 Hz, 1H), 3.98 (d, J = 13.0 Hz, 2H), 3.82 (s, 3H), 3.57 (d, J = 6.3 Hz, 1H), 3.41 (d, J = 10.4 Hz, 1H), 3.17-3.09 (m, 1H), 3.08-2.96 (m, 3H), 2.96-2.81 (m, 3H), 2.81-2.63 (m, 3H), 2.56-2.39 (m, 2H), 2.35 (q, J = 6.9 Hz, 1H), 2.29 (s, 6H), 2.26 (d, J = 13.4 Hz, 1H), 2.21-2.10 (m, 1H), 2.06-1.92 (m, 2H), 1.39 (d, J = 6.3 Hz, 3H). |
| Cpd. 76 | LC/MS 827.3 [M + H]+<br>1H NMR (500 MHz, DMSO-d6) δ 11.10 (s, 1H), 10.34 (s, 1H), 10.13 (s, 1H), 8.59 (s, 1H), 8.46 (s, 1H), 7.72 (d, J = 2.2 Hz, 1H), 7.70-7.66 (m, 2H), 7.38 (d, J = 2.3 Hz, 1H), 7.29 (dd, J = 8.8, 2.3 Hz, 1H), 7.22 (d, J = 8.6 Hz, 1H), 7.16-7.08 (m, 3H), 5.08 (dd, J = 12.8, 5.4 Hz, 1H), 4.61 (d, J = 15.2 Hz, 1H), 4.33 (dd, J = 15.7, 7.6 Hz, 1H), 4.12 (d, J = 13.1 Hz, 2H), 3.76-3.68 (m, 2H), 3.64 (s, 3H), 3.49 (ddd, J = 13.2, 5.8, 2.9 Hz, 1H), 3.45-3.29 (m, 2H), 3.26-3.18 (m, 1H), 3.15 (t, J = 6.0 Hz, 2H), 3.10-2.96 (m, 3H), 2.95-2.83 (m, 1H), 2.64-2.54 (m, 2H), 2.36-2.27 (m, 1H), 2.21 (s, 6H), 2.05-1.89 (m, 3H), 1.32 (q, J = 12.2, 11.5 Hz, 2H). |
| Cpd. 77 | 1H NMR (300 MHz, DMSO) δ 11.09 (s, 1H), 9.82 (s, 1H), 8.37 (s, 1H), 8.12 (s, 1H), 8.03 (s, 1H), 7.83-7.68 (m, 2H), 7.33 (d, J = 8.4 Hz, 1H), 7.11 (dt, J = 8.7, 4.5 Hz, 3H), 6.98 (d, J = 8.5 Hz, 1H), 5.09 (dt, J = 12.6, 5.4 Hz, 1H), 4.80 (d, J = 19.6 Hz, 4H), 3.65 (s, 3H), 3.03-2.70 (m, 2H), 2.59 (d, J = 15.1 Hz, 2H), 2.21 (s, 6H), 2.08-1.96 (m, 1H). |
| Cpd. 78 | LC/MS 795.3 [M + H]+<br>1H NMR (400 MHz, Chloroform-d) δ 8.66 (s, 1H), 7.70 (dd, J = 12.7, 8.5 Hz, 1H), 7.48 (d, J = 12.7 Hz, 2H), 7.39 (d, J = 8.0 Hz, 1H), 7.35-7.31 (m, 1H), 7.18 (d, J = 3.1 Hz, 3H), 7.06 (dd, J = 8.6, 2.5 Hz, 2H), 5.98 (s, 1H), 5.01-4.92 (m, 1H), 3.97 (q, J = 11.4, 9.4 Hz, 2H), 3.81 (s, 4H), 3.45-3.15 (m, 1H), 3.04 (dt, J = 23.5, 9.3 Hz, 3H), 2.95-2.68 (m, 6H), 2.56 (d, J = 16.6 Hz, 1H), 2.49-2.37 (m, 1H), 2.29 (s, 6H), 2.25 (d, J = 6.6 Hz, 1H), 2.21-2.09 (m, 1H), 2.09-2.01 (m, 1H), 1.95 (d, J = 13.2 Hz, 3H), 1.86-1.75 (m, 1H), 1.09 (d, J = 6.3 Hz, 3H), 0.97 (d, J = 6.5 Hz, 3H). |
| Cpd. 79 | LC/MS: 768.0 [M + H]+<br>1H NMR (400 MHz, DMSO-d6) δ 9.53 (s, 1H), 8.32 (s, 1H), 8.08 (s, 1H), 7.65 (d, J = 8.8Hz, 1H), 7.58 (dd, J = 8.0 2.4Hz, 1H), 7.54 (s, 1H), (d, J = 2.2 Hz, 1H), 7.24 (dd, J = 8.8, 2.4 Hz, 1H), 7.15-7.06 (m, 3H), 7.02 (d, J = 8.4 Hz, 1H), 5.13 (dd, J = 12.8, 5.4 Hz, 1H), 4.05 (d, J = 12.8 Hz, 2H), 3.61 (s, 3H), 3.54 (s, 2H), 3.06-2.90 (m, 6H), 2.82-2.72 (m, 3H), 2.70-2.54 (m, 3H), 2.34 (d, J = 6.8 Hz, 2H), 2.20 (s, 6H), 2.07-1.94 (m, 2H), 1.84 (d, J = 12.8 Hz, 2H), 1.23-1.13 (m, 2H). |
| Cpd. 80 | LC/MS [M + 2H]+ 797.0.<br>1H NMR (300 MHz, DMSO-d6) δ 10.93 (s, 1H), 9.55 (s, 1H), 8.33 (s, 1H), 8.09 (s, 1H), 7.65-7.48 (m, 2H), 7.41 (d, J = 8.5 Hz, 1H), 7.17-7.05 (m, 3H), 7.02 (d, J = 8.5 Hz, 1H), 6.80 (d, J = 8.5 Hz, 1H), 6.75 (s, 1H), 6.36-6.24 (h, J = 3.0 Hz, 1H), 5.02 (dd, J = 17.6, 6.8 Hz, 1H), 4.37 (s, 1H), 4.05-3.86 (m, 2H), 3.61 (s, 3H), 3.53 (s, 2H), 3.14-2.82 (m, 5H), 2.82-2.59 (m, 6H), 2.44-2.26 (m, 3H), 2.20 (s, 6H), 2.04-1.87 (m, 3H), 1.87-1.69 (m, 3H). |
| Cpd. 81 | LC/MS: 699.2 [M + H]+<br>1H NMR (400 MHz, DMSO-d6) δ 10.92 (s, 1H), 9.64 (d, J = 20.8 Hz, 1H), 8.34 (s, 1H), 8.10 (s, 1H), 7.74-7.61 (m, 2H), 7.41 (d, J = 8.4 Hz, 1H), 7.21-7.04 (m, 4H), 6.81 (d, J = 8.4 Hz, 1H), 6.77 (s, 1H), 6.39 (s, 1H), 5.01 (dd, J = 13.3, 5.1 Hz, 1H), 4.73 (s, 1H), 4.64 (s, 1H), 4.28 (d, J = 16.8 Hz, 1H), 4.21-4.07 (m, 3H), 3.79-3.69 (m, 2H), 3.63 (d, J = 6.5 Hz, 3H), 2.97-2.83 (m, 2H), 2.79-2.71 (m, 1H), 2.58 (d, J = 16.7 Hz, 1H), 2.36 (dd, J = 14.0, 9.4 Hz, 1H), 2.20 (d, J = 1.7 Hz, 6H), 2.03-1.92 (m, 1H). |
| Cpd. 82 | LC/MS : 793.50 [M + H+]<br>1H NMR (400 MHz, CDCl3) δ 9.09 (s, 1H), 8.11 (s, 1H), 7.67 (d, J = 8.5 Hz, 1H), 7.58 (s, 1H), 7.54-7.46 (m, 1H), 7.39 (t, J = 5.9 Hz, 3H), 7.28 (d, J = 2.4 Hz, 1H), 7.15-7.02 (m, 3H), 6.38 (s, 1H), 4.94 (dd, J = 12.2, 5.4 Hz, 1H), 3.95 (d, J = 12.7 Hz, 2H), 3.82 (s, 3H), 3.63 (s, 2H), 2.99 (t, |

TABLE 1-continued

| Cpd. No. | 1H NMR/Mass Spec(LCMS) |
| --- | --- |
| | J = 12.5 Hz, 2H), 2.93-2.81 (m, 4H), 2.75 (dt, J = 11.8, 7.3 Hz, 3H), 2.40 (d, J = 6.5 Hz, 2H), 2.12 (dd, J = 11.4, 5.7 Hz, 1H), 1.93 (t, J = 14.7 Hz, 3H), 1.34 (dd, J = 19.0, 7.4 Hz, 2H). |
| Cpd. 83 | 1H NMR (500 MHz, DMSO) δ 11.09 (s, 1H), 9.89-9.88 (m, 1H), 8.85 (s, 1H), 8.09 (d, J = 9.2 Hz, 1H), 7.87-7.77 (m, 1H), 7.77-7.72 (m, 1H), 7.68-7.66 (m, 2H), 7.38 (s, 1H), 7.33-7.26 (m, 1H), 7.22-7.21 (m, 1H), 7.02 (s, 1H), 6.98-6.96 (m, 1H), 5.09-5.07 (m, 1H), 4.62 (m, 1H), 4.37-4.36 (m, 1H), 4.13-4.12 (m, 2H), 3.75-3.74 (m, 3H), 3.18 (s, 3H), 3.07-2.99 (m, 3H), 2.95-2.85 (m, 1H), 2.67-2.55 (m, 2H), 2.53 (s, 1H), 2.28 (s, 3H), 2.26 (s, 3H), 2.06-1.99 (m, 1H), 1.96-1.89 (m, 2H), 1.37-1.27 (m, 2H).<br>LC/MS : 753.74 [M + H+] |
| Cpd. 84 | LC/MS : 739.56 [M + H+]<br>1H NMR (500 MHz, CDCl3) δ 9.14 (s, 1H), 8.41 (d, J = 15.9 Hz, 1H), 7.67 (d, J = 8.4 Hz, 1H), 7.55 (d, J = 8.3 Hz, 1H), 7.53-7.47 (m, 1H), 7.45 (s, 1H), 7.40 (s, 1H), 7.28 (d, J = 2.3 Hz, 1H), 7.23-7.17 (m, 2H), 7.13-7.02 (m, 2H), 6.99 (q, J = 7.5, 6.4 Hz, 1H), 6.18 (d, J = 27.8 Hz, 1H), 4.93 (dd, J = 12.4, 5.4 Hz, 1H), 3.96 (d, J = 13.2 Hz, 2H), 3.85 (d, J = 5.5 Hz, 3H), 3.63 (s, 2H), 3.49 (s, 1H), 3.00 (t, J = 12.3 Hz, 2H), 2.90-2.86 (m, 2H), 2.85-2.78 (m, 1H), 2.74 (q, J = 6.0, 5.5 Hz, 2H), 2.40 (d, J = 6.7 Hz, 2H), 2.33 (s, 3H), 2.14 (dd, J = 19.7, 11.7 Hz, 2H), 1.95 (d, J = 13.9 Hz, 2H), 1.33 (d, J = 11.9 Hz, 2H). |
| Cpd. 85 | LC/MS: 773.51 [M + H+]<br>1H NMR (400 MHz, CDCl3) δ 8.32 (s, br,1H), 7.84 (s, 1H), 7.67 (d, J = 8.5 Hz, 1H), 7.45 (dd, J = 8.2, 2.3 Hz, 1H), 7.35-7.34 (m, 1H), 7.35-7.31 (m, 1H), 7.28 (d, J = 2.3 Hz, 1H), 7.24 (s, 1H), 7.22-7.18 (m, 1H), 7.15-7.11 (m, 1H), 7.11-7.06 (m, 1H), 7.07-7.02 (m, 1H), 6.12 (s, 1H), 4.94-4.91 (m, 1H), 3.97-3.94 (m, 2H), 3.81 (s, 3H), 3.63 (s, 2H), 3.03-3.00 (m, 2H), 2.93-2.83 (m, 3H), 2.82-2.81 (m, 1H), 2.77-2.70 (m, 2H), 2.41-2.40 (m, 2H), 2.28 (s, 3H), 2.16-2.09 (m, 1H), 1.97-1.93 (m, 2H), 1.37-1.34 (m, 2H). |
| Cpd. 86 | LC/MS: 781.62 [M + H+]<br>1H NMR (500 MHz, CDCl3) δ 8.03 (s, 1H), 7.67 (d, J = 8.5 Hz, 1H), 7.46-7.44 (m, 1H), 7.35 (s, 1H), 7.28 (s, 2H), 7.15 (s, 2H), 7.11-7.00 (m, 3H), 5.85 (s, 1H), 4.96-4.91 (m, 1H), 4.90-4.84 (m, 1H), 3.97-3.95 (m, 2H), 3.61 (s, 2H), 3.00-2.99 (m, 2H), 2.87-2.76 (m, 4H), 2.73 (s, 2H), 2.40 (s, 2H), 2.27 (s, 6H), 2.19-2.08 (m, 2H), 1.95 (s, 2H), 1.53 (s, 3H), 1.52 (s, 3H), 0.88 (s, 2H). |
| Cpd. 87 | 1H NMR (500 MHz, Acetone) δ 9.95 (s, 1H), 8.77 (s, 1H), 8.08-7.99 (m, 2H), 7.92-7.89 (m, 1H), 7.75-7.69 (m, 1H), 7.60-7.49 (m, 2H), 7.47-7.40 (m, 1H), 7.32-7.27 (m, 1H), 7.20-7.15 (m, 2H), 7.13-7.09 (m, 2H), 4.83 (s, 2H), 4.45 (s, 1H), 3.90-3.82 (m, 1H), 3.72 (s, 3H), 3.62-3.60 (m, 2H), 3.52-3.49 (m, 2H), 2.85-2.77 (m, 4H), 2.64 (d, J = 18.0, 2H), 2.28 (s, 6H), 2.21-2.12 (m, 2H). |
| Cpd. 88 | LC/MS 739.56 [M + H+].<br>1H NMR (500 MHz, chloroform-d) δ 8.72 (s, 1H), 7.69 (d, J = 8.5 Hz, 1H), 7.43 (d, J = 7.5 Hz, 2H), 7.36 (d, J = 2.5 Hz, 1H), 7.31 (d, J = 2.5 Hz, 1H), 7.20-7.12 (m, 3H), 7.10-7.03 (m, 2H), 5.96 (s, 1H), 4.98-4.91 (dd, 1H), 4.03 (d, J = 13.0 Hz, 2H), 3.80 (d, J = 8.5 Hz, 5H), 3.08-2.99 (m, 2H), 2.90-2.82 (m, 5H), 2.82-2.68 (m, 2H), 2.16-2.11 (m, 1H), 2.05 (d, J = 12.5 Hz, 2H), 1.78-1.72 (m, 3H); |
| Cpd. 89 | 1H NMR (500 MHz, Methanol-d4) δ 8.28 (m, 1H), 7.93-7.86 (m, 1H), 7.64-7.57 (m, 1H), 7.52 (s, 1H), 7.46-7.38 (m, 3H), 7.35-7.31 (m, 1H), 7.25-7.22 (m, 1H), 7.17 (m, 4H), 4.65 (m, 1H), 4.46 (s, 1H), 4.01-3.90 (m, 1H), 3.69 (s, 3H), 3.62 (s, 2H), 3.53 (d, J = 6.5 Hz, 2H), 3.01 (s, 1H), 2.88 (s, 2H), 2.79-2.70 (m, 1H), 2.68-2.63 (m, 2H), 2.28 (d, J = 3.0 Hz, 6H), 2.26 (s, 3H), 2.16-2.13 (m, 2H), 2.06-1.96 (m, 1H). |
| Cpd. 90 | LC/MS: 810.2 [M + H]+<br>1H NMR (400 MHz, DMSO-d6) δ 11.12 (s, 1H), 10.35 (s, 1H), 9.53 (s, 1H), 8.33 (s, 1H), 8.31 (d, J = 1.8 Hz, 1H), 8.09-8.04 (m, 2H), 7.88 (d, J = 8.2 Hz, 1H), 7.60-7.55 (m, 1H), 7.55-7.52 (m, 1H), 7.14-7.06 (m, 3H), 7.01 (d, J = 8.4 Hz, 1H), 5.13 (dd, J = 12.9, 5.3 Hz, 1H), 3.61 (s, 3H), 3.52 (s, 2H), 3.30 (s, 2H), 3.19 (s, 2H), 2.95-2.84 (m, 3H), 2.78-2.72 (m, 2H), 2.63 (t, J = 5.6 Hz, 3H), 2.36-2.29 (m, 2H), 2.20 (s, 6H), 2.17 (d, J = 10.8 Hz, 2H), 2.09-1.94 (m, 1H), 1.73 (d, J = 12.5 Hz, 2H), 1.64 (s, 1H), 1.35-1.26 (m, 2H). |
| Cpd. 91 | LC/MS: 796.4 [ M + H]+<br>1H NMR (400 MHz, Methanol-d4) δ 8.13-8.04 (m, 2H), 7.78 (d, J = 8.3 Hz, 1H), 7.63 (dd, J = 8.3, 1.8 Hz, 1H), 7.58-7.53 (m, 2H), 7.20-7.13 (m, 3H), 7.10 (d, J = 8.2 Hz, 1H), 5.15 (dd, J = 13.3, 5.1 Hz, 1H), 4.59 (s, 2H), 4.55-4.43 (m, 2H), 3.74 (s, 2H), 3.69 (s, 3H), 3.25 (s, 2H), 3.02 (d, J = 11.3 Hz, 2H), 2.98-2.90 (m, 3H), 2.90-2.76 (m, 4H), 2.58-2.51 (m, 2H), 2.37-2.30 (m, 2H), 2.28 (s, 6H), 2.22-2.14 (m, 1H), 2.05 (d, J = 9.4 Hz, 1H), 1.89 (d, J = 13.2 Hz, 2H), 1.80 (s, 1H), 1.52-1.41 (m, 2H). |
| Cpd. 92 | LC/MS: 782.3<br>1H NMR (400 MHz, DMSO-d6) δ 10.96 (s, 1H), 9.54 (s, 1H), 8.82 (s, 1H), 8.33 (s, 1H), 8.08 (s, 1H), 7.82-7.77 (m, 1H), 7.62-7.51 (m, 4H), 7.11 (q, J = 5.4 Hz, 3H), 7.02 (d, J = 8.3 Hz, 1H), 5.07 (dd, J = 13.3, 5.1 Hz, |

TABLE 1-continued

| Cpd. No. | 1H NMR/Mass Spec(LCMS) |
| --- | --- |
| | 1H), 4.43-4.34 (m, 1H), 4.29-4.21 (m, 1H), 4.14 (d, J = 12.7 Hz, 2H), 3.61 (s, 3H), 3.54 (s, 2H), 2.98-2.72 (m, 6H), 2.70-2.60 (m, 3H), 2.36-2.31 (m, 2H), 2.20 (s, 6H), 2.04-1.84 (m, 3H), 1.79 (d, J = 12.3 Hz, 2H), 1.14-1.03 (m, 2H). |
| Cpd. 93 | LC/MS: 782.4 [M + H]+ 1H NMR (400 MHz, DMSO-d6) δ 11.14 (s, 1H), 9.67-9.55 (m, 1H), 8.37-8.30 (m, 1H), 8.09 (d, J = 8.8 Hz, 1H), 8.05-7.95 (m, 1H), 7.76-7.58 (m, 3H), 7.43-7.33 (m, 1H), 7.10 (dt, J = 9.4, 4.7 Hz, 4H), 5.90 (dd, J = 12.2, 5.3 Hz, 1H), 4.77 (s, 0.7H), 4.61 (s, 1.3H), 3.78 (t, J = 5.7 Hz, 1H), 3.69 (t, J = 6.0 Hz, 1H), 3.62 (d, J = 2.9 Hz, 3H), 3.54-3.48 (m, 2H), 3.45-3.40 (m, 2H), 3.04-2.81 (m, 2H), 2.77-2.57 (m, 8H), 2.28-2.23 (m, 1H), 2.20 (s, 6H). |
| Cpd. 94 | LC/MS: 713.3 [M + H]+ 1H NMR (500 MHz, DMSO-d6) δ 11.00 (s, 1H), 9.58 (s, 1H), 8.51 (t, J = 6.3 Hz, 1H), 8.35 (s, 1H), 8.10 (s, 1H), 7.69 (d, J = 7.8 Hz, 1H), 7.63 (dd, J = 8.5, 2.2 Hz, 1H), 7.58-7.52 (m, 1H), 7.49 (s, 1H), 7.43 (d, J = 7.8 Hz, 1H), 7.16-7.08 (m, 3H), 7.04 (d, J = 8.4 Hz, 1H), 5.11 (dd, J = 13.4, 5.1 Hz, 1H), 4.48-4.39 (m, 3H), 4.34-4.27 (m, 1H), 3.65 (s, 2H), 3.60 (s, 3H), 3.19 (s, 2H), 2.96-2.87 (m, 1H), 2.87-2.80 (m, 2H), 2.77-2.68 (m, 2H), 2.63-2.55 (m, 1H), 2.43-2.32 (m, 1H), 2.20 (s, 6H), 2.05-1.90 (m, 1H). |
| Cpd. 95 | LC/MS: 782.4 [M + H]+. 1H NMR (400 MHz, DMSO-d6) δ 11.08 (s, 1H), 9.55 (s, 1H), 8.33 (s, 1H), 8.08 (s, 1H), 7.68 (d, J = 8.5 Hz, 1H), 7.62-7.52 (m, 2H), 7.35 (d, J = 2.3 Hz, 1H), 7.25 (dd, J = 8.7, 2.3 Hz, 1H), 7.18-7.06 (m, 3H), 7.02 (d, J = 8.4 Hz, 1H), 5.07 (dd, J = 12.9, 5.4 Hz, 1H), 3.85-3.72 (m, 2H), 3.70-3.57 (m, 7H), 3.50 (s, 4H), 3.41 (s, 2H), 2.94-2.81 (m, 1H), 2.81-2.67 (m, 4H), 2.63-2.54 (m, 2H), 2.20 (s, 6H), 2.07-2.00 (m, 1H). |
| Cpd. 96 | LC/MS: 685.3. 1H NMR (500 MHz, DMSO-d6) δ 10.99 (s, 1H), 9.69 (s, 1H), 8.97 (s, 1H), 8.36 (s, 1H), 8.12 (s, 1H), 7.85 (s, 1H), 7.71 (s, 1H), 7.67 (d, J = 9.1 Hz, 1H), 7.60 (h, J = 5.4, 4.5 Hz, 2H), 7.16-7.06 (m, 4H), 5.09 (dd, J = 13.3, 5.1 Hz, 1H), 4.68 (s, 2H), 4.41 (d, J = 17.2 Hz, 1H), 4.27 (d, J = 17.0 Hz, 1H), 3.74 (t, J = 5.9 Hz, 2H), 3.64 (s, 3H), 2.96-2.86 (m, 1H), 2.81 (t, J = 5.9 Hz, 2H), 2.66-2.57 (m, 1H), 2.44-2.33 (m, 1H), 2.21 (s, 6H), 2.04-1.95 (m, 1H). |
| Cpd. 97 | LC/MS: 796.2 [M + H]+ 1H NMR (300 MHz, DMSO-d6) δ 11.07 (s, 1H), 9.55 (s, 1H), 8.33 (s, 1H), 8.09 (s, 1H), 7.76 (d, J = 8.2 Hz, 1H), 7.65 (d, J = 8.5 Hz, 1H), 7.57 (d, J = 9.1 Hz, 2H), 7.33 (s, 1H), 7.30-7.20 (m, 1H), 7.17-7.05 (m, 3H), 7.02 (d, J = 8.1 Hz, 1H), 5.06 (dd, J = 12.7, 5.3 Hz, 1H), 4.02 (d, J = 13.5 Hz, 2H), 3.72-3.53 (m, 5H), 3.19-3.04 (m, 4H), 2.89-2.59 (m, 6H), 2.20 (s, 6H), 2.09-1.91 (m, 3H), 1.78 (d, J = 8.2 Hz, 2H), 1.63-1.48 (m, 2H). |
| Cpd. 98 | LC/MS: 713.0 [M + H]+. 1H NMR (500 MHz, DMSO-d6) δ 10.76 (s, 1H), 9.35 (s, 1H), 8.28-8.24 (m, 1H), 7.90 (s, 1H), 7.71-7.52 (m, 3H), 7.40 (s, 1H), 7.16-7.01 (m, 4H), 5.01 (s, 1H), 4.88-4.50 (m, 3H), 4.35-4.10 (m, 2H), 3.90 (s, 1H), 3.76-3.43 (m, 8H), 2.85 (s, 1H), 2.77-2.58 (m, 3H), 2.22 (s, 6H), 2.05-1.89 (m, 1H). |
| Cpd. 99 | LC/MS: 699.0 [M + H]+. 1H NMR (400 MHz, DMSO-d6) δ 10.97 (s, 1H), 9.64 (s, 1H), 8.34 (s, 1H), 8.10 (s, 1H), 7.78-7.56 (m, 3H), 7.48 (s, 1H), 7.42 (d, J = 7.9 Hz, 1H), 7.29 (t, J = 5.8 Hz, 1H), 7.20-7.02 (m, 4H), 5.10 (dd, J = 13.3, 5.1 Hz, 1H), 4.53 (s, 2H), 4.49-4.23 (m, 4H), 3.63 (s, 3H), 3.62-3.57 (m, 1H), 2.99-2.84 (m, 1H), 2.73 (t, J = 6.0 Hz, 2H), 2.70-2.56 (m, 2H), 2.45-2.32 (m, 2H), 2.20 (s, 6H), 2.05-1.95 (m, 1H). |
| Cpd. 100 | 1H NMR (400 MHz, DMSO-d6) δ 11.08 (s, 1H), 9.61 (s, 1H), 8.35 (s, 1H), 8.09 (s, 1H), 7.90 (t, J = 5.6 Hz, 1H), 7.80-7.72 (m, 2H), 7.65 (d, J = 8.5 Hz, 1H), 7.33 (d, J = 2.3 Hz, 1H), 7.24 (dd, J = 8.7, 2.3 Hz, 1H), 7.17-7.04 (m, 5H), 5.07 (dd, J = 12.9, 5.4 Hz, 1H), 4.05 (d, J = 13.1 Hz, 2H), 3.62 (s, 3H), 3.29-3.21 (m, 3H), 3.07-2.83 (m, 4H), 2.70-2.63 (m, 2H), 2.20 (s, 6H), 2.06-1.96 (m, 2H), 1.79-1.70 (m, 2H), 1.68-1.55 (m, 2H). |
| Cpd. 101 | 1H NMR (400 MHz, DMSO-d6) δ 11.12 (s, 1H), 10.33 (s, 1H), 9.60 (s, 1H), 8.34 (s, 1H), 8.31 (d, J = 1.6 Hz, 1H), 8.11-8.03 (m, 2H), 7.88 (d, J = 8.4 Hz, 1H), 7.83 (t, J = 5.6 Hz, 1H), 7.75 (d, J = 8.8 Hz, 2H), 7.15-7.06 (m, 4H), 5.13 (dd, J = 13.0, 5.6 Hz, 1H), 3.61 (s, 3H), 3.29-3.21 (m, 3H), 3.18 (s, 2H), 2.96-2.83 (m, 3H), 2.70-2.59 (m, 3H), 2.20 (s, 6H), 2.15-1.97 (m, 4H), 1.79-1.67 (m, 2H), 1.67-1.59 (m, 2H). |
| Cpd. 102 | 1H NMR (500 MHz, DMSO-d6) δ 10.98 (s, 1H), 9.63 (s, 1H), 8.86 (s, 1H), 8.36 (s, 1H), 8.10 (s, 1H), 7.90 (t, J = 5.6 Hz, 1H), 7.82-7.74 (m, 3H), 7.58 (d, J = 8.3 Hz, 1H), 7.53 (d, J = 8.2 Hz, 1H), 7.18-7.06 (m, 5H), 5.08 (dd, J = 13.3, 5.1 Hz, 1H), 4.39 (d, J = 17.1 Hz, 1H), 4.25 (d, J = 17.1 Hz, 1H), 4.14 (d, J = 13.0 Hz, 2H), 3.62 (s, 3H), 3.26 (m, 2H), 2.98-2.87 (m, 1H), 2.83 (t, J = 12.6 Hz, 2H), 2.72-2.61 (m, 3H), 2.42-2.30 (m, 2H), 2.21 (s, 6H), 2.04-1.96 (m, 1H), 1.69 (d, J = 12.5 Hz, 2H), 1.57-1.43 (m, 2H). |

TABLE 1-continued

| Cpd. No. | 1H NMR/Mass Spec(LCMS) |
|---|---|
| Cpd. 103 | 1H NMR (400 MHz, DMSO) δ 9.56 (s, 1H), 8.33 (s, 1H), 8.09 (s, 1H), 7.96 (s, 1H), 7.67 (d, J = 8.3 Hz, 1H), 7.61-7.58 (m, 1H), 7.54 (s, 1H), 7.49 (s, 1H), 7.38 (s, 1H), 7.11-7.08 (m, 4H), 5.13 (d, J = 8.2 Hz, 1H), 5.07-5.01 (m, 2H), 4.35 (d, J = 16.8 Hz, 1H), 4.20 (dd, J = 17.0, 3.5 Hz, 1H), 3.75 (s, 2H), 3.65 (t, J = 7.6 Hz, 4H), 3.61 (d, J = 1.6 Hz, 3H), 3.04 (s, 2H), 2.76 (dd, J = 11.0, 6.3 Hz, 6H), 2.34 (td, J = 7.8, 4.8 Hz, 2H), 2.20 (s, 6H), 2.03-1.93 (m, 2H). |
| Cpd. 104 | 1H NMR (400 MHz, DMSO) δ 10.95 (s, 1H), 9.62 (s, 1H), 8.34 (d, J = 1.8 Hz, 1H), 8.10 (s, 1H), 7.77 (s, 1H), 7.70 (s, 1H), 7.60 (d, J = 6.7 Hz, 1H), 7.50 (d, J = 12.7 Hz, 1H), 7.11 (s, 3H), 7.08 (s, 2H), 5.06-5.02 (m, 1H), 4.77 (s, 1H), 4.61 (s, 1H), 4.31 (s, 1H), 4.19 (s, 1H), 3.78 (s, 1H), 3.68 (d, J = 5.9 Hz, 2H), 3.62 (s, 3H), 2.87 (d, J = 19.0 Hz, 4H), 2.73 (s, 2H), 2.61 (s, 6H), 2.39-2.32 (m, 2H), 2.20 (s, 6H). |
| Cpd. 105 | 1H NMR (400 MHz, Methanol-d4) δ 8.71-8.65 (m, 1H), 8.40-8.37 (m, 1H), 8.12-8.08 (m, 1H), 7.79-7.69 (m, 1H), 7.68-7.55 (m, 1H), 7.49-7.43 (m, 1H), 7.22-7.11 (m, 6H), 5.16-5.08 (m, 1H), 5.09-5.02 (m, 1H), 4.82-4.74 (m, 1H), 4.47-4.41 (m, 1H), 4.39 (s, 1H), 3.87-3.80 (m, 1H), 3.70 (s, 3H), 3.69 (s, 1H), 3.53 (t, J = 6.3 Hz, 1H), 3.11 (t, J = 6.3 Hz, 1H), 3.03-2.86 (m, 3H), 2.82-2.75 (m, 1H), 2.53-2.40 (m, 1H), 2.28 (s, 6H), 2.19-2.12 (m, 1H). |
| Cpd. 106 | 1H NMR (500 MHz, Methanol-d4) δ 8.11 (s, 1H), 7.76-7.69 (m, 1H), 7.63 (s, 1H), 7.59-7.56 (m, 1H), 7.36-7.29 (m, 1H), 7.21-7.11 (m, 6H), 5.31-5.22 (m, 1H), 5.20-5.12 (m, 1H), 4.82 (s, 1H), 4.50-4.40 (m, 2H), 4.01 (s, 2H), 3.95-3.87 (m, 1H), 3.86-3.77 (m, 2H), 3.70 (s, 3H), 3.67-3.56 (m, 2H), 3.11 (s, 2H), 3.05-3.00 (m, 2H), 2.97-2.88 (m, 1H), 2.84-2.77 (m, 1H), 2.52-2.42 (m, 1H), 2.29 (s, 6H), 2.20-2.15 (m, 1H), 2.12-2.03 (m, 2H), 1.88-1.77 (m, 2H). |
| Cpd. 107 | 1H NMR (500 MHz, DMSO-d6) δ 9.57 (s, 1H), 8.34 (s, 1H), 8.09 (s, 1H), 7.67 (d, J = 8.5 Hz, 1H), 7.59 (d, J = 8.3 Hz, 1H), 7.55 (s, 1H), 7.33 (s, 1H), 7.25 (d, J = 8.6 Hz, 1H), 7.16-7.06 (m, 3H), 7.02 (d, J = 8.4 Hz, 1H), 5.65 (s, 2H), 5.26 (dd, J = 13.0, 5.3 Hz, 1H), 4.07 (d, J = 12.9 Hz, 2H), 3.61 (s, 3H), 3.54 (s, 2H), 3.11-2.97 (m, 3H), 2.83 (d, J = 16.9 Hz, 1H), 2.80-2.72 (m, 2H), 2.69-2.62 (m, 2H), 2.58 (dd, J = 13.3, 4.4 Hz, 1H), 2.33 (d, J = 7.1 Hz, 2H), 2.20 (s, 6H), 2.12-2.05 (m, 1H), 1.98 (s, 1H), 1.84 (d, J = 12.8 Hz, 2H), 1.20 (d, J = 11.9 Hz, 2H), 1.11 (s, 9H). |
| Cpd. 108 | LCMS: 699.2 [M + H]+<br>1H NMR (400 MHz, DMSO-d6) δ 10.98 (s, 1H), 10.15 (s, 1H), 9.57 (d, J = 5.6 Hz, 1H), 8.33 (s, 1H), 8.09 (s, 1H), 8.03 (d, J = 1.7 Hz, 1H), 7.72 (dd, J = 8.4, 1.7 Hz, 1H), 7.66 (d, J = 8.3 Hz, 1H), 7.62 (dd, J = 8.4, 2.2 Hz, 1H), 7.58-7.52 (m, 1H), 7.16-7.03 (m, 4H), 5.09 (dd, J = 13.3, 5.1 Hz, 1H), 4.43 (d, J = 17.3 Hz, 1H), 4.29 (d, J = 17.4 Hz, 1H), 3.74 (s, 2H), 3.60 (s, 3H), 3.38 (s, 2H), 2.98-2.66 (m, 5H), 2.67-2.55 (m, 1H), 2.46-2.31 (m, 1H), 2.20 (s, 6H), 2.05-1.95 (m, 1H). |
| Cpd. 109 | LCMS: 753.1 [M + H]+<br>1H NMR (400 MHz, Chloroform-d) δ 8.45 (s, 1H), 7.69 (d, J = 8.5 Hz, 1H), 7.51-7.40 (m, 3H), 7.31 (d, J = 2.4 Hz, 1H), 7.24-7.13 (m, 4H), 7.07 (dd, J = 8.6, 2.4 Hz, 1H), 7.01 (d, J = 8.2 Hz, 1H), 5.93 (s, 1H), 4.96 (dd, J = 12.3, 5.4 Hz, 1H), 3.99 (d, J = 13.1 Hz, 2H), 3.82 (s, 3H), 3.62 (s, 2H), 3.02 (t, J = 12.3 Hz, 2H), 2.96-2.85 (m, 3H), 2.85-2.70 (m, 3H), 2.48-2.36 (m, 2H), 2.29 (s, 6H), 2.18-2.09 (m, 1H), 2.07-2.02 (m, 1H), 1.98 (d, J = 12.9 Hz, 3H), 1.36-1.31 (m, 2H). |
| Cpd. 110 | LCMS: 810.2 [M + H]+.<br>1H NMR (400 MHz, Chloroform-d) δ 9.04 (s, 1H), 7.65 (d, J = 8.3 Hz, 1H), 7.51-7.41 (m, 3H), 7.35 (s, 1H), 7.17 (s, 3H), 7.04-6.94 (m, 2H), 6.85 (dd, J = 8.3, 2.2 Hz, 1H), 6.04 (s, 1H), 5.97 (t, J = 3.9 Hz, 1H), 4.95 (dd, J = 12.2, 5.4 Hz, 1H), 4.66 (d, J = 13.2 Hz, 1H), 3.97 (d, J = 3.9 Hz, 2H), 3.88-3.73 (m, 4H), 3.67-3.53 (m, 2H), 3.13 (t, J = 12.7 Hz, 2H), 2.99-2.66 (m, 8H), 2.41 (d, J = 6.8 Hz, 2H), 2.29 (s, 6H), 2.19-2.10 (m, 1H), 2.08-1.99 (m, 1H), 1.92 (d, J = 12.8 Hz, 2H), 1.25-1.14 (m, 2H). |
| Cpd. 111 | LCMS: 771.4 [M + H]+<br>1H NMR (400 MHz, Chloroform-d) δ 8.99 (s, 1H), 7.81-7.70 (m, 1H), 7.58 (s, 1H), 7.53 (s, 1H), 7.50-7.36 (m, 3H), 7.22-7.15 (m, 3H), 7.14-7.05 (m, 1H), 7.01 (dd, J = 8.6, 2.0 Hz, 1H), 6.16 (s, 1H), 4.72 (s, 1H), 4.60 (s, 1H), 3.91 (s, 3H), 3.87-3.80 (m, 4H), 3.78-3.65 (m, 3H), 3.19-2.97 (m, 1H), 2.94-2.78 (m, 5H), 2.44-2.32 (m, 2H), 2.28 (s, 6H), 2.27-2.14 (m, 2H), 1.99-1.62 (m, 4H). |
| Cpd. 112 | LC/MS 771.5 [M + H]<br>1H NMR (300 MHz, DMSO-d6) δ 10.46-10.23 (m, 2H), 9.79-9.64 (m, 1H), 8.39 (s, 1H), 8.19 (s, 1H), 7.73-7.53 (m, 2H), 7.42-7.26 (m, 2H), 7.20-7.01 (m, 5H), 4.71-4.55 (m, 2H), 4.50-4.23 (m, 1H), 3.87-3.81 (m, 3H), 3.74-3.65 (m, 5H), 3.60-3.55 (m, 2H), 2.84-2.75 (m, 2H), 2.75-2.62 (m, 3H), 2.44-2.33 (m, 2H), 2.20 (s, 6H), 2.09-1.96 (m, 1H), 1.72 (s, 2H), 1.30-1.07 (m, 3H). |
| Cpd. 113 | LC/MS 703.98 [M + H+].<br>1H NMR (300 MHz, DMSO) δ 10.37 (s, 1H), 9.67 (d, J = 10.0 Hz, 1H), 8.55-8.53 (m, 1H), 8.37-8.35 (m, 1H), 8.11 (s, 1H), 7.89 (d, J = 8.5 Hz, 1H), 7.82 (d, J = 2.1 Hz, 1H), 7.75-7.69 (m, 1H), 7.65-7.62 (m, 1H), 7.21-7.17 (m, 1H), 7.12-7.08 (m, 3H), 4.71 (s, 1H), 4.60 (s, 1H), 4.21 (d, |

TABLE 1-continued

| Cpd. No. | 1H NMR/Mass Spec(LCMS) |
|---|---|
| | J = 6.7 Hz, 2H), 3.86 (s, 3H), 3.77-3.66 (m, 2H), 3.62 (d, J = 6.9 Hz, 4H), 3.31 (s, 3H), 2.84 (s, 1H), 2.75-2.67 (m, 2H), 2.19 (s, 6H). |
| Cpd. 114 | 1H NMR (400 MHz, DMSO-d6) δ 10.42-10.32 (m, 1H), 9.65 (s, 1H), 8.38-8.30 (m, 1H), 8.11 (s, 1H), 7.63 (s, 2H), 7.51-7.41 (m, 2H), 7.22-7.04 (m, 5H), 4.69 (s, 2H), 3.94-3.82 (m, 3H), 3.69-3.53 (m, 6H), 2.87 (d, J = 45.8 Hz, 5H), 2.19 (d, J = 5.7 Hz, 5H), 1.87 (d, J = 89.4 Hz, 4H), 1.32-1.14 (m, 6H). |
| Cpd. 115 | 1H NMR (400 MHz, CDCl3) δ 8.12 (s, 1H), 8.07 (s, 1H), 7.81 (d, J = 8.5 Hz, 1H), 7.52 (s, 1H), 7.43-7.41 (m, 2H), 7.19-7.18 (m, 3H), 7.14-7.11 (m, 2H), 7.04-7.01 (m, 1H), 6.92 (s, 1H), 5.25-5.21 (m, 1H), 4.51 (s, 2H), 4.48-4.44 (m, 1H), 4.33-4.30 (m, 1H), 3.94 (s, 2H), 3.86-3.83 (m, 2H), 3.81 (s, 3H), 3.60-3.57 (m, 2H), 3.40 (s, 4H), 2.95-2.89 (m, 4H), 2.39-2.34 (m, 1H), 2.29 (s, 6H), 2.25-2.20 (m, 1H). |
| Cpd. 116 | 1H NMR (500 MHz, MeOD) δ 8.64 (d, J = 4.6 Hz, 1H), 8.34 (d, J = 8.6 Hz, 1H), 8.14 (s, 1H), 7.84 (s, 1H), 7.63 (d, J = 8.9 Hz, 1H), 7.51 (d, J = 8.0 Hz, 1H), 7.47-7.42 (m, 1H), 7.32 (d, J = 8.6 Hz, 1H), 7.24 (d, J = 8.6 Hz, 1H), 7.16 (d, J = 5.1 Hz, 1H), 5.31-5.29 (m, 1H), 5.24-5.21 (m, 1H), 4.54-4.43 (m, 3H), 4.39 (d, J = 16.9 Hz, 1H), 3.83 (s, 3H), 3.71 (s, 5H), 3.62 (s, 2H), 3.46 (s, 1H), 3.37 (s, 2H), 3.22 (s, 2H), 3.07-2.84 (m, 3H), 2.53-2.50 (m, 1H), 2.29 (s, 6H), 2.13-1.98 (m, 2H), 1.88 (s, 2H). |
| Cpd. 117 | 1H NMR (500 MHz, MeOD) δ 8.14-8.11 (m, 2H), 7.84-7.71 (m, 1H), 7.67-7.57 (m, 1H), 7.52-7.50 (m, 1H), 7.45-7.43 (m, 1H), 7.32-7.30 (m, 1H), 7.17-7.13 (m, 3H), 5.19-5.16 (m, 1H), 4.77 (s, 1H), 4.69 (s, 1H), 4.59-4.47 (m, 2H), 4.32-4.30 (m, 2H), 3.86 (s, 1H), 3.72-3.71 (m, 5H), 3.45 (s, 2H), 3.37-3.36 (m, 2H), 3.05-3.00 (m, 1H), 2.99-2.85 (m, 3H), 2.82-2.80 (m, 1H), 2.63-2.60 (m, 1H), 2.28 (s, 6H), 2.19 (s, 2H), 2.09-1.97 (m, 2H). |
| Cpd. 118 | 1H NMR (400 MHz, Chloroform-d) δ 8.89 (s, 1H), 8.00 (s, 1H), 7.67 (d, J = 8.5 Hz, 1H), 7.49-7.46 (m, 1H), 7.42 (s, 1H), 7.40-7.34 (m, 2H), 7.28 (d, J = 2.3 Hz, 1H), 7.10-7.03 (m, 2H), 6.81 (d, J = 2.9 Hz, 1H), 6.76-6.73 (m, 1H), 5.99 (s, 1H), 4.95-4.92 (m, 1H), 3.96 (d, J = 12.6 Hz, 2H), 3.88-3.83 (m, 1H), 3.80 (d, J = 4.8 Hz, 6H), 3.63 (s, 2H), 3.00 (t, J = 11.8 Hz, 2H), 2.87 (t, J = 5.5 Hz, 3H), 2.79-2.72 (m, J = 12.6, 6.0 Hz, 3H), 2.40 (d, J = 6.5 Hz, 2H), 2.29 (s, 3H), 2.19-2.08 (m, 2H), 1.95 (d, J = 12.9 Hz, 2H), 1.32 (d, J = 11.9 Hz, 2H). |
| Cpd. 119 | 1H NMR (400 MHz, Chloroform-d) δ 8.58 (s, 1H), 8.56 (s, 1H), 7.70 (d, J = 8.5 Hz, 1H), 7.55-7.52 (m, 1H), 7.49-7.41 (m, 3H), 7.31 (d, J = 2.4 Hz, 1H), 7.19-7.06 (m, 3H), 6.95 (d, J = 7.4 Hz, 1H), 6.14 (s, 1H), 4.99-4.94 (m, 1H), 3.99 (d, J = 12.9 Hz, 2H), 3.88 (s, 3H), 3.67 (s, 2H), 3.07-2.98 (m, 4H), 2.95-2.87 (m, 5H), 2.82-2.71 (m, 3H), 2.44 (d, J = 6.5H z, 2H), 2.21-2.13 (m, 3H), 2.09-1.95 (m, 4H), 1.36 (d, J = 12.1 Hz, 2H). |
| Cpd. 120 | 1H NMR (400 MHz, Chloroform-d) δ 8.88 (s, 1H), 8.64 (s, 1H), 7.96 (t, J = 8.5 Hz, 1H), 7.67 (d, J = 8.6 Hz, 1H), 7.62 (s, 1H), 7.55-7.53 (m, 1H), 7.40 (d, J = 2.2 Hz, 1H), 7.29 (d, J = 2.3 Hz, 1H), 7.10 (d, J = 8.3 Hz, 1H), 7.06-7.02 (m, 1H), 6.93 (d, J = 10.2 Hz, 2H), 6.48 (d, J = 3. 2Hz, 1H), 4.97-4.92 (m, 1H), 3.96 (d, J = 12.8 Hz, 2H), 3.86 (s, 3H), 3.64 (s, 2H), 3.04-2.95 (m, 2H), 2.93-2.81 (m, 5H), 2.79-2.70 (m, 3H), 2.41 (d, J = 6.6 Hz, 2H), 2.31 (s, 3H), 2.16-2.10 (m, 1H), 1.96 (d, J = 13.1 Hz, 2H), 1.33 (d, J = 11.6 Hz, 2H). |
| Cpd. 121 | 1H NMR (400 MHz, Chloroform-d) δ 8.59 (s, 1H), 8.24 (s, 1H), 7.67 (d, J = 8.6 Hz, 1H), 7.52-7.46 (m, 2H), 7.39-7.33 (m, 2H), 7.29 (d, J = 2.4 Hz, 1H), 7.13-7.03 (m, 2H), 6.98-6.85 (m, 2H), 5.97 (s, 1H), 4.96-4.92 (m, 1H), 3.96 (d, J = 13.0 Hz, 2H), 3.83 (s, 3H), 3.63 (s, 2H), 3.00 (t, J = 12.5 Hz, 2H), 2.93-2.84 (m, 4H), 2.83-2.71 (m, 4H), 2.41 (d, J = 6.6 Hz, 2H), 2.32 (s, 3H), 2.17-2.11 (m, 1H), 1.96 (d, J = 13.1 Hz, 2H), 1.33 (d, J = 11.4 Hz, 2H). |
| Cpd. 122 | 1H NMR (400 MHz, Chloroform-d) δ 8.38 (s, 1H), 8.32 (s, 1H), 8.14 (s, 1H), 8.10-8.05 (m, 1H), 7.85-7.76 (m, 2H), 7.70-7.56 (m, 4H), 7.53-7.46 (m, 1H), 7.41 (d, J = 9.6 Hz, 2H), 7.32-7.28 (m, 2H), 7.10 (d, J = 8.4 Hz, 1H), 7.06-7.04 (m, 1H), 6.08 (s, 1H), 4.96-4.92 (m, 1H), 3.96 (d, J = 12.9 Hz, 2H), 3.86 (s, 3H), 3.64 (s, 2H), 3.05-2.94 (m, 2H), 2.94-2.84 (m, 4H), 2.82-2.79 (m, 1H), 2.74 (q, J = 6.8, 6.1 Hz, 3H), 2.41 (d, J = 6.6 Hz, 2H), 2.37 (s, 3H), 2.17-2.08 (m, 1H), 1.96 (d, J = 13.0 Hz, 2H), 1.33 (d, J = 11.8 Hz, 2H). |
| Cpd. 123 | LCMS: 699.2 [M + H]+<br>1H NMR (400 MHz, Chloroform-d) δ 7.72-7.53 (m, 2H), 7.52-7.41 (m, 2H), 7.37 (s, 1H), 7.17 (d, J = 13.9 Hz, 5H), 7.02 (s, 1H), 6.90 (s, 1H), 5.92 (s, 1H), 4.95 (dd, J = 12.2, 5.4 Hz, 1H), 3.81 (s, 5H), 3.52 (s, 1H), 3.15-2.69 (m, 8H), 2.29 (s, 6H), 2.25-2.09 (m, 2H), 2.06 (d, J = 8.0 Hz, 1H). |
| Cpd. 124 | 1H NMR (600 MHz, DMSO) δ 11.07 (s, 1H), 9.62 (s, 1H), 8.34 (d, J = 4.9 Hz, 1H), 8.09 (s, 1H), 7.68 (s, 1H), 7.69-7.61 (m, 2H), 7.32 (s, 1H), 7.24 (s, 1H), 7.17-6.97 (m, 4H), 5.05 (m, 1H), 4.59 (s, 1H), 4.52 (s, 1H), 3.68 (m, 1H), 3.62 (s, 3H), 3.58 (m, 1H), 3.51-3.41 (m, 3H), 3.37 (s, 2H), 2.88 (t, J = 12.8 Hz, 1H), 2.73 (d, J = 36.2 Hz, 2H), 2.64-2.54 (m, 2H), 2.20 (d, J = 2.5 Hz, 6H), 2.07 (s, 2H), 2.03-1.92 (m, 3H), 1.71 (s, 2H), 1.51 (s, 2H). m/z 807.35 [M + H]+. |

TABLE 1-continued

| Cpd. No. | 1H NMR/Mass Spec(LCMS) |
|---|---|
| Cpd. 125 | 1H NMR (600 MHz, DMSO) δ 11.06 (s, 1H), 9.62 (d, J = 8.5 Hz, 1H), 8.32 (m, 1H), 8.08 (m, 1H), 7.68 (s, 1H), 7.65-7.59 (m, 2H), 7.29 (s, 1H), 7.23-7.18 (m, 1H), 7.11-7.08 (m, 4H), 5.07-5.02 (m, 1H), 4.63 (s, 1H), 4.59 (s, 1H), 4.02 (m, 2H), 3.69-3.65 (m, 2H), 3.60 (d, J = 5.4 Hz, 3H), 3.18 (s, 1H), 3.15 (s, 1H), 3.00-2.93 (m, 2H), 2.88-2.84 (m, 2H), 2.80-2.74 (m, 2H), 2.71-2.65 (m, 1H), 2.61-2.55 (m, 3H), 2.40-2.35 (m, 2H), 2.20-2.16 (m, 6H), 1.77 (d, J = 12.0 Hz, 2H), 1.27-1.23 (m, 2H). m/z 781.31 [M + H]+. |
| Cpd. 126 | 1H NMR (600 MHz, DMSO) δ 11.05 (s, 1H), 9.62 (d, J = 15.6 Hz, 1H), 8.33 (s, 1H), 8.08 (s, 1H), 7.72-7.59 (m, 3H), 7.29 (d, J = 3.8 Hz, 1H), 7.23-7.18 (m, 1H), 7.16-7.00 (m, 4H), 5.05 (dd, J = 12.8, 5.4 Hz, 1H), 4.63 (s, 1H), 4.56 (s, 1H), 4.04-4.00 (m, 2H), 3.66 (dd, J = 11.7, 5.8 Hz, 2H), 3.61 (d, J = 5.8 Hz, 3H), 2.88 (m, 3H), 2.78 (t, J = 5.6 Hz, 1H), 2.67 (t, J = 5.7 Hz, 1H), 2.61-2.51 (m, 2H), 2.43 (m, 2H), 2.18 (s, 6H), 1.99 (m, 1H), 1.77 (d, J = 12.8 Hz, 2H), 1.59-1.51 (m, 1H), 1.48 (m, 2H), 1.20-1.13 (m, 2H). m/z 795.39 [M + H]+. |
| Cpd. 127 | 1H NMR (600 MHz, DMSO) δ 11.08 (s, 1H), 9.64 (d, J = 5.8 Hz, 1H), 8.35 (s, 1H), 8.10 (s, 1H), 7.74-7.57 (m, 3H), 7.33 (d, J = 15.0 Hz, 1H), 7.28-7.21 (m, 1H), 7.10 (m, 4H), 5.06 (dd, J = 12.8, 5.3 Hz, 1H), 4.64 (s, 1H), 4.58 (s, 1H), 4.31 (d, J = 16.9 Hz, 2H), 3.82-3.75 (m, 2H), 3.72-3.65 (m, 2H), 3.62 (s, 3H), 3.28-3.19 (m, 2H), 2.91-2.86 (m, 2H), 2.84-2.77 (m, 1H), 2.74-2.68 (m, 1H), 2.63-2.57 (m, 2H), 2.20 (s, 6H), 2.02-2.00 (m, 1H), 1.97-1.94 (m, 2H), 1.58-1.49 (m, 2H). m/z 797.35 [M + H]+. |
| Cpd. 128 | 1H NMR (600 MHz, DMSO) δ 11.08 (s, 1H), 9.63 (d, J = 11.0 Hz, 1H), 8.34 (d, J = 4.3 Hz, 1H), 8.10 (s, 1H), 7.75-7.56 (m, 3H), 7.32 (s, 1H), 7.24 (d, J = 8.6 Hz, 1H), 7.18-7.00 (m, 4H), 5.06 (dd, J = 12.8, 5.4 Hz, 1H), 4.68 (s, 1H), 4.57 (s, 1H), 3.84-3.76 (m, 2H), 3.74-3.69 (m, 2H), 3.68-3.64 (m, 1H), 3.62 (d, J = 3.9 Hz, 2H), 3.26-3.19 (m, 2H), 2.93-2.84 (m, 1H), 2.80 (s, 1H), 2.66 (d, J = 18.9 Hz, 2H), 2.63-2.56 (m, 2H), 2.55-2.52 (m, 2H), 2.20 (s, 6H), 2.04-1.93 (m, 2H), 1.92-1.83 (m, 2H), 1.76-1.64 (m, 2H), 1.50-1.38 (m, 4H), 1.30-1.23 (m, 2H). m/z 865.43 [M + H]+. |
| Cpd. 129 | 1H NMR (600 MHz, DMSO) δ 11.06 (s, 1H), 9.62 (d, J = 15.2 Hz, 1H), 8.32 (d, J = 9.0 Hz, 1H), 8.08 (s, 1H), 7.68 (s, 1H), 7.65-7.58 (m, 2H), 7.30 (d, J = 6.8 Hz, 1H), 7.22-7.24 (m, 1H), 7.14-7.00 (m, 4H), 5.11 (d, J = 10.9 Hz, 1H), 5.04 (dd, J = 12.6, 5.8 Hz, 1H), 4.69 (s, 1H), 4.60 (s, 1H), 3.81-3.75 (m, 1H), 3.73-3.65 (m, 2H), 3.60 (d, J = 2.0 Hz, 3H), 2.90-2.85 (m, 2H), 2.80-2.78 (m, 1H), 2.72-2.68 (m, 2H), 2.64-2.57 (m, 3H), 2.40-2.33 (m, 2H), 2.18 (d, J = 2.9 Hz, 6H), 2.01-1.96 (m, 1H), 1.70-1.61 (m, 2H). m/z 797.32 [M + H]+. |
| Cpd. 130 | 1H NMR (600 MHz, DMSO) δ 11.05 (s, 1H), 9.51 (s, 1H), 8.30 (s, 1H), 8.06 (s, 1H), 7.62 (d, J = 8.6 Hz, 1H), 7.56 (d, J = 8.3 Hz, 1H), 7.48 (s, 1H), 7.29 (d, J = 1.9 Hz, 1H), 7.22 (dd, J = 8.7, 2.2 Hz, 1H), 7.10-7.05 (m, 3H), 6.97 (d, J = 8.4 Hz, 1H), 5.03 (dd, J = 12.8, 5.5 Hz, 1H), 4.40 (s, 1H), 3.74 (d, J = 13.0 Hz, 2H), 3.68 (s, 2H), 3.58 (s, 3H), 2.89-2.82 (m, 2H), 2.79 (d, J = 5.3 Hz, 2H), 2.71 (d, J = 5.2 Hz, 2H), 2.60-2.56 (m, 2H), 2.54 (m, 1H), 2.52-2.50 (m, 1H), 2.45 (s, 1H), 2.17 (s, 6H), 2.00-1.96 (m, 1H), 1.65-1.54 (m, 4H). m/z 796.47 [M + H]+. |
| Cpd. 131 | 1H NMR (600 MHz, DMSO) δ 11.08 (s, 1H), 9.56 (s, 1H), 8.33 (s, 1H), 8.09 (s, 1H), 7.65 (d, J = 8.6 Hz, 1H), 7.60-7.53 (m, 2H), 7.32 (s, 1H), 7.24 (dd, J = 8.7, 2.2 Hz, 1H), 7.10 (m, 3H), 7.02 (d, J = 8.1 Hz, 1H), 5.06 (dd, J = 12.8, 5.5 Hz, 1H), 3.78 (d, J = 12.9 Hz, 2H), 3.61 (s, 3H), 3.57 (s, 2H), 3.31-3.26 (m, 2H), 2.95-2.82 (m, 2H), 2.74 (s, 2H), 2.65-2.60 (m, 3H), 2.63-2.59 (m, 2H), 2.57 (m, 2H), 2.40-2.37 (m, 1H), 2.20 (s, 6H), 2.04-2.00 (m, 1H), 1.72-1.54 (m, 4H). m/z 783.34 [M + H]+ |
| Cpd. 132 | 1H NMR (600 MHz, DMSO) δ 10.94 (s, 1H), 9.55 (s, 1H), 8.33 (s, 1H), 8.08 (s, 1H), 7.73 (d, J = 8.9 Hz, 1H), 7.57 (d, J = 8.3 Hz, 1H), 7.54 (s, 1H), 7.14-7.06 (m, 3H), 7.01 (d, J = 8.5 Hz, 1H), 6.90 (d, J = 9.0 Hz, 1H), 5.06 (dd, J = 13.3, 5.1 Hz, 1H), 4.44 (d, J = 12.3 Hz, 1H), 4.26 (d, J = 17.3 Hz, 1H), 4.08 (d, J = 17.3 Hz, 1H), 3.60 (s, 3H), 3.53 (s, 2H), 3.02-2.95 (m, 2H), 2.94-2.86 (m, 2H), 2.85-2.73 (m, 2H), 2.66-2.62 (m, 2H), 2.59-2.57 (d, J = 15.2 Hz, 2H), 2.37 (m, 1H), 2.35-2.32 (d, J = 7.1 Hz, 1H), 2.19 (s, 6H), 1.98-1.94 (m, 1H), 1.89 (s, 2H), 1.83 (d, J = 10.6 Hz, 2H). m/z 740.42 [M + H]+. |
| Cpd. 133 | 1H NMR (600 MHz, DMSO) δ 10.94 (s, 1H), 9.54 (s, 1H), 8.32 (s, 1H), 8.08 (s, 1H), 7.72 (d, J = 8.9 Hz, 1H), 7.57 (d, J = 8.3 Hz, 1H), 7.50 (s, 1H), 7.12-7.07 (m, 3H), 6.99 (d, J = 8.4 Hz, 1H), 6.90 (d, J = 9.0 Hz, 1H), 5.05 (dd, J = 13.3, 5.1 Hz, 2H), 4.40 (s, 1H), 4.24 (d, J = 17.3 Hz, 1H), 4.11-4.09 (m, 2H), 3.69 (s, 2H), 3.60 (s, 3H), 2.94-2.84 (m, 2H), 2.81 (m, 2H), 2.73 (m, 2H), 2.61 (d, J = 1.8 Hz, 1H), 2.59-2.53 (m, 1H), 2.46 (s, 2H), 2.39-2.31 (m, 1H), 2.19 (s, 6H), 1.97-1.93 (m, 1H), 1.59 (s, 4H). m/z 756.38 [M + H]+. |
| Cpd. 134 | 1H NMR (600 MHz, CDCl3) δ 8.42 (s, 1H), 8.29 (s, 1H), 7.85 (dd, J = 9.0, 2.6 Hz, 1H), 7.67 (d, J = 8.5 Hz, 1H), 7.40 (s, 1H), 7.29 (d, J = 2.3 Hz, 1H), 7.17-7.12 (m, 3H), 7.06-7.03 (m, 1H), 6.94 (s, 1H), 6.67 (d, J = 9.1 Hz, 1H), 5.85 (s, 1H), 4.94 (m, 1H), 3.96 (d, J = 13.1 Hz, 2H), 3.77 |

TABLE 1-continued

| Cpd. No. | 1H NMR/Mass Spec(LCMS) |
|---|---|
| | (s, 3H), 3.50 (m, 4H), 2.99 (m, 2H), 2.92-2.79 (m, 3H), 2.76-2.69 (m, 2H), 2.57-2.50 (m, 4H), 2.26 (s, 6H), 2.13 (m,1H), 1.93 (d, J = 12.7 Hz, 2H), 1.85 (s, 1H), 1.34-1.27 (m, 2H). m/z 783.53 [M + H]+. |
| Cpd. 135 | 1H NMR (600 MHz, CDCl3) δ 8.42 (s, 1H), 8.23 (d, J = 14.0 Hz, 1H), 7.74 (d, J = 7.4 Hz, 1H), 7.71 (d, J = 8.5 Hz, 1H), 7.38 (s, 1H), 7.30 (d, J = 2.2 Hz, 1H), 7.18-7.12 (m, 3H), 7.09-7.06 (m, 1H), 6.95 (s, 1H), 6.39 (d, J = 9.5 Hz, 1H), 5.86 (s, 1H), 4.94 (m, 1H), 3.76 (s, 3H), 3.64 (s, 4H), 3.57 (m, 2H), 3.46 (m, 4H), 3.12 (m, 1H), 2.90 (m, 1H), 2.84-2.79 (m, 2H), 2.77-2.71 (m, 2H), 2.67 (s, 2H), 2.55 (s, 2H), 2.26 (s, 6H), 2.16-2.12 (m, 1H), 1.73 (m, 2H). m/z 783.45 [M + H]+. |
| Cpd. 136 | 1H NMR (600 MHz, CDCl3) δ 8.47 (s, 1H), 7.68 (d, J = 8.5 Hz, 1H), 7.44 (s, 2H), 7.29 (s, 1H), 7.24 (s, 1H), 7.22-7.19 (m, 1H), 7.18-7.12 (m, 3H), 7.12-7.08 (m, 1H), 7.05 (d, J = 8.5 Hz, 1H), 6.63 (d, J = 8.0 Hz, 1H), 5.89 (s, 1H), 4.94 (m, 1H), 3.97 (d, J = 12.8 Hz, 2H), 3.81 (s, 3H), 3.23 (s, 4H), 2.98 (m, 2H), 2.84 (m, 3H), 2.77-2.69 (m, 2H), 2.58 (s, 4H), 2.27 (s, 6H), 2.16-2.09 (m, 1H), 1.91 (d, J = 13.2 Hz, 2H), 1.84 (s, 1H), 1.32 (m, 2H). m/z 782.49 [M + H]+. |
| Cpd. 137 | 1H NMR (600 MHz, DMSO) δ 10.84 (s, 1H), 9.55 (s, 1H), 8.62 (d, J = 8.2 Hz, 1H), 8.33 (s, 1H), 8.08 (s, 1H), 7.91 (d, J = 2.8 Hz, 1H), 7.83 (d, J = 8.7 Hz, 1H), 7.59-7.52 (m, 2H), 7.09 (m, 3H), 7.03-6.94 (m, 2H), 4.76-4.70 (m, 1H), 3.67-3.58 (s, 3H), 3.57 (d, J = 10.4 Hz, 1H), 3.51-3.44 (m, 2H), 3.44-3.40 (m, 2H), 3.37 (m, 3H), 3.03-2.99 (m, 1H), 2.82-2.73 (m, 2H), 2.70-2.64 (m, 2H), 2.62-2.59 (m, 1H), 2.57-2.53 (m, 2H), 2.40-2.34 (m, 1H), 2.22-2.13 (s, 6H), 2.05-1.97 (m, 1H), 1.78-1.65 (m, 3H). m/z 728.52 [M + H]+. |
| Cpd. 138 | 1H NMR (600 MHz, CDCl3) δ 7.65 (d, J = 12.0 Hz, 1H), 7.53 (d, J = 6.0 Hz, 1H), 7.45 (s, 1H), 7.29 (s, 1H), 7.19-7.15 (m, 3H), 7.05 (d, J = 6.0 Hz, 1H), 6.80 (d, J = 1.8 Hz, 1H), 6.51 (dd, J = 8.4, 1.8 Hz, 1H), 5.90 (s, 1 H), 4.94 (dd, J = 12.0, 6.0 Hz, 1H), 4.19-4.16 (m, 2H), 3.79 (s, 2H), 3.72(s, 3H), 3.74-3.71 (m, 2H), 3.05-3.00 (m, 2 H), 2.95 (d, J = 10.8 Hz, 2H), 2.91-2.90 (m, 1H), 2.87- 2.81 (m, 4H), 2.75-2.72 (m, 2H), 2.65 (d, J = 12.0 Hz, 2H), 2.55 (t, J = 10.8 Hz, 2H), 2.27 (s, 6H), 2.14-2.07 (m, 3H), 1.87 (d, J = 12.0 Hz, 2H). m/z 404.89 [M + 2H]2+. |
| Cpd. 139 | 1H NMR (600 MHz, CDCl3) δ 8.66 (brs, 1H), 7.67 (d, J = 12.0 Hz, 1H), 7.46 (d, J = 8.4 Hz, 1H), 7.43 (s, 1H), 7.37 (s, 1H), 7.33 (d, J = 1.8 Hz, 1H), 7.28 (d, J = 1.8 Hz, 1H), 7.18-7.15 (m, 3H), 7.06-7.03 (m, 2H), 5.93 (s, 1H), 4.94 (dd, J = 12.6, 5.4 Hz, 1H), 3.96 (d, J = 12.6 Hz, 2H), 3.80 (s, 2H), 3.78 (s, 1H), 3.74 (s, 1H), 2.99 (d, J = 12.0 Hz, 2H), 2.96-2.93 (m, 2H), 2.91 (t, J = 3.0 Hz, 1H), 2.88-2.87 (m, 1H), 2.85 (s, 3H), 2.81 (dd, J = 12.6, 4.2 Hz, 1H), 2.76-2.70 (m, 2H), 2.52-2.47 (m, 1H), 2.27 (s, 6H), 2.21 (d, J = 6.6 Hz, 2H), 2.15-2.11 (m, 1H), 2.0 (t, J = 11.4 Hz, 2H), 1.86 (d, J = 12.0 Hz, 4H), 1.72-1.66 (m, 2H), 1.34-1.28 (m, 3H). m/z 418.83 [M + 2H]2+. |
| Cpd. 140 | 1H NMR (600 MHz, CDCl3) δ 7.67 (d, J = 8.4 Hz, 1H), 7.47 (s, 1H), 7.41 (s, 1H), 7.38 (s, 1H), 7.33 (d, J = 1.8 Hz, 1H), 7.20 (s, 1H), 7.15 (s, 2H), 7.08-7.03 (m, 3H), 6.27 (s, 1H), 6.00 (s, 1H), 4.94 (dd, J = 12.6, 5.4 Hz, 1H), 3.97 (d, J = 13.2 Hz, 1H), 3.88 (d, J = 13.2 Hz, 1H), 3.84-3.80 (m, 4H), 3.71-3.68 (m, 1H), 3.14-3.10 (m, 1H), 3.07-3.02 (m, 2H), 2.87 (s, 3H), 2.77-2.70 (m, 2H), 2.59-2.49 (m, 3H), 2.29 (d, J = 4..2 Hz, 6H), 2.17-2.10 (m, 3H), 2.06 (t, J = 10.5 Hz, 2H), 1.90-1.75 (m, 8H), 1.2-1.18 (m, 2H). m/z 418.99 [M + 2H]2+. |
| Cpd. 141 | 1H NMR (600 MHz, CDCl3) δ 7.67 (d, J = 9.0 Hz, 1H), 7.47 (s, 1H), 7.41 (s, 1H), 7.36 (dd, J = 8.4, 1.8 Hz 1H), 7.33 (d, J = 2.4 Hz, 1H), 7.21-7.18 (m, 1H), 7.15 (s, 2H), 7.09-7.03 (m, 3H), 6.27 (s, 1H), 6.01 (s, 1H), 4.94 (dd, J = 12.6, 5.4 Hz, 1H), 3.96 (d, J = 11.4 Hz, 1H), 3.89 (d, J = 13.8 Hz, 1H), 3.81 (s, 4H), 3.74-3.68 (m, 1H), 3.12 (t, J = 12.0 Hz, 1H), 3.06-3.01 (m, 2H), 2.88 (s, 3H), 2.77-2.70 (m, 2H), 2.57-2.52 (m, 3H), 2.29 (s, 6H), 2.16-2.12 (m, 3H), 2.06 (t, J = 10.5 Hz, 2H), 1.88-1.73 (m, 8H), 1.25-1.22 (m, 2H). m/z 418.97 [M + 2H]2+. |
| Cpd. 142 | 1H NMR (600 MHz, CDCl3) δz 7.66 (dd, J = 8.4, 1.2 Hz, 1H), 7.58 (s, 1H), 7.47 (s, 1H), 7.39 (d, J = 16.2 Hz, 1H), 7.33 (d, J = 8.4 Hz, 1H), 7.17-7.14 (m, 3H), 7.04 (dd, J = 8.4, 3.6 Hz, 1H), 6.99 (d, J = 1.8 Hz, 1H), 6.68 (dd, J = 8.4,1.8 Hz, 1H), 6.17 (s, 1H), 6.05 (s, 1H), 4.95-4.92 (m, 1H), 3.80 (s, 4H), 3.59 (t, J = 8.7 Hz, 1H), 3.53-3.49 (m, 1H), 3.46-3.40 (m, 2H), 3.20 (dd, J = 9.6, 7.2 Hz, 1H), 3.05- 3.03 (m, 1H), 2.95 (d, J = 8.4 Hz, 1H), 2.92-2.90 (m, 1H), 2.86 (s, 3H), 2.84-2.80 (m, 1H), 2.76-2.73 (m, 1H), 2.65-2.58 (m, 1H), 2.56-2.51 (m, 1H), 2.45 (dd, J = 12.0, 5.4 Hz, 1H), 2.39-2.34 (m, 2H), 2.27 (s, 6H), 2.23-2.19 (m, 1H), 2.17-2.14 (m, 1H), .2.09 (d, J = 11.4 Hz, 1H), 2.00-1.93 (m, 2H), 1.87-1.80 (m, 2H), 1.76-1.68 (m, 2H). m/z 411.93 [M + 2H]2+. |
| Cpd. 143 | 1H NMR (600 MHz, CDCl3) δ 7.66 (dd, J = 8.4, 1.8 Hz, 1H), 7.59 (s, 1H), 7.47 (s, 1H), 7.38 (d, J = 16.2 Hz, 1H), 7.21 (s, 1H), 7.18-7.14 (m, 3H), 7.04 (dd, J = 7.8, 3.6 Hz, 1H), 6.99 (d, J = 2.4 Hz, 1H), 6.68 (dd, J = 8.4, 2.4 Hz, 1H), 6.19 (s, 1H), 6.06 (s, 1H), 4.96-4.92 (m, 1H), 3.80 (s, 3H), 3.75 (s, 1H), 3.59 (dd, J = 10.2, 7.2 Hz, 1H), 3.53-3.49 (m, 1H), 3.46-3.39 (m, 2H), 3.20 (dd, J = 10.2, 7.8 Hz, 1H), 3.06- 3.02 (m, 1H), 2.94 (d, J = 12.6 Hz, 1H), 2.87 (s, 3H), 2.84-2.79 (m, 1H), 2.76-2.72 (m, 1H), 2.64-2.58 (m, 1H), 2.57-2.52 (m, 1H), 2.45 (dd, J = 12.0, 6.0 Hz, |

| Cpd. No. | 1H NMR/Mass Spec(LCMS) |
| --- | --- |
| | 1H), 2.38-2.34 (m, 2H), 2.28 (s, 6H), 2.23-2.20 (m, 1H), 2.17-2.14 (m, 1H), 2.16-2.08 (m, 1H), 2.00-1.93 (m, 2H), 1.87-1.81 (m, 3H), 1.78-1.72 (m, 2H). m/z 411.98 [M + 2H]2+. |
| Cpd. 144 | 1H NMR (600 MHz, CDCl3) δ 8.28 (s, 1H), 8.09 (s, 1H), 7.67 (d, J = 8.4 Hz, 1H), 7.47 (s, 1H), 7.43 (d, J = 7.2 Hz, 1H), 7.39 (s, 1H), 7.34 (s, 1H), 7.19 (m, 3H), 7.10 (d, J = 8.0 Hz, 1H), 6.98 (s, 1H), 6.71 (d, J = 8.5 Hz, 1H), 5.86 (s, 1H), 4.95 (m, 1H), 3.81 (s, 3H), 3.73-3.68 (m, 2H), 3.62 (m, 2H), 3.53 (m, 1H), 3.48-3.43 (m, 1H), 3.33-3.25 (m, 2H), 2.89 (m, 2H), 2.84-2.81 (m, 1H), 2.77 (m, 1H), 2.72 (m, 1H), 2.62 (m, 1H), 2.56 (m, 1H), 2.27 (s, 6H), 2.16-2.12 (m, 1H), 1.90 (m, 2H). m/z 739.43 [M + H]+. |
| Cpd. 145 | 1H NMR (600 MHz, CDCl3) δ 8.25 (s, 1H), 8.06 (s, 1H), 7.66-7.61 (m, 1H), 7.46 (d, J = 8.3 Hz, 1H), 7.43-7.40 (m, 1H), 7.37 (s, 1H), 7.33 (s, 1H), 7.16 (m, 3H), 7.09-7.05 (m, 1H), 6.97-6.93 (m, 1H), 6.69 (dd, J = 8.5, 2.1 Hz, 1H), 5.85 (s, 1H), 4.93 (m, 1H), 3.79 (s, 3H), 3.72-3.55 (m, 4H), 3.54-3.48 (m, 1H), 3.44 (m, 1H), 3.31-3.22 (m, 2H), 2.88 (m, 2H), 2.80 (m, 1H), 2.77-2.71 (m, 2H), 2.62 (m, 2H), 2.26 (s, 6H), 2.13 (m, 1H), 1.89 (m, 2H). m/z 739.45 [M + H]+. |
| Cpd. 146 | 1H NMR (600 MHz, CDCl3) δ 8.40 (s, 1H), 7.67 (d, J = 8.5 Hz, 1H), 7.44 (d, J = 2.0 Hz, 1H), 7.43 (d, J = 3.7 Hz, 1H), 7.33 (d, J = 1.6 Hz, 1H), 7.27 (d, J = 2.3 Hz, 1H), 7.17 (t, J = 4.7 Hz, 1H), 7.16-7.12 (m, 3H), 7.06 (d, J = 8.3 Hz, 1H), 7.03 (dd, J = 8.6, 2.3 Hz, 1H), 5.88 (s, 1H), 4.94 (m, 1H), 3.94 (d, J = 12.8 Hz, 2H), 3.79 (s, 3H), 3.62 (s, 2H), 2.98 (t, J = 12.2 Hz, 2H), 2.91-2.89 (m, 1H), 2.89-2.86 (m, 2H), 2.84-2.78 (m, 2H), 2.76-2.72 (m, 3H), 2.58-2.55 (m, 2H), 2.27 (s, 6H), 2.13 (m, 1H), 1.85 (d, J = 12.1 Hz, 2H), 1.68 (m, 2H), 1.35 (m, 2H). m/z 767.48 [M + H]+. |
| Cpd. 147 | 1H NMR (600 MHz, CDCl3) δ 8.18 (s, 1H), 7.63 (d, J = 8.3 Hz, 1H), 7.42-7.39 (m, 2H), 7.33 (d, J = 2.0 Hz, 1H), 7.18-7.14 (m, 3H), 7.09 (d, J = 5.4 Hz, 1H), 7.06 (d, J = 8.3 Hz, 1H), 6.78 (d, J = 2.1 Hz, 1H), 6.52 (dd, J = 8.3, 2.1 Hz, 1H), 5.86 (s, 1H), 4.93 (m, 1H), 4.10 (t, J = 7.5 Hz, 2H), 3.89 (dd, J = 8.2, 5.4 Hz, 2H), 3.79 (s, 3H), 3.60 (s, 2H), 3.36-3.32 (m, 1H), 2.91-2.87 (m, 2H), 2.85 (m, 2H), 2.79 (m, 1H), 2.75 (d, J = 5.0 Hz, 1H), 2.70 (m, 2H), 2.37 (d, J = 7.2 Hz, 2H), 2.26 (s, 6H), 2.12 (m, 1H), 1.94-1.86 (m, 4H), 1.66 (m, 2H), 1.32-1.28 (m, 2H). m/z 808.49 [M + H]+. |
| Cpd. 148 | 1H NMR (600 MHz, CDCl3) δ 8.81 (s, 1H), 7.64 (d, J = 8.4 Hz, 1H), 7.47 (dd, J = 8.3, 2.0 Hz, 1H), 7.43 (s, 1H), 7.32 (d, J = 2.0 Hz, 1H), 7.23 (s, 1H), 7.17-7.11 (m, 3H), 7.06 (d, J = 8.3 Hz, 1H), 6.95 (d, J = 2.2 Hz, 1H), 6.67 (dd, J = 8.5, 2.2 Hz, 1H), 5.95 (s, 1H), 4.92 (m, 1H), 3.78 (s, 3H), 3.71 (s, 2H), 3.66 (dd, J = 9.8, 2.2 Hz, 2H), 3.52-3.48 (m, 2H), 2.89 (m, 2H), 2.86 (m, 1H), 2.84-2.77 (m, 3H), 2.75-2.68 (m, 1H), 2.58-2.50 (m, 2H), 2.26 (s, 6H), 2.14-2.09 (m, 1H), 1.71 (s, 2H), 0.97 (m, 1H). m/z 751.48 [M + H]+. |
| Cpd. 149 | 1H NMR (600 MHz, CDCl3) δ 8.59 (s, 1H), 7.67 (d, J = 8.5 Hz, 1H), 7.43-7.39 (m, 2H), 7.33 (d, J = 2.0 Hz, 1H), 7.27 (d, J = 2.5 Hz, 1H), 7.18-7.10 (m, 4H), 7.07-7.00 (m, 2H), 5.91 (s, 1H), 4.93 (m, 1H), 3.94 (d, J = 12.9 Hz, 2H), 3.79 (s, 3H), 3.66-3.62 (m, 2H), 3.48 (d, J = 5.5 Hz, 2H), 3.19-3.13 (m, 1H), 3.02-2.97 (m, 2H), 2.96-2.92 (m, 2H), 2.91-2.89 (m, 1H), 2.87-2.83 (m, 2H), 2.82-2.79 (m, 1H), 2.76-2.68 (m, 2H), 2.58 (t, J = 5.9 Hz, 2H), 2.44 (d, J = 6.8 Hz, 2H), 2.25 (s, 6H), 2.14-2.10 (m, 1H), 1.83 (d, J = 12.8 Hz, 2H), 1.34-1.27 (m, 2H). m/z 808.54 [M + H]+. |
| Cpd. 150 | 1H NMR (600 MHz, CDCl3) δ 9.04 (s, 1H), 7.65 (dd, J = 8.4, 1.5 Hz, 1H), 7.53 (dd, J = 16.9, 7.9 Hz, 1H), 7.46 (d, J = 2.3 Hz, 1H), 7.44-7.35 (m, 1H), 7.28-7.26 (m, 1H), 7.18-7.13 (m, 3H), 7.05 (d, J = 8.4 Hz, 1H), 6.95 (t, J = 2.1 Hz, 1H), 6.69-6.65 (m, 1H), 5.89 (d, J = 6.2 Hz, 1H), 4.95-4.91 (m, 1H), 3.79 (s, 3H), 3.69-3.60 (m, 2H), 3.55 (dd, J = 10.1, 7.3 Hz, 1H), 3.50-3.45 (m, 1H), 3.43-3.36 (m, 3H), 3.23-3.11 (m, 2H), 2.99 (m, 2H), 2.93-2.78 (m, 5H), 2.76-2.69 (m, 1H), 2.65-2.52 (m, 4H), 2.45 (m, 1H), 2.27 (s, 6H), 2.23-2.18 (m, 1H), 2.16-2.11 (m, 1H). m/z 794.35 [M + H]+. |
| Cpd. 151 | 1H NMR (600 MHz, CDCl3) δ 9.12 (s, 1H), 7.65 (dd, J = 8.4, 1.0 Hz, 1H), 7.53 (dd, J = 15.4, 8.7 Hz, 1H), 7.46 (d, J = 2.3 Hz, 1H), 7.44-7.40 (m, 1H), 7.28 (s, 1H), 7.20-7.12 (m, 3H), 7.05 (d, J = 8.4 Hz, 1H), 6.95 (t, J = 2.0 Hz, 1H), 6.68 (d, J = 8.5 Hz, 1H), 5.92 (d, J = 5.9 Hz, 1H), 4.93 (m, 1H), 3.79 (s, 3H), 3.65 (m, 2H), 3.55 (dd, J = 10.0, 7.3 Hz, 1H), 3.48 (m, 1H), 3.43-3.37 (m, 3H), 3.22-3.12 (m, 2H), 3.00 (m, 2H), 2.91-2.80 (m, 5H), 2.75-2.69 (m, 1H), 2.61-2.51 (m, 4H), 2.45 (m, 1H), 2.27 (s, 6H), 2.23-2.17 (m, 1H), 2.13 (dd, J = 9.0, 3.7 Hz, 1H). m/z 794.38 [M + H]+. |
| Cpd. 152 | 1H NMR (400 MHz, CDCl3) δ 9.59 (s, 1H), 7.62 (d, J = 8.3 Hz, 1H), 7.44 (dd, J = 8.2, 1.9 Hz, 1H), 7.40 (s, 1H), 7.32 (s, 2H), 7.14 (m, 3H), 7.04 (d, J = 8.3 Hz, 1H), 6.85 (d, J = 1.7 Hz, 1H), 6.46 (dd, J = 8.3, 2.0 Hz, 1H), 5.93 (s, 1H), 4.89 (m, 1H), 4.08 (m, 2H), 3.78 (s, 3H), 3.70 (m, 2H), 3.65 (m, 1H), 3.45 (s, 2H), 3.13 (m, 1H), 3.05 (m, 2H), 2.94-2.71 (m, 8H), 2.65 (m, 1H), 2.56 (t, J = 5.9 Hz, 2H), 2.25 (s, 6H), 2.14-2.09 (m, 1H). m/z 780.33 [M + H]+. |

| Cpd. No. | 1H NMR/Mass Spec(LCMS) |
| --- | --- |
| Cpd. 153 | 1H NMR (600 MHz, CDCl3) δ 8.46 (s, 1H), 7.64 (d, J = 8.4 Hz, 1H), 7.43 (d, J = 8.8 Hz, 1H), 7.38 (s, 1H), 7.35 (d, J = 2.0 Hz, 1H), 7.30 (s, 1H), 7.18-7.15 (m, 3H), 7.06 (d, J = 8.3 Hz, 1H), 6.93 (d, J = 2.2 Hz, 1H), 6.66 (dd, J = 8.5, 2.2 Hz, 1H), 5.92 (s, 1H), 4.93 (m, 1H), 3.79 (s, 3H), 3.62 (dd, J = 9.8, 2.7 Hz, 2H), 3.49-3.46 (m, 4H), 3.23 (s, 1H), 3.08 (s, 2H), 2.90 (dd, J = 4.0, 2.6 Hz, 1H), 2.86 (m, 4H), 2.82-2.78 (m, 1H), 2.76-2.69 (m, 1H), 2.58 (t, J = 5.9 Hz, 2H), 2.55 (s, 2H), 2.26 (s, 6H), 2.14-2.11 (m, 1H), 1.67 (s, 2H), 0.81-0.78 (m, 1H). m/z 806.38 [M + H]+. |
| Cpd. 154 | 1H NMR (600 MHz, CDCl3) δ 8.43 (s, 1H), 8.37 (s, 1H), 7.85 (dd, J = 9.0, 2.6 Hz, 1H), 7.66 (d, J = 8.4 Hz, 1H), 7.40 (s, 1H), 7.19-7.08 (m, 3H), 7.02 (s, 1H), 6.97 (d, J = 2.1 Hz, 1H), 6.71-6.66 (m, 2H), 5.87 (s, 1H), 4.94 (m, 1H), 3.80-3.71 (m, 3H), 3.55-3.49 (m, 4H), 3.47 (d, J = 22.3 Hz, 3H), 3.23 (dd, J = 9.6, 7.3 Hz, 1H), 2.96-2.79 (m, 3H), 2.76-2.66 (m, 2H), 2.65-2.60 (m, 2H), 2.58-2.52 (m, 2H), 2.45 (m, 2H), 2.34-2.20 (m, 6H), 2.13 (m, 1H), 1.90-1.83 (m, 1H). m/z 769.44 [M + H]+. |
| Cpd. 155 | 1H NMR (600 MHz, CDCl3) δ 8.43 (s, 1H), 8.14 (s, 1H), 7.85 (d, J = 9.0, 1H), 7.66 (dd, J = 8.4, 2.4 Hz, 1H), 7.39 (d, J = 2.3 Hz, 1H), 7.15 (s, 3H), 6.96 (d, J = 11.7 Hz, 2H), 6.73-6.66 (m, 2H), 5.85 (s, 1H), 4.94 (m, 1H), 3.76 (s, 3H), 3.52 (m, 4H), 3.50 (s, 3H), 3.25-3.20 (m, 1H), 2.86 (m, 3H), 2.77-2.68 (m, 2H), 2.63 (s, 2H), 2.57 (s, 2H), 2.50-2.42 (m, 2H), 2.27 (d, J = 2.1 Hz, 6H), 2.17-2.10 (m, 1H), 1.90-1.83 (m, 1H). m/z 769.43 [M + H]+. |
| Cpd. 156 | 1H NMR (600 MHz, CDCl3) δ 8.43 (s, 1H), 8.21 (s, 1H), 7.88-7.82 (m, 1H), 7.68 (d, J = 8.5 Hz, 1H), 7.38 (s, 1H), 7.29 (d, J = 2.1 Hz, 1H), 7.17-7.11 (m, 3H), 7.06 (dd, J = 8.6, 2.2 Hz, 1H), 6.97 (s, 1H), 6.68 (d, J = 9.1 Hz, 1H), 5.85 (s, 1H), 4.94 (m, 1H), 4.01 (d, J = 13.0 Hz, 2H), 3.76 (s, 3H), 3.51 (s, 4H), 3.02 (t, J = 11.6 Hz, 2H), 2.89 (dd, J = 16.8, 2.8 Hz, 1H), 2.84-2.79 (m, 2H), 2.76 (d, J = 5.2 Hz, 1H), 2.74-2.67 (m, 4H), 2.58 (s, 2H), 2.27 (s, 6H), 2.15-2.11 (m, 1H), 2.01 (m, 2H). m/z 769.45 [M + H]+. |
| Cpd. 157 | 1H NMR (600 MHz, CDCl3) δ 8.42 (d, J = 7.3 Hz, 2H), 7.84 (dd, J = 9.0, 2.7 Hz, 1H), 7.67 (d, J = 8.5 Hz, 1H), 7.39 (d, J = 2.9 Hz, 1H), 7.29-7.26 (m, 1H), 7.18-7.11 (m, 3H), 7.04 (dd, J = 8.6, 2.4 Hz, 1H), 6.98 (s, 1H), 6.68 (d, J = 9.1 Hz, 1H), 5.87 (m, 1H), 4.94 (m, 1H), 3.94 (d, J = 13.1 Hz, 2H), 3.75 (d, J = 9.9 Hz, 3H), 3.54-3.47 (m, 4H), 2.98 (m, 2H), 2.92-2.85 (m, 1H), 2.82 (m, 1H), 2.76-2.69 (m, 1H), 2.60-2.52 (m, 4H), 2.49-2.41 (m, 2H), 2.26 (s, 6H), 2.15-2.09 (m, 1H), 1.84 (d, J = 11.3 Hz, 2H), 1.65-1.61 (m, 1H), 1.53 (dd, J = 15.1, 7.0 Hz, 2H), 1.34 (m, 2H). m/z 797.47 [M + H]+. |
| Cpd. 158 | 1H NMR (600 MHz, CDCl3) δ 8.44 (s, 1H), 8.31 (s, 1H), 7.87 (d, J = 6.7 Hz, 1H), 7.66 (d, J = 7.6 Hz, 1H), 7.40 (d, J = 4.5 Hz, 1H), 7.15 (s, 3H), 6.98 (s, 1H), 6.81 (s, 1H), 6.69 (d, J = 8.0 Hz, 1H), 6.55 (d, J = 7.4 Hz, 1H), 5.86 (s, 1H), 4.96-4.90 (m, 1H), 4.14 (s, 2H), 3.96 (d, J = 5.2 Hz, 2H), 3.77 (d, J = 3.1 Hz, 3H), 3.56 (s, 4H), 3.44 (s, 1H), 2.89 (d, J = 16.8 Hz, 1H), 2.85-2.78 (m, 1H), 2.77-2.69 (m, 1H), 2.61 (dd, J = 15.4, 14.0 Hz, 4H), 2.27 (s, 6H), 2.15 (s, 1H). m/z 741.45 [M + H]+. |
| Cpd. 159 | 1H NMR (600 MHz, CDCl3) δ 8.48 (s, 1H), 8.43 (s, 1H), 7.86 (dd, J = 9.0, 2.7 Hz, 1H), 7.65 (d, J = 8.3 Hz, 1H), 7.40 (s, 1H), 7.19-7.11 (m, 3H), 7.02 (s, 1H), 6.80 (d, J = 2.1 Hz, 1H), 6.68 (d, J = 9.1 Hz, 1H), 6.51 (dd, J = 8.3, 2.1 Hz, 1H), 5.88 (s, 1H), 4.93 (m, 1H), 4.17 (t, J = 8.0 Hz, 2H), 3.76 (s, 3H), 3.74 (m, 2H), 3.54-3.47 (m, 4H), 3.11-3.05 (m, 1H), 2.91-2.86 (m, 1H), 2.84-2.78 (m, 1H), 2.76-2.69 (m, 3H), 2.64-2.55 (m, 4H), 2.26 (s, 6H), 2.15-2.10 (m, 1H). m/z 755.41 [M + H]+. |
| Cpd. 160 | 1H NMR (600 MHz, CDCl3) δ 8.84 (d, J = 21.0 Hz, 1H), 8.45 (s, 1H), 7.58 (d, J = 9.0 Hz 1H), 7.66 (d, J = 8.4 Hz, 1H), 7.42 (d, J = 3.0 Hz, 1H), 7.30 (d, J = 1.8 Hz, 1H), 7.17-7.11 (m, 3H), 7.06 (dd, J = 8.4, 1.8 Hz, 1H), 6.68 (d, J = 9.0 Hz, 1H), 5.97 (s, 1H), 4.93 (dd, J = 12.6, 6.0 Hz, 1H), 3.93 (t, J = 8.7 Hz, 1H), 3.76 (s, 3H), 3.56-3.50 (m, 4H), 3.16-3.11 (m, 1H), 2.34-2.89 (m, 1H), 2.88-2.87 (m, 1H), 2.84-2.81 (m, 1H), 2.72 (m, 1H), 2.64-2.60 (m, 2H), 2.48-2.45 (m, 2H), 2.36-2.32 (m, 1H), 2.26 (s, 6H), 2.23 (dd, J = 12.6, 5.4 Hz, 1H), 2.14-2.10 (m, 1H), 1.95-1.89 (m, 2H), 1.81-1.78 (m, 1H), 1.67-1.61 (m, 3H). m/z 783.48 [M + H]+. |
| Cpd. 161 | 1H NMR (600 MHz, CDCl3) δ 8.50 (d, J = 15.6 Hz, 1H), 8.43 (s, 1H), 7.84 (d, J = 9.0 Hz, 1H), 7.66 (d, J = 9.0 Hz, 1H), 7.41 (s, 1H), 7.30 (s, 1H), 7.17-7.13 (m, 3H), 7.06 (d, J = 6.0 Hz, 1H), 6.68 (d, J = 9.0 Hz, 1H), 5.90 (s, 1H), 4.93 (dd, J = 12.6, 5.4 Hz, 1H), 3.92 (s, 1H), 3.77 (s, 3H), 3.56-3.49 (m, 4H), 3.13 (t, J = 11.7 Hz, 1H), 2.94-2.87 (m, 2H), 2.82 (t, J = 12.6 Hz, 1H), 2.76-2.70 (m, 1H), 2.65-2.57 (m, 2H), .2.49-2.42 (m, 2H), 2.34 (t, J = 10.5 Hz, 1H), 2.26 (s, 6H), 2.16-2.10 (m, 1H), 1.95-1.89 (m, 2H), 1.81-1.75 (m, 1H), 1.67-1.62 (m, 1H), 1.58 (s, 3H). m/z 392.34 [M + 2H]2+. |
| Cpd. 162 | 1H NMR (600 MHz, CDCl3) δ 8.55 (s, 1H), 8.37 (s, 1H), 8.01-7.94 (m, 2H), 7.68 (d, J = 8.5 Hz, 1H), 7.45 (s, 1H), 7.36-7.32 (m, 1H), 7.28 (s, 1H), 7.18-7.09 (m, 3H), 7.07-7.03 (m, 1H), 5.88 (s, 1H), 4.92 (m, 1H), 3.96 (d, J = 12.7 Hz, 2H), 3.83 (s, 3H), 3.16 (s, 4H), 3.01-2.94 (m, |

TABLE 1-continued

| Cpd. No. | 1H NMR/Mass Spec(LCMS) |
|---|---|
| | 2H), 2.88 (m, 2H), 2.82 (m, 1H), 2.77-2.71 (m, 2H), 2.60 (s, 4H), 2.27 (s, 6H), 2.12 (m, 1H), 1.92 (m, 2H), 1.83 (s, 1H), 1.30 (d, J = 14.5 Hz, 2H). m/z 783.46 [M + H]+. |
| Cpd. 163 | 1H NMR (600 MHz, CDCl3) δ 8.23 (s, 1H), 7.70 (d, J = 8.5 Hz, 1H), 7.55 (d, J = 8.9 Hz, 2H), 7.42 (s, 1H), 7.31 (d, J = 2.3 Hz, 1H), 7.19-7.14 (m, 3H), 7.07 (dd, J = 8.7, 2.3 Hz, 2H), 6.95 (d, J = 9.0 Hz, 2H), 5.87 (s, 1H), 5.00-4.95 (m, 1H), 3.98 (d, J = 12.9 Hz, 2H), 3.81 (s, 3H), 3.18 (s, 4H), 3.04-2.98 (m, 2H), 2.94-2.88 (m, 2H), 2.86-2.81 (m, 1H), 2.78-2.71 (m, 2H), 2.62 (s, 4H), 2.30 (s, 6H), 2.16 (m, 1H), 1.95 (d, J = 12.1 Hz, 2H), 1.86 (s, 1H), 1.33 (dd, J = 21.9, 11.7 Hz, 2H). m/z 782.47 [M + H]+. |
| Cpd. 164 | 1H NMR (600 MHz, CDCl3) δ 8.82 (d, J = 2.4 Hz, 2H), 8.07 (dd, J = 8.5, 2.5 Hz, 1H), 7.67 (d, J = 8.5 Hz, 1H), 7.47 (s, 1H), 7.38 (s, 1H), 7.28 (d, J = 2.2 Hz, 1H), 7.18-7.13 (m, 4H), 7.05 (dd, J = 8.6, 2.3 Hz, 1H), 5.95 (s, 1H), 4.94 (m, 1H), 3.96 (d, J = 12.9 Hz, 2H), 3.81 (s, 3H), 2.97 (m, 4H), 2.91-2.86 (m, 2H), 2.85-2.79 (m, 1H), 2.76-2.72 (m, 1H), 2.71-2.66 (m, 1H), 2.27 (s, 6H), 2.25 (s, 1H), 2.15-2.11 (m, 2H), 2.09 (s, 2H), 1.93 (d, J = 10.7 Hz, 4H), 1.83 (s, 1H), 1.33-1.25 (m, 2H). m/z 782.42 [M + H]+. |
| Cpd. 165 | 1H NMR (600 MHz, CDCl3) δ 8.12 (s, 1H), 7.67 (d, J = 8.5 Hz, 1H), 7.59 (d, J = 8.4 Hz, 2H), 7.41 (s, 1H), 7.28 (d, J = 2.1 Hz, 2H), 7.20 (d, J = 8.5 Hz, 2H), 7.18-7.13 (m, 3H), 7.05 (dd, J = 8.6, 2.2 Hz, 1H), 5.86 (s, 1H), 4.94 (m, 1H), 3.96 (d, J = 12.8 Hz, 2H), 3.81 (s, 3H), 2.98 (m, 4H), 2.89 (m, 2H), 2.82 (m, 1H), 2.76-2.71 (m, 1H), 2.48 (s, 2H), 2.27 (s, 6H), 2.25 (s, 2H), 2.15-2.12 (m, 1H), 2.05 (m, 2H), 1.93 (d, J = 12.6 Hz, 2H), 1.82 (d, J = 11.0 Hz, 3H), 1.34-1.29 (m, 2H). m/z 781.48 [M + H]+. |
| Cpd. 166 | 1H NMR (600 MHz, CDCl3) δ 8.10 (s, 1H), 7.66 (d, J = 8.4 Hz, 1H), 7.60 (d, J = 8.5 Hz, 2H), 7.41 (s, 1H), 7.22 (d, J = 8.5 Hz, 2H), 7.19-7.12 (m, 4H), 6.97 (d, J = 2.1 Hz, 1H), 6.70 (dd, J = 8.5, 2.2 Hz, 1H), 5.86 (s, 1H), 4.94 (m, 1H), 3.81 (s, 3H), 3.60 (dd, J = 9.9, 7.4 Hz, 1H), 3.54-3.47 (m, 2H), 3.42 (d, J = 9.8 Hz, 1H), 3.23-3.18 (m, 1H), 3.07 (d, J = 10.9 Hz, 1H), 2.99 (d, J = 10.8 Hz, 1H), 2.92-2.86 (m, 2H), 2.85-2.79 (m, 2H), 2.77-2.70 (m, 2H), 2.67-2.63 (m, 1H), 2.48-2.45 (m, 1H), 2.42 (d, J = 8.7 Hz, 1H), 2.27 (s, 6H), 2.16-2.12 (m, 1H), 2.06 (d, J = 2.4 Hz, 1H), 1.86-1.79 (m, 4H). m/z 767.32 [M + H]+. |
| Cpd. 167 | 1H NMR (600 MHz, CDCl3) δ 8.03 (s, 1H), 7.66 (d, J = 8.4 Hz, 1H), 7.60 (d, J = 8.4 Hz, 2H), 7.41 (s, 1H), 7.22 (d, J = 8.5 Hz, 2H), 7.15 (m, 2H), 6.97 (d, J = 2.0 Hz, 1H), 6.70 (d, J = 8.3 Hz, 1H), 5.83 (s, 1H), 4.96-4.93 (m, 1H), 3.81 (s, 3H), 3.60 (s, 1H), 3.50 (d, J = 7.2 Hz, 1H), 3.42 (d, J = 9.3 Hz, 2H), 3.25-3.19 (m, 1H), 3.07 (s, 1H), 2.98 (s, 1H), 2.92-2.86 (m, 2H), 2.83 (m, 2H), 2.76-2.70 (m, 2H), 2.66 (s, 1H), 2.46 (s, 1H), 2.41 (s, 1H), 2.25 (s, 6H), 2.15-2.12 (m, 1H), 2.06 (s, 1H), 1.83 (s, 4H). m/z 767.34 [M + H]+. |
| Cpd. 168 | 1H NMR (600 MHz, CDCl3) δ 8.11 (s, 1H), 7.69 (d, J = 6.0 Hz, 1H), 7.59 (d, J = 6.0 Hz, 2H), 7.42 (s, 1H), 7.30 (d, J = 1.8 Hz, 1H), 7.20 (d, J = 12.0 Hz, 2H), 7.17-7.14 (m, 3H), 7.07 (dd, J = 8.4, 2.4 Hz, 1H), 5.85 (s, 1 H), 4.95 (dd, J = 12.0, 6.0 Hz, 1H), 4.03 (d, J = 12.0 Hz, 2H), 3.81 (s, 3H), 3.08 (d, J = 6.0 Hz, 2H), 3.01 (t, J = 12.0 Hz, 2H), 2.9 (dt, J = 16.8, 3.3 Hz, 1H), 2.83 (td, J = 13.2, 4.8 Hz, 1H), 2.77-2.71 (m, 1H), 2.49 (t, J = 12.0 Hz, 1H), 2.32 (t, J = 9.0 Hz, 2H), 2.27 (s, 6H), 2.17-2.12 (m, 1H), 2.0 (d, J = 11.4 Hz, 2H), 1.88 (d, J = 12.6 Hz, 2H), 1.80-1.74 (m, 2H), 1.71-1.67 (m, 3H). m/z 384.42 [M + 2H]2+. |
| Cpd. 169 | 1H NMR (600 MHz, CDCl3) δ 8.03 (s, 1H), 7.65 (d, J = 8.3 Hz, 1H), 7.59 (d, J = 8.4 Hz, 2H), 7.41 (s, 1H), 7.20 (d, J = 8.5 Hz, 2H), 7.17-7.13 (m, 3H), 7.12 (s, 1H), 6.78 (d, J = 2.0 Hz, 1H), 6.51 (dd, J = 8.3, 2.1 Hz, 1H), 5.83 (s, 1H), 4.93 (m, 1H), 4.21-4.14 (m, 2H), 3.81 (s, 3H), 3.76-3.70 (m, 2H), 3.08 (s, 1H), 3.00 (s, 2H), 2.89 (m, 2H), 2.85-2.80 (m, 2H), 2.75 (m, 1H), 2.73-2.70 (m, 2H), 2.49 (m, 1H), 2.27 (s, 6H), 2.15-2.12 (m, 1H), 1.85 (d, J = 12.4 Hz, 2H), 1.79 (m, 3H). m/z 753.35 [M + H]+. |
| Cpd. 170 | 1H NMR (600 MHz, CDCl3) δ 8.02 (s, 1H), 7.82 (d, J = 8.9 Hz, 1H), 7.59 (d, J = 8.4 Hz, 2H), 7.41 (s, 1H), 7.22-7.18 (m, 2H), 7.15 (m, 3H), 6.67 (d, J = 8.9 Hz, 1H), 5.86 (s, 1H), 5.20 (m, 1H), 4.47 (d, J = 11.6 Hz, 2H), 4.30 (d, J = 16.2 Hz, 1H), 4.17 (d, J = 16.1 Hz, 1H), 3.81 (s, 3H), 3.02 (s, 2H), 2.95 (m, 2H), 2.90 (s, 1H), 2.84 (m, 2H), 2.48 (s, 2H), 2.37-2.32 (m, 2H), 2.30-2.24 (s, 6H), 2.23-2.19 (m, 1H), 2.09-2.01 (m, 3H), 1.91 (d, J = 13.1 Hz, 3H), 1.82 (s, 5H). m/z 768.40 [M + H]+. |
| Cpd. 171 | 1H NMR (600 MHz, CDCl3) δ 8.61 (s, 3H), 7.68 (d, J = 8.5 Hz, 1H), 7.41 (s, 1H), 7.29 (d, J = 2.3 Hz, 1H), 7.16 (m, 3H), 7.05 (dd, J = 8.6, 2.3 Hz, 1H), 7.02 (s, 1H), 5.89 (s, 1H), 4.94 (m, 1H), 3.97 (d, J = 13.0 Hz, 2H), 3.80 (s, 4H), 3.76 (s, 3H), 2.99 (dd, J = 17.9, 7.4 Hz, 2H), 2.89 (m, 2H), 2.85-2.79 (m, 1H), 2.76-2.69 (m, 2H), 2.49 (s, 4H), 2.26 (s, J = 10.2 Hz, 6H), 2.16-2.11 (m, 1H), 1.93 (d, J = 13.0 Hz, 2H), 1.85 (s, 1H), 1.31 (m, 2H). m/z 784.37 [M + H]+. |
| Cpd. 172 | 1H NMR (600 MHz, CDCl3) δ 8.05 (s, 1H), 7.67 (d, J = 8.6 Hz, 1H), 7.44 (d, J = 5.3 Hz, 1H), 7.41 (s, 1H), 7.40 (s, 1H), 7.28 (d, J = 2.3 Hz, 1H), 7.18-7.13 (m, 3H), 7.06 (d, J = 2.3 Hz, 1H), 7.04 (d, J = 2.4 Hz, |

| Cpd. No. | 1H NMR/Mass Spec(LCMS) |
|---|---|
| | 1H), 6.99 (d, J = 8.3 Hz, 1H), 5.83 (s, 1H), 4.94 (dd, J = 12.5, 5.4 Hz, 1H), 3.96 (d, J = 13.1 Hz, 2H), 3.80 (s, 3H), 3.59 (s, 2H), 3.00 (t, J = 11.7 Hz, 2H), 2.90 (t, J = 5.4 Hz, 2H), 2.89- 2.87 (m, 1H), 2.85-2.79 (m, 1H), 2.74-2.69 (m, 3H), 2.39 (d, J = 6.9 Hz, 2H), 2.27 (s, 6H), 2.16-2.10 (m, 1H), 1.95 (d, J = 12.8 Hz, 2H), 1.91-1.89 (m, 1H), 1.35-1.29 (m, 2H). m/z 753.34 [M + H]+. |
| Cpd. 173 | 1H NMR (600 MHz, CDCl3) δ 8.15 (s, 1H), 7.65 (d, J = 8.5 Hz, 1H), 7.45 (dd, J = 8.4, 1.8, 1H), 7.42 (s, 2H), 7.19-7.13 (m, 3H), 7.11 (s, 1H), 6.99 (d, J = 8.3 Hz, 1H), 6.95 (d, J = 2.2 Hz, 1H), 6.69 (dd, J = 8.5, 2.2 Hz, 1H), 5.85 (s, 1H), 4.93 (dd, J = 12.5, 5.4 Hz, 1H), 3.80 (s, 3H), 3.68 (d, J = 14.4 Hz, 1H), 3.62 (s, 1H), 3.60 (dd, J = 7.0, 2.7 Hz, 1H), 3.54-3.48 (m, 1H), 3.47-3.42 (m, 1H), 3.25 (dd, J = 9.9, 7.1 Hz, 1H), 2.94-2.91 (m, 2H), 2.91-2.89 (m, 1H), 2.88-2.86 (m, 1H), 2.82 (dd, J = 13.0, 4.3 Hz, 1H), 2.80-2.78 (m, 1H), 2.76-2.74 (m, 1H), 2.72 (dd, J = 5.1, 3.5 Hz, 1H), 2.62-2.54 (m, 2H), 2.27 (s, 6H), 2.24-2.22 (m, 1H), 2.15-2.10 (m, 1H), 1.93-1.85 (m, 1H). m/z 739.33 [M + H]+. |
| Cpd. 174 | 1H NMR (600 MHz, CDCl3) δ 8.24 (s, 1H), 7.65 (d, J = 8.4 Hz, 1H), 7.45 (d, J = 8.3 Hz, 1H), 7.42 (s, 2H), 7.17-7.13 (m, 3H), 6.99 (d, J = 8.3 Hz, 1H), 6.95 (d, J = 2.1 Hz, 1H), 6.69 (dd, J = 8.5, 2.2 Hz, 1H), 5.88 (s, 1H), 4.93 (dd, J = 12.5, 5.4 Hz, 1H), 3.80 (s, 3H), 3.68 (d, J = 14.4 Hz, 1H), 3.63 (d, J = 12.0 Hz, 1H), 3.51 (dd, J = 10.2, 6.3 Hz, 1H), 3.47-3.40 (m, 1H), 3.46-3.42 (m, 1H), 3.25 (dd, J = 9.9, 7.1 Hz, 1H), 2.94-2.91 (m, 2H), 2.91-2.89 (m, 1H), 2.88-2.85 (m, 1H), 2.84-2.81 (m, 1H), 2.80-2.78 (m, 1H), 2.76-2.74 (m, 1H), 2.73-2.71 (m, 1H), 2.62-2.54 (m, 2H), 2.27 (s, 6H), 2.25-2.22 (m, 1H), 2.15-2.09 (m, 1H), 1.92-1.86 (m, 1H). m/z 739.31 [M + H]+. |
| Cpd. 175 | 1H NMR (600 MHz, CDCl3) δ 8.42 (s, 1H), 7.67 (d, J = 8.5 Hz, 1H), 7.61 (d, J = 8.5 Hz, 2H), 7.43 (s, 1H), 7.29-7.27 (m, 3H), 7.19-7.13 (m, 3H), 7.05 (dd, J = 8.6, 2.4 Hz, 1H), 5.85 (s, 1H), 4.94 (dd, J = 12.6, 5.4 Hz, 1H), 3.98-3.93 (m, 2H), 3.81 (s, 3H), 3.75 (t, J = 7.4 Hz, 2H), 3.69-3.64 (m, 1H), 3.13 (td, J = 7.2, 3.7 Hz, 2H), 2.98 (td, J = 13.0, 2.0 Hz, 2H), 2.92-2.88 (m, 1H), 2.86-2.80 (m, 1H), 2.77-2.70 (m, 1H), 2.42 (d, J = 6.7 Hz, 2H), 2.27 (s, 6H), 2.17-2.11 (m, 1H), 1.86 (d, J = 11.1 Hz, 2H), 1.68-1.64 (m, 1H), 1.39-1.30 (m, 2H). m/z 753.43 [M + H]+. |
| Cpd. 176 | 1H NMR (600 MHz, CDCl3) δ 7.66 (dd, J = 8.4, 2.0 Hz, 1H), 7.62 (dd, J = 8.5, 3.0 Hz, 2H), 7.43 (d, J = 1.2 Hz, 1H), 7.28-7.26 (m, 2H), 7.19-7.14 (m, 3H), 6.96 (d, J = 2.2 Hz, 1H), 6.69 (dt, J = 8.5, 1.9 Hz, 1H), 5.83 (s, 1H), 4.94 (dd, J = 12.5, 5.4 Hz, 1H), 3.81 (s, 3H), 3.77 (t, J = 6.8 Hz, 2H), 3.73-3.67 (m, 1H), 3.58 (q, J = 8.6 Hz, 1H), 3.52-3.48 (m, 1H), 3.44-3.39 (m, 1H), 3.23-3.13 (m, 3H), 2.89 (dt, J = 9.6, 3.4 Hz, 1H), 2.85-2.78 (m, 1H), 2.77-2.69 (m, 1H), 2.59 (t, J = 6.6 Hz, 2H), 2.48-2.40 (m, 1H), 2.27 (s, 6H), 2.25-2.20 (m, 1H), 2.16-2.10 (m, 1H), 1.86-1.79 (m, 1H). m/z 739.28 [M + H]+. |
| Cpd. 177 | 1H NMR (600 MHz, CDCl3) δ 7.66 (dd, J = 8.4, 2.1 Hz, 1H), 7.62 (dd, J = 8.6, 3.0 Hz, 2H), 7.43 (d, J = 1.2 Hz, 1H), 7.28-7.26 (m, 2H), 7.20-7.13 (m, 3H), 6.96 (d, J = 2.2 Hz, 1H), 6.69 (dt, J = 9.0, 2.1 Hz, 1H), 5.85 (s, 1H), 4.94 (dd, J = 12.5, 5.4 Hz, 1H), 3.81 (s, 3H), 3.78 (t, J = 6.8 Hz, 2H), 3.72-3.69 (m, 1H), 3.58 (q, J = 8.6 Hz, 1H), 3.52-3.47 (m, 1H), 3.44-3.39 (m, 1H), 3.23-3.14 (m, 3H), 2.92-2.86 (m, 1H), 2.85-2.80 (m, 1H), 2.76-2.70 (m, 1H), 2.59 (t, J = 6.5 Hz, 2H), 2.46-2.41 (m, 1H), 2.27 (s, 6H), 2.25-2.19 (m, 1H), 2.17-2.11 (m, 1H), 1.87-1.80 (m, 1H). m/z 739.26 [M + H]+. |
| Cpd. 178 | 1H NMR (600 MHz, CDCl3) δ 8.27 (s, 1H), 7.70 (d, J = 8.5 Hz, 1H), 7.45-7.40 (m, 2H), 7.36 (s, 1H), 7.29 (d, J = 2.3 Hz, 1H), 7.20-7.12 (m, 4H), 7.10-7.05 (m, 2H), 5.88 (s, 1H), 4.94 (m, 1H), 4.04 (m, 2H), 3.80 (s, 3H), 3.68 (d, J = 14.9 Hz, 2H), 3.48 (s, 4H), 2.93-2.91 (m, 1H), 2.90-2.86 (m, 3H), 2.82 (m, 1H), 2.81-2.78 (m, 1H), 2.75 (m, 2H), 2.71 (m, 2H), 2.59-2.54 (m, 2H), 2.50 (m, 2H), 2.27 (s, 6H), 2.16-2.10 (m, 1H). m/z 798.41 [M + H]+. |
| Cpd. 179 | 1H NMR (400 MHz, CDCl3) δ 8.61 (s, 1H), 7.66 (d, J = 8.5 Hz, 1H), 7.58-7.52 (m, 2H), 7.42 (s, 1H), 7.19 (s, 1H), 7.16-7.12 (m, 3H), 6.98-6.91 (m, 3H), 6.70 (dd, J = 8.5, 2.3 Hz, 1H), 5.93 (s, 1H), 4.94 (m, 1H), 3.78 (s, 3H), 3.63-3.56 (m, 1H), 3.54-3.48 (m, 1H), 3.42 (m, 1H), 3.25-3.12 (m, 5H), 2.87 (m, 2H), 2.78 (m, 1H), 2.73-2.64 (m, 4H), 2.60 (m, 2H), 2.52-2.41 (m, 2H), 2.27 (s, 6H), 2.16-2.09 (m, 1H), 1.86 (m, 1H). m/z 768.43 [M + H]+. |
| Cpd. 180 | 1H NMR (400 MHz, CDCl3) δ 8.48 (s, 1H), 7.66 (d, J = 8.4 Hz, 1H), 7.54 (m, 2H), 7.41 (s, 1H), 7.15 (m, 4H), 6.97-6.91 (m, 3H), 6.70 (dd, J = 8.5, 2.2 Hz, 1H), 5.90 (s, 1H), 4.94 (m, 1H), 3.78 (s, 3H), 3.60 (m, 1H), 3.54-3.48 (m, 1H), 3.46-3.40 (m, 1H), 3.25-3.13 (m, 5H), 2.93-2.83 (m, 2H), 2.77 (m, 1H), 2.73-2.65 (m, 4H), 2.61 (m, 2H), 2.51-2.42 (m, 2H), 2.27 (s, 6H), 2.17-2.09 (m, 1H), 1.91-1.81 (m, 1H). m/z 768.43 [M + H]+. |
| Cpd. 181 | 1H NMR (400 MHz, CDCl3) δ 8.32 (s, 1H), 7.65 (d, J = 8.0 Hz, 1H), 7.53 (d, J = 12.0 Hz, 2H), 7.40 (s, 1H), 7.16-7.14 (m, 3H), 7.04 (s, 1H), 6.93 (d, J = 8.0 Hz, 2H), 6.80 (d, J = 2.0 Hz, 1H), 6.51 (dd, J = 8.0, 2.0 Hz, 1H), 5.84 (s, 1H), 4.93 (dd, J = 12.0, 4.0 Hz, 1H), 4.17 (t, J = 8.0 Hz, |

TABLE 1-continued

| Cpd. No. | 1H NMR/Mass Spec(LCMS) |
|---|---|
| | 2H), 3.79 (s, 3H), 3.76-3.72 (m, 2H), 3.16 (t, J = 6.0 Hz, 4H), 3.10-3.04 (m 1H), 2.91-2.87 (m, 1H), 2.81-2.80 (m, 1H), 2.78-2.72 (m, 3H), 2.64 (t, J = 4.0 Hz, 4H), 2.27 (s, 6H), 2.15-2.11 (m, 1H). m/z 755.88 [M + H]2+. |
| Cpd. 182 | 1H NMR (400 MHz, CDCl3) δ 8.43 (s, 1H), 7.65-7.59 (m, 3H), 7.42 (s, 1H), 7.30 (s, 1H), 7.24 (s, 2H), 7.19-7.13 (m, 3H), 6.80 (d, J = 2.1 Hz, 1H), 6.51 (dd, J = 8.3, 1.9 Hz, 1H), 5.85 (s, 1H), 4.93 (m, 1H), 4.17-4.09 (m, 2H), 3.92-3.59 (m, 9H), 3.21 (s, 1H), 2.81 (m, 6H), 2.27 (s, 6H), 2.12 (m, 1H). m/z 725.41 [M + H]+. |
| Cpd. 183 | 1H NMR (400 MHz, CDCl3) δ 7.97 (s, 1H), 7.65 (d, J = 8.0 Hz, 1H), 7.53 (d, J = 8.8 Hz, 2H), 7.40 (s, 1H), 7.16-7.12 (m, 3H), 6.99 (s, 1H), 6.95 (d, J = 8.8 Hz, 2H), 6.78 (d, J = 2.0 Hz, 1H), 6.52 (dd, J = 8.4, 2.0 Hz, 1H), 5.80 (s, 1H), 4.93 (dd, J = 12.0, 4.8 Hz, 1H), 4.18-4.13 (m, 2H), 3.79 (s, 3H), 3.77-3.72 (m, 2H), 3.69-3.62 (m, 1H), 3.49 (m, 1H), 3.12-3.01 (m, 2H), 3.08-3.03 (m, 1H), 2.91-2.87 (m, 1H), 2.85-2.80 (m, 1H), 2.78-2.74 (m, 1H), 2.72-2.67 (m, 3H), 2.63 (dd, J = 10.8, 3.2 Hz, 1H), 2.51-2.46 (m, 2H), 2.27 (s, 6H), 2.15-2.10 (m, 1H), 1.03 (d, J = 6.4 Hz, 3H). m/z 768.46 [M + H]+. |
| Cpd. 184 | 1H NMR (400 MHz, CDCl3) δ 8.07 (s, 1H), 7.65 (d, J = 8.4 Hz, 1H), 7.55 (d, J = 8.8 Hz, 2H), 7.40 (s, 1H), 7.16-7.14 (m, 3H), 7.12 (s, 1H), 6.95 (d, J = 8.8 Hz, 2H), 6.78 (d, J = 2.0 Hz, 1H), 6.52 (dd, J = 8.4, 2.0 Hz, 1H), 5.85 (s, 1H), 4.93 (dd, J = 12.4, 5.2 Hz, 1H), 4.18-4.13 (m, 2H), 3.79 (s, 3H), 3.77-3.73 (m, 2H), 3.69-3.62 (m, 1H), 3.12-3.01 (m, 2H), 3.08-3.03 (m, 1H), 2.91-2.87 (m, 1H), 2.85-2.80 (m, 1H), 2.78-2.74 (m, 1H), 2.72-2.67 (m, 3H), 2.63 (dd, J = 10.8, 3.2 Hz, 1H), 2.51-2.46 (m, 2H), 2.26 (s, 6H), 2.15-2.11 (m, 1H), 1.03 (d, J = 6.4 Hz, 3H). m/z 768.44 [M + H]+. |
| Cpd. 185 | 1H NMR (400 MHz, CDCl3) δ 8.08 (d, J = 4.8 Hz 1H), 7.65 (d, J = 8.4 Hz, 1H), 7.53 (d, J = 8.4 Hz, 2H), 7.39 (s, 1H), 7.16-7.12 (m, 3H), 7.00 (s, 1H), 6.92 (d, J = 5.6 Hz, 2H), 6.79 (s, 1H), 6.52 (dd, J = 8.4, 2.0 Hz, 1H), 5.82 (s, 1H), 4.93 (dd, J = 12.4, 5.2 Hz, 1H), 4.19-4.12 (m, 2H), 3.78 (s, 3H), 3.76-3.67 (m, 2H), 3.40-3.34 (m, 2H), 3.14-3.03 (m, 2H), 2.95-2.88 (m, 3H), 2.85-2.72 (m, 2H), 2.65-2.52 (m, 3H), 2.45 (t, J = 10.4 Hz, 1H), 2.26 (s, 6H), 2.18-2.10 (m, 1H), 1.16 (d, J = 5.2 Hz, 3H). m/z 768.43 [M + H]+ |
| Cpd. 186 | 1H NMR (400 MHz, CDCl3) δ 8.19 (d, J = 6.4 Hz 1H), 7.65 (d, J = 8.4 Hz, 1H), 7.53 (d, J = 8.8 Hz, 2H), 7.40 (s, 1H), 7.16-7.12 (m, 3H), 7.04 (s, 1H), 6.92 (d, J = 8.8 Hz, 2H), 6.79 (s, 1H), 6.52 (dd, J = 8.4, 1.6 Hz, 1H), 5.84 (s, 1H), 4.93 (dd, J = 12.0, 5.2 Hz, 1H), 4.20-4.13 (m, 2H), 3.78 (s, 3H), 3.77-3.74 (m, 1H), 3.70-3.67 (m, 1H), 3.40-3.34 (m, 2H), 3.14-3.06 (m, 2H), 2.96-2.88 (m, 3H), 2.85-2.72 (m, 2H), 2.65-2.59 (m, 2H), 2.57-2.52 (m, 1H), 2.45 (t, J = 9.8 Hz, 1H), 2.27 (s, 6H), 2.15-2.10 (m, 1H), 1.16 (d, J = 5.2 Hz, 3H). m/z 768.44 [M + H]+ |
| Cpd. 187 | 1H NMR (400 MHz, CDCl3) δ 8.17 (s, 1H), 7.82 (d, J = 8.6 Hz, 1H), 7.54 (d, J = 6.9 Hz, 2H), 7.38 (s, 1H), 7.22 (s, 1H), 7.17-7.11 (m, 3H), 6.93 (d, J = 9.0 Hz, 2H), 6.24 (d, J = 8.6 Hz, 1H), 5.90 (s, 1H), 5.19 (m, 1H), 4.32 (d, J = 16.4 Hz, 1H), 4.25 (m, 2H), 4.19 (d, J = 16.4 Hz, 1H), 3.87-3.80 (m, 2H), 3.78 (s, 3H), 3.19-3.12 (m, 4H), 3.08-3.01 (m, 1H), 2.90 (m, 1H), 2.84 (m, 1H), 2.75 (d, J = 7.4 Hz, 2H), 2.67-2.60 (m, 4H), 2.36-2.29 (m, 1H), 2.27 (s, 6H), 2.24-2.17 (m, 1H). m/z 741.24 [M + H]+. |
| Cpd. 188 | 1H NMR (400 MHz, CDCl3) δ 8.41 (s, 1H), 7.82 (d, J = 8.0 Hz, 1H), 7.53 (d, J = 12.0, 2H), 7.41 (s, 1H), 7.15-7.12 (m, 3H), 7.12 (s, 1H), 6.93 (d, J = 8.8 Hz, 2H), 6.67 (d, J = 8.0 Hz, 1H), 5.90 (s, 1H), 5.21 (dd, J = 12.0, 4.0 Hz, 1H), 4.50-4.44 (m, 2H), 4.31 (d, J = 16.0 Hz, 1H), 4.17 (d, J = 16.0 Hz, 1H), 3.78 (s, 3H), 3.16 (t, J = 4.8, 4H), 2.99-2.92 (m, 2H), 2.90 (s, 1H), 2.86-2.81 (m, 1H), 2.59 (t, J = 4.8 Hz, 4H), 2.32 (dd, J = 12.8, 4.8 Hz, 1H), 2.27 (s, 6H), 2.24-2.17 (m, 2H), 1.90 (d, J = 12.0 Hz, 3H), 1.86-1.81 (m, 1H), 1.27-1.18 (m, 2H). m/z 770.42 [M + H]2+. |
| Cpd. 189 | LC/MS 832.3 [M − H]/834.3 [M + H]<br>1H NMR (400 MHz, DMSO-d6) δ 10.77 (s, 1H), 9.87 (s, 1H), 9.54 (s, 1H), 8.33 (s, 1H), 8.19 (d, J = 2.3 Hz, 1H), 8.13 (d, J = 8.8 Hz, 1H), 8.09 (s, 1H), 7.77 (dd, J = 8.1, 2.3 Hz, 1H), 7.57 (d, J = 8.4 Hz, 1H), 7.53 (s, 1H), 7.31 (d, J = 8.3 Hz, 1H), 7.18-7.05 (m, 3H), 7.01 (d, J = 8.4 Hz, 1H), 4.13-4.01 (m, 1H), 3.61 (s, 3H), 3.54-3.49 (m, 2H), 3.10 (s, 2H), 2.92-2.82 (m, 2H), 2.76-2.72 (m, 2H), 2.69-2.60 (m, 4H), 2.57-2.54 (m, 4H), 2.48-2.37 (m, 2H), 2.36-2.28 (m, 2H), 2.20 (s, 6H), 2.17-2.11 (m, 1H), 1.91-1.82 (m, 2H), 1.79-1.69 (m, 2H), 1.63 (s, 1H). |
| Cpd. 190 | LC/MS 721.33 [M − H]/723.15 [M + H]<br>1H NMR (400 MHz, DMSO-d6) δ 10.76 (s, 1H), 9.66 (s, 1H), 8.81 (s, 1H), 8.34 (s, 1H), 8.14-7.96 (m, 3H), 7.74-7.56 (m, 3H), 7.24 (d, J = 8.4 Hz, 1H), 7.15-7.02 (m, 4H), 4.64 (s, 2H), 4.06-3.98 (m, 2H), 3.70 (t, J = 5.6 Hz, 2H), 3.63 (s, 3H), 2.85-2.74 (m, 2H), 2.65-2.54 (m, 4H), 2.45-2.37 (m, 1H), 2.20 (s, 6H), 2.02-1.78 (m, 2H). |
| Cpd. 192 | 1H NMR (500 MHz, DMSO) δ 11.09 (s, 1H), 9.85 (s, 1H), 9.67 (d, J = 10.2 Hz, 1H), 8.36 (d, J = 3.6 Hz, 1H), 8.12 (s, 1H), 7.69 (d, J = 3.8 Hz, 1H), 7.62 (d, J = 8.3 Hz, 1H), 7.36-7.28 (m, 4H), 7.12-7.01 (m, 5H), |

TABLE 1-continued

| Cpd. No. | 1H NMR/Mass Spec(LCMS) |
|---|---|
| | 4.99-4.95 (m, 1H), 4.72 (s, 1H), 4.63 (s, 1H), 3.89-3.86 (m, 2H), 3.75-3.70 (m, 2H), 3.62 (s, 3H), 2.87-2.81 (m, 2H), 2.73-2.71 (m, 2H), 2.20 (s, 6H), 2.00-1.98 (m, 2H).<br>LC/MS (ESI) m/z [M + H]+: 739.09 |
| Cpd. 193 | 1H NMR (500 MHz, DMSO) δ 11.09 (s, 1H), 9.86 (s, 1H), 9.58 (s, 1H), 8.35 (s, 1H), 8.11 (s, 1H), 7.59-7.52 (m, 2H), 7.33-7.28 (m, 3H), 7.13-7.08 (m, 4H), 7.01-6.98 (m, 2H), 4.99-4.96 (m, 1H), 4.40-4.38 (m, 1H), 3.98-3.96 (m, 1H), 3.75 (s, 2H), 3.61 (s, 3H), 3.51-3.50 (m, 2H), 3.18-3.16 (m, 1H), 3.05-3.00 (m, 1H), 2.90-2.82 (m, 1H), 2.73-2.72 (m, 2H), 2.62-2.59 (m, 4H), 2.28-2.26 (m, 2H), 2.20 (s, 6H), 2.18-2.15 (m, 1H), 2.06-1.98 (m, 2H), 1.88 (s, 1H), 1.75-1.69 (m, 2H).<br>LC/MS (ESI) m/z [M + H]+: 836.7 |
| Cpd. 194 | LC/MS (ESI) m/z [M + H]+: 714.6<br>1H NMR (400 MHz, DMSO) δ 11.11 (s, 1H), 9.74-7.69 (m, 1H), 8.37 (d, J = 3.2 Hz, 1H), 8.15 (s, 1H), 7.85-7.82 (m, 1H), 7.72-7.68 (m, 1H), 7.67-7.62 (m, 1H), 7.48 (d, J = 2.3 Hz, 1H), 7.39-7.36 (m, 1H), 7.15-7.09 (m, 4H), 5.28-5.24 (m, 2H), 5.15-5.10 (m, 1H), 4.70 (s, 1H), 4.61 (s, 1H), 3.70 (d, J = 5.6 Hz, 2H), 3.62 (s, 3H), 3.43 (s, 2H), 2.90-2.87 (m, 1H), 2.76-2.73 (m, 1H), 2.62-2.57 (m, 1H), 2.20 (s, 6H), 2.08-2.01 (m, 1H). |
| Cpd. 195 | LC/MS: 817.53 [M + H]+<br>1H NMR (400 MHz, DMSO-d6) δ 11.07 (s, 1H), 9.59 (s, 1H), 8.51 (s, 1H), 8.38 (s, 1H), 7.65 (d, J = 8.6 Hz, 1H), 7.63-7.50 (m, 2H), 7.35-7.28 (m, 1H), 7.24 (d, J = 8.6 Hz, 1H), 7.13 (t, J = 7.8 Hz, 1H), 7.02 (d, J = 8.4 Hz, 1H), 5.07 (dd, J = 12.8, 5.4 Hz, 1H), 4.06 (d, J = 12.8 Hz, 2H), 3.58 (d, J = 29.9 Hz, 3H), 3.15-2.92 (m, 2H), 2.95-2.82 (m, 1H), 2.76 (s, 2H), 2.72-2.55 (m, 3H), 2.29 (d, J = 32.2 Hz, 3H), 2.01 (d, J = 15.0 Hz, 1H), 1.84 (d, J = 12.7 Hz, 1H), 1.26-1.17 (m, 1H). |
| Cpd. 199 | LCMS: 836.3 [M + H]+<br>1H NMR (500 MHz, DMSO-d6) δ 11.08 (s, 1H), 7.63 (d, J = 8.6 Hz, 1H), 7.35 (s, 1H), 7.26 (s, 2H), 7.21-6.96 (m, 5H), 5.06 (dd, J = 12.9, 5.4 Hz, 1H), 4.07-3.79 (m, 5H), 3.62 (s, 1H), 3.00-2.69 (m, 6H), 2.66-2.58 (m, 2H), 2.37 (s, 2H), 2.25-2.13 (m, 6H), 2.05-1.96 (m, 1H), 1.82-1.41 (m, 4H), 1.24 (s, 2H), 1.08 (s, 2H), 0.86 (s, 2H), 0.75 (s, 2H). |
| Cpd. 201 | LC/MS: 703.31 [M + H]+<br>1H NMR (500 MHz, DMSO-d6) δ 11.02 (s, 1H), 9.59 (s, 1H), 8.35 (s, 2H), 8.11 (s, 1H), 7.62-7.51 (m, 2H), 7.23-7.06 (m, 3H), 7.01 (d, J = 8.5 Hz, 1H), 5.23 (s, 1H), 4.86 (dd, J = 12.8, 5.5 Hz, 1H), 3.61 (s, 3H), 3.53 (s, 2H), 3.09 (t, J = 12.5 Hz, 2H), 2.89-2.78 (m, 1H), 2.79-2.61 (m, 4H), 2.61-2.54 (m, 4H), 2.46-2.29 (m, 3H), 2.20 (s, 6H), 2.03-1.77 (m, 2H), 1.23-1.13 (m, 2H). |
| Cpd. 204 | LCMS: 836.2 [M + H]+<br>1H NMR (400 MHz, DMSO-d6) δ 11.08 (s, 1H), 9.55 (s, 1H), 8.34 (s, 1H), 8.13-8.01 (m, 2H), 7.64 (d, J = 8.5 Hz, 1H), 7.63-7.49 (m, 2H), 7.30 (s, 1H), 7.20 (d, J = 8.5 Hz, 1H), 7.16-7.06 (m, 3H), 7.01 (d, J = 8.5 Hz, 1H), 5.06 (dd, J = 12.9, 5.3 Hz, 1H), 4.01 (d, J = 13.1 Hz, 2H), 3.62 (s, 5H), 2.96 (t, J = 12.7 Hz, 2H), 2.92-2.82 (m, 1H), 2.72 (s, 4H), 2.59 (s, 3H), 2.20 (s, 6H), 2.06-1.93 (m, 1H), 1.77-1.52 (m, 3H), 1.19-1.13 (m, 3H), 0.71-0.58 (m, 4H). |
| Cpd. 205 | LC/MS. 783.6 [M + H]+<br>1H NMR (400 MHz, DMSO-d6) δ 11.11 (s, 1H), 9.54 (s, 1H), 8.40 (d, J = 9.5 Hz, 1H), 8.33 (s, 1H), 8.08 (s, 1H), 7.74 (d, J = 8.8 Hz, 1H), 7.58 (d, J = 8.7 Hz, 1H), 7.52 (s, 1H), 7.38-7.30 (m, 1H), 7.17-7.06 (m, 3H), 7.02-6.95 (m, 2H), 5.10 (dd, J = 12.7, 5.4 Hz, 1H), 4.64 (s, 2H), 3.62 (d, J = 8.1 Hz, 5H), 2.88 (d, J = 5.7 Hz, 2H), 2.69 (d, J = 14.9 Hz, 4H), 2.61 (s, 2H), 2.20 (s, 6H), 2.07-1.97 (m, 2H), 0.77 (s, 2H), 0.69 (s, 2H). |
| Cpd. 206 | LCMS 894.4 [M + H].<br>1H NMR (400 MHz, DMSO-d6) δ 9.81 (s, 1H), 9.66 (s, 1H), 8.59 (s, 1H), 8.37 (s, 1H), 8.29 (s, 1H), 8.14 (s, 1H), 7.78 (s, 1H), 7.74-7.65 (m, 2H), 7.38 (s, 1H), 7.30 (d, J = 8.7 Hz, 1H), 7.20 (d, J = 8.6 Hz, 1H), 7.16-7.02 (m, 3H), 5.70 (s, 2H), 5.26 (dd, J = 13.0, 5.4 Hz, 1H), 4.61 (d, J = 15.0 Hz, 1H), 4.35 (dd, J = 15.4, 7.5 Hz, 1H), 4.12 (d, J = 12.9 Hz, 2H), 3.64 (s, 3H), 3.41-3.30 (m, 2H), 3.28-3.15 (m, 4H), 3.15-2.98 (m, 5H), 2.98-2.84 (m, 3H), 2.76-2.59 (m, 3H), 2.20 (s, 6H), 2.10 (d, J = 8.7 Hz, 1H), 2.01-1.86 (m, 4H), 1.76-1.63 (m, 2H), 1.36-1.26 (m, 2H). |
| Cpd. 207 | LC/MS 881.1<br>1H NMR (400 MHz, DMSO-d6) δ 9.56 (s, 1H), 8.33 (s, 1H), 8.09 (s, 1H), 7.66 (d, J = 8.5 Hz, 1H), 7.61-7.48 (m, 2H), 7.37-7.29 (m, 1H), 7.29-7.22 (m, 1H), 7.16-7.06 (m, 3H), 7.02 (d, J = 8.2 Hz, 1H), 5.64 (s, 2H), 5.25 (dd, J = 13.1, 5.4 Hz, 1H), 4.06 (d, J = 12.7 Hz, 2H), 3.61 (s, 3H), 3.53 (s, 2H), 3.13-2.94 (m, 3H), 2.88-2.54 (m, 6H), 2.39-2.31 (m, 2H), 2.28 (t, J = 7.7 Hz, 2H), 2.20 (s, 6H), 2.13-2.03 (m, 1H), 2.02-1.93 (m, 1H), 1.90-1.77 (m, 2H), 1.57-1.46 (m, 1H), 1.40 (q, J = 7.3 Hz, 2H), 1.23-1.12 (m, 2H), 0.85 (s, 3H), 0.83 (s, 3H). |
| Cpd. 208 | LC/MS: 771.2 [M + H]+.<br>1H NMR (400 MHz, DMSO-d6) δ 11.11 (s, 1H), 9.56 (s, 1H), 8.33 (s, 1H), 8.09 (s, 1H), 7.71 (d, J = 11.5 Hz, 1H), 7.57 (d, J = 15.1 Hz, 2H), 7.45 (d, J = 7.4 Hz, 1H), 7.11 (q, J = 5.3 Hz, 3H), 7.02 (d, J = 8.3 Hz, |

TABLE 1-continued

| Cpd. No. | 1H NMR/Mass Spec(LCMS) |
|---|---|
| | 1H), 5.10 (dd, J = 12.8, 5.4 Hz, 1H), 3.68-3.57 (m, 5H), 3.54 (s, 2H), 2.93 (t, J = 12.8 Hz, 3H), 2.76 (s, 2H), 2.66 (d, J = 6.0 Hz, 2H), 2.63-2.54 (m, 2H), 2.42-2.32 (m, 2H), 2.20 (s, 6H), 2.07-1.98 (m, 1H), 1.93-1.80 (m, 3H), 1.37-1.27 (m, 2H). |
| Cpd. 209 | LCMS: 769.7 [M + H]+ <br> 1H NMR (400 MHz, DMSO-d6) δ 10.97 (s, 1H), 9.63 (s, 1H), 8.35 (d, J = 6.5 Hz, 1H), 8.09 (s, 1H), 7.62 (d, J = 7.8 Hz, 3H), 7.49-7.28 (m, 2H), 7.18-7.02 (m, 4H), 5.08 (dd, J = 13.5, 5.0 Hz, 1H), 4.57 (d, J = 12.7 Hz, 1H), 4.28-4.06 (m, 2H), 3.83-3.44 (m, 5H), 3.22-3.07 (m, 1H), 3.03-2.65 (m, 7H), 2.63-2.56 (m, 2H), 2.42-2.27 (m, 2H), 2.27-2.13 (m, 7H), 2.06-1.90 (m, 1H), 1.82 (t, J = 14.8 Hz, 2H), 1.73-1.59 (m, 1H), 1.58-1.43 (m, 1H). |
| Cpd. 210 | LC/MS 882.1 [M + H]+ <br> 1H NMR (400 MHz, DMSO-d6) δ 11.11 (s, 1H), 9.55 (s, 1H), 8.33 (s, 1H), 8.09 (s, 1H), 7.72 (d, J = 11.4 Hz, 1H), 7.58 (d, J = 8.4 Hz, 1H), 7.54 (s, 1H), 7.44 (d, J = 7.4 Hz, 1H), 7.18-7.05 (m, 3H), 7.01 (d, J = 8.4 Hz, 1H), 5.10 (dd, J = 12.8, 5.4 Hz, 1H), 4.40 (d, J = 12.6 Hz, 1H), 4.01 (d, J = 13.2 Hz, 1H), 3.72-3.57 (m, 5H), 3.53 (s, 2H), 3.11-2.82 (m, 6H), 2.75 (s, 2H), 2.70-2.55 (m, 5H), 2.32 (d, J = 7.5 Hz, 2H), 2.20 (s, 6H), 2.07-2.00 (m, 1H), 1.87-1.80 (m, 1H), 1.73 (m, 5H), 1.11-1.02 (m, 1H), 0.99-0.91 (m, 1H). |
| Cpd. 211 | 1H NMR (400 MHz, DMSO-d6) δ 11.09 (s, 1H), 9.97 (s, 1H), 9.82 (s, 1H), 8.40 (s, 1H), 8.18 (s, 1H), 7.78 (s, 1H), 7.73-7.57 (m, 2H), 7.30-7.06 (m, 4H), 6.53 (s, 1H), 5.07 (dd, J = 12.8, 5.4 Hz, 1H), 4.61 (d, J = 16.0 Hz, 1H), 4.47-4.11 (m, 5H), 4.09-3.87 (m, 2H), 3.83-3.59 (m, 4H), 3.25-3.05 (m, 4H), 3.04-2.80 (m, 3H), 2.72 (dd, J = 23.8, 11.4 Hz, 2H), 2.61 (s, 2H), 2.33-2.14 (m, 6H), 2.08-1.99 (m, 1H), 1.98-1.82 (m, 2H). |
| Cpd. 217 | 1H NMR (400 MHz, DMSO-d6) δ 11.10 (s, 1H), 9.72 (s, 1H), 8.73 (s, 1H), 8.62 (s, 1H), 7.76 (d, J = 8.0 Hz, 1H), 7.65 (t, J = 8.4 Hz, 1H), 7.60 (s, 1H), 7.33 (s, 1H), 7.25 (d, J = 8.7 Hz, 1H), 7.15 (q, J = 8.3 Hz, 1H), 5.07 (dd, J = 12.8, 5.4 Hz, 1H), 4.59 (d, J = 14.7 Hz, 1H), 4.26-4.14 (m, 1H), 4.03 (d, J = 12.9 Hz, 2H), 3.64 (s, 3H), 3.48-3.24 (m, 4H), 3.10 (q, J = 12.9, 12.1 Hz, 3H), 2.95-2.82 (m, 1H), 2.73 (d, J = 16.0 Hz, 1H), 2.59 (d, J = 15.5 Hz, 2H), 2.05 (dd, J = 24.6, 11.9 Hz, 3H), 1.84 (s, 1H), 1.37 (dd, J = 28.9, 17.2 Hz, 3H). |
| Cpd. 218 | LC/MS: 881.12 [M + H+] <br> 1H NMR (400 MHz, DMSO-d6) δ 11.08 (s, 1H), 9.63 (s, 1H), 8.71 (d, J = 11.0 Hz, 1H), 8.65 (d, J = 9.2 Hz, 1H), 7.77-7.50 (m, 5H), 7.32 (s, 1H), 7.23 (td, J = 8.3, 2.0 Hz, 2H), 7.03 (d, J = 8.3 Hz, 1H), 5.07 (dd, J = 12.9, 5.4 Hz, 1H), 4.06 (d, J = 13.1 Hz, 2H), 3.64 (d, J = 8.6 Hz, 3H), 3.54 (s, 2H), 3.01 (t, J = 12.4 Hz, 2H), 2.97-2.81 (m, 2H), 2.76 (d, J = 6.0 Hz, 2H), 2.70-2.57 (m, 3H), 2.34 (d, J = 6.3 Hz, 2H), 2.01 (d, J = 13.0 Hz, 2H), 1.84 (d, J = 13.0 Hz, 2H). |
| Cpd. 219 | LC/MS: 878.22 [M + Na+] <br> 1H NMR (400 MHz, DMSO-d6) δ 11.08 (s, 1H), 9.62 (s, 1H), 8.71 (d, J = 11.0 Hz, 1H), 8.57 (d, J = 8.3 Hz, 1H), 7.98-7.86 (m, 1H), 7.72-7.51 (m, 3H), 7.32 (d, J = 2.3 Hz, 1H), 7.24 (dd, J = 8.7, 2.3 Hz, 1H), 7.09-7.01 (m, 1H), 5.07 (dd, J = 12.8, 5.4 Hz, 1H), 4.06 (d, J = 13.0 Hz, 2H), 3.64 (d, J = 8.5 Hz, 3H), 3.54 (s, 1H), 3.01 (t, J = 12.4 Hz, 2H), 2.98-2.81 (m, 2H), 2.76 (s, 1H), 2.71-2.56 (m, 3H), 2.41-2.27 (m, 2H), 2.01 (d, J = 13.6 Hz, 2H), 1.84 (d, J = 13.0 Hz, 2H), 1.29-1.12 (m, 3H). |
| Cpd. 220 | LC/MS 883.15 [M + H-] <br> LC/MS 757.2 [M + H]+ <br> 1H NMR (400 MHz, Methanol-d4) δ 8.09 (s, 1H), 7.63-7.48 (m, 2H), 7.42 (d, J = 11.5 Hz, 1H), 7.22 (d, J = 7.3 Hz, 1H), 7.16 (s, 3H), 7.09 (d, J = 8.2 Hz, 1H), 5.13 (dd, J = 13.4, 5.1 Hz, 1H), 4.51-4.31 (m, 2H), 3.70 (s, 4H), 3.61 (d, J = 11.4 Hz, 2H), 2.98-2.75 (m, 7H), 2.49 (dd, J = 20.0, 6.0 Hz, 3H), 2.28 (s, 6H), 2.22-2.14 (m, 1H), 1.97 (d, J = 13.5 Hz, 3H), 1.50 (t, J = 11.9 Hz, 2H), 1.33 (d, J = 17.6 Hz, 2H). |
| Cpd. 221 | 1H NMR (300 MHz, DMSO-d6) δ 11.09 (s, 1H), 9.59 (s, 1H), 8.43 (d, J = 3.0 Hz, 1H), 8.32 (d, J = 3.1 Hz, 1H), 8.06 (d, J = 2.8 Hz, 1H), 7.66 (d, J = 8.8 Hz, 1H), 7.57 (s, 2H), 7.32 (s, 1H), 7.24 (d, J = 8.7 Hz, 1H), 7.04-7.02 (m, 1H), 7.00-6.96 (m, 1H), 5.07 (d, J = 12.1 Hz, 1H), 4.06 (d, J = 12.7 Hz, 2H), 3.58 (s, 3H), 3.34-3.01 (m, 2H), 2.97-2.67 (m, 5H), 2.37-2.07 (m, 6H), 2.01 (s, 2H), 1.93-1.71 (m, 2H), 1.22-1.18 (m, 2H). |
| Cpd. 222 | LC/MS: 771.42 [M + H+] <br> 1H NMR (500 MHz, DMSO-d6) δ 11.09 (s, 1H), 9.63 (s, 1H), 8.36 (s, 1H), 8.10 (s, 1H), 7.78-7.76 (m, 2H), 7.66 (d, J = 8.6 Hz, 1H), 7.33 (s, 1H), 7.26-7.24 (m, 1H), 7.18-7.16 (m, 2H), 7.13-7.08 (m, 3H), 5.09-5.06 (m, 1H), 4.08-4.04 (m, 1H), 3.61 (s, 3H), 3.12-3.07 (m, 1H), 3.02-2.97 (m, 2H), 2.61-2.55 (m, 3H), 2.33-2.32 (m, 2H), 2.20 (s, 8H), 2.03-1.98 (m, 4H), 1.81-1.78 (m, 4H), 1.57-1.37 (m, 4H). |
| Cpd. 225 | LC/MS (ESI) m/z [M + H]+ : 809.50 <br> 1H NMR (400 MHz, DMSO-d6) δ 11.09 (s, 1H), 9.61 (s, 1H), 8.74 (d, J = 4.4 Hz, 1H), 8.52 (d, J = 8.4 Hz, 1H), 8.34 (s, 1H), 8.09 (s, 1H), 7.77 (s, 1H), 7.69 (d, J = 8.5 Hz, 1H), 7.52-7.48 (m, 1H), 7.37 (s, 1H), 7.28 (d, J = 8.6 Hz, 1H), 7.15 (s, 1H), 7.13-7.10 (m, 2H), 5.10-5.06 (m, 1H), 4.17-4.14 (m, 1H), 3.60 (s, 3H), 3.51-3.49 (m, 4H), 3.13-3.07 (m, 2H), |

TABLE 1-continued

| Cpd. No. | 1H NMR/Mass Spec(LCMS) |
|---|---|
| | 2.93-2.84 (m, 2H), 2.73-2.63 (m, 6H), 2.57-2.55 (m, 2H), 2.20 (s, 6H), 2.05-1.91 (m, 2H), 1.86-1.77 (m, 2H), 1.66-1.60 (m, 1H), 1.48-1.38 (m, 1H). LC/MS (ESI) m/z [M + H]+: 810.51 |
| Cpd. 226 | 1H NMR (400 MHz, DMSO-d6) δ 11.09 (s, 1H), 9.85 (s, 1H), 8.74 (d, J = 4.4 Hz, 1H), 8.51 (d, J = 8.4 Hz, 1H), 8.39 (s, 1H), 8.14-8.09 (m, 1H), 7.84-7.80 (m, 1H), 7.70 (d, J = 8.5 Hz, 1H), 7.51-7.48 (m, 1H), 7.38 (s, 1H), 7.28 (d, J = 8.6 Hz, 1H), 7.23-7.18 (m, 1H), 7.14-7.09 (m, 1H), 5.10-5.06 (m, 1H), 4.17-4.14 (m, 1H), 3.62 (s, 3H), 3.51-3.49 (m, 4H), 3.06-3.00 (m, 2H), 2.93-2.84 (m, 2H), 2.67-2.60 (m, 6H), 2.57-2.53 (m, 2H), 2.20 (s, 6H), 2.04-1.94 (m, 2H), 1.80-1.74 (m, 2H), 1.70-1.67 (m, 1H), 1.52-1.47 (m, 1H). LC/MS (ESI) m/z [M + H]+: 828.60. |
| Cpd. 227 | 1H NMR (400 MHz, DMSO-d6) δ 11.08 (s, 1H), 9.85 (s, 1H), 8.39 (s, 1H), 8.14-8.09 (m, 1H), 7.84-7.81 (m, 1H), 7.65 (d, J = 8.5 Hz, 1H), 7.53 (d, J = 8.5 Hz, 1H), 7.32 (d, J = 2.3 Hz, 1H), 7.25-7.19 (m, 2H), 7.14-7.07 (m, 3H), 5.09-5.04 (m, 1H), 4.60-4.57 (m, 1H), 4.07-4.04 (m, 3H), 3.63 (s, 3H), 3.18-3.10 (m, 1H), 3.03-2.95 (m, 2H), 2.90-2.82 (m, 1H), 2.65-2.57 (m, 2H), 2.32 (d, J = 7.0 Hz, 2H), 2.20 (s, 6H), 2.03-2.00 (m, 2H), 1.81-1.78 (m, 4H), 1.62-1.53 (m, 1H), 1.49-1.40 (m, 1H), 1.26-1.24 (m, 4H). LC/MS (ESI) m/z [M + H]+: 829.55 |
| Cpd. 228 | 1H NMR (400 MHz, DMSO-d6) δ 11.08 (s, 1H), 9.62 (s, 1H), 8.35 (s, 1H), 8.09 (s, 1H), 7.77 (d, J = 8.2 Hz, 2H), 7.66 (d, J = 8.2 Hz, 1H), 7.19 (d, J = 8.4 Hz, 2H), 7.14-7.07 (m, 3H), 6.86 (d, J = 2.1 Hz, 1H), 6.73-6.70 (m, 1H), 5.09-5.04 (m, 1H), 4.57-4.54 (m, 1H), 4.30-4.15 (m, 4H), 4.00-3.91 (m, 1H), 3.73 (d, J = 13.4 Hz, 1H), 3.61 (s, 3H), 3.16-3.10 (m, 1H), 2.85 (d, J = 5.6 Hz, 1H), 2.77 (s, 1H), 2.61-2.53 (m, 2H), 2.20 (s, 6H), 2.03-2.02 (m, 2H), 1.83-1.78 (m, 2H), 1.63-1.56 (m, 1H), 1.50-1.43 (m, 1H). LC/MS (ESI) m/z [M + H]+: 767.51 |
| Cpd. 229 | 1H NMR (500 MHz, DMSO-d6) δ 11.09 (s, 1H), 9.87 (s, 1H), 8.41 (s, 1H), 8.15 (s, 1H), 7.68-7.65 (m, 2H), 7.56-7.53 (m, 1H), 7.28-7.24(m, 1H), 7.14-7.09 (m, 3H), 6.86-6.84 (m, 1H), 6.73-6.68 (m, 1H), 5.08-5.05 (m, 1H), 4.58-4.56 (m, 1H), 4.27-4.20 (m, 4H), 4.11-4.08 (m, 1H), 3.97-3.91 (m, 1H), 3.76-3.70 (m, 1H), 3.63 (s, 3H), 2.8-2.87 (m, 1H), 2.86-2.85 (m, 1H), 2.61 (s, 1H), 2.57 (s, 1H), 2.21 (s, 6H), 2.05-1.97 (m, 4H), 1.78 (s, 2H). LC/MS (ESI) m/z [M + H]+: 785.46 |
| Cpd. 230 | 1H NMR (400 MHz, DMSO-d6) δ 11.08 (s, 1H), 9.73 (s, 1H), 8.37 (s, 1H), 8.10 (d, J = 6.7 Hz, 1H), 7.83 (d, J = 8.6 Hz, 2H), 7.65 (d, J = 8.5 Hz, 1H), 7.38 (d, J = 8.5 Hz, 2H), 7.32 (s, 1H), 7.24 (d, J = 8.8 Hz, 1H), 7.14-7.09 (m, 3H), 6.09 (s, 1H), 5.09-5.04 (m, 1H), 4.24 (d, J = 5.8 Hz, 1H), 4.07-4.04 (m, 2H), 3.63 (s, 3H), 3.08 (s, 2H), 3.02-2.93 (m, 3H), 2.90-2.85 (m, 1H), 2.64-2.60 (m, 4H), 2.28 (d, J = 7.0 Hz, 2H), 2.20 (s, 6H), 2.04-1.97 (m, 2H), 1.94-1.89 (m, 2H), 1.85-1.82 (m, 2H). LC/MS (ESI) m/z [M + H]+: 779.46 |
| Cpd. 231 | 1H NMR (400 MHz, DMSO-d6) δ 11.08 (s, 1H), 8.98 (s, 1H), 8.28 (s, 1H), 8.10 (d, J = 4.2 Hz, 1H), 7.76-7.71 (m, 1H), 7.67-7.65 (m, 1H), 7.48-7.44 (m, 1H), 7.32 (s, 1H), 7.25-7.20 (m, 1H), 7.13-7.05 (m, 4H), 5.09-5.05 (m, 1H), 4.25-4.24 (m, 1H), 4.07-4.04 (m, 2H), 3.55 (s, 3H), 3.02-2.92 (m, 5H), 2.90-2.83 (m, 1H), 2.62-2.55 (m, 3H), 2.25-2.24 (m, 2H), 2.19 (s, 6H), 2.09-2.00 (m, 4H), 1.84-1.77 (m, 4H), 1.72-1.66 (m, 2H). LC/MS (ESI) m/z [M + H]+: 799.51 |
| Cpd. 232 | LC/MS: 783.0 [M + H]+ 1H NMR (400 MHz, DMSO-d6) δ 11.08 (s, 1H), 9.70 (d, J = 7.4 Hz, 1H), 8.36 (d, J = 6.3 Hz, 1H), 8.11 (s, 1H), 7.85-7.60 (m, 3H), 7.35 (s, 1H), 7.31-7.23 (m, 2H), 7.18 (d, J = 9.2 Hz, 1H), 7.15-7.06 (m, 3H), 5.33 (t, J = 4.9 Hz, 1H), 5.27 (s, 1H), 5.16-5.01 (m, 1H), 4.31 (t, J = 6.0 Hz, 1H), 4.23-4.07 (m, 3H), 3.63 (d, J = 8.1 Hz, 3H), 3.22-3.08 (m, 2H), 3.00-2.80 (m, 3H), 2.64-2.54 (m, 2H), 2.20 (s, 6H), 2.05-1.98 (m, 2H), 1.97-1.85 (m, 2H), 1.79-1.63 (m, 2H). |
| Cpd. 233 | LC/MS: 801.5 [M + H]+ 1H NMR (500 MHz, DMSO-d6) δ 11.13 (s, 1H), 9.70 (s, 1H), 8.37 (s, 0.6H), 8.35 (s, 0.4H), 8.12 (s, 1H), 7.78-7.70 (m, 2H), 7.68 (d, J = 2.2 Hz, 1H), 7.66-7.63 (m, 0.6H), 7.49-7.44 (m, 0.4H), 7.20-7.15 (m, 1H), 7.15-7.07 (m, 3H), 5.29 (s, 1H), 5.14-5.10 (m, 1H), 5.09 (s, 1H), 4.32 (t, J = 6.1 Hz, 1H), 4.14 (t, J = 6.0 Hz, 1H), 3.70 (t, J = 10.7 Hz, 2H), 3.63 (d, J = 4.9 Hz, 3H), 3.10 (q, J = 11.5 Hz, 2H), 2.98-2.85 (m, 3H), 2.64-2.54 (m, 2H), 2.20 (d, J = 2.3 Hz, 6H), 2.10-1.96 (m, 4H), 1.75 (dd, J = 27.3, 12.7 Hz, 2H). |
| Cpd. 234 | LC/MS: 894.6 [M + H]+. 1H NMR (500 MHz, DMSO-d6) δ 11.09 (s, 1H), 9.70 (d, J = 5.4 Hz, 1H), 8.36 (d, J = 8.9 Hz, 1H), 8.12 (s, 1H), 7.80-7.70 (m, 1H), 7.66 (dt, J = 9.1, 4.3 Hz, 2H), 7.34 (d, J = 5.3 Hz, 1H), 7.29-7.21 (m, 1H), 7.17 (d, J = 10.0 Hz, 1H), 7.16-7.06 (m, 3H), 5.31-5.20 (m, 1H), 5.16-5.00 (m, 2H), 4.54-4.42 (m, 1H), 4.18-4.03 (m, 4H), 3.65-3.61 (m, 3H), 3.33-3.14 |

| Cpd. No. | 1H NMR/Mass Spec(LCMS) |
|---|---|
| | (m, 3H), 3.14-2.98 (m, 2H), 2.97-2.83 (m, 3H), 2.72-2.54 (m, 3H), 2.20 (s, 7H), 2.08-1.95 (m, 1H), 1.90-1.49 (m, 8H). |
| Cpd. 235 | LC/MS: 840.6 [M + H]+.<br>1H NMR (400 MHz, DMSO-d6) δ 11.07 (s, 1H), 9.69 (d, J = 5.8 Hz, 1H), 8.35 (d, J = 6.3 Hz, 1H), 8.11 (s, 1H), 7.78 (s, 0.4H), 7.72 (d, J = 8.4 Hz, 0.6H), 7.67 (s, 0.6H), 7.63 (d, J = 8.4 Hz, 0.4H), 7.57 (dd, J = 8.3, 4.2 Hz, 1H), 7.26-6.95 (m, 7H), 5.27 (s, 1H), 5.13-4.98 (m, 2H), 4.60-4.24 (m, 3H), 4.24-3.93 (m, 5H), 3.63 (d, J = 7.7 Hz, 3H), 3.00-2.85 (m, 3H), 2.85-2.73 (m, 1H), 2.20 (s, 6H), 2.08-1.93 (m, 2H), 1.70 (s, 3H). |
| Cpd. 236 | LC/MS: 841.6 [M + H]+<br>1H NMR (400 MHz, DMSO-d6) δ 11.12 (s, 1H), 9.68 (d, J = 4.0 Hz, 1H), 8.35 (d, J = 7.3 Hz, 1H), 8.10 (d, J = 6.7 Hz, 1H), 7.83 (dd, J = 8.4, 3.8 Hz, 1H), 7.80-7.60 (m, 2H), 7.44 (d, J = 5.1 Hz, 1H), 7.35 (d, J = 7.4 Hz, 1H), 7.23-7.03 (m, 4H), 5.27 (s, 1H), 5.25-5.00 (m, 4H), 4.50-4.31 (m, 2H), 4.30-4.21 (m, 1H), 4.17-4.09 (m, 1H), 3.92-3.80 (m, 1H), 3.63 (d, J = 5.9 Hz, 3H), 2.99-2.81 (m, 4H), 2.69-2.58 (m, 2H), 2.20 (s, 6H), 2.11-1.83 (m, 3H), 1.77-1.61 (m, 3H). |
| Cpd. 237 | LC/MS: 739.6 [M + H]+<br>1H NMR (400 MHz, Methanol-d4) δ 8.08 (s, 1H), 7.65-7.50 (m, 3H), 7.16 (s, 3H), 7.11 (d, J = 8.2 Hz, 1H), 6.73-6.60 (m, 2H), 5.09 (dd, J = 13.3, 5.2 Hz, 1H), 4.44-4.33 (m, 2H), 3.81 (s, 2H), 3.69 (s, 3H), 3.66-3.48 (m, 3H), 3.46-3.40 (m, 1H), 3.09 (t, J = 8.8 Hz, 1H), 2.93 (d, J = 16.3 Hz, 4H), 2.85-2.68 (m, 3H), 2.53-2.36 (m, 2H), 2.28 (s, 6H), 2.25-2.10 (m, 2H), 1.93-1.83 (m, 2H), 1.83-1.73 (m, 1H). |
| Cpd. 238 | LCMS: 683.33 M − H, 685.35 M + H<br>1H NMR (300 MHz, DMSO-d6) δ 11.10 (s, 1H), 9.49 (s, 1H), 8.31 (s, 1H), 8.06 (s, 1H), 7.82-7.66 (m, 3H), 7.43 (s, 1H), 7.35 (d, J = 8.5 Hz, 1H), 7.16-7.05 (m, 3H), 6.98 (d, J = 9.0 Hz, 2H), 5.09 (dd, J = 12.5, 5.4 Hz, 1H), 3.68-3.56 (m, 4H), 3.68-3.56 (s, 3H) 3.28-3.18 (m, 4H), 3.01-2.79 (m, 1H), 2.65-2.55 (m, 1H), 2.20 (s, 6H), 2.07-1.89 (m, 2H). |
| Cpd. 239 | LCMS: 786.4 M + H<br>1H NMR (300 MHz, DMSO-d6) δ 11.13 (s, 1H), 9.49 (s, 1H), 8.33-8.31 (m, 1H), 8.07 (s, 1H), 7.84-7.66 (m, 3H), 7.54 (d, J = 7.4 Hz, 1H), 7.17-7.07 (m, 3H), 6.99 (d, J = 8.9 Hz, 2H), 5.13 (dd, J = 12.9, 5.4 Hz, 1H), 3.60 (s, 3H), 3.45-3.39 (m, 4H), 3.30-3.21 (m, 4H), 2.99-2.81 (m, 1H), 2.69-2.55 (m, 2H), 2.20 (s, 6H), 2.14-1.97 (m, 1H). |
| Cpd. 240 | LC/MS 929.7 [M + H]+<br>1H NMR (300 MHz, DMSO-d6) δ 11.09 (s, 1H), 9.68 (s, 1H), 8.36 (s, 1H), 8.10 (d, J = 4.7 Hz, 1H), 7.83-7.58 (m, 3H), 7.33 (s, 1H), 7.25 (d, J = 8.9 Hz, 1H), 7.19-6.95 (m, 4H), 5.07 (dd, J = 12.7, 5.4 Hz, 1H), 4.70 (d, J = 19.4 Hz, 2H), 4.41 (d, J = 13.7 Hz, 1H), 4.07 (d, J = 12.5 Hz, 3H), 3.75 (s, 1H), 3.63 (s, 3H), 3.17-2.97 (m, 3H), 2.87 (d, J = 11.6 Hz, 3H), 2.58 (d, J = 16.0 Hz, 3H), 2.19 (d, J = 4.9 Hz, 6H), 2.08-1.92 (m, 2H), 1.68 (s, 6H), 1.20 (d, J = 23.4 Hz, 4H). |
| Cpd. 241 | LC/MS 876.6 [M + H]+<br>1H NMR (300 MHz, DMSO-d6) δ11.12 (s, 1H), 9.68 (s, 1H), 8.36 (s, 1H), 8.10 (d, J = 4.3 Hz, 1H), 7.84 (d, J = 8.3 Hz, 1H), 7.74 (s, 1H), 7.64 (s, 1H), 7.45 (s, 1H), 7.34 (d, J = 8.9 Hz, 1H), 7.05 (d, J = 38.4 Hz, 5H), 5.12 (d, J = 14.8 Hz, 3H), 4.70 (d, J = 18.6 Hz, 3H), 4.33 (d, J = 13.0 Hz, 1H), 3.80 (d, J = 30.9 Hz, 4H), 3.63 (s, 3H), 2.84 (t, J = 14.3 Hz, 5H), 2.63 (s, 2H), 2.20 (s, 6H), 2.03 (dd, J = 20.1, 12.3 Hz, 2H), 1.77 (s, 2H). |
| Cpd. 243 | 1H NMR (400 MHz, Chloroform-d) δ 10.75-10.48 (m, 1H), 8.15 (s, 1H), 7.93-7.79 (m, 1H), 7.73 (d, J = 8.3 Hz, 1H), 7.65 (s, 0.6H), 7.55 (s, 0.4H), 7.46 (d, J = 7.0 Hz, 1H), 7.40-7.30 (m, 2H), 7.27-7.17 (m, 3H), 7.16-7.07 (m, 1H), 6.66 (s, 1H), 5.06-4.89 (m, 2H), 4.79 (s, 1H), 4.04 (s, 1H), 3.96-3.78 (m, 5H), 3.79-3.62 (m, 1H), 3.45 (t, J = 12.4 Hz, 2H), 3.03-2.69 (m, 5H), 2.56-2.35 (m, 2H), 2.30 (s, 6H), 2.21-2.04 (m, 3H). |
| Cpd. 244 | LC/MS: 803.6 [M + H]+<br>1H NMR (400 MHz, DMSO-d6) δ 11.11 (s, 1H), 9.61 (s, 1H), 8.34 (s, 1H), 8.10 (s, 1H), 7.73 (d, J = 11.2 Hz, 1H), 7.69-7.57 (m, 2H), 7.53 (d, J = 7.3 Hz, 1H), 7.26-6.96 (m, 4H), 5.10 (dd, J = 12.7, 5.4 Hz, 1H), 4.89 (s, 0.8H), 4.66 (s, 1.2H), 3.96 (s, 2H), 3.74 (s, 2H), 3.62 (s, 3H), 2.93-2.73 (m, 4H), 2.69-2.56 (m, 3H), 2.20 (s, 6H), 2.17-1.87 (m, 5H). |
| Cpd. 245 | LCMS: 786.4 M + H<br>1H NMR (400 MHz, DMSO-d6) δ 10.98 (s, 1H), 9.43 (s, 1H), 8.30 (s, 1H), 8.05 (s, 1H), 7.68 (d, J = 8.5 Hz, 2H), 7.41 (d, J = 11.5 Hz, 1H), 7.24 (d, J = 7.5 Hz, 1H), 7.10 (q, J = 5.5 Hz, 3H), 6.90 (d, J = 8.7 Hz, 2H), 5.07 (dd, J = 13.2, 5.1 Hz, 1H), 4.36 (d, J = 17.1 Hz, 1H), 4.24 (d, J = 17.0 Hz, 1H), 3.59 (s, 3H), 3.52-3.43 (m, 2H), 3.16-3.05 (m, 5H), 2.98-2.84 (m, 2H), 2.81-2.71 (m, 2H), 2.65-2.55 (m, 2H), 2.43-2.31 (m, 2H), 2.30-2.23 (m, 2H), 2.20 (s, 6H), 2.03-1.93 (m, 2H), 1.89-1.81 (m, 2H), 1.79-1.64 (m, 2H). |
| Cpd. 246 | 1H NMR (500 MHz, Chloroform-d) δ 10.76-10.39 (m, 1H), 8.22 (s, 1H), 7.88-7.82 (m, 0.5H), 7.71 (d, J = 8.2 Hz, 1H), 7.68-7.61 (m, 0.5H), 7.48 (d, J = 12.5 Hz, 1H), 7.31 (s, 1H), 7.27 (s, 1H), 7.25-7.13 (m, 4H), 7.09 (d, J = 8.6 Hz, 1H), 6.68 (s, 1H), 4.97 (dd, J = 12.3, 5.4 Hz, 1H), 4.91-4.84 (m, 1H), 4.74-4.63 (m, 1H), 4.55-4.46 (m, 1H), 4.17-4.06 (m, 1H), 4.00 (d, J = 12.9 Hz, 2H), 3.92-3.85 (m, 2H), 3.82 (s, 3H), 3.62 (s, 0.7H), |

TABLE 1-continued

| Cpd. No. | 1H NMR/Mass Spec(LCMS) |
|---|---|
| | 3.52 (t, J = 12.6 Hz, 1.3H), 3.17-3.04 (m, 3H), 2.97-2.88 (m, 3H), 2.87-2.72 (m, 3H), 2.30 (s, 6H), 2.20-2.14 (m, 2H), 2.08 (d, J = 19.6 Hz, 2H), 1.96 (m, 1.98-1.93, 1H), 1.89 (m, 1.93-1.84, 2H). |
| Cpd. 247 | 1H NMR (500 MHz, Chloroform-d) δ 10.79-10.40 (m, 1H), 8.24 (s, 1H), 7.86 (s, 0.4H), 7.67 (d, J = 8.2 Hz, 1.6H), 7.53-7.40 (m, 1H), 7.28-7.12 (m, 5H), 6.98 (s, 1H), 6.91-6.82 (m, 1H), 6.69 (s, 1H), 5.88 (s, 1H), 5.02-4.90 (m, 2H), 4.84 (d, J = 17.0 Hz, 1H), 4.72 (d, J = 17.4 Hz, 1H), 4.52 (s, 1H), 4.08 (s, 1H), 4.02 (s, 2H), 3.98-3.70 (m, 6H), 3.54 (t, J = 12.6 Hz, 1H), 3.25 (s, 1H), 3.01-2.88 (m, 3H), 2.87-2.70 (m, 2H), 2.30 (s, 6H), 2.19-2.10 (m, 3H). |
| Cpd. 248 | 1H NMR (400 MHz, Chloroform-d) δ 8.44-8.18 (m, 1H), 7.83 (d, J = 8.4 Hz, 1.3H), 7.65 (d, J = 14.0 Hz, 0.7H), 7.50-7.36 (m, 2H), 7.35-7.29 (m, 2H), 7.27-7.09 (m, 4H), 6.65 (s, 1H), 4.98 (dd, J = 12.0, 5.2 Hz, 1H), 4.94-4.78 (m, 3.3H), 4.70 (d, J = 17.0 Hz, 0.7H), 4.43 (s, 1.3H), 4.07 (s, 0.7H), 3.96-3.77 (m, 5H), 3.55 (t, J = 12.7 Hz, 1H), 3.20 (t, J = 11.7 Hz, 1H), 3.04-2.88 (m, 3H), 2.88-2.72 (m, 2H), 2.29 (s, 6H), 2.15 (m, 2.21-2.00, 5H). |
| Cpd. 250 | 1H NMR (400 MHz, DMSO-d6) δ 11.08 (s, 1H), 9.70 (s, 1H), 8.39 (s, 1H), 8.11 (s, 1H), 7.91-7.86 (m, 1H), 7.76-7.72 (m, 1H), 7.67-7.65 (m, 1H), 7.32 (d, J = 2.3 Hz, 1H), 7.26-7.23 (m, 1H), 7.14-7.07 (m, 4H), 6.03 (s, 1H), 5.09-5.05 (m, 1H), 4.08-4.04 (m, 2H), 3.62 (s, 3H), 3.10 (s, 2H), 3.02-3.00 (m, 2H), 2.92-2.82 (m, 1H), 2.68-2.54 (m, 6H), 2.30-2.28 (m, 2H), 2.20 (s, 6H), 2.06-1.93 (m, 2H), 1.91-1.82 (m, 4H).<br>LC/MS (ESI) m/z [M + H]+: 797.48 |
| Cpd. 253 | LC/MS: 813 [M + H]+<br>1H NMR (400 MHz, Chloroform-d) δ 10.50 (s, 1H), 8.27 (s, 1H), 7.80-7.60 (m, 4H), 7.37-7.31 (m, 1H), 7.26-7.16 (m, 5H), 7.13 (dd, J = 8.6, 2.3 Hz, 1.25H), 6.95 (s, 0.75H), 4.97 (dd, J = 12.2, 5.2 Hz, 1H), 4.83-4.52 (m, 2H), 3.94-3.83 (m, 2H), 3.81 (s, 3H), 3.44 (t, J = 12.4 Hz, 2H), 3.27-3.10 (m, 1H), 2.96-2.70 (m, 5H), 2.57-2.33 (m, 1H), 2.30 (s, 6H), 2.21-2.09 (m, 3H), 1.98 (d, J = 13.5 Hz, 2H), 1.79-1.69 (m, 3H). |
| Cpd. 254 | LC/MS: 831.0 [M + H]+<br>1H NMR (400 MHz, DMSO-d6) δ 11.12 (s, 1H), 9.62 (s, 1H), 8.34 (d, J = 11.0 Hz, 2H), 8.09 (s, 1H), 7.84-7.69 (m, 3H), 7.54 (d, J = 7.3 Hz, 1H), 7.19 (d, J = 8.3 Hz, 2H), 7.14-7.07 (m, 2H), 5.12 (dd, J = 12.8, 5.4 Hz, 1H), 4.59 4.41 (m, 2H), 3.70-3.45 (m, 5H), 3.24 (t, J = 11.9 Hz, 2H), 2.98-2.70 (m, 3H), 2.65-2.55 (m, 2H), 2.39-2.28 (m, 2H), 2.20 (s, 6H), 2.17-1.95 (m, 4H), 1.86 (d, J = 12.7 Hz, 2H), 1.64-1.47 (m, 2H). |
| Cpd. 255 | LC/MS: 799.0 [M + H]+<br>1H NMR (400 MHz, DMSO-d6) δ 11.01 (s, 1H), 9.63 (s, 1H), 8.35 (s, 1H), 8.10 (s, 1H), 7.79 (d, J = 7.7 Hz, 1H), 7.73-7.60 (m, 3H), 7.56 (d, J = 7.7 Hz, 1H), 7.19-7.02 (m, 4H), 5.14 (dd, J = 13.3, 5.1 Hz, 1H), 4.87 (s, 1H), 4.65 (s, 1H), 4.51 (d, J = 17.6 Hz, 1H), 4.38 (d, J = 17.5 Hz, 2H), 4.03-3.67 (m, 3H), 3.62 (s, 3H), 3.51 (s, 1H), 3.23 (s, 1H), 3.02-2.86 (m, 2H), 2.82 (s, 2H), 2.70-2.57 (m, 2H), 2.47-2.36 (m, 1H), 2.20 (s, 6H), 2.14-2.07 (m, 1H), 2.05-1.92 (m, 2H). |
| Cpd. 256 | LC/MS: 796.6 [M + H]+<br>1H NMR (400 MHz, DMSO-d6) δ 11.01 (s, 1H), 9.42 (s, 1H), 8.29 (s, 1H), 8.05 (s, 1H), 7.79 (d, J = 7.7 Hz, 1H), 7.67 (d, J = 8.6 Hz, 2H), 7.62 (s, 1H), 7.49 (d, J = 7.8 Hz, 1H), 7.18-7.01 (m, 3H), 6.89 (d, J = 8.9 Hz, 2H), 5.14 (dd, J = 13.2, 5.1 Hz, 1H), 4.51 (d, J = 17.4 Hz, 2H), 4.38 (d, J = 17.7 Hz, 1H), 3.59 (s, 3H), 3.56-3.50 (m, 1H), 3.06 (s, 5H), 2.98-2.72 (m, 4H), 2.65-2.57 (m, 2H), 2.45-2.37 (m, 2H), 2.28-2.15 (m, 7H), 2.01 (dd, J = 15.4, 8.6 Hz, 1H), 1.95-1.60 (m, 4H), 1.12 (s, 2H). |
| Cpd. 257 | LC/MS 698.0 [M + H]+<br>1H NMR (400 MHz, DMSO-d6) δ 11.01 (s, 1H), 9.62 (s, 1H), 8.35 (s, 1H), 8.09 (s, 1H), 7.84-7.73 (m, 3H), 7.69 (s, 1H), 7.57 (d, J = 7.8 Hz, 1H), 7.21 (d, J = 8.3 Hz, 2H), 7.15-7.04 (m, 3H), 5.14 (dd, J = 13.2, 5.1 Hz, 1H), 4.70-4.59 (m, 1H), 4.53 (d, J = 17.6 Hz, 1H), 4.39 (d, J = 17.6 Hz, 1H), 3.61 (s, 3H), 2.98-2.86 (m, 3H), 2.82-2.73 (m, 1H), 2.66-2.56 (m, 2H), 2.43-2.36 (m, 1H), 2.20 (s, 6H), 2.07-1.97 (m, 1H), 1.92-1.82 (m, 1H), 1.65 (s, 3H). |
| Cpd. 258 | LC/MS: 767.2 [M + H]+<br>1H NMR (400 MHz, DMSO-d6) δ 11.01 (s, 1H), 9.54 (s, 1H), 8.32 (s, 1H), 8.08 (s, 1H), 7.78 (d, J = 7.7 Hz, 1H), 7.62 (s, 1H), 7.57 (d, J = 8.5 Hz, 1H), 7.54 (s, 1H), 7.49 (d, J = 7.8 Hz, 1H), 7.16-7.05 (m, 3H), 7.01 (d, J = 8.3 Hz, 1H), 5.14 (dd, J = 13.2, 5.1 Hz, 1H), 4.51 (d, J = 17.2 Hz, 2H), 4.38 (d, J = 17.5 Hz, 1H), 3.61 (s, 3H), 3.53 (s, 2H), 3.16-2.99 (m, 2H), 2.99-2.79 (m, 3H), 2.74 (s, 2H), 2.70-2.57 (m, 4H), 2.36-2.31 (m, 2H), 2.20 (s, 6H), 2.07-1.92 (m, 3H), 1.90-1.82 (m, 1H), 1.74-1.66 (m, 1H). |

TABLE 1-continued

| Cpd. No. | 1H NMR/Mass Spec(LCMS) |
|---|---|
| Cpd. 259 | LC/MS 832.6 [M + H]+<br>1H NMR (400 MHz, DMSO-d6) δ 11.01 (s, 1H), 9.66 (s, 1H), 8.35 (s, 1H), 8.10 (s, 1H), 7.80 (d, J = 8.1 Hz, 1H), 7.73 (s, 1H), 7.63 (s, 2H), 7.50 (t, J = 9.5 Hz, 1H), 7.19-6.96 (m, 5H), 5.14 (dd, J = 13.2, 5.2 Hz, 1H), 4.69 (d, J = 25.4 Hz, 2H), 4.52 (d, J = 17.2 Hz, 2H), 4.38 (d, J = 17.5 Hz, 1H), 3.74 (s, 2H), 3.62 (s, 4H), 2.90 (dd, J = 30.9, 13.9 Hz, 4H), 2.65 (d, J = 18.6 Hz, 3H), 2.33 (s, 1H), 2.20 (s, 6H), 2.09-1.90 (m, 3H), 1.55 (s, 2H). |
| Cpd. 260 | LC/MS 875.8 [M + H]+<br>1H NMR (400 MHz, DMSO-d6) δ 11.07 (s, 1H), 9.66 (s, 1H), 8.36 (s, 1H), 8.10 (s, 1H), 7.77 (d, J = 20.1 Hz, 2H), 7.65-7.50 (m, 2H), 7.17-7.07 (m, 5H), 7.07-6.93 (m, 2H), 5.04 (dd, J = 12.8, 5.4 Hz, 1H), 4.82-4.55 (m, 3H), 4.41 (d, J = 12.7 Hz, 1H), 4.20-3.97 (m, 3H), 3.75 (s, 2H), 3.63 (d, J = 3.0 Hz, 3H), 3.20 (t, J = 12.4 Hz, 1H), 2.94-2.77 (m, 4H), 2.60 (s, 1H), 2.20 (s, 6H), 2.04-1.91 (m, 2H), 1.78 (s, 2H), 1.55 (d, J = 29.5 Hz, 1H), 1.42 (d, J = 15.3 Hz, 1H). |
| Cpd. 261 | LC/MS 903.8 [M + H]+<br>1H NMR (300 MHz, DMSO-d6) δ 11.07 (s, 1H), 9.63 (s, 1H), 8.35 (s, 1H), 8.09 (s, 1H), 7.77 (d, J = 8.6 Hz, 2H), 7.58 (d, J = 8.3 Hz, 1H), 7.19 (d, J = 8.5 Hz, 2H), 7.17-7.09 (m, 4H), 7.09-7.01 (m, 2H), 6.93 (d, J = 9.8 Hz, 1H), 5.05 (dd, J = 12.7, 5.3 Hz, 1H), 4.41 (d, J = 13.2 Hz, 1H), 4.15 (s, 2H), 3.99 (s, 2H), 3.61 (d, J = 1.3 Hz, 3H), 3.17 (d, J = 5.3 Hz, 2H), 2.98-2.68 (m, 6H), 2.61 (s, 1H), 2.20 (s, 6H), 2.09-1.91 (m, 3H), 1.89-1.70 (m, 4H), 1.58 (s, 3H). |
| Cpd. 262 | 1H NMR (400 MHz, DMSO-d6) δ 9.62 (s, 1H), 8.74 (d, J = 4.4 Hz, 1H), 8.51 (d, J = 8.4 Hz, 1H), 8.35 (s, 1H), 8.09 (s, 1H), 7.78 (s, 1H), 7.22-7.19 (m, 3H), 7.17-7.09 (m, 2H), 6.87-6.85 (m, 2H), 6.59 (d, J = 8.5 Hz, 1H), 5.46-5.42 (m, 1H), 4.84-4.74 (m, 2H), 4.60-4.57 (m, 1H), 4.15-4.11 (m, 1H), 3.73 (s, 3H), 3.61 (s, 3H), 3.14-3.02 (m, 2H), 2.83-2.68 (m, 6H), 2.20 (s, 6H), 2.05-1.99 (m, 2H), 1.79-1.70 (m, 4H), 1.45-1.42 (m, 4H).<br>LC/MS (ESI) m/z [M + H]+: 796.42 |
| Cpd. 263 | 1H NMR (400 MHz, DMSO-d6) δ 11.08 (s, 1H), 9.73 (s, 1H), 8.38 (s, 1H), 8.11 (s, 1H), 7.92 (d, J = 7.0 Hz, 1H), 7.78-7.74 (m, 1H), 7.66 (d, J = 8.2 Hz, 1H), 7.18-7.06 (m, 4H), 6.86-6.84 (m, 1H), 6.72-6.69 (m, 1H), 6.09-6.06 (m, 1H), 5.09-5.04 (m, 1H), 4.31-4.25 (m, 2H), 4.21-4.14 (m, 3H), 4.10 (s, 1H), 4.04-3.97 (m, 1H), 3.75-3.73 (m, 1H), 3.63 (s, 3H), 3.58-3.55 (m, 1H), 3.13-3.07 (m, 1H), 2.93-2.82 (m, 1H), 2.63-2.53 (m, 3H), 2.20 (s, 6H), 2.07-1.97 (m, 1H).<br>LC/MS (ESI) m/z [M + H]+ : 783.57 |
| Cpd. 264 | 1H NMR (400 MHz, DMSO-d6) δ 11.07 (s, 1H), 9.63 (s, 1H), 8.35 (d, J = 3.0 Hz, 1H), 8.10 (d, J = 2.9 Hz, 1H), 7.69 (s, 1H), 7.63 (d, J = 8.4 Hz, 1H), 7.14-7.08 (m, 4H), 6.95-6.93 (m, 1H), 6.87-6.83 (m, 1H), 6.66-6.64 (m, 1H), 5.32-5.27 (m, 1H), 4.74 (s, 1H), 4.61 (s, 1H), 3.79-3.77 (m, 2H), 3.70-3.69 (m, 2H), 3.63 (s, 3H), 3.32 (s, 3H), 2.94-2.80 (m, 4H), 2.78-2.68 (m, 4H), 2.20 (s, 6H), 2.02-1.96 (m, 1H), 1.77-1.73 (m, 4H).<br>LC/MS (ESI) m/z [M + H]+: 768.65 |
| Cpd. 268 | 1H NMR (400 MHz, DMSO-d6) δ 11.07 (s, 1H), 9.95 (s, 1H), 8.35 (s, 1H), 8.27 (d, J = 9.8 Hz, 1H), 8.15 (s, 1H), 7.65 (d, J = 8.5 Hz, 1H), 7.39-7.27 (m, 2H), 7.24 (dd, J = 8.9, 2.3 Hz, 1H), 7.10 (q, J = 5.2 Hz, 3H), 5.06 (dd, J = 12.8, 5.4 Hz, 1H), 4.06 (d, J = 12.9 Hz, 2H), 3.59 (s, 3H), 3.51 (s, 4H), 2.97 (d, J = 12.3 Hz, 2H), 2.92-2.80 (m, 1H), 2.54 (s, 6H), 2.19 (s, 8H), 2.06-1.93 (m, 2H), 1.83 (d, J = 13.4 Hz, 2H), 1.18 (d, J= 12.5 Hz, 2H).<br>LC/MS (ESI) m/z [M + H]+: 784.59 |
| Cpd. 272 | LC/MS: 785.4 M + H<br>1H NMR (400 MHz, DMSO-d6) δ 10.98 (s, 1H), 9.60 (s, 1H), 8.35 (s, 1H), 8.09 (s, 1H), 7.76 (d, J = 8.6 Hz, 2H), 7.41 (d, J = 11.6 Hz, 1H), 7.24 (d, J = 7.6 Hz, 1H), 7.17 (d, J = 8.6 Hz, 2H), 7.14-7.05 (m, 3H), 5.07 (dd, J = 13.2, 5.1 Hz, 1H), 4.36 (d, J = 17.2 Hz, 1H), 4.24 (d, J = 17.1 Hz, 1H), 3.61 (s, 3H), 3.54-3.45 (m, 2H), 3.09-2.84 (m, 3H), 2.80-2.72 (m, 2H), 2.64-2.55 (m, 2H), 2.46-2.32 (m, 2H), 2.27-2.24 (m, 1H), 2.20 (s, 6H), 2.05-1.91 (m, 3H), 1.88-1.80 (m, 2H), 1.80-1.58 (m, 5H), 1.39-1.27 (m, 2H). |

Experimental Example 1: Assay for BTK Protein Degradation

TMD-8, RAMOS, or 293T BTK MUT (C481S) cells were treated with the synthesized compounds and measured for intracellular BTK protein levels by Western blotting. The protocol of the experiment using TMD-8 cells is as follows.

[Culture]

TMD-8 cells were resuspended in an RPMI1640 medium (Hyclone, SH30027.01, 10% FBS (Hyclone, SV30207.02), 1% penicillin-streptomycin (Welgene, LS 202-02) and the cell suspension was seeded at a density of 1×106 cells/mL in an amount of 1 mL per well into 12-well plates.

[Treatment with Compound]

The 12-well plates were treated as follows. A 10 mM stock was 1/10 diluted in series with DMSO (3 mL+27 mL DMSO) to form final concentrations of 10, 1, 0.1, 0.01, 0.001, and 0.0001 mM. The compounds with such concentrations were applied to cells, followed by harvesting the cells 24 hours later. For a negative control, a 1/10 dilution of DMSO in the medium (3 mL DMSO+27 mL medium) was used.

[Harvest]

The 1-mL cell culture in each well was passed many times through a pipette and then transferred into a 1.5-mL microtube before centrifugation (500 g, 5 min, 4° C.). The supernatant was discarded and the cell pellet was washed with PBS. After centrifugation (500 g, 5 min, 4° C.) again, the supernatant was discarded and the cell pellet was taken.

[Cell Lysis and Sample Preparation]

A lysis buffer was prepared as follows. RIPA buffer (Biosesang, RC2038-050-00)+0.5 mM PMSF (SIGMA, P7626)+1×Protease/Phosphatase Inhibitor (Cell signaling, 5872S) was added in an amount 60-70 mL per well and left for 30 minutes on ice (vortexing at 0 and 30 minutes) before sonication (5 cycles of pulse for 10 seconds and rest for 30 seconds, 70% amplification). The supernatant obtained by centrifugation (15000 g, 15 min, 4° C.) was transferred into a new microtube. Cells in each well of 96-well plates were 1/2 diluted with the RIPA buffer and incubated at 37° C. for 30 minutes with 200 ml of a 50:1 mixture of BCA reagents A and B in BCA Protein Assay Kit (iNtRON, 21071). After being cooled for 10 minutes, the 96-well plates were measured for absorbance at 562 nm on the BioTek, SYNERGY $H_1$ microplate reader. Samples were prepared by protein quantification based on the absorbance measurements and then boiled at 70° C. for 10 minutes. The sample buffer used in the case was prepared by mixing a NuPAGE or a Bolt 4× sample buffer (Invitrogen) and its 10× sample reducing agent depending on the gel to be used, and protein dilution was made in a RIPI buffer.

[Western Blotting Assay]

The samples were loaded in the same amount into a NuPAGE or Bolt Bis-tris 4-12% gradient gel and allowed to run therein (200 V, 35 minutes). The separated proteins were transferred onto a 0.2-mm NC membrane, using Trans-blot Turbo (BIO-RAD) (1.3 A constant, 25V limit, 15 minutes). The membrane was blocked at room temperature for 1 hour with skim milk or Intercept Blocking Buffer (LI-COR, 927-60001):0.1% TBST=1:1. The membrane was incubated with Anti BTK Rabbit (1:1,000 in 5% skim milk/0.2% TBST, size: 77 kDa, Cell signaling Technology) at 4° C. overnight O/N or at room temperature for 2 hours and with Anti GAPDH Rabbit (1:10,000 in 5% BSA/0.2% TBST, size: 36 kDa, GENETEX) and Anti β-actin mouse (1:10,000 in 5% BSA/0.2% TBST, RT, size: 43 kDa, GENETEX) at room temperature for 1 or 3 hours. Then, the membrane was washed three times with 0.5% TBST for 5 minutes each time before incubation with the second antibody Anti-Rabbit IgG (1:5,000 in 5% Skim milk/TBST, CST), IRDye® 800CW Goat anti-Rabbit IgG Secondary Antibody (1:10,000 in 5% skim/TBST, RT 45 min), or IRDye® 680RD Goat anti-Mouse IgG Secondary Antibody (1:10,000 in 5% skim/TBST, RT 45 min) for 45 minutes at room temperature in a rocker. The membrane was washed five times with 0.5% TBST for 5 minutes in each time, followed by detection with LI-COR, Odyssey. In this regard, the detection proceeded, as it was, for house-keeping genes while using SuperSignal West Pico PLUS Chemiluminescent Substrate or SuperSignal West femto Maximum Sensitivity Substrate for BTK detection.

BTK protein degradation activities of the compounds of the present disclosure are summarized in Table 2, below. According to the concentration ranges of compounds accounting for 50% degradation of WT BTK protein and C481S BTK protein, the activities are expressed as +++ (0.0001-0.01 µM), ++(0.01-1 µM), +(1-10 µM), −(>10 µM), and NT (not tested). For comparison for BTK protein degradation activity, MT-802 (BTK degrader) was used as a control.

TABLE 2

| Compound No. | WT BTK Degradation ($DC_{50}$ %) | C481S BTK Degradation ($DC_{50}$ %) |
| --- | --- | --- |
| Compound 1 | ++ | − |
| Compound 2 | +++ | ++ |
| Compound 3 | +++ | + |
| Compound 4 | ++ | + |
| Compound 5 | ++ | ++ |
| Compound 6 | ++ | ++ |
| Compound 7 | +++ | − |
| Compound 8 | +++ | ++ |
| Compound 9 | ++ | − |
| Compound 10 | ++ | − |
| Compound 11 | +++ | − |
| Compound 12 | ++ | − |
| Compound 13 | +++ | + |
| Compound 14 | +++ | − |
| Compound 15 | +++ | + |
| Compound 16 | +++ | + |
| Compound 17 | +++ | − |
| Compound 18 | +++ | − |
| Compound 19 | ++ | − |
| Compound 20 | +++ | + |
| Compound 21 | +++ | + |
| Compound 22 | +++ | − |
| Compound 23 | +++ | + |
| Compound 24 | +++ | + |
| Compound 25 | +++ | + |
| Compound 26 | +++ | + |
| Compound 27 | +++ | + |
| Compound 28 | +++ | +++ |
| Compound 29 | +++ | ++ |
| Compound 30 | +++ | ++ |
| Compound 31 | +++ | ++ |
| Compound 32 | ++ | + |
| Compound 33 | ++ | NT |
| Compound 34 | ++ | NT |
| Compound 35 | +++ | ++ |
| Compound 36 | +++ | NT |
| Compound 37 | +++ | +++ |
| Compound 39 | +++ | NT |
| Compound 40 | +++ | NT |
| Compound 41 | ++ | NT |
| Compound 42 | +++ | NT |
| Compound 43 | +++ | NT |
| Compound 44 | +++ | NT |
| Compound 45 | +++ | NT |
| Compound 46 | ++ | ++ |
| Compound 47 | +++ | NT |
| Compound 48 | +++ | NT |
| Compound 49 | ++ | NT |
| Compound 50 | ++ | NT |
| Compound 51 | +++ | NT |
| Compound 52 | +++ | NT |
| Compound 53 | +++ | ++ |
| Compound 54 | +++ | ++ |
| Compound 55 | +++ | ++ |
| Compound 56 | ++ | ++ |
| Compound 57 | +++ | ++ |
| Compound 58 | +++ | ++ |
| Compound 59 | +++ | + |
| Compound 60 | +++ | ++ |
| Compound 61 | +++ | +++ |
| Compound 62 | +++ | ++ |
| Compound 63 | +++ | ++ |
| Compound 64 | +++ | NT |
| Compound 66 | ++ | NT |
| Compound 67 | ++ | NT |
| Compound 68 | ++ | NT |
| Compound 69 | ++ | NT |
| Compound 72 | ++ | NT |
| Compound 73 | ++ | NT |
| Compound 74 | ++ | NT |

TABLE 2-continued

| Compound No. | WT BTK Degradation (DC$_{50}$ %) | C481S BTK Degradation (DC$_{50}$ %) |
|---|---|---|
| Compound 75 | ++ | NT |
| Compound 76 | ++ | NT |
| Compound 80 | +++ | NT |
| Compound 81 | +++ | NT |
| Compound 82 | +++ | NT |
| Compound 83 | ++ | NT |
| Compound 84 | +++ | NT |
| Compound 85 | +++ | +++ |
| Compound 86 | +++ | NT |
| Compound 88 | +++ | +++ |
| Compound 90 | ++ | NT |
| Compound 91 | +++ | NT |
| Compound 92 | +++ | NT |
| Compound 93 | ++ | NT |
| Compound 94 | ++ | NT |
| Compound 95 | ++ | NT |
| Compound 96 | +++ | NT |
| Compound 97 | +++ | NT |
| Compound 98 | +++ | NT |
| Compound 100 | +++ | NT |
| Compound 101 | ++ | NT |
| Compound 102 | ++ | NT |
| Compound 103 | ++ | NT |
| Compound 104 | +++ | NT |
| Compound 105 | +++ | NT |
| Compound 106 | ++ | NT |
| Compound 107 | +++ | NT |
| Compound 108 | +++ | NT |
| Compound 109 | ++ | NT |
| Compound 110 | +++ | NT |
| Compound 111 | ++ | NT |
| Compound 112 | + | NT |
| Compound 116 | + | NT |
| Compound 117 | + | NT |
| Compound 118 | + | NT |
| Compound 121 | ++ | NT |
| Compound 122 | ++ | NT |
| Compound 123 | ++ | NT |
| Compound 124 | +++ | NT |
| Compound 125 | +++ | NT |
| Compound 126 | +++ | NT |
| Compound 127 | +++ | NT |
| Compound 128 | +++ | NT |
| Compound 129 | +++ | NT |
| Compound 130 | +++ | NT |
| Compound 131 | +++ | NT |
| Compound 132 | +++ | NT |
| Compound 133 | +++ | NT |
| Compound 134 | +++ | NT |
| Compound 135 | +++ | NT |
| Compound 136 | +++ | NT |
| Compound 137 | +++ | NT |
| Compound 138 | +++ | NT |
| Compound 139 | +++ | NT |
| Compound 140 | +++ | NT |
| Compound 141 | +++ | NT |
| Compound 142 | +++ | NT |
| Compound 143 | +++ | NT |
| Compound 144 | +++ | +++ |
| Compound 145 | +++ | NT |
| Compound 146 | +++ | NT |
| Compound 147 | +++ | NT |
| Compound 148 | +++ | NT |
| Compound 149 | +++ | +++ |
| Compound 150 | +++ | NT |
| Compound 151 | +++ | NT |
| Compound 152 | +++ | NT |
| Compound 153 | +++ | NT |
| Compound 154 | +++ | NT |
| Compound 155 | +++ | NT |
| Compound 156 | +++ | NT |
| Compound 157 | +++ | NT |
| Compound 158 | +++ | NT |
| Compound 159 | +++ | NT |
| Compound 160 | +++ | NT |
| Compound 161 | +++ | NT |
| Compound 162 | ++ | NT |
| Compound 163 | +++ | NT |
| Compound 164 | +++ | NT |
| Compound 165 | +++ | NT |
| Compound 166 | +++ | NT |
| Compound 167 | +++ | NT |
| Compound 168 | +++ | NT |
| Compound 169 | +++ | NT |
| Compound 170 | +++ | NT |
| Compound 171 | +++ | NT |
| Compound 172 | +++ | NT |
| Compound 173 | +++ | NT |
| Compound 174 | +++ | NT |
| Compound 175 | +++ | NT |
| Compound 176 | +++ | NT |
| Compound 177 | +++ | NT |
| Compound 178 | +++ | NT |
| Compound 179 | +++ | NT |
| Compound 180 | +++ | NT |
| Compound 181 | +++ | NT |
| Compound 182 | +++ | NT |
| Compound 183 | +++ | NT |
| Compound 184 | +++ | NT |
| Compound 185 | +++ | NT |
| Compound 186 | +++ | NT |
| Compound 187 | +++ | NT |
| Compound 188 | +++ | NT |
| Compound 192 | ++ | NT |
| Compound 193 | +++ | NT |
| Compound 194 | ++ | NT |
| Compound 195 | +++ | NT |
| Compound 199 | ++ | NT |
| Compound 201 | +++ | NT |
| Compound 204 | +++ | NT |
| Compound 205 | ++ | NT |
| Compound 208 | +++ | NT |
| Compound 209 | +++ | NT |
| Compound 210 | +++ | NT |
| Compound 211 | +++ | NT |
| Compound 217 | +++ | NT |
| Compound 218 | +++ | NT |
| Compound 219 | +++ | NT |
| Compound 220 | +++ | NT |
| Compound 221 | +++ | NT |
| Compound 222 | +++ | NT |
| Compound 225 | +++ | NT |
| Compound 226 | +++ | NT |
| Compound 227 | +++ | NT |
| Compound 228 | +++ | NT |
| Compound 229 | ++ | NT |
| Compound 230 | +++ | NT |
| Compound 231 | ++ | NT |
| Compound 232 | +++ | NT |
| Compound 233 | +++ | NT |
| Compound 234 | +++ | NT |
| Compound 235 | +++ | NT |
| Compound 236 | +++ | NT |
| Compound 237 | +++ | NT |
| Compound 238 | +++ | NT |
| Compound 239 | ++ | NT |
| Compound 240 | +++ | NT |
| Compound 241 | +++ | NT |
| Compound 243 | +++ | NT |
| Compound 244 | +++ | NT |
| Compound 245 | +++ | NT |
| Compound 246 | +++ | NT |
| Compound 247 | +++ | NT |
| Compound 248 | +++ | NT |
| Compound 250 | +++ | NT |
| Compound 253 | +++ | NT |
| Compound 254 | ++ | NT |
| Compound 255 | +++ | NT |
| Compound 256 | +++ | NT |
| Compound 257 | +++ | NT |
| Compound 258 | +++ | NT |
| Compound 259 | ++ | NT |

TABLE 2-continued

| Compound No. | WT BTK Degradation (DC$_{50}$ %) | C481S BTK Degradation (DC$_{50}$ %) |
|---|---|---|
| Compound 260 | +++ | NT |
| Compound 261 | +++ | NT |
| Compound 262 | +++ | NT |
| Compound 263 | +++ | NT |
| Compound 264 | +++ | NT |
| Compound 268 | +++ | NT |
| Compound 272 | +++ | NT |
| MT-802 (Comparative Compound) | ++ | + |

It can be understood from the data of Table 1 that the compounds according to the present disclosure have excellent degradative effects on Bruton's tyrosine kinase (BTK).

With excellent degradative effects on Bruton's tyrosine kinase (BTK), the novel heterocyclic compounds according to the present disclosure can find advantageous applications as an active ingredient in pharmaceutical compositions for prevention or treatment of cancer, autoimmune diseases, and Parkinson's disease.

Preparation Example 1. Preparation of Pulvis

A pulvis was prepared by mixing 2 g of Compound 28 of the present disclosure and 1 g of lactose and loading the mixture into an airtight bag.

Preparation Example 2. Preparation of Tablet

A tablet was preparing by mixing 100 mg of Compound 28 of the present disclosure, 100 mg of microcrystalline cellulose, 60 mg of lactose hydrate, 20 mg of low-substituted hydroxypropyl cellulose, and 2 mg of magnesium stearate and tableting the mixture according to a typical tablet formulation method.

Preparation Example 3. Preparation of Capsule

A capsule was prepared by mixing 100 g of Compound 28 of the present disclosure, 100 mg of microcrystalline cellulose, 60 mg of lactose hydrate, 20 mg of low-substituted hydroxypropyl cellulose, and 2 mg of magnesium stearate and loading the mixture into a gelatin capsule.

Preparation Example 4. Preparation of Pill

Together with anti-hygroscopic additives including dextrin, maltodextrin, corn starch, and microcrystalline cellulose (MCC), 90 mg of Compound 28 of the present disclosure, 5 mg of glutinous rice starch, and 5 mg of pure water were mixed and formulated into a pill weighing 100 mg according to a typical method.

Preparation Example 5. Preparation of Injection

In each ampoule (2 mL), 10 mg of Compound 28 of the present disclosure was mixed with an appropriate amount of injectable sterile distilled water and an appropriate amount of a pH adjustor, and formulated according to a typical injection method.

The invention claimed is:

1. A bifunctional compound or pharmaceutically acceptable salt thereof, wherein the compound is selected from the group consisting of:

4-((6-(7-((3-((2,6-dimethylphenyl)amino)-1-methyl-1H-pyrazolo[3,4-d]pyrimidin-6-yl)amino)-3,4-dihydroisoquinolin-2 (1H)-yl)-6-oxohexyl)amino)-2-(2,6-dioxopiperidin-3-yl)isoindoline-1,3-dione (Compound 1), 5-((2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)amino)-2-(2,6-dioxopiperidin-3-yl)isoindoline-1,3-dione (Compound 2), 4-((2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)amino)-2-(2,6-dioxopiperidin-3-yl)isoindoline-1,3-dione (Compound 3), N-(2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)ethoxy)ethyl)-1-(2-(2,6-dioxopiperidin-3-yl)-1,3-dioxoisoindolin-4-yl)piperidine-4-carboxamide (Compound 4), N-(14-(7-((3-((2,6-dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)-1-(2-(2,6-dioxopiperidin-3-yl)-1,3-dioxoisoindolin-4-yl)piperidine-4-carboxamide (Compound 5), N-(4-(2-(2-(2-((2-(2,6-dioxopiperidin-3-yl)-1,3-dioxoisoindolin-4-yl)amino)ethoxy)ethoxy)ethoxy)phenyl)-4-(7-((3-((4-(2-methoxyethoxy)-2,6-dimethylphenyl)amino)-1-methyl-1H-pyrazolo[3,4-d]pyrimidin-6-yl)amino)-1,1-dimethyl-3,4-dihydroisoquinolin-2 (1H)-yl)-4-oxobutanamide (Compound 6), 4-((12-(7-((3-((2,6-dimethylphenyl)amino)-1-methyl-1H-pyrazolo[3,4-d]pyrimidin-6-yl)amino)-3,4-dihydroisoquinolin-2 (1H)-yl)-12-oxododecyl)amino)-2-(2,6-dioxopiperidin-3-yl)isoindoline-1,3-dione (Compound 7), 5-((14-(7-((3-((2,6-dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)amino)-2-(2,6-dioxopiperidin-3-yl)isoindoline-1,3-dione (Compound 8), N-(14-(7-((3-((2,6-dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)-2-((2-(2,6-dioxopiperidin-3-yl)-1,3-dioxoisoindolin-5-yl)oxy)acetamide (Compound 9), N-(14-(7-((3-((2,6-dimethylphenyl)amino)-1-methyl-1H-pyrazolo[3,4-d]pyrimidin-6-yl)amino)-3,4-dihydroisoquinolin-2 (1H)-yl)-14-oxo-3,6,9,12-tetraoxatetradecyl)-2-((2-(2,6-dioxopiperidin-3-yl)-1,3-dioxoisoindolin-4-yl)amino)acetamide (Compound 10), tert-butyl 1-((2-(2,6-dioxopiperidin-3-yl)-1,3-dioxoisoindolin-4-yl)amino)-2-oxo-6,9,12,15-tetraoxa-3-azaheptadecan-17-oate (Compound 11), N-(2-(2-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-1H-1,2,3-triazol-1-yl)ethoxy)ethoxy)ethyl)-2-((2-(2,6-dioxopiperidin-3-yl)-1,3-dioxoisoindolin-5-yl)amino)acetamide (Compound 12), 4-((14-(7-((3-((2,6-dimethylphenyl)amino)-1-methyl-1H-pyrazolo[3,4-d])pyrimidin-6-yl)amino)-3,4-dihydroisoquinolin-2 (1H)-yl)-14-oxo-3,6,9,12-tetraoxatetradecyl)amino)-2-(2,6-dioxopiperidin-3-yl) isoindoline-1,3-dione (Compound 13), tert-butyl 2-(2-(2-((2-(2,6-dioxopiperidin-3-yl)-1,3-dioxoisoindolin-5-yl)amino)ethoxy)ethoxy)acetate (Compound 14), 5-((15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)amino)-2-(2,6-dioxopiperidin-3-yl) isoindoline-1,3-dione (Compound 15), N-(15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-5-yl)oxy)acetamide (Compound 16), N-(15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-4-yl)oxy)acetamide (Compound 17), N-(15-(7-((3-((2,6-dimethylphenyl)amino)-1-methyl)-1H-pyrazolo[3,4-d]pyrimidin-6-yl)amino)-3,4-dihydroisoquinolin-2 (1H)-yl)-15-oxo-3,6,9,12-tetraoxapentadecyl)-2-(4-(2-(2,6-dioxopiperidin-3-yl)-1,3-dioxoisoindolin-5-yl)piperazin-1-yl)acetamide (Compound 18), N-(2-(2-(2-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-1H-1,2,3-triazol-1-yl)ethoxy)ethoxy)ethyl)-2-((2-(2,6-dioxopiperidin-3-yl)-1,3-dioxoisoindolin-4-yl)amino) acetamide (Compound 19), N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-(4-(2-(2,6-dioxopiperidin-3-yl)-1,3-dioxoisoindolin-5-yl) piperazin-1-yl)acetamide (Compound 20), N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-5-yl) piperidine-4-carboxamide (Compound 21), N-(15-(7-((3-((2,6-dimethylphenyl)amino)-1-methyl-1H-pyrazolo[3,4-d]pyrimidin-6-yl)amino)-3,4-dihydroisoquinolin-2 (1H)-yl)-15-oxo-3,6,9,12-tetraoxapentadecyl)-2-((2-(2,6-dioxopiperidin-3-yl)-1,3-dioxoisoindolin-5-yl)amino)acetamide (Compound 22), 2-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethoxy)-N-(2-(2,6-dioxopiperidin-3-yl)-1,3-dioxoisoindolin-5-yl)acetamide (Compound 23), N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-4-yl) piperidine-4-carboxamide (Compound 24), N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-2-((2-(2,6-dioxopiperidin-3-yl)-1,3-dioxoisoindolin-5-yl)oxy) acetamide (Compound 25), 5-(4-((R)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl) isoindoline-1,3-dione (Compound 26), N-(2-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethoxy)ethyl)-1-(2-(2,6-dioxopiperidin-3-yl)-1,3-dioxoisoindolin-5-yl)azetidine-3-carboxamide (Compound 27), 5-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-2-(2,6-dioxopiperidin-3-yl) isoindoline-1,3-dione (Compound 28), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 29), 5-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethoxy)-2-(2,6-dioxopiperidin-3-yl)isoindoline-1,3-dione (Compound 30), 5-(4-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)piperazin-1-yl)-2-(2,6-dioxopiperidin-3-yl) isoindoline-1,3-dione (Compound 31), 5-(4-(2-((R)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)piperazin-1-yl)-2-(2,6-dioxopiperidin-3-yl)isoindoline-1,3-dione (Compound 32), 5-(4-(2-((S)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)piperazin-1-yl)-2-(2,6-dioxopiperidin-3-yl)isoindoline-1,3-dione (Compound 33), 5-(2-((S)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethoxy)-2-(2,6-dioxopiperidin-3-yl) isoindoline-1,3-dione (Compound 34), 5-((2-((S)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidin-1-yl)-2-oxoethyl)amino)-2-(2,6-dioxopiperidin-3-yl) isoindoline-1,3-dione (Compound 35), 5-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-2-(2,6-dioxopiperidin-3-yl) isoindoline-1,3-dione (Compound 36), 3-(6-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-dione (Compound 37), 1-(5-(4-((7-((3-((2,6-dimethylphenyl))amino)-1-methyl-1H-pyrazolo[3,4-d]pyrimidin-6-yl)amino)-3,4-dihydroisoquinolin-2 (1H)-yl)methyl)piperidine-1-carbonyl)-2-methoxyphenyl)dihydropyrimidine-2,4 (1H, 3H)-dione (Compound 38), 5-(4-(2-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethyl)piperazin-1-yl)-2-(2,6-dioxopiperidin-3-yl) isoindoline-1,3-dione (Compound 39), 5-(4-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidine-1-carbonyl)piperidin-1-yl)-2-(2,6-dioxopiperidin-3-yl)isoindoline-1,3-dione (Compound 40), 5-(4-(((3-((3-((2,6-dimethylphenyl)amino)-1-methyl-1H-pyrazolo[3,4-d]pyrimidin-6-yl)amino)benzyl)amino)methyl)piperidin-1-yl)-2-(2,6-dioxopiperidin-3-yl)isoindoline-1,3-dione (Compound 41), 5-(4-(4-(((3-((3-((2,6-dimethylphenyl)amino)-1-methyl-1H-pyrazolo[3,4-d]pyrimidin-6-yl)amino)benzyl)amino)methyl)piperidine-1-carbonyl)piperidin-1-yl)-2-(2,6-dioxopiperidin-3-yl)isoindoline-1,3-dione (Compound 42), 5-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethoxy)-2-(2,6-dioxopiperidin-3-yl)isoindoline-1,3-dione (Compound 43), 5-(4-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)piperazin-1-yl)-2-(2,6-dioxopiperidin-3-yl)isoindoline-1,3-dione (Compound 44), 5-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)amino)-2-(2,6-dioxopiperidin-3-yl)isoindoline-1,3-dione (Compound 45), 3-(6-((4-((7-((3-((2,6-dimethylphenyl))amino)-1-methyl-1H-pyrazolo[3,4-d]pyrimidin-6-yl)amino)-3,4-dihydroisoquinolin-2 (1H)-yl)methyl)piperidin-1-yl)methyl)-4-oxobenzo[d][1,2,3]triazin-3 (4H)-yl)piperidin-2,6-dione (Compound 46), 5-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-(2,6-dioxopiperidin-3-yl)isoindoline-1,3-dione (Compound 47), 3-(6-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethoxy)-4-oxobenzo[d][1,2,3]triazin-3 (4H)-yl)piperidin-2,6-dione (Compound 48), 5-(2-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethoxy)-2-(2,6-dioxopiperidin-3-yl)isoindoline-1,3-dione (Compound 49), 5-(3-((4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)methyl)azetidin-1-yl)-2-(2,6-dioxopiperidin-3-yl)isoindoline-1,3-dione (Compound 50), 5-((2-(3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)azetidin-1-yl)-2-oxoethyl)amino)-2-(2,6-dioxopiperidin-3-yl)isoindoline-1,3-dione (Compound 51), 3-(6-((2-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidin-1-yl)-2-oxoethyl)amino)-4-oxobenzo[d][1,2,3]triazin-3 (4H)-yl)piperidin-2,6-dione (Compound 52), 3-(7-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-4-oxobenzo[d][1,2,3]triazin-3 (4H)-yl)piperidin-2,6-dione (Compound 53), 5-(4-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)piperidine-1-carbonyl)piperidin-1-yl)-2-(2,6-dioxopiperidin-3-yl)isoindoline-1, 3-dione (Compound 54), 3-(6-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethoxy)-4-oxobenzo[d][1,2,3]triazin-3 (4H)-yl)piperidin-2,6-dione (Compound 55), 5-(4-(7-((3-((2,6-dimethylphenyl)amino)-1-methyl-H-pyrazolo[3,4-d]pyrimidin-6-yl)amino)-1,2,3,4-tetrahydroisoquinoline-2-carbonyl)piperidin-1-yl)-2-(2,6-dioxopiperidin-3-yl)isoindoline-1,3-dione (Compound 56), 3-(6-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)amino)-4-oxobenzo[d][1,2,3]triazin-3 (4H)-yl)piperidin-2,6-dione (Compound 57), 3-(6-(4-(7-((3-((2,6-dimethylphenyl)amino)-1-methyl-1H-pyrazolo[3,4-d]pyrimidin-6-yl)amino)-,2,3,4-tetrahydroisoquinoline-2-carbonyl)piperidin-1-yl)-4-oxobenzo[d][1,2,3]triazin-3 (4H)-yl)piperidin-2,6-dione (Compound 58), 3-(5-(4-(7-((3-((2,6-dimethylphenyl))amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3 (4H)-yl)piperidin-2,6-dione (Compound 59), 3-(7-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidine-1-carbonyl)piperidin-1-yl)-4-oxobenzo[d][1,2,3]triazin-3 (4H)-yl)piperidin-2,6-dione (Compound 60), 3-(7-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-dione (Compound 61), 3-(5-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-4-oxobenzo[d][1,2,3]triazin-3 (4H)-yl)piperidin-2,6-dione (Compound 62), 3-(7-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-4-oxobenzo[d][1,2,3]triazin-3 (4H)-yl)piperidin-2,6-dione (Compound 63), 3-(4-(3-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-3-oxopropyl)-1-oxoisoindolin-2-yl)piperidin-2,6-dione (Compound 64), 3-(4-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)-3-oxopropyl)-1-oxoisoindolin-2-yl)piperidin-2,6-dione (Compound 65), 5-(3-(7-((3-((2,6-dimethylphenyl))amino)-1-methyl-1H-pyrazolo[3,4-d]pyrimidin-6-yl)amino)-1,2,3,4-tetrahydroisoquinoline-2-carbonyl)pyrrolidin-1-yl)-2-(2,6-dioxopiperidin-3-yl)isoindoline-1,3-dione (Compound 66), 5-(4-(3-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)pyrrolidine-1-carbonyl)piperidin-1-yl)-2-(2,6-dioxopiperidin-3-yl)isoindoline-1,3-dione (Compound 67), 3-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-2-oxoethyl)amino)-4-oxobenzo[d][1,2,3]triazin-3 (4H)-yl)piperidin-2,6-dione (Compound 68), 3-(7-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-4-oxobenzo[d][1,2,3]triazin-3 (4H)-yl)piperidin-2,6-dione (Compound 69), 5-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-(2,6-dioxopiperidin-3-yl)isoindoline-1,3-dione (Compound 70), 3-(7-(7-((3-((2,6-dimethylphenyl)amino)-1-methyl-1H-pyrazolo[3,4-d]pyrimidin-6-yl)amino)-3,4-dihydroisoquinolin-2 (1H)-yl)-4-oxobenzo[d][1,2,3]triazin-3 (4H)-yl)piperidin-2,6-dione (Compound 71), 5-((2-(7-((3-((2,6-dimethylphenyl)amino)-1-methyl-1H-pyrazolo[3,4-d]pyrinidin-6-yl)amino)-3,4-dihydroisoquinolin-2 (1H)-yl)-2-oxoethyl)amino)-2-(2,6-dioxopiperidin-3-yl)isoindoline-1,3-dione (Compound 72), 5-(4-((5-((3-((2,6-dimethylphenyl)amino)-1-methyl-1H-pyrazolo[3,4-d]pyrimidin-6-yl)amino)isoindolin-2-yl)methyl)piperidin-1-yl)-2-(2,6-dioxopiperidin-3-yl)isoindoline-1,3-dione (Compound 73), 3-(7-(4-((5-((3-((2,6-dimethylphenyl)amino)-1-methyl-1H-pyrazolo[3,4-d]pyrimidin-6-yl)amino)isoindolin-2-yl)methyl)piperidin-1-yl)-4-oxobenzo[d][1,2,3]triazin-3 (4H)-yl)piperidin-2,6-dione (Compound 74), 5-(4-((7-((3-((2,6-dimethylphenyl)amino)-1-methyl-1H-pyrazolo[3,4-d]pyrimidin-6-yl)amino)-1-methyl-3,4-dihydroisoquinolin-2 (1H)-yl)methyl)piperidin-1-yl)-2-(2,6-dioxopiperidin-3-yl)isoindoline-1,3-dione (Compound 75), 2-(2,6-dioxopiperidin-3-yl)-5-(4-((7-((3-((4-(2-methoxyethoxy)-2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 76), 5-((3-((2,6-dimethylphenyl)amino)-1-methyl-1H-pyrazolo[3,4-d]pyrimidin-6-yl)amino)-2'-(2,6-dioxopiperidin-3-yl)-[2,5'-biisoindoline]-1',3'-dione (Compound 77), 5-(4-((7-((3-((2,6-dimethylphenyl)amino)-1-methyl-1H-pyrazolo[3,4-d]pyrimidin-6-yl)amino)-1-isopropyl-3,4-dihydroisoquinolin-2 (1H)-yl)methyl)piperidin-1-yl)-2-(2,6-dioxopiperidin-3-yl)isoindoline-1,3-dione (Compound 78), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(1-methyl-2,6-dioxopiperidin-3-yl)isoindoline-1,3-dione (Compound 79), 3-(5-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-1-oxoisoindolin-2-yl)piperidin-2,6-dione (Compound 80), 3-(5-((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)amino)-1-oxoisoindolin-2-yl)piperidin-2,6-dione (Compound 81), 5-(4-((7-((3-((2,6-dichlorophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 82), 5-(4-((7-((3-((2,4-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 83), 2-(2,6-dioxopiperidin-3-yl)-5-(4-((7-((1-methyl-3-(o-tolylamino)-1H-pyrazolo[3,4-d]pyrimidin-6-yl)amino)-3,4-dihydroisoquinolin-2 (1H)-yl)methyl)piperidin-1-yl)isoindoline-1,3-dione (Compound 84), 5-(4-((7-((3-((2-chloro-6-methylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 85), 5-(4-((7-((3-((2,6-dimethylphenyl)amino)-1-isopropyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 86), 5-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)-2-(2,6-dioxopiperidin-3-yl)isoindoline-1,3-dione (Compound 87), 5-(4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)-2-(2,6-dioxopiperidin-3-yl)isoindoline-1,3-dione (Compound 88), 5-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)pyrrolidin-1-yl)-2-(2,6-dioxopiperidin-3-yl)isoindoline-1,3-dione (Compound 89), 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1,3-dioxoisoindolin-5-yl) acetamide (Compound 90), 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2-(2,6-dioxopiperidin-3-yl)-1-oxoisoindolin-5-yl)acetamide (Compound 91), 4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-N-(2-(2,6-dioxopiperidin-3-yl)-1-oxoisoindolin-5-yl)piperidine-1-carboxamide (Compound 92), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperazin-1-yl)-2-(2,6-dioxopiperidin-3-yl)isoindoline-1,3-dione (Compound 93), 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-((2-(2,6-dioxopiperidin-3-yl)-1-oxoisoindolin-5-yl)methyl)acetamide (Compound 94), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-2-(2,6-dioxopiperidin-3-yl)isoindoline-1,3-dione (Compound 95), 7-((3-((2,6-dimethylphenyl)amino)-1-methyl-1H-pyrazolo[3,4-d]pyrimidin-6-yl)amino)-N-(2-(2,6-dioxopiperidin-3-yl)-1-oxoisoindolin-5-yl)-3,4-dihydroisoquinoline-2 (1H)-carboxamide (Compound 96), 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-(1-(2-(2,6-dioxopiperidin-3-yl)-1,3-dioxoisoindolin-5-yl)piperidin-4-yl)acetamide (Compound 97), 3-(5-(((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)amino)methyl)-1-oxoisoindolin-2-yl)piperidin-2,6-dione (Compound 98), 7-((3-((2,6-dimethylphenyl)amino)-1-methyl-1H-pyrazolo[3,4-d]pyrimidin-6-yl)amino)-N-((2-(2,6-dioxopiperidin-3-yl)-1-oxoisoindolin-5-yl)methyl)-3,4-dihydroisoquinoline-2 (1H)-carboxamide (Compound 99), N-(4-((3-((2,6-dimethylphenyl)amino)-1-methyl-1H-pyrazolo[3,4-d]pyrimidin-6-yl)amino)phenethyl)-1-(2-(2,6-dioxopiperidin-3-yl)-1,3-dioxoisoindolin-5-yl)piperidine-4-carboxamide (Compound 100), N-(4-((3-((2,6-dimethylphenyl)amino)-1-methyl-1H-pyrazolo[3,4-d]pyrimidin-6-yl)amino)phenethyl)-1-(2-((2-(2,6-dioxopiperidin-3-yl)-1,3-dioxoisoindolin-5-yl)amino)-2-oxoethyl)piperidine-4-carboxamide (Compound 101), N4-(4-((3-((2,6-dimethylphenyl)amino)-1-methyl-1H-pyrazolo[3,4-d]pyrimidin-6-yl)amino)phenethyl)-N1-(2-(2,6-dioxopiperidin-3-yl)-1-oxoisoindolin-5-yl)piperidine-1,4-dicarboxamide (Compound 102), 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperazin-1-yl)-1-oxoisoindolin-2-yl)piperidin-2,6-dione (Compound 103), 3-(5-(4-(2-(7-((3-((2,6-dimethylphenyl)amino)-1-methyl-1H-pyrazolo[3,4-d]pyrimidin-6-yl)amino)-3,4-dihydroisoquinolin-2(1H)-yl)-2-oxoethyl)piperazin-1-yl)-1-oxoisoindolin-2-yl)piperidin-2,6-dione (Compound 104), 3-(5-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)-1-oxoisoindolin-2-yl)piperidin-2,6-dione (Compound 105), 3-(5-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)oxy)-1-oxoisoindolin-2-yl)piperidin-2,6-dione (Compound 106), (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methyl pivalate (Compound 107), 2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-N-(2-(2,6-dioxopiperidin-3-yl)-1-oxoisoindolin-5-yl)acetamide (Compound 108), 5-(4-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 109), 5-((2-(4-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-2-(2,6-dioxopiperidin-3-yl)isoindoline-1,3-dione (Compound 110), 1-(5-(4-(2-(6-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidine-1-carbonyl)-2-methoxyphenyl)dihydropyrimidine-2,4 (1H, 3H)-dione (Compound 111), 1-(5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidine-t-carbonyl)-2-methoxyphenyl)dihydropyrimidine-2,4 (1H, 3H)-dione (Compound 112), N-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)-3-(2,4-dioxotetrahydropyrimidin-t (2H)-yl)-4-methoxybenzamide (Compound 113), N-(4-((3-((2,6-dimethylphenyl)amino)-1-methyl-1H-pyrazolo[3,4-d]pyrimidin-6-yl)amino)phenethyl)-1-(2-((2-(2,6-dioxopiperidin-3-yl)-1,3-dioxoisoindolin-5-yl)amino)-2-oxoethyl)piperidine-4-carboxamide (Compound 114), 3-(5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperazin-1-yl)-1-oxoisoindolin-2-yl)piperidin-2,6-dione (Compound 115), 3-(6-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)oxy)-1-oxoisoindolin-2-yl)piperidin-2,6-dione (Compound 116), 3-(6-((1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidin-4-yl)oxy)-1-oxoisoindolin-2-yl)piperidin-2,6-dione (Compound 117), 2-(2,6-dioxopiperidin-3-yl)-5-(4-((7-((3-((4-methoxy-2-methylphenyl)amino)-1-methyl-1H-pyrazolo[3,4-d]pyrimidin-6-yl)amino)-3,4-dihydroisoquinolin-2(1H)-yl)methyl)piperidin-1-yl)isoindoline-1,3-dione (Compound 118), 5-(4-((7-((3-((2,3-dihydro-1H-inden-4-yl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 119), 2-(2,6-dioxopiperidin-3-yl)-5-(4-((7-((3-((2-fluoro-4-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 120), 2-(2,6-dioxopiperidin-3-yl)-5-(4-((7-((3-((4-fluoro-2-methylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 121), N-(4-((6-((2-((1-(2-(2,6-dioxopiperidin-3-yl)-1,3-dioxoisoindolin-5-yl)piperidin-4-yl)methyl)-1,2,3,4-tetrahydroisoquinolin-7-yl)amino)-1-methyl-1H-pyrazolo[3,4-d]pyrimidin-3-yl)amino)-3-methylphenyl)-3-(trifluoromethyl)benzamide (Compound 122), 5-((2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)amino)-2-(2,6-dioxopiperidin-3-yl)isoindoline-1,3-dione (Compound 123), 5-(2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-7-azaspiro[3.5]nonan-7-yl)-2-(2,6-dioxopiperidin-3-yl)isoindoline-1,3-dione (Compound 124), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)piperidin-1-yl)-2-(2,6-dioxopiperidin-3-yl)isoindoline-1,3-dione (Compound 125), 5-(4-(3-(7-((3-((2,6-dimethylphenyl)amino)-1-methyl-H-pyrazolo[3,4-d]pyrimidin-6-yl)amino)-3,4-dihydroisoquinolin-2 (1H)-yl)-3-oxopropyl)piperidin-1-yl)-2-(2,6-dioxopiperidin-3-yl)isoindoline-1,3-dione (Compound 126), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)piperidin-1-yl)-2-(2,6-dioxopiperidin-3-yl)isoindoline-1,3-dione (Compound 127), 5-(4-(((1r,4r)-4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)cyclohexyl)oxy)piperidin-1-yl)-2-(2,6-dioxopiperidin-3-yl)isoindoline-1,3-dione (Compound 128), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)-4-hydroxypiperidin-1-yl)-2-(2,6-dioxopiperidin-3-yl)isoindoline-1,3-dione (Compound 129), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidin-1-yl)-2-(2,6-dioxopiperidin-3-yl)isoindoline-1,3-dione (Compound 130), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)-4-hydroxypiperidin-1-yl)-2-(2,6-dioxopiperidin-3-yl)isoindoline-1,3-dione (Compound 131), 3-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-5-oxo-5,7-dihydro-6H-pyrrolo[3,4-b]pyridin-6-yl)piperidin-2,6-dione (Compound 132), 3-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-4-hydroxypiperidin-1-yl)-5-oxo-5,7-dihydro-6H-pyrrolo[3,4-b]pyridin-6-yl)piperidin-2,6-dione (Compound 133), 5-(4-((4-(5-((3-((2,6-dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione (Compound 134), 5-(4-((1-(5-((3-((2,6-dimethylphenyl)amino)-1-methyl-1H-pyrazolo[3,4-d]pyrimidin-6-yl)amino)pyridin-2-yl)piperidin-4-yl)methyl)piperazin-1-yl)-2-(2,6-dioxopiperidin-3-yl)isoindoline-1,3-dione (Compound 135), 5-(4-((4-(3-((3-((2,6-dimethylphenyl)amino)-1-methyl-1H-pyrazolo[3,4-d]pyrimidin-6-yl)amino)phenyl)piperazin-1-yl)methyl)piperidin-1-yl)-2-(2,6-dioxopiperidin-3-yl)isoindoline-1,3-dione (Compound 136), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(2,6-dioxopiperidin-3-yl)picolinamide (Compound 137), 5-(3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)azetidin-1-yl)-2-(2,6-dioxopiperidin-3-yl)isoindoline-1,3-dione (Compound 138), 5-(4-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)piperidin-1-yl)-2-(2,6-dioxopiperidin-3-yl)isoindoline-1,3-dione (Compound 139), 5-((R)-3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)piperidin-1-yl)-2-(2,6-dioxopiperidin-3-yl)isoindoline-1,3-dione (Compound 140), 5-((S)-3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)piperidin-1-yl)-2-(2,6-dioxopiperidin-3-yl)isoindoline-1,3-dione (Compound 141), 5-((R)-3-((4-(7-((3-((2,6-dimethylphenyl)amino)-1-methyl-H-pyrazolo[3,4-d]pyrimidin-6-yl)amino)-3,4-dihydroisoquinolin-2 (1H)-yl)piperidin-1-yl)methyl)pyrrolidin-1-yl)-2-(2,6-dioxopiperidin-3-yl)isoindoline-1,3-dione (Compound 142), 5-((S)-3-((4-(7-((3-((2,6-dimethylphenyl)amino)-1-methyl-1H-pyrazolo[3,4-d]pyrimidin-6-yl)amino)-3,4-dihydroisoquinolin-2 (1H)-yl)piperidin-1-yl)methyl)pyrrolidin-1-yl)-2-(2,6-dioxopiperidin-3-yl)isoindoline-1,3-dione (Compound 143), 5-((R)-3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione (Compound 144), 5-((S)-3-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione (Compound 145), 5-(4-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)ethyl)piperidin-1-yl)-2-(2,6-dioxopiperidin-3-yl)isoindoline-1,3-dione (Compound 146), 5-(3-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)azetidin-1-yl)-2-(2,6-dioxopiperidin-3-yl)isoindoline-1,3-dione (Compound 147), 5-((1R,5S,6S)-6-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)-3-azabicyclo[3.1.0]hexan-3-yl)-2-(2,6-dioxopiperidin-3-yl)isoindoline-1,3-dione (Compound 148), 5-(4-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)piperidin-1-yl)-2-(2,6-dioxopiperidin-3-yl)isoindoline-1,3-dione (Compound 149), 5-((R)-3-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)pyrrolidin-1-yl)-2-(2,6-dioxopiperidin-3-yl)isoindoline-1,3-dione (Compound 150), 5-((S)-3-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)pyrrolidin-1-yl)-2-(2,6-dioxopiperidin-3-yl)isoindoline-1,3-dione (Compound 151), 5-(3-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)azetidin-1-yl)-2-(2,6-dioxopiperidin-3-yl)isoindoline-1,3-dione (Compound 152), 5-((1R,5S,6S)-6-((3-(7-((3-((2,6-dimethylphenyl)amino)-1-methyl-1H-pyrazolo[3,4-d]pyrimidin-6-yl)amino)-3,4-dihydroisoquinolin-2 (1H)-yl)azetidin-1-yl)methyl)-3-azabicyclo[3.1.0]hexan-3-yl)-2-(2,6-dioxopiperidin-3-yl)isoindoline-1,3-dione (Compound 153), 5-((R)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)pyrrolidin-1-yl)-2-(2,6-dioxopiperidin-3-yl)isoindoline-1,3-dione (Compound 154), 5-((S)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)pyrrolidin-1-yl)-2-(2,6-dioxopiperidin-3-yl)isoindoline-1,3-dione (Compound 155), 5-(4-(4-(5-((3-((2,6-dimethylphenyl)amino)-1-methyl-1H-pyrazolo[3,4-d]pyrimidin-6-yl)amino)pyridin-2-yl)piperazin-1-yl)piperidin-1-yl)-2-(2,6-dioxopiperidin-3-yl)isoindoline-1,3-dione (Compound 156), 5-(4-(2-(4-(5-((3-((2,6-dimethylphenyl)amino)-1-methyl-1H-pyrazolo[3,4-d]pyrimidin-6-yl)amino)pyridin-2-yl)piperazin-1-yl)ethyl)piperidin-1-yl)-2-(2,6-dioxopiperidin-3-yl)isoindoline-1,3-dione (Compound 157), 5-(3-(4-(5-((3-((2,6-dimethylphenyl)amino)-1-methyl-1H-pyrazolo[3,4-d]pyrimidin-6-yl)amino)pyridin-2-yl)piperazin-1-yl)azetidin-1-yl)-2-(2,6-dioxopiperidin-3-yl)isoindoline-1,3-dione (Compound 158), 5-((4-(5-((3-((2,6-dimethylphenyl)amino)-1-methyl-1H-pyrazolo[3,4-d]pyrimidin-6-yl)amino)pyridin-2-yl)piperazin-1-yl)methyl)azetidin-1-yl)-2-(2,6-dioxopiperidin-3-yl)isoindoline-1,3-dione (Compound 159), 5-((R)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione (Compound 160), 5-((S)-3-((4-(5-((3-((2,6-dimethylphenyl)amino)-1-methyl-1H-pyrazolo[3,4-d]pyrimidin-6-yl)amino)pyridin-2-yl)piperazin-1-yl)methyl)piperidin-1-yl)-2-(2,6-dioxopiperidin-3-yl)isoindoline-1,3-dione (Compound 161), 5-(4-((4-(6-((3-((2,6-dimethylphenyl)amino)-1-methyl-1H-pyrazolo[3,4-d]pyrimidin-6-yl)amino)pyridin-3-yl)piperazin-1-yl)methyl)piperidin-1-yl)-2-(2,6-dioxopiperidin-3-yl)isoindoline-1,3-dione (Compound 162), 5-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidin-1-yl)-2-(2,6-dioxopiperidin-3-yl)isoindoline-1,3-dione (Compound 163), 5-(4-((4-(5-((3-((2,6-dimethylphenyl)amino)-1-methyl-1H-pyrazolo[3,4-d]pyrimidin-6-yl)amino)pyridin-2-yl)piperidin-1-yl)methyl)piperidin-1-yl)-2-(2,6-dioxopiperidin-3-yl)isoindoline-1,3-dione (Compound 164), 5-(4-((4-(4-((3-((2,6-dimethylphenyl)amino)-1-methyl-1H-pyrazolo[3,4-d]pyrimidin-6-yl)amino)phenyl)piperidin-1-yl)methyl)piperidin-1-yl)-2-(2,6-dioxopiperidin-3-yl)isoindoline-1,3-dione (Compound 165), 5-((R)-3-((4-(4-((3-((2,6-dimethylphenyl)amino)-1-methyl-1H-pyrazolo[3,4-d]pyrimidin-6-yl)amino)phenyl)piperidin-1-yl)methyl)pyrrolidin-1-yl)-2-(2,6-dioxopiperidin-3-yl)isoindoline-1,3-dione (Compound 166), 5-((S)-3-((4-(4-((3-((2,6-dimethylphenyl)amino)-1-methyl-1H-pyrazolo[3,4-d]pyrimidin-6-yl)amino)phenyl)piperidin-1-yl)methyl)pyrrolidin-1-yl)-2-(2,6-dioxopiperidin-3-yl)isoindoline-1,3-dione (Compound 167), 5-(4-(4-((3-((2,6-dimethylphenyl)amino)-1-methyl-1H-pyrazolo[3,4-d]pyrimidin-6-yl)amino)phenyl)-[1,4'-bipiperidin]-1'-yl)-2-(2,6-dioxopiperidin-3-yl)isoindoline-1,3-dione (Compound 168), 5-(3-((4-(4-((3-((2,6-dimethylphenyl)amino)-1-methyl-1H-pyrazolo[3,4-d]pyrimidin-6-yl)amino)phenyl)piperidin-1-yl)methyl)azetidin-1-yl)-2-(2,6-dioxopiperidin-3-yl)isoindoline-1,3-dione (Compound 169), 3-(2-(4-((4-(4-((3-((2,6-dimethylphenyl)amino)-1-methyl-1H-pyrazolo[3,4-d]pyrimidin-6-yl)amino)phenyl)piperidin-1-yl)methyl)piperidin-1-yl)-5-oxo-5,7-dihydro-6H-pyrrolo[3,4-b]pyridin-6-yl)piperidin-2,6-dione (Compound 170), 5-(4-((4-(5-((3-((2,6-dimethylphenyl)amino)-1-methyl-1H-pyrazolo[3,4-d]pyrimidin-6-yl)amino)pyrimidin-2-yl)piperazin-1-yl)methyl)piperidin-1-yl)-2-(2,6-dioxopiperidin-3-yl)isoindoline-1,3-dione (Compound 171), 5-(4-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 172), 5-((R)-3-((6-((3-((2,6-dimethylphenyl)amino)-1-methyl-1H-pyrazolo[3,4-d]pyrimidin-6-yl)amino)-3,4-dihydroisoquinolin-2(1H)-yl)methyl)pyrrolidin-1-yl)-2-(2,6-dioxopiperidin-3-yl)isoindoline-1,3-dione (Compound 173), 5-((S)-3-((6-((3-((2,6-dimethylphenyl)amino)-1-methyl-1H-pyrazolo[3,4-d]pyrimidin-6-yl)amino)-3,4-dihydroisoquinolin-2 (1H)-yl)methyl)pyrrolidin-1-yl)-2-(2,6-dioxopiperidin-3-yl)isoindoline-1,3-dione (Compound 174), 5-(4-((3-(4-((3-((2,6-dimethylphenyl)amino)-1-methyl-1H-pyrazolo[3,4-d]pyrimidin-6-yl)amino)phenyl)azetidin-1-yl)methyl)piperidin-1-yl)-2-(2,6-dioxopiperidin-3-yl)isoindoline-1,3-dione (Compound 175), 5-((R)-3-((3-(4-((3-((2,6-dimethylphenyl)amino)-1-methyl-1H-pyrazolo[3,4-d]pyrimidin-6-yl)amino)phenyl)azetidin-1-yl)methyl)pyrrolidin-1-yl)-2-(2,6-dioxopiperidin-3-yl)isoindoline-1,3-dione (Compound 176), 5-((S)-3-((3-(4-((3-((2,6-dimethylphenyl)amino)-1-methyl-1H-pyrazolo[3,4-d]pyrimidin-6-yl)amino)phenyl)azetidin-1-yl)methyl)pyrrolidin-1-yl)-2-(2,6-dioxopiperidin-3-yl)isoindoline-1,3-dione (Compound 177), 5-(4-(3-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-hydroxypropyl)piperazin-1-yl)-2-(2,6-dioxopiperidin-3-yl)isoindoline-1,3-dione (Compound 178), 5-((R)-3-((4-(4-((3-((2,6-dimethylphenyl)amino)-1-methyl-1H-pyrazolo[3,4-d]pyrimidin-6-yl)amino)phenyl)piperazin-1-yl)methyl)pyrrolidin-1-yl)-2-(2,6-dioxopiperidin-3-yl)isoindoline-1,3-dione (Compound 179), 5-((S)-3-((4-(4-((3-((2,6-dimethylphenyl)amino)-1-methyl-1H-pyrazolo[3,4-d]pyrimidin-6-yl)amino)phenyl)piperazin-1-yl)methyl)pyrrolidin-1-yl)-2-(2,6-dioxopiperidin-3-yl)isoindoline-1,3-dione (Compound 180), 5-(3-((4-(4-((3-((2,6-dimethylphenyl)amino)-1-methyl-1H-pyrazolo[3,4-d]pyrimidin-6-yl)amino)phenyl)piperazin-1-yl)methyl)azetidin-1-yl)-2-(2,6-dioxopiperidin-3-yl)isoindoline-1,3-dione (Compound 181), 5-(3-((3-(4-((3-((2,6-dimethylphenyl)amino)-1-methyl-1H-pyrazolo[3,4-d]pyrimidin-6-yl)amino)phenyl)azetidin-1-yl)methyl)azetidin-1-yl)-2-(2,6-dioxopiperidin-3-yl)isoindoline-1,3-dione (Compound 182), 5-(((S)-4-(4-((3-((2,6-dimethylphenyl)amino)-1-methyl-1H-pyrazolo[3,4-d]pyrimidin-6-yl)amino)phenyl)-3-methylpiperazin-1-yl)methyl)azetidin-1-yl)-2-(2,6-dioxopiperidin-3-yl)isoindoline-1,3-dione (Compound 183), 5-(3-(((R)-4-(4-((3-((2,6-dimethylphenyl)amino)-1-methyl-1H-pyrazolo[3,4-d]pyrimidin-6-yl)amino)phenyl)-3-methylpiperazin-1-yl)methyl)azetidin-1-yl)-2-(2,6-dioxopiperidin-3-yl)isoindoline-1,3-dione (Compound 184), 5-(3-(((S)-4-(4-((3-((2,6-dimethylphenyl)amino)-1-methyl-1H-pyrazolo[3,4-d]pyrimidin-6-yl)amino)phenyl)-2-methylpiperazin-1-yl)methyl)azetidin-1-yl)-2-(2,6-dioxopiperidin-3-yl)isoindoline-1,3-dione (Compound 185), 5-(3-(((R)-4-(4-((3-((2,6-dimethylphenyl)amino)-1-methyl-1H-pyrazolo[3,4-d]pyrimidin-6-yl)amino)phenyl)-2-methylpiperazin-1-yl)methyl)azetidin-1-yl)-2-(2,6-dioxopiperidin-3-yl)isoindoline-1,3-dione (Compound 186), 3-(2-(3-((4-(4-((3-((2,6-dimethylphenyl)amino)-1-methyl-1H-pyrazolo[3,4-d]pyrimidin-6-yl)amino)phenyl)piperazin-1-yl)methyl)azetidin-1-yl)-5-oxo-5,7-dihydro-6H-pyrrolo[3,4-b]pyridin-6-yl)piperidin-2,6-dione (Compound 187), 3-(2-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidin-1-yl)-5-oxo-5,7-dihydro-6H-pyrrolo[3,4-b]pyridin-6-yl)piperidin-2,6-dione (Compound 188), 2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-N-(3-(N-(2,6-dioxopiperidin-3-yl)sulfamoyl)-4-methylphenyl)acetamide (Compound 189), 7-((3-((2,6-dimethylphenyl)amino)-1-methyl-1H-pyrazolo[3,4-d]pyrimidin-6-yl)amino)-N-(3-(N-(2,6-dioxopiperidin-3-yl)sulfamoyl)-4-methylphenyl)-3,4-dihydroisoquinoline-2 (1H)-carboxamide (Compound 190), 3-(3-((3-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethyl)phenyl)amino)-2,5-dioxo-2,5-dihydro-1H-pyrrol-1-yl)piperidine-2,6-dione (Compound 192), 3-((3-(3-(2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)phenyl)amino)-2,5-dioxo-2,5-dihydro-1H-pyrrol-1-yl)piperidin-2,6-dione (Compound 193), 5-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)-2-oxoethoxy)-2-(2,6-dioxopiperidin-3-yl)isoindoline-1,3-dione (Compound 194), 5-(4-((7-((2-bromo-6-methylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 195), 5-(4-((((1-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)cyclopropyl)amino)methyl)piperidin-1-yl)-2-(2,6-dioxopiperidin-3-yl)isoindoline-1,3-dione (Compound 199), 3-(3-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2,5-dioxo-2,5-dihydro-1H-pyrrol-1-yl)piperidin-2,6-dione (Compound 201), N-(1-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)cyclopropyl)-1-(2-(2,6-dioxopiperidin-3-yl)-1,3-dioxoisoindolin-5-yl)piperidine-4-carboxamide (Compound 204), N-(1-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)cyclopropyl)-2-((2-(2,6-dioxopiperidin-3-yl)-1,3-dioxoisoindolin-5-yl)oxy)acetamide (Compound 205), (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methyl piperidine-4-carboxylate bistrifluoroacetic acid (Compound 206), (3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1,3-dioxoisoindolin-2-yl)-2,6-dioxopiperidin-1-yl)methyl 4-methylpentanoate (Compound 207), 5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)-6-fluoroisoindoline-1,3-dione (Compound 208), 3-(5-(1-(2-(7-((3-((2,6-dimethylphenyl)amino)-1-methyl-1H-pyrazolo[3,4-d]pyrimidin-6-yl)amino)-3,4-dihydroisoquinolin-2 (1H)-yl)acetyl)piperidin-4-yl)-1-oxoisoindolin-2-yl)piperidin-2,6-dione (Compound 209), 5-(4-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidine-1-carbonyl)piperidin-1-yl)-2-(2,6-dioxopiperidin-3-yl)-6-fluoroisoindoline-1,3-dione (Compound 210), 5-((2-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-2-oxoethyl)amino)-2-(2,6-dioxopiperidin-3-yl)-6-fluoroisoindoline-1,3-dione (Compound 211), 5-(4-((7-((3-((2,6-dibromophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 217), 5-(4-((7-((3-((2-bromo-6-chlorophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 218), 5-(4-((7-((3-((2-chloro-6-iodophenyl)amino)-1-methyl-1H-pyrazolo[3,4-d]pyrimidin-6-yl)amino)-3,4-dihydroisoquinolin-2 (1H)-yl)methyl)piperidin-1-yl)-2-(2,6-dioxopiperidin-3-yl)isoindoline-1,3-dione (Compound 219), 3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-6-fluoro-1-oxoisoindolin-2-yl)piperidin-2,6-dione (Compound 220), 2-(2,6-dioxopiperidin-3-yl)-5-(4-((7-((3-((4-fluoro-2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)isoindoline-1,3-dione (Compound 221), 5-(4-(2-(4-(4-((3-((2,6-dimethylphenyl)amino)-1-methyl-1H-pyrazolo[3,4-d]pyrimidin-6-yl)amino)phenyl)piperidin-1-yl)-2-oxoethyl)piperidin-1-yl)-2-(2,6-dioxopiperidin-3-yl)isoindoline-1,3-dione (Compound 222), 5-(4-(2-(4-(4-((3-((2,6-dimethylphenyl)amino)-1-methyl-1H-pyrazolo[3,4-d]pyrimidin-6-yl)amino)phenyl)piperidin-1-yl)-2-oxoethyl)piperazin-1-yl)-2-(2,6-dioxopiperidin-3-yl)isoindoline-1,3-dione (Compound 225), 5-(4-(2-(4-(4-((3-((2,6-dimethylphenyl)amino)-1-methyl-1H-pyrazolo[3,4-d]pyrimidin-6-yl)amino)-2-fluorophenyl)piperidin-1-yl)-2-oxoethyl)piperazin-1-yl)-2-(2,6-dioxopiperidin-3-yl)isoindoline-1,3-dione (Compound 226), 5-(4-(2-(4-(4-((3-((2,6-dimethylphenyl)amino)-1-methyl-1H-pyrazolo[3,4-d]pyrimidin-6-yl)amino)-2-fluorophenyl)piperidin-1-yl)-2-oxoethyl)piperidin-1-yl)-2-(2,6-dioxopiperidin-3-yl)isoindoline-1,3-dione (Compound 227), 5-(3-(4-(4-((3-((2,6-dimethylphenyl)amino)-1-methyl-1H-pyrazolo[3,4-d]pyrimidin-6-yl)amino)phenyl)piperidine-1-carbonyl)azetidin-1-yl)-2-(2,6-dioxopiperidin-3-yl)isoindoline-1,3-dione (Compound 228), 5-(3-(4-(4-((3-((2,6-dimethylphenyl)amino)-1-methyl-1H-pyrazolo[3,4-d]pyrimidin-6-yl)amino)-2-fluorophenyl)piperidine-1-carbonyl)azetidin-1-yl)-2-(2,6-dioxopiperidin-3-yl)isoindoline-1,3-dione (Compound 229), 5-(4-((4-(4-((3-((2,6-dimethylphenyl)amino)-1-methyl-1H-pyrazolo[3,4-d]pyrimidin-6-yl)amino)phenyl)-3,6-dihydropyridin-1 (2H)-yl)methyl)piperidin-1-yl)-2-(2,6-dioxopiperidin-3-yl)isoindoline-1,3-dione (Compound 230), 5-(4-((4-(4-((3-((2,6-dimethylphenyl)amino)-1-methyl-1H-pyrazolo[3,4-d]pyrimidin-6-yl)amino)-3-fluorophenyl)piperidin-1-yl)methyl)piperidin-1-yl)-2-(2,6-dioxopiperidin-3-yl)isoindoline-1,3-dione (Compound 231), 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-(2,6-dioxopiperidin-3-yl)isoindoline-1,3-dione (Compound 232), 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-(2,6-dioxopiperidin-3-yl)-6-fluoroisoindoline-1,3-dione (Compound 233), 5-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidine-1-carbonyl)piperidin-1-yl)-2-(2,6-dioxopiperidin-3-yl)isoindoline-1,3-dione (Compound 234), 5-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-oxoethyl)amino)-2-(2,6-dioxopiperidin-3-yl)isoindoline-1,3-dione (Compound 235), 5-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonothioyl)piperidin-1-yl)-2-oxoethoxy)-2-(2,6-dioxopiperidin-3-yl)isoindoline-1,3-dione (Compound 236), 3-(5-(4-((7-((3-((2,6-dimethylphenyl)amino)-1-methyl-1H-pyrazolo[3,4-d]pyrimidin-6-yl)amino)-3,4-dihydroisoquinolin-2 (1H)-yl)methyl)piperidin-1-yl)-1-oxoisoindolin-2-yl)piperidin-2,6-dione (Compound 237), 5-(4-(4-((3-((2,6-dimethylphenyl)amino)-1-methyl-1H-pyrazolo[3,4-d]pyrimidin-6-yl)amino)phenyl)piperazin-1-yl)-2-(2,6-dioxopiperidin-3-yl)isoindoline-1,3-dione (Compound 238), 5-(4-(4-((3-((2,6-dimethylphenyl)amino)-1-methyl-1H-pyrazolo[3,4-d]pyrinidin-6-yl)amino)phenyl)piperazin-1-yl)-2-(2,6-dioxopiperidin-3-yl)-6-fluoroisoindoline-1,3-dione (Compound 239), (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(1-(1-(2-(2,6-dioxopiperidin-3-yl)-1,3-dioxoisoindolin-5-yl)piperidine-4-carbonyl)piperidin-4-yl)acrylonitrile (Compound 240), (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(1-(2-((2-(2,6-dioxopiperidin-3-yl)-1,3-dioxoisoindolin-5-yl)oxy)acetyl)piperidin-4-yl)acrylonitrile (Compound 241), 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-(2,6-dioxopiperidin-3-yl)isoindoline-1,3-dione (Compound 243), 5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-(2,6-dioxopiperidin-3-yl)-6-fluoroisoindoline-1,3-dione (Compound 244), 3-(5-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidin-1-yl)-6-fluoro-1-oxoisoindolin-2-yl)piperidin-2,6-dione (Compound 245), 5-(4-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidine-1-carbonyl)piperidin-1-yl)-2-(2,6-dioxopiperidin-3-yl)isoindoline-1,3-dione (Compound 246), 5-((2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-oxoethyl)amino)-2-(2,6-dioxopiperidin-3-yl)isoindoline-1,3-dione (Compound 247), 5-(2-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidin-1-yl)-2-oxoethoxy)-2-(2,6-dioxopiperidin-3-yl)isoindoline-1,3-dione (Compound 248), 5-(4-((4-(5-((3-((2,6-dimethylphenyl)amino)-1-methyl-1H-pyrazolo[3,4-d]pyrimidin-6-yl)amino)-2-fluorophenyl)-3,6-dihydropyridin-1 (2H)-yl)methyl)piperidin-1-yl)-2-(2,6-dioxopiperidin-3-yl)isoindoline-1,3-dione (Compound 250), 5-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidin-1-yl)-2-(2,6-dioxopiperidin-3-yl)isoindoline-1,3-dione (Compound 253), 5-(4-(4-(4-((3-((2,6-dimethylphenyl)amino)-1-methyl-1H-pyrazolo[3,4-d]pyrimidin-6-yl)amino)phenyl)piperidine-1-carbonyl)-4-fluoropiperidin-1-yl)-2-(2,6-dioxopiperidin-3-yl)-6-fluoroisoindoline-1,3-dione (Compound 254), 3-(5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-4-fluoropiperidine-1-carbonyl)-1-oxoisoindolin-2-yl)piperidin-2,6-dione (Compound 255), 3-(5-(4-((4-(4-((3-((2,6-dimethylphenyl)amino)-1-methyl-1H-pyrazolo[3,4-d]pyrimidin-6-yl)amino)phenyl)piperazin-1-yl)methyl)piperidine-1-carbonyl)-1-oxoisoindolin-2-yl)piperidin-2,6-dione (Compound 256), 3-(5-(4-(4-((3-((2,6-dimethylphenyl)amino)-1-methyl-1H-pyrazolo[3,4-d]pyrimidin-6-yl)amino)phenyl)piperidine-1-carbonyl)-1-oxoisoindolin-2-yl)piperidin-2,6-dione (Compound 257), 3-(5-(4-((7-((3-((2,6-dimethylphenyl)amino)-1-methyl-H-pyrazolo[3,4-d]pyrimidin-6-yl)amino)-3,4-dihydroisoquinolin-2 (1H)-yl)methyl)piperidine-1-carbonyl)-1-oxoisoindolin-2-yl)piperidin-2,6-dione (Compound 258), (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(1-(2-(2,6-dioxopiperidin-3-yl)-1-oxoisoindoline-5-carbonyl)piperidin-4-yl)acrylonitrile (Compound 259), (E)-2-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)-3-(1-((2-(2,6-dioxopiperidin-3-yl)-1,3-dioxoisoindolin-5-yl)glycyl)piperidin-4-yl)acrylonitrile (Compound 260), (E)-2-(4-(4-((3-((2,6-dimethylphenyl)amino)-1-methyl-1H-pyrazolo[3,4-d]pyrimidin-6-yl)amino)phenyl)piperidine-1-carbonyl)-3-(1-((2-(2,6-dioxopiperidin-3-yl)-1,3-dioxoisoindolin-5-yl)glycyl)piperidin-4-yl)acrylonitrile (Compound 261), 3-(5-(4-(4-(4-((3-((2,6-dimethylphenyl)amino)-1-methyl-1H-pyrazolo[3,4-d]pyrinidin-6-yl)amino)phenyl)piperidine-1-carbonyl)piperidin-1-yl)-3-methyl-2-oxo-2,3-dihydro-1H-benzo[d]imidazol-1-yl)piperidin-2,6-dione (Compound 262), 5-(3-(4-(5-((3-((2,6-dimethylphenyl)amino)-1-methyl-1H-pyrazolo[3,4-d]pyrimidin-6-yl)amino)-2-fluorophenyl)-1,2,3,6-tetrahydropyridine-1-carbonyl)azetidin-1-yl)-2-(2,6-dioxopiperidin-3-yl)isoindoline-1,3-dione (Compound 263), 3-(5-(4-(7-((3-((2,6-dimethylphenyl)amino)-1-methyl-1H-pyrazolo[3,4-d]pyrimidin-6-yl)amino)-1,2,3,4-tetrahydroisoquinoline-2-carbonyl)piperidin-1-yl)-3-methyl-2-oxo-2,3-dihydro-1H-benzo[d]imidazol-1-yl)piperidin-2,6-dione (Compound 264), 5-(4-((4-(6-((3-((2,6-dimethylphenyl)amino)-1-methyl-1H-pyrazolo[3,4-d]pyrimidin-6-yl)amino)pyridazin-3-yl)piperazin-1-yl)methyl)piperidin-1-yl)-2-(2,6-dioxopiperidin-3-yl)isoindoline-1,3-dione (Compound 268), and 3-(5-(4-((4-(4-((3-((2,6-dimethylphenyl)amino)-1-methyl-1H-pyrazolo[3,4-d]pyrimidin-6-yl)amino)phenyl)piperidin-1-yl)methyl)piperidin-1-yl)-6-fluoro-1-oxoisoindolin-2-yl)piperidin-2,6-dione (Compound 272).

2. A pharmaceutical composition comprising a compound according to claim 1, and a pharmaceutically acceptable carrier.

\* \* \* \* \*